(12) United States Patent
Klaenhammer et al.

(10) Patent No.: US 7,550,576 B2
(45) Date of Patent: Jun. 23, 2009

(54) NUCLEIC ACID SEQUENCES ENCODING TWO-COMPONENT SENSING AND REGULATORY PROTEINS, ANTIMICROBIAL PROTEINS AND USES THEREFOR

(75) Inventors: Todd R. Klaenhammer, Raleigh, NC (US); William M. Russell, Newburgh, IN (US); Eric Altermann, Apex, NC (US); Andrea Azcarate-Peril, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 160 days.

(21) Appl. No.: 11/199,489

(22) Filed: Aug. 8, 2005

(65) Prior Publication Data

US 2006/0134745 A1 Jun. 22, 2006

Related U.S. Application Data

(60) Provisional application No. 60/599,972, filed on Aug. 9, 2004.

(51) Int. Cl.
*C07H 21/04* (2006.01)
*C12N 1/20* (2006.01)
*C12N 15/00* (2006.01)
*C12P 21/06* (2006.01)

(52) U.S. Cl. .................. 536/23.7; 435/69.1; 435/252.3; 435/320.1

(58) Field of Classification Search .................. 536/23.1
See application file for complete search history.

(56) References Cited

U.S. PATENT DOCUMENTS

| 5,302,527 | A * | 4/1994 | Birkett et al. ............ 435/254.5 |
| 5,837,509 | A | 11/1998 | Israelsen et al. |
| 6,451,584 | B2 | 9/2002 | Tomita et al. |
| 6,476,209 | B1 | 11/2002 | Glenn et al. |
| 6,544,772 | B1 | 4/2003 | Glenn et al. |
| 6,635,460 | B1 | 10/2003 | Van Hijum et al. |
| 2002/0159976 | A1 | 10/2002 | Glenn et al. |
| 2003/0138822 | A1 | 7/2003 | Glenn et al. |
| 2004/0009490 | A1 | 1/2004 | Glenn et al. |
| 2004/0208863 | A1 | 10/2004 | Versalovic et al. |
| 2005/0003510 | A1 | 1/2005 | Chang et al. |
| 2005/0112612 | A1 | 5/2005 | Klaenhammer et al. |
| 2005/0123941 | A1 | 6/2005 | Klaenhammer et al. |
| 2005/0250135 | A1 | 11/2005 | Klaenhammer et al. |

FOREIGN PATENT DOCUMENTS

| EP | 0 888 118 B1 | 1/1999 |
| WO | WO 02/12506 A1 | 2/2002 |
| WO | WO 02/074798 A2 | 9/2002 |
| WO | WO 03/084989 A2 | 10/2003 |
| WO | WO 2004/020467 A2 | 3/2004 |
| WO | WO 2004/031389 A1 | 4/2004 |
| WO | WO 2004/069178 A2 | 8/2004 |
| WO | WO 2004/096992 A2 | 11/2004 |
| WO | WO 2005/001057 A2 | 1/2005 |
| WO | WO 2005/012491 A2 | 2/2005 |
| WO | WO 2005/081959 A2 | 9/2005 |
| WO | WO 2005/086794 A2 | 9/2005 |

OTHER PUBLICATIONS

Abee et al. (1994) "Kinetic studies of the action of lactacin F, a bacteriocin produced by *Lactobacillus johnsonii* that forms poration complexes in the cytoplasmic membrane" *Appl. Environ. Microbiol.* 60:1006-10013.

Allison and Klaenhammer (1996) "Functional analysis of the gene encoding immunity to lactacin F, *lafI*, and its use as a *Lactobacillus*-specific, food-grade genetic marker" *Appl. Environ. Microbiol.* 62:4450-4460.

Allison and Klaenhammer (1999) "Genetics of bacteriocins produced by lactic acid bacteria and their use in novel industrial applications" in *Manual of Industrial Microbiology and Biotechnology*. DeMain and Davies (eds.), ASM Press, Washington, D.C., pp. 789-808.

Allison et al. (1994) "Expansion of bacteriocin activity and host range upon complementation of two peptides encoded with the lactacin F operon" *J. Bacteriol.* 176:2235-2241.

Altermann et al. (2004) "Identification and phenotypic characterization of the cell-division protein CdpA" *Gene* 342:189-197.

Altermann et al. (2005) "Complete genome sequence of the probiotic lactic acid bacterium *Lactobacillus acidophilus* NCFM" *Proc. Natl. Acad. Sci. U.S.A.* Early Edition 10.1073/pnas.0409188102, online publication date Jan. 25, 2005.

Azcarate-Peril et al. (2004) "Identification and inactivation of genetic loci involved with *Lactobacillus acidophilus* acid tolerance" *Appl. Environ. Microbiol.* 70:5315-5322.

Barefoot and Klaenhammer (1983) "Detection and activity of lactacin B, a bacteriocin produced by *Lactobacillus acidophilus*" *Appl. Environ. Microbiol.* 45:1808-1815.

Barefoot and Klaenhammer (1984) "Purification and characterization of the *Lactobacillus acidophilus* bacteriocin lactacin B" *Antimicrob. Agents Chemother.* 26:328-334.

Barefoot et al. (1994) "Identification and purification of a protein that induces production of the *Lactobacillus acidophilus* bacteriocin lactacin B" *Appl. Environ. Microbiol.* 60:3522-3528.

Barrangou et al. (2003) "Functional and comparative genomic analyses of an operon involved in fructooligosaccharide utilization by *Lactobacillus acidophilus*" *Proc. Natl. Acad. Sci. U.S.A.* 100:8957-8962.

(Continued)

*Primary Examiner*—Mark Navarro
(74) *Attorney, Agent, or Firm*—Alston & Bird LLP

(57) ABSTRACT

Stress-related nucleic acid molecules and polypeptides and fragments and variants thereof are disclosed in the current invention. In addition, stress-related fusion proteins, antigenic peptides, and anti-stress-related antibodies are encompassed. The invention also provides recombinant expression vectors containing a nucleic acid molecule of the invention and cells into which the expression vectors have been introduced. Methods for producing the polypeptides and methods of use for the polypeptides of the invention are further disclosed.

22 Claims, 8 Drawing Sheets

OTHER PUBLICATIONS

Boels et al. (2001) "Functional analysis of the *Lactococcus lactis* galU and galE genes and their impact on sugar nucleotide and exopolysaccharide biosynthesis" *Appl. Environ. Microbiol.* 67:3033-3040.

Bruno-Barcena et al. (2004) "Expression of heterologous manganese superoxide dismutase gene in intestinal lactobacilli provides protection against hydrogen peroxide toxicity" *Appl. Environ. Microbiol.* 70:4702-4710.

Christensen et al. (1999) "Peptidases and Amino Acid Catabolism in Lactic Acid Bacteria" *Antonie van Leeuwenhoek* 76:217-246.

Coconnier et al. (1992) "Protein-mediated adhesion of *Lactobacillus acidophilus* BG2FO4 on human enterocyte and mucus-secreting cell lines in culture" *Appl. Environ. Microbiol.* 58:2034-2039.

Contreras et al. (1997) "Isolation, purification and amino acid sequence of lactobin A, one of the two bacteriocins produced by *Lactobacillus amylovorus* LMG P-13139" *Appl. Environ. Microbiol.* 63:13-20.

De Vuyst and Degeest (1998) "Heteropolysaccharides from lactic acid bacteria" *FEMS Microbiol. Rev.* 23:153-177.

Dodd and Gasson (1994) "Bacteriocins of lactic acid bacteria" in *Genetics and Biotechnology of Lactic Acid Bacteria.* Gasson and de Vos (eds.), Blackie Academic and Professional, London, pp. 211-251.

Fremaux et al. (1993) "Molecular analysis of the lactacin F operon" *Appl. Environ. Microbiol.* 59:3906-3915.

Girgis et al. (2002) "Stress adaptations of lactic acid bacteria" in *Microbial adaptation to stress and safety of new-generation foods.* Yousef and Juneja (eds.) CRC Press, NY, pp. 159-212.

Greene and Klaenhammer (1994) "Factors involved in adherence of lactobacilli to human Caco-2 cells" *Appl. Environ. Microbiol.* 60:4487-4494.

Holzapfel et al. (2001) "Taxonomy and Important Features of Probiotic Microorganisms in Food and Nutrition" *Am J of Clil Nutr* 73 Suppl: 365S-373S.

Hugenholtz (1999) "Metabolic Engineering of Lactic Acid Bacteria: Overview of the Approaches and Results of Pathway Rerouting Involved in Food Fermentations" *Current Opinion in Biotechnology* 10: 492-497.

Joerger and Klaenhammer (1986) "Characterization and purification of helveticin J and evidence for a chromosomally determined bacteriocin produced by *Lactobacillus helveticus*" *J. Bacteriol.* 167:439-446.

Joerger et al. (1990) "Cloning, expression, and nucleotide sequence of the *Lactobacillus helveticus* 481 gene encoding the bactericin helveticin J" *J. Bacteriol.* 172:6339-6347.

Jolly et al. (2002) "Exploiting exopolysaccharides from lactic acid bacteria" *Antonie van Leeuwenhoek* 82:367-374.

Klaenhammer (1988) "Bacteriocins of lactic acid bacteria" *Biochimie* 70:337-349.

Klaenhammer (1993) "Genetics of bacteriocins produced by lactic acid bacteria" *FEMS Microbiol. Rev.* 12:39-85.

Klaenhammer (2000) "Probiotic bacteria: today and tomorrow" *J. Nutr.* 130(2S Suppl.):415S-416S.

Klaenhammer and Kullen (1999) "Selection and design of probiotics" *Int. J. Food Microbiol.* 50:45-57.

Klaenhammer and Sutherland (1980) "Detection of plasmid deoxyribonucleic acid in an isolate of *Lactobacillus acidophilus*" *Appl. Environ. Microbiol.* 39:671-674.

Klaenhammer et al. (2002) "Discovering lactic acid bacteria by genomics" *Antonie van Leeuenhoek* 82:29-58'.

Klaenhammer et al. (2005) "*Lactobacillus acidophilus* Nucleic Acid Sequences Encoding Protease Homologues and Uses Therefore" U.S. Appl. No. 11/062,665, filed Feb. 22, 2005.

Klaenhammer et al. (2005) "*Lactobacillus acidophilus* Nucleic Acid Sequences Encoding Carbohydrate Utilization-Related Proteins and Uses Therefor" U.S. Appl. No. 11/074,226, filed Mar. 7, 2005.

Kleeman and Klaenhammer (1982) "Adherence of *Lactobacillus* species to human fetal intestinal cells" *J. Dairy Sci.* 65:2063-2069.

Kleerebezem et al. (1999) "Exopolysaccharides produced by *Lactococcus lactis*: from genetic engineering to improved rheological properties?" *Antonie van Leeuwenhoek* 76:357-365.

Kleerebezem et al. (2003) "Complete genome sequence of *Lactobacillus plantarum* WCFS1" *Proc. Natl. Acad. Sci. U.S.A.* 100:1990-1995.

Kok et al. (1994) "The Proteolytic System of Lactic Acid Bacteria" *Genetics and Biotechnology of Lactic Acid Bacteria* pp. 169-210.

Konigs et al. (1997) "The role of transport processes in survival of lactic acid bacteria" *Antonie van Leeuwenhoek* 71:117-128.

Konigs et al. (2000) "Lactic acid bacteria: the bugs of a new millennium" *Curr. Opin. Microbiol.* 3:276-282.

Kuipers et al. (2000) "Current Strategies for Improving Food Bacteria" *Res Microbiol* 151: 815-822.

Kullen and Klaenhammer (1999) Identification of the pH-inducible, proton-translocating $F_1F_0$-ATPase (atpBEFHAGDC) operon of *Lactobacillus acidophilus* by differential display: gene structure, cloning and characterization *Mol. Microbiol.* 33:1152-1161.

Kullen and Klaenhammer (2000) "Genetic modification of intestinal lactobacilli and bifidobacteria" *Curr. Issues Mol. Biol.* 2:41-50.

Kullen et al. (2000) "Use of the DNA sequence of variable regions of the 16S rRNA gene for rapid and accurate identification of bacteria in the *Lactobacillus acidophilus* complex" *J. Appl. Microbiol.* 89:511-516.

Law et al. (1997) "Proteolytic Enzymes of Lactic Acid Bacteria" *Int Dairy Journal* 7: 1-11.

Luchansky et al. (1988) "Application of electroporation for transfer of plasmid DNA to *Lactobacillus, Lactococcus, Leuconostoc, Listeria, Pediococcus, Bacillus, Staphylococcus, Enterococcus* and *Propionobacterium*" *Mol. Microbiol.* 2:637-646.

Luchansky et al. (1989) "Genetic transfer systems for delivery of plasmid deoxyribonucleic acid to *Lactobacillus acidophilus* ADH: conjugation, electroporation, and transduction" *J. Dairy Sci.* 72:1408-1417.

Luchansky et al. (1991) "Molecular cloning and deoxyribonucleic acid polymorphisms in *Lactobacillus acidophilus* and *Lactobacillus gasseri*" *J. Dairy Sci.* 74:3293-3302.

Majhenic et al. (2004) "DNA analysis of the genes encoding acidocin LF221 A and acidocin LF221 B, two bacteriocins produced by *Lactobacillus gasseri* LF221" *Appl. Microbiol. Biotechnol.* 63:705-714.

Mohamadzadeh et al. (2005) "Lactobacilli activate human dendritic cells that skew T cells toward T helper 1 polarization" *Proc. Nat. Acad. Sci. USA* 102:2880-2885.

Muriana and Klaenhammer (1991) "Cloning, phenotypic expression, and DNA sequence of the gene for lactacin F, an antimicrobial peptide produced by *Lactobacillus* spp." *J. Bacteriol.* 173:1779-1788.

Muriana and Klaenhammer (1991) "Purification and partial characterization of lactacin F, a bacteriocin produced by *Lactobacillus acidophilus* 11088" *Appl. Environ. Microbiol.* 57:114-121.

Pao et al. (1998) "Major Facilitator Superfamily" *Microbiol. Mol. Biol. Rev.* 62:1-34.

Poolman (2002) "Transporters and their roles in LAB cell physiology" *Antonie van Leeuwenhoek* 82:147-164.

Pridmore et al. (2004) "The genome sequence of the probiotic intestinal bacterium *Lactobacillus johnsonii* NCC 533" *Proc. Natl. Acad. Sci. U.S.A.* 101:2512-2517.

Putman et al. (2000) "Molecular properties of bacterial multidrug transporters" *Microbiol. Mol. Biol. Rev.* 64:672-693.

Rastall et al. (2005). Modulation of the microbial ecology of the human colon by probiotics, prebiotics and synbiotics to enhance human health: An overview of enabling science and potential applications. *FEMS Microbiol. Ecol.* 52:145-152.

Roy et al. (1993) "Cloning and expression of the manganese superoxide dismutase gene of *Escherichia coli* in *Lactococcus lactis* and *Lactobacillus gasseri*" *Mol. Gen. Genet.* 239:33-40.

Russell and Klaenhammer (2001) "Efficient system for directed integration into the *Lactobacillus acidophilus* and *Lactobacillus gasseri* chromosomes via homologous recombination" *Appl. Environ. Microbiol.* 67:4361-4364.

Russell and Klaenhammer (2001) "Identification and cloning of gusA, encoding a new β-glucuronidase from *Lactobacillus gasseri* ADH" *Appl. Environ. Microbiol.* 67:1253-1261.

Sablon et al. (2000) "Antimicrobiol peptides of lactic acid bacteria: mode of action, genetics and biosynthesis" in *Advances in Biochemical Engineering/Biotechnology.* vol. 68. Schleper (ed.), Springer-Verlag, Berlin, pp. 21-60.

Sanders and Klaenhammer (2001) "Invited review: the scientific basis of *Lactobacillus acidophilus* NCFM functionality as a probiotic" *J. Dairy Sci.* 84:319-331.

Sanders et al. (1996) "Performance of commercial cultures in fluid milk applications" *J. Dairy Sci.* 79:943-955.

Steidler et al. (1998) "Functional display of a heterologous protein on the surface of *Lactococcus lactis* by means of the cell wall anchor of *Staphylococcus aureus* protein A" *Appl. Environ. Microbiol.* 64:342-345.

Sturino and Klaenhammer (2004) "Bacteriophage defense systems for lactic acid bacteria" *Adv. Appl. Microbiol.* 56:331-378.

Ventura et al. (2003) "Analysis, characterization, and loci of *tuf* genes in *Lactobacillus and Bifidobacterium* species and their direct application for species identification" *Appl. Environ. Microbiol.* 69:6908-6922

Walker et al. (1999) "The groESL chaperone operon of *Lactobacillus johnsonii*" *Appl. Environ. Microbiol.* 65:3033-3041.

Yother et al. (2002) Genetics of streptococci, lactococci, and enterococci: review of the sixth international conference *J. Bacteriol.* 184:6085-6092.

GenBank Accession No. AAA19050; filed Jan. 17, 1994; Prolinase; Source: *Lactobacillus helveticus.*

GenBank Accession No. AAA25250; filed Jan. 13, 1994; Aminopeptidase C.; Source: *Lactobacillus helveticus.*

GenBank Accession No. AAB52540; filed Nov. 1, 1996; Endopeptidase; Source: *Lactobacillus helveticus.*

GenBank Accession No. AAB66326; filed Aug. 7, 1997; GroEL; Source: *Lactobacillus zeae.*

GenBank Accession No. AAC29003; filed Aug. 7, 1998; cochaperonin GroES; Source: *Lactobacillus helveticus.*

GenBank Accession No. AAC99363; filed Sep. 10, 1999; D-lactate dehydrogenase; Source: *Lactobacillus johnsonii.*

GenBank Accession No. AAF22492; filed Aug. 30, 2001; F1F0-ATPase subunit a; Source: *Lactobacillus acidophilus.*

GenBank Accession No. AAF22494; filed Aug. 30, 2001; F1F0-ATPase subunit b; Source: *Lactobacillus acidophilus.*

GenBank Accession No. AAF22495; filed Aug. 30, 2001; F1F0-ATPase subunit delta; Source: *Lactobacillus acidophilus.*

GenBank Accession No. AAF22496; filed Aug. 30, 2001; F1F0-ATPase subunit alpha; Source: *Lactobacillus acidophilus.*

GenBank Accession No. AAF22497; filed Aug. 30, 2001; FiF0-ATPase subunit gamma; Source: *Lactobacillus acidophilus.*

GenBank Accession No. AAF22498; filed Aug. 30, 2001; F1F0-ATPase subunit beta; Source: *Lactobacillus acidophilus.*

GenBank Accession No. AAF22499; filed Aug. 30, 2001; F1F0-ATPase subunit epsilon; Source: *Lactobacillus acidophilus.*

GenBank Accession No. AAF75593; filed Jun. 13, 2000; GroEL; Source: *Lactobacillus johnsonii.*

GenBank Accession No. AAK97217; filed Sep. 2, 2001; cochaperonin GroES; Source: *Lactobacillus acidophilus.*

GenBank Accession No. AAK97218; filed Sep. 2, 2001; chaperonin GroEL; Source: *Lactobacillus acidophilus.*

GenBank Accession No. AAK97220; filed Sep. 2, 2001; cochaperonin GrpE; Source: *Lactobacillus acidophilus.*

GenBank Accession No. AAK97221; filed Sep. 2, 2001; heat shock protein DnaK; Source: *Lactobacillus acidophilus.*

GenBank Accession No. AAQ72431; filed Aug. 11, 2003; Endopeptidase E2; Source: *Lactobacillus helveticus.*

GenBank Accession No. AAR25444; filed Dec. 3, 2003; Tuf; *Lactobacillus johnsonii.*

GenBank Accession No. AAT09141; filed Sep. 7, 2004; amino acid permease La995; Source: *Lactobacillus acidophilus.*

GenBank Accession No. AF010281; filed Aug. 9, 1997; *Lactobacillus zeae* GroES; Source: *Lactobacillus zeae.*

GenBank Accession No. AF031929; filed Aug. 8, 1998; *Lactobacillus helveticus* cochaperonin GroES and chaperonin GroEL genes, complete cds and DNA mismatch repair enzyme (hexA) gene, partial cds; Source: *Lactobacillus helveticus.*

GenBank Accession No. AF071558; filed Sep. 10, 1999; *Lactobacillus johnsonii* D-lactate dehydrogenase (ldhD) gene, complete cds; Source: *Lactobacillus johnsonii.*

GenBank Accession No. AF098522; filed Aug. 30, 2001; *Lactobacillus acidophilus* uracil phosphoribosyltransferase; Source: *Lactobacillus acidophilus.*

GenBank Accession No. AF214488; filed Jun. 13, 2000; *Lactobacillus johnsonii* groESL operon, complete sequence and unknown gene; Source: *Lactobacillus johnsonii.*

GenBank Accession No. AF300645; filed Sep. 2, 2001; *Lactobacillus acidophilus* groESL operon, complete sequence; Source: *Lactobacillus acidophilus.*

GenBank Accession No. AF300646; filed Sep. 2, 2001; *Lactobacillus acidophilus* repressor protein HrcA (hrcA) gene, partial cds; cochaperonin GrpE (grpE) and heat shock protein DnaK (dnaK) genes, complete cds, and DnaJ (dnaJ) gene, partical cds; Source: *Lactobacillus acidophilus.*

GenBank Accession No. B59088; filed Oct. 22, 1999; Prolyl Aminopeptidase; Source: *Lactobacillus helveticus.*

GenBank Accession No. CAA42781; filed Nov. 5, 1992; D-lactate dehydrogenase; Source: *Lactobacillus delbrueckii.*

GenBank Accession No. CAA59019; filed Apr. 18, 2005; heat shock induced protein HtpI; Source: *Lactobacillus leichmannii.*

GenBank Accession No. CAA61561; filed Jan. 22, 1996; SB-protein; *Lactobacillus acidophilus.*

GenBank Accession No. CAA86210; filed Oct. 10, 1994; Dipeptidase; Source: *Lactobacillus helveticus.*

GenBank Accession No. CAB72938; filed Jun. 23, 1999; Tripeptidase Enzyme; Source: *Lactobacillus helveticus.*

GenBank Accession No. NP_964658; filed Jan. 26, 2007; probable xylulose-5-phosphate/fructose-6-phosphate phosphoketolase; Source: *Lactobacillus johnsonii NCC 533.*

GenBank Accession No. NP_964694; filed Jan. 26, 2007; RecA protein; Source: *Lactobacillus johnsonii NCC 533.*

GenBank Accession No. NP_964728; filed Jan. 26, 2007; phosphoglycerate kinase; Source: *Lactobacillus johnsonii NCC 533.*

GenBank Accession No. NP_964948; filed Jan. 26, 2007; DNA-binding protein HU; Source: *Lactobacillus johsonii NCC 533.*

GenBank Accession No. NP_965314; filed Jan. 26, 2007; 50S ribosomal protein L19; Source: *Lactobacillus johnsonii NCC 533.*

GenBank Accession No. NP_965472; filed Jan. 26, 2007; thioredoxin; Source: *Lactobacillus johnsonii NCC 533.*

GenBank Accession No. NP_966600; filed Jan. 26, 2007; hypothetica protein LJ1693; Source: *Lactobacillus johnsonii NC 533.*

GenBank Accession No. O07684; filed Oct. 17, 2006; Beta-galactosidase large subunit; Source: *Lactobacillus acidophilus.*

GenBank Accession No. O07685; filed Nov. 28, 2006; Beta-galactosidase small subunit; Source: *Lactobacillus acidophilus.*

Genbank Accession No. O32755; filed Oct. 17, 2006; Glyceraldehyde-3-phosphate dehydrogenase; Source: *Lactobacillus delbrueckii* subsp. *Bulgaricus.*

GenBank Accession No. O32756; filed Apr. 18, 2006; Phosphoglycerate kinase; Source: *Lactobacillus delbrueckii* subsp. *Bulgaricus.*

GenBank Accession No. O32765; filed Nov. 28, 2006; L-lactate dehydrogenase; Source: *Lactobacillus helveticus.*

GenBank Accession No. O68324; filed Mar. 21, 2006; 60 kDa chaperonin; Source: *Lactobacillus helveticus.*

GenBank Accession No. O84913; filed Jul. 1, 1997; Xaa-Pro dipeptidase; Source: *Lactobacillus helveticus.*

GenBank Accession No. P26297; filed Jan. 23, 2007; D-lactate dehydrogenase; Source: *Lactobacillus delbrueckii* subsp. *Bulgaricus.*

GenBank Accession No. P30901; filed Jan. 23, 2007; D-lactate dehydrogenase; Source: *Lactobacillus helveticus.*

GenBank Accession No. P34038; filed Nov. 28, 2006; Pyruvate kinase; Source: *Lactobacillus delbrueckii* subsp. *Bulgaricus.*

GenBank Accession No. P35829; filed Jan. 9, 2007; S-layer protein precursor; Source: *Lactobacilus acidophilus.*

GenBank Accession No. P43451; filed Oct. 17, 2006; ATP synthase beta chain; Source: *Enterococcus hirae.*

GenBank Accession No. P94870; filed May 1, 1997; Aminopeptidase E.; Source: *Lactobacillus helveticus*.

GenBank Accession No. Q00052; filed Mar. 21, 2006; Galactokinase; Source: *Lactobacillus helveticus*.

GenBank Accession No. Q10730; filed Oct. 1, 1996; Aminopeptidase N; Source: *Lactobacillus helveticus*.

GenBank Accession No. Q10744; filed Nov. 1, 1996; Aminopeptidase C.; Source: *Lactobacillus helveticus*.

GenBank Accession No. Q48558; filed Sep. 26, 2001; Dipeptidase A.; Source: *Lactobacillus helveticus*.

GenBank Accession No. Q9Z4H7; filed Oct. 17, 2006; Serine protease do-like htrA; Source: *Lactobacillus helveticus*.

GenBank Accession No. S47274; filed Feb. 1, 1994; Membrane Alanyl Aminopeptidase; Source: *Lactobacillus helveticus*.

GenBank Accession No. S47276; filed Jan. 6, 1995; Prolinase; Source: *Lactobacillus helveticus*.

GenBank Accession No. X60220; filed Nov. 5, 1992; *L. delbrueckii* subsp. *Bulgaricus* 1dhA gene for D-lactate dehydrogenase; Source: *Lactobacillus delbrueckii*.

GenBank Accession No. X84261; filed Apr. 18, 2005; *L.leichmannii* xerC, hslU and HslV; Source: *Lactobacillus leichmannii*.

GenBank Accession No. X89376; filed Jan. 22, 1996; *L. acidphilus* DNA for SB-protein gene; Source: *Lactobacillus acidophilus*.

GenBank Accession No. ZP_00046537; filed May 25, 2006; COG0124: Histidyl-tRNA sythetase; Source: *Lactobacillus gasseri*.

GenBank Accession No. ZP_00046557; filed May 25, 2006; COG0148: Enolase; Source: *Lactobacillus gasseri*.

GenBank Accession No. ZP_00046583; filed May 25, 2006; COG0195: Transcription elongation factor; Source: *Lactobacillus gasseri*.

GenBank Accession No. ZP_00047305; filed May 25, 2006; COG4690: Dipeptidase; Source: *Lactobacillus gasseri*.

GenBank Accession No. ZP_00341831; filed May 25, 2006; COG0522: Ribosomal protein S4 and related proteins; Source: *Lactobacillus gasseri*.

GenBank Accession No. Q03234; filed Oct. 17, 2006; ATP synthesis beta chain; *Lactobacillus casei*.

* cited by examiner

```
                        SEQUENCE LISTING

<160> NUMBER OF SEQ ID NOS: 180

<210> SEQ ID NO 1
<211> LENGTH: 714
<212> TYPE: DNA
<213> ORGANISM: Lactobacillus acidophilus
<220> FEATURE:
<221> NAME/KEY: CDS
<222> LOCATION: (1)..(714)
<223> OTHER INFORMATION: vicR response regulator consisting of a Che
      Y-like receiver domain and a winged-helix DNA-binding domain ORF#
      78

<400> SEQUENCE: 1 atg cca aaa aaa att ctc gtc gtc gac gat gaa aag cct att tcc gat      48
Met Pro Lys Lys Ile Leu Val Val Asp Asp Glu Lys Pro Ile Ser Asp
1               5                   10                  15 att atc aaa ttt aat tta act aag gaa ggc ttt gac gtc gac act gcc      96
Ile Ile Lys Phe Asn Leu Thr Lys Glu Gly Phe Asp Val Asp Thr Ala
            20                  25                  30 tat gat ggc gaa gaa gct gtt aaa aaa gtt gac gaa tac gac cca gat     144
Tyr Asp Gly Glu Glu Ala Val Lys Lys Val Asp Glu Tyr Asp Pro Asp
        35                  40                  45 cta atg atc ttg gat tta atg ttg cca aaa aag gat gga cta gag gtt     192
Leu Met Ile Leu Asp Leu Met Leu Pro Lys Lys Asp Gly Leu Glu Val
    50                  55                  60 gct cgt gaa gtc cgt caa acg cat gat atg cca att att atg gta act     240
Ala Arg Glu Val Arg Gln Thr His Asp Met Pro Ile Ile Met Val Thr
65                  70                  75                  80 gca aaa gat act gaa atc gat aaa gtt tta gga ctc gaa atg ggt gcg     288
Ala Lys Asp Thr Glu Ile Asp Lys Val Leu Gly Leu Glu Met Gly Ala
```

```
                 85                  90                  95
gat gat tac gta act aaa cca ttt tct aac cgt gaa tta gtt gct cgg      336
Asp Asp Tyr Val Thr Lys Pro Phe Ser Asn Arg Glu Leu Val Ala Arg
            100                 105                 110 gtt aag gct aac tta cgt cgc cgc gat att gtt aaa aaa gca gaa gct      384
Val Lys Ala Asn Leu Arg Arg Arg Asp Ile Val Lys Lys Ala Glu Ala
        115                 120                 125 gca aat caa gaa gaa ccc gat aag aat att aag atc ggt aat ttg gtt      432
Ala Asn Gln Glu Glu Pro Asp Lys Asn Ile Lys Ile Gly Asn Leu Val
    130                 135                 140 atc atg cct gat gcc tat att gta gaa aag aat ggt aag aag att gaa      480
Ile Met Pro Asp Ala Tyr Ile Val Glu Lys Asn Gly Lys Lys Ile Glu
145                 150                 155                 160 ctt aca cat cgt gaa ttt gaa ctt ctt tac tat tta gct caa cat atg      528
Leu Thr His Arg Glu Phe Glu Leu Leu Tyr Tyr Leu Ala Gln His Met
                165                 170                 175 ggc caa gtt atg aca cgt gaa cat tta tta caa act gtt tgg ggt tat      576
Gly Gln Val Met Thr Arg Glu His Leu Leu Gln Thr Val Trp Gly Tyr
            180                 185                 190 gac tac ttt ggt gat gta cgt act gtt gat gta act gtt cac cgt ttg      624
Asp Tyr Phe Gly Asp Val Arg Thr Val Asp Val Thr Val His Arg Leu
        195                 200                 205 aga gaa aag att gag gat aac cca att caa cct caa att ttg gtt act      672
Arg Glu Lys Ile Glu Asp Asn Pro Ile Gln Pro Gln Ile Leu Val Thr
    210                 215                 220 cgt cgt ggt gtc ggc tac tat gta aaa cag cca agt gaa gga              714
Arg Arg Gly Val Gly Tyr Tyr Val Lys Gln Pro Ser Glu Gly
225                 230                 235

<210> SEQ ID NO 2
<211> LENGTH: 238
<212> TYPE: PRT
<213> ORGANISM: Lactobacillus acidophilus

<400> SEQUENCE: 2

Met Pro Lys Lys Ile Leu Val Val Asp Asp Glu Lys Pro Ile Ser Asp
1               5                   10                  15

Ile Ile Lys Phe Asn Leu Thr Lys Glu Gly Phe Asp Val Asp Thr Ala
            20                  25                  30

Tyr Asp Gly Glu Glu Ala Val Lys Lys Val Asp Glu Tyr Asp Pro Asp
        35                  40                  45

Leu Met Ile Leu Asp Leu Met Leu Pro Lys Lys Asp Gly Leu Glu Val
    50                  55                  60

Ala Arg Glu Val Arg Gln Thr His Asp Met Pro Ile Ile Met Val Thr
65                  70                  75                  80

Ala Lys Asp Thr Glu Ile Asp Lys Val Leu Gly Leu Glu Met Gly Ala
                85                  90                  95

Asp Asp Tyr Val Thr Lys Pro Phe Ser Asn Arg Glu Leu Val Ala Arg
            100                 105                 110

Val Lys Ala Asn Leu Arg Arg Arg Asp Ile Val Lys Lys Ala Glu Ala
        115                 120                 125

Ala Asn Gln Glu Glu Pro Asp Lys Asn Ile Lys Ile Gly Asn Leu Val
    130                 135                 140

Ile Met Pro Asp Ala Tyr Ile Val Glu Lys Asn Gly Lys Lys Ile Glu
145                 150                 155                 160

Leu Thr His Arg Glu Phe Glu Leu Leu Tyr Tyr Leu Ala Gln His Met
                165                 170                 175
```

```
Gly Gln Val Met Thr Arg Glu His Leu Leu Gln Thr Val Trp Gly Tyr
            180                 185                 190

Asp Tyr Phe Gly Asp Val Arg Thr Val Asp Thr Val His Arg Leu
        195                 200                 205

Arg Glu Lys Ile Glu Asp Asn Pro Ile Gln Pro Gln Ile Leu Val Thr
        210                 215                 220

Arg Arg Gly Val Gly Tyr Tyr Val Lys Gln Pro Ser Glu Gly
225                 230                 235

<210> SEQ ID NO 3
<211> LENGTH: 1854
<212> TYPE: DNA
<213> ORGANISM: Lactobacillus acidophilus
<220> FEATURE:
<221> NAME/KEY: CDS
<222> LOCATION: (1)..(1854)
<223> OTHER INFORMATION: vicK signal transduction histidine kinase ORF#
      79

<400> SEQUENCE: 3 atg aaa aaa ctc aga ata aaa cta aac act aca ttt aat tca att aat      48
Met Lys Lys Leu Arg Ile Lys Leu Asn Thr Thr Phe Asn Ser Ile Asn
1               5                   10                  15 act aaa tta gca att gta ttt atg ctg atg ttg ctt gca act att gaa     96
Thr Lys Leu Ala Ile Val Phe Met Leu Met Leu Leu Ala Thr Ile Glu
                20                  25                  30 gtt att ggt gct tat ttt act aga cag ctc gaa caa act agc att gaa    144
Val Ile Gly Ala Tyr Phe Thr Arg Gln Leu Glu Gln Thr Ser Ile Glu
            35                  40                  45 aac ttt caa tca tct att caa att caa act att gta agt aat cag tta    192
Asn Phe Gln Ser Ser Ile Gln Ile Gln Thr Ile Val Ser Asn Gln Leu
        50                  55                  60 gcc aat caa tta gct agt gat aat aaa aat gct aat gat cgc tta aac    240
Ala Asn Gln Leu Ala Ser Asp Asn Lys Asn Ala Asn Asp Arg Leu Asn
65                  70                  75                  80 cag att gtt aat gat tat aac aac gat gca att agt gaa att att gta    288
Gln Ile Val Asn Asp Tyr Asn Asn Asp Ala Ile Ser Glu Ile Ile Val
                85                  90                  95 gtt gat aat aag gac acg atc cgt gct gta tct aac tta aat gat aaa    336
Val Asp Asn Lys Asp Thr Ile Arg Ala Val Ser Asn Leu Asn Asp Lys
            100                 105                 110 agt aag att ggg caa aga att aat aat acg gat gtc aaa caa gta att    384
Ser Lys Ile Gly Gln Arg Ile Asn Asn Thr Asp Val Lys Gln Val Ile
        115                 120                 125 tca acg ggg cat cag atc aat aaa gtg att gat gat cat gga aat tat    432
Ser Thr Gly His Gln Ile Asn Lys Val Ile Asp Asp His Gly Asn Tyr
    130                 135                 140 atg att cag att tct cca cta acg agt gga aat ggt tct aat aat aat    480
Met Ile Gln Ile Ser Pro Leu Thr Ser Gly Asn Gly Ser Asn Asn Asn
145                 150                 155                 160 gta ggg gcg atc tat gtc aaa gca agc atg cag gat gtc ttt aat aac    528
Val Gly Ala Ile Tyr Val Lys Ala Ser Met Gln Asp Val Phe Asn Asn
                165                 170                 175 tta cga caa att tct ctt act ttc tta att gct tct tta att gca gct    576
Leu Arg Gln Ile Ser Leu Thr Phe Leu Ile Ala Ser Leu Ile Ala Ala
            180                 185                 190 tta ctt gga gca ttt ttg gca cta gtt att tcc cgt gca att acg caa    624
Leu Leu Gly Ala Phe Leu Ala Leu Val Ile Ser Arg Ala Ile Thr Gln
        195                 200                 205 cca att gaa gaa atg caa aaa caa gcg tta cat att gct gac gga gat    672
Pro Ile Glu Glu Met Gln Lys Gln Ala Leu His Ile Ala Asp Gly Asp
```

-continued

```
          210                 215                 220
tat tca agc cag gta aaa att tac tct aac gat gaa tta gga cag tta       720
Tyr Ser Ser Gln Val Lys Ile Tyr Ser Asn Asp Glu Leu Gly Gln Leu
225                 230                 235                 240 gga aaa gca ttc aat aca ctt tca gtt cgt att gaa cgg tcg caa gaa       768
Gly Lys Ala Phe Asn Thr Leu Ser Val Arg Ile Glu Arg Ser Gln Glu
                245                 250                 255 gaa tca gac agt gaa cgc cgt aga tta gac agc gta ctt tcc cat atg       816
Glu Ser Asp Ser Glu Arg Arg Arg Leu Asp Ser Val Leu Ser His Met
            260                 265                 270 agc gac gga gtg cta gca acc gat cgt cat ggt aat gtt agt gta gta       864
Ser Asp Gly Val Leu Ala Thr Asp Arg His Gly Asn Val Ser Val Val
        275                 280                 285 aat cat atg gtt ctt acc ttt ttg aat gct aaa gaa gaa gat gta atc       912
Asn His Met Val Leu Thr Phe Leu Asn Ala Lys Glu Glu Asp Val Ile
    290                 295                 300 aat aag cca att gcg gaa gta tta gga tta aaa gat act tcg tct cag       960
Asn Lys Pro Ile Ala Glu Val Leu Gly Leu Lys Asp Thr Ser Ser Gln
305                 310                 315                 320 gat ctt att tca agt cag aaa gag att gtg att act ctt gat gaa ggt      1008
Asp Leu Ile Ser Ser Gln Lys Glu Ile Val Ile Thr Leu Asp Glu Gly
                325                 330                 335 acg cgt gat gaa atg att ttg cat gct agc ttt tct tta ata aaa cgt      1056
Thr Arg Asp Glu Met Ile Leu His Ala Ser Phe Ser Leu Ile Lys Arg
            340                 345                 350 gta aca gga ttt gtt tct ggt agc gta tgt gtt ctg cat gat gta acg      1104
Val Thr Gly Phe Val Ser Gly Ser Val Cys Val Leu His Asp Val Thr
        355                 360                 365 gaa caa caa aag aat gaa aat tca caa cgc caa ttc gtt tct aat gta      1152
Glu Gln Gln Lys Asn Glu Asn Ser Gln Arg Gln Phe Val Ser Asn Val
    370                 375                 380 tct cat gaa ctt aga act cca tta acg agt ctg cag gca tat att gaa      1200
Ser His Glu Leu Arg Thr Pro Leu Thr Ser Leu Gln Ala Tyr Ile Glu
385                 390                 395                 400 gcg tta aat gaa ggg gca tgg aag gat cca gaa att gca cca aaa ttc      1248
Ala Leu Asn Glu Gly Ala Trp Lys Asp Pro Glu Ile Ala Pro Lys Phe
                405                 410                 415 ttg gaa gta acg caa caa gaa aca ggt cga atg att cgc atg att aac      1296
Leu Glu Val Thr Gln Gln Glu Thr Gly Arg Met Ile Arg Met Ile Asn
            420                 425                 430 gat tta ctt agt ctt tca aga atg gat cgt ggt gtt tca aag atg gat      1344
Asp Leu Leu Ser Leu Ser Arg Met Asp Arg Gly Val Ser Lys Met Asp
        435                 440                 445 tta gaa ttt gtt aat tta aac gat ttc gtt aac cac att ctt aat cgt      1392
Leu Glu Phe Val Asn Leu Asn Asp Phe Val Asn His Ile Leu Asn Arg
    450                 455                 460 ttt gat atg atc gtt aaa acg gat aaa aat aaa gat cat aaa aag aaa      1440
Phe Asp Met Ile Val Lys Thr Asp Lys Asn Lys Asp His Lys Lys Lys
465                 470                 475                 480 tat act att aaa cgc gaa tta gga aat caa gct ctt tgg gta gaa att      1488
Tyr Thr Ile Lys Arg Glu Leu Gly Asn Gln Ala Leu Trp Val Glu Ile
                485                 490                 495 gat act gat aag atg atg cag gta atc gat aat att atg aat aat gcg      1536
Asp Thr Asp Lys Met Met Gln Val Ile Asp Asn Ile Met Asn Asn Ala
            500                 505                 510 att aag tat tcg cca gac ggt ggt gta atc act gtt aga tta acg caa      1584
Ile Lys Tyr Ser Pro Asp Gly Gly Val Ile Thr Val Arg Leu Thr Gln
        515                 520                 525 aat cag aat cat gtt atc ttg agt att tct gac caa gga ttg ggt att      1632
```

```
Asn Gln Asn His Val Ile Leu Ser Ile Ser Asp Gln Gly Leu Gly Ile
            530                 535                 540 cca aga aaa gac tta gct aag atc ttt gat cga ttc tat cgt gta gat      1680
Pro Arg Lys Asp Leu Ala Lys Ile Phe Asp Arg Phe Tyr Arg Val Asp
545                 550                 555                 560 aag gct cgt tca cgt gca caa ggt ggt aca gga tta ggg ttg gca att      1728
Lys Ala Arg Ser Arg Ala Gln Gly Gly Thr Gly Leu Gly Leu Ala Ile
                565                 570                 575 gcc aaa gaa att gta gaa gct cac cac ggc cgt att tgg gct gat agt      1776
Ala Lys Glu Ile Val Glu Ala His His Gly Arg Ile Trp Ala Asp Ser
            580                 585                 590 agc gaa ggt aaa ggt tcg aca ttt tat att tcc tta cct tat gaa cca      1824
Ser Glu Gly Lys Gly Ser Thr Phe Tyr Ile Ser Leu Pro Tyr Glu Pro
        595                 600                 605 atg aca gag gag gat gac tgg gat gag att                              1854
Met Thr Glu Glu Asp Asp Trp Asp Glu Ile
610                 615

<210> SEQ ID NO 4
<211> LENGTH: 618
<212> TYPE: PRT
<213> ORGANISM: Lactobacillus acidophilus

<400> SEQUENCE: 4

Met Lys Lys Leu Arg Ile Lys Leu Asn Thr Thr Phe Asn Ser Ile Asn
1               5                   10                  15

Thr Lys Leu Ala Ile Val Phe Met Leu Met Leu Ala Thr Ile Glu
            20                  25                  30

Val Ile Gly Ala Tyr Phe Thr Arg Gln Leu Glu Gln Thr Ser Ile Glu
            35                  40                  45

Asn Phe Gln Ser Ser Ile Gln Ile Gln Thr Ile Val Ser Asn Gln Leu
        50                  55                  60

Ala Asn Gln Leu Ala Ser Asp Asn Lys Asn Ala Asn Asp Arg Leu Asn
65                  70                  75                  80

Gln Ile Val Asn Asp Tyr Asn Asn Asp Ala Ile Ser Glu Ile Ile Val
                85                  90                  95

Val Asp Asn Lys Asp Thr Ile Arg Ala Val Ser Asn Leu Asn Asp Lys
            100                 105                 110

Ser Lys Ile Gly Gln Arg Ile Asn Asn Thr Asp Val Lys Gln Val Ile
            115                 120                 125

Ser Thr Gly His Gln Ile Asn Lys Val Ile Asp His Gly Asn Tyr
        130                 135                 140

Met Ile Gln Ile Ser Pro Leu Thr Ser Gly Asn Gly Ser Asn Asn
145                 150                 155                 160

Val Gly Ala Ile Tyr Val Lys Ala Ser Met Gln Asp Val Phe Asn Asn
                165                 170                 175

Leu Arg Gln Ile Ser Leu Thr Phe Leu Ile Ala Ser Leu Ile Ala Ala
            180                 185                 190

Leu Leu Gly Ala Phe Leu Ala Leu Val Ile Ser Arg Ala Ile Thr Gln
        195                 200                 205

Pro Ile Glu Glu Met Gln Lys Gln Ala Leu His Ile Ala Asp Gly Asp
    210                 215                 220

Tyr Ser Ser Gln Val Lys Ile Tyr Ser Asn Asp Glu Leu Gly Gln Leu
225                 230                 235                 240

Gly Lys Ala Phe Asn Thr Leu Ser Val Arg Ile Glu Arg Ser Gln Glu
                245                 250                 255
```

Glu Ser Asp Ser Glu Arg Arg Leu Asp Ser Val Leu Ser His Met
                260                 265                 270

Ser Asp Gly Val Leu Ala Thr Asp Arg His Gly Asn Val Ser Val Val
            275                 280                 285

Asn His Met Val Leu Thr Phe Leu Asn Ala Lys Glu Glu Asp Val Ile
        290                 295                 300

Asn Lys Pro Ile Ala Glu Val Leu Gly Leu Lys Asp Thr Ser Ser Gln
305                 310                 315                 320

Asp Leu Ile Ser Ser Gln Lys Glu Ile Val Ile Thr Leu Asp Glu Gly
                325                 330                 335

Thr Arg Asp Glu Met Ile Leu His Ala Ser Phe Ser Leu Ile Lys Arg
            340                 345                 350

Val Thr Gly Phe Val Ser Gly Ser Val Cys Val Leu His Asp Val Thr
        355                 360                 365

Glu Gln Gln Lys Asn Glu Asn Ser Gln Arg Gln Phe Val Ser Asn Val
    370                 375                 380

Ser His Glu Leu Arg Thr Pro Leu Thr Ser Leu Gln Ala Tyr Ile Glu
385                 390                 395                 400

Ala Leu Asn Glu Gly Ala Trp Lys Asp Pro Glu Ile Ala Pro Lys Phe
                405                 410                 415

Leu Glu Val Thr Gln Gln Glu Thr Gly Arg Met Ile Arg Met Ile Asn
            420                 425                 430

Asp Leu Leu Ser Leu Ser Arg Met Asp Arg Gly Val Ser Lys Met Asp
        435                 440                 445

Leu Glu Phe Val Asn Leu Asn Asp Phe Val Asn His Ile Leu Asn Arg
    450                 455                 460

Phe Asp Met Ile Val Lys Thr Asp Lys Asn Lys Asp His Lys Lys Lys
465                 470                 475                 480

Tyr Thr Ile Lys Arg Glu Leu Gly Asn Gln Ala Leu Trp Val Glu Ile
                485                 490                 495

Asp Thr Asp Lys Met Met Gln Val Ile Asp Asn Ile Met Asn Asn Ala
            500                 505                 510

Ile Lys Tyr Ser Pro Asp Gly Gly Val Ile Thr Val Arg Leu Thr Gln
        515                 520                 525

Asn Gln Asn His Val Ile Leu Ser Ile Ser Asp Gln Gly Leu Gly Ile
    530                 535                 540

Pro Arg Lys Asp Leu Ala Lys Ile Phe Asp Arg Phe Tyr Arg Val Asp
545                 550                 555                 560

Lys Ala Arg Ser Arg Ala Gln Gly Gly Thr Gly Leu Gly Leu Ala Ile
                565                 570                 575

Ala Lys Glu Ile Val Glu Ala His His Gly Arg Ile Trp Ala Asp Ser
            580                 585                 590

Ser Glu Gly Lys Gly Ser Thr Phe Tyr Ile Ser Leu Pro Tyr Glu Pro
        595                 600                 605

Met Thr Glu Glu Asp Asp Trp Asp Glu Ile
    610                 615

<210> SEQ ID NO 5
<211> LENGTH: 450
<212> TYPE: DNA
<213> ORGANISM: Lactobacillus acidophilus
<220> FEATURE:
<221> NAME/KEY: CDS
<222> LOCATION: (1)..(450)
<223> OTHER INFORMATION: Two-component response regulator ORF# 248

```
<400> SEQUENCE: 5 ttg aag gtt aaa ttt cag gaa gat tcg tct cta aag agt gga gaa ctt      48
Leu Lys Val Lys Phe Gln Glu Asp Ser Ser Leu Lys Ser Gly Glu Leu
1               5                   10                  15 caa att gaa gta aaa gct ctt caa gag gat agt acg gtt aaa aaa tta      96
Gln Ile Glu Val Lys Ala Leu Gln Glu Asp Ser Thr Val Lys Lys Leu
            20                  25                  30 att agt tac tta aat aaa ttc ggt aaa aga gat cga aat ctt tta ccg     144
Ile Ser Tyr Leu Asn Lys Phe Gly Lys Arg Asp Arg Asn Leu Leu Pro
        35                  40                  45 att aaa acc agt gat cgg att gta aca ata aag cgt gag gaa tta ata     192
Ile Lys Thr Ser Asp Arg Ile Val Thr Ile Lys Arg Glu Glu Leu Ile
    50                  55                  60 aaa att gaa gta caa tca act act tta act tat tac acg acc aat gaa     240
Lys Ile Glu Val Gln Ser Thr Thr Leu Thr Tyr Tyr Thr Thr Asn Glu
65                  70                  75                  80 gtt att aaa act aca gga aga ctt tat cag gtc tta gat gat ttg aat     288
Val Ile Lys Thr Thr Gly Arg Leu Tyr Gln Val Leu Asp Asp Leu Asn
                85                  90                  95 aaa gat ttt gtg caa gtt tca cgc cac tct gta att aat cta aat tat     336
Lys Asp Phe Val Gln Val Ser Arg His Ser Val Ile Asn Leu Asn Tyr
            100                 105                 110 tta gaa tca ctt gaa agt gga ttt gct gga aat atg att gct ata ttg     384
Leu Glu Ser Leu Glu Ser Gly Phe Ala Gly Asn Met Ile Ala Ile Leu
        115                 120                 125 gct aat aaa tta aaa act gat gta tca cgt cgg tat ttg cca gat tta     432
Ala Asn Lys Leu Lys Thr Asp Val Ser Arg Arg Tyr Leu Pro Asp Leu
    130                 135                 140 gag aaa gag ctg gga tta                                             450
Glu Lys Glu Leu Gly Leu
145                 150

<210> SEQ ID NO 6
<211> LENGTH: 150
<212> TYPE: PRT
<213> ORGANISM: Lactobacillus acidophilus

<400> SEQUENCE: 6

Leu Lys Val Lys Phe Gln Glu Asp Ser Ser Leu Lys Ser Gly Glu Leu
1               5                   10                  15

Gln Ile Glu Val Lys Ala Leu Gln Glu Asp Ser Thr Val Lys Lys Leu
            20                  25                  30

Ile Ser Tyr Leu Asn Lys Phe Gly Lys Arg Asp Arg Asn Leu Leu Pro
        35                  40                  45

Ile Lys Thr Ser Asp Arg Ile Val Thr Ile Lys Arg Glu Glu Leu Ile
    50                  55                  60

Lys Ile Glu Val Gln Ser Thr Thr Leu Thr Tyr Tyr Thr Thr Asn Glu
65                  70                  75                  80

Val Ile Lys Thr Thr Gly Arg Leu Tyr Gln Val Leu Asp Asp Leu Asn
                85                  90                  95

Lys Asp Phe Val Gln Val Ser Arg His Ser Val Ile Asn Leu Asn Tyr
            100                 105                 110

Leu Glu Ser Leu Glu Ser Gly Phe Ala Gly Asn Met Ile Ala Ile Leu
        115                 120                 125

Ala Asn Lys Leu Lys Thr Asp Val Ser Arg Arg Tyr Leu Pro Asp Leu
    130                 135                 140

Glu Lys Glu Leu Gly Leu
145                 150
```

```
<210> SEQ ID NO 7
<211> LENGTH: 1278
<212> TYPE: DNA
<213> ORGANISM: Lactobacillus acidophilus
<220> FEATURE:
<221> NAME/KEY: CDS
<222> LOCATION: (1)..(1278)
<223> OTHER INFORMATION: Predicted signal transduction protein with
      C-terminal ATPase domain ORF# 602

<400> SEQUENCE: 7 gtg gat tat gtg act aca tat gat ttt ggc ttt att tca ggt gag ata      48
Val Asp Tyr Val Thr Thr Tyr Asp Phe Gly Phe Ile Ser Gly Glu Ile
1               5                   10                  15 gtt tta gtt att atc gag ctg aca ttt ttt tat gca att acc aat act      96
Val Leu Val Ile Ile Glu Leu Thr Phe Phe Tyr Ala Ile Thr Asn Thr
            20                  25                  30 aat ttt caa aag aaa gat att tta ttc gga cta gaa atc tta ctc tgt     144
Asn Phe Gln Lys Lys Asp Ile Leu Phe Gly Leu Glu Ile Leu Leu Cys
        35                  40                  45 ggc gtg ata act tct tca gat ttg ttg cat att cct caa gga tta agc     192
Gly Val Ile Thr Ser Ser Asp Leu Leu His Ile Pro Gln Gly Leu Ser
    50                  55                  60 agt att ctt tgg gcg tca tta act att ctt agc tat tat tat tac ttc     240
Ser Ile Leu Trp Ala Ser Leu Thr Ile Leu Ser Tyr Tyr Tyr Tyr Phe
65                  70                  75                  80 cgt cga aaa gta ggt agt tta cta gta ctg gcc gca att act ttg att     288
Arg Arg Lys Val Gly Ser Leu Leu Val Leu Ala Ala Ile Thr Leu Ile
                85                  90                  95 cgt tca gtt tta att ttg aat agt tta att tgg gga ctt tta tta aca     336
Arg Ser Val Leu Ile Leu Asn Ser Leu Ile Trp Gly Leu Leu Leu Thr
            100                 105                 110 act tta cca att gat gtt gct ctt tta tgc cta cca ata aca ttg ctt     384
Thr Leu Pro Ile Asp Val Ala Leu Leu Cys Leu Pro Ile Thr Leu Leu
        115                 120                 125 tgt ctt tac gtt att ttt atg aag ttc cgc cag tat att cat cgt ttt     432
Cys Leu Tyr Val Ile Phe Met Lys Phe Arg Gln Tyr Ile His Arg Phe
    130                 135                 140 ttg att gat gaa aat cat aag aca gct gat tgg cta gta atc tac cta     480
Leu Ile Asp Glu Asn His Lys Thr Ala Asp Trp Leu Val Ile Tyr Leu
145                 150                 155                 160 tat gtt tgt gca tta att ttg gat ctt acg tgt aca tat ggg att agt     528
Tyr Val Cys Ala Leu Ile Leu Asp Leu Thr Cys Thr Tyr Gly Ile Ser
                165                 170                 175 gct cat tca gaa tcg ctt ttc ttt tta atc atg cta gtt caa tca att     576
Ala His Ser Glu Ser Leu Phe Phe Leu Ile Met Leu Val Gln Ser Ile
            180                 185                 190 ttt atc att gct gtt tac gtt tct agt gta aat ata caa aag aaa tta     624
Phe Ile Ile Ala Val Tyr Val Ser Ser Val Asn Ile Gln Lys Lys Leu
        195                 200                 205 cta aaa aga caa gag caa gag aat tta aag gtc tat tta cat agt tta     672
Leu Lys Arg Gln Glu Gln Glu Asn Leu Lys Val Tyr Leu His Ser Leu
    210                 215                 220 gaa aag agt gaa gat cgg gtt cgt aag ttt aaa cat gat tat ctc aat     720
Glu Lys Ser Glu Asp Arg Val Arg Lys Phe Lys His Asp Tyr Leu Asn
225                 230                 235                 240 ctg ctg tct act tta aga act atg gcg gta gta aat aat gat caa aaa     768
Leu Leu Ser Thr Leu Arg Thr Met Ala Val Val Asn Asn Asp Gln Lys
                245                 250                 255 cta atc cag gag ctc gaa caa tac tca agt aaa caa att aat gaa gag     816
Leu Ile Gln Glu Leu Glu Gln Tyr Ser Ser Lys Gln Ile Asn Glu Glu
```

-continued

```
Leu Ile Gln Glu Leu Glu Gln Tyr Ser Ser Lys Gln Ile Asn Glu Glu
                260                 265                 270 agt atg tgg cga ttt aaa gat gta aat cat tta cgt aat aat gca tta      864
Ser Met Trp Arg Phe Lys Asp Val Asn His Leu Arg Asn Asn Ala Leu
            275                 280                 285 aag agt tta gtc atc aat aaa ttg aac aag ata agt gaa tta ggt gtt      912
Lys Ser Leu Val Ile Asn Lys Leu Asn Lys Ile Ser Glu Leu Gly Val
        290                 295                 300 aag tat tct ttt gaa tgc gaa aag gag att gaa act ttg cct gat cag      960
Lys Tyr Ser Phe Glu Cys Glu Lys Glu Ile Glu Thr Leu Pro Asp Gln
305                 310                 315                 320 gtc aaa ttg ttt gat cta tta aga ata att ggc att gtg ttt gat aac     1008
Val Lys Leu Phe Asp Leu Leu Arg Ile Ile Gly Ile Val Phe Asp Asn
                325                 330                 335 gct att gaa gca agt cag gca atg aaa aag gaa aat gct gag att aag     1056
Ala Ile Glu Ala Ser Gln Ala Met Lys Lys Glu Asn Ala Glu Ile Lys
            340                 345                 350 gtt atg ttt tac caa gaa aag cct gga gaa tta gaa ttc aag att caa     1104
Val Met Phe Tyr Gln Glu Lys Pro Gly Glu Leu Glu Phe Lys Ile Gln
        355                 360                 365 aat aag tgt caa caa gta gat atg aat caa gtc aat aaa aaa ggc tat     1152
Asn Lys Cys Gln Gln Val Asp Met Asn Gln Val Asn Lys Lys Gly Tyr
    370                 375                 380 act act aag gaa ggt cat tat ggc tta gga tta gtt acg gct cag gaa     1200
Thr Thr Lys Glu Gly His Tyr Gly Leu Gly Leu Val Thr Ala Gln Glu
385                 390                 395                 400 att aat gat agt tat agc aat atg ttt att gaa tac agc aat aaa gat     1248
Ile Asn Asp Ser Tyr Ser Asn Met Phe Ile Glu Tyr Ser Asn Lys Asp
                405                 410                 415 ggt tgg ttt agt ttt act ttg gta att atc                             1278
Gly Trp Phe Ser Phe Thr Leu Val Ile Ile
            420                 425

<210> SEQ ID NO 8
<211> LENGTH: 426
<212> TYPE: PRT
<213> ORGANISM: Lactobacillus acidophilus

<400> SEQUENCE: 8

Val Asp Tyr Val Thr Thr Tyr Asp Phe Gly Phe Ile Ser Gly Glu Ile
1               5                   10                  15

Val Leu Val Ile Ile Glu Leu Thr Phe Phe Tyr Ala Ile Thr Asn Thr
            20                  25                  30

Asn Phe Gln Lys Lys Asp Ile Leu Phe Gly Leu Glu Ile Leu Leu Cys
        35                  40                  45

Gly Val Ile Thr Ser Ser Asp Leu Leu His Ile Pro Gln Gly Leu Ser
    50                  55                  60

Ser Ile Leu Trp Ala Ser Leu Thr Ile Leu Ser Tyr Tyr Tyr Tyr Phe
65                  70                  75                  80

Arg Arg Lys Val Gly Ser Leu Val Leu Ala Ala Ile Thr Leu Ile
                85                  90                  95

Arg Ser Val Leu Ile Leu Asn Ser Leu Ile Trp Gly Leu Leu Thr
            100                 105                 110

Thr Leu Pro Ile Asp Val Ala Leu Leu Cys Leu Pro Ile Thr Leu Leu
        115                 120                 125

Cys Leu Tyr Val Ile Phe Met Lys Phe Arg Gln Tyr Ile His Arg Phe
    130                 135                 140

Leu Ile Asp Glu Asn His Lys Thr Ala Asp Trp Leu Val Ile Tyr Leu
```

```
                145                 150                 155                 160

Tyr Val Cys Ala Leu Ile Leu Asp Leu Thr Cys Thr Tyr Gly Ile Ser
                    165                 170                 175

Ala His Ser Glu Ser Leu Phe Phe Leu Ile Met Leu Val Gln Ser Ile
                    180                 185                 190

Phe Ile Ile Ala Val Tyr Val Ser Ser Val Asn Ile Gln Lys Lys Leu
                    195                 200                 205

Leu Lys Arg Gln Glu Gln Glu Asn Leu Lys Val Tyr Leu His Ser Leu
            210                 215                 220

Glu Lys Ser Glu Asp Arg Val Arg Lys Phe Lys His Asp Tyr Leu Asn
225                 230                 235                 240

Leu Leu Ser Thr Leu Arg Thr Met Ala Val Asn Asn Asp Gln Lys
                    245                 250                 255

Leu Ile Gln Glu Leu Glu Gln Tyr Ser Ser Lys Gln Ile Asn Glu Glu
                    260                 265                 270

Ser Met Trp Arg Phe Lys Asp Val Asn His Leu Arg Asn Asn Ala Leu
                275                 280                 285

Lys Ser Leu Val Ile Asn Lys Leu Asn Lys Ile Ser Glu Leu Gly Val
            290                 295                 300

Lys Tyr Ser Phe Glu Cys Glu Lys Glu Ile Glu Thr Leu Pro Asp Gln
305                 310                 315                 320

Val Lys Leu Phe Asp Leu Leu Arg Ile Ile Gly Ile Val Phe Asp Asn
                    325                 330                 335

Ala Ile Glu Ala Ser Gln Ala Met Lys Lys Glu Asn Ala Glu Ile Lys
                340                 345                 350

Val Met Phe Tyr Gln Glu Lys Pro Gly Glu Leu Glu Phe Lys Ile Gln
                355                 360                 365

Asn Lys Cys Gln Gln Val Asp Met Asn Gln Val Asn Lys Lys Gly Tyr
            370                 375                 380

Thr Thr Lys Glu Gly His Tyr Gly Leu Gly Leu Val Thr Ala Gln Glu
385                 390                 395                 400

Ile Asn Asp Ser Tyr Ser Asn Met Phe Ile Glu Tyr Ser Asn Lys Asp
                    405                 410                 415

Gly Trp Phe Ser Phe Thr Leu Val Ile Ile
                420                 425

<210> SEQ ID NO 9
<211> LENGTH: 795
<212> TYPE: DNA
<213> ORGANISM: Lactobacillus acidophilus
<220> FEATURE:
<221> NAME/KEY: CDS
<222> LOCATION: (1)..(795)
<223> OTHER INFORMATION: LytR/AlgR family response regulator ORF# 603

<400> SEQUENCE: 9 atg aaa tat aca gta ata att tgt gat gac aat ctt aat cat gcc agt      48
Met Lys Tyr Thr Val Ile Ile Cys Asp Asp Asn Leu Asn His Ala Ser
1               5                   10                  15 aat tta gct ttg aaa att ggc ata gcc gca atg gtt gac tcg ggt gat      96
Asn Leu Ala Leu Lys Ile Gly Ile Ala Ala Met Val Asp Ser Gly Asp
                20                  25                  30 aat cct gat aca gaa att gat tta gaa ata ggc aaa att gcg caa aat     144
Asn Pro Asp Thr Glu Ile Asp Leu Glu Ile Gly Lys Ile Ala Gln Asn
            35                  40                  45 gct tta gat gta att gag tat ttg aaa gag aat ccc att agc ggt gga     192
Ala Leu Asp Val Ile Glu Tyr Leu Lys Glu Asn Pro Ile Ser Gly Gly
```

```
                50                  55                  60
ata tat ttt tta gat att gaa ctg agt caa gaa aaa aat gca atg aat     240
Ile Tyr Phe Leu Asp Ile Glu Leu Ser Gln Glu Lys Asn Ala Met Asn
 65                  70                  75                  80 ggt atc gat ctg gct gaa caa gtt aaa caa tta gat cca cgt gct caa     288
Gly Ile Asp Leu Ala Glu Gln Val Lys Gln Leu Asp Pro Arg Ala Gln
                 85                  90                  95 atc att ttt gtt act gcc tat aac gaa tac atg gaa atg acg ttt gag     336
Ile Ile Phe Val Thr Ala Tyr Asn Glu Tyr Met Glu Met Thr Phe Glu
            100                 105                 110 cga cga ata ggc gca gtt gat tac att aat aaa agt aat cct aat ttg     384
Arg Arg Ile Gly Ala Val Asp Tyr Ile Asn Lys Ser Asn Pro Asn Leu
        115                 120                 125 caa aat cgc ctg aat gag aca ttg cag gat act gta aga agg att tca     432
Gln Asn Arg Leu Asn Glu Thr Leu Gln Asp Thr Val Arg Arg Ile Ser
    130                 135                 140 aag gaa aat tat agt aaa aaa atg act ttt tcc tat cgt ctg gga aga     480
Lys Glu Asn Tyr Ser Lys Lys Met Thr Phe Ser Tyr Arg Leu Gly Arg
145                 150                 155                 160 att att aaa aat atc aat att gat gat att tac tac att tca act acg     528
Ile Ile Lys Asn Ile Asn Ile Asp Asp Ile Tyr Tyr Ile Ser Thr Thr
                165                 170                 175 aag gca cca cat aaa ttg aaa tta gtt aaa aat gat gga act gcc gaa     576
Lys Ala Pro His Lys Leu Lys Leu Val Lys Asn Asp Gly Thr Ala Glu
            180                 185                 190 ttt gca ggg gat att aaa agt gta gat aag caa aat gag ttt ttg act     624
Phe Ala Gly Asp Ile Lys Ser Val Asp Lys Gln Asn Glu Phe Leu Thr
        195                 200                 205 aag gtc tca caa tca tat ttg gtg aat cct aaa aat att gtc cag atc     672
Lys Val Ser Gln Ser Tyr Leu Val Asn Pro Lys Asn Ile Val Gln Ile
    210                 215                 220 aat ttg aag aaa aaa gag att act tta tct aat ggg gat gca att aag     720
Asn Leu Lys Lys Lys Glu Ile Thr Leu Ser Asn Gly Asp Ala Ile Lys
225                 230                 235                 240 ttt tct cgt cga ttt act cac gtg atg aaa gac atg atc aat act tac     768
Phe Ser Arg Arg Phe Thr His Val Met Lys Asp Met Ile Asn Thr Tyr
                245                 250                 255 aat tta aag caa aat aat tac cag att                                 795
Asn Leu Lys Gln Asn Asn Tyr Gln Ile
            260                 265

<210> SEQ ID NO 10
<211> LENGTH: 265
<212> TYPE: PRT
<213> ORGANISM: Lactobacillus acidophilus

<400> SEQUENCE: 10

Met Lys Tyr Thr Val Ile Ile Cys Asp Asp Asn Leu Asn His Ala Ser
  1               5                  10                  15

Asn Leu Ala Leu Lys Ile Gly Ile Ala Ala Met Val Asp Ser Gly Asp
                 20                  25                  30

Asn Pro Asp Thr Glu Ile Asp Leu Glu Ile Gly Lys Ile Ala Gln Asn
             35                  40                  45

Ala Leu Asp Val Ile Glu Tyr Leu Lys Glu Asn Pro Ile Ser Gly Gly
         50                  55                  60

Ile Tyr Phe Leu Asp Ile Glu Leu Ser Gln Glu Lys Asn Ala Met Asn
 65                  70                  75                  80

Gly Ile Asp Leu Ala Glu Gln Val Lys Gln Leu Asp Pro Arg Ala Gln
                 85                  90                  95
```

```
Ile Ile Phe Val Thr Ala Tyr Asn Glu Tyr Met Glu Met Thr Phe Glu
            100                 105                 110

Arg Arg Ile Gly Ala Val Asp Tyr Ile Asn Lys Ser Asn Pro Asn Leu
        115                 120                 125

Gln Asn Arg Leu Asn Glu Thr Leu Gln Asp Thr Val Arg Arg Ile Ser
    130                 135                 140

Lys Glu Asn Tyr Ser Lys Lys Met Thr Phe Ser Tyr Arg Leu Gly Arg
145                 150                 155                 160

Ile Ile Lys Asn Ile Asn Ile Asp Asp Ile Tyr Tyr Ile Ser Thr Thr
                165                 170                 175

Lys Ala Pro His Lys Leu Lys Leu Val Lys Asn Asp Gly Thr Ala Glu
            180                 185                 190

Phe Ala Gly Asp Ile Lys Ser Val Asp Lys Gln Asn Glu Phe Leu Thr
        195                 200                 205

Lys Val Ser Gln Ser Tyr Leu Val Asn Pro Lys Asn Ile Val Gln Ile
    210                 215                 220

Asn Leu Lys Lys Lys Glu Ile Thr Leu Ser Asn Gly Asp Ala Ile Lys
225                 230                 235                 240

Phe Ser Arg Arg Phe Thr His Val Met Lys Asp Met Ile Asn Thr Tyr
                245                 250                 255

Asn Leu Lys Gln Asn Asn Tyr Gln Ile
            260                 265

<210> SEQ ID NO 11
<211> LENGTH: 720
<212> TYPE: DNA
<213> ORGANISM: Lactobacillus acidophilus
<220> FEATURE:
<221> NAME/KEY: CDS
<222> LOCATION: (1)..(720)
<223> OTHER INFORMATION: Response regulator consisting of a Che Y-like
      receiver domain and a winged-helix DNA-binding domain ORF# 746

<400> SEQUENCE: 11 atg agt tta aat ata tta atg gtt gaa gat gac aac tcc gtt gct gaa      48
Met Ser Leu Asn Ile Leu Met Val Glu Asp Asp Asn Ser Val Ala Glu
1               5                   10                  15 atg atg ggg atg ttt ttc aaa aaa gaa ggt tgg caa caa gat att gct     96
Met Met Gly Met Phe Phe Lys Lys Glu Gly Trp Gln Gln Asp Ile Ala
            20                  25                  30 gtt gac ggt gtc gaa gcc gtc gac atg ttt aga aaa aat gca gat aag    144
Val Asp Gly Val Glu Ala Val Asp Met Phe Arg Lys Asn Ala Asp Lys
        35                  40                  45 tat gat tta att act ttg gat ttg aat tta cct aaa aaa gac ggt att    192
Tyr Asp Leu Ile Thr Leu Asp Leu Asn Leu Pro Lys Lys Asp Gly Ile
50                  55                  60 caa gtt gcc aaa gaa gtg aga gca att tca cct act gta cca att att    240
Gln Val Ala Lys Glu Val Arg Ala Ile Ser Pro Thr Val Pro Ile Ile
65                  70                  75                  80 atg ctt act gct agg gga agt gaa tca gat caa gta cta ggt ctt ggt    288
Met Leu Thr Ala Arg Gly Ser Glu Ser Asp Gln Val Leu Gly Leu Gly
                85                  90                  95 att gga gct gat gaa tat gtc act aaa cct ttt agt cca att gct tta    336
Ile Gly Ala Asp Glu Tyr Val Thr Lys Pro Phe Ser Pro Ile Ala Leu
            100                 105                 110 att gct aga atc aag gca ctt cat cgt aga gtt atg atg gaa gaa gag    384
Ile Ala Arg Ile Lys Ala Leu His Arg Arg Val Met Met Glu Glu Glu
        115                 120                 125
```

```
ccg gat act gct aaa gaa gat aag caa gat tat gaa att acc aca aaa      432
Pro Asp Thr Ala Lys Glu Asp Lys Gln Asp Tyr Glu Ile Thr Thr Lys
    130                 135                 140 cac cta aaa att tct aaa aat aga cga gaa gta ttg ttt gac aag caa      480
His Leu Lys Ile Ser Lys Asn Arg Arg Glu Val Leu Phe Asp Lys Gln
145                 150                 155                 160 cct gta act aat tta act cca aag gaa ttt gac ttg ctt tat acg atg      528
Pro Val Thr Asn Leu Thr Pro Lys Glu Phe Asp Leu Leu Tyr Thr Met
                165                 170                 175 gct caa aag cct aag caa gtc ttt tct cgt gaa caa tta tta gag ctg      576
Ala Gln Lys Pro Lys Gln Val Phe Ser Arg Glu Gln Leu Leu Glu Leu
            180                 185                 190 gtt tgg gga tat gaa tac tac gga gaa gaa aga aca gta gat gct cat      624
Val Trp Gly Tyr Glu Tyr Tyr Gly Glu Glu Arg Thr Val Asp Ala His
        195                 200                 205 att aag aaa ctg cgc caa aaa tta gag aaa gtt gga gct aaa gtt atc      672
Ile Lys Lys Leu Arg Gln Lys Leu Glu Lys Val Gly Ala Lys Val Ile
    210                 215                 220 caa acc gtt tgg gga gtt gga tat aag ttt gat gat ttg cag gta gaa      720
Gln Thr Val Trp Gly Val Gly Tyr Lys Phe Asp Asp Leu Gln Val Glu
225                 230                 235                 240

<210> SEQ ID NO 12
<211> LENGTH: 240
<212> TYPE: PRT
<213> ORGANISM: Lactobacillus acidophilus

<400> SEQUENCE: 12

Met Ser Leu Asn Ile Leu Met Val Glu Asp Asp Asn Ser Val Ala Glu
1               5                   10                  15

Met Met Gly Met Phe Phe Lys Lys Glu Gly Trp Gln Gln Asp Ile Ala
            20                  25                  30

Val Asp Gly Val Glu Ala Val Asp Met Phe Arg Lys Asn Ala Asp Lys
        35                  40                  45

Tyr Asp Leu Ile Thr Leu Asp Leu Asn Leu Pro Lys Lys Asp Gly Ile
    50                  55                  60

Gln Val Ala Lys Glu Val Arg Ala Ile Ser Pro Thr Val Pro Ile Ile
65                  70                  75                  80

Met Leu Thr Ala Arg Gly Ser Glu Ser Asp Gln Val Leu Gly Leu Gly
                85                  90                  95

Ile Gly Ala Asp Glu Tyr Val Thr Lys Pro Phe Ser Pro Ile Ala Leu
            100                 105                 110

Ile Ala Arg Ile Lys Ala Leu His Arg Arg Val Met Glu Glu Glu
        115                 120                 125

Pro Asp Thr Ala Lys Glu Asp Lys Gln Asp Tyr Glu Ile Thr Thr Lys
    130                 135                 140

His Leu Lys Ile Ser Lys Asn Arg Arg Glu Val Leu Phe Asp Lys Gln
145                 150                 155                 160

Pro Val Thr Asn Leu Thr Pro Lys Glu Phe Asp Leu Leu Tyr Thr Met
                165                 170                 175

Ala Gln Lys Pro Lys Gln Val Phe Ser Arg Glu Gln Leu Leu Glu Leu
            180                 185                 190

Val Trp Gly Tyr Glu Tyr Tyr Gly Glu Glu Arg Thr Val Asp Ala His
        195                 200                 205

Ile Lys Lys Leu Arg Gln Lys Leu Glu Lys Val Gly Ala Lys Val Ile
    210                 215                 220

Gln Thr Val Trp Gly Val Gly Tyr Lys Phe Asp Asp Leu Gln Val Glu
```

-continued

```
                225                 230                 235                 240

<210> SEQ ID NO 13
<211> LENGTH: 1449
<212> TYPE: DNA
<213> ORGANISM: Lactobacillus acidophilus
<220> FEATURE:
<221> NAME/KEY: CDS
<222> LOCATION: (1)..(1449)
<223> OTHER INFORMATION: Signal transduction histidine kinase ORF# 747

<400> SEQUENCE: 13 atg aaa tta att tac caa aat atg cta ggg ttt cta tta att att gta        48
Met Lys Leu Ile Tyr Gln Asn Met Leu Gly Phe Leu Leu Ile Ile Val
1               5                   10                  15 act aca att tca att att gga tat tcc gag ata ggc tat gca cgt gat        96
Thr Thr Ile Ser Ile Ile Gly Tyr Ser Glu Ile Gly Tyr Ala Arg Asp
                20                  25                  30 caa gca tat atg caa aat tat caa aga atg gaa ggt tat gct aat tct       144
Gln Ala Tyr Met Gln Asn Tyr Gln Arg Met Glu Gly Tyr Ala Asn Ser
            35                  40                  45 tta gga aat tta gca gca gct gag gga aaa gac gat aca gca ata tta       192
Leu Gly Asn Leu Ala Ala Ala Glu Gly Lys Asp Asp Thr Ala Ile Leu
        50                  55                  60 agc aat agc ttt tta aat cag tta gaa ttt att ctt cgc ggg gat gat       240
Ser Asn Ser Phe Leu Asn Gln Leu Glu Phe Ile Leu Arg Gly Asp Asp
65                  70                  75                  80 gtt cat tta cga att ttt aat gaa aaa aat gag caa att tat cct aag       288
Val His Leu Arg Ile Phe Asn Glu Lys Asn Glu Gln Ile Tyr Pro Lys
                85                  90                  95 act aga gaa aaa ata caa tta tct aaa aat att ttt gct act tta aaa       336
Thr Arg Glu Lys Ile Gln Leu Ser Lys Asn Ile Phe Ala Thr Leu Lys
                100                 105                 110 aat ggt caa gag att cgt att caa aat aat cac aat gaa aat gcg cca       384
Asn Gly Gln Glu Ile Arg Ile Gln Asn Asn His Asn Glu Asn Ala Pro
            115                 120                 125 att gca tca act aag gat gcc tat aca ggt gtt tta gtt cct tgg atg       432
Ile Ala Ser Thr Lys Asp Ala Tyr Thr Gly Val Leu Val Pro Trp Met
        130                 135                 140 aat ggg aaa aat tta att ggt gta gcg tgg ata agt tcc aga gtt aag       480
Asn Gly Lys Asn Leu Ile Gly Val Ala Trp Ile Ser Ser Arg Val Lys
145                 150                 155                 160 cat gtt gaa aga ccg ata tat atg gcc aaa cgc aat ttg ctt aga gcg       528
His Val Glu Arg Pro Ile Tyr Met Ala Lys Arg Asn Leu Leu Arg Ala
                165                 170                 175 ttg ttg act aca gtt gca gtt ggt ttg att ctg agt ttt att att tca       576
Leu Leu Thr Thr Val Ala Val Gly Leu Ile Leu Ser Phe Ile Ile Ser
                180                 185                 190 tat tac tct act aaa cga att aaa cgt tta tca cgc gct acg caa aaa       624
Tyr Tyr Ser Thr Lys Arg Ile Lys Arg Leu Ser Arg Ala Thr Gln Lys
            195                 200                 205 gta gct tca ggt aac ttt aat gtg cag atc aaa cat aaa gat agc gat       672
Val Ala Ser Gly Asn Phe Asn Val Gln Ile Lys His Lys Asp Ser Asp
        210                 215                 220 gaa att gat cag tta gct gaa aac ttt aat caa atg gta tta gca tta       720
Glu Ile Asp Gln Leu Ala Glu Asn Phe Asn Gln Met Val Leu Ala Leu
225                 230                 235                 240 aag cga tcc aat gaa gaa gtc aag gcg caa gaa aat cgg cgg gac caa       768
Lys Arg Ser Asn Glu Glu Val Lys Ala Gln Glu Asn Arg Arg Asp Gln
                245                 250                 255 ttt atg gca gat gct gct cat gaa atg aga aca cca tta act act att       816
Phe Met Ala Asp Ala Ala His Glu Met Arg Thr Pro Leu Thr Thr Ile
```

```
Phe Met Ala Asp Ala Ala His Glu Met Arg Thr Pro Leu Thr Thr Ile
            260                 265                 270 aat gga att ctc gaa gga tta caa tat gat gca att cca gaa gaa tct       864
Asn Gly Ile Leu Glu Gly Leu Gln Tyr Asp Ala Ile Pro Glu Glu Ser
            275                 280                 285 aaa cct aaa tcg ata gca ttg atg cag aga gaa act aaa cga tta att       912
Lys Pro Lys Ser Ile Ala Leu Met Gln Arg Glu Thr Lys Arg Leu Ile
            290                 295                 300 aga tta gtt aat gaa aat ttg gat tat gaa aaa att cgt aat aat caa       960
Arg Leu Val Asn Glu Asn Leu Asp Tyr Glu Lys Ile Arg Asn Asn Gln
305                 310                 315                 320 atc aat tta att aaa act aat ttt aat gct acg ccg gta tta tta gac      1008
Ile Asn Leu Ile Lys Thr Asn Phe Asn Ala Thr Pro Val Leu Leu Asp
                325                 330                 335 tta aaa tcg caa tta atg cag aat gct aaa aaa gct ggc gat aag ttg      1056
Leu Lys Ser Gln Leu Met Gln Asn Ala Lys Lys Ala Gly Asp Lys Leu
            340                 345                 350 att ttt gaa gta ccg act gat cta cca att tat gcg aat cgt gat cgt      1104
Ile Phe Glu Val Pro Thr Asp Leu Pro Ile Tyr Ala Asn Arg Asp Arg
            355                 360                 365 ttc act caa gta atg gtc aat ttg gta caa aat gca att caa ttt act      1152
Phe Thr Gln Val Met Val Asn Leu Val Gln Asn Ala Ile Gln Phe Thr
            370                 375                 380 cat gat ggt aaa att aaa gtc tct ggt aaa aga tta aag cat gga gct      1200
His Asp Gly Lys Ile Lys Val Ser Gly Lys Arg Leu Lys His Gly Ala
385                 390                 395                 400 gaa ttt agt gtt aaa gat aat ggt att ggt atg agt gac gat caa att      1248
Glu Phe Ser Val Lys Asp Asn Gly Ile Gly Met Ser Asp Asp Gln Ile
                405                 410                 415 aaa tat att ttt gag cgt ttc ttt aaa gct gat cca tcc cgt gcg cga      1296
Lys Tyr Ile Phe Glu Arg Phe Phe Lys Ala Asp Pro Ser Arg Ala Arg
            420                 425                 430 atg gga aca ggt gaa tca gga cta gga ctt gct atc gta tct tcg ttg      1344
Met Gly Thr Gly Glu Ser Gly Leu Gly Leu Ala Ile Val Ser Ser Leu
            435                 440                 445 att aag cag cat ggt ggt aag ata acc gtt gat tct aag cct ggt caa      1392
Ile Lys Gln His Gly Gly Lys Ile Thr Val Asp Ser Lys Pro Gly Gln
450                 455                 460 gga gct aca ttt acg gta act ttt tat gat aaa ggt tat gaa caa ttt      1440
Gly Ala Thr Phe Thr Val Thr Phe Tyr Asp Lys Gly Tyr Glu Gln Phe
465                 470                 475                 480 att gaa aaa                                                          1449
Ile Glu Lys <210> SEQ ID NO 14
<211> LENGTH: 483
<212> TYPE: PRT
<213> ORGANISM: Lactobacillus acidophilus

<400> SEQUENCE: 14

Met Lys Leu Ile Tyr Gln Asn Met Leu Gly Phe Leu Leu Ile Ile Val
1               5                   10                  15

Thr Thr Ile Ser Ile Ile Gly Tyr Ser Glu Ile Gly Tyr Ala Arg Asp
            20                  25                  30

Gln Ala Tyr Met Gln Asn Tyr Gln Arg Met Glu Gly Tyr Ala Asn Ser
        35                  40                  45

Leu Gly Asn Leu Ala Ala Ala Glu Gly Lys Asp Asp Thr Ala Ile Leu
    50                  55                  60

Ser Asn Ser Phe Leu Asn Gln Leu Glu Phe Ile Leu Arg Gly Asp Asp
```

```
             65                  70                  75                  80
Val His Leu Arg Ile Phe Asn Glu Lys Asn Glu Gln Ile Tyr Pro Lys
                     85                  90                  95

Thr Arg Glu Lys Ile Gln Leu Ser Lys Asn Ile Phe Ala Thr Leu Lys
                    100                 105                 110

Asn Gly Gln Glu Ile Arg Ile Gln Asn Asn His Asn Glu Asn Ala Pro
                    115                 120                 125

Ile Ala Ser Thr Lys Asp Ala Tyr Thr Gly Val Leu Val Pro Trp Met
            130                 135                 140

Asn Gly Lys Asn Leu Ile Gly Val Ala Trp Ile Ser Ser Arg Val Lys
145                 150                 155                 160

His Val Glu Arg Pro Ile Tyr Met Ala Lys Arg Asn Leu Leu Arg Ala
                165                 170                 175

Leu Leu Thr Thr Val Ala Val Gly Leu Ile Leu Ser Phe Ile Ile Ser
                180                 185                 190

Tyr Tyr Ser Thr Lys Arg Ile Lys Arg Leu Ser Arg Ala Thr Gln Lys
            195                 200                 205

Val Ala Ser Gly Asn Phe Asn Val Gln Ile Lys His Lys Asp Ser Asp
            210                 215                 220

Glu Ile Asp Gln Leu Ala Glu Asn Phe Asn Gln Met Val Leu Ala Leu
225                 230                 235                 240

Lys Arg Ser Asn Glu Glu Val Lys Ala Gln Glu Asn Arg Arg Asp Gln
                245                 250                 255

Phe Met Ala Asp Ala Ala His Glu Met Arg Thr Pro Leu Thr Thr Ile
                260                 265                 270

Asn Gly Ile Leu Glu Gly Leu Gln Tyr Asp Ala Ile Pro Glu Glu Ser
            275                 280                 285

Lys Pro Lys Ser Ile Ala Leu Met Gln Arg Glu Thr Lys Arg Leu Ile
        290                 295                 300

Arg Leu Val Asn Glu Asn Leu Asp Tyr Glu Lys Ile Arg Asn Asn Gln
305                 310                 315                 320

Ile Asn Leu Ile Lys Thr Asn Phe Asn Ala Thr Pro Val Leu Leu Asp
                325                 330                 335

Leu Lys Ser Gln Leu Met Gln Asn Ala Lys Lys Ala Gly Asp Lys Leu
                340                 345                 350

Ile Phe Glu Val Pro Thr Asp Leu Pro Ile Tyr Ala Asn Arg Asp Arg
            355                 360                 365

Phe Thr Gln Val Met Val Asn Leu Val Gln Asn Ala Ile Gln Phe Thr
370                 375                 380

His Asp Gly Lys Ile Lys Val Ser Gly Lys Arg Leu Lys His Gly Ala
385                 390                 395                 400

Glu Phe Ser Val Lys Asp Asn Gly Ile Gly Met Ser Asp Gln Ile
                405                 410                 415

Lys Tyr Ile Phe Glu Arg Phe Lys Ala Asp Pro Ser Arg Ala Arg
            420                 425                 430

Met Gly Thr Gly Glu Ser Gly Leu Gly Leu Ala Ile Val Ser Ser Leu
            435                 440                 445

Ile Lys Gln His Gly Gly Lys Ile Thr Val Asp Ser Lys Pro Gly Gln
            450                 455                 460

Gly Ala Thr Phe Thr Val Thr Phe Tyr Asp Lys Gly Tyr Glu Gln Phe
465                 470                 475                 480

Ile Glu Lys
```

-continued

```
<210> SEQ ID NO 15
<211> LENGTH: 1101
<212> TYPE: DNA
<213> ORGANISM: Lactobacillus acidophilus
<220> FEATURE:
<221> NAME/KEY: CDS
<222> LOCATION: (1)..(1101)
<223> OTHER INFORMATION: Regulatory component of sensory transduction
      system ORF# 1413

<400> SEQUENCE: 15 gtg ttt ttt caa gtc tta agc tca att tta ttt ctt cca ttt tta gtt      48
Val Phe Phe Gln Val Leu Ser Ser Ile Leu Phe Leu Pro Phe Leu Val
1               5                   10                  15 atg agc atg ata att gct caa gtc cac ttg gaa gga tat tgg gat tct      96
Met Ser Met Ile Ile Ala Gln Val His Leu Glu Gly Tyr Trp Asp Ser
            20                  25                  30 aaa att acc aag tgg cga gga aga caa tgg tct gtt ttt tat att ata     144
Lys Ile Thr Lys Trp Arg Gly Arg Gln Trp Ser Val Phe Tyr Ile Ile
        35                  40                  45 ttt tta tac ata gtt caa gaa ata tgt atc atg gaa cta acg cta cta     192
Phe Leu Tyr Ile Val Gln Glu Ile Cys Ile Met Glu Leu Thr Leu Leu
    50                  55                  60 aat ttg aac att atg gct ttt att tat gtt atc ccc atc aca atg att     240
Asn Leu Asn Ile Met Ala Phe Ile Tyr Val Ile Pro Ile Thr Met Ile
65                  70                  75                  80 tta aga aat aaa cat caa att tgg tgg ggc ctt ttt gct ctg acc cct     288
Leu Arg Asn Lys His Gln Ile Trp Trp Gly Leu Phe Ala Leu Thr Pro
                85                  90                  95 gtt tta gca tgg atg tta gat gca tat tta aaa cga tat caa ttt ata     336
Val Leu Ala Trp Met Leu Asp Ala Tyr Leu Lys Arg Tyr Gln Phe Ile
            100                 105                 110 aat tta aga gcg act tta tta caa ctt gcc cta att ggc cta gtt tgt     384
Asn Leu Arg Ala Thr Leu Leu Gln Leu Ala Leu Ile Gly Leu Val Cys
        115                 120                 125 tgg tct gtc tta cat aat aag aga ctt tcc tac tat tat aag tat aca     432
Trp Ser Val Leu His Asn Lys Arg Leu Ser Tyr Tyr Tyr Lys Tyr Thr
    130                 135                 140 ata gct tta tac agt aac tgc ttt att cat atg tta cat tta tat ctt     480
Ile Ala Leu Tyr Ser Asn Cys Phe Ile His Met Leu His Leu Tyr Leu
145                 150                 155                 160 gaa cat cag ctt caa ctt gat ttc aca gtt agt ata cta gca gga act     528
Glu His Gln Leu Gln Leu Asp Phe Thr Val Ser Ile Leu Ala Gly Thr
                165                 170                 175 ttt ttc att atc ata gct gaa aat tca aga atg tat tat gaa caa aag     576
Phe Phe Ile Ile Ile Ala Glu Asn Ser Arg Met Tyr Tyr Glu Gln Lys
            180                 185                 190 caa aaa gaa gaa att gaa aaa cta cat tac gaa agt gtc cgt gac gac     624
Gln Lys Glu Glu Ile Glu Lys Leu His Tyr Glu Ser Val Arg Asp Asp
        195                 200                 205 cta acg ggt tta ctc aac tat cga gcc ttt gat gaa gaa atg cag gga     672
Leu Thr Gly Leu Leu Asn Tyr Arg Ala Phe Asp Glu Glu Met Gln Gly
    210                 215                 220 tta tca aaa gac gag agc aac atg cct att ttt att gca gtt ctt gat     720
Leu Ser Lys Asp Glu Ser Asn Met Pro Ile Phe Ile Ala Val Leu Asp
225                 230                 235                 240 att gat cac ttt aag cag gtt aat gat act tat ggt cat cta aat ggc     768
Ile Asp His Phe Lys Gln Val Asn Asp Thr Tyr Gly His Leu Asn Gly
                245                 250                 255 aat acc gtt ttg agt act ttt tct aaa aaa tta aaa tta gat att cac     816
Asn Thr Val Leu Ser Thr Phe Ser Lys Lys Leu Lys Leu Asp Ile His
```

```
                   260                 265                 270
cat aac ttt gat cct cat tgt gct gta tat cgc ttt ggc ggt gaa gaa    864
His Asn Phe Asp Pro His Cys Ala Val Tyr Arg Phe Gly Gly Glu Glu
        275                 280                 285 ttc acc atc tta att aaa act aaa gat aat act aaa att att aaa atc    912
Phe Thr Ile Leu Ile Lys Thr Lys Asp Asn Thr Lys Ile Ile Lys Ile
290                 295                 300 ctt aat agt atc aat aaa tat tac tca aag cat ccc gtt ata aca gat    960
Leu Asn Ser Ile Asn Lys Tyr Tyr Ser Lys His Pro Val Ile Thr Asp
305                 310                 315                 320 gaa gga caa aaa atc ttt ttc tct ttc tca ggt ggt tta acc gag cat   1008
Glu Gly Gln Lys Ile Phe Phe Ser Phe Ser Gly Gly Leu Thr Glu His
                325                 330                 335 cat aat aat gaa aag ttc act aaa acc ctt gaa aga gcc gat gag tta   1056
His Asn Asn Glu Lys Phe Thr Lys Thr Leu Glu Arg Ala Asp Glu Leu
        340                 345                 350 gtt tat caa gca aaa aag aca ggt cga gca aaa atc cta att ggt       1101
Val Tyr Gln Ala Lys Lys Thr Gly Arg Ala Lys Ile Leu Ile Gly
        355                 360                 365

<210> SEQ ID NO 16
<211> LENGTH: 367
<212> TYPE: PRT
<213> ORGANISM: Lactobacillus acidophilus

<400> SEQUENCE: 16

Val Phe Phe Gln Val Leu Ser Ser Ile Leu Phe Leu Pro Phe Leu Val
1               5                   10                  15

Met Ser Met Ile Ile Ala Gln Val His Leu Glu Gly Tyr Trp Asp Ser
            20                  25                  30

Lys Ile Thr Lys Trp Arg Gly Arg Gln Trp Ser Val Phe Tyr Ile Ile
        35                  40                  45

Phe Leu Tyr Ile Val Gln Glu Ile Cys Ile Met Glu Leu Thr Leu Leu
    50                  55                  60

Asn Leu Asn Ile Met Ala Phe Ile Tyr Val Ile Pro Ile Thr Met Ile
65                  70                  75                  80

Leu Arg Asn Lys His Gln Ile Trp Trp Gly Leu Phe Ala Leu Thr Pro
                85                  90                  95

Val Leu Ala Trp Met Leu Asp Ala Tyr Leu Lys Arg Tyr Gln Phe Ile
            100                 105                 110

Asn Leu Arg Ala Thr Leu Leu Gln Leu Ala Leu Ile Gly Leu Val Cys
        115                 120                 125

Trp Ser Val Leu His Asn Lys Arg Leu Ser Tyr Tyr Tyr Lys Tyr Thr
    130                 135                 140

Ile Ala Leu Tyr Ser Asn Cys Phe Ile His Met Leu His Leu Tyr Leu
145                 150                 155                 160

Glu His Gln Leu Gln Leu Asp Phe Thr Val Ser Ile Leu Ala Gly Thr
                165                 170                 175

Phe Phe Ile Ile Ile Ala Glu Asn Ser Arg Met Tyr Tyr Glu Gln Lys
            180                 185                 190

Gln Lys Glu Glu Ile Glu Lys Leu His Tyr Glu Ser Val Arg Asp Asp
        195                 200                 205

Leu Thr Gly Leu Leu Asn Tyr Arg Ala Phe Asp Glu Glu Met Gln Gly
    210                 215                 220

Leu Ser Lys Asp Glu Ser Asn Met Pro Ile Phe Ile Ala Val Leu Asp
225                 230                 235                 240
```

```
Ile Asp His Phe Lys Gln Val Asn Asp Thr Tyr Gly His Leu Asn Gly
            245                 250                 255

Asn Thr Val Leu Ser Thr Phe Ser Lys Lys Leu Lys Leu Asp Ile His
        260                 265                 270

His Asn Phe Asp Pro His Cys Ala Val Tyr Arg Phe Gly Gly Glu Glu
            275                 280                 285

Phe Thr Ile Leu Ile Lys Thr Lys Asp Asn Thr Lys Ile Ile Lys Ile
    290                 295                 300

Leu Asn Ser Ile Asn Lys Tyr Tyr Ser Lys His Pro Val Ile Thr Asp
305                 310                 315                 320

Glu Gly Gln Lys Ile Phe Phe Ser Phe Ser Gly Gly Leu Thr Glu His
                325                 330                 335

His Asn Asn Glu Lys Phe Thr Lys Thr Leu Glu Arg Ala Asp Glu Leu
            340                 345                 350

Val Tyr Gln Ala Lys Lys Thr Gly Arg Ala Lys Ile Leu Ile Gly
        355                 360                 365

<210> SEQ ID NO 17
<211> LENGTH: 708
<212> TYPE: DNA
<213> ORGANISM: Lactobacillus acidophilus
<220> FEATURE:
<221> NAME/KEY: CDS
<222> LOCATION: (1)..(708)
<223> OTHER INFORMATION: FOG: EAL ORF# 1414

<400> SEQUENCE: 17 ttg aaa gga gaa aaa atg tat aag tgg cat aat gtg ttt caa cct att        48
Leu Lys Gly Glu Lys Met Tyr Lys Trp His Asn Val Phe Gln Pro Ile
1               5                   10                  15 ttt cag ata gat caa aac atg aat cat aaa gtt gac cac tac gag atg        96
Phe Gln Ile Asp Gln Asn Met Asn His Lys Val Asp His Tyr Glu Met
            20                  25                  30 tta tta cgt gat gaa aac gac caa ttc cct aat cat gat ttt ttc aga       144
Leu Leu Arg Asp Glu Asn Asp Gln Phe Pro Asn His Asp Phe Phe Arg
        35                  40                  45 atc att agt act gag gaa gat aat caa aaa tgg atc caa ata gaa gaa       192
Ile Ile Ser Thr Glu Glu Asp Asn Gln Lys Trp Ile Gln Ile Glu Glu
    50                  55                  60 aag tca tta aaa aat cta ttt tcc ctt cat ccc aat att cat gta aat       240
Lys Ser Leu Lys Asn Leu Phe Ser Leu His Pro Asn Ile His Val Asn
65                  70                  75                  80 tta aat gtt gaa ccc att caa ttc gct tat cca agc gta tgg gaa ttc       288
Leu Asn Val Glu Pro Ile Gln Phe Ala Tyr Pro Ser Val Trp Glu Phe
                85                  90                  95 tta aga cga att tat gat aaa tat ggt caa aag gta att att gaa att       336
Leu Arg Arg Ile Tyr Asp Lys Tyr Gly Gln Lys Val Ile Ile Glu Ile
            100                 105                 110 act gag cgt caa tta caa gct gga aat att ggg aat cgc caa ttc gat       384
Thr Glu Arg Gln Leu Gln Ala Gly Asn Ile Gly Asn Arg Gln Phe Asp
        115                 120                 125 tgc gct ttt caa aga att aat gat att gga ttt aaa att gct tta gac       432
Cys Ala Phe Gln Arg Ile Asn Asp Ile Gly Phe Lys Ile Ala Leu Asp
    130                 135                 140 gat gtt gat tcc ggt agt aat agt ttt agt ttt gtc aat cat cat gtt       480
Asp Val Asp Ser Gly Ser Asn Ser Phe Ser Phe Val Asn His His Val
145                 150                 155                 160 aat cag atc agt gtg att aaa ctt tca tta ctt atc ttc gat aat gtt       528
Asn Gln Ile Ser Val Ile Lys Leu Ser Leu Leu Ile Phe Asp Asn Val
                165                 170                 175
```

```
tct tca gga act acc att agt ttt att gat tct tgg gca gcc ttt gct      576
Ser Ser Gly Thr Thr Ile Ser Phe Ile Asp Ser Trp Ala Ala Phe Ala
        180                 185                 190 aaa gaa aaa cac tta gat tta gtg ata gaa gct gtt aga tca aaa gaa      624
Lys Glu Lys His Leu Asp Leu Val Ile Glu Ala Val Arg Ser Lys Glu
        195                 200                 205 att gct aag cgt ttt gcc ggc aac aag cat att ttc caa caa ggc tat      672
Ile Ala Lys Arg Phe Ala Gly Asn Lys His Ile Phe Gln Gln Gly Tyr
        210                 215                 220 tac tgg gaa aaa gca ctc aaa tta gaa gac att tat                      708
Tyr Trp Glu Lys Ala Leu Lys Leu Glu Asp Ile Tyr
225                 230                 235

<210> SEQ ID NO 18
<211> LENGTH: 236
<212> TYPE: PRT
<213> ORGANISM: Lactobacillus acidophilus

<400> SEQUENCE: 18

Leu Lys Gly Glu Lys Met Tyr Lys Trp His Asn Val Phe Gln Pro Ile
1               5                   10                  15

Phe Gln Ile Asp Gln Asn Met Asn His Lys Val Asp His Tyr Glu Met
            20                  25                  30

Leu Leu Arg Asp Glu Asn Asp Gln Phe Pro Asn His Asp Phe Phe Arg
        35                  40                  45

Ile Ile Ser Thr Glu Glu Asp Asn Gln Lys Trp Ile Gln Ile Glu Glu
    50                  55                  60

Lys Ser Leu Lys Asn Leu Phe Ser Leu His Pro Asn Ile His Val Asn
65                  70                  75                  80

Leu Asn Val Glu Pro Ile Gln Phe Ala Tyr Pro Ser Val Trp Glu Phe
                85                  90                  95

Leu Arg Arg Ile Tyr Asp Lys Tyr Gly Gln Lys Val Ile Ile Glu Ile
            100                 105                 110

Thr Glu Arg Gln Leu Gln Ala Gly Asn Ile Gly Asn Arg Gln Phe Asp
        115                 120                 125

Cys Ala Phe Gln Arg Ile Asn Asp Ile Gly Phe Lys Ile Ala Leu Asp
    130                 135                 140

Asp Val Asp Ser Gly Ser Asn Ser Phe Ser Phe Val Asn His His Val
145                 150                 155                 160

Asn Gln Ile Ser Val Ile Lys Leu Ser Leu Leu Ile Phe Asp Asn Val
                165                 170                 175

Ser Ser Gly Thr Thr Ile Ser Phe Ile Asp Ser Trp Ala Ala Phe Ala
            180                 185                 190

Lys Glu Lys His Leu Asp Leu Val Ile Glu Ala Val Arg Ser Lys Glu
        195                 200                 205

Ile Ala Lys Arg Phe Ala Gly Asn Lys His Ile Phe Gln Gln Gly Tyr
    210                 215                 220

Tyr Trp Glu Lys Ala Leu Lys Leu Glu Asp Ile Tyr
225                 230                 235

<210> SEQ ID NO 19
<211> LENGTH: 1281
<212> TYPE: DNA
<213> ORGANISM: Lactobacillus acidophilus
<220> FEATURE:
<221> NAME/KEY: CDS
<222> LOCATION: (1)..(1281)
<223> OTHER INFORMATION: Signal transduction histidine kinase ORF# 1430
```

<400> SEQUENCE: 19

```
gtg ata agg atg att cag aaa ttt cgc tgg aag ttt att gga gct tct        48
Val Ile Arg Met Ile Gln Lys Phe Arg Trp Lys Phe Ile Gly Ala Ser
 1               5                  10                  15 gtt gca gca tta cta cta gtt ttg ata att act tta ggc gga ttg gtc        96
Val Ala Ala Leu Leu Leu Val Leu Ile Ile Thr Leu Gly Gly Leu Val
             20                  25                  30 ggt att act cgt gtt caa agc caa aat gaa gtt aat cgc gtg ctg aca       144
Gly Ile Thr Arg Val Gln Ser Gln Asn Glu Val Asn Arg Val Leu Thr
         35                  40                  45 gca ttg gta aaa aat gaa ggt cgt tta tcg ccg cgt aat gca caa cca       192
Ala Leu Val Lys Asn Glu Gly Arg Leu Ser Pro Arg Asn Ala Gln Pro
     50                  55                  60 gct ttt ggt aat caa aaa gat att att aat cgt aat ttt tta ggc gga       240
Ala Phe Gly Asn Gln Lys Asp Ile Ile Asn Arg Asn Phe Leu Gly Gly
 65                  70                  75                  80 caa tat aat ccg gag gct gtg tat cag tac cgt tat ttt gca gta act       288
Gln Tyr Asn Pro Glu Ala Val Tyr Gln Tyr Arg Tyr Phe Ala Val Thr
                 85                  90                  95 gta gat cct acg cag cga ata aat gtg att aat gat aat aat gtt tat       336
Val Asp Pro Thr Gln Arg Ile Asn Val Ile Asn Asp Asn Asn Val Tyr
            100                 105                 110 aag att aat aat act gaa ata aag agt gtt aca aaa aga gct cta gct       384
Lys Ile Asn Asn Thr Glu Ile Lys Ser Val Thr Lys Arg Ala Leu Ala
        115                 120                 125 aat cga gat caa ttt gga gat gta aaa att ggg cag aac cga tac gca       432
Asn Arg Asp Gln Phe Gly Asp Val Lys Ile Gly Gln Asn Arg Tyr Ala
    130                 135                 140 tat aga gtt gat aaa aac gct gct gga cag aca atg atc gtt ttc ttg       480
Tyr Arg Val Asp Lys Asn Ala Ala Gly Gln Thr Met Ile Val Phe Leu
145                 150                 155                 160 aat gaa aca ctt att ttt aat cga ttc tgg ttg tta ttt aga gtg tca       528
Asn Glu Thr Leu Ile Phe Asn Arg Phe Trp Leu Leu Phe Arg Val Ser
                165                 170                 175 ctt gtt tta gga gca ttt gca tta ttg atc ttt gca gca gtt tta atc       576
Leu Val Leu Gly Ala Phe Ala Leu Leu Ile Phe Ala Ala Val Leu Ile
            180                 185                 190 ttg gtt tct ggt aaa gca att aag ccg att gtt gat aca tat cat aag       624
Leu Val Ser Gly Lys Ala Ile Lys Pro Ile Val Asp Thr Tyr His Lys
        195                 200                 205 caa caa gaa ttt att acc aac gcg ggt cat gaa tta aag aca cca cta       672
Gln Gln Glu Phe Ile Thr Asn Ala Gly His Glu Leu Lys Thr Pro Leu
    210                 215                 220 gcg gtt att tca gct aat act gaa atg gaa gag atg cta ggc aat aat       720
Ala Val Ile Ser Ala Asn Thr Glu Met Glu Glu Met Leu Gly Asn Asn
225                 230                 235                 240 tct gaa tgg aat gaa agt aca aaa gag caa gtt gaa aaa tta tct gag       768
Ser Glu Trp Asn Glu Ser Thr Lys Glu Gln Val Glu Lys Leu Ser Glu
                245                 250                 255 tta att aat cgt cta att tct ttg gct aga act ggt gaa aat ggt gaa       816
Leu Ile Asn Arg Leu Ile Ser Leu Ala Arg Thr Gly Glu Asn Gly Glu
            260                 265                 270 gtt gct tta agt aaa gtg gat ttt tca cag att gtt gaa gat gtg aca       864
Val Ala Leu Ser Lys Val Asp Phe Ser Gln Ile Val Glu Asp Val Thr
        275                 280                 285 caa aat ttt aaa tcg gtt atg aag caa aat gat tta gtg tat cag gtt       912
Gln Asn Phe Lys Ser Val Met Lys Gln Asn Asp Leu Val Tyr Gln Val
    290                 295                 300
```

-continued

```
tcc att cgt gag ggg att aat gta att gca gaa aag cat tct tta act      960
Ser Ile Arg Glu Gly Ile Asn Val Ile Ala Glu Lys His Ser Leu Thr
305                 310                 315                 320 gaa gtg gtc aat att tta ctt gat aat gct aga aaa tat tgt gat cca     1008
Glu Val Val Asn Ile Leu Leu Asp Asn Ala Arg Lys Tyr Cys Asp Pro
                325                 330                 335 cat ggc aga gta aaa gta gag tta gtc aaa agt acg cta agt aaa aat     1056
His Gly Arg Val Lys Val Glu Leu Val Lys Ser Thr Leu Ser Lys Asn
            340                 345                 350 gca att tta cga gta att aat act tat aag gaa gga aaa aat aaa gac     1104
Ala Ile Leu Arg Val Ile Asn Thr Tyr Lys Glu Gly Lys Asn Lys Asp
        355                 360                 365 tat acg cac ttc ttt gat cgt ttt tat cgt gaa gat gaa tct cac aat     1152
Tyr Thr His Phe Phe Asp Arg Phe Tyr Arg Glu Asp Glu Ser His Asn
    370                 375                 380 tct aaa aaa ggt ggc ttt ggt att gga tta gct atg gct caa gaa tta     1200
Ser Lys Lys Gly Gly Phe Gly Ile Gly Leu Ala Met Ala Gln Glu Leu
385                 390                 395                 400 att cat act ttc cac ggt aaa att tca gta aat cat aga gaa gaa aat     1248
Ile His Thr Phe His Gly Lys Ile Ser Val Asn His Arg Glu Glu Asn
                405                 410                 415 atc gtt ttt agt gtt agt cta aaa att gtc aaa                         1281
Ile Val Phe Ser Val Ser Leu Lys Ile Val Lys
                420                 425

<210> SEQ ID NO 20
<211> LENGTH: 427
<212> TYPE: PRT
<213> ORGANISM: Lactobacillus acidophilus

<400> SEQUENCE: 20

Val Ile Arg Met Ile Gln Lys Phe Arg Trp Lys Phe Ile Gly Ala Ser
1               5                   10                  15

Val Ala Ala Leu Leu Leu Val Leu Ile Ile Thr Leu Gly Gly Leu Val
            20                  25                  30

Gly Ile Thr Arg Val Gln Ser Gln Asn Glu Val Asn Arg Val Leu Thr
        35                  40                  45

Ala Leu Val Lys Asn Glu Gly Arg Leu Ser Pro Arg Asn Ala Gln Pro
    50                  55                  60

Ala Phe Gly Asn Gln Lys Asp Ile Ile Asn Arg Asn Phe Leu Gly Gly
65                  70                  75                  80

Gln Tyr Asn Pro Glu Ala Val Tyr Gln Tyr Arg Tyr Phe Ala Val Thr
                85                  90                  95

Val Asp Pro Thr Gln Arg Ile Asn Val Ile Asp Asn Asn Val Tyr
            100                 105                 110

Lys Ile Asn Asn Thr Glu Ile Lys Ser Val Thr Lys Arg Ala Leu Ala
        115                 120                 125

Asn Arg Asp Gln Phe Gly Asp Val Lys Ile Gly Gln Asn Arg Tyr Ala
    130                 135                 140

Tyr Arg Val Asp Lys Asn Ala Ala Gly Gln Thr Met Ile Val Phe Leu
145                 150                 155                 160

Asn Glu Thr Leu Ile Phe Asn Arg Phe Trp Leu Leu Phe Arg Val Ser
                165                 170                 175

Leu Val Leu Gly Ala Phe Ala Leu Leu Ile Phe Ala Ala Val Leu Ile
            180                 185                 190

Leu Val Ser Gly Lys Ala Ile Lys Pro Ile Val Asp Thr Tyr His Lys
        195                 200                 205
```

```
Gln Gln Glu Phe Ile Thr Asn Ala Gly His Glu Leu Lys Thr Pro Leu
    210                 215                 220

Ala Val Ile Ser Ala Asn Thr Glu Met Glu Met Leu Gly Asn Asn
225                 230                 235                 240

Ser Glu Trp Asn Glu Ser Thr Lys Glu Gln Val Glu Lys Leu Ser Glu
                245                 250                 255

Leu Ile Asn Arg Leu Ile Ser Leu Ala Arg Thr Gly Glu Asn Gly Glu
            260                 265                 270

Val Ala Leu Ser Lys Val Asp Phe Ser Gln Ile Val Glu Asp Val Thr
        275                 280                 285

Gln Asn Phe Lys Ser Val Met Lys Gln Asn Asp Leu Val Tyr Gln Val
    290                 295                 300

Ser Ile Arg Glu Gly Ile Asn Val Ile Ala Glu Lys His Ser Leu Thr
305                 310                 315                 320

Glu Val Val Asn Ile Leu Leu Asp Asn Ala Arg Lys Tyr Cys Asp Pro
                325                 330                 335

His Gly Arg Val Lys Val Glu Leu Val Lys Ser Thr Leu Ser Lys Asn
            340                 345                 350

Ala Ile Leu Arg Val Ile Asn Thr Tyr Lys Glu Gly Lys Asn Lys Asp
        355                 360                 365

Tyr Thr His Phe Phe Asp Arg Phe Tyr Arg Glu Asp Glu Ser His Asn
    370                 375                 380

Ser Lys Lys Gly Gly Phe Gly Ile Gly Leu Ala Met Ala Gln Glu Leu
385                 390                 395                 400

Ile His Thr Phe His Gly Lys Ile Ser Val Asn His Arg Glu Glu Asn
                405                 410                 415

Ile Val Phe Ser Val Ser Leu Lys Ile Val Lys
            420                 425

<210> SEQ ID NO 21
<211> LENGTH: 663
<212> TYPE: DNA
<213> ORGANISM: Lactobacillus acidophilus
<220> FEATURE:
<221> NAME/KEY: CDS
<222> LOCATION: (1)..(663)
<223> OTHER INFORMATION: Response regulator consisting of a Che Y-like
      receiver domain and a winged-helix DNA-binding domain ORF# 1431

<400> SEQUENCE: 21 atg aag att tta gtg gca gaa gat gaa ccg cag cta cta cgt gta tta      48
Met Lys Ile Leu Val Ala Glu Asp Glu Pro Gln Leu Leu Arg Val Leu
1               5                   10                  15 aca gtt gct atg caa aaa gca gga tat gag gtt gat cca gtt gat aat      96
Thr Val Ala Met Gln Lys Ala Gly Tyr Glu Val Asp Pro Val Asp Asn
            20                  25                  30 ggc tta aag gct gtg gaa cat gcc aaa aaa aat tgc tat gac gtg atc     144
Gly Leu Lys Ala Val Glu His Ala Lys Lys Asn Cys Tyr Asp Val Ile
        35                  40                  45 att ttg gat atc atg atg ccc gtc atg gat gga att acc gct ctt aaa     192
Ile Leu Asp Ile Met Met Pro Val Met Asp Gly Ile Thr Ala Leu Lys
    50                  55                  60 caa att aga gaa agt ggt gat aag act tat att tta atg tta aca gcg     240
Gln Ile Arg Glu Ser Gly Asp Lys Thr Tyr Ile Leu Met Leu Thr Ala
65                  70                  75                  80 aaa gct gaa att gat gat cgt gta act gga ttg gat agt gga gct gac     288
Lys Ala Glu Ile Asp Asp Arg Val Thr Gly Leu Asp Ser Gly Ala Asp
                85                  90                  95
```

```
gat tat ctt act aag cct ttt tca tta aaa gaa tta tta gca aga ttg     336
Asp Tyr Leu Thr Lys Pro Phe Ser Leu Lys Glu Leu Leu Ala Arg Leu
            100                 105                 110 cgc tca aaa gag cga cgt gaa gaa gac ttt aca cct aat gaa tta aaa     384
Arg Ser Lys Glu Arg Arg Glu Glu Asp Phe Thr Pro Asn Glu Leu Lys
            115                 120                 125 gta ggt gat gtt tca ctg aac gtt tct gag caa gaa tta gcg agt cac     432
Val Gly Asp Val Ser Leu Asn Val Ser Glu Gln Glu Leu Ala Ser His
        130                 135                 140 aat tca atc aga tta agc ggt caa gaa acg caa cta atg aat tac ttt     480
Asn Ser Ile Arg Leu Ser Gly Gln Glu Thr Gln Leu Met Asn Tyr Phe
145                 150                 155                 160 tta tta aat gaa ggt aaa gaa ctt tca act gat gaa tta ttg aat cat     528
Leu Leu Asn Glu Gly Lys Glu Leu Ser Thr Asp Glu Leu Leu Asn His
                165                 170                 175 gtt tgg aaa aat gat gag gat gct aat tca gat gtt gtt tgg att tat     576
Val Trp Lys Asn Asp Glu Asp Ala Asn Ser Asp Val Val Trp Ile Tyr
            180                 185                 190 gta tcg tat ttg cga caa aaa tta caa tca att cgc agc tcg gta aaa     624
Val Ser Tyr Leu Arg Gln Lys Leu Gln Ser Ile Arg Ser Ser Val Lys
        195                 200                 205 att gag ggt gaa aaa ggt ggt aat tat gaa tta gtt gag                 663
Ile Glu Gly Glu Lys Gly Gly Asn Tyr Glu Leu Val Glu
210                 215                 220
```

<210> SEQ ID NO 22
<211> LENGTH: 221
<212> TYPE: PRT
<213> ORGANISM: Lactobacillus acidophilus

<400> SEQUENCE: 22

```
Met Lys Ile Leu Val Ala Glu Asp Glu Pro Gln Leu Leu Arg Val Leu
1               5                   10                  15

Thr Val Ala Met Gln Lys Ala Gly Tyr Glu Val Asp Pro Val Asp Asn
            20                  25                  30

Gly Leu Lys Ala Val Glu His Ala Lys Lys Asn Cys Tyr Asp Val Ile
        35                  40                  45

Ile Leu Asp Ile Met Met Pro Val Met Asp Gly Ile Thr Ala Leu Lys
    50                  55                  60

Gln Ile Arg Glu Ser Gly Asp Lys Thr Tyr Ile Leu Met Leu Thr Ala
65                  70                  75                  80

Lys Ala Glu Ile Asp Asp Arg Val Thr Gly Leu Asp Ser Gly Ala Asp
                85                  90                  95

Asp Tyr Leu Thr Lys Pro Phe Ser Leu Lys Glu Leu Leu Ala Arg Leu
            100                 105                 110

Arg Ser Lys Glu Arg Arg Glu Glu Asp Phe Thr Pro Asn Glu Leu Lys
        115                 120                 125

Val Gly Asp Val Ser Leu Asn Val Ser Glu Gln Glu Leu Ala Ser His
    130                 135                 140

Asn Ser Ile Arg Leu Ser Gly Gln Glu Thr Gln Leu Met Asn Tyr Phe
145                 150                 155                 160

Leu Leu Asn Glu Gly Lys Glu Leu Ser Thr Asp Glu Leu Leu Asn His
                165                 170                 175

Val Trp Lys Asn Asp Glu Asp Ala Asn Ser Asp Val Val Trp Ile Tyr
            180                 185                 190

Val Ser Tyr Leu Arg Gln Lys Leu Gln Ser Ile Arg Ser Ser Val Lys
        195                 200                 205
```

-continued

```
Ile Glu Gly Glu Lys Gly Gly Asn Tyr Glu Leu Val Glu
    210             215                 220
```

<210> SEQ ID NO 23
<211> LENGTH: 1575
<212> TYPE: DNA
<213> ORGANISM: Lactobacillus acidophilus
<220> FEATURE:
<221> NAME/KEY: CDS
<222> LOCATION: (1)..(1575)
<223> OTHER INFORMATION: lisK two-component sensor histidine kinase ORF# 1524

<400> SEQUENCE: 23

```
atg aag atg atg atc aag aat aat aaa gaa gcg cag gaa gag acc aag      48
Met Lys Met Met Ile Lys Asn Asn Lys Glu Ala Gln Glu Glu Thr Lys
1               5                   10                  15 cat tca tcg cta atc att cga tgg gta agt atc gtt gca ttg acg att      96
His Ser Ser Leu Ile Ile Arg Trp Val Ser Ile Val Ala Leu Thr Ile
            20                  25                  30 acg gtc tct ttt gtc ata ttt tca gtt gtc gtt tat caa att gtt agt     144
Thr Val Ser Phe Val Ile Phe Ser Val Val Val Tyr Gln Ile Val Ser
        35                  40                  45 caa cag tca ctt aat caa caa gaa gaa act tcg gcc aat gtg gca gta     192
Gln Gln Ser Leu Asn Gln Gln Glu Glu Thr Ser Ala Asn Val Ala Val
    50                  55                  60 aca ttg gat aga act ttg agt tcg att cca aat gaa tta gaa att tct     240
Thr Leu Asp Arg Thr Leu Ser Ser Ile Pro Asn Glu Leu Glu Ile Ser
65                  70                  75                  80 aat gtg att ccg tcg ctt tct ccg tct act aga cgt gta tta aaa ggt     288
Asn Val Ile Pro Ser Leu Ser Pro Ser Thr Arg Arg Val Leu Lys Gly
                85                  90                  95 ggt cca gct att agt agt aaa gat gct aat aat aat gct ttt agt gac     336
Gly Pro Ala Ile Ser Ser Lys Asp Ala Asn Asn Asn Ala Phe Ser Asp
            100                 105                 110 aat ttg att tca tca att tct aat cca gat att agt gtt gct gtt tat     384
Asn Leu Ile Ser Ser Ile Ser Asn Pro Asp Ile Ser Val Ala Val Tyr
        115                 120                 125 aat aag cat aat gaa gtt gtt ttt gct aac ggt gat aca acg cct aaa     432
Asn Lys His Asn Glu Val Val Phe Ala Asn Gly Asp Thr Thr Pro Lys
    130                 135                 140 ttt aag cct ttt aaa ggt gat tca aat gtg gtg aag atc aaa caa aat     480
Phe Lys Pro Phe Lys Gly Asp Ser Asn Val Val Lys Ile Lys Gln Asn
145                 150                 155                 160 cgg cgt ttg cta tta ata act tat caa aaa gtt tat tca tca gtt aat     528
Arg Arg Leu Leu Leu Ile Thr Tyr Gln Lys Val Tyr Ser Ser Val Asn
                165                 170                 175 aat aaa tta acg ggt tat att gtc gtc tcg aat agt atg aga tat tac     576
Asn Lys Leu Thr Gly Tyr Ile Val Val Ser Asn Ser Met Arg Tyr Tyr
            180                 185                 190 aat aat ttg atg aac aac ttg ctg cgc tta atg cta gta ctt tct ctg     624
Asn Asn Leu Met Asn Asn Leu Leu Arg Leu Met Leu Val Leu Ser Leu
        195                 200                 205 att gct att gtg gca ttt ata ggt att tct tat ata ttg gtt gtt agt     672
Ile Ala Ile Val Ala Phe Ile Gly Ile Ser Tyr Ile Leu Val Val Ser
    210                 215                 220 gtt gtt aaa ccg att aag aat atg tct aaa gtg gct aag gaa gtt aat     720
Val Val Lys Pro Ile Lys Asn Met Ser Lys Val Ala Lys Glu Val Asn
225                 230                 235                 240 gct gat cct aat agt gtg gca aga att aaa gag ctt aac cgg gat gat     768
Ala Asp Pro Asn Ser Val Ala Arg Ile Lys Glu Leu Asn Arg Asp Asp
                245                 250                 255
```

```
gaa tta gaa gaa ttg gca acg tca att aat aaa atg ctt gat cga atg      816
Glu Leu Glu Glu Leu Ala Thr Ser Ile Asn Lys Met Leu Asp Arg Met
            260                 265                 270 caa agt tat att gag caa caa aag caa ttt gtt ggg gat gta tct cat      864
Gln Ser Tyr Ile Glu Gln Gln Lys Gln Phe Val Gly Asp Val Ser His
        275                 280                 285 gaa ttg aga act cca gtg gcc gta att gag ggg cat ttg aat atg cta      912
Glu Leu Arg Thr Pro Val Ala Val Ile Glu Gly His Leu Asn Met Leu
    290                 295                 300 gag cgc tgg ggt aaa gat gat cca caa att ttg gat gaa tca att aag      960
Glu Arg Trp Gly Lys Asp Asp Pro Gln Ile Leu Asp Glu Ser Ile Lys
305                 310                 315                 320 gcg tct ctt caa gaa gct gat cga atg aaa cat ttg att cag gaa atg     1008
Ala Ser Leu Gln Glu Ala Asp Arg Met Lys His Leu Ile Gln Glu Met
                325                 330                 335 ctt gat tta act aga gct gaa caa att gat gtt caa tat cct tat gaa     1056
Leu Asp Leu Thr Arg Ala Glu Gln Ile Asp Val Gln Tyr Pro Tyr Glu
            340                 345                 350 gta aca aat gtt aac gaa aca gta aaa cga gtt gtt tct gat ttg gca     1104
Val Thr Asn Val Asn Glu Thr Val Lys Arg Val Val Ser Asp Leu Ala
        355                 360                 365 atg gtt cat tca gac ttt aag att caa ctt gat gaa gat gat tta cca     1152
Met Val His Ser Asp Phe Lys Ile Gln Leu Asp Glu Asp Asp Leu Pro
    370                 375                 380 cca gat aca gaa att caa att tat cat ggt cac ttg gag cag ctg tta     1200
Pro Asp Thr Glu Ile Gln Ile Tyr His Gly His Leu Glu Gln Leu Leu
385                 390                 395                 400 gta att tta ata gat aat ggt att aag tat tct act gat ata aaa caa     1248
Val Ile Leu Ile Asp Asn Gly Ile Lys Tyr Ser Thr Asp Ile Lys Gln
                405                 410                 415 att aat gtt tca gct ggt gtg act aaa aaa gaa gtt aat atc att gtt     1296
Ile Asn Val Ser Ala Gly Val Thr Lys Lys Glu Val Asn Ile Ile Val
            420                 425                 430 cag gac ttc ggt gaa ggt att tct caa gaa gat caa gag aag atc ttt     1344
Gln Asp Phe Gly Glu Gly Ile Ser Gln Glu Asp Gln Glu Lys Ile Phe
        435                 440                 445 aat cgt ttc tac cgt gtt gat aaa gca aga act cgt gaa aaa ggt ggt     1392
Asn Arg Phe Tyr Arg Val Asp Lys Ala Arg Thr Arg Glu Lys Gly Gly
    450                 455                 460 aac ggt tta gga tta tca ata gct caa aag tta gtt gat agc tat gat     1440
Asn Gly Leu Gly Leu Ser Ile Ala Gln Lys Leu Val Asp Ser Tyr Asp
465                 470                 475                 480 ggt gaa atc agt gtt gag tcc gtt gaa gga caa ggt agt cag ttt aag     1488
Gly Glu Ile Ser Val Glu Ser Val Glu Gly Gln Gly Ser Gln Phe Lys
                485                 490                 495 cta cgc ttc cca cgg tta acc aag aaa cag gca gct aaa ctt aga aaa     1536
Leu Arg Phe Pro Arg Leu Thr Lys Lys Gln Ala Ala Lys Leu Arg Lys
            500                 505                 510 tta agt gaa aat gct aaa aag cca aaa agt aat tta gaa                 1575
Leu Ser Glu Asn Ala Lys Lys Pro Lys Ser Asn Leu Glu
        515                 520                 525

<210> SEQ ID NO 24
<211> LENGTH: 525
<212> TYPE: PRT
<213> ORGANISM: Lactobacillus acidophilus

<400> SEQUENCE: 24

Met Lys Met Met Ile Lys Asn Asn Lys Glu Ala Gln Glu Glu Thr Lys
1               5                   10                  15
```

```
His Ser Ser Leu Ile Ile Arg Trp Val Ser Ile Val Ala Leu Thr Ile
             20                  25                  30

Thr Val Ser Phe Val Ile Phe Ser Val Val Tyr Gln Ile Val Ser
         35                  40                  45

Gln Gln Ser Leu Asn Gln Gln Glu Thr Ser Ala Asn Val Ala Val
     50                  55                  60

Thr Leu Asp Arg Thr Leu Ser Ser Ile Pro Asn Glu Leu Glu Ile Ser
 65                  70                  75                  80

Asn Val Ile Pro Ser Leu Ser Pro Ser Thr Arg Arg Val Leu Lys Gly
                 85                  90                  95

Gly Pro Ala Ile Ser Ser Lys Asp Ala Asn Asn Asn Ala Phe Ser Asp
                100                 105                 110

Asn Leu Ile Ser Ser Ile Ser Asn Pro Asp Ile Ser Val Ala Val Tyr
             115                 120                 125

Asn Lys His Asn Glu Val Val Phe Ala Asn Gly Asp Thr Thr Pro Lys
    130                 135                 140

Phe Lys Pro Phe Lys Gly Asp Ser Asn Val Val Lys Ile Lys Gln Asn
145                 150                 155                 160

Arg Arg Leu Leu Leu Ile Thr Tyr Gln Lys Val Tyr Ser Ser Val Asn
                165                 170                 175

Asn Lys Leu Thr Gly Tyr Ile Val Val Ser Asn Ser Met Arg Tyr Tyr
            180                 185                 190

Asn Asn Leu Met Asn Asn Leu Leu Arg Leu Met Leu Val Leu Ser Leu
        195                 200                 205

Ile Ala Ile Val Ala Phe Ile Gly Ile Ser Tyr Ile Leu Val Val Ser
    210                 215                 220

Val Val Lys Pro Ile Lys Asn Met Ser Lys Val Ala Lys Glu Val Asn
225                 230                 235                 240

Ala Asp Pro Asn Ser Val Ala Arg Ile Lys Glu Leu Asn Arg Asp Asp
                245                 250                 255

Glu Leu Glu Glu Leu Ala Thr Ser Ile Asn Lys Met Leu Asp Arg Met
            260                 265                 270

Gln Ser Tyr Ile Glu Gln Gln Lys Gln Phe Val Gly Asp Val Ser His
        275                 280                 285

Glu Leu Arg Thr Pro Val Ala Val Ile Glu Gly His Leu Asn Met Leu
    290                 295                 300

Glu Arg Trp Gly Lys Asp Asp Pro Gln Ile Leu Asp Glu Ser Ile Lys
305                 310                 315                 320

Ala Ser Leu Gln Glu Ala Asp Arg Met Lys His Leu Ile Gln Glu Met
                325                 330                 335

Leu Asp Leu Thr Arg Ala Glu Gln Ile Asp Val Gln Tyr Pro Tyr Glu
            340                 345                 350

Val Thr Asn Val Asn Glu Thr Val Lys Arg Val Val Ser Asp Leu Ala
        355                 360                 365

Met Val His Ser Asp Phe Lys Ile Gln Leu Asp Glu Asp Asp Leu Pro
    370                 375                 380

Pro Asp Thr Glu Ile Gln Ile Tyr His Gly His Leu Glu Gln Leu Leu
385                 390                 395                 400

Val Ile Leu Ile Asp Asn Gly Ile Lys Tyr Ser Thr Asp Ile Lys Gln
                405                 410                 415

Ile Asn Val Ser Ala Gly Val Thr Lys Lys Glu Val Asn Ile Ile Val
            420                 425                 430
```

```
Gln Asp Phe Gly Glu Gly Ile Ser Gln Glu Asp Gln Glu Lys Ile Phe
            435                 440                 445
Asn Arg Phe Tyr Arg Val Asp Lys Ala Arg Thr Arg Glu Lys Gly Gly
        450                 455                 460
Asn Gly Leu Gly Leu Ser Ile Ala Gln Lys Leu Val Asp Ser Tyr Asp
465                 470                 475                 480
Gly Glu Ile Ser Val Glu Ser Val Glu Gly Gln Gly Ser Gln Phe Lys
                485                 490                 495
Leu Arg Phe Pro Arg Leu Thr Lys Lys Gln Ala Ala Lys Leu Arg Lys
            500                 505                 510
Leu Ser Glu Asn Ala Lys Lys Pro Lys Ser Asn Leu Glu
        515                 520                 525

<210> SEQ ID NO 25
<211> LENGTH: 714
<212> TYPE: DNA
<213> ORGANISM: Lactobacillus acidophilus
<220> FEATURE:
<221> NAME/KEY: CDS
<222> LOCATION: (1)..(714)
<223> OTHER INFORMATION: lisR two-component response regulator ORF# 1525

<400> SEQUENCE: 25 atg gca aaa att cta att att gaa gat gaa aag aat ttg gct cga ttt     48
Met Ala Lys Ile Leu Ile Ile Glu Asp Glu Lys Asn Leu Ala Arg Phe
1               5                   10                  15 gtt gag cta gaa tta caa cac gaa aat tat gag act gta gta gaa aat     96
Val Glu Leu Glu Leu Gln His Glu Asn Tyr Glu Thr Val Val Glu Asn
            20                  25                  30 aat ggt cgt aaa ggg tta gat gac gct ctt gcc caa gat ttt gat gca    144
Asn Gly Arg Lys Gly Leu Asp Asp Ala Leu Ala Gln Asp Phe Asp Ala
        35                  40                  45 ata tta ctt gac ttg atg ttg cca gat ttg aat ggt ctg gaa att gct    192
Ile Leu Leu Asp Leu Met Leu Pro Asp Leu Asn Gly Leu Glu Ile Ala
    50                  55                  60 cgt cga gtt cgt caa gta aag act aca cca att att atg atg act gcg    240
Arg Arg Val Arg Gln Val Lys Thr Thr Pro Ile Ile Met Met Thr Ala
65                  70                  75                  80 cgt gat tct gta att gat cgt gta tct ggc tta gac cat ggt gca gat    288
Arg Asp Ser Val Ile Asp Arg Val Ser Gly Leu Asp His Gly Ala Asp
                85                  90                  95 gat tac att gtt aag cct ttt gct att gaa gaa ctt ctt gca cgt tta    336
Asp Tyr Ile Val Lys Pro Phe Ala Ile Glu Glu Leu Leu Ala Arg Leu
            100                 105                 110 cgt gcc gtc tta cgc cga gta aag att gaa aaa gat gct tct aaa gtt    384
Arg Ala Val Leu Arg Arg Val Lys Ile Glu Lys Asp Ala Ser Lys Val
        115                 120                 125 aca gtt gca aaa caa aag ata gtt aag ttt aaa gat tta act att gaa    432
Thr Val Ala Lys Gln Lys Ile Val Lys Phe Lys Asp Leu Thr Ile Glu
    130                 135                 140 act gct aac aga att gtt cac cgc gga gat ggt aaa gca att gac ttg    480
Thr Ala Asn Arg Ile Val His Arg Gly Asp Gly Lys Ala Ile Asp Leu
145                 150                 155                 160 act aaa cgt gaa tat aac ttg tta atg acc tta att gaa aac aag aac    528
Thr Lys Arg Glu Tyr Asn Leu Leu Met Thr Leu Ile Glu Asn Lys Asn
                165                 170                 175 aac gta gtc agt cgt gat caa ttg ctg aac aaa att tgg ggt cca gaa    576
Asn Val Val Ser Arg Asp Gln Leu Leu Asn Lys Ile Trp Gly Pro Glu
            180                 185                 190 tca aat att gaa act aat gtt gtt gaa gtt tat gtt cgt tac tta cgt    624
```

```
Ser Asn Ile Glu Thr Asn Val Val Glu Val Tyr Val Arg Tyr Leu Arg
        195                 200                 205 aat aag atc gat gct cca ggt caa cca tct tac att aag acg gtt cgt      672
Asn Lys Ile Asp Ala Pro Gly Gln Pro Ser Tyr Ile Lys Thr Val Arg
        210                 215                 220 ggt acc ggt tat atg gta aga gat gaa gat gat caa gaa                  714
Gly Thr Gly Tyr Met Val Arg Asp Glu Asp Asp Gln Glu
225                 230                 235

<210> SEQ ID NO 26
<211> LENGTH: 238
<212> TYPE: PRT
<213> ORGANISM: Lactobacillus acidophilus

<400> SEQUENCE: 26

Met Ala Lys Ile Leu Ile Ile Glu Asp Glu Lys Asn Leu Ala Arg Phe
1               5                   10                  15

Val Glu Leu Glu Leu Gln His Glu Asn Tyr Glu Thr Val Val Glu Asn
            20                  25                  30

Asn Gly Arg Lys Gly Leu Asp Asp Ala Leu Ala Gln Asp Phe Asp Ala
        35                  40                  45

Ile Leu Leu Asp Leu Met Leu Pro Asp Leu Asn Gly Leu Glu Ile Ala
    50                  55                  60

Arg Arg Val Arg Gln Val Lys Thr Thr Pro Ile Ile Met Met Thr Ala
65                  70                  75                  80

Arg Asp Ser Val Ile Asp Arg Val Ser Gly Leu Asp His Gly Ala Asp
                85                  90                  95

Asp Tyr Ile Val Lys Pro Phe Ala Ile Glu Glu Leu Leu Ala Arg Leu
            100                 105                 110

Arg Ala Val Leu Arg Arg Val Lys Ile Glu Lys Asp Ala Ser Lys Val
        115                 120                 125

Thr Val Ala Lys Gln Lys Ile Val Lys Phe Lys Asp Leu Thr Ile Glu
    130                 135                 140

Thr Ala Asn Arg Ile Val His Arg Gly Asp Gly Lys Ala Ile Asp Leu
145                 150                 155                 160

Thr Lys Arg Glu Tyr Asn Leu Leu Met Thr Leu Ile Glu Asn Lys Asn
                165                 170                 175

Asn Val Val Ser Arg Asp Gln Leu Leu Asn Lys Ile Trp Gly Pro Glu
            180                 185                 190

Ser Asn Ile Glu Thr Asn Val Val Glu Val Tyr Val Arg Tyr Leu Arg
        195                 200                 205

Asn Lys Ile Asp Ala Pro Gly Gln Pro Ser Tyr Ile Lys Thr Val Arg
        210                 215                 220

Gly Thr Gly Tyr Met Val Arg Asp Glu Asp Asp Gln Glu
225                 230                 235

<210> SEQ ID NO 27
<211> LENGTH: 741
<212> TYPE: DNA
<213> ORGANISM: Lactobacillus acidophilus
<220> FEATURE:
<221> NAME/KEY: CDS
<222> LOCATION: (1)..(741)
<223> OTHER INFORMATION: Putative response regulator ORF# 1659

<400> SEQUENCE: 27 ttg gaa tta att ttc cag ccg ttt ttt tct aga ggt gaa aat atg gat    48
Leu Glu Leu Ile Phe Gln Pro Phe Phe Ser Arg Gly Glu Asn Met Asp
1               5                   10                  15
```

```
gaa aaa gat gtc aaa att ctc tta gta gaa gat gaa gaa gcc gta gcc      96
Glu Lys Asp Val Lys Ile Leu Leu Val Glu Asp Glu Glu Ala Val Ala
             20                  25                  30 agc ttc gtt aaa act gaa cta gaa ttt gaa ggt tac caa gta att tgg     144
Ser Phe Val Lys Thr Glu Leu Glu Phe Glu Gly Tyr Gln Val Ile Trp
         35                  40                  45 gct caa gat ggc aaa gaa gct tta gaa ctc ttt caa aaa gaa aaa ccc     192
Ala Gln Asp Gly Lys Glu Ala Leu Glu Leu Phe Gln Lys Glu Lys Pro
     50                  55                  60 act tta atc ctg ctc gac tgg atg ctt cct gta tat gat ggg atc act     240
Thr Leu Ile Leu Leu Asp Trp Met Leu Pro Val Tyr Asp Gly Ile Thr
 65                  70                  75                  80 gtt tta aga cgg att cgt aaa aaa agc gag gtc cct att att atg ctt     288
Val Leu Arg Arg Ile Arg Lys Lys Ser Glu Val Pro Ile Ile Met Leu
                 85                  90                  95 act gct aaa aat tcc act tct gac att agc tca gcc ctt gat caa gga     336
Thr Ala Lys Asn Ser Thr Ser Asp Ile Ser Ser Ala Leu Asp Gln Gly
            100                 105                 110 tta gat gac tat att act aag cca ttt gaa att gaa gaa ctt ttt gct     384
Leu Asp Asp Tyr Ile Thr Lys Pro Phe Glu Ile Glu Glu Leu Phe Ala
        115                 120                 125 aga att cga gta att ttg cgt cgc tta gaa aaa agt aac aaa caa aaa     432
Arg Ile Arg Val Ile Leu Arg Arg Leu Glu Lys Ser Asn Lys Gln Lys
    130                 135                 140 gaa aac tcg aca att tca ttt aac ttt gga cct ttt aaa att gat ttg     480
Glu Asn Ser Thr Ile Ser Phe Asn Phe Gly Pro Phe Lys Ile Asp Leu
145                 150                 155                 160 gtt aaa cac gaa ttc ttc tct aat gat gaa aaa atc tat ttg act cca     528
Val Lys His Glu Phe Phe Ser Asn Asp Glu Lys Ile Tyr Leu Thr Pro
                165                 170                 175 aag gaa ttt gct cta atg act gaa tta atg cgt gac ccg gaa aaa gtc     576
Lys Glu Phe Ala Leu Met Thr Glu Leu Met Arg Asp Pro Glu Lys Val
            180                 185                 190 aaa agc cgc gat gaa ttg ctt gat gta gtc tgg gga tat gac ttt gtg     624
Lys Ser Arg Asp Glu Leu Leu Asp Val Val Trp Gly Tyr Asp Phe Val
        195                 200                 205 ggg caa act aac aca gtt gat gtc tat atc aga acc atc cgg aat aaa     672
Gly Gln Thr Asn Thr Val Asp Val Tyr Ile Arg Thr Ile Arg Asn Lys
    210                 215                 220 ata ggt gat cct aat aaa aag tta att cag act gtc cgt gga tta ggg     720
Ile Gly Asp Pro Asn Lys Lys Leu Ile Gln Thr Val Arg Gly Leu Gly
225                 230                 235                 240 tat tgt tta aga aaa gcc gaa                                         741
Tyr Cys Leu Arg Lys Ala Glu
                245

<210> SEQ ID NO 28
<211> LENGTH: 247
<212> TYPE: PRT
<213> ORGANISM: Lactobacillus acidophilus

<400> SEQUENCE: 28

Leu Glu Leu Ile Phe Gln Pro Phe Phe Ser Arg Gly Glu Asn Met Asp
1               5                   10                  15

Glu Lys Asp Val Lys Ile Leu Leu Val Glu Asp Glu Glu Ala Val Ala
            20                  25                  30

Ser Phe Val Lys Thr Glu Leu Glu Phe Glu Gly Tyr Gln Val Ile Trp
        35                  40                  45

Ala Gln Asp Gly Lys Glu Ala Leu Glu Leu Phe Gln Lys Glu Lys Pro
```

```
                50                  55                  60
Thr Leu Ile Leu Leu Asp Trp Met Leu Pro Val Tyr Asp Gly Ile Thr
 65                  70                  75                  80

Val Leu Arg Arg Ile Arg Lys Lys Ser Glu Val Pro Ile Ile Met Leu
                 85                  90                  95

Thr Ala Lys Asn Ser Thr Ser Asp Ile Ser Ser Ala Leu Asp Gln Gly
                100                 105                 110

Leu Asp Asp Tyr Ile Thr Lys Pro Phe Glu Ile Glu Glu Leu Phe Ala
                115                 120                 125

Arg Ile Arg Val Ile Leu Arg Arg Leu Glu Lys Ser Asn Lys Gln Lys
        130                 135                 140

Glu Asn Ser Thr Ile Ser Phe Asn Phe Gly Pro Phe Lys Ile Asp Leu
145                 150                 155                 160

Val Lys His Glu Phe Phe Ser Asn Asp Glu Lys Ile Tyr Leu Thr Pro
                165                 170                 175

Lys Glu Phe Ala Leu Met Thr Glu Leu Met Arg Asp Pro Glu Lys Val
                180                 185                 190

Lys Ser Arg Asp Glu Leu Leu Asp Val Val Trp Gly Tyr Asp Phe Val
        195                 200                 205

Gly Gln Thr Asn Thr Val Asp Val Tyr Ile Arg Thr Ile Arg Asn Lys
        210                 215                 220

Ile Gly Asp Pro Asn Lys Lys Leu Ile Gln Thr Val Arg Gly Leu Gly
225                 230                 235                 240

Tyr Cys Leu Arg Lys Ala Glu
                245

<210> SEQ ID NO 29
<211> LENGTH: 1323
<212> TYPE: DNA
<213> ORGANISM: Lactobacillus acidophilus
<220> FEATURE:
<221> NAME/KEY: CDS
<222> LOCATION: (1)..(1323)
<223> OTHER INFORMATION: Sensor protein kinase ORF# 1660

<400> SEQUENCE: 29 atg aaa aaa aac act act tct gct caa tta act cgc ctt ttt gtg gga      48
Met Lys Lys Asn Thr Thr Ser Ala Gln Leu Thr Arg Leu Phe Val Gly
 1               5                  10                  15 tta ttt gta gcg att ttg ctg tta gtt aat att gct ttc ttg att att      96
Leu Phe Val Ala Ile Leu Leu Leu Val Asn Ile Ala Phe Leu Ile Ile
             20                  25                  30 tct tca agt tat att tat tac cat gct aaa agt caa agt gaa caa gtt     144
Ser Ser Ser Tyr Ile Tyr Tyr His Ala Lys Ser Gln Ser Glu Gln Val
         35                  40                  45 att caa gcc gta gaa gaa aat tta gaa ccc aaa tac gat tgg tct tct     192
Ile Gln Ala Val Glu Glu Asn Leu Glu Pro Lys Tyr Asp Trp Ser Ser
     50                  55                  60 cta ctt gat gct ttt tta gcc aaa caa gat gat gat gca att att cta     240
Leu Leu Asp Ala Phe Leu Ala Lys Gln Asp Asp Asp Ala Ile Ile Leu
 65                  70                  75                  80 act acg cct aca gga aga acc tac tac tct gag gat gca cat gaa act     288
Thr Thr Pro Thr Gly Arg Thr Tyr Tyr Ser Glu Asp Ala His Glu Thr
                 85                  90                  95 ttt aaa gta att ggt caa aaa cgg cac tac caa aat ttt gtt ttt gcc     336
Phe Lys Val Ile Gly Gln Lys Arg His Tyr Gln Asn Phe Val Phe Ala
                100                 105                 110 aaa aaa cat gtc tat ttt tta aat caa gaa cga cac cgt gca tat caa     384
Lys Lys His Val Tyr Phe Leu Asn Gln Glu Arg His Arg Ala Tyr Gln
```

```
            Lys Lys His Val Tyr Phe Leu Asn Gln Glu Arg His Arg Ala Tyr Gln
                115                 120                 125 att cac gtg gcg ata aat gta gat gaa ttg ctt aac tta att acc tgg        432
Ile His Val Ala Ile Asn Val Asp Glu Leu Leu Asn Leu Ile Thr Trp
    130                 135                 140 tta tta ttc acg atg ctt ggc att aat att gct gct atg ctt atc agt        480
Leu Leu Phe Thr Met Leu Gly Ile Asn Ile Ala Ala Met Leu Ile Ser
145                 150                 155                 160 atc cct tta att cgt aga ttg tca tat agg tgg agt cgt ccg att caa        528
Ile Pro Leu Ile Arg Arg Leu Ser Tyr Arg Trp Ser Arg Pro Ile Gln
                165                 170                 175 aat atg aat atg gaa att aaa gat att cga aaa aat ggt aag aaa gat        576
Asn Met Asn Met Glu Ile Lys Asp Ile Arg Lys Asn Gly Lys Lys Asp
            180                 185                 190 caa att acc gtt cct act caa cct cta gaa ata aag aac cta gct aaa        624
Gln Ile Thr Val Pro Thr Gln Pro Leu Glu Ile Lys Asn Leu Ala Lys
        195                 200                 205 tcg ttt aat aac tta tta gct ttt caa aag aaa gca ttg gaa cgt gaa        672
Ser Phe Asn Asn Leu Leu Ala Phe Gln Lys Lys Ala Leu Glu Arg Glu
    210                 215                 220 caa caa ttt gtt agt gat gct tca cat gaa tta aaa acg cca att gcc        720
Gln Gln Phe Val Ser Asp Ala Ser His Glu Leu Lys Thr Pro Ile Ala
225                 230                 235                 240 gct atc cgc ggt cat gtc aat tta att aaa cgc cgt gga aaa agc aat        768
Ala Ile Arg Gly His Val Asn Leu Ile Lys Arg Arg Gly Lys Ser Asn
                245                 250                 255 cca gaa att att cct act tca tta aat tat att gac gtt gaa tca aag        816
Pro Glu Ile Ile Pro Thr Ser Leu Asn Tyr Ile Asp Val Glu Ser Lys
            260                 265                 270 aaa tta gaa aca cta gta aat gag ctt ctt act tta ggt aga ata gat        864
Lys Leu Glu Thr Leu Val Asn Glu Leu Leu Thr Leu Gly Arg Ile Asp
        275                 280                 285 cat tat act aat aat gac caa aat aca gat tta gta aaa att gtt caa        912
His Tyr Thr Asn Asn Asp Gln Asn Thr Asp Leu Val Lys Ile Val Gln
    290                 295                 300 gaa gta att agt gaa gta caa aca gta tat cct cat act att caa gcc        960
Glu Val Ile Ser Glu Val Gln Thr Val Tyr Pro His Thr Ile Gln Ala
305                 310                 315                 320 aaa tta ccc aac caa tta att tat tct att tca aca act gat ttt tat       1008
Lys Leu Pro Asn Gln Leu Ile Tyr Ser Ile Ser Thr Thr Asp Phe Tyr
                325                 330                 335 aat atc gca cat aat ctg atc gaa aat gct gct aaa tat tcc cca gaa       1056
Asn Ile Ala His Asn Leu Ile Glu Asn Ala Ala Lys Tyr Ser Pro Glu
            340                 345                 350 aat agc gac att gac att aca ctg gta gaa aaa gac aaa cat att atc       1104
Asn Ser Asp Ile Asp Ile Thr Leu Val Glu Lys Asp Lys His Ile Ile
        355                 360                 365 ttt aaa gta gct gat cat ggc att ggt att aac tca gaa aat aaa gat       1152
Phe Lys Val Ala Asp His Gly Ile Gly Ile Asn Ser Glu Asn Lys Asp
    370                 375                 380 aag att ttt gaa cgt ttt tat cgt gaa gac aat tca cat tca agc aaa       1200
Lys Ile Phe Glu Arg Phe Tyr Arg Glu Asp Asn Ser His Ser Ser Lys
385                 390                 395                 400 att tct ggc tcc ggt tta ggg ctt gca att gta caa act gag gtc aac       1248
Ile Ser Gly Ser Gly Leu Gly Leu Ala Ile Val Gln Thr Glu Val Asn
                405                 410                 415 aaa tat cat ggt aaa atc gta tta aag gat aat act cct caa ggt agt       1296
Lys Tyr His Gly Lys Ile Val Leu Lys Asp Asn Thr Pro Gln Gly Ser
            420                 425                 430
```

```
ata ttc ata gta agc ttg ccc caa aaa                                    1323
Ile Phe Ile Val Ser Leu Pro Gln Lys
        435                 440

<210> SEQ ID NO 30
<211> LENGTH: 441
<212> TYPE: PRT
<213> ORGANISM: Lactobacillus acidophilus

<400> SEQUENCE: 30

Met Lys Lys Asn Thr Thr Ser Ala Gln Leu Thr Arg Leu Phe Val Gly
1               5                   10                  15

Leu Phe Val Ala Ile Leu Leu Val Asn Ile Ala Phe Leu Ile Ile
            20                  25                  30

Ser Ser Ser Tyr Ile Tyr Tyr His Ala Lys Ser Gln Ser Glu Gln Val
        35                  40                  45

Ile Gln Ala Val Glu Glu Asn Leu Glu Pro Lys Tyr Asp Trp Ser Ser
    50                  55                  60

Leu Leu Asp Ala Phe Leu Ala Lys Gln Asp Asp Ala Ile Ile Leu
65                  70                  75                  80

Thr Thr Pro Thr Gly Arg Thr Tyr Tyr Ser Glu Asp Ala His Glu Thr
                85                  90                  95

Phe Lys Val Ile Gly Gln Lys Arg His Tyr Gln Asn Phe Val Phe Ala
            100                 105                 110

Lys Lys His Val Tyr Phe Leu Asn Gln Glu Arg His Arg Ala Tyr Gln
        115                 120                 125

Ile His Val Ala Ile Asn Val Asp Glu Leu Leu Asn Leu Ile Thr Trp
    130                 135                 140

Leu Leu Phe Thr Met Leu Gly Ile Asn Ile Ala Ala Met Leu Ile Ser
145                 150                 155                 160

Ile Pro Leu Ile Arg Arg Leu Ser Tyr Arg Trp Ser Arg Pro Ile Gln
                165                 170                 175

Asn Met Asn Met Glu Ile Lys Asp Ile Arg Lys Asn Gly Lys Lys Asp
            180                 185                 190

Gln Ile Thr Val Pro Thr Gln Pro Leu Glu Ile Lys Asn Leu Ala Lys
        195                 200                 205

Ser Phe Asn Asn Leu Leu Ala Phe Gln Lys Lys Ala Leu Glu Arg Glu
    210                 215                 220

Gln Gln Phe Val Ser Asp Ala Ser His Glu Leu Lys Thr Pro Ile Ala
225                 230                 235                 240

Ala Ile Arg Gly His Val Asn Leu Ile Lys Arg Arg Gly Lys Ser Asn
                245                 250                 255

Pro Glu Ile Ile Pro Thr Ser Leu Asn Tyr Ile Asp Val Glu Ser Lys
            260                 265                 270

Lys Leu Glu Thr Leu Val Asn Glu Leu Leu Thr Leu Gly Arg Ile Asp
        275                 280                 285

His Tyr Thr Asn Asn Asp Gln Asn Thr Asp Leu Val Lys Ile Val Gln
    290                 295                 300

Glu Val Ile Ser Glu Val Gln Thr Val Tyr Pro His Thr Ile Gln Ala
305                 310                 315                 320

Lys Leu Pro Asn Gln Leu Ile Tyr Ser Ile Thr Thr Asp Phe Tyr
                325                 330                 335

Asn Ile Ala His Asn Leu Ile Glu Asn Ala Ala Lys Tyr Ser Pro Glu
            340                 345                 350

Asn Ser Asp Ile Asp Ile Thr Leu Val Glu Lys Asp Lys His Ile Ile
```

```
                355                 360                 365
Phe Lys Val Ala Asp His Gly Ile Gly Ile Asn Ser Glu Asn Lys Asp
    370                 375                 380

Lys Ile Phe Glu Arg Phe Tyr Arg Glu Asp Asn Ser His Ser Ser Lys
385                 390                 395                 400

Ile Ser Gly Ser Gly Leu Gly Leu Ala Ile Val Gln Thr Glu Val Asn
                405                 410                 415

Lys Tyr His Gly Lys Ile Val Leu Lys Asp Asn Thr Pro Gln Gly Ser
            420                 425                 430

Ile Phe Ile Val Ser Leu Pro Gln Lys
            435                 440

<210> SEQ ID NO 31
<211> LENGTH: 822
<212> TYPE: DNA
<213> ORGANISM: Lactobacillus acidophilus
<220> FEATURE:
<221> NAME/KEY: CDS
<222> LOCATION: (1)..(822)
<223> OTHER INFORMATION: sapR sakacin A production response regulator
      ORF# 1798

<400> SEQUENCE: 31 ttg ata cgg aag atg gtg aag atg atg agt aaa ttt cca att att gtg      48
Leu Ile Arg Lys Met Val Lys Met Met Ser Lys Phe Pro Ile Ile Val
1               5                   10                  15 tgc gac gac gat aaa gac ttg gct aat caa ttg gct aag aat att aat      96
Cys Asp Asp Asp Lys Asp Leu Ala Asn Gln Leu Ala Lys Asn Ile Asn
            20                  25                  30 gca tct att caa gat tta act gat gac aat gaa agt tat acc gaa ttg     144
Ala Ser Ile Gln Asp Leu Thr Asp Asp Asn Glu Ser Tyr Thr Glu Leu
        35                  40                  45 gat gaa tct gtt aca ttt gtt gct aat gat ttt gct caa gca gta gga     192
Asp Glu Ser Val Thr Phe Val Ala Asn Asp Phe Ala Gln Ala Val Gly
    50                  55                  60 tat gtc gtt gca aat gat att aaa aac tgt att tac ttc tta gat att     240
Tyr Val Val Ala Asn Asp Ile Lys Asn Cys Ile Tyr Phe Leu Asp Ile
65                  70                  75                  80 gaa tta agc cgt gag tct aaa gct aag aat ggc gta gat cta gct gaa     288
Glu Leu Ser Arg Glu Ser Lys Ala Lys Asn Gly Val Asp Leu Ala Glu
                85                  90                  95 ttc att aag aag aat gat gag aat gcc cag atc atc ttt gta acg gcg     336
Phe Ile Lys Lys Asn Asp Glu Asn Ala Gln Ile Ile Phe Val Thr Ala
            100                 105                 110 tac gac aag tac gct ccg tta aca tat cgc cgt cgt atc ggt gca att     384
Tyr Asp Lys Tyr Ala Pro Leu Thr Tyr Arg Arg Arg Ile Gly Ala Ile
        115                 120                 125 gac tat ata agt aag tcc atg tca tct gat aag att att cag cgt att     432
Asp Tyr Ile Ser Lys Ser Met Ser Ser Asp Lys Ile Ile Gln Arg Ile
    130                 135                 140 gag gaa act ttg cgt aat gct ttc gat aat tta tct agc agg att aag     480
Glu Glu Thr Leu Arg Asn Ala Phe Asp Asn Leu Ser Ser Arg Ile Lys
145                 150                 155                 160 ttt ggt caa cgt gat ttt act tat aaa att ggt cgg cgt ata tgt aaa     528
Phe Gly Gln Arg Asp Phe Thr Tyr Lys Ile Gly Arg Arg Ile Cys Lys
                165                 170                 175 gta gct gaa gac aat ata ctt ttt att gaa cat agt act acg cag cat     576
Val Ala Glu Asp Asn Ile Leu Phe Ile Glu His Ser Thr Thr Gln His
            180                 185                 190
```

```
aag gta cat atg gtt acc gaa aat gga gag gta gaa tac aag gga aat      624
Lys Val His Met Val Thr Glu Asn Gly Glu Val Glu Tyr Lys Gly Asn
            195                 200                 205 att agt cag att gat aaa gaa aac cca ttt tta gta aaa gtc tct cag      672
Ile Ser Gln Ile Asp Lys Glu Asn Pro Phe Leu Val Lys Val Ser Gln
        210                 215                 220 tct tat tta gtg aat cca aga aat att aat gcg att gat atg aaa gaa      720
Ser Tyr Leu Val Asn Pro Arg Asn Ile Asn Ala Ile Asp Met Lys Glu
225                 230                 235                 240 cat act att ata ttt gat aat gat aag atg gta act tat tct aga gcg      768
His Thr Ile Ile Phe Asp Asn Asp Lys Met Val Thr Tyr Ser Arg Ala
                245                 250                 255 tac aaa gat gtg gtt aaa aca ctt gta aat aaa ttt aaa gat att gaa      816
Tyr Lys Asp Val Val Lys Thr Leu Val Asn Lys Phe Lys Asp Ile Glu
            260                 265                 270 gtt aaa                                                              822
Val Lys <210> SEQ ID NO 32
<211> LENGTH: 274
<212> TYPE: PRT
<213> ORGANISM: Lactobacillus acidophilus

<400> SEQUENCE: 32

Leu Ile Arg Lys Met Val Lys Met Met Ser Lys Phe Pro Ile Ile Val
1               5                   10                  15

Cys Asp Asp Lys Asp Leu Ala Asn Gln Leu Ala Lys Asn Ile Asn
            20                  25                  30

Ala Ser Ile Gln Asp Leu Thr Asp Asp Asn Glu Ser Tyr Thr Glu Leu
        35                  40                  45

Asp Glu Ser Val Thr Phe Val Ala Asn Asp Phe Ala Gln Ala Val Gly
    50                  55                  60

Tyr Val Val Ala Asn Asp Ile Lys Asn Cys Ile Tyr Phe Leu Asp Ile
65                  70                  75                  80

Glu Leu Ser Arg Glu Ser Lys Ala Lys Asn Gly Val Asp Leu Ala Glu
                85                  90                  95

Phe Ile Lys Lys Asn Asp Glu Asn Ala Gln Ile Ile Phe Val Thr Ala
            100                 105                 110

Tyr Asp Lys Tyr Ala Pro Leu Thr Tyr Arg Arg Ile Gly Ala Ile
        115                 120                 125

Asp Tyr Ile Ser Lys Ser Met Ser Ser Asp Lys Ile Ile Gln Arg Ile
    130                 135                 140

Glu Glu Thr Leu Arg Asn Ala Phe Asp Asn Leu Ser Ser Arg Ile Lys
145                 150                 155                 160

Phe Gly Gln Arg Asp Phe Thr Tyr Lys Ile Gly Arg Ile Cys Lys
                165                 170                 175

Val Ala Glu Asp Asn Ile Leu Phe Ile Glu His Ser Thr Thr Gln His
            180                 185                 190

Lys Val His Met Val Thr Glu Asn Gly Glu Val Glu Tyr Lys Gly Asn
        195                 200                 205

Ile Ser Gln Ile Asp Lys Glu Asn Pro Phe Leu Val Lys Val Ser Gln
    210                 215                 220

Ser Tyr Leu Val Asn Pro Arg Asn Ile Asn Ala Ile Asp Met Lys Glu
225                 230                 235                 240

His Thr Ile Ile Phe Asp Asn Asp Lys Met Val Thr Tyr Ser Arg Ala
                245                 250                 255
```

```
                Tyr Lys Asp Val Val Lys Thr Leu Val Asn Lys Phe Lys Asp Ile Glu
                                260                 265                 270

Val Lys

<210> SEQ ID NO 33
<211> LENGTH: 1320
<212> TYPE: DNA
<213> ORGANISM: Lactobacillus acidophilus
<220> FEATURE:
<221> NAME/KEY: CDS
<222> LOCATION: (1)..(1320)
<223> OTHER INFORMATION: Putative sensor histidine kinase ORF# 1799

<400> SEQUENCE: 33 atg gtc tta tac cta tct ata gtt caa ttt tta ttg tcg agt gcc ata          48
Met Val Leu Tyr Leu Ser Ile Val Gln Phe Leu Leu Ser Ser Ala Ile
1               5                   10                  15 gat tta tgg atg ttt ctt aaa ata act cgt ata aaa ttg aat ata aat          96
Asp Leu Trp Met Phe Leu Lys Ile Thr Arg Ile Lys Leu Asn Ile Asn
            20                  25                  30 tta aaa ctg gga cta aca tta gta gtt att act ata gga tcg ata ata         144
Leu Lys Leu Gly Leu Thr Leu Val Val Ile Thr Ile Gly Ser Ile Ile
        35                  40                  45 agc ata ata tta gat gaa tat ggt ggc tta ctt tta gca aat ata tct         192
Ser Ile Ile Leu Asp Glu Tyr Gly Gly Leu Leu Leu Ala Asn Ile Ser
    50                  55                  60 gag ata ata ggt ttt tat gta ata tat aaa aag aaa aat aac aaa ata         240
Glu Ile Ile Gly Phe Tyr Val Ile Tyr Lys Lys Lys Asn Asn Lys Ile
65                  70                  75                  80 ctt gta gca ggt gca ata gtt ttt gta tgt act tta gat cta ttt att         288
Leu Val Ala Gly Ala Ile Val Phe Val Cys Thr Leu Asp Leu Phe Ile
                85                  90                  95 aat ata att cta gct ttt gcg gca gtt ttt att aaa gta gaa ggt tat         336
Asn Ile Ile Leu Ala Phe Ala Ala Val Phe Ile Lys Val Glu Gly Tyr
            100                 105                 110 atg agt ata atc ctt tta ttt gtt gaa gcc tgg att gta aaa aaa tat         384
Met Ser Ile Ile Leu Leu Phe Val Glu Ala Trp Ile Val Lys Lys Tyr
        115                 120                 125 aat aaa aat att tat agt act tta gta gga caa aat aaa aaa tca ttt         432
Asn Lys Asn Ile Tyr Ser Thr Leu Val Gly Gln Asn Lys Lys Ser Phe
    130                 135                 140 ttg tac ata tta tgt tat att ttc ttg tca agt gaa ata gta ttg ttg         480
Leu Tyr Ile Leu Cys Tyr Ile Phe Leu Ser Ser Glu Ile Val Leu Leu
145                 150                 155                 160 att att tta tta act aaa tca tat aat gct ttt tat act gta gca atg         528
Ile Ile Leu Leu Thr Lys Ser Tyr Asn Ala Phe Tyr Thr Val Ala Met
                165                 170                 175 gtg ttg ttt gct ttg caa att ata ttt tca atc gtt gca tat cat gaa         576
Val Leu Phe Ala Leu Gln Ile Ile Phe Ser Ile Val Ala Tyr His Glu
            180                 185                 190 att gtt agt atc cag caa gaa ctt tta aat aaa caa aag caa aaa gag         624
Ile Val Ser Ile Gln Gln Glu Leu Leu Asn Lys Gln Lys Gln Lys Glu
        195                 200                 205 atc ctt gat aat caa cat cag ctc gaa gaa tat gcc tct tat ctt gaa         672
Ile Leu Asp Asn Gln His Gln Leu Glu Glu Tyr Ala Ser Tyr Leu Glu
    210                 215                 220 aaa agt gaa gat gat ctc cgt gcc ttc aga cat gat tac aaa aat att         720
Lys Ser Glu Asp Asp Leu Arg Ala Phe Arg His Asp Tyr Lys Asn Ile
225                 230                 235                 240 ctt aat tct tta aag gta agt gct caa gag ggc aac gtt aaa gaa gta         768
Leu Asn Ser Leu Lys Val Ser Ala Gln Glu Gly Asn Val Lys Glu Val
```

```
att cag aaa cta gat aaa tac act gaa act aac tta aat tct aag gct      816
Ile Gln Lys Leu Asp Lys Tyr Thr Glu Thr Asn Leu Asn Ser Lys Ala
            260                 265                 270 cta ctc aaa tat aaa gac gta aat cac att tac gtt aaa tca att aag      864
Leu Leu Lys Tyr Lys Asp Val Asn His Ile Tyr Val Lys Ser Ile Lys
        275                 280                 285 agt att att att tcc aag tta aca gaa tta tac aat ttg aat att cca      912
Ser Ile Ile Ile Ser Lys Leu Thr Glu Leu Tyr Asn Leu Asn Ile Pro
    290                 295                 300 tat aac ttc gaa tgt cga agc aat att cat aat tta cca gat cat gta      960
Tyr Asn Phe Glu Cys Arg Ser Asn Ile His Asn Leu Pro Asp His Val
305                 310                 315                 320 aat gag ctt gat cta gta cgt att att ggt att acc ttt gat aat gca     1008
Asn Glu Leu Asp Leu Val Arg Ile Ile Gly Ile Thr Phe Asp Asn Ala
                325                 330                 335 att gaa gaa agc aaa gcc ttg gtt gct gag aaa cat gat att aga agc     1056
Ile Glu Glu Ser Lys Ala Leu Val Ala Glu Lys His Asp Ile Arg Ser
            340                 345                 350 gct gaa gtt caa ata atg gtc tac tct gat ggt cct gat gag ttt gag     1104
Ala Glu Val Gln Ile Met Val Tyr Ser Asp Gly Pro Asp Glu Phe Glu
        355                 360                 365 ttc gaa atc aga aat aaa att caa aat aaa aag atc tca act agt cag     1152
Phe Glu Ile Arg Asn Lys Ile Gln Asn Lys Lys Ile Ser Thr Ser Gln
    370                 375                 380 att caa caa cgt ggc ttt act act aag aaa gat cat aag gga ctc gga     1200
Ile Gln Gln Arg Gly Phe Thr Thr Lys Lys Asp His Lys Gly Leu Gly
385                 390                 395                 400 tta gct aat att aaa gaa att gag ggt aaa tat cct gat atg tct att     1248
Leu Ala Asn Ile Lys Glu Ile Glu Gly Lys Tyr Pro Asp Met Ser Ile
                405                 410                 415 tct tat aca att caa gat ggc tgg ttt gac ttc tat atg aca att gat     1296
Ser Tyr Thr Ile Gln Asp Gly Trp Phe Asp Phe Tyr Met Thr Ile Asp
            420                 425                 430 acg gaa gat ggt gaa gat gat gag                                     1320
Thr Glu Asp Gly Glu Asp Asp Glu
        435                 440

<210> SEQ ID NO 34
<211> LENGTH: 440
<212> TYPE: PRT
<213> ORGANISM: Lactobacillus acidophilus

<400> SEQUENCE: 34

Met Val Leu Tyr Leu Ser Ile Val Gln Phe Leu Leu Ser Ser Ala Ile
1               5                   10                  15

Asp Leu Trp Met Phe Leu Lys Ile Thr Arg Ile Lys Leu Asn Ile Asn
            20                  25                  30

Leu Lys Leu Gly Leu Thr Leu Val Val Ile Thr Ile Gly Ser Ile Ile
        35                  40                  45

Ser Ile Ile Leu Asp Glu Tyr Gly Gly Leu Leu Leu Ala Asn Ile Ser
    50                  55                  60

Glu Ile Ile Gly Phe Tyr Val Ile Tyr Lys Lys Lys Asn Asn Lys Ile
65                  70                  75                  80

Leu Val Ala Gly Ala Ile Val Phe Val Cys Thr Leu Asp Leu Phe Ile
                85                  90                  95

Asn Ile Ile Leu Ala Phe Ala Ala Val Phe Ile Lys Val Glu Gly Tyr
            100                 105                 110
```

```
Met Ser Ile Ile Leu Leu Phe Val Glu Ala Trp Ile Val Lys Lys Tyr
        115                 120                 125

Asn Lys Asn Ile Tyr Ser Thr Leu Val Gly Gln Asn Lys Lys Ser Phe
    130                 135                 140

Leu Tyr Ile Leu Cys Tyr Ile Phe Leu Ser Ser Glu Ile Val Leu Leu
145                 150                 155                 160

Ile Ile Leu Leu Thr Lys Ser Tyr Asn Ala Phe Tyr Thr Val Ala Met
                165                 170                 175

Val Leu Phe Ala Leu Gln Ile Ile Phe Ser Ile Val Ala Tyr His Glu
            180                 185                 190

Ile Val Ser Ile Gln Gln Glu Leu Asn Lys Gln Lys Gln Lys Glu
        195                 200                 205

Ile Leu Asp Asn Gln His Gln Leu Glu Glu Tyr Ala Ser Tyr Leu Glu
    210                 215                 220

Lys Ser Glu Asp Asp Leu Arg Ala Phe Arg His Asp Tyr Lys Asn Ile
225                 230                 235                 240

Leu Asn Ser Leu Lys Val Ser Ala Gln Glu Gly Asn Val Lys Glu Val
                245                 250                 255

Ile Gln Lys Leu Asp Lys Tyr Thr Glu Thr Asn Leu Asn Ser Lys Ala
            260                 265                 270

Leu Leu Lys Tyr Lys Asp Val Asn His Ile Tyr Val Lys Ser Ile Lys
        275                 280                 285

Ser Ile Ile Ile Ser Lys Leu Thr Glu Leu Tyr Asn Leu Asn Ile Pro
    290                 295                 300

Tyr Asn Phe Glu Cys Arg Ser Asn Ile His Asn Leu Pro Asp His Val
305                 310                 315                 320

Asn Glu Leu Asp Leu Val Arg Ile Ile Gly Ile Thr Phe Asp Asn Ala
                325                 330                 335

Ile Glu Glu Ser Lys Ala Leu Val Ala Glu Lys His Asp Ile Arg Ser
            340                 345                 350

Ala Glu Val Gln Ile Met Val Tyr Ser Asp Gly Pro Asp Glu Phe Glu
        355                 360                 365

Phe Glu Ile Arg Asn Lys Ile Gln Asn Lys Lys Ile Ser Thr Ser Gln
    370                 375                 380

Ile Gln Gln Arg Gly Phe Thr Thr Lys Lys Asp His Lys Gly Leu Gly
385                 390                 395                 400

Leu Ala Asn Ile Lys Glu Ile Glu Gly Lys Tyr Pro Asp Met Ser Ile
                405                 410                 415

Ser Tyr Thr Ile Gln Asp Gly Trp Phe Asp Phe Tyr Met Thr Ile Asp
            420                 425                 430

Thr Glu Asp Gly Glu Asp Glu
        435                 440

<210> SEQ ID NO 35
<211> LENGTH: 1143
<212> TYPE: DNA
<213> ORGANISM: Lactobacillus acidophilus
<220> FEATURE:
<221> NAME/KEY: CDS
<222> LOCATION: (1)..(1143)
<223> OTHER INFORMATION: Putative histidine kinase ORF# 1819

<400> SEQUENCE: 35 atg aaa aaa gag cgc gtt aaa tta aca ggc gct gaa aaa agc gaa tta      48
Met Lys Lys Glu Arg Val Lys Leu Thr Gly Ala Glu Lys Ser Glu Leu
1               5                   10                  15
```

-continued

| | |
|---|---|
| ttt gca gaa gga atc gta acg att atc ctt ctg ctt ttg cta aat tta<br>Phe Ala Glu Gly Ile Val Thr Ile Ile Leu Leu Leu Leu Leu Asn Leu<br>20        25        30 | 96 |
| tca att atc att tta att cac cta gcc att ttg caa gat gag agc ttg<br>Ser Ile Ile Ile Leu Ile His Leu Ala Ile Leu Gln Asp Glu Ser Leu<br>   35        40        45 | 144 |
| gta aat ggt att tac ttt ttg aaa aag tcg atg act ttt gtt ggt gga<br>Val Asn Gly Ile Tyr Phe Leu Lys Lys Ser Met Thr Phe Val Gly Gly<br>50        55        60 | 192 |
| cga cat gtt tgg tct tgg cag aat atc ttc att atc ata atg gca gtt<br>Arg His Val Trp Ser Trp Gln Asn Ile Phe Ile Ile Ile Met Ala Val<br>65        70        75        80 | 240 |
| ggc gat tta gcc gtg tta tat tgg cgg cta att aga aga tat cat cag<br>Gly Asp Leu Ala Val Leu Tyr Trp Arg Leu Ile Arg Arg Tyr His Gln<br>       85        90        95 | 288 |
| atg cag tta cgc cac gtt att tcg gag ttg cat tat att gct aat ggg<br>Met Gln Leu Arg His Val Ile Ser Glu Leu His Tyr Ile Ala Asn Gly<br>       100        105        110 | 336 |
| cat ttt gat cat aga att aat ttt aga gtt cga cca gaa ctt caa aga<br>His Phe Asp His Arg Ile Asn Phe Arg Val Arg Pro Glu Leu Gln Arg<br>       115        120        125 | 384 |
| gta gtt gat tca att aat tcg tta gtt gat agt acg gtc aac tct att<br>Val Val Asp Ser Ile Asn Ser Leu Val Asp Ser Thr Val Asn Ser Ile<br>130        135        140 | 432 |
| aac gaa gaa cgt gcc att gaa aag tct aag gac gaa ttg att act aat<br>Asn Glu Glu Arg Ala Ile Glu Lys Ser Lys Asp Glu Leu Ile Thr Asn<br>145        150        155        160 | 480 |
| gta tca cat gat att aga acg ccg cta acg tca att att ggc tat tta<br>Val Ser His Asp Ile Arg Thr Pro Leu Thr Ser Ile Ile Gly Tyr Leu<br>       165        170        175 | 528 |
| ggg cta tta aaa act ggc ata tca tca aaa gag gat caa caa aag tat<br>Gly Leu Leu Lys Thr Gly Ile Ser Ser Lys Glu Asp Gln Gln Lys Tyr<br>       180        185        190 | 576 |
| gtt gat atc gct tat act aaa gca gag caa atg aaa tca tta gct gat<br>Val Asp Ile Ala Tyr Thr Lys Ala Glu Gln Met Lys Ser Leu Ala Asp<br>       195        200        205 | 624 |
| gat tta ttt gaa tac aca aca cta aaa tca acc agt act aag tta aac<br>Asp Leu Phe Glu Tyr Thr Thr Leu Lys Ser Thr Ser Thr Lys Leu Asn<br>210        215        220 | 672 |
| ttg aat gag cta cat att tat tca atg ctt gag caa gta gct gca ggt<br>Leu Asn Glu Leu His Ile Tyr Ser Met Leu Glu Gln Val Ala Ala Gly<br>225        230        235        240 | 720 |
| ttt gaa tta gaa gct gaa aaa aag ggt att gat att gag ata gaa gca<br>Phe Glu Leu Glu Ala Glu Lys Lys Gly Ile Asp Ile Glu Ile Glu Ala<br>       245        250        255 | 768 |
| cgg cct aag aat tta acg ata cag gct gat gca gaa aag tta gtg cgt<br>Arg Pro Lys Asn Leu Thr Ile Gln Ala Asp Ala Glu Lys Leu Val Arg<br>       260        265        270 | 816 |
| gta tat aac aat ttg att tct aat gct ttt aaa tat ggt aca ggt gct<br>Val Tyr Asn Asn Leu Ile Ser Asn Ala Phe Lys Tyr Gly Thr Gly Ala<br>       275        280        285 | 864 |
| aca aaa att aag ttg gta gca aat ttg gtt aac aaa agt gaa gta gaa<br>Thr Lys Ile Lys Leu Val Ala Asn Leu Val Asn Lys Ser Glu Val Glu<br>290        295        300 | 912 |
| tta cga gtt gaa aat aac ggt gaa cca att cct gta tca gcc caa aag<br>Leu Arg Val Glu Asn Asn Gly Glu Pro Ile Pro Val Ser Ala Gln Lys<br>305        310        315        320 | 960 |
| aaa att ttt gat cgt ttc tat cga gta gaa aca tca cgt aat acg aaa<br>Lys Ile Phe Asp Arg Phe Tyr Arg Val Glu Thr Ser Arg Asn Thr Lys<br>       325        330        335 | 1008 |

```
act ggt ggt aca gga ttg ggg tta tca att act aaa agt gta gta gac      1056
Thr Gly Gly Thr Gly Leu Gly Leu Ser Ile Thr Lys Ser Val Val Asp
            340                 345                 350 tta cat cat ggg aca att cgt tgt caa tca gat gaa aac tgg aca agt      1104
Leu His His Gly Thr Ile Arg Cys Gln Ser Asp Glu Asn Trp Thr Ser
        355                 360                 365 ttt att att cgt ttg cca ctt gat ccc aat aag gca aag                   1143
Phe Ile Ile Arg Leu Pro Leu Asp Pro Asn Lys Ala Lys
    370                 375                 380

<210> SEQ ID NO 36
<211> LENGTH: 381
<212> TYPE: PRT
<213> ORGANISM: Lactobacillus acidophilus

<400> SEQUENCE: 36
```

Met Lys Lys Glu Arg Val Lys Leu Thr Gly Ala Glu Lys Ser Glu Leu
1               5                   10                  15

Phe Ala Glu Gly Ile Val Thr Ile Ile Leu Leu Leu Leu Asn Leu
            20                  25                  30

Ser Ile Ile Ile Leu Ile His Leu Ala Ile Leu Gln Asp Glu Ser Leu
        35                  40                  45

Val Asn Gly Ile Tyr Phe Leu Lys Lys Ser Met Thr Phe Val Gly Gly
    50                  55                  60

Arg His Val Trp Ser Trp Gln Asn Ile Phe Ile Ile Met Ala Val
65                  70                  75                  80

Gly Asp Leu Ala Val Leu Tyr Trp Arg Leu Ile Arg Arg Tyr His Gln
                85                  90                  95

Met Gln Leu Arg His Val Ile Ser Glu Leu His Tyr Ile Ala Asn Gly
            100                 105                 110

His Phe Asp His Arg Ile Asn Phe Arg Val Arg Pro Glu Leu Gln Arg
        115                 120                 125

Val Val Asp Ser Ile Asn Ser Leu Val Asp Ser Thr Val Asn Ser Ile
    130                 135                 140

Asn Glu Glu Arg Ala Ile Glu Lys Ser Lys Asp Glu Leu Ile Thr Asn
145                 150                 155                 160

Val Ser His Asp Ile Arg Thr Pro Leu Thr Ser Ile Ile Gly Tyr Leu
                165                 170                 175

Gly Leu Leu Lys Thr Gly Ile Ser Ser Lys Glu Asp Gln Gln Lys Tyr
            180                 185                 190

Val Asp Ile Ala Tyr Thr Lys Ala Glu Gln Met Lys Ser Leu Ala Asp
        195                 200                 205

Asp Leu Phe Glu Tyr Thr Thr Leu Lys Ser Thr Ser Thr Lys Leu Asn
    210                 215                 220

Leu Asn Glu Leu His Ile Tyr Ser Met Leu Glu Gln Val Ala Ala Gly
225                 230                 235                 240

Phe Glu Leu Glu Ala Glu Lys Lys Gly Ile Asp Ile Glu Ile Glu Ala
                245                 250                 255

Arg Pro Lys Asn Leu Thr Ile Gln Ala Asp Ala Glu Lys Leu Val Arg
            260                 265                 270

Val Tyr Asn Asn Leu Ile Ser Asn Ala Phe Lys Tyr Gly Thr Gly Ala
        275                 280                 285

Thr Lys Ile Lys Leu Val Ala Asn Leu Val Asn Lys Ser Glu Val Glu
    290                 295                 300

Leu Arg Val Glu Asn Asn Gly Glu Pro Ile Pro Val Ser Ala Gln Lys

```
                305                 310                 315                 320
Lys Ile Phe Asp Arg Phe Tyr Arg Val Glu Thr Ser Arg Asn Thr Lys
                    325                 330                 335

Thr Gly Gly Thr Gly Leu Gly Leu Ser Ile Thr Lys Ser Val Val Asp
                340                 345                 350

Leu His His Gly Thr Ile Arg Cys Gln Ser Asp Glu Asn Trp Thr Ser
            355                 360                 365

Phe Ile Ile Arg Leu Pro Leu Asp Pro Asn Lys Ala Lys
        370                 375                 380

<210> SEQ ID NO 37
<211> LENGTH: 684
<212> TYPE: DNA
<213> ORGANISM: Lactobacillus acidophilus
<220> FEATURE:
<221> NAME/KEY: CDS
<222> LOCATION: (1)..(684)
<223> OTHER INFORMATION: Putative response regulator ORF# 1820

<400> SEQUENCE: 37
```

| | | | | | | | | | | | | | | | | |
|---|---|---|---|---|---|---|---|---|---|---|---|---|---|---|---|---|
| gtg | aaa | att | tta | gtt | gtt | gat | gat | gat | aaa | gaa | att | gta | gaa | ctt | tta | 48 |
| Val | Lys | Ile | Leu | Val | Val | Asp | Asp | Asp | Lys | Glu | Ile | Val | Glu | Leu | Leu | |
| 1 | | | | 5 | | | | | 10 | | | | | 15 | | |
| agt | att | tat | ctt | aaa | aac | gaa | gga | tat | gag | cca | gtt | act | gcc | tat | agc | 96 |
| Ser | Ile | Tyr | Leu | Lys | Asn | Glu | Gly | Tyr | Glu | Pro | Val | Thr | Ala | Tyr | Ser | |
| | | | 20 | | | | | 25 | | | | | 30 | | | |
| ggt | aaa | gaa | gca | att | act | aag | cta | aca | act | act | cca | gat | att | gct | ttg | 144 |
| Gly | Lys | Glu | Ala | Ile | Thr | Lys | Leu | Thr | Thr | Thr | Pro | Asp | Ile | Ala | Leu | |
| | | 35 | | | | | 40 | | | | | 45 | | | | |
| atg | att | tta | gac | gta | atg | atg | cct | aat | atg | tca | ggg | att | gaa | gta | att | 192 |
| Met | Ile | Leu | Asp | Val | Met | Met | Pro | Asn | Met | Ser | Gly | Ile | Glu | Val | Ile | |
| | 50 | | | | | 55 | | | | | 60 | | | | | |
| aag | gaa | gtt | aga | aaa | gat | tcc | gat | att | cca | att | att | att | gtt | tct | gct | 240 |
| Lys | Glu | Val | Arg | Lys | Asp | Ser | Asp | Ile | Pro | Ile | Ile | Ile | Val | Ser | Ala | |
| 65 | | | | | 70 | | | | | 75 | | | | | 80 | |
| aaa | aca | ggt | gat | atg | gat | aag | att | caa | ggt | tta | att | acc | ggt | gca | gat | 288 |
| Lys | Thr | Gly | Asp | Met | Asp | Lys | Ile | Gln | Gly | Leu | Ile | Thr | Gly | Ala | Asp | |
| | | | | 85 | | | | | 90 | | | | | 95 | | |
| gat | tat | gtt | tca | aaa | cca | ttt | aat | cca | ctt | gaa | gta | atg | gct | cga | gta | 336 |
| Asp | Tyr | Val | Ser | Lys | Pro | Phe | Asn | Pro | Leu | Glu | Val | Met | Ala | Arg | Val | |
| | | | 100 | | | | | 105 | | | | | 110 | | | |
| cgt | tca | ctt | ctt | cgt | aga | agt | caa | aag | caa | gtt | aag | gat | gaa | aag | cct | 384 |
| Arg | Ser | Leu | Leu | Arg | Arg | Ser | Gln | Lys | Gln | Val | Lys | Asp | Glu | Lys | Pro | |
| | | 115 | | | | | 120 | | | | | 125 | | | | |
| gat | att | ttg | gaa | gta | ggg | cct | ttg | gta | att | aat | cgt | gat | tcg | cat | gaa | 432 |
| Asp | Ile | Leu | Glu | Val | Gly | Pro | Leu | Val | Ile | Asn | Arg | Asp | Ser | His | Glu | |
| | 130 | | | | | 135 | | | | | 140 | | | | | |
| gtt | aag | act | att | gat | ggt | aaa | gca | att | cag | tta | act | gca | ctt | gaa | ttt | 480 |
| Val | Lys | Thr | Ile | Asp | Gly | Lys | Ala | Ile | Gln | Leu | Thr | Ala | Leu | Glu | Phe | |
| 145 | | | | | 150 | | | | | 155 | | | | | 160 | |
| ggt | att | cta | tat | ctt | ttg | gct | agt | cac | cct | aat | cga | gta | ttt | tca | gct | 528 |
| Gly | Ile | Leu | Tyr | Leu | Leu | Ala | Ser | His | Pro | Asn | Arg | Val | Phe | Ser | Ala | |
| | | | | 165 | | | | | 170 | | | | | 175 | | |
| gat | gaa | ata | ttt | gaa | cgt | gta | tgg | caa | caa | gaa | tct | att | gtt | tct | gct | 576 |
| Asp | Glu | Ile | Phe | Glu | Arg | Val | Trp | Gln | Gln | Glu | Ser | Ile | Val | Ser | Ala | |
| | | | 180 | | | | | 185 | | | | | 190 | | | |
| aag | act | gta | atg | gtt | cac | gta | tcc | cat | ctt | cgt | gac | aag | atc | caa | aag | 624 |
| Lys | Thr | Val | Met | Val | His | Val | Ser | His | Leu | Arg | Asp | Lys | Ile | Gln | Lys | |
| | | 195 | | | | | 200 | | | | | 205 | | | | |
| gca | acg | gat | ggt | gaa | gat | gtt | att | caa | act | gtt | tgg | ggt | gta | gga | tac | 672 |

```
Ala Thr Asp Gly Glu Asp Val Ile Gln Thr Val Trp Gly Val Gly Tyr
    210                 215                 220 aag gtc gag gca                                                      684
Lys Val Glu Ala
225

<210> SEQ ID NO 38
<211> LENGTH: 228
<212> TYPE: PRT
<213> ORGANISM: Lactobacillus acidophilus

<400> SEQUENCE: 38

Val Lys Ile Leu Val Asp Asp Lys Glu Ile Val Glu Leu Leu
1               5                   10                  15

Ser Ile Tyr Leu Lys Asn Glu Gly Tyr Glu Pro Val Thr Ala Tyr Ser
            20                  25                  30

Gly Lys Glu Ala Ile Thr Lys Leu Thr Thr Thr Pro Asp Ile Ala Leu
        35                  40                  45

Met Ile Leu Asp Val Met Met Pro Asn Met Ser Gly Ile Glu Val Ile
    50                  55                  60

Lys Glu Val Arg Lys Asp Ser Asp Ile Pro Ile Ile Val Ser Ala
65                  70                  75                  80

Lys Thr Gly Asp Met Asp Lys Ile Gln Gly Leu Ile Thr Gly Ala Asp
                85                  90                  95

Asp Tyr Val Ser Lys Pro Phe Asn Pro Leu Glu Val Met Ala Arg Val
            100                 105                 110

Arg Ser Leu Leu Arg Arg Ser Gln Lys Val Lys Asp Glu Lys Pro
        115                 120                 125

Asp Ile Leu Glu Val Gly Pro Leu Val Ile Asn Arg Asp Ser His Glu
    130                 135                 140

Val Lys Thr Ile Asp Gly Lys Ala Ile Gln Leu Thr Ala Leu Glu Phe
145                 150                 155                 160

Gly Ile Leu Tyr Leu Leu Ala Ser His Pro Asn Arg Val Phe Ser Ala
                165                 170                 175

Asp Glu Ile Phe Glu Arg Val Trp Gln Gln Glu Ser Ile Val Ser Ala
            180                 185                 190

Lys Thr Val Met Val His Val Ser His Leu Arg Asp Lys Ile Gln Lys
        195                 200                 205

Ala Thr Asp Gly Glu Asp Val Ile Gln Thr Val Trp Gly Val Gly Tyr
    210                 215                 220

Lys Val Glu Ala
225

<210> SEQ ID NO 39
<211> LENGTH: 762
<212> TYPE: DNA
<213> ORGANISM: Lactobacillus acidophilus
<220> FEATURE:
<221> NAME/KEY: CDS
<222> LOCATION: (1)..(762)
<223> OTHER INFORMATION: Translocation regulator ORF# 599

<400> SEQUENCE: 39 atg att caa gaa gaa cga tta ata caa att aag cat ttg ctc aaa aaa    48
Met Ile Gln Glu Glu Arg Leu Ile Gln Ile Lys His Leu Leu Lys Lys
1               5                   10                  15 gag cat caa gta tca act aaa gaa att gcc caa aaa ttt ggt gta tcg    96
Glu His Gln Val Ser Thr Lys Glu Ile Ala Gln Lys Phe Gly Val Ser
            20                  25                  30
```

```
ttt gat act gcc cgc cga gat gta atc cat ctg acc aca aca ggc caa      144
Phe Asp Thr Ala Arg Arg Asp Val Ile His Leu Thr Thr Thr Gly Gln
        35                  40                  45 gct gta aga ata cat ggc ggt atg atg gaa att aat caa aat gac gta      192
Ala Val Arg Ile His Gly Gly Met Met Glu Ile Asn Gln Asn Asp Val
 50                  55                  60 cct aat ttt tta gct aga aat caa gtt cag tct cct gtg aaa ttg aaa      240
Pro Asn Phe Leu Ala Arg Asn Gln Val Gln Ser Pro Val Lys Leu Lys
 65                  70                  75                  80 atg gcc caa atg gca aaa aga ttc gtc cat cca ggc caa tgc gat ttt      288
Met Ala Gln Met Ala Lys Arg Phe Val His Pro Gly Gln Cys Asp Phe
             85                  90                  95 ata ggt cct tct acc att ctc aag cag ctc tgc cca atg ctt aat ggt      336
Ile Gly Pro Ser Thr Ile Leu Lys Gln Leu Cys Pro Met Leu Asn Gly
            100                 105                 110 ata aat atg caa ata gta acc aac tca att gac aat gct ctg agc tta      384
Ile Asn Met Gln Ile Val Thr Asn Ser Ile Asp Asn Ala Leu Ser Leu
            115                 120                 125 ctt act acc gaa ttt cct tct gtt aga tta ttg ggc ggt atg att aat      432
Leu Thr Thr Glu Phe Pro Ser Val Arg Leu Leu Gly Gly Met Ile Asn
130                 135                 140 aag caa caa cgt tat att tat tct gaa act aca ctt gaa act atc agg      480
Lys Gln Gln Arg Tyr Ile Tyr Ser Glu Thr Thr Leu Glu Thr Ile Arg
145                 150                 155                 160 aga att cgt ttt aat act gct ttt ata ggt ggt tct aaa gtt gat act      528
Arg Ile Arg Phe Asn Thr Ala Phe Ile Gly Gly Ser Lys Val Asp Thr
                165                 170                 175 gat ggt gtt tat aca act tca atg gca gat gcc gaa gtt gta cgt gca      576
Asp Gly Val Tyr Thr Thr Ser Met Ala Asp Ala Glu Val Val Arg Ala
            180                 185                 190 gca atc aat cga gcc aat caa att gta tta gtt gct gaa aag tat aaa      624
Ala Ile Asn Arg Ala Asn Gln Ile Val Leu Val Ala Glu Lys Tyr Lys
        195                 200                 205 ttc acg aat caa att act tct cca tat atg tca att ccg ttg gat aaa      672
Phe Thr Asn Gln Ile Thr Ser Pro Tyr Met Ser Ile Pro Leu Asp Lys
210                 215                 220 gtt gat gtc tta atc act gac gca cct tta tct gat gaa att aaa cag      720
Val Asp Val Leu Ile Thr Asp Ala Pro Leu Ser Asp Glu Ile Lys Gln
225                 230                 235                 240 cat ttt aat tct aaa gca caa att atc cca gtt cta aag gag              762
His Phe Asn Ser Lys Ala Gln Ile Ile Pro Val Leu Lys Glu
                245                 250

<210> SEQ ID NO 40
<211> LENGTH: 254
<212> TYPE: PRT
<213> ORGANISM: Lactobacillus acidophilus

<400> SEQUENCE: 40

Met Ile Gln Glu Glu Arg Leu Ile Gln Ile Lys His Leu Leu Lys Lys
 1               5                  10                  15

Glu His Gln Val Ser Thr Lys Glu Ile Ala Gln Lys Phe Gly Val Ser
            20                  25                  30

Phe Asp Thr Ala Arg Arg Asp Val Ile His Leu Thr Thr Thr Gly Gln
        35                  40                  45

Ala Val Arg Ile His Gly Gly Met Met Glu Ile Asn Gln Asn Asp Val
 50                  55                  60

Pro Asn Phe Leu Ala Arg Asn Gln Val Gln Ser Pro Val Lys Leu Lys
 65                  70                  75                  80
```

```
Met Ala Gln Met Ala Lys Arg Phe Val His Pro Gly Gln Cys Asp Phe
                85                  90                  95

Ile Gly Pro Ser Thr Ile Leu Lys Gln Leu Cys Pro Met Leu Asn Gly
            100                 105                 110

Ile Asn Met Gln Ile Val Thr Asn Ser Ile Asp Asn Ala Leu Ser Leu
        115                 120                 125

Leu Thr Thr Glu Phe Pro Ser Val Arg Leu Leu Gly Gly Met Ile Asn
    130                 135                 140

Lys Gln Gln Arg Tyr Ile Tyr Ser Glu Thr Thr Leu Glu Thr Ile Arg
145                 150                 155                 160

Arg Ile Arg Phe Asn Thr Ala Phe Ile Gly Gly Ser Lys Val Asp Thr
                165                 170                 175

Asp Gly Val Tyr Thr Thr Ser Met Ala Asp Ala Glu Val Val Arg Ala
            180                 185                 190

Ala Ile Asn Arg Ala Asn Gln Ile Val Leu Val Ala Glu Lys Tyr Lys
        195                 200                 205

Phe Thr Asn Gln Ile Thr Ser Pro Tyr Met Ser Ile Pro Leu Asp Lys
    210                 215                 220

Val Asp Val Leu Ile Thr Asp Ala Pro Leu Ser Asp Glu Ile Lys Gln
225                 230                 235                 240

His Phe Asn Ser Lys Ala Gln Ile Ile Pro Val Leu Lys Glu
                245                 250

<210> SEQ ID NO 41
<211> LENGTH: 2415
<212> TYPE: DNA
<213> ORGANISM: Lactobacillus acidophilus
<220> FEATURE:
<221> NAME/KEY: CDS
<222> LOCATION: (1)..(2415)
<223> OTHER INFORMATION: Transketolase ORF# 600

<400> SEQUENCE: 41 gtg ctc aaa gga gaa aaa atg aca gtt aat tac gat tcc aaa gat tac      48
Val Leu Lys Gly Glu Lys Met Thr Val Asn Tyr Asp Ser Lys Asp Tyr
1               5                   10                  15 tta aag agc gtt gac gca tat tgg cgt gca gct aat tat ttg tca gtt      96
Leu Lys Ser Val Asp Ala Tyr Trp Arg Ala Ala Asn Tyr Leu Ser Val
            20                  25                  30 gga caa tta ttt tta atg aaa aat ccg ttg tta aag aaa cct tta aca     144
Gly Gln Leu Phe Leu Met Lys Asn Pro Leu Leu Lys Lys Pro Leu Thr
        35                  40                  45 gct gaa gat gta aaa cct aag cca atc ggt cac tgg ggt act att gct     192
Ala Glu Asp Val Lys Pro Lys Pro Ile Gly His Trp Gly Thr Ile Ala
    50                  55                  60 cca caa aac ttt att tat gct cac tta aat cgt gcg ctt aaa aaa tat     240
Pro Gln Asn Phe Ile Tyr Ala His Leu Asn Arg Ala Leu Lys Lys Tyr
65                  70                  75                  80 gac ttg gat atg ttc tat att gaa ggt tca ggt cac ggt ggc caa gtg     288
Asp Leu Asp Met Phe Tyr Ile Glu Gly Ser Gly His Gly Gly Gln Val
                85                  90                  95 atg gtt tca aat tca tat ctt gat ggt tca tat act gaa cgt tat cca     336
Met Val Ser Asn Ser Tyr Leu Asp Gly Ser Tyr Thr Glu Arg Tyr Pro
            100                 105                 110 gaa att acc caa gat gaa aag ggt atg gct aaa ttg ttt aag cgc ttt     384
Glu Ile Thr Gln Asp Glu Lys Gly Met Ala Lys Leu Phe Lys Arg Phe
        115                 120                 125 agt ttc cca ggt ggt gta gct tct cac gct gct cct gaa act cca ggt     432
```

```
                Ser Phe Pro Gly Gly Val Ala Ser His Ala Ala Pro Glu Thr Pro Gly
                    130                 135                 140 tct att cat gaa ggt ggg gaa tta gga tac gca ctt tca cat ggg gta    480
Ser Ile His Glu Gly Gly Glu Leu Gly Tyr Ala Leu Ser His Gly Val
145                 150                 155                 160 ggt gct att tta gac aat cca gat gta att gct gcc gtt gaa att ggt    528
Gly Ala Ile Leu Asp Asn Pro Asp Val Ile Ala Ala Val Glu Ile Gly
                    165                 170                 175 gat ggt gaa gca gaa act ggt cca ctt gca gct agc tgg ttc agt gac    576
Asp Gly Glu Ala Glu Thr Gly Pro Leu Ala Ala Ser Trp Phe Ser Asp
                180                 185                 190 aag ttt att aat cca att aag gat ggt gca gtt tta cca att ctt caa    624
Lys Phe Ile Asn Pro Ile Lys Asp Gly Ala Val Leu Pro Ile Leu Gln
            195                 200                 205 att aat ggt ttc aag att tct aac cca act atc gtt tca aga atg agc    672
Ile Asn Gly Phe Lys Ile Ser Asn Pro Thr Ile Val Ser Arg Met Ser
        210                 215                 220 gat gaa gaa tta act gaa tac ttc cgt ggc atg ggt tgg gat ccg cac    720
Asp Glu Glu Leu Thr Glu Tyr Phe Arg Gly Met Gly Trp Asp Pro His
225                 230                 235                 240 ttt gtt tca gta ttt aag ggt ggc cgc ttt gac ggt gaa aag gat cca    768
Phe Val Ser Val Phe Lys Gly Gly Arg Phe Asp Gly Glu Lys Asp Pro
                245                 250                 255 atg caa gtc cac gaa gaa atg gct aaa acc atg gac gaa gta att gaa    816
Met Gln Val His Glu Glu Met Ala Lys Thr Met Asp Glu Val Ile Glu
                    260                 265                 270 gaa att aag gct att caa aag cat gct cgt gaa aat aat gat gct act    864
Glu Ile Lys Ala Ile Gln Lys His Ala Arg Glu Asn Asn Asp Ala Thr
                275                 280                 285 ttg cca cat tgg cca ttg att atc ttc caa tgt cca aag ggc tgg acc    912
Leu Pro His Trp Pro Leu Ile Ile Phe Gln Cys Pro Lys Gly Trp Thr
            290                 295                 300 ggt cca aag aag gat ctt gac ggc aat cca att gaa aac tca ttt aga    960
Gly Pro Lys Lys Asp Leu Asp Gly Asn Pro Ile Glu Asn Ser Phe Arg
305                 310                 315                 320 gca cac caa att cca att cct gtc tca caa tac gat atg aaa cat gtt    1008
Ala His Gln Ile Pro Ile Pro Val Ser Gln Tyr Asp Met Lys His Val
                325                 330                 335 gat atg ttg act gat tgg ctt gaa agt tat aag cca aac gaa tta ttc    1056
Asp Met Leu Thr Asp Trp Leu Glu Ser Tyr Lys Pro Asn Glu Leu Phe
                    340                 345                 350 aac gaa gat ggt tca cca aag gaa att gtt act gaa aac act gct aag    1104
Asn Glu Asp Gly Ser Pro Lys Glu Ile Val Thr Glu Asn Thr Ala Lys
                355                 360                 365 ggt gat caa cgt atg gca atg aat ccg atc act aat ggt ggt aag gat    1152
Gly Asp Gln Arg Met Ala Met Asn Pro Ile Thr Asn Gly Gly Lys Asp
370                 375                 380 cct aaa cga ttg aac cta cca gat tat cgc aac ttt gca ctt aag ttt    1200
Pro Lys Arg Leu Asn Leu Pro Asp Tyr Arg Asn Phe Ala Leu Lys Phe
385                 390                 395                 400 gac aag cca ggt tca gtt gaa gca caa gac atg gtt gaa tgg gct aaa    1248
Asp Lys Pro Gly Ser Val Glu Ala Gln Asp Met Val Glu Trp Ala Lys
                405                 410                 415 tat tta aac gaa gtt gct aaa ctt aac cca act act ttc cgt ggc ttt    1296
Tyr Leu Asn Glu Val Ala Lys Leu Asn Pro Thr Thr Phe Arg Gly Phe
                    420                 425                 430 ggt cct gat gaa tct aaa tca aac cgt tta ttt aaa ctt tta gat gat    1344
Gly Pro Asp Glu Ser Lys Ser Asn Arg Leu Phe Lys Leu Leu Asp Asp
                435                 440                 445
```

```
                                           -continued caa aag cgt caa tgg gaa cct gaa gtt cat gaa cca aat gat gaa aac    1392
Gln Lys Arg Gln Trp Glu Pro Glu Val His Glu Pro Asn Asp Glu Asn
    450                 455                 460 ttg gca cca agt ggc cgc gtt atc gat tca caa tta tca gaa cac caa    1440
Leu Ala Pro Ser Gly Arg Val Ile Asp Ser Gln Leu Ser Glu His Gln
465                 470                 475                 480 gac gaa ggc ttc ctt gaa ggc tac gtt tta act ggt cgt cac ggc ttc    1488
Asp Glu Gly Phe Leu Glu Gly Tyr Val Leu Thr Gly Arg His Gly Phe
                485                 490                 495 ttt gca acc tac gaa gca ttt ggt cgt gta gta gat tcg atg ctt act    1536
Phe Ala Thr Tyr Glu Ala Phe Gly Arg Val Val Asp Ser Met Leu Thr
            500                 505                 510 caa cat atg aag tgg ctt aga aaa gct aaa gaa caa tat tgg cgt cat    1584
Gln His Met Lys Trp Leu Arg Lys Ala Lys Glu Gln Tyr Trp Arg His
        515                 520                 525 gat tat cca tca ctt aac ttt gtt gct act tca aca gta ttc caa caa    1632
Asp Tyr Pro Ser Leu Asn Phe Val Ala Thr Ser Thr Val Phe Gln Gln
    530                 535                 540 gat cac aat ggt tac act cac caa gat cca ggc att tta act cac tta    1680
Asp His Asn Gly Tyr Thr His Gln Asp Pro Gly Ile Leu Thr His Leu
545                 550                 555                 560 tat gaa aag aat cgt cca gat tta gtt cat gaa tac ttg cca tca gat    1728
Tyr Glu Lys Asn Arg Pro Asp Leu Val His Glu Tyr Leu Pro Ser Asp
                565                 570                 575 act aat act tta ctt gct gta ggt aac aag gca ttt act gat cgt gaa    1776
Thr Asn Thr Leu Leu Ala Val Gly Asn Lys Ala Phe Thr Asp Arg Glu
            580                 585                 590 tgt att aat gtt tta gta act tca aag caa cct cgt cca caa tgg ttc    1824
Cys Ile Asn Val Leu Val Thr Ser Lys Gln Pro Arg Pro Gln Trp Phe
        595                 600                 605 tca att gag gaa gca caa aag tta gtt gat aaa ggt tta agt tac att    1872
Ser Ile Glu Glu Ala Gln Lys Leu Val Asp Lys Gly Leu Ser Tyr Ile
    610                 615                 620 gat tgg gct tca act gat aaa ggt gta aaa cca gat att gtc ttt gct    1920
Asp Trp Ala Ser Thr Asp Lys Gly Val Lys Pro Asp Ile Val Phe Ala
625                 630                 635                 640 tca aca gaa act gaa cca aca att gaa act ttg gca gca att gat att    1968
Ser Thr Glu Thr Glu Pro Thr Ile Glu Thr Leu Ala Ala Ile Asp Ile
                645                 650                 655 ttg cat gac aag ttc cca gat ctt aag att cgc tac att aac gta att    2016
Leu His Asp Lys Phe Pro Asp Leu Lys Ile Arg Tyr Ile Asn Val Ile
            660                 665                 670 gat gtg atg aaa tta atg tca cca aag gac aat aag aat ggt att tct    2064
Asp Val Met Lys Leu Met Ser Pro Lys Asp Asn Lys Asn Gly Ile Ser
        675                 680                 685 gat gaa gaa ttt gat cgc tta ttc cca aag gac gtt cct gta atc ttt    2112
Asp Glu Glu Phe Asp Arg Leu Phe Pro Lys Asp Val Pro Val Ile Phe
    690                 695                 700 gca tgg cac ggc tac aag agt atg atg gaa tca att tgg ttt gca cgt    2160
Ala Trp His Gly Tyr Lys Ser Met Met Glu Ser Ile Trp Phe Ala Arg
705                 710                 715                 720 aac cgt cat aat gta cat att cac tgc tac gaa gaa aac ggt gat att    2208
Asn Arg His Asn Val His Ile His Cys Tyr Glu Glu Asn Gly Asp Ile
                725                 730                 735 act acc cca ttt gat atg cgt gtt ttg aac cac ctt gac aga ttt gat    2256
Thr Thr Pro Phe Asp Met Arg Val Leu Asn His Leu Asp Arg Phe Asp
            740                 745                 750 ctt gcc aaa gat gct gtt gaa agt gtt gat aaa ttg aag ggc aag aac    2304
Leu Ala Lys Asp Ala Val Glu Ser Val Asp Lys Leu Lys Gly Lys Asn
        755                 760                 765
```

```
gct gac ttt atc agt cat atg gat gac ttg ctt gaa aag cac cac caa      2352
Ala Asp Phe Ile Ser His Met Asp Asp Leu Leu Glu Lys His His Gln
770                 775                 780 tac att cgt gat aat ggt aaa gat atg cca gaa gtt act gaa tgg aag      2400
Tyr Ile Arg Asp Asn Gly Lys Asp Met Pro Glu Val Thr Glu Trp Lys
785                 790                 795                 800 tgg aag ggc ttg aag                                                  2415
Trp Lys Gly Leu Lys
                805

<210> SEQ ID NO 42
<211> LENGTH: 805
<212> TYPE: PRT
<213> ORGANISM: Lactobacillus acidophilus

<400> SEQUENCE: 42
```

| | | | | | | | | | | | | | | |
|---|---|---|---|---|---|---|---|---|---|---|---|---|---|---|
| Val | Leu | Lys | Gly | Glu | Lys | Met | Thr | Val | Asn | Tyr | Asp | Ser | Lys | Asp | Tyr |
| 1 | | | | 5 | | | | | 10 | | | | | 15 | |

Leu Lys Ser Val Asp Ala Tyr Trp Arg Ala Ala Asn Tyr Leu Ser Val
            20                  25                  30

Gly Gln Leu Phe Leu Met Lys Asn Pro Leu Leu Lys Lys Pro Leu Thr
            35                  40                  45

Ala Glu Asp Val Lys Pro Lys Pro Ile Gly His Trp Gly Thr Ile Ala
50                  55                  60

Pro Gln Asn Phe Ile Tyr Ala His Leu Asn Arg Ala Leu Lys Lys Tyr
65                  70                  75                  80

Asp Leu Asp Met Phe Tyr Ile Glu Gly Ser Gly His Gly Gly Gln Val
                85                  90                  95

Met Val Ser Asn Ser Tyr Leu Asp Gly Ser Tyr Thr Glu Arg Tyr Pro
            100                 105                 110

Glu Ile Thr Gln Asp Glu Lys Gly Met Ala Lys Leu Phe Lys Arg Phe
            115                 120                 125

Ser Phe Pro Gly Gly Val Ala Ser His Ala Ala Pro Glu Thr Pro Gly
130                 135                 140

Ser Ile His Glu Gly Gly Glu Leu Gly Tyr Ala Leu Ser His Gly Val
145                 150                 155                 160

Gly Ala Ile Leu Asp Asn Pro Asp Val Ile Ala Ala Val Glu Ile Gly
                165                 170                 175

Asp Gly Glu Ala Glu Thr Gly Pro Leu Ala Ala Ser Trp Phe Ser Asp
            180                 185                 190

Lys Phe Ile Asn Pro Ile Lys Asp Gly Ala Val Leu Pro Ile Leu Gln
            195                 200                 205

Ile Asn Gly Phe Lys Ile Ser Asn Pro Thr Ile Val Ser Arg Met Ser
210                 215                 220

Asp Glu Glu Leu Thr Glu Tyr Phe Arg Gly Met Gly Trp Asp Pro His
225                 230                 235                 240

Phe Val Ser Val Phe Lys Gly Gly Arg Phe Asp Gly Glu Lys Asp Pro
                245                 250                 255

Met Gln Val His Glu Glu Met Ala Lys Thr Met Asp Glu Val Ile Glu
            260                 265                 270

Glu Ile Lys Ala Ile Gln Lys His Ala Arg Glu Asn Asn Asp Ala Thr
            275                 280                 285

Leu Pro His Trp Pro Leu Ile Ile Phe Gln Cys Pro Lys Gly Trp Thr
290                 295                 300

Gly Pro Lys Lys Asp Leu Asp Gly Asn Pro Ile Glu Asn Ser Phe Arg

-continued

```
            305                 310                 315                 320
        Ala His Gln Ile Pro Ile Pro Val Ser Gln Tyr Asp Met Lys His Val
                        325                 330                 335

Asp Met Leu Thr Asp Trp Leu Glu Ser Tyr Lys Pro Asn Glu Leu Phe
                        340                 345                 350

Asn Glu Asp Gly Ser Pro Lys Glu Ile Val Thr Glu Asn Thr Ala Lys
                        355                 360                 365

Gly Asp Gln Arg Met Ala Met Asn Pro Ile Thr Asn Gly Gly Lys Asp
                        370                 375                 380

Pro Lys Arg Leu Asn Leu Pro Asp Tyr Arg Asn Phe Ala Leu Lys Phe
        385                 390                 395                 400

Asp Lys Pro Gly Ser Val Glu Ala Gln Asp Met Val Glu Trp Ala Lys
                        405                 410                 415

Tyr Leu Asn Glu Val Ala Lys Leu Asn Pro Thr Thr Phe Arg Gly Phe
                        420                 425                 430

Gly Pro Asp Glu Ser Lys Ser Asn Arg Leu Phe Lys Leu Leu Asp Asp
                        435                 440                 445

Gln Lys Arg Gln Trp Glu Pro Glu Val His Glu Pro Asn Asp Glu Asn
                        450                 455                 460

Leu Ala Pro Ser Gly Arg Val Ile Asp Ser Gln Leu Ser Glu His Gln
        465                 470                 475                 480

Asp Glu Gly Phe Leu Glu Gly Tyr Val Leu Thr Gly Arg His Gly Phe
                        485                 490                 495

Phe Ala Thr Tyr Glu Ala Phe Gly Arg Val Val Asp Ser Met Leu Thr
                        500                 505                 510

Gln His Met Lys Trp Leu Arg Lys Ala Lys Glu Gln Tyr Trp Arg His
                        515                 520                 525

Asp Tyr Pro Ser Leu Asn Phe Val Ala Thr Ser Thr Val Phe Gln Gln
                        530                 535                 540

Asp His Asn Gly Tyr Thr His Gln Asp Pro Gly Ile Leu Thr His Leu
        545                 550                 555                 560

Tyr Glu Lys Asn Arg Pro Asp Leu Val His Glu Tyr Leu Pro Ser Asp
                        565                 570                 575

Thr Asn Thr Leu Leu Ala Val Gly Asn Lys Ala Phe Thr Asp Arg Glu
                        580                 585                 590

Cys Ile Asn Val Leu Val Thr Ser Lys Gln Pro Arg Pro Gln Trp Phe
                        595                 600                 605

Ser Ile Glu Glu Ala Gln Lys Leu Val Asp Lys Gly Leu Ser Tyr Ile
                        610                 615                 620

Asp Trp Ala Ser Thr Asp Lys Gly Val Lys Pro Asp Ile Val Phe Ala
        625                 630                 635                 640

Ser Thr Glu Thr Glu Pro Thr Ile Glu Thr Leu Ala Ala Ile Asp Ile
                        645                 650                 655

Leu His Asp Lys Phe Pro Asp Leu Lys Ile Arg Tyr Ile Asn Val Ile
                        660                 665                 670

Asp Val Met Lys Leu Met Ser Pro Lys Asp Lys Asn Gly Ile Ser
                        675                 680                 685

Asp Glu Glu Phe Asp Arg Leu Phe Pro Lys Asp Val Pro Val Ile Phe
                        690                 695                 700

Ala Trp His Gly Tyr Lys Ser Met Met Glu Ser Ile Trp Phe Ala Arg
        705                 710                 715                 720

Asn Arg His Asn Val His Ile His Cys Tyr Glu Glu Asn Gly Asp Ile
                        725                 730                 735
```

<210> SEQ ID NO 43
<211> LENGTH: 858
<212> TYPE: DNA
<213> ORGANISM: Lactobacillus acidophilus
<220> FEATURE:
<221> NAME/KEY: CDS
<222> LOCATION: (1)..(858)
<223> OTHER INFORMATION: Serine protease ORF# 601

<400> SEQUENCE: 43

| | | | | | | | | | | | | | | | | |
|---|---|---|---|---|---|---|---|---|---|---|---|---|---|---|---|---|
| Thr | Thr | Pro | Phe | Asp | Met | Arg | Val | Leu | Asn | His | Leu | Asp | Arg | Phe | Asp | |
| | | | 740 | | | | | 745 | | | | 750 | | | | |
| Leu | Ala | Lys | Asp | Ala | Val | Glu | Ser | Val | Asp | Lys | Leu | Lys | Gly | Lys | Asn | |
| | | 755 | | | | | 760 | | | | | 765 | | | | |
| Ala | Asp | Phe | Ile | Ser | His | Met | Asp | Asp | Leu | Leu | Glu | Lys | His | His | Gln | |
| | 770 | | | | | 775 | | | | | 780 | | | | | |
| Tyr | Ile | Arg | Asp | Asn | Gly | Lys | Asp | Met | Pro | Glu | Val | Thr | Glu | Trp | Lys | |
| 785 | | | | | 790 | | | | | 795 | | | | | 800 | |
| Trp | Lys | Gly | Leu | Lys | | | | | | | | | | | | |
| | | | | 805 | | | | | | | | | | | | |

```
ttg gag gaa aaa atg aaa act ggg tta gtg tta gaa ggc ggt gca atg      48
Leu Glu Glu Lys Met Lys Thr Gly Leu Val Leu Glu Gly Gly Ala Met
1               5                   10                  15 cgt gga tta ttt acc gct ggt gtg atc gat gtc tta atg gaa aac aag      96
Arg Gly Leu Phe Thr Ala Gly Val Ile Asp Val Leu Met Glu Asn Lys
                20                  25                  30 att aat ttt gat gta gca att gga gtt tcc gct gga gct gct ttt ggc     144
Ile Asn Phe Asp Val Ala Ile Gly Val Ser Ala Gly Ala Ala Phe Gly
            35                  40                  45 gtt aat ctg aaa tcc aaa caa att ggc cga gtt ctg cgt tat aat tta     192
Val Asn Leu Lys Ser Lys Gln Ile Gly Arg Val Leu Arg Tyr Asn Leu
        50                  55                  60 cgt ttt gca ggt aaa tct tat tat gca agt tgg aag tca tgg cgt aga     240
Arg Phe Ala Gly Lys Ser Tyr Tyr Ala Ser Trp Lys Ser Trp Arg Arg
65                  70                  75                  80 tct ggt aat ttg tat gct gct aat ttt tgc tat cat att ttg cca gat     288
Ser Gly Asn Leu Tyr Ala Ala Asn Phe Cys Tyr His Ile Leu Pro Asp
                85                  90                  95 aag tta gat att ttt gat aaa gaa act ttt atg gct aat cca atg cga     336
Lys Leu Asp Ile Phe Asp Lys Glu Thr Phe Met Ala Asn Pro Met Arg
                100                 105                 110 ttc tgt tgt gta gcg act gat gct gca acg gga gag cct gtt tat cat     384
Phe Cys Cys Val Ala Thr Asp Ala Ala Thr Gly Glu Pro Val Tyr His
            115                 120                 125 gag ttg tac gat gct ggg tat gta gat tta gag tgg att agg gca tcc     432
Glu Leu Tyr Asp Ala Gly Tyr Val Asp Leu Glu Trp Ile Arg Ala Ser
        130                 135                 140 tct tca att cca ttt ttt gct cat cct gtt gct att ggt ggc cat tat     480
Ser Ser Ile Pro Phe Phe Ala His Pro Val Ala Ile Gly Gly His Tyr
145                 150                 155                 160 tat ttt gac ggc gga gtt tct gat tct att cca tat gat ttt ttg ata     528
Tyr Phe Asp Gly Gly Val Ser Asp Ser Ile Pro Tyr Asp Phe Leu Ile
                165                 170                 175 aag aac ggt gtt tct aaa agg gta gta att aca acg caa cct aaa gaa     576
Lys Asn Gly Val Ser Lys Arg Val Val Ile Thr Thr Gln Pro Lys Glu
                180                 185                 190 tat cgt aaa aag caa agt aag cta tat cca att gaa aaa att gta cta     624
Tyr Arg Lys Lys Gln Ser Lys Leu Tyr Pro Ile Glu Lys Ile Val Leu
            195                 200                 205
```

```
cgt gaa tat cct gct gtt tta aag aaa tta gct act aga gca gaa gat      672
Arg Glu Tyr Pro Ala Val Leu Lys Lys Leu Ala Thr Arg Ala Glu Asp
    210                 215                 220 tat aat gcg gtt tta gat aag atg gaa gaa gat gaa aat cag ggg aat      720
Tyr Asn Ala Val Leu Asp Lys Met Glu Glu Asp Glu Asn Gln Gly Asn
225                 230                 235                 240 gca ttt att att cgt ccg cca tat ccg cta gaa att ggt act gtt gaa      768
Ala Phe Ile Ile Arg Pro Pro Tyr Pro Leu Glu Ile Gly Thr Val Glu
                245                 250                 255 caa aat aaa gaa gag att aaa cgg gta tat gag atc gga cga aaa aag      816
Gln Asn Lys Glu Glu Ile Lys Arg Val Tyr Glu Ile Gly Arg Lys Lys
            260                 265                 270 gca gaa gaa att ctg cca gat ttg gtt gaa tat ttg aaa gac              858
Ala Glu Glu Ile Leu Pro Asp Leu Val Glu Tyr Leu Lys Asp
        275                 280                 285

<210> SEQ ID NO 44
<211> LENGTH: 286
<212> TYPE: PRT
<213> ORGANISM: Lactobacillus acidophilus

<400> SEQUENCE: 44

Leu Glu Glu Lys Met Lys Thr Gly Leu Val Leu Glu Gly Gly Ala Met
1               5                   10                  15

Arg Gly Leu Phe Thr Ala Gly Val Ile Asp Val Leu Met Glu Asn Lys
                20                  25                  30

Ile Asn Phe Asp Val Ala Ile Gly Val Ser Ala Gly Ala Ala Phe Gly
            35                  40                  45

Val Asn Leu Lys Ser Lys Gln Ile Gly Arg Val Leu Arg Tyr Asn Leu
        50                  55                  60

Arg Phe Ala Gly Lys Ser Tyr Tyr Ala Ser Trp Lys Ser Trp Arg Arg
65                  70                  75                  80

Ser Gly Asn Leu Tyr Ala Ala Asn Phe Cys Tyr His Ile Leu Pro Asp
                85                  90                  95

Lys Leu Asp Ile Phe Asp Lys Glu Thr Phe Met Ala Asn Pro Met Arg
            100                 105                 110

Phe Cys Cys Val Ala Thr Asp Ala Ala Thr Gly Glu Pro Val Tyr His
        115                 120                 125

Glu Leu Tyr Asp Ala Gly Tyr Val Asp Leu Glu Trp Ile Arg Ala Ser
    130                 135                 140

Ser Ser Ile Pro Phe Phe Ala His Pro Val Ala Ile Gly Gly His Tyr
145                 150                 155                 160

Tyr Phe Asp Gly Gly Val Ser Asp Ser Ile Pro Tyr Asp Phe Leu Ile
                165                 170                 175

Lys Asn Gly Val Ser Lys Arg Val Ile Thr Thr Gln Pro Lys Glu
            180                 185                 190

Tyr Arg Lys Lys Gln Ser Lys Leu Tyr Pro Ile Glu Lys Ile Val Leu
        195                 200                 205

Arg Glu Tyr Pro Ala Val Leu Lys Lys Leu Ala Thr Arg Ala Glu Asp
    210                 215                 220

Tyr Asn Ala Val Leu Asp Lys Met Glu Glu Asp Glu Asn Gln Gly Asn
225                 230                 235                 240

Ala Phe Ile Ile Arg Pro Pro Tyr Pro Leu Glu Ile Gly Thr Val Glu
                245                 250                 255

Gln Asn Lys Glu Glu Ile Lys Arg Val Tyr Glu Ile Gly Arg Lys Lys
            260                 265                 270
```

```
Ala Glu Glu Ile Leu Pro Asp Leu Val Glu Tyr Leu Lys Asp
        275                 280                 285

<210> SEQ ID NO 45
<211> LENGTH: 1206
<212> TYPE: DNA
<213> ORGANISM: Lactobacillus acidophilus
<220> FEATURE:
<221> NAME/KEY: CDS
<222> LOCATION: (1)..(1206)
<223> OTHER INFORMATION: PlnI ORF# 604

<400> SEQUENCE: 45 gtg aag caa aga aaa atg aac tta aaa aag tgg gat ttt gga ttt agg      48
Val Lys Gln Arg Lys Met Asn Leu Lys Lys Trp Asp Phe Gly Phe Arg
1               5                   10                  15 tat gaa act gcc atc gtt atc cta gtt tgg tgg gga atg gca atc ttt     96
Tyr Glu Thr Ala Ile Val Ile Leu Val Trp Trp Gly Met Ala Ile Phe
                20                  25                  30 aat att agt aaa gga aaa tca gct aca gca gga tta tgt att gca gct    144
Asn Ile Ser Lys Gly Lys Ser Ala Thr Ala Gly Leu Cys Ile Ala Ala
            35                  40                  45 agt gtt ttg cca gta ctt gtc ttt gtg ttt gat tta ctc aag cgg cat    192
Ser Val Leu Pro Val Leu Val Phe Val Phe Asp Leu Leu Lys Arg His
        50                  55                  60 tca gac aaa tgg aca gtg gca gca aat tgg ctg gca att gta tta atg    240
Ser Asp Lys Trp Thr Val Ala Ala Asn Trp Leu Ala Ile Val Leu Met
65                  70                  75                  80 cca gca att ttg tcg att acg tgg tac ata ctt ttt aga aat att ttg    288
Pro Ala Ile Leu Ser Ile Thr Trp Tyr Ile Leu Phe Arg Asn Ile Leu
                85                  90                  95 cag cat gtc att ttt aaa atg ttc att acg atc gtt ttt agt tta att    336
Gln His Val Ile Phe Lys Met Phe Ile Thr Ile Val Phe Ser Leu Ile
                100                 105                 110 tta ctg gtg atg gac tta ccg gtt gca gtt gta gca att gga caa ttg    384
Leu Leu Val Met Asp Leu Pro Val Ala Val Val Ala Ile Gly Gln Leu
            115                 120                 125 aga aat tgg ctt gga cga tta att gca gta tgt tat ttc aac atg gta    432
Arg Asn Trp Leu Gly Arg Leu Ile Ala Val Cys Tyr Phe Asn Met Val
        130                 135                 140 ctt tta tca tct act gta att gaa tta aag ccc cag gga att aat gtt    480
Leu Leu Ser Ser Thr Val Ile Glu Leu Lys Pro Gln Gly Ile Asn Val
145                 150                 155                 160 tta att act tca ggc tta atg gca gca atc gct acc ttt tta gct gca    528
Leu Ile Thr Ser Gly Leu Met Ala Ala Ile Ala Thr Phe Leu Ala Ala
                165                 170                 175 ata tta att gca aaa agg tgg agc ttt agt ttt aat ccc gat ttg aaa    576
Ile Leu Ile Ala Lys Arg Trp Ser Phe Ser Phe Asn Pro Asp Leu Lys
            180                 185                 190 tgg cag ggg tca aac gta act tta att tgg ttg gta cta ttt tgt ctt    624
Trp Gln Gly Ser Asn Val Thr Leu Ile Trp Leu Val Leu Phe Cys Leu
        195                 200                 205 att ttc gcc ttc tgg gca gaa ttt tgc ggt caa gga aat agt cta gga    672
Ile Phe Ala Phe Trp Ala Glu Phe Cys Gly Gln Gly Asn Ser Leu Gly
        210                 215                 220 gaa att tta tta aaa cca gat ctt gct ccg cta aaa cca act tgg gtg    720
Glu Ile Leu Leu Lys Pro Asp Leu Ala Pro Leu Lys Pro Thr Trp Val
225                 230                 235                 240 tca ttt tgt aga gca ata gaa gca ggg gtc ttt gag gaa act aac cgc    768
Ser Phe Cys Arg Ala Ile Glu Ala Gly Val Phe Glu Glu Thr Asn Arg
                245                 250                 255
```

| | | | | | | | | | | | | | | | | |
|---|---|---|---|---|---|---|---|---|---|---|---|---|---|---|---|---|
| tat | tta | acg | att | tta | gct | ttg | att | gct | ggt | ttt | gct | tat | agt | aga | tat | 816 |
| Tyr | Leu | Thr | Ile | Leu | Ala | Leu | Ile | Ala | Gly | Phe | Ala | Tyr | Ser | Arg | Tyr | |
| | | 260 | | | | | 265 | | | | | 270 | | | | |
| cgg | gtt | caa | att | gct | ttg | att | gtc | agt | gcc | ata | ttc | ttt | ggt | tta | cta | 864 |
| Arg | Val | Gln | Ile | Ala | Leu | Ile | Val | Ser | Ala | Ile | Phe | Phe | Gly | Leu | Leu | |
| | | | 275 | | | | | 280 | | | | | 285 | | | |
| cat | ttt | act | aat | ttg | ggt | ggt | caa | gct | ttt | gcg | gct | acg | cta | aac | caa | 912 |
| His | Phe | Thr | Asn | Leu | Gly | Gly | Gln | Ala | Phe | Ala | Ala | Thr | Leu | Asn | Gln | |
| | | | | 290 | | | | | 295 | | | | | 300 | | |
| gct | gtc | tat | gcc | gca | gca | ctg | ggc | tta | gtt | ttc | gca | att | atg | tat | tta | 960 |
| Ala | Val | Tyr | Ala | Ala | Ala | Leu | Gly | Leu | Val | Phe | Ala | Ile | Met | Tyr | Leu | |
| 305 | | | | | 310 | | | | | 315 | | | | | 320 | |
| tat | act | ggt | aaa | tta | tgg | cta | gcc | atg | ttg | tat | cac | ttc | ggg | atc | gat | 1008 |
| Tyr | Thr | Gly | Lys | Leu | Trp | Leu | Ala | Met | Leu | Tyr | His | Phe | Gly | Ile | Asp | |
| | | | | 325 | | | | | 330 | | | | | 335 | | |
| ttt | ctt | aat | tat | gca | gtt | aat | ggt | gga | gtt | aaa | gca | cag | gtt | tgg | tct | 1056 |
| Phe | Leu | Asn | Tyr | Ala | Val | Asn | Gly | Gly | Val | Lys | Ala | Gln | Val | Trp | Ser | |
| | | | 340 | | | | | 345 | | | | | 350 | | | |
| ggt | acg | ctt | agt | gat | tgg | gtc | agc | tca | ttt | gta | tta | gtt | ctg | gtg | cca | 1104 |
| Gly | Thr | Leu | Ser | Asp | Trp | Val | Ser | Ser | Phe | Val | Leu | Val | Leu | Val | Pro | |
| | | | 355 | | | | | 360 | | | | | 365 | | | |
| gta | gct | att | gcc | gtc | tgg | atg | atg | aca | ggt | aag | aga | aag | caa | gtt | atg | 1152 |
| Val | Ala | Ile | Ala | Val | Trp | Met | Met | Thr | Gly | Lys | Arg | Lys | Gln | Val | Met | |
| | 370 | | | | | 375 | | | | | 380 | | | | | |
| gat | gaa | aat | att | gat | gaa | aaa | ttg | aaa | acg | aat | gaa | tgg | caa | ata | gga | 1200 |
| Asp | Glu | Asn | Ile | Asp | Glu | Lys | Leu | Lys | Thr | Asn | Glu | Trp | Gln | Ile | Gly | |
| 385 | | | | | 390 | | | | | 395 | | | | | 400 | |
| ctt | agt | | | | | | | | | | | | | | | 1206 |
| Leu | Ser | | | | | | | | | | | | | | | |

<210> SEQ ID NO 46
<211> LENGTH: 402
<212> TYPE: PRT
<213> ORGANISM: Lactobacillus acidophilus

<400> SEQUENCE: 46

Val Lys Gln Arg Lys Met Asn Leu Lys Lys Trp Asp Phe Gly Phe Arg
1               5                   10                  15

Tyr Glu Thr Ala Ile Val Ile Leu Val Trp Trp Gly Met Ala Ile Phe
            20                  25                  30

Asn Ile Ser Lys Gly Lys Ser Ala Thr Ala Gly Leu Cys Ile Ala Ala
        35                  40                  45

Ser Val Leu Pro Val Leu Val Phe Val Phe Asp Leu Leu Lys Arg His
    50                  55                  60

Ser Asp Lys Trp Thr Val Ala Ala Asn Trp Leu Ala Ile Val Leu Met
65                  70                  75                  80

Pro Ala Ile Leu Ser Ile Thr Trp Tyr Ile Leu Phe Arg Asn Ile Leu
                85                  90                  95

Gln His Val Ile Phe Lys Met Phe Ile Thr Ile Val Phe Ser Leu Ile
            100                 105                 110

Leu Leu Val Met Asp Leu Pro Val Ala Val Ala Ile Gly Gln Leu
        115                 120                 125

Arg Asn Trp Leu Gly Arg Leu Ile Ala Val Cys Tyr Phe Asn Met Val
    130                 135                 140

Leu Leu Ser Ser Thr Val Ile Glu Leu Lys Pro Gln Gly Ile Asn Val
145                 150                 155                 160

Leu Ile Thr Ser Gly Leu Met Ala Ala Ile Ala Thr Phe Leu Ala Ala

```
                          165                 170                 175
Ile Leu Ile Ala Lys Arg Trp Ser Phe Ser Phe Asn Pro Asp Leu Lys
            180                 185                 190

Trp Gln Gly Ser Asn Val Thr Leu Ile Trp Leu Val Leu Phe Cys Leu
            195                 200                 205

Ile Phe Ala Phe Trp Ala Glu Phe Cys Gly Gln Gly Asn Ser Leu Gly
            210                 215                 220

Glu Ile Leu Leu Lys Pro Asp Leu Ala Pro Leu Lys Pro Thr Trp Val
225                 230                 235                 240

Ser Phe Cys Arg Ala Ile Glu Ala Gly Val Phe Glu Glu Thr Asn Arg
                245                 250                 255

Tyr Leu Thr Ile Leu Ala Leu Ile Ala Gly Phe Ala Tyr Ser Arg Tyr
                260                 265                 270

Arg Val Gln Ile Ala Leu Ile Val Ser Ala Ile Phe Phe Gly Leu Leu
                275                 280                 285

His Phe Thr Asn Leu Gly Gly Gln Ala Phe Ala Ala Thr Leu Asn Gln
                290                 295                 300

Ala Val Tyr Ala Ala Leu Gly Leu Val Phe Ala Ile Met Tyr Leu
305                 310                 315                 320

Tyr Thr Gly Lys Leu Trp Leu Ala Met Leu Tyr His Phe Gly Ile Asp
                325                 330                 335

Phe Leu Asn Tyr Ala Val Asn Gly Val Lys Ala Gln Val Trp Ser
                340                 345                 350

Gly Thr Leu Ser Asp Trp Val Ser Ser Phe Val Leu Val Leu Val Pro
                355                 360                 365

Val Ala Ile Ala Val Trp Met Met Thr Gly Lys Arg Lys Gln Val Met
                370                 375                 380

Asp Glu Asn Ile Asp Glu Lys Leu Lys Thr Asn Glu Trp Gln Ile Gly
385                 390                 395                 400

Leu Ser
```

<210> SEQ ID NO 47
<211> LENGTH: 690
<212> TYPE: DNA
<213> ORGANISM: Lactobacillus acidophilus
<220> FEATURE:
<221> NAME/KEY: CDS
<222> LOCATION: (1)..(690)
<223> OTHER INFORMATION: Flavodoxin ORF# 1563

<400> SEQUENCE: 47

```
ttg agg ata aga ggg aaa atg aaa att atg tta ggt cgt gtt tat tca     48
Leu Arg Ile Arg Gly Lys Met Lys Ile Met Leu Gly Arg Val Tyr Ser
1               5                   10                  15 gat tta ggt ccc gtt gta gga caa att aat ggt gaa gat att cat gct    96
Asp Leu Gly Pro Val Val Gly Gln Ile Asn Gly Glu Asp Ile His Ala
            20                  25                  30 aac caa cta gaa aga cgt ggt tac gac tgg gag aac ggt tat ggt act   144
Asn Gln Leu Glu Arg Arg Gly Tyr Asp Trp Glu Asn Gly Tyr Gly Thr
        35                  40                  45 cca tcg gat ggg aaa gat acc aac cgt gat ggt caa cca gtt aga aaa   192
Pro Ser Asp Gly Lys Asp Thr Asn Arg Asp Gly Gln Pro Val Arg Lys
    50                  55                  60 tta act aaa gat gcc aaa agt atc att atc ttt tgg tca cgt tct ggt   240
Leu Thr Lys Asp Ala Lys Ser Ile Ile Ile Phe Trp Ser Arg Ser Gly
65                  70                  75                  80 tca act aag tta tta gca agt aaa atc gcg cgt gaa acc ggt gct gat   288
```

-continued

```
Ser Thr Lys Leu Leu Ala Ser Lys Ile Ala Arg Glu Thr Gly Ala Asp
            85                  90                  95 att tta gaa atc act tta aag acg ctt tat cca gca aac tat cgt aaa      336
Ile Leu Glu Ile Thr Leu Lys Thr Leu Tyr Pro Ala Asn Tyr Arg Lys
            100                 105                 110 acg cta agt cgt gct aac cgg gag aga att caa gat gct cca cca gag      384
Thr Leu Ser Arg Ala Asn Arg Glu Arg Ile Gln Asp Ala Pro Pro Glu
            115                 120                 125 ctt gcg atg cag tta ccc gat ttg agc caa tat gac aca att tac tta      432
Leu Ala Met Gln Leu Pro Asp Leu Ser Gln Tyr Asp Thr Ile Tyr Leu
        130                 135                 140 ggt tat caa act tgg gca atg act tta agc cag cca atg aag gca ttt      480
Gly Tyr Gln Thr Trp Ala Met Thr Leu Ser Gln Pro Met Lys Ala Phe
145                 150                 155                 160 tta ctt caa tat ggt ggc gaa ttt tct aat aaa aag att gcc cca ttt      528
Leu Leu Gln Tyr Gly Gly Glu Phe Ser Asn Lys Lys Ile Ala Pro Phe
                165                 170                 175 ctt tct gaa ggt ggc tac ggc aca ggt gat agt atc gaa ttg atc cgt      576
Leu Ser Glu Gly Gly Tyr Gly Thr Gly Asp Ser Ile Glu Leu Ile Arg
                180                 185                 190 gaa att att gct caa aat ggt ggc aaa aat aat act tat act tct gca      624
Glu Ile Ile Ala Gln Asn Gly Gly Lys Asn Asn Thr Tyr Thr Ser Ala
                195                 200                 205 ttg gta gtt gat ggc aat cgt gtt gat gaa agt gat gcg gaa gtt aaa      672
Leu Val Val Asp Gly Asn Arg Val Asp Glu Ser Asp Ala Glu Val Lys
        210                 215                 220 aga tgg ttg aaa aat att                                              690
Arg Trp Leu Lys Asn Ile
225                 230

<210> SEQ ID NO 48
<211> LENGTH: 230
<212> TYPE: PRT
<213> ORGANISM: Lactobacillus acidophilus

<400> SEQUENCE: 48

Leu Arg Ile Arg Gly Lys Met Lys Ile Met Leu Gly Arg Val Tyr Ser
1               5                   10                  15

Asp Leu Gly Pro Val Val Gly Gln Ile Asn Gly Glu Asp Ile His Ala
            20                  25                  30

Asn Gln Leu Glu Arg Arg Gly Tyr Asp Trp Glu Asn Gly Tyr Gly Thr
        35                  40                  45

Pro Ser Asp Gly Lys Asp Thr Asn Arg Asp Gly Gln Pro Val Arg Lys
    50                  55                  60

Leu Thr Lys Asp Ala Lys Ser Ile Ile Phe Trp Ser Arg Ser Gly
65                  70                  75                  80

Ser Thr Lys Leu Leu Ala Ser Lys Ile Ala Arg Glu Thr Gly Ala Asp
            85                  90                  95

Ile Leu Glu Ile Thr Leu Lys Thr Leu Tyr Pro Ala Asn Tyr Arg Lys
            100                 105                 110

Thr Leu Ser Arg Ala Asn Arg Glu Arg Ile Gln Asp Ala Pro Pro Glu
            115                 120                 125

Leu Ala Met Gln Leu Pro Asp Leu Ser Gln Tyr Asp Thr Ile Tyr Leu
        130                 135                 140

Gly Tyr Gln Thr Trp Ala Met Thr Leu Ser Gln Pro Met Lys Ala Phe
145                 150                 155                 160

Leu Leu Gln Tyr Gly Gly Glu Phe Ser Asn Lys Lys Ile Ala Pro Phe
                165                 170                 175
```

```
Leu Ser Glu Gly Gly Tyr Gly Thr Gly Asp Ser Ile Glu Leu Ile Arg
            180                 185                 190

Glu Ile Ile Ala Gln Asn Gly Gly Lys Asn Asn Thr Tyr Thr Ser Ala
        195                 200                 205

Leu Val Val Asp Gly Asn Arg Val Asp Glu Ser Asp Ala Glu Val Lys
    210                 215                 220

Arg Trp Leu Lys Asn Ile
225             230

<210> SEQ ID NO 49
<211> LENGTH: 879
<212> TYPE: DNA
<213> ORGANISM: Lactobacillus acidophilus
<220> FEATURE:
<221> NAME/KEY: CDS
<222> LOCATION: (1)..(879)
<223> OTHER INFORMATION: Hypothetical membrane protein ORF# 1564

<400> SEQUENCE: 49
```

| | | | | | | | | | | | | | | | | |
|---|---|---|---|---|---|---|---|---|---|---|---|---|---|---|---|---|
| atg | atg | ata | aga | att | ata | ctt | gga | gta | att | att | gtt | cta | gct | atc | gtt | 48 |
| Met | Met | Ile | Arg | Ile | Ile | Leu | Gly | Val | Ile | Ile | Val | Leu | Ala | Ile | Val | |
| 1 | | | | 5 | | | | | 10 | | | | | 15 | | |
| tat | att | tgt | tgt | ggt | ttt | aga | att | gta | ccg | caa | aat | aat | gaa | ggt | ttg | 96 |
| Tyr | Ile | Cys | Cys | Gly | Phe | Arg | Ile | Val | Pro | Gln | Asn | Asn | Glu | Gly | Leu | |
| | | | 20 | | | | | 25 | | | | | 30 | | | |
| gtt | gaa | act | tta | ggt | aaa | tat | tct | aag | acg | gtt | aag | gca | ggt | ttt | atc | 144 |
| Val | Glu | Thr | Leu | Gly | Lys | Tyr | Ser | Lys | Thr | Val | Lys | Ala | Gly | Phe | Ile | |
| | | 35 | | | | | 40 | | | | | 45 | | | | |
| ttt | att | tgg | cca | ctt | ttc | caa | aga | ctt | cgt | aaa | gtt | cct | ttg | gca | ctt | 192 |
| Phe | Ile | Trp | Pro | Leu | Phe | Gln | Arg | Leu | Arg | Lys | Val | Pro | Leu | Ala | Leu | |
| | 50 | | | | | 55 | | | | | 60 | | | | | |
| cag | ccc | ctt | gag | att | tct | aaa | tat | tca | att | att | act | aaa | gat | aac | gct | 240 |
| Gln | Pro | Leu | Glu | Ile | Ser | Lys | Tyr | Ser | Ile | Ile | Thr | Lys | Asp | Asn | Ala | |
| 65 | | | | | 70 | | | | | 75 | | | | | 80 | |
| gaa | atc | act | act | agt | ttg | act | ttg | aac | tac | ttg | gtt | act | gat | tct | tac | 288 |
| Glu | Ile | Thr | Thr | Ser | Leu | Thr | Leu | Asn | Tyr | Leu | Val | Thr | Asp | Ser | Tyr | |
| | | | | 85 | | | | | 90 | | | | | 95 | | |
| cgt | tat | ttc | tac | aac | aac | aca | gat | tca | gtt | gaa | tca | atg | gtg | cag | cta | 336 |
| Arg | Tyr | Phe | Tyr | Asn | Asn | Thr | Asp | Ser | Val | Glu | Ser | Met | Val | Gln | Leu | |
| | | | 100 | | | | | 105 | | | | | 110 | | | |
| atc | aga | gga | cat | tta | cgt | gac | att | att | ggt | cga | atg | gat | ctg | aac | tca | 384 |
| Ile | Arg | Gly | His | Leu | Arg | Asp | Ile | Ile | Gly | Arg | Met | Asp | Leu | Asn | Ser | |
| | | 115 | | | | | 120 | | | | | 125 | | | | |
| gct | ctt | ggt | tca | act | aag | gaa | att | aat | gat | caa | tta | ttt | gta | gcg | act | 432 |
| Ala | Leu | Gly | Ser | Thr | Lys | Glu | Ile | Asn | Asp | Gln | Leu | Phe | Val | Ala | Thr | |
| | 130 | | | | | 135 | | | | | 140 | | | | | |
| ggc | gat | tta | act | gac | att | tac | ggt | att | aaa | gtg | gtt | cgt | gtt | aat | gtc | 480 |
| Gly | Asp | Leu | Thr | Asp | Ile | Tyr | Gly | Ile | Lys | Val | Val | Arg | Val | Asn | Val | |
| 145 | | | | | 150 | | | | | 155 | | | | | 160 | |
| gat | gaa | ctt | tta | cct | agt | cct | gaa | att | caa | aga | gcc | atg | gat | aaa | caa | 528 |
| Asp | Glu | Leu | Leu | Pro | Ser | Pro | Glu | Ile | Gln | Arg | Ala | Met | Asp | Lys | Gln | |
| | | | | 165 | | | | | 170 | | | | | 175 | | |
| ttg | acg | gct | gat | cgt | gaa | aag | acc | gcc | gca | att | gcc | aag | gca | gaa | ggt | 576 |
| Leu | Thr | Ala | Asp | Arg | Glu | Lys | Thr | Ala | Ala | Ile | Ala | Lys | Ala | Glu | Gly | |
| | | | 180 | | | | | 185 | | | | | 190 | | | |
| gaa | gca | cgc | acg | att | gaa | atg | act | act | aaa | gct | aag | aat | gac | gct | ttg | 624 |
| Glu | Ala | Arg | Thr | Ile | Glu | Met | Thr | Thr | Lys | Ala | Lys | Asn | Asp | Ala | Leu | |
| | | 195 | | | | | 200 | | | | | 205 | | | | |
| gta | gct | aca | gcc | aag | gcc | aat | gct | gaa | gca | gtg | aag | acc | caa | gct | gat | 672 |
| Val | Ala | Thr | Ala | Lys | Ala | Asn | Ala | Glu | Ala | Val | Lys | Thr | Gln | Ala | Asp | |

```
                   210                 215                 220
gcg gat gcc tac cgt gtg aaa aag atg gaa gaa gct ttg tcc aat gct      720
Ala Asp Ala Tyr Arg Val Lys Lys Met Glu Glu Ala Leu Ser Asn Ala
225                 230                 235                 240 ggt gaa ggg tac ttc aga aat caa agt tta gac agc ttc aat caa tta      768
Gly Glu Gly Tyr Phe Arg Asn Gln Ser Leu Asp Ser Phe Asn Gln Leu
                245                 250                 255 gct caa ggt cct aac aac tta gtt gtt gta ggt aaa gat gaa atg act      816
Ala Gln Gly Pro Asn Asn Leu Val Val Val Gly Lys Asp Glu Met Thr
            260                 265                 270 gat cta ggt aag gtt cca gct ttg aaa aag gtg tgg gat gaa agt ggt      864
Asp Leu Gly Lys Val Pro Ala Leu Lys Lys Val Trp Asp Glu Ser Gly
        275                 280                 285 caa aat gaa gat gaa                                                  879
Gln Asn Glu Asp Glu
    290

<210> SEQ ID NO 50
<211> LENGTH: 293
<212> TYPE: PRT
<213> ORGANISM: Lactobacillus acidophilus

<400> SEQUENCE: 50

Met Met Ile Arg Ile Ile Leu Gly Val Ile Val Leu Ala Ile Val
1               5                   10                  15

Tyr Ile Cys Cys Gly Phe Arg Ile Val Pro Gln Asn Asn Glu Gly Leu
                20                  25                  30

Val Glu Thr Leu Gly Lys Tyr Ser Lys Thr Val Lys Ala Gly Phe Ile
            35                  40                  45

Phe Ile Trp Pro Leu Phe Gln Arg Leu Arg Lys Val Pro Leu Ala Leu
        50                  55                  60

Gln Pro Leu Glu Ile Ser Lys Tyr Ser Ile Ile Thr Lys Asp Asn Ala
65                  70                  75                  80

Glu Ile Thr Thr Ser Leu Thr Leu Asn Tyr Leu Val Thr Asp Ser Tyr
                85                  90                  95

Arg Tyr Phe Tyr Asn Asn Thr Asp Ser Val Glu Ser Met Val Gln Leu
                100                 105                 110

Ile Arg Gly His Leu Arg Asp Ile Ile Gly Arg Met Asp Leu Asn Ser
            115                 120                 125

Ala Leu Gly Ser Thr Lys Glu Ile Asn Asp Gln Leu Phe Val Ala Thr
        130                 135                 140

Gly Asp Leu Thr Asp Ile Tyr Gly Ile Lys Val Val Arg Val Asn Val
145                 150                 155                 160

Asp Glu Leu Leu Pro Ser Pro Glu Ile Gln Arg Ala Met Asp Lys Gln
                165                 170                 175

Leu Thr Ala Asp Arg Glu Lys Thr Ala Ala Ile Ala Lys Ala Glu Gly
            180                 185                 190

Glu Ala Arg Thr Ile Glu Met Thr Thr Lys Ala Lys Asn Asp Ala Leu
        195                 200                 205

Val Ala Thr Ala Lys Ala Asn Ala Glu Ala Val Lys Thr Gln Ala Asp
    210                 215                 220

Ala Asp Ala Tyr Arg Val Lys Lys Met Glu Glu Ala Leu Ser Asn Ala
225                 230                 235                 240

Gly Glu Gly Tyr Phe Arg Asn Gln Ser Leu Asp Ser Phe Asn Gln Leu
                245                 250                 255

Ala Gln Gly Pro Asn Asn Leu Val Val Val Gly Lys Asp Glu Met Thr
```

```
                    260                 265                 270
Asp Leu Gly Lys Val Pro Ala Leu Lys Lys Val Trp Asp Glu Ser Gly
            275                 280                 285

Gln Asn Glu Asp Glu
        290
```

<210> SEQ ID NO 51
<211> LENGTH: 315
<212> TYPE: DNA
<213> ORGANISM: Lactobacillus acidophilus
<220> FEATURE:
<221> NAME/KEY: CDS
<222> LOCATION: (1)..(315)
<223> OTHER INFORMATION: Hypothetical protein ORF# 1565

<400> SEQUENCE: 51

```
atg acg att atg gca gaa aaa aca acg gga ctt tat gtc aga atg aat      48
Met Thr Ile Met Ala Glu Lys Thr Thr Gly Leu Tyr Val Arg Met Asn
1               5                   10                  15 cca gaa aag aag gaa aag gcg gaa gct att ttg aaa aag ctg ggt ttg      96
Pro Glu Lys Lys Glu Lys Ala Glu Ala Ile Leu Lys Lys Leu Gly Leu
            20                  25                  30 aat tcg gct acg gca att aac atg ttt tat gat caa att att ttg cat     144
Asn Ser Ala Thr Ala Ile Asn Met Phe Tyr Asp Gln Ile Ile Leu His
        35                  40                  45 aat ggt att cct ttt aga gtt gag att cca aat gca tgg gat aat ttg     192
Asn Gly Ile Pro Phe Arg Val Glu Ile Pro Asn Ala Trp Asp Asn Leu
    50                  55                  60 gat caa atg aat aag tat gaa tac acc agg ttg ctt gac gaa cgt ctt     240
Asp Gln Met Asn Lys Tyr Glu Tyr Thr Arg Leu Leu Asp Glu Arg Leu
65                  70                  75                  80 aat acg ctt agt gga agg gaa gat ttg tta gga gaa att gcc aag caa     288
Asn Thr Leu Ser Gly Arg Glu Asp Leu Leu Gly Glu Ile Ala Lys Gln
                85                  90                  95 ctt gat gat gac aaa aag aaa gat gaa                                 315
Leu Asp Asp Asp Lys Lys Lys Asp Glu
            100                 105
```

<210> SEQ ID NO 52
<211> LENGTH: 105
<212> TYPE: PRT
<213> ORGANISM: Lactobacillus acidophilus

<400> SEQUENCE: 52

```
Met Thr Ile Met Ala Glu Lys Thr Thr Gly Leu Tyr Val Arg Met Asn
1               5                   10                  15

Pro Glu Lys Lys Glu Lys Ala Glu Ala Ile Leu Lys Lys Leu Gly Leu
            20                  25                  30

Asn Ser Ala Thr Ala Ile Asn Met Phe Tyr Asp Gln Ile Ile Leu His
        35                  40                  45

Asn Gly Ile Pro Phe Arg Val Glu Ile Pro Asn Ala Trp Asp Asn Leu
    50                  55                  60

Asp Gln Met Asn Lys Tyr Glu Tyr Thr Arg Leu Leu Asp Glu Arg Leu
65                  70                  75                  80

Asn Thr Leu Ser Gly Arg Glu Asp Leu Leu Gly Glu Ile Ala Lys Gln
                85                  90                  95

Leu Asp Asp Asp Lys Lys Lys Asp Glu
            100                 105
```

<210> SEQ ID NO 53

<211> LENGTH: 975
<212> TYPE: DNA
<213> ORGANISM: Lactobacillus acidophilus
<220> FEATURE:
<221> NAME/KEY: CDS
<222> LOCATION: (1)..(975)
<223> OTHER INFORMATION: Helveticin ORF# 1566

<400> SEQUENCE: 53

| | | | | | | | | | | | | | | | | |
|---|---|---|---|---|---|---|---|---|---|---|---|---|---|---|---|---|
| atg | gtc | gga | agt | att | aca | cct | aaa | ttg | gtt | tat | cgc | ttg | aat | ggg | atg | 48 |
| Met | Val | Gly | Ser | Ile | Thr | Pro | Lys | Leu | Val | Tyr | Arg | Leu | Asn | Gly | Met | |
| 1 | | | | 5 | | | | | 10 | | | | | 15 | | |
| cac | cat | gta | gta | gca | caa | gtt | ggt | gca | gta | aat | ggt | gat | cat | gtt | ttt | 96 |
| His | His | Val | Val | Ala | Gln | Val | Gly | Ala | Val | Asn | Gly | Asp | His | Val | Phe | |
| | | | 20 | | | | | 25 | | | | | 30 | | | |
| gct | ttg | caa | ctg | ctt | cac | agc | gcg | cat | gat | gta | tta | gtt | tat | aga | aag | 144 |
| Ala | Leu | Gln | Leu | Leu | His | Ser | Ala | His | Asp | Val | Leu | Val | Tyr | Arg | Lys | |
| | | 35 | | | | | 40 | | | | | 45 | | | | |
| cat | aag | gga | ctg | acc | aag | gat | att | aat | tat | act | aat | cct | cac | tta | gta | 192 |
| His | Lys | Gly | Leu | Thr | Lys | Asp | Ile | Asn | Tyr | Thr | Asn | Pro | His | Leu | Val | |
| | 50 | | | | | 55 | | | | | 60 | | | | | |
| atg | acc | ggc | ttt | ggt | cat | aca | caa | acc | tgg | gtt | cca | gca | aat | gat | aac | 240 |
| Met | Thr | Gly | Phe | Gly | His | Thr | Gln | Thr | Trp | Val | Pro | Ala | Asn | Asp | Asn | |
| 65 | | | | | 70 | | | | | 75 | | | | | 80 | |
| gat | gaa | tat | ttc | gtt | ggt | gct | aaa | cct | aat | tct | ggt | aac | tgg | act | aca | 288 |
| Asp | Glu | Tyr | Phe | Val | Gly | Ala | Lys | Pro | Asn | Ser | Gly | Asn | Trp | Thr | Thr | |
| | | | | 85 | | | | | 90 | | | | | 95 | | |
| caa | att | gca | cgt | gta | aaa | tat | cca | aga | tta | ctg | tca | gaa | aat | tat | act | 336 |
| Gln | Ile | Ala | Arg | Val | Lys | Tyr | Pro | Arg | Leu | Leu | Ser | Glu | Asn | Tyr | Thr | |
| | | | 100 | | | | | 105 | | | | | 110 | | | |
| tca | aat | acg | caa | ttg | cca | cgt | ttg | tca | cat | tta | aac | cgt | gta | act | gac | 384 |
| Ser | Asn | Thr | Gln | Leu | Pro | Arg | Leu | Ser | His | Leu | Asn | Arg | Val | Thr | Asp | |
| | | 115 | | | | | 120 | | | | | 125 | | | | |
| gtt | cct | tat | gat | ggt | cac | aat | cat | ttg | cac | aga | gtt | gaa | gct | tca | gtt | 432 |
| Val | Pro | Tyr | Asp | Gly | His | Asn | His | Leu | His | Arg | Val | Glu | Ala | Ser | Val | |
| | 130 | | | | | 135 | | | | | 140 | | | | | |
| tca | cca | aac | ggt | aaa | tat | ttt | atg | att | gct | tca | atc | tgg | aat | aat | ggt | 480 |
| Ser | Pro | Asn | Gly | Lys | Tyr | Phe | Met | Ile | Ala | Ser | Ile | Trp | Asn | Asn | Gly | |
| 145 | | | | | 150 | | | | | 155 | | | | | 160 | |
| tct | ggt | cac | ttt | ggt | ttg | ttt | gat | cta | gat | gaa | gta | aat | caa | aaa | tta | 528 |
| Ser | Gly | His | Phe | Gly | Leu | Phe | Asp | Leu | Asp | Glu | Val | Asn | Gln | Lys | Leu | |
| | | | | 165 | | | | | 170 | | | | | 175 | | |
| gat | gag | aat | ggt | aca | act | aat | aca | cca | att | act | gac | ctt | cac | tgc | tta | 576 |
| Asp | Glu | Asn | Gly | Thr | Thr | Asn | Thr | Pro | Ile | Thr | Asp | Leu | His | Cys | Leu | |
| | | | 180 | | | | | 185 | | | | | 190 | | | |
| agt | gca | ttt | cat | att | gat | aac | ttt | gat | aat | cca | agt | gtt | gct | cct | gat | 624 |
| Ser | Ala | Phe | His | Ile | Asp | Asn | Phe | Asp | Asn | Pro | Ser | Val | Ala | Pro | Asp | |
| | | 195 | | | | | 200 | | | | | 205 | | | | |
| gaa | gaa | gaa | cca | aca | atg | att | gat | tca | gtc | cag | ggt | tat | gct | att | gat | 672 |
| Glu | Glu | Glu | Pro | Thr | Met | Ile | Asp | Ser | Val | Gln | Gly | Tyr | Ala | Ile | Asp | |
| | 210 | | | | | 215 | | | | | 220 | | | | | |
| aat | gac | aag | aat | att | tat | ata | tct | aat | caa | tta | tca | cca | aag | att | aac | 720 |
| Asn | Asp | Lys | Asn | Ile | Tyr | Ile | Ser | Asn | Gln | Leu | Ser | Pro | Lys | Ile | Asn | |
| 225 | | | | | 230 | | | | | 235 | | | | | 240 | |
| cat | gaa | act | ggt | gaa | gta | acc | act | tgg | gca | cgt | aag | att | gtt | aag | ttc | 768 |
| His | Glu | Thr | Gly | Glu | Val | Thr | Thr | Trp | Ala | Arg | Lys | Ile | Val | Lys | Phe | |
| | | | | 245 | | | | | 250 | | | | | 255 | | |
| cca | tgg | ggc | gag | act | gat | agc | aat | aat | tgg | caa | gta | gca | atg | att | gat | 816 |
| Pro | Trp | Gly | Glu | Thr | Asp | Ser | Asn | Asn | Trp | Gln | Val | Ala | Met | Ile | Asp | |
| | | | 260 | | | | | 265 | | | | | 270 | | | |
| ggt | att | gat | tta | cct | gat | cgc | tac | agc | gaa | gta | gaa | agt | att | cat | gtt | 864 |

```
Gly Ile Asp Leu Pro Asp Arg Tyr Ser Glu Val Glu Ser Ile His Val
            275                 280                 285 aat gct ccc gac gat att tat tta aca gtt gct tac cac caa aag att      912
Asn Ala Pro Asp Asp Ile Tyr Leu Thr Val Ala Tyr His Gln Lys Ile
        290                 295                 300 gtg aag ggc gat gaa tat gct tta aga aca ttg gaa aac caa atc ttt      960
Val Lys Gly Asp Glu Tyr Ala Leu Arg Thr Leu Glu Asn Gln Ile Phe
305                 310                 315                 320 cat att gat aat tta                                                  975
His Ile Asp Asn Leu
                325

<210> SEQ ID NO 54
<211> LENGTH: 325
<212> TYPE: PRT
<213> ORGANISM: Lactobacillus acidophilus

<400> SEQUENCE: 54

Met Val Gly Ser Ile Thr Pro Lys Leu Val Tyr Arg Leu Asn Gly Met
1               5                   10                  15

His His Val Val Ala Gln Val Gly Ala Val Asn Gly Asp His Val Phe
            20                  25                  30

Ala Leu Gln Leu Leu His Ser Ala His Asp Val Leu Val Tyr Arg Lys
        35                  40                  45

His Lys Gly Leu Thr Lys Asp Ile Asn Tyr Thr Asn Pro His Leu Val
    50                  55                  60

Met Thr Gly Phe Gly His Thr Gln Thr Trp Val Pro Ala Asn Asp Asn
65                  70                  75                  80

Asp Glu Tyr Phe Val Gly Ala Lys Pro Asn Ser Gly Asn Trp Thr Thr
                85                  90                  95

Gln Ile Ala Arg Val Lys Tyr Pro Arg Leu Leu Ser Glu Asn Tyr Thr
            100                 105                 110

Ser Asn Thr Gln Leu Pro Arg Leu Ser His Leu Asn Arg Val Thr Asp
        115                 120                 125

Val Pro Tyr Asp Gly His Asn His Leu His Arg Val Glu Ala Ser Val
    130                 135                 140

Ser Pro Asn Gly Lys Tyr Phe Met Ile Ala Ser Ile Trp Asn Asn Gly
145                 150                 155                 160

Ser Gly His Phe Gly Leu Phe Asp Leu Asp Glu Val Asn Gln Lys Leu
                165                 170                 175

Asp Glu Asn Gly Thr Thr Asn Thr Pro Ile Thr Asp Leu His Cys Leu
            180                 185                 190

Ser Ala Phe His Ile Asp Asn Phe Asp Asn Pro Ser Val Ala Pro Asp
        195                 200                 205

Glu Glu Glu Pro Thr Met Ile Asp Ser Val Gln Gly Tyr Ala Ile Asp
    210                 215                 220

Asn Asp Lys Asn Ile Tyr Ile Ser Asn Gln Leu Ser Pro Lys Ile Asn
225                 230                 235                 240

His Glu Thr Gly Glu Val Thr Thr Trp Ala Arg Lys Ile Val Lys Phe
                245                 250                 255

Pro Trp Gly Glu Thr Asp Ser Asn Asn Trp Gln Val Ala Met Ile Asp
            260                 265                 270

Gly Ile Asp Leu Pro Asp Arg Tyr Ser Glu Val Glu Ser Ile His Val
        275                 280                 285

Asn Ala Pro Asp Asp Ile Tyr Leu Thr Val Ala Tyr His Gln Lys Ile
    290                 295                 300
```

Val Lys Gly Asp Glu Tyr Ala Leu Arg Thr Leu Glu Asn Gln Ile Phe
305                 310                 315                 320

His Ile Asp Asn Leu
            325

<210> SEQ ID NO 55
<211> LENGTH: 816
<212> TYPE: DNA
<213> ORGANISM: Lactobacillus acidophilus
<220> FEATURE:
<221> NAME/KEY: CDS
<222> LOCATION: (1)..(816)
<223> OTHER INFORMATION: Consensus hypothtical ORF# 595

<400> SEQUENCE: 55

```
atg agt aaa tta ccc ttt aaa gtt gtt gct gtc gat atg gac ggc act        48
Met Ser Lys Leu Pro Phe Lys Val Val Ala Val Asp Met Asp Gly Thr
1               5                   10                  15 ttt atg cgt aac gat caa acc ttt gat cat caa aga ttt aat cgt att        96
Phe Met Arg Asn Asp Gln Thr Phe Asp His Gln Arg Phe Asn Arg Ile
            20                  25                  30 ttg aat caa tta cga gca gac ggc gct cac ttt atc gtt tca agt ggt       144
Leu Asn Gln Leu Arg Ala Asp Gly Ala His Phe Ile Val Ser Ser Gly
        35                  40                  45 cga cct tac act aga ttg cga gaa gac ttt gca gga ttt tta act aga       192
Arg Pro Tyr Thr Arg Leu Arg Glu Asp Phe Ala Gly Phe Leu Thr Arg
    50                  55                  60 att gat atg att gca gat aat ggg tca tta ctc ctc aag gat aat gaa       240
Ile Asp Met Ile Ala Asp Asn Gly Ser Leu Leu Leu Lys Asp Asn Glu
65                  70                  75                  80 att atc agt agc cac ctg ctt act tat caa act act gtt gat cta atc       288
Ile Ile Ser Ser His Leu Leu Thr Tyr Gln Thr Thr Val Asp Leu Ile
                85                  90                  95 aaa ttt gtg caa aag cat tat cct gaa agc tca gtt atc gtc acc ggg       336
Lys Phe Val Gln Lys His Tyr Pro Glu Ser Ser Val Ile Val Thr Gly
            100                 105                 110 gta tat cat tca tat acc acc att gat gca tcc cct gac ttt aag aaa       384
Val Tyr His Ser Tyr Thr Thr Ile Asp Ala Ser Pro Asp Phe Lys Lys
        115                 120                 125 aaa atg agc ttt tac tat cca gaa agc att gaa gtc aac gat ctc tta       432
Lys Met Ser Phe Tyr Tyr Pro Glu Ser Ile Glu Val Asn Asp Leu Leu
    130                 135                 140 gcg gca gtc aca cct gat gat caa att aca aaa atc act tta agt tac       480
Ala Ala Val Thr Pro Asp Asp Gln Ile Thr Lys Ile Thr Leu Ser Tyr
145                 150                 155                 160 cga aaa gac ttt tcg gcg gaa ctt gaa aaa gaa ttt aac aaa cac cac       528
Arg Lys Asp Phe Ser Ala Glu Leu Glu Lys Glu Phe Asn Lys His His
                165                 170                 175 act gaa aaa att cac tgt act tca agt ggt ttc ggc ttg ctt gat att       576
Thr Glu Lys Ile His Cys Thr Ser Ser Gly Phe Gly Leu Leu Asp Ile
            180                 185                 190 gtg cca tac agc gtt aat aaa ggt agt gct tta caa tac ttc cta cgc       624
Val Pro Tyr Ser Val Asn Lys Gly Ser Ala Leu Gln Tyr Phe Leu Arg
        195                 200                 205 tac ttt gac gct aag cct agc gaa tta att gcc ttt ggc gat gga atg       672
Tyr Phe Asp Ala Lys Pro Ser Glu Leu Ile Ala Phe Gly Asp Gly Met
    210                 215                 220 aat gat aaa gaa atg cta gag ctg gct ggc tac agc tac gca atg gaa       720
Asn Asp Lys Glu Met Leu Glu Leu Ala Gly Tyr Ser Tyr Ala Met Glu
225                 230                 235                 240
```

```
aat gct gag cct gca ctc aaa aaa ata gct aaa tat gaa gcc cct tct    768
Asn Ala Glu Pro Ala Leu Lys Lys Ile Ala Lys Tyr Glu Ala Pro Ser
            245                 250                 255 aat aac acc gat ggc gtt ttg gaa gtg cta gat agt tac ttg aat aaa    816
Asn Asn Thr Asp Gly Val Leu Glu Val Leu Asp Ser Tyr Leu Asn Lys
260                 265                 270
```

<210> SEQ ID NO 56
<211> LENGTH: 272
<212> TYPE: PRT
<213> ORGANISM: Lactobacillus acidophilus

<400> SEQUENCE: 56

```
Met Ser Lys Leu Pro Phe Lys Val Val Ala Val Asp Met Asp Gly Thr
1               5                   10                  15

Phe Met Arg Asn Asp Gln Thr Phe Asp His Gln Arg Phe Asn Arg Ile
            20                  25                  30

Leu Asn Gln Leu Arg Ala Asp Gly Ala His Phe Ile Val Ser Ser Gly
        35                  40                  45

Arg Pro Tyr Thr Arg Leu Arg Glu Asp Phe Ala Gly Phe Leu Thr Arg
    50                  55                  60

Ile Asp Met Ile Ala Asp Asn Gly Ser Leu Leu Leu Lys Asp Asn Glu
65                  70                  75                  80

Ile Ile Ser Ser His Leu Leu Thr Tyr Gln Thr Thr Val Asp Leu Ile
                85                  90                  95

Lys Phe Val Gln Lys His Tyr Pro Glu Ser Ser Val Ile Val Thr Gly
            100                 105                 110

Val Tyr His Ser Tyr Thr Thr Ile Asp Ala Ser Pro Asp Phe Lys Lys
        115                 120                 125

Lys Met Ser Phe Tyr Tyr Pro Glu Ser Ile Glu Val Asn Asp Leu Leu
    130                 135                 140

Ala Ala Val Thr Pro Asp Asp Gln Ile Thr Lys Ile Thr Leu Ser Tyr
145                 150                 155                 160

Arg Lys Asp Phe Ser Ala Glu Leu Glu Lys Glu Phe Asn Lys His His
                165                 170                 175

Thr Glu Lys Ile His Cys Thr Ser Ser Gly Phe Gly Leu Leu Asp Ile
            180                 185                 190

Val Pro Tyr Ser Val Asn Lys Gly Ser Ala Leu Gln Tyr Phe Leu Arg
        195                 200                 205

Tyr Phe Asp Ala Lys Pro Ser Glu Leu Ile Ala Phe Gly Asp Gly Met
    210                 215                 220

Asn Asp Lys Glu Met Leu Glu Leu Ala Gly Tyr Ser Tyr Ala Met Glu
225                 230                 235                 240

Asn Ala Glu Pro Ala Leu Lys Lys Ile Ala Lys Tyr Glu Ala Pro Ser
                245                 250                 255

Asn Asn Thr Asp Gly Val Leu Glu Val Leu Asp Ser Tyr Leu Asn Lys
            260                 265                 270
```

<210> SEQ ID NO 57
<211> LENGTH: 438
<212> TYPE: DNA
<213> ORGANISM: Lactobacillus acidophilus
<220> FEATURE:
<221> NAME/KEY: CDS
<222> LOCATION: (1)..(438)
<223> OTHER INFORMATION: Transcriptional regulator ORF# 596

<400> SEQUENCE: 57

```
atg cca aca aaa aaa gaa aaa ttt gct gaa gta aat cgc ttg ctt cgg     48
Met Pro Thr Lys Lys Glu Lys Phe Ala Glu Val Asn Arg Leu Leu Arg
1               5                   10                  15 ctt tac atg att caa aca cag cgt ttc att atg caa caa atc tcc att     96
Leu Tyr Met Ile Gln Thr Gln Arg Phe Ile Met Gln Gln Ile Ser Ile
            20                  25                  30 cta caa gtt aca ccg caa caa gcc cat aca tta gct tat att aaa aag    144
Leu Gln Val Thr Pro Gln Gln Ala His Thr Leu Ala Tyr Ile Lys Lys
        35                  40                  45 cat ccg ggt tta att cag cgt gaa ctt agt gat ttc ttt cat tta cgt    192
His Pro Gly Leu Ile Gln Arg Glu Leu Ser Asp Phe Phe His Leu Arg
    50                  55                  60 aat gct tcg gtt acg aat atg gtg aaa aat tta gag cgt gat gga tta    240
Asn Ala Ser Val Thr Asn Met Val Lys Asn Leu Glu Arg Asp Gly Leu
65              70                  75                  80 att gaa cga aaa att gat cct aag tct gcc agg aat aaa cga att tat    288
Ile Glu Arg Lys Ile Asp Pro Lys Ser Ala Arg Asn Lys Arg Ile Tyr
            85                  90                  95 tta act aaa aaa ggt gaa gaa att gcc caa gat atc gag gat caa atg    336
Leu Thr Lys Lys Gly Glu Glu Ile Ala Gln Asp Ile Glu Asp Gln Met
        100                 105                 110 aat cgt tta aac cag caa att gtt gat aga tta gat gag aaa gat att    384
Asn Arg Leu Asn Gln Gln Ile Val Asp Arg Leu Asp Glu Lys Asp Ile
    115                 120                 125 gat aat ttg ctt act agt ttg gaa aac gtt atc caa agt ctt gat agt    432
Asp Asn Leu Leu Thr Ser Leu Glu Asn Val Ile Gln Ser Leu Asp Ser
130                 135                 140 aaa aat                                                             438
Lys Asn
145

<210> SEQ ID NO 58
<211> LENGTH: 146
<212> TYPE: PRT
<213> ORGANISM: Lactobacillus acidophilus

<400> SEQUENCE: 58

Met Pro Thr Lys Lys Glu Lys Phe Ala Glu Val Asn Arg Leu Leu Arg
1               5                   10                  15

Leu Tyr Met Ile Gln Thr Gln Arg Phe Ile Met Gln Gln Ile Ser Ile
            20                  25                  30

Leu Gln Val Thr Pro Gln Gln Ala His Thr Leu Ala Tyr Ile Lys Lys
        35                  40                  45

His Pro Gly Leu Ile Gln Arg Glu Leu Ser Asp Phe Phe His Leu Arg
    50                  55                  60

Asn Ala Ser Val Thr Asn Met Val Lys Asn Leu Glu Arg Asp Gly Leu
65              70                  75                  80

Ile Glu Arg Lys Ile Asp Pro Lys Ser Ala Arg Asn Lys Arg Ile Tyr
            85                  90                  95

Leu Thr Lys Lys Gly Glu Glu Ile Ala Gln Asp Ile Glu Asp Gln Met
        100                 105                 110

Asn Arg Leu Asn Gln Gln Ile Val Asp Arg Leu Asp Glu Lys Asp Ile
    115                 120                 125

Asp Asn Leu Leu Thr Ser Leu Glu Asn Val Ile Gln Ser Leu Asp Ser
130                 135                 140

Lys Asn
145
```

-continued

```
<210> SEQ ID NO 59
<211> LENGTH: 1770
<212> TYPE: DNA
<213> ORGANISM: Lactobacillus acidophilus
<220> FEATURE:
<221> NAME/KEY: CDS
<222> LOCATION: (1)..(1770)
<223> OTHER INFORMATION: Multidrug resistance ABC transporter ATP
      binding protein ORF# 597

<400> SEQUENCE: 59 ttg gga ggg tat acc atg aac cat gaa gat att tct ata gat aat ggt      48
Leu Gly Gly Tyr Thr Met Asn His Glu Asp Ile Ser Ile Asp Asn Gly
1               5                   10                  15 gct aaa gcg aat aag ttt aaa ttt agc agc ttt ttc aaa tta att aat      96
Ala Lys Ala Asn Lys Phe Lys Phe Ser Ser Phe Phe Lys Leu Ile Asn
            20                  25                  30 agt tta aaa cca cat tat tcc aaa cta att att gga aca att ttg gga     144
Ser Leu Lys Pro His Tyr Ser Lys Leu Ile Ile Gly Thr Ile Leu Gly
        35                  40                  45 ttt att gct aca gct gct aat tta ttt gtt cct caa cta gca cag cgt     192
Phe Ile Ala Thr Ala Ala Asn Leu Phe Val Pro Gln Leu Ala Gln Arg
    50                  55                  60 tta att aat ggc ttt aaa aat ttg agt cct aat ttg att att tta acg     240
Leu Ile Asn Gly Phe Lys Asn Leu Ser Pro Asn Leu Ile Ile Leu Thr
65                  70                  75                  80 att gtt att ttt att ggt gga tta gtt att agt gca cta tca gga ctt     288
Ile Val Ile Phe Ile Gly Gly Leu Val Ile Ser Ala Leu Ser Gly Leu
                85                  90                  95 att tta ggt att ttt ggt gaa gat gtt gtt gct aaa ctg cgc aaa aaa     336
Ile Leu Gly Ile Phe Gly Glu Asp Val Val Ala Lys Leu Arg Lys Lys
            100                 105                 110 tta tgg caa aaa ttg ctc aat atg cct gtt tca tat ttt gat aat act     384
Leu Trp Gln Lys Leu Leu Asn Met Pro Val Ser Tyr Phe Asp Asn Thr
        115                 120                 125 aaa act ggt gag ata agt tcg cgt tta gta aat gat act tca cag gtt     432
Lys Thr Gly Glu Ile Ser Ser Arg Leu Val Asn Asp Thr Ser Gln Val
    130                 135                 140 aaa gaa tta ctt gct tca acc ttg cct aat gca atg act tca att tta     480
Lys Glu Leu Leu Ala Ser Thr Leu Pro Asn Ala Met Thr Ser Ile Leu
145                 150                 155                 160 caa ttt ttt ggt gca ttg att att atg atg gca atg gat tgg cag atg     528
Gln Phe Phe Gly Ala Leu Ile Ile Met Met Ala Met Asp Trp Gln Met
                165                 170                 175 aca tta tta atg ttt att ggt gta cca tta atc gtc tta gct gtt atc     576
Thr Leu Leu Met Phe Ile Gly Val Pro Leu Ile Val Leu Ala Val Ile
            180                 185                 190 cca att atg caa aag tcg cgt agt att ggg cgt aaa cgg caa gat gag     624
Pro Ile Met Gln Lys Ser Arg Ser Ile Gly Arg Lys Arg Gln Asp Glu
        195                 200                 205 ttg gct aat ttt tca agc gat tca acc agt gtt tta agc gaa att cgt     672
Leu Ala Asn Phe Ser Ser Asp Ser Thr Ser Val Leu Ser Glu Ile Arg
    210                 215                 220 ttg gtt aaa tca tct act ggt gaa aaa aaa gaa cta aga gat ggt aat     720
Leu Val Lys Ser Ser Thr Gly Glu Lys Lys Glu Leu Arg Asp Gly Asn
225                 230                 235                 240 cac cgt atc gat aat ctt tat gga att ggt gta aaa gaa gct tgg att     768
His Arg Ile Asp Asn Leu Tyr Gly Ile Gly Val Lys Glu Ala Trp Ile
                245                 250                 255 agt tca ctt act tca cct att act aac atg tta atg atc atg ttc         816
Ser Ser Leu Thr Ser Pro Ile Thr Asn Met Leu Met Met Ile Met Phe
            260                 265                 270
```

| | | |
|---|---|---|
| ttg ggt att tta ggt tat ggc gca att cga gta atg aat ggt tca atg<br>Leu Gly Ile Leu Gly Tyr Gly Ala Ile Arg Val Met Asn Gly Ser Met<br>              275                         280                      285 | | 864 |
| acc atg ggt gca tta gtt tct ttc tta atg tat ctt ttc caa ata atg<br>Thr Met Gly Ala Leu Val Ser Phe Leu Met Tyr Leu Phe Gln Ile Met<br>       290                           295                            300 | | 912 |
| tct cca gta att att att agt caa ttc ttt aat cgc ctt tcc caa act<br>Ser Pro Val Ile Ile Ile Ser Gln Phe Phe Asn Arg Leu Ser Gln Thr<br>305                    310                        315                      320 | | 960 |
| agt ggt tca aca gaa aga atc aac cag att ttg caa gaa gat gag gaa<br>Ser Gly Ser Thr Glu Arg Ile Asn Gln Ile Leu Gln Glu Asp Glu Glu<br>                      325                        330                      335 | | 1008 |
| aca aag act gac aaa aag aag ata gat att gct gat aag act tta aaa<br>Thr Lys Thr Asp Lys Lys Lys Ile Asp Ile Ala Asp Lys Thr Leu Lys<br>       340                           345                            350 | | 1056 |
| ttt gaa gat gtt agt ttt gaa tat gaa aaa gat aag cca att ctt cat<br>Phe Glu Asp Val Ser Phe Glu Tyr Glu Lys Asp Lys Pro Ile Leu His<br>              355                         360                      365 | | 1104 |
| aac gtt aat cta aag gca gaa cct aat act gtt gta gct ttt gct gga<br>Asn Val Asn Leu Lys Ala Glu Pro Asn Thr Val Val Ala Phe Ala Gly<br>370                    375                        380 | | 1152 |
| cca tct ggt ggt ggt aaa tcg act atc ttt tca tta att gaa caa ttt<br>Pro Ser Gly Gly Gly Lys Ser Thr Ile Phe Ser Leu Ile Glu Gln Phe<br>385                    390                        395                      400 | | 1200 |
| tat cag cca act tct ggc aaa att gta att ggt aat act gaa att gat<br>Tyr Gln Pro Thr Ser Gly Lys Ile Val Ile Gly Asn Thr Glu Ile Asp<br>                            405                            410                      415 | | 1248 |
| gat att gat tta agt gat tgg cgt aag caa att ggc ttg gta ggg caa<br>Asp Ile Asp Leu Ser Asp Trp Arg Lys Gln Ile Gly Leu Val Gly Gln<br>                    420                        425                      430 | | 1296 |
| aat tct gcg gta atg cct ggc aca att cgt gaa aat tta gtt tat gga<br>Asn Ser Ala Val Met Pro Gly Thr Ile Arg Glu Asn Leu Val Tyr Gly<br>       435                           440                            445 | | 1344 |
| ttg aat aaa gat gtt acc gag gcc gag cta tgg cgt gtt ttg aaa atg<br>Leu Asn Lys Asp Val Thr Glu Ala Glu Leu Trp Arg Val Leu Lys Met<br>450                    455                        460 | | 1392 |
| gca tat gct gat caa ttt gta aaa gaa atg gat gat gga ctt gat acg<br>Ala Tyr Ala Asp Gln Phe Val Lys Glu Met Asp Asp Gly Leu Asp Thr<br>465                    470                        475                      480 | | 1440 |
| caa att ggt gaa cgt gga att aaa ttg tct gga ggt caa agg caa aga<br>Gln Ile Gly Glu Arg Gly Ile Lys Leu Ser Gly Gly Gln Arg Gln Arg<br>                            485                            490                      495 | | 1488 |
| atc gca att gcg cgt gca ttt tta cgt gat cca aag att tta atg ctt<br>Ile Ala Ile Ala Arg Ala Phe Leu Arg Asp Pro Lys Ile Leu Met Leu<br>                    500                        505                      510 | | 1536 |
| gat gaa gca act gct agc ctt gat tca gaa tct gaa gca atg gta caa<br>Asp Glu Ala Thr Ala Ser Leu Asp Ser Glu Ser Glu Ala Met Val Gln<br>              515                         520                      525 | | 1584 |
| aaa gca ttg aat acc tta atg aag gat aga act act cta gtt att gcg<br>Lys Ala Leu Asn Thr Leu Met Lys Asp Arg Thr Thr Leu Val Ile Ala<br>530                    535                        540 | | 1632 |
| cac aga ttg agt aca att gtt gat gcc gat tgt att tac ttt att gat<br>His Arg Leu Ser Thr Ile Val Asp Ala Asp Cys Ile Tyr Phe Ile Asp<br>545                    550                        555                      560 | | 1680 |
| cac gga aca gtt tca ggc tct gga act cat gaa gaa tta atc aag tca<br>His Gly Thr Val Ser Gly Ser Gly Thr His Glu Glu Leu Ile Lys Ser<br>                            565                            570                      575 | | 1728 |
| aca ccg ctt tat gca caa tat gtt cat aat caa ttt aag aag<br>Thr Pro Leu Tyr Ala Gln Tyr Val His Asn Gln Phe Lys Lys | | 1770 |

-continued

```
              580              585              590

<210> SEQ ID NO 60
<211> LENGTH: 590
<212> TYPE: PRT
<213> ORGANISM: Lactobacillus acidophilus

<400> SEQUENCE: 60

Leu Gly Gly Tyr Thr Met Asn His Glu Asp Ile Ser Ile Asp Asn Gly
1               5                   10                  15

Ala Lys Ala Asn Lys Phe Lys Phe Ser Ser Phe Phe Lys Leu Ile Asn
            20                  25                  30

Ser Leu Lys Pro His Tyr Ser Lys Leu Ile Ile Gly Thr Ile Leu Gly
        35                  40                  45

Phe Ile Ala Thr Ala Ala Asn Leu Phe Val Pro Gln Leu Ala Gln Arg
    50                  55                  60

Leu Ile Asn Gly Phe Lys Asn Leu Ser Pro Asn Leu Ile Ile Leu Thr
65                  70                  75                  80

Ile Val Ile Phe Ile Gly Gly Leu Val Ile Ser Ala Leu Ser Gly Leu
                85                  90                  95

Ile Leu Gly Ile Phe Gly Glu Asp Val Val Ala Lys Leu Arg Lys Lys
            100                 105                 110

Leu Trp Gln Lys Leu Leu Asn Met Pro Val Ser Tyr Phe Asp Asn Thr
        115                 120                 125

Lys Thr Gly Glu Ile Ser Ser Arg Leu Val Asn Asp Thr Ser Gln Val
    130                 135                 140

Lys Glu Leu Leu Ala Ser Thr Leu Pro Asn Ala Met Thr Ser Ile Leu
145                 150                 155                 160

Gln Phe Phe Gly Ala Leu Ile Ile Met Met Ala Met Asp Trp Gln Met
                165                 170                 175

Thr Leu Leu Met Phe Ile Gly Val Pro Leu Ile Val Leu Ala Val Ile
            180                 185                 190

Pro Ile Met Gln Lys Ser Arg Ser Ile Gly Arg Lys Arg Gln Asp Glu
        195                 200                 205

Leu Ala Asn Phe Ser Ser Asp Ser Thr Ser Val Leu Ser Glu Ile Arg
    210                 215                 220

Leu Val Lys Ser Ser Thr Gly Glu Lys Lys Glu Leu Arg Asp Gly Asn
225                 230                 235                 240

His Arg Ile Asp Asn Leu Tyr Gly Ile Gly Val Lys Glu Ala Trp Ile
                245                 250                 255

Ser Ser Leu Thr Ser Pro Ile Thr Asn Met Leu Met Met Ile Met Phe
            260                 265                 270

Leu Gly Ile Leu Gly Tyr Gly Ala Ile Arg Val Met Asn Gly Ser Met
        275                 280                 285

Thr Met Gly Ala Leu Val Ser Phe Leu Met Tyr Leu Phe Gln Ile Met
    290                 295                 300

Ser Pro Val Ile Ile Ile Ser Gln Phe Phe Asn Arg Leu Ser Gln Thr
305                 310                 315                 320

Ser Gly Ser Thr Glu Arg Ile Asn Gln Ile Leu Gln Glu Asp Glu Glu
                325                 330                 335

Thr Lys Thr Asp Lys Lys Ile Asp Ile Ala Asp Lys Thr Leu Lys
            340                 345                 350

Phe Glu Asp Val Ser Phe Glu Tyr Glu Lys Asp Lys Pro Ile Leu His
        355                 360                 365
```

```
Asn Val Asn Leu Lys Ala Glu Pro Asn Thr Val Val Ala Phe Ala Gly
    370                 375                 380

Pro Ser Gly Gly Gly Lys Ser Thr Ile Phe Ser Leu Ile Glu Gln Phe
385                 390                 395                 400

Tyr Gln Pro Thr Ser Gly Lys Ile Val Ile Gly Asn Thr Glu Ile Asp
                405                 410                 415

Asp Ile Asp Leu Ser Asp Trp Arg Lys Gln Ile Gly Leu Val Gly Gln
            420                 425                 430

Asn Ser Ala Val Met Pro Gly Thr Ile Arg Glu Asn Leu Val Tyr Gly
        435                 440                 445

Leu Asn Lys Asp Val Thr Glu Ala Glu Leu Trp Arg Val Leu Lys Met
    450                 455                 460

Ala Tyr Ala Asp Gln Phe Val Lys Glu Met Asp Asp Gly Leu Asp Thr
465                 470                 475                 480

Gln Ile Gly Glu Arg Gly Ile Lys Leu Ser Gly Gly Gln Arg Gln Arg
                485                 490                 495

Ile Ala Ile Ala Arg Ala Phe Leu Arg Asp Pro Lys Ile Leu Met Leu
            500                 505                 510

Asp Glu Ala Thr Ala Ser Leu Asp Ser Glu Ser Glu Ala Met Val Gln
        515                 520                 525

Lys Ala Leu Asn Thr Leu Met Lys Asp Arg Thr Thr Leu Val Ile Ala
    530                 535                 540

His Arg Leu Ser Thr Ile Val Asp Ala Asp Cys Ile Tyr Phe Ile Asp
545                 550                 555                 560

His Gly Thr Val Ser Gly Ser Gly Thr His Glu Leu Ile Lys Ser
                565                 570                 575

Thr Pro Leu Tyr Ala Gln Tyr Val His Asn Gln Phe Lys Lys
            580                 585                 590

<210> SEQ ID NO 61
<211> LENGTH: 363
<212> TYPE: DNA
<213> ORGANISM: Lactobacillus acidophilus
<220> FEATURE:
<221> NAME/KEY: CDS
<222> LOCATION: (1)..(363)
<223> OTHER INFORMATION: Unknown ORF# 598

<400> SEQUENCE: 61 gtg att att atg ttc agc ctt ttt aaa tca cat aca act aat gaa aaa      48
Val Ile Ile Met Phe Ser Leu Phe Lys Ser His Thr Thr Asn Glu Lys
1               5                   10                  15 gaa gta tat caa gaa ctt aaa gaa ttc tat gat agc ttt ttc agt gat      96
Glu Val Tyr Gln Glu Leu Lys Glu Phe Tyr Asp Ser Phe Phe Ser Asp
            20                  25                  30 att tac aat gaa atg aat atc gat cgt tac cgt caa atc aga gat gta     144
Ile Tyr Asn Glu Met Asn Ile Asp Arg Tyr Arg Gln Ile Arg Asp Val
        35                  40                  45 att ggt ctc gtt atc aat aag ttc gat gaa aac gat cat ccc ctt gaa     192
Ile Gly Leu Val Ile Asn Lys Phe Asp Glu Asn Asp His Pro Leu Glu
    50                  55                  60 tat acg agt aaa tta gta atg tac att caa gcc aga gtt gca atg agt     240
Tyr Thr Ser Lys Leu Val Met Tyr Ile Gln Ala Arg Val Ala Met Ser
65                  70                  75                  80 cat tta cac ctt act gat gaa caa gta aaa att atg aga aag tta aca     288
His Leu His Leu Thr Asp Glu Gln Val Lys Ile Met Arg Lys Leu Thr
                85                  90                  95 gaa tct aca aaa tat ata aat ctt tct tat gtt tat ctg agt cca att     336
```

```
Glu Ser Thr Lys Tyr Ile Asn Leu Ser Tyr Val Tyr Leu Ser Pro Ile
            100                 105                 110 gat tca gca gaa caa ttt gtt aag att                                    363
Asp Ser Ala Glu Gln Phe Val Lys Ile
        115                 120

<210> SEQ ID NO 62
<211> LENGTH: 121
<212> TYPE: PRT
<213> ORGANISM: Lactobacillus acidophilus

<400> SEQUENCE: 62

Val Ile Ile Met Phe Ser Leu Phe Lys Ser His Thr Thr Asn Glu Lys
1               5                   10                  15

Glu Val Tyr Gln Glu Leu Lys Glu Phe Tyr Asp Ser Phe Phe Ser Asp
            20                  25                  30

Ile Tyr Asn Glu Met Asn Ile Asp Arg Tyr Arg Gln Ile Arg Asp Val
        35                  40                  45

Ile Gly Leu Val Ile Asn Lys Phe Asp Glu Asn Asp His Pro Leu Glu
    50                  55                  60

Tyr Thr Ser Lys Leu Val Met Tyr Ile Gln Ala Arg Val Ala Met Ser
65                  70                  75                  80

His Leu His Leu Thr Asp Glu Gln Val Lys Ile Met Arg Lys Leu Thr
                85                  90                  95

Glu Ser Thr Lys Tyr Ile Asn Leu Ser Tyr Val Tyr Leu Ser Pro Ile
            100                 105                 110

Asp Ser Ala Glu Gln Phe Val Lys Ile
        115                 120

<210> SEQ ID NO 63
<211> LENGTH: 1530
<212> TYPE: DNA
<213> ORGANISM: Lactobacillus acidophilus
<220> FEATURE:
<221> NAME/KEY: CDS
<222> LOCATION: (1)..(1530)
<223> OTHER INFORMATION: Aminopeptidase ORF# 1567

<400> SEQUENCE: 63 ttg gag gta aaa cgt atg aaa aaa aga aca aca ctt tta tta tca agt     48
Leu Glu Val Lys Arg Met Lys Lys Arg Thr Thr Leu Leu Leu Ser Ser
1               5                   10                  15 gca ata aca att gca gca tta ttt agt ttt aat tca aag gct cag gcc     96
Ala Ile Thr Ile Ala Ala Leu Phe Ser Phe Asn Ser Lys Ala Gln Ala
            20                  25                  30 gct gcc gat ccc gca gtc aaa gca acc aac tac aat atg act gta aaa    144
Ala Ala Asp Pro Ala Val Lys Ala Thr Asn Tyr Asn Met Thr Val Lys
        35                  40                  45 cta aat act cgc aaa aat caa cta acc gaa aaa gtt acc atg cat gtc    192
Leu Asn Thr Arg Lys Asn Gln Leu Thr Glu Lys Val Thr Met His Val
    50                  55                  60 gtt aat aac ggc aat gaa cca gtt aag aac tta ctg atc aga aat att    240
Val Asn Asn Gly Asn Glu Pro Val Lys Asn Leu Leu Ile Arg Asn Ile
65                  70                  75                  80 gct aat ggt gtt tta aag tat gac cat cag cat ttt aaa att gcc aaa    288
Ala Asn Gly Val Leu Lys Tyr Asp His Gln His Phe Lys Ile Ala Lys
                85                  90                  95 aat gca aaa act aca gtt aaa agt att tcc tca gct gga gaa aat ctt    336
Asn Ala Lys Thr Thr Val Lys Ser Ile Ser Ser Ala Gly Glu Asn Leu
            100                 105                 110
```

|   |   |   |   |   |   |   |   |   |   |   |   |   |   |   |   |     |
|---|---|---|---|---|---|---|---|---|---|---|---|---|---|---|---|-----|
| tcc | tat | acc | act | ggc | aaa | gat | aag | agc | aac | cta | ttc | gtt | gat | aaa | agc | 384 |
| Ser | Tyr | Thr | Thr | Gly | Lys | Asp | Lys | Ser | Asn | Leu | Phe | Val | Asp | Lys | Ser |     |
|     |     | 115 |     |     |     | 120 |     |     |     |     | 125 |     |     |     |     |     |

| tta | aat | gca | ggt | gaa | tct | acc | gac | tta | act | gtt | aat | gta | gtc | acc | agc | 432 |
|---|---|---|---|---|---|---|---|---|---|---|---|---|---|---|---|---|
| Leu | Asn | Ala | Gly | Glu | Ser | Thr | Asp | Leu | Thr | Val | Asn | Val | Val | Thr | Ser |     |
|  | 130 |  |  |  |  | 135 |  |  |  |  | 140 |  |  |  |  |  |

| gtt | ccc | aaa | aga | caa | gat | cgt | ttt | ggc | tac | caa | aat | att | aat | ggc | ggt | 480 |
|---|---|---|---|---|---|---|---|---|---|---|---|---|---|---|---|---|
| Val | Pro | Lys | Arg | Gln | Asp | Arg | Phe | Gly | Tyr | Gln | Asn | Ile | Asn | Gly | Gly |  |
| 145 |  |  |  |  | 150 |  |  |  |  | 155 |  |  |  |  | 160 |  |

| aaa | gtt | tat | aac | tta | tcc | ttc | tgt | ttt | cct | tac | cta | agc | gat | tat | cgc | 528 |
|---|---|---|---|---|---|---|---|---|---|---|---|---|---|---|---|---|
| Lys | Val | Tyr | Asn | Leu | Ser | Phe | Cys | Phe | Pro | Tyr | Leu | Ser | Asp | Tyr | Arg |  |
|  |  |  |  |  | 165 |  |  |  |  | 170 |  |  |  |  | 175 |  |

| aac | gga | aaa | tgg | aat | tac | cat | cca | tat | tat | gac | ggt | ggt | gaa | aac | cgt | 576 |
|---|---|---|---|---|---|---|---|---|---|---|---|---|---|---|---|---|
| Asn | Gly | Lys | Trp | Asn | Tyr | His | Pro | Tyr | Tyr | Asp | Gly | Gly | Glu | Asn | Arg |  |
|  |  |  |  | 180 |  |  |  |  | 185 |  |  |  |  | 190 |  |  |

| aat | acc | act | gtc | agc | aat | ttt | cat | gtt | agc | ttt | tat | gca | cca | aag | agt | 624 |
|---|---|---|---|---|---|---|---|---|---|---|---|---|---|---|---|---|
| Asn | Thr | Thr | Val | Ser | Asn | Phe | His | Val | Ser | Phe | Tyr | Ala | Pro | Lys | Ser |  |
|  |  | 195 |  |  |  |  | 200 |  |  |  |  | 205 |  |  |  |  |

| tac | aag | gtt | gct | gct | tca | gga | caa | aat | agc | acc | aaa | aat | ggc | aag | act | 672 |
|---|---|---|---|---|---|---|---|---|---|---|---|---|---|---|---|---|
| Tyr | Lys | Val | Ala | Ala | Ser | Gly | Gln | Asn | Ser | Thr | Lys | Asn | Gly | Lys | Thr |  |
| 210 |  |  |  |  | 215 |  |  |  |  | 220 |  |  |  |  |  |  |

| aca | atc | gtt | gcg | gaa | aat | atg | aga | gat | ttt | gct | atc | gtt | gct | tct | aat | 720 |
|---|---|---|---|---|---|---|---|---|---|---|---|---|---|---|---|---|
| Thr | Ile | Val | Ala | Glu | Asn | Met | Arg | Asp | Phe | Ala | Ile | Val | Ala | Ser | Asn |  |
| 225 |  |  |  |  | 230 |  |  |  |  | 235 |  |  |  |  | 240 |  |

| aaa | ttc | aag | gtt | tct | cat | act | tat | gca | gat | ggt | ata | aga | att | aat | aat | 768 |
|---|---|---|---|---|---|---|---|---|---|---|---|---|---|---|---|---|
| Lys | Phe | Lys | Val | Ser | His | Thr | Tyr | Ala | Asp | Gly | Ile | Arg | Ile | Asn | Asn |  |
|  |  |  |  | 245 |  |  |  |  | 250 |  |  |  |  | 255 |  |  |

| tat | tat | ttt | gcc | ggt | aaa | aat | agt | aag | caa | tat | aac | aaa | ctt | gcc | tta | 816 |
|---|---|---|---|---|---|---|---|---|---|---|---|---|---|---|---|---|
| Tyr | Tyr | Phe | Ala | Gly | Lys | Asn | Ser | Lys | Gln | Tyr | Asn | Lys | Leu | Ala | Leu |  |
|  |  |  | 260 |  |  |  |  | 265 |  |  |  |  | 270 |  |  |  |

| ttg | act | gct | aaa | gat | agt | ttc | aat | att | ttc | acc | aag | aaa | att | ggt | aaa | 864 |
|---|---|---|---|---|---|---|---|---|---|---|---|---|---|---|---|---|
| Leu | Thr | Ala | Lys | Asp | Ser | Phe | Asn | Ile | Phe | Thr | Lys | Lys | Ile | Gly | Lys |  |
|  |  | 275 |  |  |  |  | 280 |  |  |  |  | 285 |  |  |  |  |

| tat | cct | tat | aaa | gaa | atc | gat | atg | act | gaa | ggc | tta | ctt | ggt | aaa | gat | 912 |
|---|---|---|---|---|---|---|---|---|---|---|---|---|---|---|---|---|
| Tyr | Pro | Tyr | Lys | Glu | Ile | Asp | Met | Thr | Glu | Gly | Leu | Leu | Gly | Lys | Asp |  |
| 290 |  |  |  |  | 295 |  |  |  |  | 300 |  |  |  |  |  |  |

| acc | ggt | gga | atg | gaa | tat | cct | agt | tta | att | atg | atc | gat | gcg | agt | ggc | 960 |
|---|---|---|---|---|---|---|---|---|---|---|---|---|---|---|---|---|
| Thr | Gly | Gly | Met | Glu | Tyr | Pro | Ser | Leu | Ile | Met | Ile | Asp | Ala | Ser | Gly |  |
| 305 |  |  |  |  | 310 |  |  |  |  | 315 |  |  |  |  | 320 |  |

| ttt | gta | caa | aag | aaa | cac | cca | atc | aac | aga | tac | aat | gaa | tta | acc | gaa | 1008 |
|---|---|---|---|---|---|---|---|---|---|---|---|---|---|---|---|---|
| Phe | Val | Gln | Lys | Lys | His | Pro | Ile | Asn | Arg | Tyr | Asn | Glu | Leu | Thr | Glu |  |
|  |  |  |  | 325 |  |  |  |  | 330 |  |  |  |  | 335 |  |  |

| gat | gtt | tcc | cat | gaa | att | ggt | cac | caa | tgg | ttc | tac | gct | act | gtt | ggc | 1056 |
|---|---|---|---|---|---|---|---|---|---|---|---|---|---|---|---|---|
| Asp | Val | Ser | His | Glu | Ile | Gly | His | Gln | Trp | Phe | Tyr | Ala | Thr | Val | Gly |  |
|  |  |  | 340 |  |  |  |  | 345 |  |  |  |  | 350 |  |  |  |

| aat | gac | gaa | tac | acc | gag | cca | tgg | ctt | gat | gaa | gga | ctt | act | aat | ttc | 1104 |
|---|---|---|---|---|---|---|---|---|---|---|---|---|---|---|---|---|
| Asn | Asp | Glu | Tyr | Thr | Glu | Pro | Trp | Leu | Asp | Glu | Gly | Leu | Thr | Asn | Phe |  |
|  |  |  |  | 355 |  |  |  |  | 360 |  |  |  |  | 365 |  |  |

| ctt | gaa | aac | agt | gtt | tat | gat | tta | act | tat | act | aag | agt | aaa | gcc | tat | 1152 |
|---|---|---|---|---|---|---|---|---|---|---|---|---|---|---|---|---|
| Leu | Glu | Asn | Ser | Val | Tyr | Asp | Leu | Thr | Tyr | Thr | Lys | Ser | Lys | Ala | Tyr |  |
|  | 370 |  |  |  |  | 375 |  |  |  |  | 380 |  |  |  |  |  |

| act | gct | aaa | ctt | atg | cac | aac | aaa | ctt | tat | aat | cgt | aaa | aca | gtg | aaa | 1200 |
|---|---|---|---|---|---|---|---|---|---|---|---|---|---|---|---|---|
| Thr | Ala | Lys | Leu | Met | His | Asn | Lys | Leu | Tyr | Asn | Arg | Lys | Thr | Val | Lys |  |
| 385 |  |  |  |  | 390 |  |  |  |  | 395 |  |  |  |  | 400 |  |

| aag | gca | aat | caa | gtt | ctg | gct | aac | tta | gct | aat | acc | ttt | tta | acc | gat | 1248 |
|---|---|---|---|---|---|---|---|---|---|---|---|---|---|---|---|---|
| Lys | Ala | Asn | Gln | Val | Leu | Ala | Asn | Leu | Ala | Asn | Thr | Phe | Leu | Thr | Asp |  |
|  |  |  |  | 405 |  |  |  |  | 410 |  |  |  |  | 415 |  |  |

| cat | cgt | caa | aaa | ggt | atc | tac | gtt | aac | cgt | cct | ctc | aac | aat | cca | cca | 1296 |
|---|---|---|---|---|---|---|---|---|---|---|---|---|---|---|---|---|
| His | Arg | Gln | Lys | Gly | Ile | Tyr | Val | Asn | Arg | Pro | Leu | Asn | Asn | Pro | Pro |  |
|  |  |  | 420 |  |  |  |  | 425 |  |  |  |  | 430 |  |  |  |

```
aaa gga atc gat act gac gag atg gct tat gaa gcc ggt agt tct ttc       1344
Lys Gly Ile Asp Thr Asp Glu Met Ala Tyr Glu Ala Gly Ser Ser Phe
        435                 440                 445 cca gca atc tta atg atc gct atg ggt aaa aag aaa ttc ttt aat gct       1392
Pro Ala Ile Leu Met Ile Ala Met Gly Lys Lys Lys Phe Phe Asn Ala
    450                 455                 460 ttg cat gat tat gaa acc tac tac tta aaa caa gct act aca cag           1440
Leu His Asp Tyr Tyr Glu Thr Tyr Tyr Leu Lys Gln Ala Thr Thr Gln
465                 470                 475                 480 gat ttt ttg aat atc att cgt aag tat gac aac tca aag aaa gta aac       1488
Asp Phe Leu Asn Ile Ile Arg Lys Tyr Asp Asn Ser Lys Lys Val Asn
                485                 490                 495 tat gtg att aat caa ttt atc gat cct gat tat ttg aac aaa               1530
Tyr Val Ile Asn Gln Phe Ile Asp Pro Asp Tyr Leu Asn Lys
            500                 505                 510

<210> SEQ ID NO 64
<211> LENGTH: 510
<212> TYPE: PRT
<213> ORGANISM: Lactobacillus acidophilus

<400> SEQUENCE: 64

Leu Glu Val Lys Arg Met Lys Lys Arg Thr Thr Leu Leu Leu Ser Ser
1               5                   10                  15

Ala Ile Thr Ile Ala Ala Leu Phe Ser Phe Asn Ser Lys Ala Gln Ala
            20                  25                  30

Ala Ala Asp Pro Ala Val Lys Ala Thr Asn Tyr Asn Met Thr Val Lys
        35                  40                  45

Leu Asn Thr Arg Lys Asn Gln Leu Thr Glu Lys Val Thr Met His Val
    50                  55                  60

Val Asn Asn Gly Asn Glu Pro Val Lys Asn Leu Leu Ile Arg Asn Ile
65                  70                  75                  80

Ala Asn Gly Val Leu Lys Tyr Asp His Gln His Phe Lys Ile Ala Lys
                85                  90                  95

Asn Ala Lys Thr Thr Val Lys Ser Ile Ser Ser Ala Gly Glu Asn Leu
            100                 105                 110

Ser Tyr Thr Thr Gly Lys Asp Lys Ser Asn Leu Phe Val Asp Lys Ser
        115                 120                 125

Leu Asn Ala Gly Glu Ser Thr Asp Leu Thr Val Asn Val Val Thr Ser
    130                 135                 140

Val Pro Lys Arg Gln Asp Arg Phe Gly Tyr Gln Asn Ile Asn Gly Gly
145                 150                 155                 160

Lys Val Tyr Asn Leu Ser Phe Cys Phe Pro Tyr Leu Ser Asp Tyr Arg
                165                 170                 175

Asn Gly Lys Trp Asn Tyr His Pro Tyr Tyr Asp Gly Gly Glu Asn Arg
            180                 185                 190

Asn Thr Thr Val Ser Asn Phe His Val Ser Phe Tyr Ala Pro Lys Ser
        195                 200                 205

Tyr Lys Val Ala Ala Ser Gly Gln Asn Ser Thr Lys Asn Gly Lys Thr
    210                 215                 220

Thr Ile Val Ala Glu Asn Met Arg Asp Phe Ala Ile Val Ala Ser Asn
225                 230                 235                 240

Lys Phe Lys Val Ser His Thr Tyr Ala Asp Gly Ile Arg Ile Asn Asn
                245                 250                 255

Tyr Tyr Phe Ala Gly Lys Asn Ser Lys Gln Tyr Asn Lys Leu Ala Leu
            260                 265                 270
```

```
Leu Thr Ala Lys Asp Ser Phe Asn Ile Phe Thr Lys Lys Ile Gly Lys
        275                 280                 285

Tyr Pro Tyr Lys Glu Ile Asp Met Thr Glu Gly Leu Leu Gly Lys Asp
        290                 295                 300

Thr Gly Gly Met Glu Tyr Pro Ser Leu Ile Met Ile Asp Ala Ser Gly
305                 310                 315                 320

Phe Val Gln Lys Lys His Pro Ile Asn Arg Tyr Asn Glu Leu Thr Glu
                325                 330                 335

Asp Val Ser His Glu Ile Gly His Gln Trp Phe Tyr Ala Thr Val Gly
            340                 345                 350

Asn Asp Glu Tyr Thr Glu Pro Trp Leu Asp Glu Gly Leu Thr Asn Phe
        355                 360                 365

Leu Glu Asn Ser Val Tyr Asp Leu Thr Tyr Thr Lys Ser Lys Ala Tyr
    370                 375                 380

Thr Ala Lys Leu Met His Asn Lys Leu Tyr Asn Arg Lys Thr Val Lys
385                 390                 395                 400

Lys Ala Asn Gln Val Leu Ala Asn Leu Ala Asn Thr Phe Leu Thr Asp
                405                 410                 415

His Arg Gln Lys Gly Ile Tyr Val Asn Arg Pro Leu Asn Asn Pro Pro
            420                 425                 430

Lys Gly Ile Asp Thr Asp Glu Met Ala Tyr Glu Ala Gly Ser Ser Phe
        435                 440                 445

Pro Ala Ile Leu Met Ile Ala Met Gly Lys Lys Lys Phe Phe Asn Ala
    450                 455                 460

Leu His Asp Tyr Tyr Glu Thr Tyr Tyr Leu Lys Gln Ala Thr Thr Gln
465                 470                 475                 480

Asp Phe Leu Asn Ile Ile Arg Lys Tyr Asp Asn Ser Lys Lys Val Asn
                485                 490                 495

Tyr Val Ile Asn Gln Phe Ile Asp Pro Asp Tyr Leu Asn Lys
            500                 505                 510

<210> SEQ ID NO 65
<211> LENGTH: 1059
<212> TYPE: DNA
<213> ORGANISM: Lactobacillus acidophilus
<220> FEATURE:
<221> NAME/KEY: CDS
<222> LOCATION: (1)..(1059)
<223> OTHER INFORMATION: Surface protein ORF# 1568

<400> SEQUENCE: 65 ttg ttt tcg gag att ttt att tta att tta gca ctt atg aaa gtg tta     48
Leu Phe Ser Glu Ile Phe Ile Leu Ile Leu Ala Leu Met Lys Val Leu
1               5                   10                  15 aaa tca act tgt agg ttt cat tat aag gag aat att atg aag aat aaa     96
Lys Ser Thr Cys Arg Phe His Tyr Lys Glu Asn Ile Met Lys Asn Lys
            20                  25                  30 aaa tta gta gct att gca gcg aca ctt tta atc agc gct tct cca gta    144
Lys Leu Val Ala Ile Ala Ala Thr Leu Leu Ile Ser Ala Ser Pro Val
        35                  40                  45 gtt gca ctg att aat caa cca atc cat cca gtt caa gcc gtt aat caa    192
Val Ala Leu Ile Asn Gln Pro Ile His Pro Val Gln Ala Val Asn Gln
    50                  55                  60 aca cta aaa gat aaa atc aaa tta aaa aag act ttt aac aac act att    240
Thr Leu Lys Asp Lys Ile Lys Leu Lys Lys Thr Phe Asn Asn Thr Ile
65                  70                  75                  80 caa gtt ttc aac agc aaa ggt aac gct tct aca act acc aag act att    288
```

```
Gln Val Phe Asn Ser Lys Gly Asn Ala Ser Thr Thr Lys Thr Ile
             85                  90                  95 aat ggt aaa aag atg acc gaa gcc tca aca gtt aaa gct ggt caa act        336
Asn Gly Lys Lys Met Thr Glu Ala Ser Thr Val Lys Ala Gly Gln Thr
        100                 105                 110 ttt aaa tat tat ggc agt cca gta ctg atc caa ggt aaa aag ata act        384
Phe Lys Tyr Tyr Gly Ser Pro Val Leu Ile Gln Gly Lys Lys Ile Thr
        115                 120                 125 gat agt acc aat aag aat tat cac tac gca acc gct tct tat atc aat        432
Asp Ser Thr Asn Lys Asn Tyr His Tyr Ala Thr Ala Ser Tyr Ile Asn
130                 135                 140 att ggt aaa aaa cgt tat att aaa tca ata aat gtt agt tca atg gat        480
Ile Gly Lys Lys Arg Tyr Ile Lys Ser Ile Asn Val Ser Ser Met Asp
145                 150                 155                 160 gga caa aat gtc tta gtc tta agt gct aat tca cgt atc tat gat aaa        528
Gly Gln Asn Val Leu Val Leu Ser Ala Asn Ser Arg Ile Tyr Asp Lys
                165                 170                 175 aat gga cat cgt act acc ttt aac ggg ctt aca tta att cca aaa tat        576
Asn Gly His Arg Thr Thr Phe Asn Gly Leu Thr Leu Ile Pro Lys Tyr
            180                 185                 190 atg tta ctt aag aca cct gat aaa aca cat gtg aca acc aaa aat gat        624
Met Leu Leu Lys Thr Pro Asp Lys Thr His Val Thr Thr Lys Asn Asp
        195                 200                 205 atg ttt tac tat ttt tca aat ctt aat ggt tct aaa aaa aga agc tta        672
Met Phe Tyr Tyr Phe Ser Asn Leu Asn Gly Ser Lys Lys Arg Ser Leu
        210                 215                 220 aat aca aca act att aat ggc aaa ttg tat tat tca tta ggt aag gat        720
Asn Thr Thr Thr Ile Asn Gly Lys Leu Tyr Tyr Ser Leu Gly Lys Asp
225                 230                 235                 240 gct tat att aga gct tca aat gtt ggc tac atc aat ggt aat act gta        768
Ala Tyr Ile Arg Ala Ser Asn Val Gly Tyr Ile Asn Gly Asn Thr Val
                245                 250                 255 tat caa gcc tct ggt aca act act gcc act att ttg aat aag att cac        816
Tyr Gln Ala Ser Gly Thr Thr Thr Ala Thr Ile Leu Asn Lys Ile His
            260                 265                 270 gtt ttg gat aat aaa tta aaa aca act aac aag gcc tta aaa gtt ggt        864
Val Leu Asp Asn Lys Leu Lys Thr Thr Asn Lys Ala Leu Lys Val Gly
        275                 280                 285 aaa aag gtt aag gtt gat gca aca aaa gtt act gga caa ggc gat agt        912
Lys Lys Val Lys Val Asp Ala Thr Lys Val Thr Gly Gln Gly Asp Ser
        290                 295                 300 gct gcc ctt tac ttt aga att gct ggt act aaa ggt aac aat gct caa        960
Ala Ala Leu Tyr Phe Arg Ile Ala Gly Thr Lys Gly Asn Asn Ala Gln
305                 310                 315                 320 tat atc tat tgg ggc gac tat tcc gaa tat ggt atg gat cag gag agt       1008
Tyr Ile Tyr Trp Gly Asp Tyr Ser Glu Tyr Gly Met Asp Gln Glu Ser
                325                 330                 335 act acc gat gaa ttt caa ggt aac ttc aac tta gca aat cat tta gca       1056
Thr Thr Asp Glu Phe Gln Gly Asn Phe Asn Leu Ala Asn His Leu Ala
            340                 345                 350 aat                                                                    1059
Asn

<210> SEQ ID NO 66
<211> LENGTH: 353
<212> TYPE: PRT
<213> ORGANISM: Lactobacillus acidophilus

<400> SEQUENCE: 66

Leu Phe Ser Glu Ile Phe Ile Leu Ile Leu Ala Leu Met Lys Val Leu
```

```
                1               5                  10                 15
Lys Ser Thr Cys Arg Phe His Tyr Lys Glu Asn Ile Met Lys Asn Lys
                    20                  25                  30
Lys Leu Val Ala Ile Ala Ala Thr Leu Leu Ile Ser Ala Ser Pro Val
                    35                  40                  45
Val Ala Leu Ile Asn Gln Pro Ile His Pro Val Gln Ala Val Asn Gln
                    50                  55                  60
Thr Leu Lys Asp Lys Ile Lys Leu Lys Lys Thr Phe Asn Asn Thr Ile
65                      70                  75                  80
Gln Val Phe Asn Ser Lys Gly Asn Ala Ser Thr Thr Lys Thr Lys Ile
                    85                  90                  95
Asn Gly Lys Lys Met Thr Glu Ala Ser Thr Val Lys Ala Gly Gln Thr
                    100                 105                 110
Phe Lys Tyr Tyr Gly Ser Pro Val Leu Ile Gln Gly Lys Lys Ile Thr
                    115                 120                 125
Asp Ser Thr Asn Lys Asn Tyr His Tyr Ala Thr Ala Ser Tyr Ile Asn
                    130                 135                 140
Ile Gly Lys Lys Arg Tyr Ile Lys Ser Ile Asn Val Ser Ser Met Asp
145                     150                 155                 160
Gly Gln Asn Val Leu Val Leu Ser Ala Asn Ser Arg Ile Tyr Asp Lys
                    165                 170                 175
Asn Gly His Arg Thr Thr Phe Asn Gly Leu Thr Leu Ile Pro Lys Tyr
                    180                 185                 190
Met Leu Leu Lys Thr Pro Asp Lys Thr His Val Thr Thr Lys Asn Asp
                    195                 200                 205
Met Phe Tyr Tyr Phe Ser Asn Leu Asn Gly Ser Lys Lys Arg Ser Leu
                    210                 215                 220
Asn Thr Thr Thr Ile Asn Gly Lys Leu Tyr Tyr Ser Leu Gly Lys Asp
225                     230                 235                 240
Ala Tyr Ile Arg Ala Ser Asn Val Gly Tyr Ile Asn Gly Asn Thr Val
                    245                 250                 255
Tyr Gln Ala Ser Gly Thr Thr Thr Ala Thr Ile Leu Asn Lys Ile His
                    260                 265                 270
Val Leu Asp Asn Lys Leu Lys Thr Thr Asn Lys Ala Leu Lys Val Gly
                    275                 280                 285
Lys Lys Val Lys Val Asp Ala Thr Lys Val Thr Gly Gln Gly Asp Ser
                    290                 295                 300
Ala Ala Leu Tyr Phe Arg Ile Ala Gly Thr Lys Gly Asn Asn Ala Gln
305                     310                 315                 320
Tyr Ile Tyr Trp Gly Asp Tyr Ser Glu Tyr Gly Met Asp Gln Glu Ser
                    325                 330                 335
Thr Thr Asp Glu Phe Gln Gly Asn Phe Asn Leu Ala Asn His Leu Ala
                    340                 345                 350
Asn
```

<210> SEQ ID NO 67
<211> LENGTH: 603
<212> TYPE: DNA
<213> ORGANISM: Lactobacillus acidophilus
<220> FEATURE:
<221> NAME/KEY: CDS
<222> LOCATION: (1)..(603)
<223> OTHER INFORMATION: Transposase ORF# 1569

<400> SEQUENCE: 67

```
atg att aaa aca caa gta gta aag cta aaa gtt aat aag acc atg caa      48
Met Ile Lys Thr Gln Val Val Lys Leu Lys Val Asn Lys Thr Met Gln
1               5                  10                  15 aag cag ctc gat gct ttg tgc gac tat cgg cga tac tgc tgg aat aaa      96
Lys Gln Leu Asp Ala Leu Cys Asp Tyr Arg Arg Tyr Cys Trp Asn Lys
            20                  25                  30 ggc tta gaa act tgg caa tta atg tat gaa gct cat aca cta aac aaa     144
Gly Leu Glu Thr Trp Gln Leu Met Tyr Glu Ala His Thr Leu Asn Lys
        35                  40                  45 aaa gat aat ccc agt cct aac gaa cgc aga gtc cgt gat gaa cta gtc     192
Lys Asp Asn Pro Ser Pro Asn Glu Arg Arg Val Arg Asp Glu Leu Val
    50                  55                  60 gca aat aaa gct gac tgg caa tat gat ttg tca gct cga tgc ttg caa     240
Ala Asn Lys Ala Asp Trp Gln Tyr Asp Leu Ser Ala Arg Cys Leu Gln
65                  70                  75                  80 tta gct gtt aaa gac ttg gct aat gca tgg aag aac ttc ttt gat aag     288
Leu Ala Val Lys Asp Leu Ala Asn Ala Trp Lys Asn Phe Phe Asp Lys
                85                  90                  95 tca caa tct gat tgg gga ata cct agt ttt aaa tca aag aaa gct ccc     336
Ser Gln Ser Asp Trp Gly Ile Pro Ser Phe Lys Ser Lys Lys Ala Pro
            100                 105                 110 aga caa ggc ttt aaa act gat agg gct aag att gtt aat ggc aag ctt     384
Arg Gln Gly Phe Lys Thr Asp Arg Ala Lys Ile Val Asn Gly Lys Leu
        115                 120                 125 cgc ctt gat cgt cca aga agt att tca aaa gaa gat tgg ttt gat tta     432
Arg Leu Asp Arg Pro Arg Ser Ile Ser Lys Glu Asp Trp Phe Asp Leu
    130                 135                 140 aaa agc tat gaa gct cta aag atg agt gaa gtc aaa gta ata agt atc     480
Lys Ser Tyr Glu Ala Leu Lys Met Ser Glu Val Lys Val Ile Ser Ile
145                 150                 155                 160 ttc aaa gaa aaa gga gct tat tat gcg gct ttg cct tat gaa gaa gag     528
Phe Lys Glu Lys Gly Ala Tyr Tyr Ala Ala Leu Pro Tyr Glu Glu Glu
                165                 170                 175 att tca agt aag gct aaa act tat caa aag aca gca gta gat gtc aat     576
Ile Ser Ser Lys Ala Lys Thr Tyr Gln Lys Thr Ala Val Asp Val Asn
            180                 185                 190 gtt gga cat ttt aac tat acc gag ggg                                 603
Val Gly His Phe Asn Tyr Thr Glu Gly
        195                 200
```

<210> SEQ ID NO 68
<211> LENGTH: 201
<212> TYPE: PRT
<213> ORGANISM: Lactobacillus acidophilus

<400> SEQUENCE: 68

```
Met Ile Lys Thr Gln Val Val Lys Leu Lys Val Asn Lys Thr Met Gln
1               5                  10                  15

Lys Gln Leu Asp Ala Leu Cys Asp Tyr Arg Arg Tyr Cys Trp Asn Lys
            20                  25                  30

Gly Leu Glu Thr Trp Gln Leu Met Tyr Glu Ala His Thr Leu Asn Lys
        35                  40                  45

Lys Asp Asn Pro Ser Pro Asn Glu Arg Arg Val Arg Asp Glu Leu Val
    50                  55                  60

Ala Asn Lys Ala Asp Trp Gln Tyr Asp Leu Ser Ala Arg Cys Leu Gln
65                  70                  75                  80

Leu Ala Val Lys Asp Leu Ala Asn Ala Trp Lys Asn Phe Phe Asp Lys
                85                  90                  95

Ser Gln Ser Asp Trp Gly Ile Pro Ser Phe Lys Ser Lys Lys Ala Pro
```

```
                    100              105              110
Arg Gln Gly Phe Lys Thr Asp Arg Ala Lys Ile Val Asn Gly Lys Leu
            115                  120              125

Arg Leu Asp Arg Pro Arg Ser Ile Ser Lys Glu Asp Trp Phe Asp Leu
        130                  135              140

Lys Ser Tyr Glu Ala Leu Lys Met Ser Glu Val Lys Val Ile Ser Ile
145                  150              155              160

Phe Lys Glu Lys Gly Ala Tyr Ala Ala Leu Pro Tyr Glu Glu Glu
                165              170              175

Ile Ser Ser Lys Ala Lys Thr Tyr Gln Lys Thr Ala Val Asp Val Asn
            180              185              190

Val Gly His Phe Asn Tyr Thr Glu Gly
        195              200

<210> SEQ ID NO 69
<211> LENGTH: 540
<212> TYPE: DNA
<213> ORGANISM: Lactobacillus acidophilus
<220> FEATURE:
<221> NAME/KEY: CDS
<222> LOCATION: (1)..(540)
<223> OTHER INFORMATION: Transposase ORF# 1570

<400> SEQUENCE: 69 ttg cct gct aaa ttg caa aag ctt tat aag cgt att aag cat tat caa        48
Leu Pro Ala Lys Leu Gln Lys Leu Tyr Lys Arg Ile Lys His Tyr Gln
1               5                   10                  15 aga atg ctg gca cgt aaa aga gaa gtt aac ggt aag tta gct aca aaa        96
Arg Met Leu Ala Arg Lys Arg Glu Val Asn Gly Lys Leu Ala Thr Lys
            20                  25                  30 tca aat aat tac ttt gca gtg aga acc aaa ttg caa aga gat tat cgc       144
Ser Asn Asn Tyr Phe Ala Val Arg Thr Lys Leu Gln Arg Asp Tyr Arg
        35                  40                  45 aag gta gct aat atc caa aat gat ctt tta cag cag ttc act act aag       192
Lys Val Ala Asn Ile Gln Asn Asp Leu Leu Gln Gln Phe Thr Thr Lys
    50                  55                  60 ctt gta gat aat tac gac caa ata gta att gaa gat ttg gca gta aag       240
Leu Val Asp Asn Tyr Asp Gln Ile Val Ile Glu Asp Leu Ala Val Lys
65                  70                  75                  80 caa atg atg atg acc cat gta gct tca aaa gga atg cag aga tct ctt       288
Gln Met Met Met Thr His Val Ala Ser Lys Gly Met Gln Arg Ser Leu
                85                  90                  95 ttc agt aga ttt agg cag ata tta act tat aag tgt gat tgg tat ggc       336
Phe Ser Arg Phe Arg Gln Ile Leu Thr Tyr Lys Cys Asp Trp Tyr Gly
            100                 105                 110 aaa gag tta atc tta gct gat aaa aca tac cca tca act caa aga tgt       384
Lys Glu Leu Ile Leu Ala Asp Lys Thr Tyr Pro Ser Thr Gln Arg Cys
        115                 120                 125 gct gcg tgc ggt tat gtc aaa aaa ggc gag gaa aag atc act ttg caa       432
Ala Ala Cys Gly Tyr Val Lys Lys Gly Glu Glu Lys Ile Thr Leu Gln
    130                 135                 140 ggc aat aaa aag cat ggc act aag cat aat gaa tat atc tgt tat gag       480
Gly Asn Lys Lys His Gly Thr Lys His Asn Glu Tyr Ile Cys Tyr Glu
145                 150                 155                 160 tgt ggc tac agt aat gat cga gat gaa aat gcg gtt tta aac ctt tta       528
Cys Gly Tyr Ser Asn Asp Arg Asp Glu Asn Ala Val Leu Asn Leu Leu
                165                 170                 175 gct tta gtg aaa                                                       540
Ala Leu Val Lys
            180
```

<210> SEQ ID NO 70
<211> LENGTH: 180
<212> TYPE: PRT
<213> ORGANISM: Lactobacillus acidophilus

<400> SEQUENCE: 70

| Leu | Pro | Ala | Lys | Leu | Gln | Lys | Leu | Tyr | Lys | Arg | Ile | Lys | His | Tyr | Gln |
|---|---|---|---|---|---|---|---|---|---|---|---|---|---|---|---|
| 1 | | | | 5 | | | | | 10 | | | | | 15 | |

| Arg | Met | Leu | Ala | Arg | Lys | Arg | Glu | Val | Asn | Gly | Lys | Leu | Ala | Thr | Lys |
|---|---|---|---|---|---|---|---|---|---|---|---|---|---|---|---|
| | | | 20 | | | | | 25 | | | | | 30 | | |

| Ser | Asn | Asn | Tyr | Phe | Ala | Val | Arg | Thr | Lys | Leu | Gln | Arg | Asp | Tyr | Arg |
|---|---|---|---|---|---|---|---|---|---|---|---|---|---|---|---|
| | | 35 | | | | | 40 | | | | | 45 | | | |

| Lys | Val | Ala | Asn | Ile | Gln | Asn | Asp | Leu | Leu | Gln | Gln | Phe | Thr | Thr | Lys |
|---|---|---|---|---|---|---|---|---|---|---|---|---|---|---|---|
| | 50 | | | | | 55 | | | | | 60 | | | | |

| Leu | Val | Asp | Asn | Tyr | Asp | Gln | Ile | Val | Ile | Glu | Asp | Leu | Ala | Val | Lys |
|---|---|---|---|---|---|---|---|---|---|---|---|---|---|---|---|
| 65 | | | | | 70 | | | | | 75 | | | | | 80 |

| Gln | Met | Met | Met | Thr | His | Val | Ala | Ser | Lys | Gly | Met | Gln | Arg | Ser | Leu |
|---|---|---|---|---|---|---|---|---|---|---|---|---|---|---|---|
| | | | | 85 | | | | | 90 | | | | | 95 | |

| Phe | Ser | Arg | Phe | Arg | Gln | Ile | Leu | Thr | Tyr | Lys | Cys | Asp | Trp | Tyr | Gly |
|---|---|---|---|---|---|---|---|---|---|---|---|---|---|---|---|
| | | | 100 | | | | | 105 | | | | | 110 | | |

| Lys | Glu | Leu | Ile | Leu | Ala | Asp | Lys | Thr | Tyr | Pro | Ser | Thr | Gln | Arg | Cys |
|---|---|---|---|---|---|---|---|---|---|---|---|---|---|---|---|
| | | 115 | | | | | 120 | | | | | 125 | | | |

| Ala | Ala | Cys | Gly | Tyr | Val | Lys | Lys | Gly | Glu | Glu | Lys | Ile | Thr | Leu | Gln |
|---|---|---|---|---|---|---|---|---|---|---|---|---|---|---|---|
| | 130 | | | | | 135 | | | | | 140 | | | | |

| Gly | Asn | Lys | Lys | His | Gly | Thr | Lys | His | Asn | Glu | Tyr | Ile | Cys | Tyr | Glu |
|---|---|---|---|---|---|---|---|---|---|---|---|---|---|---|---|
| 145 | | | | | 150 | | | | | 155 | | | | | 160 |

| Cys | Gly | Tyr | Ser | Asn | Asp | Arg | Asp | Glu | Asn | Ala | Val | Leu | Asn | Leu | Leu |
|---|---|---|---|---|---|---|---|---|---|---|---|---|---|---|---|
| | | | | 165 | | | | | 170 | | | | | 175 | |

| Ala | Leu | Val | Lys |
|---|---|---|---|
| | | | 180 |

<210> SEQ ID NO 71
<211> LENGTH: 1356
<212> TYPE: DNA
<213> ORGANISM: Lactobacillus acidophilus
<220> FEATURE:
<221> NAME/KEY: CDS
<222> LOCATION: (1)..(1356)
<223> OTHER INFORMATION: Membrane protein ORF# 1571

<400> SEQUENCE: 71

| atg | ttt | tat | ata | gca | gaa | aaa | tat | atg | gat | gaa | cta | ttt | gct | aaa | gcg | | 48 |
|---|---|---|---|---|---|---|---|---|---|---|---|---|---|---|---|---|---|
| Met | Phe | Tyr | Ile | Ala | Glu | Lys | Tyr | Met | Asp | Glu | Leu | Phe | Ala | Lys | Ala | | |
| 1 | | | | 5 | | | | | 10 | | | | | 15 | | | |

| cca | atc | aag | aag | gtc | tat | ttt | aag | cta | gca | ctg | cca | gtc | gtc | cta | ggg | | 96 |
|---|---|---|---|---|---|---|---|---|---|---|---|---|---|---|---|---|---|
| Pro | Ile | Lys | Lys | Val | Tyr | Phe | Lys | Leu | Ala | Leu | Pro | Val | Val | Leu | Gly | | |
| | | | 20 | | | | | 25 | | | | | 30 | | | | |

| atg | atc | act | act | atg | atc | tac | aac | cta | gct | gac | aca | atg | ttt | gtt | gct | | 144 |
|---|---|---|---|---|---|---|---|---|---|---|---|---|---|---|---|---|---|
| Met | Ile | Thr | Thr | Met | Ile | Tyr | Asn | Leu | Ala | Asp | Thr | Met | Phe | Val | Ala | | |
| | | 35 | | | | | 40 | | | | | 45 | | | | | |

| aaa | acc | agc | gat | act | aat | cta | gta | gcc | gga | att | aca | att | ggt | gca | cca | | 192 |
|---|---|---|---|---|---|---|---|---|---|---|---|---|---|---|---|---|---|
| Lys | Thr | Ser | Asp | Thr | Asn | Leu | Val | Ala | Gly | Ile | Thr | Ile | Gly | Ala | Pro | | |
| | 50 | | | | | 55 | | | | | 60 | | | | | | |

| ctc | ttt | act | ttt | cta | atc | gct | gtt | tct | gac | att | ttc | ggt | tta | ggt | ggc | | 240 |
|---|---|---|---|---|---|---|---|---|---|---|---|---|---|---|---|---|---|
| Leu | Phe | Thr | Phe | Leu | Ile | Ala | Val | Ser | Asp | Ile | Phe | Gly | Leu | Gly | Gly | | |
| 65 | | | | | 70 | | | | | 75 | | | | | 80 | | |

| tct | tca | tta | att | tca | cgt | ttg | ttt | ggt | gaa | aga | aat | tat | caa | cta | agt | | 288 |
|---|---|---|---|---|---|---|---|---|---|---|---|---|---|---|---|---|---|
| Ser | Ser | Leu | Ile | Ser | Arg | Leu | Phe | Gly | Glu | Arg | Asn | Tyr | Gln | Leu | Ser | | |

-continued

```
              85                  90                  95
aaa cgt gta agt agc ttt tgt atg atc ggt gga ttt gtc act ggt tta      336
Lys Arg Val Ser Ser Phe Cys Met Ile Gly Gly Phe Val Thr Gly Leu
            100                 105                 110 ata ctg aca gct att tta tta att ttt gaa aat cca att ctt cac ctt      384
Ile Leu Thr Ala Ile Leu Leu Ile Phe Glu Asn Pro Ile Leu His Leu
        115                 120                 125 ttg ggt gcg aaa gcc gct act tat caa gat gcg gcc gac ttt tat cgc      432
Leu Gly Ala Lys Ala Ala Thr Tyr Gln Asp Ala Ala Asp Phe Tyr Arg
    130                 135                 140 ata ata tca att ggt gct gct cca att gtc ttt tca att att cca caa      480
Ile Ile Ser Ile Gly Ala Ala Pro Ile Val Phe Ser Ile Ile Pro Gln
145                 150                 155                 160 aat ctg atc aga aca gaa ggc tta gcc act caa gca atg att gcc aca      528
Asn Leu Ile Arg Thr Glu Gly Leu Ala Thr Gln Ala Met Ile Ala Thr
                165                 170                 175 atg aca ggg aca att tta gct atc att ctc gat ccc att ttc ctg ttt      576
Met Thr Gly Thr Ile Leu Ala Ile Ile Leu Asp Pro Ile Phe Leu Phe
            180                 185                 190 gtt ttc aaa atg gga gcc atc ggt gtt ggg atc gcc aat att aca ggc      624
Val Phe Lys Met Gly Ala Ile Gly Val Gly Ile Ala Asn Ile Thr Gly
        195                 200                 205 tat cta gtt act gat att att ctt att tat tac gtc cta tgt aaa act      672
Tyr Leu Val Thr Asp Ile Ile Leu Ile Tyr Tyr Val Leu Cys Lys Thr
    210                 215                 220 gaa tac atc aaa tta aag cta aaa tat act aaa atc agt ggc aaa acc      720
Glu Tyr Ile Lys Leu Lys Leu Lys Tyr Thr Lys Ile Ser Gly Lys Thr
225                 230                 235                 240 atc aaa gat atc gtg gca atc ggc atc ccc ggt tca att act aac ttt      768
Ile Lys Asp Ile Val Ala Ile Gly Ile Pro Gly Ser Ile Thr Asn Phe
                245                 250                 255 gca caa agc ttc ggt atg gct ctt ctt aac tca tct tta gcc tta tac      816
Ala Gln Ser Phe Gly Met Ala Leu Leu Asn Ser Ser Leu Ala Leu Tyr
            260                 265                 270 ggt gca aat aaa gtt gct gca atg gga atc aca caa aag att tac agt      864
Gly Ala Asn Lys Val Ala Ala Met Gly Ile Thr Gln Lys Ile Tyr Ser
        275                 280                 285 atc gtc atc tta gta atc gtc ggt ttt gcc ttt ggt tca caa ccc tta      912
Ile Val Ile Leu Val Ile Val Gly Phe Ala Phe Gly Ser Gln Pro Leu
    290                 295                 300 att ggt tac aac tat ggt gcc aaa aac tgg aaa cga tta aag aag att      960
Ile Gly Tyr Asn Tyr Gly Ala Lys Asn Trp Lys Arg Leu Lys Lys Ile
305                 310                 315                 320 tta aac ttc gat att ctt gtc caa gtt gtc tat gcc gta gtt tcc ggt     1008
Leu Asn Phe Asp Ile Leu Val Gln Val Val Tyr Ala Val Val Ser Gly
                325                 330                 335 gga tta tta att cta ttt gct cgt cca gtc act gct tta ttt atg aat     1056
Gly Leu Leu Ile Leu Phe Ala Arg Pro Val Thr Ala Leu Phe Met Asn
            340                 345                 350 caa cca gac atc gtc aat gcc ggt agt tac atg tta att gca act atc     1104
Gln Pro Asp Ile Val Asn Ala Gly Ser Tyr Met Leu Ile Ala Thr Ile
        355                 360                 365 att act aca cca att gtt ggt att att ctg gtt tac act acc gtt ttc     1152
Ile Thr Thr Pro Ile Val Gly Ile Ile Leu Val Tyr Thr Thr Val Phe
    370                 375                 380 caa tca gtt ggt aat gcc tgg gct gcc ttc atc atg gca atc gca cgt     1200
Gln Ser Val Gly Asn Ala Trp Ala Ala Phe Ile Met Ala Ile Ala Arg
385                 390                 395                 400 caa gga gta gtt tac ttt atc gca tta gag act ttg aaa aac atc ttc     1248
```

```
Gln Gly Val Val Tyr Phe Ile Ala Leu Glu Thr Leu Lys Asn Ile Phe
                405                 410                 415
ggc tat cac ggc att gtc tgg gct caa gca gta agt gat gta atc acc      1296
Gly Tyr His Gly Ile Val Trp Ala Gln Ala Val Ser Asp Val Ile Thr
            420                 425                 430
tgc atc atc ggt tac ttc atc tat gaa aag agt cta gat ctc aag gat      1344
Cys Ile Ile Gly Tyr Phe Ile Tyr Glu Lys Ser Leu Asp Leu Lys Asp
            435                 440                 445
aaa ata aaa aat                                                      1356
Lys Ile Lys Asn
        450

<210> SEQ ID NO 72
<211> LENGTH: 452
<212> TYPE: PRT
<213> ORGANISM: Lactobacillus acidophilus

<400> SEQUENCE: 72

Met Phe Tyr Ile Ala Glu Lys Tyr Met Asp Glu Leu Phe Ala Lys Ala
1               5                   10                  15

Pro Ile Lys Lys Val Tyr Phe Lys Leu Ala Leu Pro Val Val Leu Gly
            20                  25                  30

Met Ile Thr Thr Met Ile Tyr Asn Leu Ala Asp Thr Met Phe Val Ala
        35                  40                  45

Lys Thr Ser Asp Thr Asn Leu Val Ala Gly Ile Thr Ile Gly Ala Pro
    50                  55                  60

Leu Phe Thr Phe Leu Ile Ala Val Ser Asp Ile Phe Gly Leu Gly Gly
65                  70                  75                  80

Ser Ser Leu Ile Ser Arg Leu Phe Gly Glu Arg Asn Tyr Gln Leu Ser
                85                  90                  95

Lys Arg Val Ser Ser Phe Cys Met Ile Gly Phe Val Thr Gly Leu
            100                 105                 110

Ile Leu Thr Ala Ile Leu Leu Ile Phe Glu Asn Pro Ile Leu His Leu
        115                 120                 125

Leu Gly Ala Lys Ala Ala Thr Tyr Gln Asp Ala Ala Asp Phe Tyr Arg
    130                 135                 140

Ile Ile Ser Ile Gly Ala Ala Pro Ile Val Phe Ser Ile Ile Pro Gln
145                 150                 155                 160

Asn Leu Ile Arg Thr Glu Gly Leu Ala Thr Gln Ala Met Ile Ala Thr
                165                 170                 175

Met Thr Gly Thr Ile Leu Ala Ile Ile Leu Asp Pro Ile Phe Leu Phe
            180                 185                 190

Val Phe Lys Met Gly Ala Ile Gly Val Gly Ile Ala Asn Ile Thr Gly
        195                 200                 205

Tyr Leu Val Thr Asp Ile Ile Leu Ile Tyr Tyr Val Leu Cys Lys Thr
    210                 215                 220

Glu Tyr Ile Lys Leu Lys Leu Lys Tyr Thr Lys Ile Ser Gly Lys Thr
225                 230                 235                 240

Ile Lys Asp Ile Val Ala Ile Gly Ile Pro Gly Ser Ile Thr Asn Phe
                245                 250                 255

Ala Gln Ser Phe Gly Met Ala Leu Leu Asn Ser Ser Leu Ala Leu Tyr
            260                 265                 270

Gly Ala Asn Lys Val Ala Ala Met Gly Ile Thr Gln Lys Ile Tyr Ser
        275                 280                 285

Ile Val Ile Leu Val Ile Val Gly Phe Ala Phe Gly Ser Gln Pro Leu
    290                 295                 300
```

```
Ile Gly Tyr Asn Tyr Gly Ala Lys Asn Trp Lys Arg Leu Lys Lys Ile
305                 310                 315                 320

Leu Asn Phe Asp Ile Leu Val Gln Val Val Tyr Ala Val Val Ser Gly
            325                 330                 335

Gly Leu Leu Ile Leu Phe Ala Arg Pro Val Thr Ala Leu Phe Met Asn
            340                 345                 350

Gln Pro Asp Ile Val Asn Ala Gly Ser Tyr Met Leu Ile Ala Thr Ile
            355                 360                 365

Ile Thr Thr Pro Ile Val Gly Ile Ile Leu Val Tyr Thr Thr Val Phe
370                 375                 380

Gln Ser Val Gly Asn Ala Trp Ala Ala Phe Ile Met Ala Ile Ala Arg
385                 390                 395                 400

Gln Gly Val Val Tyr Phe Ile Ala Leu Glu Thr Leu Lys Asn Ile Phe
                405                 410                 415

Gly Tyr His Gly Ile Val Trp Ala Gln Ala Val Ser Asp Val Ile Thr
            420                 425                 430

Cys Ile Ile Gly Tyr Phe Ile Tyr Glu Lys Ser Leu Asp Leu Lys Asp
            435                 440                 445

Lys Ile Lys Asn
    450
```

```
<210> SEQ ID NO 73
<211> LENGTH: 192
<212> TYPE: DNA
<213> ORGANISM: Lactobacillus acidophilus
<220> FEATURE:
<221> NAME/KEY: CDS
<222> LOCATION: (1)..(192)
<223> OTHER INFORMATION: Unknown ORF# 1791

<400> SEQUENCE: 73 atg aat aaa ttt aaa gat ttg aat gaa tta gaa tta agt aat att gct       48
Met Asn Lys Phe Lys Asp Leu Asn Glu Leu Glu Leu Ser Asn Ile Ala
1               5                   10                  15 ggg gga agt aac aac att ttt tgg aca aga gtc gga gtt ggt tgg gct       96
Gly Gly Ser Asn Asn Ile Phe Trp Thr Arg Val Gly Val Gly Trp Ala
            20                  25                  30 gca gaa gcg aga tgc atg atc aaa ccc agt ctc ggt aat tgg act acg     144
Ala Glu Ala Arg Cys Met Ile Lys Pro Ser Leu Gly Asn Trp Thr Thr
        35                  40                  45 aaa gca gta agc tgt gga gca aaa gga tta tat gca gcg gtg agg gga     192
Lys Ala Val Ser Cys Gly Ala Lys Gly Leu Tyr Ala Ala Val Arg Gly
    50                  55                  60
```

```
<210> SEQ ID NO 74
<211> LENGTH: 64
<212> TYPE: PRT
<213> ORGANISM: Lactobacillus acidophilus

<400> SEQUENCE: 74

Met Asn Lys Phe Lys Asp Leu Asn Glu Leu Glu Leu Ser Asn Ile Ala
1               5                   10                  15

Gly Gly Ser Asn Asn Ile Phe Trp Thr Arg Val Gly Val Gly Trp Ala
            20                  25                  30

Ala Glu Ala Arg Cys Met Ile Lys Pro Ser Leu Gly Asn Trp Thr Thr
        35                  40                  45

Lys Ala Val Ser Cys Gly Ala Lys Gly Leu Tyr Ala Ala Val Arg Gly
    50                  55                  60
```

<210> SEQ ID NO 75
<211> LENGTH: 189
<212> TYPE: DNA
<213> ORGANISM: Lactobacillus acidophilus
<220> FEATURE:
<221> NAME/KEY: CDS
<222> LOCATION: (1)..(189)
<223> OTHER INFORMATION: Unknown ORF# 1792

<400> SEQUENCE: 75

```
atg aag caa att att att act gag aac aaa gtg att tta agt aaa att      48
Met Lys Gln Ile Ile Ile Thr Glu Asn Lys Val Ile Leu Ser Lys Ile
1               5                   10                  15 tta ggt gga tcg agt tct ata gat gat att ggt ctg aat gat act gaa      96
Leu Gly Gly Ser Ser Ser Ile Asp Asp Ile Gly Leu Asn Asp Thr Glu
                20                  25                  30 cat atg cta cct ttg tat agt aag aaa ggg agc aat cat aaa aga gat     144
His Met Leu Pro Leu Tyr Ser Lys Lys Gly Ser Asn His Lys Arg Asp
            35                  40                  45 gtt tat ttg gag aat cct aga tac caa aca cat ttt aaa ttt atg         189
Val Tyr Leu Glu Asn Pro Arg Tyr Gln Thr His Phe Lys Phe Met
        50                  55                  60
```

<210> SEQ ID NO 76
<211> LENGTH: 63
<212> TYPE: PRT
<213> ORGANISM: Lactobacillus acidophilus

<400> SEQUENCE: 76

```
Met Lys Gln Ile Ile Ile Thr Glu Asn Lys Val Ile Leu Ser Lys Ile
1               5                   10                  15

Leu Gly Gly Ser Ser Ser Ile Asp Asp Ile Gly Leu Asn Asp Thr Glu
                20                  25                  30

His Met Leu Pro Leu Tyr Ser Lys Lys Gly Ser Asn His Lys Arg Asp
            35                  40                  45

Val Tyr Leu Glu Asn Pro Arg Tyr Gln Thr His Phe Lys Phe Met
        50                  55                  60
```

<210> SEQ ID NO 77
<211> LENGTH: 1314
<212> TYPE: DNA
<213> ORGANISM: Lactobacillus acidophilus
<220> FEATURE:
<221> NAME/KEY: CDS
<222> LOCATION: (1)..(1314)
<223> OTHER INFORMATION: Hypothetical ORF# 1793

<400> SEQUENCE: 77

```
atg aat aag aaa aat gta tca atg cta atg tta agt cca gca atc tta      48
Met Asn Lys Lys Asn Val Ser Met Leu Met Leu Ser Pro Ala Ile Leu
1               5                   10                  15 tta atg atg aat agt act att gtg cat gcg gat aaa ggt agt act tct      96
Leu Met Met Asn Ser Thr Ile Val His Ala Asp Lys Gly Ser Thr Ser
                20                  25                  30 cat gag att agt agt aaa gta gta tct aaa aca aaa aat gat gat aaa     144
His Glu Ile Ser Ser Lys Val Val Ser Lys Thr Lys Asn Asp Asp Lys
            35                  40                  45 aat gtt cct gaa tcc gag caa gaa act agt agt aat aac gaa att gat     192
Asn Val Pro Glu Ser Glu Gln Glu Thr Ser Ser Asn Asn Glu Ile Asp
        50                  55                  60 caa tct caa gat aag cag gaa aaa gaa gaa caa gca att cct gaa gat     240
Gln Ser Gln Asp Lys Gln Glu Lys Glu Glu Gln Ala Ile Pro Glu Asp
65                  70                  75                  80
```

-continued

```
caa aat gat caa tct cag aat aca aat aat caa gat cct aat gac gca      288
Gln Asn Asp Gln Ser Gln Asn Thr Asn Asn Gln Asp Pro Asn Asp Ala
                85                  90                  95 agt gaa gaa gat gat gaa gat gaa gta tct gtt gaa gat tat gaa aac      336
Ser Glu Glu Asp Asp Glu Asp Glu Val Ser Val Glu Asp Tyr Glu Asn
            100                 105                 110 aat gta aaa gat ttt cat aga gtg aaa atg caa gag gtg aaa gat ctt      384
Asn Val Lys Asp Phe His Arg Val Lys Met Gln Glu Val Lys Asp Leu
        115                 120                 125 cta gca gag aaa aat aat caa gaa cat ctt atg tac att ggt cgc cca      432
Leu Ala Glu Lys Asn Asn Gln Glu His Leu Met Tyr Ile Gly Arg Pro
    130                 135                 140 aca tgt tat tac tgc cga caa ttt tca cct gat tta aaa gat ttc aat      480
Thr Cys Tyr Tyr Cys Arg Gln Phe Ser Pro Asp Leu Lys Asp Phe Asn
145                 150                 155                 160 gaa atc gtt aaa ggt aag ctg ctt tat ttc aat att gat gat gaa gaa      528
Glu Ile Val Lys Gly Lys Leu Leu Tyr Phe Asn Ile Asp Asp Glu Glu
                165                 170                 175 gga gca cat gat tat gct ttt aag gtt att ggt att cca gga aca cct      576
Gly Ala His Asp Tyr Ala Phe Lys Val Ile Gly Ile Pro Gly Thr Pro
            180                 185                 190 aca acg atg aga ttt atg aat gga aaa ttg ata agt gct tgg ata ggt      624
Thr Thr Met Arg Phe Met Asn Gly Lys Leu Ile Ser Ala Trp Ile Gly
        195                 200                 205 gga gaa aaa aca gga caa gag cta cat gat ttt ttg tat tct gac aca      672
Gly Glu Lys Thr Gly Gln Glu Leu His Asp Phe Leu Tyr Ser Asp Thr
    210                 215                 220 gct aat aaa tta gta gaa cag gtt gta att aaa aat caa tcg aat gat      720
Ala Asn Lys Leu Val Glu Gln Val Val Ile Lys Asn Gln Ser Asn Asp
225                 230                 235                 240 acg gct act caa gca gat aat gat gtc gtt gca tct gag agc gat aaa      768
Thr Ala Thr Gln Ala Asp Asn Asp Val Val Ala Ser Glu Ser Asp Lys
                245                 250                 255 aca cct gaa gtg act gta gag gaa aat aat caa gcg cag tct aat aat      816
Thr Pro Glu Val Thr Val Glu Glu Asn Asn Gln Ala Gln Ser Asn Asn
            260                 265                 270 gat gtc gct att act aac ttc gct gag aat agt gta ttt gaa aat gct      864
Asp Val Ala Ile Thr Asn Phe Ala Glu Asn Ser Val Phe Glu Asn Ala
        275                 280                 285 aaa aat gtt gct agt tct act gcg gat tta act caa gta gcg acg ggc      912
Lys Asn Val Ala Ser Ser Thr Ala Asp Leu Thr Gln Val Ala Thr Gly
    290                 295                 300 gat caa gat gat gta gct cct aaa gct gaa act aaa aat aaa act gtg      960
Asp Gln Asp Asp Val Ala Pro Lys Ala Glu Thr Lys Asn Lys Thr Val
305                 310                 315                 320 aag aaa cca ata aaa cat aaa att gta gcc aat aag gtt aag aaa caa     1008
Lys Lys Pro Ile Lys His Lys Ile Val Ala Asn Lys Val Lys Lys Gln
                325                 330                 335 gct aaa ttg cat aag acg aat att att ata cct atg tcc gct aaa aaa     1056
Ala Lys Leu His Lys Thr Asn Ile Ile Ile Pro Met Ser Ala Lys Lys
            340                 345                 350 cgt gaa gat gta aaa gaa aat aat caa tat gat acg gta aaa gta cac     1104
Arg Glu Asp Val Lys Glu Asn Asn Gln Tyr Asp Thr Val Lys Val His
        355                 360                 365 ggt aca tct cct aat gca att aag gac aaa caa gct aga att act atg     1152
Gly Thr Ser Pro Asn Ala Ile Lys Asp Lys Gln Ala Arg Ile Thr Met
    370                 375                 380 ttg aag gaa ctt gag aat gat act tca gat act att tct act gtg tct     1200
Leu Lys Glu Leu Glu Asn Asp Thr Ser Asp Thr Ile Ser Thr Val Ser
```

```
                385                 390                 395                 400
ttg ccg tct act ggt gag aag aaa aat atc tgg att caa tta atg gga      1248
Leu Pro Ser Thr Gly Glu Lys Lys Asn Ile Trp Ile Gln Leu Met Gly
                405                 410                 415 atg att agt gtt cta gtt agt gta gtt tta ggt att tcg tta aga aag      1296
Met Ile Ser Val Leu Val Ser Val Val Leu Gly Ile Ser Leu Arg Lys
                420                 425                 430 aaa act aag gag gaa aag                                              1314
Lys Thr Lys Glu Glu Lys
        435

<210> SEQ ID NO 78
<211> LENGTH: 438
<212> TYPE: PRT
<213> ORGANISM: Lactobacillus acidophilus

<400> SEQUENCE: 78

Met Asn Lys Lys Asn Val Ser Met Leu Met Leu Ser Pro Ala Ile Leu
1               5                   10                  15

Leu Met Met Asn Ser Thr Ile Val His Ala Asp Lys Gly Ser Thr Ser
                20                  25                  30

His Glu Ile Ser Ser Lys Val Val Ser Lys Thr Lys Asn Asp Asp Lys
            35                  40                  45

Asn Val Pro Glu Ser Glu Gln Glu Thr Ser Ser Asn Glu Ile Asp
        50                  55                  60

Gln Ser Gln Asp Lys Gln Glu Lys Glu Glu Ala Ile Pro Glu Asp
65                  70                  75                  80

Gln Asn Asp Gln Ser Gln Asn Thr Asn Asn Gln Asp Pro Asn Asp Ala
                85                  90                  95

Ser Glu Glu Asp Asp Glu Asp Val Ser Val Glu Asp Tyr Glu Asn
                100                 105                 110

Asn Val Lys Asp Phe His Arg Val Lys Met Gln Glu Val Lys Asp Leu
                115                 120                 125

Leu Ala Glu Lys Asn Asn Gln Glu His Leu Met Tyr Ile Gly Arg Pro
        130                 135                 140

Thr Cys Tyr Tyr Cys Arg Gln Phe Ser Pro Asp Leu Lys Asp Phe Asn
145                 150                 155                 160

Glu Ile Val Lys Gly Lys Leu Leu Tyr Phe Asn Ile Asp Asp Glu Glu
                165                 170                 175

Gly Ala His Asp Tyr Ala Phe Lys Val Ile Gly Ile Pro Gly Thr Pro
                180                 185                 190

Thr Thr Met Arg Phe Met Asn Gly Lys Leu Ile Ser Ala Trp Ile Gly
            195                 200                 205

Gly Glu Lys Thr Gly Gln Glu Leu His Asp Phe Leu Tyr Ser Asp Thr
        210                 215                 220

Ala Asn Lys Leu Val Glu Gln Val Val Ile Lys Asn Gln Ser Asn Asp
225                 230                 235                 240

Thr Ala Thr Gln Ala Asp Asn Asp Val Val Ala Ser Glu Ser Asp Lys
                245                 250                 255

Thr Pro Glu Val Thr Val Glu Glu Asn Asn Gln Ala Gln Ser Asn Asn
                260                 265                 270

Asp Val Ala Ile Thr Asn Phe Ala Glu Asn Ser Val Phe Glu Asn Ala
            275                 280                 285

Lys Asn Val Ala Ser Ser Thr Ala Asp Leu Thr Gln Val Ala Thr Gly
        290                 295                 300
```

```
Asp Gln Asp Asp Val Ala Pro Lys Ala Glu Thr Lys Asn Lys Thr Val
305                 310                 315                 320

Lys Lys Pro Ile Lys His Lys Ile Val Ala Asn Val Lys Lys Gln
            325                 330                 335

Ala Lys Leu His Lys Thr Asn Ile Ile Ile Pro Met Ser Ala Lys Lys
            340                 345                 350

Arg Glu Asp Val Lys Glu Asn Asn Gln Tyr Asp Thr Val Lys Val His
            355                 360                 365

Gly Thr Ser Pro Asn Ala Ile Lys Asp Lys Gln Ala Arg Ile Thr Met
            370                 375                 380

Leu Lys Glu Leu Glu Asn Asp Thr Ser Asp Thr Ile Ser Thr Val Ser
385                 390                 395                 400

Leu Pro Ser Thr Gly Glu Lys Lys Asn Ile Trp Ile Gln Leu Met Gly
                405                 410                 415

Met Ile Ser Val Leu Val Ser Val Val Leu Gly Ile Ser Leu Arg Lys
                420                 425                 430

Lys Thr Lys Glu Glu Lys
            435

<210> SEQ ID NO 79
<211> LENGTH: 588
<212> TYPE: DNA
<213> ORGANISM: Lactobacillus acidophilus
<220> FEATURE:
<221> NAME/KEY: CDS
<222> LOCATION: (1)..(588)
<223> OTHER INFORMATION: orf2 Lactobacillus ORF#1794

<400> SEQUENCE: 79 atg aat agc aaa gac tat gaa agt act gaa ttc tat tct tat aaa ttt     48
Met Asn Ser Lys Asp Tyr Glu Ser Thr Glu Phe Tyr Ser Tyr Lys Phe
1               5                   10                  15 aaa aat ttt tca act atg att atc att cct atg gca ctt tta gta ttt    96
Lys Asn Phe Ser Thr Met Ile Ile Ile Pro Met Ala Leu Leu Val Phe
                20                  25                  30 atc ttg ata att ggc tct ttc ttt gca atc aga cag agt aca gtt aca    144
Ile Leu Ile Ile Gly Ser Phe Phe Ala Ile Arg Gln Ser Thr Val Thr
            35                  40                  45 tct act gga att gta gaa cca caa agt aca ctt gat att gcc aat aaa    192
Ser Thr Gly Ile Val Glu Pro Gln Ser Thr Leu Asp Ile Ala Asn Lys
        50                  55                  60 aat tat cat gag gga caa att att aaa aga aat aga agt aaa tgg atg    240
Asn Tyr His Glu Gly Gln Ile Ile Lys Arg Asn Arg Ser Lys Trp Met
65                  70                  75                  80 gtt cat cta gat gat aaa aaa gaa aat ata gtg cat tta tta cca ata    288
Val His Leu Asp Asp Lys Lys Glu Asn Ile Val His Leu Leu Pro Ile
                85                  90                  95 att aaa gca aaa aaa tca gtt aat atc gtt aca tat ttc cct ggt aat    336
Ile Lys Ala Lys Lys Ser Val Asn Ile Val Thr Tyr Phe Pro Gly Asn
            100                 105                 110 aaa att ggt gca att aaa aaa gga caa ccc tta cat ttt caa tta tct    384
Lys Ile Gly Ala Ile Lys Lys Gly Gln Pro Leu His Phe Gln Leu Ser
        115                 120                 125 aac gcc aat gga aca aca gat aga cta gtt ggg gaa gtg aaa gaa gta    432
Asn Ala Asn Gly Thr Thr Asp Arg Leu Val Gly Glu Val Lys Glu Val
130                 135                 140 gga ata tac cct gtt aac tta cac gga aac aat gtt tac gaa gtg att    480
Gly Ile Tyr Pro Val Asn Leu His Gly Asn Asn Val Tyr Glu Val Ile
145                 150                 155                 160
```

```
tgt aaa gct aaa tta gat aaa gat gtg aag tat gga atg gaa ggc aat    528
Cys Lys Ala Lys Leu Asp Lys Asp Val Lys Tyr Gly Met Glu Gly Asn
            165                 170                 175 gca cca att att aca gga aag agc aca tat ttt gaa tat ttt aag gat    576
Ala Pro Ile Ile Thr Gly Lys Ser Thr Tyr Phe Glu Tyr Phe Lys Asp
            180                 185                 190 aaa att ctt aac                                                    588
Lys Ile Leu Asn
        195

<210> SEQ ID NO 80
<211> LENGTH: 196
<212> TYPE: PRT
<213> ORGANISM: Lactobacillus acidophilus

<400> SEQUENCE: 80

Met Asn Ser Lys Asp Tyr Glu Ser Thr Glu Phe Tyr Ser Tyr Lys Phe
1               5                   10                  15

Lys Asn Phe Ser Thr Met Ile Ile Pro Met Ala Leu Leu Val Phe
            20                  25                  30

Ile Leu Ile Ile Gly Ser Phe Phe Ala Ile Arg Gln Ser Thr Val Thr
            35                  40                  45

Ser Thr Gly Ile Val Glu Pro Gln Ser Thr Leu Asp Ile Ala Asn Lys
        50                  55                  60

Asn Tyr His Glu Gly Gln Ile Ile Lys Arg Asn Arg Ser Lys Trp Met
65              70                  75                  80

Val His Leu Asp Asp Lys Lys Glu Asn Ile Val His Leu Leu Pro Ile
                85                  90                  95

Ile Lys Ala Lys Lys Ser Val Asn Ile Val Thr Tyr Phe Pro Gly Asn
            100                 105                 110

Lys Ile Gly Ala Ile Lys Lys Gly Gln Pro Leu His Phe Gln Leu Ser
        115                 120                 125

Asn Ala Asn Gly Thr Thr Asp Arg Leu Val Gly Glu Val Lys Glu Val
    130                 135                 140

Gly Ile Tyr Pro Val Asn Leu His Gly Asn Asn Val Tyr Glu Val Ile
145                 150                 155                 160

Cys Lys Ala Lys Leu Asp Lys Asp Val Lys Tyr Gly Met Glu Gly Asn
                165                 170                 175

Ala Pro Ile Ile Thr Gly Lys Ser Thr Tyr Phe Glu Tyr Phe Lys Asp
            180                 185                 190

Lys Ile Leu Asn
        195

<210> SEQ ID NO 81
<211> LENGTH: 2160
<212> TYPE: DNA
<213> ORGANISM: Lactobacillus acidophilus
<220> FEATURE:
<221> NAME/KEY: CDS
<222> LOCATION: (1)..(2160)
<223> OTHER INFORMATION: PlnG ORF# 1796

<400> SEQUENCE: 81 atg cta cta caa tat aaa tca atc tat gta cca caa gta gac gaa tca    48
Met Leu Leu Gln Tyr Lys Ser Ile Tyr Val Pro Gln Val Asp Glu Ser
1               5                   10                  15 gat tgc ggt gtt gcc tgt ttg gct atg att ctt aag aaa tat cat tct    96
Asp Cys Gly Val Ala Cys Leu Ala Met Ile Leu Lys Lys Tyr His Ser
            20                  25                  30
```

```
aga gta tca tta gca cat ttg cgc cat tca gca cgt act aat tta gaa    144
Arg Val Ser Leu Ala His Leu Arg His Ser Ala Arg Thr Asn Leu Glu
         35                  40                  45 gga act acc gcc ctt ggc tta gtc aaa aca gca caa aca ttt aat ttg    192
Gly Thr Thr Ala Leu Gly Leu Val Lys Thr Ala Gln Thr Phe Asn Leu
 50                  55                  60 aaa act gaa gcg gtc aaa gct gat atg tcc ttg ttt gat cca gat acg    240
Lys Thr Glu Ala Val Lys Ala Asp Met Ser Leu Phe Asp Pro Asp Thr
65                  70                  75                  80 gat atc caa tat cct ttt att gtt cat gtc tta aaa caa ggc gaa tta    288
Asp Ile Gln Tyr Pro Phe Ile Val His Val Leu Lys Gln Gly Glu Leu
                 85                  90                  95 ctc cac tat tat gtt gta ctt aaa gca act aaa aat tat tta gta att    336
Leu His Tyr Tyr Val Val Leu Lys Ala Thr Lys Asn Tyr Leu Val Ile
            100                 105                 110 gct gat cca gat cct agc gtt ggt tta acg aaa atg tct aaa gaa aaa    384
Ala Asp Pro Asp Pro Ser Val Gly Leu Thr Lys Met Ser Lys Glu Lys
        115                 120                 125 ttc tct caa gaa tgg act ggt att gcc ctt ttt atg gtt cct aat gac    432
Phe Ser Gln Glu Trp Thr Gly Ile Ala Leu Phe Met Val Pro Asn Asp
130                 135                 140 gat ttt gag cca gtt aag gag aaa aaa cga aat ctt tgg tcg ttg ttt    480
Asp Phe Glu Pro Val Lys Glu Lys Lys Arg Asn Leu Trp Ser Leu Phe
145                 150                 155                 160 cca tat atg ttc aag caa aag aaa tta gtt act aat att att ttg gcc    528
Pro Tyr Met Phe Lys Gln Lys Lys Leu Val Thr Asn Ile Ile Leu Ala
                165                 170                 175 gcc ctt tta atg aca att att agt att tgt agt tca tat ttc tta caa    576
Ala Leu Leu Met Thr Ile Ile Ser Ile Cys Ser Ser Tyr Phe Leu Gln
            180                 185                 190 ggt tta att gat act tat att cct aat ggc aca tat caa acc tta tca    624
Gly Leu Ile Asp Thr Tyr Ile Pro Asn Gly Thr Tyr Gln Thr Leu Ser
        195                 200                 205 att cta gcc atc ggt tta ttg ata gca tat gtc ttt aat tcc atc ttt    672
Ile Leu Ala Ile Gly Leu Leu Ile Ala Tyr Val Phe Asn Ser Ile Phe
210                 215                 220 tct tat ggt caa aac ttt ttg tta aat atc tta gga caa cga tta agt    720
Ser Tyr Gly Gln Asn Phe Leu Leu Asn Ile Leu Gly Gln Arg Leu Ser
225                 230                 235                 240 att gat ctt aat tta caa tat att cgc cat att ttt gaa tta cca atg    768
Ile Asp Leu Asn Leu Gln Tyr Ile Arg His Ile Phe Glu Leu Pro Met
                245                 250                 255 gaa ttt ttt gtg act cgt aga aca ggt gaa atc act tct aga ttc tct    816
Glu Phe Phe Val Thr Arg Arg Thr Gly Glu Ile Thr Ser Arg Phe Ser
            260                 265                 270 gat gct agt cga att att gac gcc tta gct agt aca gtt att tca tta    864
Asp Ala Ser Arg Ile Ile Asp Ala Leu Ala Ser Thr Val Ile Ser Leu
        275                 280                 285 ttt ctt gac ctt tca att gta att gta atg gga att gtt ttg gca att    912
Phe Leu Asp Leu Ser Ile Val Ile Val Met Gly Ile Val Leu Ala Ile
290                 295                 300 caa aac tct act tta ttc atg att act ttg tta gca ctg cca gta tac    960
Gln Asn Ser Thr Leu Phe Met Ile Thr Leu Leu Ala Leu Pro Val Tyr
305                 310                 315                 320 gct gta gtg att ctt agc ttt tct aag aaa ttt gaa aag ctg aac aat   1008
Ala Val Val Ile Leu Ser Phe Ser Lys Lys Phe Glu Lys Leu Asn Asn
                325                 330                 335 gat cag atg gaa agt aat gca gtt tta agt tct tca gta att gag gat   1056
Asp Gln Met Glu Ser Asn Ala Val Leu Ser Ser Ser Val Ile Glu Asp
            340                 345                 350
```

```
att caa ggg att gaa acg atc aag gct tta aat agt gaa cag aca cgg    1104
Ile Gln Gly Ile Glu Thr Ile Lys Ala Leu Asn Ser Glu Gln Thr Arg
        355                 360                 365 tac cgt aag att gat agt caa ttt gtc gat tat cta aag aaa tcc ttt    1152
Tyr Arg Lys Ile Asp Ser Gln Phe Val Asp Tyr Leu Lys Lys Ser Phe
370                 375                 380 cgt tac agt aaa act gaa tct ttg cag tca gct cta aag act ttc att    1200
Arg Tyr Ser Lys Thr Glu Ser Leu Gln Ser Ala Leu Lys Thr Phe Ile
385                 390                 395                 400 caa ctg tct ctc aat gtg att atc ctt tgg gta gga gcc aaa gtt gta    1248
Gln Leu Ser Leu Asn Val Ile Ile Leu Trp Val Gly Ala Lys Val Val
            405                 410                 415 atg aac ggt cag atg agt atc ggt caa tta atg aca ttt aat gca ttg    1296
Met Asn Gly Gln Met Ser Ile Gly Gln Leu Met Thr Phe Asn Ala Leu
            420                 425                 430 cta tca tat ttt gta gat cca ctt cag agt att att aat ctt cag cca    1344
Leu Ser Tyr Phe Val Asp Pro Leu Gln Ser Ile Ile Asn Leu Gln Pro
        435                 440                 445 acc tta cag tct gct aat gta gct caa aat cga ttg aat gaa gta tac    1392
Thr Leu Gln Ser Ala Asn Val Ala Gln Asn Arg Leu Asn Glu Val Tyr
450                 455                 460 atg gtt aag agc gag ttt cag aaa gat gtc cag att agg gat gca aag    1440
Met Val Lys Ser Glu Phe Gln Lys Asp Val Gln Ile Arg Asp Ala Lys
465                 470                 475                 480 caa tta gta gga gat att gaa tac cat aat gtc gat tat cat tat ggt    1488
Gln Leu Val Gly Asp Ile Glu Tyr His Asn Val Asp Tyr His Tyr Gly
            485                 490                 495 tat gga gtt gat gtt tta aag gac gtt aat tta aag att aag cag aat    1536
Tyr Gly Val Asp Val Leu Lys Asp Val Asn Leu Lys Ile Lys Gln Asn
            500                 505                 510 gat aag ttg gcg atc gta gga atg agt ggc tca ggc aag tca acc atg    1584
Asp Lys Leu Ala Ile Val Gly Met Ser Gly Ser Gly Lys Ser Thr Met
        515                 520                 525 gta aag ctt tta gtt gat ttt ttc tct cca agc aaa ggc aag tta act    1632
Val Lys Leu Leu Val Asp Phe Phe Ser Pro Ser Lys Gly Lys Leu Thr
530                 535                 540 ttt aat gga ttt gat tct act aaa gta gat aag cat gtc tta cgg tca    1680
Phe Asn Gly Phe Asp Ser Thr Lys Val Asp Lys His Val Leu Arg Ser
545                 550                 555                 560 tac gta aac tat gtt ccc caa aca cca tac atc ttt tca gga aca atc    1728
Tyr Val Asn Tyr Val Pro Gln Thr Pro Tyr Ile Phe Ser Gly Thr Ile
            565                 570                 575 aaa gaa aat ctg ctc tta ggt agt cga cca gat att aca gaa gaa gat    1776
Lys Glu Asn Leu Leu Leu Gly Ser Arg Pro Asp Ile Thr Glu Glu Asp
            580                 585                 590 gta ttg aaa gct tgc cag ata gca gag att gag tct gaa atc gag caa    1824
Val Leu Lys Ala Cys Gln Ile Ala Glu Ile Glu Ser Glu Ile Glu Gln
        595                 600                 605 tta cca ttg caa ttt gaa act aag atg gat gaa aat gcc aag att tta    1872
Leu Pro Leu Gln Phe Glu Thr Lys Met Asp Glu Asn Ala Lys Ile Leu
610                 615                 620 tcc ggt gga caa aag caa agg tta act att gca cgt gca tta ttg tca    1920
Ser Gly Gly Gln Lys Gln Arg Leu Thr Ile Ala Arg Ala Leu Leu Ser
625                 630                 635                 640 cca gct aag gtt ttg att ttt gat gaa gcc aca agt gga ctt gat acg    1968
Pro Ala Lys Val Leu Ile Phe Asp Glu Ala Thr Ser Gly Leu Asp Thr
            645                 650                 655 att acg gag aaa aaa gta gta gat aac tta atg aaa ttg aag aat aaa    2016
Ile Thr Glu Lys Lys Val Val Asp Asn Leu Met Lys Leu Lys Asn Lys
```

```
                         660                 665                 670
act att att ttt atc gcc cat cgt tta gca att gcg caa agg act aat   2064
Thr Ile Ile Phe Ile Ala His Arg Leu Ala Ile Ala Gln Arg Thr Asn
            675                 680                 685 aat att gtg gtt gta gac cat ggt caa att gtt gag caa gga agc cat   2112
Asn Ile Val Val Val Asp His Gly Gln Ile Val Glu Gln Gly Ser His
        690                 695                 700 gat gaa tta atg caa aaa cat gga ttc tat tat aac tta gtt gaa aat   2160
Asp Glu Leu Met Gln Lys His Gly Phe Tyr Tyr Asn Leu Val Glu Asn
705                 710                 715                 720
```

<210> SEQ ID NO 82
<211> LENGTH: 720
<212> TYPE: PRT
<213> ORGANISM: Lactobacillus acidophilus

<400> SEQUENCE: 82

```
Met Leu Leu Gln Tyr Lys Ser Ile Tyr Val Pro Gln Val Asp Glu Ser
1               5                   10                  15

Asp Cys Gly Val Ala Cys Leu Ala Met Ile Leu Lys Lys Tyr His Ser
            20                  25                  30

Arg Val Ser Leu Ala His Leu Arg His Ser Ala Arg Thr Asn Leu Glu
        35                  40                  45

Gly Thr Thr Ala Leu Gly Leu Val Lys Thr Ala Gln Thr Phe Asn Leu
    50                  55                  60

Lys Thr Glu Ala Val Lys Ala Asp Met Ser Leu Phe Asp Pro Asp Thr
65                  70                  75                  80

Asp Ile Gln Tyr Pro Phe Ile Val His Val Leu Lys Gln Gly Glu Leu
                85                  90                  95

Leu His Tyr Tyr Val Val Leu Lys Ala Thr Lys Asn Tyr Leu Val Ile
            100                 105                 110

Ala Asp Pro Asp Pro Ser Val Gly Leu Thr Lys Met Ser Lys Glu Lys
        115                 120                 125

Phe Ser Gln Glu Trp Thr Gly Ile Ala Leu Phe Met Val Pro Asn Asp
    130                 135                 140

Asp Phe Glu Pro Val Lys Glu Lys Lys Arg Asn Leu Trp Ser Leu Phe
145                 150                 155                 160

Pro Tyr Met Phe Lys Gln Lys Lys Leu Val Thr Asn Ile Ile Leu Ala
                165                 170                 175

Ala Leu Leu Met Thr Ile Ile Ser Ile Cys Ser Ser Tyr Phe Leu Gln
            180                 185                 190

Gly Leu Ile Asp Thr Tyr Ile Pro Asn Gly Thr Tyr Gln Thr Leu Ser
        195                 200                 205

Ile Leu Ala Ile Gly Leu Leu Ile Ala Tyr Val Phe Asn Ser Ile Phe
    210                 215                 220

Ser Tyr Gly Gln Asn Phe Leu Leu Asn Ile Leu Gly Gln Arg Leu Ser
225                 230                 235                 240

Ile Asp Leu Asn Leu Gln Tyr Ile Arg His Ile Phe Glu Leu Pro Met
                245                 250                 255

Glu Phe Phe Val Thr Arg Arg Thr Gly Glu Ile Thr Ser Arg Phe Ser
            260                 265                 270

Asp Ala Ser Arg Ile Ile Asp Ala Leu Ala Ser Thr Val Ile Ser Leu
        275                 280                 285

Phe Leu Asp Leu Ser Ile Val Ile Val Met Gly Ile Val Leu Ala Ile
    290                 295                 300
```

```
Gln Asn Ser Thr Leu Phe Met Ile Thr Leu Leu Ala Leu Pro Val Tyr
305                 310                 315                 320

Ala Val Val Ile Leu Ser Phe Ser Lys Lys Phe Glu Lys Leu Asn Asn
                325                 330                 335

Asp Gln Met Glu Ser Asn Ala Val Leu Ser Ser Val Ile Glu Asp
            340                 345                 350

Ile Gln Gly Ile Glu Thr Ile Lys Ala Leu Asn Ser Glu Gln Thr Arg
        355                 360                 365

Tyr Arg Lys Ile Asp Ser Gln Phe Val Asp Tyr Leu Lys Lys Ser Phe
    370                 375                 380

Arg Tyr Ser Lys Thr Glu Ser Leu Gln Ser Ala Leu Lys Thr Phe Ile
385                 390                 395                 400

Gln Leu Ser Leu Asn Val Ile Ile Leu Trp Val Gly Ala Lys Val Val
                405                 410                 415

Met Asn Gly Gln Met Ser Ile Gly Gln Leu Met Thr Phe Asn Ala Leu
                420                 425                 430

Leu Ser Tyr Phe Val Asp Pro Leu Gln Ser Ile Ile Asn Leu Gln Pro
                435                 440                 445

Thr Leu Gln Ser Ala Asn Val Ala Gln Asn Arg Leu Asn Glu Val Tyr
    450                 455                 460

Met Val Lys Ser Glu Phe Gln Lys Asp Val Gln Ile Arg Asp Ala Lys
465                 470                 475                 480

Gln Leu Val Gly Asp Ile Glu Tyr His Asn Val Asp Tyr His Tyr Gly
                485                 490                 495

Tyr Gly Val Asp Val Leu Lys Asp Val Asn Leu Lys Ile Lys Gln Asn
            500                 505                 510

Asp Lys Leu Ala Ile Val Gly Met Ser Gly Ser Gly Lys Ser Thr Met
        515                 520                 525

Val Lys Leu Leu Val Asp Phe Phe Ser Pro Ser Lys Gly Lys Leu Thr
    530                 535                 540

Phe Asn Gly Phe Asp Ser Thr Lys Val Asp Lys His Val Leu Arg Ser
545                 550                 555                 560

Tyr Val Asn Tyr Val Pro Gln Thr Pro Tyr Ile Phe Ser Gly Thr Ile
                565                 570                 575

Lys Glu Asn Leu Leu Leu Gly Ser Arg Pro Asp Ile Thr Glu Glu Asp
                580                 585                 590

Val Leu Lys Ala Cys Gln Ile Ala Glu Ile Glu Ser Glu Ile Glu Gln
                595                 600                 605

Leu Pro Leu Gln Phe Glu Thr Lys Met Asp Glu Asn Ala Lys Ile Leu
    610                 615                 620

Ser Gly Gly Gln Lys Gln Arg Leu Thr Ile Ala Arg Ala Leu Leu Ser
625                 630                 635                 640

Pro Ala Lys Val Leu Ile Phe Asp Glu Ala Thr Ser Gly Leu Asp Thr
                645                 650                 655

Ile Thr Glu Lys Lys Val Val Asp Asn Leu Met Lys Leu Lys Asn Lys
                660                 665                 670

Thr Ile Ile Phe Ile Ala His Arg Leu Ala Ile Ala Gln Arg Thr Asn
            675                 680                 685

Asn Ile Val Val Asp His Gly Gln Ile Val Glu Gln Gly Ser His
            690                 695                 700

Asp Glu Leu Met Gln Lys His Gly Phe Tyr Tyr Asn Leu Val Glu Asn
705                 710                 715                 720
```

<210> SEQ ID NO 83
<211> LENGTH: 249
<212> TYPE: DNA
<213> ORGANISM: Lactobacillus acidophilus
<220> FEATURE:
<221> NAME/KEY: CDS
<222> LOCATION: (1)..(249)
<223> OTHER INFORMATION: Unknown ORF# 1797

<400> SEQUENCE: 83

```
atg gaa aag tta atg gta tta aat gaa gaa aaa ttg agt tat gta att        48
Met Glu Lys Leu Met Val Leu Asn Glu Glu Lys Leu Ser Tyr Val Ile
1               5                   10                  15 ggt gga gga aat cct aaa gta gca cat tgt gct agt caa att ggt aga        96
Gly Gly Gly Asn Pro Lys Val Ala His Cys Ala Ser Gln Ile Gly Arg
            20                  25                  30 tca acg gct tgg ggt gca gtt agc ggt gca gct act gga act gca gtt       144
Ser Thr Ala Trp Gly Ala Val Ser Gly Ala Ala Thr Gly Thr Ala Val
        35                  40                  45 ggt cag gca gtt ggt gca ttg ggt ggt gct ctt ttc ggt ggg agt atg       192
Gly Gln Ala Val Gly Ala Leu Gly Gly Ala Leu Phe Gly Gly Ser Met
    50                  55                  60 ggc gtt atc aaa ggc tca gca gca tgt gta agt tat tta acg cgt cat       240
Gly Val Ile Lys Gly Ser Ala Ala Cys Val Ser Tyr Leu Thr Arg His
65                  70                  75                  80 aga cat cat                                                           249
Arg His His
```

<210> SEQ ID NO 84
<211> LENGTH: 83
<212> TYPE: PRT
<213> ORGANISM: Lactobacillus acidophilus

<400> SEQUENCE: 84

```
Met Glu Lys Leu Met Val Leu Asn Glu Glu Lys Leu Ser Tyr Val Ile
1               5                   10                  15

Gly Gly Gly Asn Pro Lys Val Ala His Cys Ala Ser Gln Ile Gly Arg
            20                  25                  30

Ser Thr Ala Trp Gly Ala Val Ser Gly Ala Ala Thr Gly Thr Ala Val
        35                  40                  45

Gly Gln Ala Val Gly Ala Leu Gly Gly Ala Leu Phe Gly Gly Ser Met
    50                  55                  60

Gly Val Ile Lys Gly Ser Ala Ala Cys Val Ser Tyr Leu Thr Arg His
65                  70                  75                  80

Arg His His
```

<210> SEQ ID NO 85
<211> LENGTH: 141
<212> TYPE: DNA
<213> ORGANISM: Lactobacillus acidophilus
<220> FEATURE:
<221> NAME/KEY: CDS
<222> LOCATION: (1)..(141)
<223> OTHER INFORMATION: Unknown ORF# 1800

<400> SEQUENCE: 85

```
atg aag aag aaa gtt gtt aag aag act gtt ttg aag gaa aaa gaa tta        48
Met Lys Lys Lys Val Val Lys Lys Thr Val Leu Lys Glu Lys Glu Leu
1               5                   10                  15 act aag gtt gtt ggc ggg aaa aaa gca cca att tct ggt tat gta ggt        96
Thr Lys Val Val Gly Gly Lys Lys Ala Pro Ile Ser Gly Tyr Val Gly
            20                  25                  30
```

```
aga gga cta tgg gaa aac cta agt aat ata ttt aaa cat cac aag        141
Arg Gly Leu Trp Glu Asn Leu Ser Asn Ile Phe Lys His His Lys
        35                  40                  45

<210> SEQ ID NO 86
<211> LENGTH: 47
<212> TYPE: PRT
<213> ORGANISM: Lactobacillus acidophilus

<400> SEQUENCE: 86

Met Lys Lys Lys Val Val Lys Thr Val Leu Lys Glu Lys Glu Leu
1               5                   10                  15

Thr Lys Val Val Gly Gly Lys Lys Ala Pro Ile Ser Gly Tyr Val Gly
            20                  25                  30

Arg Gly Leu Trp Glu Asn Leu Ser Asn Ile Phe Lys His His Lys
        35                  40                  45

<210> SEQ ID NO 87
<211> LENGTH: 114
<212> TYPE: DNA
<213> ORGANISM: Lactobacillus acidophilus
<220> FEATURE:
<221> NAME/KEY: CDS
<222> LOCATION: (1)..(114)
<223> OTHER INFORMATION: Unknown ORF# 1801

<400> SEQUENCE: 87 ttg gca gta ttc ctc cat ggc gtc caa att ggt gga agt aga att aag    48
Leu Ala Val Phe Leu His Gly Val Gln Ile Gly Gly Ser Arg Ile Lys
1               5                   10                  15 caa gat gcc aga tcg gta cga aag tat gac cga att ggt atc ttt ttt    96
Gln Asp Ala Arg Ser Val Arg Lys Tyr Asp Arg Ile Gly Ile Phe Phe
            20                  25                  30 tat tcg ttt aaa agt gca                                            114
Tyr Ser Phe Lys Ser Ala
        35

<210> SEQ ID NO 88
<211> LENGTH: 38
<212> TYPE: PRT
<213> ORGANISM: Lactobacillus acidophilus

<400> SEQUENCE: 88

Leu Ala Val Phe Leu His Gly Val Gln Ile Gly Gly Ser Arg Ile Lys
1               5                   10                  15

Gln Asp Ala Arg Ser Val Arg Lys Tyr Asp Arg Ile Gly Ile Phe Phe
            20                  25                  30

Tyr Ser Phe Lys Ser Ala
        35

<210> SEQ ID NO 89
<211> LENGTH: 198
<212> TYPE: DNA
<213> ORGANISM: Lactobacillus acidophilus
<220> FEATURE:
<221> NAME/KEY: CDS
<222> LOCATION: (1)..(198)
<223> OTHER INFORMATION: Unknown ORF# 1802

<400> SEQUENCE: 89 gtg atg aaa atg aag ctt aga caa gaa caa ttg aat aga aaa gaa tta    48
Val Met Lys Met Lys Leu Arg Gln Glu Gln Leu Asn Arg Lys Glu Leu
1               5                   10                  15 agt cag gtt att ggt ggc cga aga gat atg atc ttg gta gcg ctt cct    96
Ser Gln Val Ile Gly Gly Arg Arg Asp Met Ile Leu Val Ala Leu Pro
```

```
Ser Gln Val Ile Gly Gly Arg Arg Asp Met Ile Leu Val Ala Leu Pro
        20                  25                  30 cat gct gta ggt cca gat ggt atg cca ggt agc ggt aga ggt ggt ggt    144
His Ala Val Gly Pro Asp Gly Met Pro Gly Ser Gly Arg Gly Gly Gly
        35                  40                  45 gct caa atg aga gcc att ggc agt att cct cca tgg cgt cca aat tgg    192
Ala Gln Met Arg Ala Ile Gly Ser Ile Pro Pro Trp Arg Pro Asn Trp
 50                  55                  60 tgg aag                                                              198
Trp Lys
 65
```

<210> SEQ ID NO 90
<211> LENGTH: 66
<212> TYPE: PRT
<213> ORGANISM: Lactobacillus acidophilus

<400> SEQUENCE: 90

```
Val Met Lys Met Lys Leu Arg Gln Glu Gln Leu Asn Arg Lys Glu Leu
 1               5                  10                  15

Ser Gln Val Ile Gly Gly Arg Arg Asp Met Ile Leu Val Ala Leu Pro
            20                  25                  30

His Ala Val Gly Pro Asp Gly Met Pro Gly Ser Gly Arg Gly Gly Gly
            35                  40                  45

Ala Gln Met Arg Ala Ile Gly Ser Ile Pro Pro Trp Arg Pro Asn Trp
 50                  55                  60

Trp Lys
 65
```

<210> SEQ ID NO 91
<211> LENGTH: 168
<212> TYPE: DNA
<213> ORGANISM: Lactobacillus acidophilus
<220> FEATURE:
<221> NAME/KEY: CDS
<222> LOCATION: (1)..(168)
<223> OTHER INFORMATION: Unknown ORF#1803

<400> SEQUENCE: 91

```
gtg aaa aat atg cag gaa tgg aag aag act acc tta agt gac aat gag     48
Val Lys Asn Met Gln Glu Trp Lys Lys Thr Thr Leu Ser Asp Asn Glu
 1               5                  10                  15 ttg att gac gta att ggt ggt tca gca aaa agc tat att cgt aga tta     96
Leu Ile Asp Val Ile Gly Gly Ser Ala Lys Ser Tyr Ile Arg Arg Leu
            20                  25                  30 gga cct gat ggt ggt tat ggc ggt cga gag agt aaa tta atc gct atg    144
Gly Pro Asp Gly Gly Tyr Gly Gly Arg Glu Ser Lys Leu Ile Ala Met
            35                  40                  45 gca gac atg att aga cga cgt att                                    168
Ala Asp Met Ile Arg Arg Arg Ile
 50                  55
```

<210> SEQ ID NO 92
<211> LENGTH: 56
<212> TYPE: PRT
<213> ORGANISM: Lactobacillus acidophilus

<400> SEQUENCE: 92

```
Val Lys Asn Met Gln Glu Trp Lys Lys Thr Thr Leu Ser Asp Asn Glu
 1               5                  10                  15

Leu Ile Asp Val Ile Gly Gly Ser Ala Lys Ser Tyr Ile Arg Arg Leu
            20                  25                  30
```

```
Gly Pro Asp Gly Gly Tyr Gly Gly Arg Glu Ser Lys Leu Ile Ala Met
            35                  40                  45

Ala Asp Met Ile Arg Arg Ile
 50                  55

<210> SEQ ID NO 93
<211> LENGTH: 633
<212> TYPE: DNA
<213> ORGANISM: Lactobacillus acidophilus
<220> FEATURE:
<221> NAME/KEY: CDS
<222> LOCATION: (1)..(633)
<223> OTHER INFORMATION: Hypothetical ORF# 1804

<400> SEQUENCE: 93 gtg aga ata atg aga act aga att gga cgg atg ttt ttt cgt tat aaa        48
Val Arg Ile Met Arg Thr Arg Ile Gly Arg Met Phe Phe Arg Tyr Lys
 1               5                  10                  15 aga cat agg ctc tct acc tgg tca gcg tta ggg atg ctt tta ttt ggt        96
Arg His Arg Leu Ser Thr Trp Ser Ala Leu Gly Met Leu Leu Phe Gly
                20                  25                  30 gta gca acc ttg gcg tta tgg att ttc aat atg cta cta ttc ttg cag       144
Val Ala Thr Leu Ala Leu Trp Ile Phe Asn Met Leu Leu Phe Leu Gln
            35                  40                  45 ttc gta ggt tat gct gca aca atc tac tac att att gat att gaa gca       192
Phe Val Gly Tyr Ala Ala Thr Ile Tyr Tyr Ile Ile Asp Ile Glu Ala
        50                  55                  60 ggg tat gcg gaa gaa aaa gta att ggt aat tcc caa cat cga tta agt       240
Gly Tyr Ala Glu Glu Lys Val Ile Gly Asn Ser Gln His Arg Leu Ser
 65                  70                  75                  80 aag tct gat cag ttc tgg ctc gga tta gct caa aca gtg act gca ata       288
Lys Ser Asp Gln Phe Trp Leu Gly Leu Ala Gln Thr Val Thr Ala Ile
                 85                  90                  95 atc ggt att gct gaa ctg gca gtg ttg atc tac tgt caa gtt act aat       336
Ile Gly Ile Ala Glu Leu Ala Val Leu Ile Tyr Cys Gln Val Thr Asn
            100                 105                 110 tat tat cac ttc atg ttg agt gca gta ttc ctt act ggg ttg tac ttt       384
Tyr Tyr His Phe Met Leu Ser Ala Val Phe Leu Thr Gly Leu Tyr Phe
        115                 120                 125 acg tac tgg act tgt ctc tat ggc tta tcc att tat caa gtc aag aga       432
Thr Tyr Trp Thr Cys Leu Tyr Gly Leu Ser Ile Tyr Gln Val Lys Arg
    130                 135                 140 aga gtt aac ata gct gct agg aaa tgg tta att ggt gaa att gta gct       480
Arg Val Asn Ile Ala Ala Arg Lys Trp Leu Ile Gly Glu Ile Val Ala
145                 150                 155                 160 ctt agc gtt atg gca gct gtt atg gtg aga att tat ttt gta caa aat       528
Leu Ser Val Met Ala Ala Val Met Val Arg Ile Tyr Phe Val Gln Asn
                165                 170                 175 tgg gta ttc ttt gta att gta ata gga att gcg att att gaa tgg atc       576
Trp Val Phe Phe Val Ile Val Ile Gly Ile Ala Ile Ile Glu Trp Ile
            180                 185                 190 gtc agt tgg cgt aat tat tat gta att aaa aat ggc gat cgg aat gca       624
Val Ser Trp Arg Asn Tyr Tyr Val Ile Lys Asn Gly Asp Arg Asn Ala
        195                 200                 205 atg gga tac                                                            633
Met Gly Tyr
    210

<210> SEQ ID NO 94
<211> LENGTH: 211
<212> TYPE: PRT
```

<210> ORGANISM: Lactobacillus acidophilus

<400> SEQUENCE: 94

```
Val Arg Ile Met Arg Thr Arg Ile Gly Arg Met Phe Phe Arg Tyr Lys
1               5                   10                  15
Arg His Arg Leu Ser Thr Trp Ser Ala Leu Gly Met Leu Leu Phe Gly
            20                  25                  30
Val Ala Thr Leu Ala Leu Trp Ile Phe Asn Met Leu Leu Phe Leu Gln
        35                  40                  45
Phe Val Gly Tyr Ala Ala Thr Ile Tyr Tyr Ile Ile Asp Ile Glu Ala
    50                  55                  60
Gly Tyr Ala Glu Glu Lys Val Ile Gly Asn Ser Gln His Arg Leu Ser
65                  70                  75                  80
Lys Ser Asp Gln Phe Trp Leu Gly Leu Ala Gln Thr Val Thr Ala Ile
                85                  90                  95
Ile Gly Ile Ala Glu Leu Ala Val Leu Ile Tyr Cys Gln Val Thr Asn
            100                 105                 110
Tyr Tyr His Phe Met Leu Ser Ala Val Phe Leu Thr Gly Leu Tyr Phe
        115                 120                 125
Thr Tyr Trp Thr Cys Leu Tyr Gly Leu Ser Ile Tyr Gln Val Lys Arg
    130                 135                 140
Arg Val Asn Ile Ala Ala Arg Lys Trp Leu Ile Gly Glu Ile Val Ala
145                 150                 155                 160
Leu Ser Val Met Ala Ala Val Met Val Arg Ile Tyr Phe Val Gln Asn
                165                 170                 175
Trp Val Phe Phe Val Ile Val Ile Gly Ile Ala Ile Ile Glu Trp Ile
            180                 185                 190
Val Ser Trp Arg Asn Tyr Tyr Val Ile Lys Asn Gly Asp Arg Asn Ala
        195                 200                 205
Met Gly Tyr
    210
```

<210> SEQ ID NO 95
<211> LENGTH: 174
<212> TYPE: DNA
<213> ORGANISM: Lactobacillus acidophilus
<220> FEATURE:
<221> NAME/KEY: CDS
<222> LOCATION: (1)..(174)
<223> OTHER INFORMATION: Unknown ORF# 1805

<400> SEQUENCE: 95

```
atg aaa aaa ttg aaa gta atg aat aat ggt gaa tta gaa aaa gta atc    48
Met Lys Lys Leu Lys Val Met Asn Asn Gly Glu Leu Glu Lys Val Ile
1               5                   10                  15 ggt ggt tca tta tat gaa atg aag aat tcg gta cca cgt ttg tta ggt    96
Gly Gly Ser Leu Tyr Glu Met Lys Asn Ser Val Pro Arg Leu Leu Gly
            20                  25                  30 cca gat gga atg gaa ggt agt atg ggt ggt agt act gga ggt att caa   144
Pro Asp Gly Met Glu Gly Ser Met Gly Gly Ser Thr Gly Gly Ile Gln
        35                  40                  45 tcg ttt cgt cat ttc cca gga ttc gga aga                           174
Ser Phe Arg His Phe Pro Gly Phe Gly Arg
    50                  55
```

<210> SEQ ID NO 96
<211> LENGTH: 58
<212> TYPE: PRT
<213> ORGANISM: Lactobacillus acidophilus

<400> SEQUENCE: 96

| Met | Lys | Lys | Leu | Lys | Val | Met | Asn | Asn | Gly | Glu | Leu | Glu | Lys | Val | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Gly | Ser | Leu | Tyr | Glu | Met | Lys | Asn | Ser | Val | Pro | Arg | Leu | Leu | Gly |
|     |     |     | 20  |     |     |     |     | 25  |     |     |     |     | 30  |     |     |

| Pro | Asp | Gly | Met | Glu | Gly | Ser | Met | Gly | Gly | Ser | Thr | Gly | Gly | Ile | Gln |
|     |     | 35  |     |     |     |     | 40  |     |     |     |     | 45  |     |     |     |

| Ser | Phe | Arg | His | Phe | Pro | Gly | Phe | Gly | Arg |
|     | 50  |     |     |     |     | 55  |     |     |     |

<210> SEQ ID NO 97
<211> LENGTH: 591
<212> TYPE: DNA
<213> ORGANISM: Lactobacillus acidophilus
<220> FEATURE:
<221> NAME/KEY: CDS
<222> LOCATION: (1)..(591)
<223> OTHER INFORMATION: Hypothetical ORF# 1808

<400> SEQUENCE: 97

```
gtg cta ctg ctc ctt ttc tca gct tat ttc cca ttt ttt aat gtg ttt      48
Val Leu Leu Leu Leu Phe Ser Ala Tyr Phe Pro Phe Phe Asn Val Phe
1               5                   10                  15 ttg ggg ata gca caa aca ccg gta caa atc ttt aac tgg gat ttt agt      96
Leu Gly Ile Ala Gln Thr Pro Val Gln Ile Phe Asn Trp Asp Phe Ser
            20                  25                  30 act ttt gaa gta acg ttg act gga ttt ctt tca gca gta gaa gcc gga     144
Thr Phe Glu Val Thr Leu Thr Gly Phe Leu Ser Ala Val Glu Ala Gly
        35                  40                  45 atc atg gaa gaa acg caa cgt tgt tta gat att gtt gta ctt tta ttt     192
Ile Met Glu Glu Thr Gln Arg Cys Leu Asp Ile Val Val Leu Leu Phe
    50                  55                  60 gtc ttt cgt aat ttt aaa gga aaa gta gtg tgg gct acc gta att tct     240
Val Phe Arg Asn Phe Lys Gly Lys Val Val Trp Ala Thr Val Ile Ser
65                  70                  75                  80 tca cta tta ttt agc ttg gat cat ttg act aat ttg ggt tca acg caa    288
Ser Leu Leu Phe Ser Leu Asp His Leu Thr Asn Leu Gly Ser Thr Gln
                85                  90                  95 ttt ggc gtt ctt tat aat ttg aca aaa gtt gaa cag caa atg atc tat    336
Phe Gly Val Leu Tyr Asn Leu Thr Lys Val Glu Gln Gln Met Ile Tyr
            100                 105                 110 acc ttt gga ttt ggc atg tta gct gca gtt ttg tac tta tat act ggt    384
Thr Phe Gly Phe Gly Met Leu Ala Ala Val Leu Tyr Leu Tyr Thr Gly
        115                 120                 125 aaa tta tgg tta agc atg ttg gtt cac ttt ggc tta gat ttc att gtc    432
Lys Leu Trp Leu Ser Met Leu Val His Phe Gly Leu Asp Phe Ile Val
    130                 135                 140 ttt agt gaa acg cca tta act gtg tcg ata tct cca ttt ttt gat aat    480
Phe Ser Glu Thr Pro Leu Thr Val Ser Ile Ser Pro Phe Phe Asp Asn
145                 150                 155                 160 tgg gct tgt gct ttt att gta atg gca gca tca tcc ttg gta gcc atc    528
Trp Ala Cys Ala Phe Ile Val Met Ala Ala Ser Ser Leu Val Ala Ile
                165                 170                 175 ttc atg tta tta gga aaa aga tgt aag ttt atg gat gat aat gca gat    576
Phe Met Leu Leu Gly Lys Arg Cys Lys Phe Met Asp Asp Asn Ala Asp
            180                 185                 190 aga att atg aaa atg                                                 591
Arg Ile Met Lys Met
            195
```

<210> SEQ ID NO 98
<211> LENGTH: 197
<212> TYPE: PRT
<213> ORGANISM: Lactobacillus acidophilus

<400> SEQUENCE: 98

| | | | | | | | | | | | | | | |
|---|---|---|---|---|---|---|---|---|---|---|---|---|---|---|
| Val | Leu | Leu | Leu | Leu | Phe | Ser | Ala | Tyr | Phe | Pro | Phe | Asn | Val | Phe |
| 1 | | | | 5 | | | | | 10 | | | | | 15 |

| | | | | | | | | | | | | | | |
|---|---|---|---|---|---|---|---|---|---|---|---|---|---|---|
| Leu | Gly | Ile | Ala | Gln | Thr | Pro | Val | Gln | Ile | Phe | Asn | Trp | Asp | Phe | Ser |
| | | | 20 | | | | | 25 | | | | | 30 | | |

Thr Phe Glu Val Thr Leu Thr Gly Phe Leu Ser Ala Val Glu Ala Gly
                35                  40                  45

Ile Met Glu Glu Thr Gln Arg Cys Leu Asp Ile Val Val Leu Leu Phe
    50                  55                  60

Val Phe Arg Asn Phe Lys Gly Lys Val Val Trp Ala Thr Val Ile Ser
65                  70                  75                  80

Ser Leu Leu Phe Ser Leu Asp His Leu Thr Asn Leu Gly Ser Thr Gln
                85                  90                  95

Phe Gly Val Leu Tyr Asn Leu Thr Lys Val Glu Gln Gln Met Ile Tyr
            100                 105                 110

Thr Phe Gly Phe Gly Met Leu Ala Ala Val Leu Tyr Leu Tyr Thr Gly
        115                 120                 125

Lys Leu Trp Leu Ser Met Leu Val His Phe Gly Leu Asp Phe Ile Val
    130                 135                 140

Phe Ser Glu Thr Pro Leu Thr Val Ser Ile Ser Pro Phe Phe Asp Asn
145                 150                 155                 160

Trp Ala Cys Ala Phe Ile Val Met Ala Ala Ser Ser Leu Val Ala Ile
                165                 170                 175

Phe Met Leu Leu Gly Lys Arg Cys Lys Phe Met Asp Asp Asn Ala Asp
            180                 185                 190

Arg Ile Met Lys Met
        195

<210> SEQ ID NO 99
<211> LENGTH: 789
<212> TYPE: DNA
<213> ORGANISM: Lactobacillus acidophilus
<220> FEATURE:
<221> NAME/KEY: CDS
<222> LOCATION: (1)..(789)
<223> OTHER INFORMATION: Hypothetical ORF# 1809

<400> SEQUENCE: 99

```
ttg ttg gcg gat aag aat aat tcg gaa aag ttg aac cgc ttg aga ata       48
Leu Leu Ala Asp Lys Asn Asn Ser Glu Lys Leu Asn Arg Leu Arg Ile
1               5                   10                  15 aat ctt tac caa att agt ata ttt tta agc aaa att agt ctt tta tgg       96
Asn Leu Tyr Gln Ile Ser Ile Phe Leu Ser Lys Ile Ser Leu Leu Trp
                20                  25                  30 cgg ttt tgc ttt ttt tgt tat ata ttt cta att aaa aag ggg atg tta      144
Arg Phe Cys Phe Phe Cys Tyr Ile Phe Leu Ile Lys Lys Gly Met Leu
            35                  40                  45 aaa gtg agt caa aaa gcg tgg aat aaa att ttc aat gtt gaa tta att      192
Lys Val Ser Gln Lys Ala Trp Asn Lys Ile Phe Asn Val Glu Leu Ile
        50                  55                  60 att ggt att gta tgg ata gtt ttg ttt agt ttt cat cct gaa aga tca      240
Ile Gly Ile Val Trp Ile Val Leu Phe Ser Phe His Pro Glu Arg Ser
65                  70                  75                  80
```

```
ttt ccg ata tat ttg cct gta ata aat tgg gta ttt ctg gca att cta      288
Phe Pro Ile Tyr Leu Pro Val Ile Asn Trp Val Phe Leu Ala Ile Leu
            85                  90                  95 gta gtg ctt ctg att tta tcc aca gta cgt aaa aag aat cgc cat att      336
Val Val Leu Leu Ile Leu Ser Thr Val Arg Lys Lys Asn Arg His Ile
            100                 105                 110 caa acc acg att agt gta tta agc gca ctt gca ttg cct ttc aca ttt      384
Gln Thr Thr Ile Ser Val Leu Ser Ala Leu Ala Leu Pro Phe Thr Phe
            115                 120                 125 aac aag cta atc caa ggc ata gtt act agt tta aat act ata ttt gca      432
Asn Lys Leu Ile Gln Gly Ile Val Thr Ser Leu Asn Thr Ile Phe Ala
            130                 135                 140 tca tgg gca ccc ttc ttt tct att gtc ggt tgc ttg gca ttg tta cta      480
Ser Trp Ala Pro Phe Phe Ser Ile Val Gly Cys Leu Ala Leu Leu Leu
145                 150                 155                 160 gtt tcg atc ccc atg gtt aag gca agc ttg cct gct gta aag aat tgg      528
Val Ser Ile Pro Met Val Lys Ala Ser Leu Pro Ala Val Lys Asn Trp
            165                 170                 175 ata tta cgt tta ata gtc gtt gaa ggc ttg gga cta agt caa tta gct      576
Ile Leu Arg Leu Ile Val Val Glu Gly Leu Gly Leu Ser Gln Leu Ala
            180                 185                 190 ccc gca tta aaa ttc tat tgt gcg ccc aaa tat gta agt gaa cta ctt      624
Pro Ala Leu Lys Phe Tyr Cys Ala Pro Lys Tyr Val Ser Glu Leu Leu
            195                 200                 205 gaa tct ggt ctt ata aat gca ctt gcc atg ttc att ctg gca ttc ttt      672
Glu Ser Gly Leu Ile Asn Ala Leu Ala Met Phe Ile Leu Ala Phe Phe
            210                 215                 220 att ttt aaa gca tgg gga tta aaa ttt gaa tgg aat ttg aaa ttt atc      720
Ile Phe Lys Ala Trp Gly Leu Lys Phe Glu Trp Asn Leu Lys Phe Ile
225                 230                 235                 240 aaa act aag aat ttt caa tgg tgg gcc att agt gct act gct cct ttt      768
Lys Thr Lys Asn Phe Gln Trp Trp Ala Ile Ser Ala Thr Ala Pro Phe
            245                 250                 255 ctc agc tta ttt ccc att ttt                                          789
Leu Ser Leu Phe Pro Ile Phe
            260
```

<210> SEQ ID NO 100
<211> LENGTH: 263
<212> TYPE: PRT
<213> ORGANISM: Lactobacillus acidophilus

<400> SEQUENCE: 100

```
Leu Leu Ala Asp Lys Asn Asn Ser Glu Lys Leu Asn Arg Leu Arg Ile
1               5                   10                  15

Asn Leu Tyr Gln Ile Ser Ile Phe Leu Ser Lys Ile Ser Leu Leu Trp
            20                  25                  30

Arg Phe Cys Phe Phe Cys Tyr Ile Phe Leu Ile Lys Lys Gly Met Leu
        35                  40                  45

Lys Val Ser Gln Lys Ala Trp Asn Lys Ile Phe Asn Val Glu Leu Ile
    50                  55                  60

Ile Gly Ile Val Trp Ile Val Leu Phe Ser Phe His Pro Glu Arg Ser
65                  70                  75                  80

Phe Pro Ile Tyr Leu Pro Val Ile Asn Trp Val Phe Leu Ala Ile Leu
            85                  90                  95

Val Val Leu Leu Ile Leu Ser Thr Val Arg Lys Lys Asn Arg His Ile
            100                 105                 110

Gln Thr Thr Ile Ser Val Leu Ser Ala Leu Ala Leu Pro Phe Thr Phe
            115                 120                 125
```

-continued

```
Asn Lys Leu Ile Gln Gly Ile Val Thr Ser Leu Asn Thr Ile Phe Ala
    130                 135                 140

Ser Trp Ala Pro Phe Phe Ser Ile Val Gly Cys Leu Ala Leu Leu Leu
145                 150                 155                 160

Val Ser Ile Pro Met Val Lys Ala Ser Leu Pro Ala Val Lys Asn Trp
                165                 170                 175

Ile Leu Arg Leu Ile Val Glu Gly Leu Gly Leu Ser Gln Leu Ala
            180                 185                 190

Pro Ala Leu Lys Phe Tyr Cys Ala Pro Lys Tyr Val Ser Glu Leu Leu
            195                 200                 205

Glu Ser Gly Leu Ile Asn Ala Leu Ala Met Phe Ile Leu Ala Phe Phe
    210                 215                 220

Ile Phe Lys Ala Trp Gly Leu Lys Phe Glu Trp Asn Leu Lys Phe Ile
225                 230                 235                 240

Lys Thr Lys Asn Phe Gln Trp Trp Ala Ile Ser Ala Thr Ala Pro Phe
                245                 250                 255

Leu Ser Leu Phe Pro Ile Phe
            260
```

<210> SEQ ID NO 101
<211> LENGTH: 1194
<212> TYPE: DNA
<213> ORGANISM: Lactobacillus acidophilus
<220> FEATURE:
<221> NAME/KEY: CDS
<222> LOCATION: (1)..(1194)
<223> OTHER INFORMATION: Hypothetical ORF# 1810

<400> SEQUENCE: 101

```
atg aaa aat aga att tat caa ttg att tta aaa att caa ttg ata gta      48
Met Lys Asn Arg Ile Tyr Gln Leu Ile Leu Lys Ile Gln Leu Ile Val
1               5                   10                  15 gga ata ctg ctc atg ctt tgc ctt aat ctg aat gtg gta cat aca ttt      96
Gly Ile Leu Leu Met Leu Cys Leu Asn Leu Asn Val Val His Thr Phe
            20                  25                  30 aag atg cct aaa cta gta tat cca act att cta tgt gca tta gta gta    144
Lys Met Pro Lys Leu Val Tyr Pro Thr Ile Leu Cys Ala Leu Val Val
        35                  40                  45 ata ttt gtt ttg act ctc ttt gaa aat aaa aac cgt tat ata cag gca    192
Ile Phe Val Leu Thr Leu Phe Glu Asn Lys Asn Arg Tyr Ile Gln Ala
    50                  55                  60 gcg gca aaa tgg ctt ggc gtt cta gca tta cca tat gca tct aat ttc    240
Ala Ala Lys Trp Leu Gly Val Leu Ala Leu Pro Tyr Ala Ser Asn Phe
65                  70                  75                  80 tta gtt tat act gga att tca gtt ctt aat att gca ttt cca agc tat    288
Leu Val Tyr Thr Gly Ile Ser Val Leu Asn Ile Ala Phe Pro Ser Tyr
                85                  90                  95 gca atg ttt ttc tca atc ata ggc tgt att ctt tta ctt gta gta aat    336
Ala Met Phe Phe Ser Ile Ile Gly Cys Ile Leu Leu Leu Val Val Asn
            100                 105                 110 att ccc tgg gta atg gtt gat ttg ccg ata gta aag aat ggt ttt ctc    384
Ile Pro Trp Val Met Val Asp Leu Pro Ile Val Lys Asn Gly Phe Leu
        115                 120                 125 cgt gtg cta agt atc gct ctt att gat atg agc ttt aca ttt aat gcc    432
Arg Val Leu Ser Ile Ala Leu Ile Asp Met Ser Phe Thr Phe Asn Ala
    130                 135                 140 aat gac ttt att aat ttg ccg gag tcg ctt cat ttt ctt gta tac gat    480
Asn Asp Phe Ile Asn Leu Pro Glu Ser Leu His Phe Leu Val Tyr Asp
145                 150                 155                 160
```

-continued

```
gcc gtg ata gtt gcc ata gaa atc ttt gtt tta ggc ttt ttt att acg      528
Ala Val Ile Val Ala Ile Glu Ile Phe Val Leu Gly Phe Phe Ile Thr
                165                 170                 175 aag gca tgg ggc ttg aaa ttc agt tgg aat ttg aag ttt gtt aaa aca      576
Lys Ala Trp Gly Leu Lys Phe Ser Trp Asn Leu Lys Phe Val Lys Thr
            180                 185                 190 agt aat ttt caa tta gga tcc tgg att gta tta att ctg gta atg atc      624
Ser Asn Phe Gln Leu Gly Ser Trp Ile Val Leu Ile Leu Val Met Ile
        195                 200                 205 tgg ctt att ttc ttt aat acg tat tta aat ctt gta aat aac tgg gca      672
Trp Leu Ile Phe Phe Asn Thr Tyr Leu Asn Leu Val Asn Asn Trp Ala
    210                 215                 220 gaa ttg ctt gct ttt tgg aac tgg aat agc ttt gaa att tca tat cac      720
Glu Leu Leu Ala Phe Trp Asn Trp Asn Ser Phe Glu Ile Ser Tyr His
225                 230                 235                 240 ttt act gca gat ata gtg agt ttt gca gct aga gcg ggt att tat gag      768
Phe Thr Ala Asp Ile Val Ser Phe Ala Ala Arg Ala Gly Ile Tyr Glu
                245                 250                 255 gaa atg ttt cgc gga cta gaa ata att gtt ttg ctt tat gct atg cgt      816
Glu Met Phe Arg Gly Leu Glu Ile Ile Val Leu Leu Tyr Ala Met Arg
            260                 265                 270 aac ttc aaa gac aga ata atg gtg gct gta gta ata tca gct att ttg      864
Asn Phe Lys Asp Arg Ile Met Val Ala Val Val Ile Ser Ala Ile Leu
        275                 280                 285 ttc agt tta ggg cat ttg agt aat ctg ggt act att acc aat ggt act      912
Phe Ser Leu Gly His Leu Ser Asn Leu Gly Thr Ile Thr Asn Gly Thr
    290                 295                 300 ttt tat tct gct gat atg atg gcg cag caa ctt ata tat gcg ttt ggt      960
Phe Tyr Ser Ala Asp Met Met Ala Gln Gln Leu Ile Tyr Ala Phe Gly
305                 310                 315                 320 ctg ggc ttg gcg ttt ggt gta ctg tat ttg tat act gga aaa tta tgg     1008
Leu Gly Leu Ala Phe Gly Val Leu Tyr Leu Tyr Thr Gly Lys Leu Trp
                325                 330                 335 cta ggg atg ctg atc cac ttt ttg tat gat tta gag act ttg agt act     1056
Leu Gly Met Leu Ile His Phe Leu Tyr Asp Leu Glu Thr Leu Ser Thr
            340                 345                 350 gat gtc aca aca ggc ttg ttt aca ggt tgg ccg gct tca att atg ttg     1104
Asp Val Thr Thr Gly Leu Phe Thr Gly Trp Pro Ala Ser Ile Met Leu
        355                 360                 365 tta atc att ggc gta gcg att ttt gtc tgg atg tta aca ggt aag aga     1152
Leu Ile Ile Gly Val Ala Ile Phe Val Trp Met Leu Thr Gly Lys Arg
    370                 375                 380 cgt aag ttc atg gaa gat aat gta gat cga att gtt ggc gga              1194
Arg Lys Phe Met Glu Asp Asn Val Asp Arg Ile Val Gly Gly
385                 390                 395

<210> SEQ ID NO 102
<211> LENGTH: 398
<212> TYPE: PRT
<213> ORGANISM: Lactobacillus acidophilus

<400> SEQUENCE: 102

Met Lys Asn Arg Ile Tyr Gln Leu Ile Leu Lys Ile Gln Leu Ile Val
1               5                   10                  15

Gly Ile Leu Leu Met Leu Cys Leu Asn Leu Asn Val Val His Thr Phe
            20                  25                  30

Lys Met Pro Lys Leu Val Tyr Pro Thr Ile Leu Cys Ala Leu Val Val
        35                  40                  45

Ile Phe Val Leu Thr Leu Phe Glu Asn Lys Asn Arg Tyr Ile Gln Ala
```

```
            50                  55                  60
Ala Ala Lys Trp Leu Gly Val Leu Ala Leu Pro Tyr Ala Ser Asn Phe
 65                  70                  75                  80

Leu Val Tyr Thr Gly Ile Ser Val Leu Asn Ile Ala Phe Pro Ser Tyr
                 85                  90                  95

Ala Met Phe Phe Ser Ile Ile Gly Cys Ile Leu Leu Leu Val Val Asn
                100                 105                 110

Ile Pro Trp Val Met Val Asp Leu Pro Ile Val Lys Asn Gly Phe Leu
                115                 120                 125

Arg Val Leu Ser Ile Ala Leu Ile Asp Met Ser Phe Thr Phe Asn Ala
                130                 135                 140

Asn Asp Phe Ile Asn Leu Pro Glu Ser Leu His Phe Leu Val Tyr Asp
145                 150                 155                 160

Ala Val Ile Val Ala Ile Glu Ile Phe Val Leu Gly Phe Phe Ile Thr
                165                 170                 175

Lys Ala Trp Gly Leu Lys Phe Ser Trp Asn Leu Lys Phe Val Lys Thr
                180                 185                 190

Ser Asn Phe Gln Leu Gly Ser Trp Ile Val Leu Ile Leu Val Met Ile
                195                 200                 205

Trp Leu Ile Phe Phe Asn Thr Tyr Leu Asn Leu Val Asn Asn Trp Ala
210                 215                 220

Glu Leu Leu Ala Phe Trp Asn Trp Asn Ser Phe Glu Ile Ser Tyr His
225                 230                 235                 240

Phe Thr Ala Asp Ile Val Ser Phe Ala Ala Arg Ala Gly Ile Tyr Glu
                245                 250                 255

Glu Met Phe Arg Gly Leu Glu Ile Ile Val Leu Leu Tyr Ala Met Arg
                260                 265                 270

Asn Phe Lys Asp Arg Ile Met Val Ala Val Ile Ser Ala Ile Leu
                275                 280                 285

Phe Ser Leu Gly His Leu Ser Asn Leu Gly Thr Ile Thr Asn Gly Thr
                290                 295                 300

Phe Tyr Ser Ala Asp Met Met Ala Gln Gln Leu Ile Tyr Ala Phe Gly
305                 310                 315                 320

Leu Gly Leu Ala Phe Gly Val Leu Tyr Leu Tyr Thr Gly Lys Leu Trp
                325                 330                 335

Leu Gly Met Leu Ile His Phe Leu Tyr Asp Leu Glu Thr Leu Ser Thr
                340                 345                 350

Asp Val Thr Thr Gly Leu Phe Thr Gly Trp Pro Ala Ser Ile Met Leu
                355                 360                 365

Leu Ile Ile Gly Val Ala Ile Phe Val Trp Met Leu Thr Gly Lys Arg
370                 375                 380

Arg Lys Phe Met Glu Asp Asn Val Asp Arg Ile Val Gly Gly
385                 390                 395
```

<210> SEQ ID NO 103
<211> LENGTH: 309
<212> TYPE: DNA
<213> ORGANISM: Lactobacillus acidophilus
<220> FEATURE:
<221> NAME/KEY: CDS
<222> LOCATION: (1)..(309)
<223> OTHER INFORMATION: Hypothetical ORF# 1811

<400> SEQUENCE: 103

```
ttg aag aga tgt gat gtt gaa agg gac gaa aat cga atg gtt agt agc     48
Leu Lys Arg Cys Asp Val Glu Arg Asp Glu Asn Arg Met Val Ser Ser
```

```
aag gaa aaa ttg caa cag gtt ctg atg gat ttg caa aaa gaa tgt gcc      96
Lys Glu Lys Leu Gln Gln Val Leu Met Asp Leu Gln Lys Glu Cys Ala
             20                  25                  30 gat gat cgg gat aca act gcg ttg att gat aat gct tta gac gat ttg     144
Asp Asp Arg Asp Thr Thr Ala Leu Ile Asp Asn Ala Leu Asp Asp Leu
         35                  40                  45 aaa cat aat gtt gat tta gat aaa gtg att ttt agg ctt aat caa aat     192
Lys His Asn Val Asp Leu Asp Lys Val Ile Phe Arg Leu Asn Gln Asn
     50                  55                  60 att agt aac tat tct tta gcg cat aat ttt aag tta tca cca gct tta     240
Ile Ser Asn Tyr Ser Leu Ala His Asn Phe Lys Leu Ser Pro Ala Leu
 65                  70                  75                  80 acg aaa tta caa att atg ttg aga gaa aat cca aat aag tgg aca gat     288
Thr Lys Leu Gln Ile Met Leu Arg Glu Asn Pro Asn Lys Trp Thr Asp
                 85                  90                  95 gct gga tta aca ggt tcg att                                         309
Ala Gly Leu Thr Gly Ser Ile
            100
```

<210> SEQ ID NO 104
<211> LENGTH: 103
<212> TYPE: PRT
<213> ORGANISM: Lactobacillus acidophilus

<400> SEQUENCE: 104

```
Leu Lys Arg Cys Asp Val Glu Arg Asp Glu Asn Arg Met Val Ser Ser
 1               5                  10                  15

Lys Glu Lys Leu Gln Gln Val Leu Met Asp Leu Gln Lys Glu Cys Ala
             20                  25                  30

Asp Asp Arg Asp Thr Thr Ala Leu Ile Asp Asn Ala Leu Asp Asp Leu
         35                  40                  45

Lys His Asn Val Asp Leu Asp Lys Val Ile Phe Arg Leu Asn Gln Asn
     50                  55                  60

Ile Ser Asn Tyr Ser Leu Ala His Asn Phe Lys Leu Ser Pro Ala Leu
 65                  70                  75                  80

Thr Lys Leu Gln Ile Met Leu Arg Glu Asn Pro Asn Lys Trp Thr Asp
                 85                  90                  95

Ala Gly Leu Thr Gly Ser Ile
            100
```

<210> SEQ ID NO 105
<211> LENGTH: 2301
<212> TYPE: DNA
<213> ORGANISM: Lactobacillus acidophilus
<220> FEATURE:
<221> NAME/KEY: CDS
<222> LOCATION: (1)..(2301)
<223> OTHER INFORMATION: Alpha-glucosidase II ORF# 1812

<400> SEQUENCE: 105

```
atg gct aac aaa ctt aaa aat ttc atc caa gat ggg caa aaa gtt acc      48
Met Ala Asn Lys Leu Lys Asn Phe Ile Gln Asp Gly Gln Lys Val Thr
 1               5                  10                  15 tta aat tat gaa gat ggg gaa ctt gaa tta agg gtt cta acg cct gaa      96
Leu Asn Tyr Glu Asp Gly Glu Leu Glu Leu Arg Val Leu Thr Pro Glu
             20                  25                  30 att gtg cgt gta ttt gaa aat cgt ggc aat gct agc aat tca tat gct     144
Ile Val Arg Val Phe Glu Asn Arg Gly Asn Ala Ser Asn Ser Tyr Ala
         35                  40                  45
```

-continued

| | | |
|---|---|---|
| atc gct ggt gat aag gaa ata aaa act aat ttt cgt att gaa gaa aaa<br>Ile Ala Gly Asp Lys Glu Ile Lys Thr Asn Phe Arg Ile Glu Glu Lys<br>50                      55                    60 | 192 | |
| gat gat cat gca gag tta tca aca gaa aag ttg ttc gta aaa att tac<br>Asp Asp His Ala Glu Leu Ser Thr Glu Lys Leu Phe Val Lys Ile Tyr<br>65                   70                    75                    80 | 240 | |
| gat gac aaa aag att gat gtt tat gat gaa aag gat cat cca ttg atc<br>Asp Asp Lys Lys Ile Asp Val Tyr Asp Glu Lys Asp His Pro Leu Ile<br>                 85                    90                    95 | 288 | |
| att gat tat cgc ggt gag cgt acg ccg att gat cgt caa atg gac gag<br>Ile Asp Tyr Arg Gly Glu Arg Thr Pro Ile Asp Arg Gln Met Asp Glu<br>                100                   105                  110 | 336 | |
| gaa cat aaa aaa tcg gca gaa tca gaa ggt cat gag gtt gct ggt agt<br>Glu His Lys Lys Ser Ala Glu Ser Glu Gly His Glu Val Ala Gly Ser<br>                115                   120                  125 | 384 | |
| aaa aaa gaa gat aaa aac tat tat gaa atc gtt aaa aaa cta gct agt<br>Lys Lys Glu Asp Lys Asn Tyr Tyr Glu Ile Val Lys Lys Leu Ala Ser<br>130                     135                   140 | 432 | |
| gat gaa caa ttt tac ggc tta ggt gat aag act ggc ttt tta aat aag<br>Asp Glu Gln Phe Tyr Gly Leu Gly Asp Lys Thr Gly Phe Leu Asn Lys<br>145                    150                   155                   160 | 480 | |
| cgt cat tat gcc tat aat aac tgg aat act gac gat cca gca cct caa<br>Arg His Tyr Ala Tyr Asn Asn Trp Asn Thr Asp Asp Pro Ala Pro Gln<br>                165                   170                  175 | 528 | |
| gtt gaa agc ttc cca agt ctt tat aag tcg gtt ccg atc ttg ctc ggc<br>Val Glu Ser Phe Pro Ser Leu Tyr Lys Ser Val Pro Ile Leu Leu Gly<br>                  180                  185                  190 | 576 | |
| tta aaa gat ggt cat ccc tat ggg att ttc ttt gac aat act tat cgt<br>Leu Lys Asp Gly His Pro Tyr Gly Ile Phe Phe Asp Asn Thr Tyr Arg<br>                195                   200                  205 | 624 | |
| aac cac att gac tta ggt aaa gaa agt aac gat tat tac tac tcc<br>Asn His Ile Asp Leu Gly Lys Glu Ser Asn Asp Tyr Tyr Tyr Ser<br>          210                   215                   220 | 672 | |
| gca gtt gat ggc aac att gat tac tac atc att ggt ggt gat tca ctt<br>Ala Val Asp Gly Asn Ile Asp Tyr Tyr Ile Ile Gly Gly Asp Ser Leu<br>225                     230                   235                   240 | 720 | |
| aaa gaa att atc acc aac tac act tac ttg act ggt cgt gta cca atg<br>Lys Glu Ile Ile Thr Asn Tyr Thr Tyr Leu Thr Gly Arg Val Pro Met<br>                  245                  250                  255 | 768 | |
| ccg cag aaa tgg acc ttg ggc tat caa cag tct cgc tgg ggc tac agt<br>Pro Gln Lys Trp Thr Leu Gly Tyr Gln Gln Ser Arg Trp Gly Tyr Ser<br>                260                   265                  270 | 816 | |
| gtc agc caa aag caa gtt gag aaa att gcg gaa aac ttg cgc aag tat<br>Val Ser Gln Lys Gln Val Glu Lys Ile Ala Glu Asn Leu Arg Lys Tyr<br>               275                   280                  285 | 864 | |
| gat ttg ccg tgt gac gtt ttg cat ctt gat atc gat tat atg cgt ggg<br>Asp Leu Pro Cys Asp Val Leu His Leu Asp Ile Asp Tyr Met Arg Gly<br>290                     295                   300 | 912 | |
| tat cgt gta ttt acc tgg aga aaa gat act tat gaa tca cca gat aaa<br>Tyr Arg Val Phe Thr Trp Arg Lys Asp Thr Tyr Glu Ser Pro Asp Lys<br>305                     310                   315                   320 | 960 | |
| ttc atc aag aag atg cgt aaa ttg ggc ttt aga atc atc acg att att<br>Phe Ile Lys Lys Met Arg Lys Leu Gly Phe Arg Ile Ile Thr Ile Ile<br>                  325                  330                  335 | 1008 | |
| gac cca ggc gta aag aaa gat gat gac tat aag att tac aag gaa ggt<br>Asp Pro Gly Val Lys Lys Asp Asp Asp Tyr Lys Ile Tyr Lys Glu Gly<br>                  340                  345                  350 | 1056 | |
| ctt gaa aaa ggc tac ttc gtt aag gct cca gat ggt acg gtt tat gta<br>Leu Glu Lys Gly Tyr Phe Val Lys Ala Pro Asp Gly Thr Val Tyr Val<br>                 355                   360                  365 | 1104 | |

|                                                                 |      |
|-----------------------------------------------------------------|------|
| aat gaa gtt tgg cca ggc gat gct gtc ttc cca gac ttt ggt cgc aaa | 1152 |
| Asn Glu Val Trp Pro Gly Asp Ala Val Phe Pro Asp Phe Gly Arg Lys |      |
|     370                 375                 380                 |      |
| gaa gta cgt aaa tgg tgg gct aga aat tgt aag tac tta gtt gat ctt | 1200 |
| Glu Val Arg Lys Trp Trp Ala Arg Asn Cys Lys Tyr Leu Val Asp Leu |      |
| 385                 390                 395                 400 |      |
| ggc gtt tca ggt atc tgg gac gat atg aat gaa cct gca tca ttt aga | 1248 |
| Gly Val Ser Gly Ile Trp Asp Asp Met Asn Glu Pro Ala Ser Phe Arg |      |
|             405                 410                 415         |      |
| ggt gaa att cca caa gat att gtc ttt cat aac gaa gag caa gct tca | 1296 |
| Gly Glu Ile Pro Gln Asp Ile Val Phe His Asn Glu Glu Gln Ala Ser |      |
|         420                 425                 430             |      |
| act cat aag aag atg cac aat gtc tat ggt cat aat atg gct aaa gca | 1344 |
| Thr His Lys Lys Met His Asn Val Tyr Gly His Asn Met Ala Lys Ala |      |
|             435                 440                 445         |      |
| act tat gaa ggt ttg aag aaa tat tca ggc aag cgt ccc ttt gtc att | 1392 |
| Thr Tyr Glu Gly Leu Lys Lys Tyr Ser Gly Lys Arg Pro Phe Val Ile |      |
|     450                 455                 460                 |      |
| acg cgt gcg gca tat gca gga acg caa aag ttt tcc aca gtt tgg act | 1440 |
| Thr Arg Ala Ala Tyr Ala Gly Thr Gln Lys Phe Ser Thr Val Trp Thr |      |
| 465                 470                 475                 480 |      |
| ggt gat aac caa agt tta tgg acg cat gtc caa atg atg att ccg caa | 1488 |
| Gly Asp Asn Gln Ser Leu Trp Thr His Val Gln Met Met Ile Pro Gln |      |
|             485                 490                 495         |      |
| tta tgt aac ttg gga atg agt gga ttt agt ttt gcc ggt act gat att | 1536 |
| Leu Cys Asn Leu Gly Met Ser Gly Phe Ser Phe Ala Gly Thr Asp Ile |      |
|             500                 505                 510         |      |
| ggt ggt ttc ggt gct gat acg acg cca gaa tta ttg act cgt tgg atc | 1584 |
| Gly Gly Phe Gly Ala Asp Thr Thr Pro Glu Leu Leu Thr Arg Trp Ile |      |
|         515                 520                 525             |      |
| gaa ggt gca tta ttt agt ccg ttg tac aga aac cat gcg gct cta ggt | 1632 |
| Glu Gly Ala Leu Phe Ser Pro Leu Tyr Arg Asn His Ala Ala Leu Gly |      |
|     530                 535                 540                 |      |
| act cgc tca caa gag cca tgg gta ttt ggt gaa cca act ttg tca att | 1680 |
| Thr Arg Ser Gln Glu Pro Trp Val Phe Gly Glu Pro Thr Leu Ser Ile |      |
| 545                 550                 555                 560 |      |
| tac cgt aaa tac ttg aaa ctt cgc tac cgc ttt att cca tat ctt tac | 1728 |
| Tyr Arg Lys Tyr Leu Lys Leu Arg Tyr Arg Phe Ile Pro Tyr Leu Tyr |      |
|             565                 570                 575         |      |
| gat gaa ttt tat cgt gaa act agg aca ggt ttg cca att atg cgg cca | 1776 |
| Asp Glu Phe Tyr Arg Glu Thr Arg Thr Gly Leu Pro Ile Met Arg Pro |      |
|             580                 585                 590         |      |
| ctt gtc ttg aat tat gaa aat gat cca cag gtg tat aac ttg aat gat | 1824 |
| Leu Val Leu Asn Tyr Glu Asn Asp Pro Gln Val Tyr Asn Leu Asn Asp |      |
|         595                 600                 605             |      |
| gag tat atg gtt ggc gag gat att ttg gca gcc cca gtt gtt caa gag | 1872 |
| Glu Tyr Met Val Gly Glu Asp Ile Leu Ala Ala Pro Val Val Gln Glu |      |
|     610                 615                 620                 |      |
| ggt caa act aag cgt gcc gta tat ttg cca aaa gga aaa tgg att gat | 1920 |
| Gly Gln Thr Lys Arg Ala Val Tyr Leu Pro Lys Gly Lys Trp Ile Asp |      |
| 625                 630                 635                 640 |      |
| ttt tgg aat ggt gtt gaa tat tct gga aag acc acg att ttg gtt gat | 1968 |
| Phe Trp Asn Gly Val Glu Tyr Ser Gly Lys Thr Thr Ile Leu Val Asp |      |
|             645                 650                 655         |      |
| gca cca att ggt aaa ttg cca ttg ttc att aag aag aat act atc ctg | 2016 |
| Ala Pro Ile Gly Lys Leu Pro Leu Phe Ile Lys Lys Asn Thr Ile Leu |      |
|             660                 665                 670         |      |
| cca tgg ggc aag gaa gta agt cac att tcc gat gag cca gac gag agt | 2064 |
| Pro Trp Gly Lys Glu Val Ser His Ile Ser Asp Glu Pro Asp Glu Ser |      |

-continued

```
              675                 680                 685
atg acc ttt aga gta ttt ggt aaa aag ggt aag tac att cac tat caa    2112
Met Thr Phe Arg Val Phe Gly Lys Lys Gly Lys Tyr Ile His Tyr Gln
    690                 695                 700 gat aac gga act gac ttc aag tac caa aag ggc gaa tac aac ttg tac    2160
Asp Asn Gly Thr Asp Phe Lys Tyr Gln Lys Gly Glu Tyr Asn Leu Tyr
705                 710                 715                 720 aag gtt aag gta agt aag gat ggt agc gta aag gtt aag ctt gaa aag    2208
Lys Val Lys Val Ser Lys Asp Gly Ser Val Lys Val Lys Leu Glu Lys
                725                 730                 735 cat ggc ttc ggt cct gta tat cgt aga att acg gtt caa ttg cct aat    2256
His Gly Phe Gly Pro Val Tyr Arg Arg Ile Thr Val Gln Leu Pro Asn
            740                 745                 750 aag aag gtt gaa ttt aag tac aag aat ggt gaa tac gtt aga aaa        2301
Lys Lys Val Glu Phe Lys Tyr Lys Asn Gly Glu Tyr Val Arg Lys
                755                 760                 765

<210> SEQ ID NO 106
<211> LENGTH: 767
<212> TYPE: PRT
<213> ORGANISM: Lactobacillus acidophilus

<400> SEQUENCE: 106

Met Ala Asn Lys Leu Lys Asn Phe Ile Gln Asp Gly Gln Lys Val Thr
1               5                   10                  15

Leu Asn Tyr Glu Asp Gly Glu Leu Glu Leu Arg Val Leu Thr Pro Glu
                20                  25                  30

Ile Val Arg Val Phe Glu Asn Arg Gly Asn Ala Ser Asn Ser Tyr Ala
            35                  40                  45

Ile Ala Gly Asp Lys Glu Ile Lys Thr Asn Phe Arg Ile Glu Glu Lys
        50                  55                  60

Asp Asp His Ala Glu Leu Ser Thr Glu Lys Leu Phe Val Lys Ile Tyr
65                  70                  75                  80

Asp Asp Lys Lys Ile Asp Val Tyr Asp Glu Lys Asp His Pro Leu Ile
                85                  90                  95

Ile Asp Tyr Arg Gly Glu Arg Thr Pro Ile Asp Arg Gln Met Asp Glu
            100                 105                 110

Glu His Lys Lys Ser Ala Glu Ser Glu Gly His Glu Val Ala Gly Ser
        115                 120                 125

Lys Lys Glu Asp Lys Asn Tyr Tyr Glu Ile Val Lys Lys Leu Ala Ser
    130                 135                 140

Asp Glu Gln Phe Tyr Gly Leu Gly Asp Lys Thr Gly Phe Leu Asn Lys
145                 150                 155                 160

Arg His Tyr Ala Tyr Asn Asn Trp Asn Thr Asp Asp Pro Ala Pro Gln
                165                 170                 175

Val Glu Ser Phe Pro Ser Leu Tyr Lys Ser Val Pro Ile Leu Leu Gly
            180                 185                 190

Leu Lys Asp Gly His Pro Tyr Gly Ile Phe Phe Asp Asn Thr Tyr Arg
        195                 200                 205

Asn His Ile Asp Leu Gly Lys Glu Ser Asn Asp Tyr Tyr Tyr Tyr Ser
    210                 215                 220

Ala Val Asp Gly Asn Ile Asp Tyr Tyr Ile Gly Gly Asp Ser Leu
225                 230                 235                 240

Lys Glu Ile Ile Thr Asn Tyr Thr Tyr Leu Thr Gly Arg Val Pro Met
                245                 250                 255

Pro Gln Lys Trp Thr Leu Gly Tyr Gln Gln Ser Arg Trp Gly Tyr Ser
```

-continued

```
                260                 265                 270
Val Ser Gln Lys Gln Val Glu Lys Ile Ala Glu Asn Leu Arg Lys Tyr
            275                 280                 285

Asp Leu Pro Cys Asp Val Leu His Leu Asp Ile Asp Tyr Met Arg Gly
        290                 295                 300

Tyr Arg Val Phe Thr Trp Arg Lys Asp Thr Tyr Glu Ser Pro Asp Lys
305                 310                 315                 320

Phe Ile Lys Lys Met Arg Lys Leu Gly Phe Arg Ile Ile Thr Ile Ile
                325                 330                 335

Asp Pro Gly Val Lys Lys Asp Asp Tyr Lys Ile Tyr Lys Glu Gly
            340                 345                 350

Leu Glu Lys Gly Tyr Phe Val Lys Ala Pro Asp Gly Thr Val Tyr Val
                355                 360                 365

Asn Glu Val Trp Pro Gly Asp Ala Val Phe Pro Asp Phe Gly Arg Lys
            370                 375                 380

Glu Val Arg Lys Trp Trp Ala Arg Asn Cys Lys Tyr Leu Val Asp Leu
385                 390                 395                 400

Gly Val Ser Gly Ile Trp Asp Asp Met Asn Glu Pro Ala Ser Phe Arg
                405                 410                 415

Gly Glu Ile Pro Gln Asp Ile Val Phe His Asn Glu Gln Ala Ser
            420                 425                 430

Thr His Lys Lys Met His Asn Val Tyr Gly His Asn Met Ala Lys Ala
                435                 440                 445

Thr Tyr Glu Gly Leu Lys Lys Tyr Ser Gly Lys Arg Pro Phe Val Ile
    450                 455                 460

Thr Arg Ala Ala Tyr Ala Gly Thr Gln Lys Phe Ser Thr Val Trp Thr
465                 470                 475                 480

Gly Asp Asn Gln Ser Leu Trp Thr His Val Gln Met Met Ile Pro Gln
                485                 490                 495

Leu Cys Asn Leu Gly Met Ser Gly Phe Ser Phe Ala Gly Thr Asp Ile
            500                 505                 510

Gly Gly Phe Gly Ala Asp Thr Thr Pro Glu Leu Leu Thr Arg Trp Ile
        515                 520                 525

Glu Gly Ala Leu Phe Ser Pro Leu Tyr Arg Asn His Ala Ala Leu Gly
    530                 535                 540

Thr Arg Ser Gln Glu Pro Trp Val Phe Gly Glu Pro Thr Leu Ser Ile
545                 550                 555                 560

Tyr Arg Lys Tyr Leu Lys Leu Arg Tyr Arg Phe Ile Pro Tyr Leu Tyr
                565                 570                 575

Asp Glu Phe Tyr Arg Glu Thr Arg Thr Gly Leu Pro Ile Met Arg Pro
        580                 585                 590

Leu Val Leu Asn Tyr Glu Asn Asp Pro Gln Val Tyr Asn Leu Asn Asp
            595                 600                 605

Glu Tyr Met Val Gly Glu Asp Ile Leu Ala Ala Pro Val Val Gln Glu
    610                 615                 620

Gly Gln Thr Lys Arg Ala Val Tyr Leu Pro Lys Gly Lys Trp Ile Asp
625                 630                 635                 640

Phe Trp Asn Gly Val Glu Tyr Ser Gly Lys Thr Thr Ile Leu Val Asp
                645                 650                 655

Ala Pro Ile Gly Lys Leu Pro Leu Phe Ile Lys Lys Asn Thr Ile Leu
        660                 665                 670

Pro Trp Gly Lys Glu Val Ser His Ile Ser Asp Glu Pro Asp Glu Ser
    675                 680                 685
```

```
Met Thr Phe Arg Val Phe Gly Lys Lys Gly Lys Tyr Ile His Tyr Gln
        690             695             700
Asp Asn Gly Thr Asp Phe Lys Tyr Gln Lys Gly Glu Tyr Asn Leu Tyr
705             710             715             720
Lys Val Lys Val Ser Lys Asp Gly Ser Val Lys Val Lys Leu Glu Lys
                725             730             735
His Gly Phe Gly Pro Val Tyr Arg Arg Ile Thr Val Gln Leu Pro Asn
            740             745             750
Lys Lys Val Glu Phe Lys Tyr Lys Asn Gly Glu Tyr Val Arg Lys
        755             760             765

<210> SEQ ID NO 107
<211> LENGTH: 189
<212> TYPE: DNA
<213> ORGANISM: Lactobacillus acidophilus
<220> FEATURE:
<221> NAME/KEY: CDS
<222> LOCATION: (1)..(189)
<223> OTHER INFORMATION: Consensus hypothetical protein ORF# 1813

<400> SEQUENCE: 107 atg ctt tat ctt ttg tac att ttt tta gga tta tta att att tta ggt        48
Met Leu Tyr Leu Leu Tyr Ile Phe Leu Gly Leu Leu Ile Ile Leu Gly
1               5                   10                  15 gtc aat ttg tta gtc aca gct ttt tgg gca ttg cat gat atg tat gtg        96
Val Asn Leu Leu Val Thr Ala Phe Trp Ala Leu His Asp Met Tyr Val
                20                  25                  30 cat aaa gat gaa gaa gca tgt gat ttg aac acc ttt aag aag tat ttt       144
His Lys Asp Glu Glu Ala Cys Asp Leu Asn Thr Phe Lys Lys Tyr Phe
            35                  40                  45 gtt aaa aat aat aat att ccg act aag atg tca gat att ttt aac           189
Val Lys Asn Asn Asn Ile Pro Thr Lys Met Ser Asp Ile Phe Asn
        50                  55                  60

<210> SEQ ID NO 108
<211> LENGTH: 63
<212> TYPE: PRT
<213> ORGANISM: Lactobacillus acidophilus

<400> SEQUENCE: 108

Met Leu Tyr Leu Leu Tyr Ile Phe Leu Gly Leu Leu Ile Ile Leu Gly
1               5                   10                  15

Val Asn Leu Leu Val Thr Ala Phe Trp Ala Leu His Asp Met Tyr Val
                20                  25                  30

His Lys Asp Glu Glu Ala Cys Asp Leu Asn Thr Phe Lys Lys Tyr Phe
            35                  40                  45

Val Lys Asn Asn Asn Ile Pro Thr Lys Met Ser Asp Ile Phe Asn
        50                  55                  60

<210> SEQ ID NO 109
<211> LENGTH: 225
<212> TYPE: DNA
<213> ORGANISM: Lactobacillus acidophilus
<220> FEATURE:
<221> NAME/KEY: CDS
<222> LOCATION: (1)..(225)
<223> OTHER INFORMATION: Unknown protein ORF# 1814

<400> SEQUENCE: 109 atg aac aaa aaa aat tca cag aat aat ttt tca att tta gga tta att        48
Met Asn Lys Lys Asn Ser Gln Asn Asn Phe Ser Ile Leu Gly Leu Ile
1               5                   10                  15
```

```
att tcg ttg att att gcc tgg gta att aca ttt ttt gca atg tgg gct        96
Ile Ser Leu Ile Ile Ala Trp Val Ile Thr Phe Phe Ala Met Trp Ala
         20                  25                  30 tcg cgt ggt ttt agt aga gat ttt ttt att atg cca cgt ttt gct ttt       144
Ser Arg Gly Phe Ser Arg Asp Phe Phe Ile Met Pro Arg Phe Ala Phe
         35                  40                  45 gtt tta gtg ttg tca att gca ggt gct att ata att ggt cca gca att       192
Val Leu Val Leu Ser Ile Ala Gly Ala Ile Ile Ile Gly Pro Ala Ile
 50                  55                  60 tac ggc ttt tta tac atc ggt aga aaa aaa gat                           225
Tyr Gly Phe Leu Tyr Ile Gly Arg Lys Lys Asp
 65                  70                  75
```

<210> SEQ ID NO 110
<211> LENGTH: 75
<212> TYPE: PRT
<213> ORGANISM: Lactobacillus acidophilus

<400> SEQUENCE: 110

```
Met Asn Lys Lys Asn Ser Gln Asn Asn Phe Ser Ile Leu Gly Leu Ile
 1               5                  10                  15

Ile Ser Leu Ile Ile Ala Trp Val Ile Thr Phe Phe Ala Met Trp Ala
             20                  25                  30

Ser Arg Gly Phe Ser Arg Asp Phe Phe Ile Met Pro Arg Phe Ala Phe
         35                  40                  45

Val Leu Val Leu Ser Ile Ala Gly Ala Ile Ile Ile Gly Pro Ala Ile
 50                  55                  60

Tyr Gly Phe Leu Tyr Ile Gly Arg Lys Lys Asp
 65                  70                  75
```

<210> SEQ ID NO 111
<211> LENGTH: 321
<212> TYPE: DNA
<213> ORGANISM: Lactobacillus acidophilus
<220> FEATURE:
<221> NAME/KEY: CDS
<222> LOCATION: (1)..(321)
<223> OTHER INFORMATION: Hypothetical protein ORF# 1815

<400> SEQUENCE: 111

```
atg tat caa gaa gaa aaa gat agt ttg aaa att tgg ctt tta gac aac        48
Met Tyr Gln Glu Glu Lys Asp Ser Leu Lys Ile Trp Leu Leu Asp Asn
 1               5                  10                  15 att act gat ttg tta gta gat aaa gaa act aag cca gaa gag cgg aaa        96
Ile Thr Asp Leu Leu Val Asp Lys Glu Thr Lys Pro Glu Glu Arg Lys
             20                  25                  30 gtt ttg ctc gat gct aag cat cag ctt gaa aat ggt gaa gcc gca aat       144
Val Leu Leu Asp Ala Lys His Gln Leu Glu Asn Gly Glu Ala Ala Asn
         35                  40                  45 tat gtt tgc aat tta att cgt gta gga ctt gat cca tta agc tgg caa       192
Tyr Val Cys Asn Leu Ile Arg Val Gly Leu Asp Pro Leu Ser Trp Gln
 50                  55                  60 agt aaa tta tca aac agc gtc atg aaa ttt cat tcc gca att att gcg       240
Ser Lys Leu Ser Asn Ser Val Met Lys Phe His Ser Ala Ile Ile Ala
 65                  70                  75                  80 gat gct cgt ccg gtg tct cag caa gct ggc gca ttg ggt ggc gct cta       288
Asp Ala Arg Pro Val Ser Gln Gln Ala Gly Ala Leu Gly Gly Ala Leu
                 85                  90                  95 ctg ggt cta gct ttc agt aac gtc ggt aga aaa                           321
Leu Gly Leu Ala Phe Ser Asn Val Gly Arg Lys
            100                 105
```

<210> SEQ ID NO 112
<211> LENGTH: 107
<212> TYPE: PRT
<213> ORGANISM: Lactobacillus acidophilus

<400> SEQUENCE: 112

Met Tyr Gln Glu Glu Lys Asp Ser Leu Lys Ile Trp Leu Leu Asp Asn
1               5                   10                  15

Ile Thr Asp Leu Leu Val Asp Lys Glu Thr Lys Pro Glu Glu Arg Lys
            20                  25                  30

Val Leu Leu Asp Ala Lys His Gln Leu Glu Asn Gly Glu Ala Ala Asn
        35                  40                  45

Tyr Val Cys Asn Leu Ile Arg Val Gly Leu Asp Pro Leu Ser Trp Gln
    50                  55                  60

Ser Lys Leu Ser Asn Ser Val Met Lys Phe His Ser Ala Ile Ile Ala
65                  70                  75                  80

Asp Ala Arg Pro Val Ser Gln Gln Ala Gly Ala Leu Gly Gly Ala Leu
                85                  90                  95

Leu Gly Leu Ala Phe Ser Asn Val Gly Arg Lys
            100                 105

<210> SEQ ID NO 113
<211> LENGTH: 351
<212> TYPE: DNA
<213> ORGANISM: Lactobacillus acidophilus
<220> FEATURE:
<221> NAME/KEY: CDS
<222> LOCATION: (1)..(351)
<223> OTHER INFORMATION: Hypothetical protein ORF# 1816

<400> SEQUENCE: 113 atg aag cta gtt cat ggc ttt tta gtt gtg cta aaa tca gga gtg aac        48
Met Lys Leu Val His Gly Phe Leu Val Val Leu Lys Ser Gly Val Asn
1               5                   10                  15 gga ggc aaa aat atg aaa aat cca atg gaa ggt gtc ggt aca cac cct        96
Gly Gly Lys Asn Met Lys Asn Pro Met Glu Gly Val Gly Thr His Pro
            20                  25                  30 gat att agc cca aaa gat aat gaa ttt atg att aag gtt aga gaa cta       144
Asp Ile Ser Pro Lys Asp Asn Glu Phe Met Ile Lys Val Arg Glu Leu
        35                  40                  45 gtt gat agt gat cct gat tta tta ggc aat agt gat att atg aaa ctg       192
Val Asp Ser Asp Pro Asp Leu Leu Gly Asn Ser Asp Ile Met Lys Leu
    50                  55                  60 gta aaa gta gct tta ttc aga gct ggc aaa aat gaa cct gtg cat gaa       240
Val Lys Val Ala Leu Phe Arg Ala Gly Lys Asn Glu Pro Val His Glu
65                  70                  75                  80 att gct aat gaa ctt gat gat ggc ttg tca ggc tac ttg gct aaa aat       288
Ile Ala Asn Glu Leu Asp Asp Gly Leu Ser Gly Tyr Leu Ala Lys Asn
                85                  90                  95 gat ttt aaa gca cca gct ggt gta aaa aaa tta caa gct gaa tta caa       336
Asp Phe Lys Ala Pro Ala Gly Val Lys Lys Leu Gln Ala Glu Leu Gln
            100                 105                 110 aaa tac att gaa gtt                                                    351
Lys Tyr Ile Glu Val
        115

<210> SEQ ID NO 114
<211> LENGTH: 117
<212> TYPE: PRT
<213> ORGANISM: Lactobacillus acidophilus

<400> SEQUENCE: 114

```
Met Lys Leu Val His Gly Phe Leu Val Val Leu Lys Ser Gly Val Asn
1               5                   10                  15
Gly Gly Lys Asn Met Lys Asn Pro Met Glu Gly Val Gly Thr His Pro
            20                  25                  30
Asp Ile Ser Pro Lys Asp Asn Glu Phe Met Ile Lys Val Arg Glu Leu
        35                  40                  45
Val Asp Ser Asp Pro Asp Leu Leu Gly Asn Ser Asp Ile Met Lys Leu
    50                  55                  60
Val Lys Val Ala Leu Phe Arg Ala Gly Lys Asn Glu Pro Val His Glu
65                  70                  75                  80
Ile Ala Asn Glu Leu Asp Asp Gly Leu Ser Gly Tyr Leu Ala Lys Asn
                85                  90                  95
Asp Phe Lys Ala Pro Ala Gly Val Lys Lys Leu Gln Ala Glu Leu Gln
            100                 105                 110
Lys Tyr Ile Glu Val
            115
```

<210> SEQ ID NO 115
<211> LENGTH: 747
<212> TYPE: DNA
<213> ORGANISM: Lactobacillus acidophilus
<220> FEATURE:
<221> NAME/KEY: CDS
<222> LOCATION: (1)..(747)
<223> OTHER INFORMATION: Aspartate racemase ORF#1817

<400> SEQUENCE: 115

```
atg aag cac ttt ttt agt att att ggc ggc atg gga act att gct acc      48
Met Lys His Phe Phe Ser Ile Ile Gly Gly Met Gly Thr Ile Ala Thr
1               5                   10                  15 gaa agt tat gta cgc cta att aat cat cgt gtt aaa att gca cgt gat      96
Glu Ser Tyr Val Arg Leu Ile Asn His Arg Val Lys Ile Ala Arg Asp
            20                  25                  30 caa gat tat tta aat tat att ttg gta aat gat gct cag gtt cct gac     144
Gln Asp Tyr Leu Asn Tyr Ile Leu Val Asn Asp Ala Gln Val Pro Asp
        35                  40                  45 cgt act gcc tat atc aag gat cat agt aag cca aat ttc ttc tat gat     192
Arg Thr Ala Tyr Ile Lys Asp His Ser Lys Pro Asn Phe Phe Tyr Asp
    50                  55                  60 tta aaa gat gac gtt gaa ggt caa gat aag tta gga act gac ttt tta     240
Leu Lys Asp Asp Val Glu Gly Gln Asp Lys Leu Gly Thr Asp Phe Leu
65                  70                  75                  80 gtc atg cca tgt aat aca gca cat tat ttt tat gat gac tta gct gca     288
Val Met Pro Cys Asn Thr Ala His Tyr Phe Tyr Asp Asp Leu Ala Ala
                85                  90                  95 ttg act gat aag cca ttt ttg cac atg atg cgt att gcc gta cat aat     336
Leu Thr Asp Lys Pro Phe Leu His Met Met Arg Ile Ala Val His Asn
            100                 105                 110 ttt ctt gat aat tat ccg gat gaa gaa aag atc ggt tta att gca aca     384
Phe Leu Asp Asn Tyr Pro Asp Glu Glu Lys Ile Gly Leu Ile Ala Thr
        115                 120                 125 gaa ggt tca atc tat gac cat ttg tat gct gat gaa att aag aag gtg     432
Glu Gly Ser Ile Tyr Asp His Leu Tyr Ala Asp Glu Ile Lys Lys Val
    130                 135                 140 ggg cgc aag gta gaa tta ggt gga ccc gaa att cag cca atg gtt aat     480
Gly Arg Lys Val Glu Leu Gly Gly Pro Glu Ile Gln Pro Met Val Asn
145                 150                 155                 160
```

```
gaa ttg att tac tca gat atc aaa gaa aag ggt act gta gat cat gat     528
Glu Leu Ile Tyr Ser Asp Ile Lys Glu Lys Gly Thr Val Asp His Asp
            165                 170                 175 tta tat cat aaa att ttg caa act atg cat gat aaa tat ggt tgt aac     576
Leu Tyr His Lys Ile Leu Gln Thr Met His Asp Lys Tyr Gly Cys Asn
            180                 185                 190 gtg att tta ctt ggt tgt acc gaa ttg tca tta gcg caa gaa aaa gca     624
Val Ile Leu Leu Gly Cys Thr Glu Leu Ser Leu Ala Gln Glu Lys Ala
            195                 200                 205 cct gat cat ccg tat aac gtc atc gat ccg caa tca att att gca gat     672
Pro Asp His Pro Tyr Asn Val Ile Asp Pro Gln Ser Ile Ile Ala Asp
        210                 215                 220 gtt tca att gaa tta gca ctt aaa atc cgt aac gga atg gat cct aaa     720
Val Ser Ile Glu Leu Ala Leu Lys Ile Arg Asn Gly Met Asp Pro Lys
225                 230                 235                 240 gaa gca tgt gca aaa tat atg tat gaa                                 747
Glu Ala Cys Ala Lys Tyr Met Tyr Glu
                245

<210> SEQ ID NO 116
<211> LENGTH: 249
<212> TYPE: PRT
<213> ORGANISM: Lactobacillus acidophilus

<400> SEQUENCE: 116

Met Lys His Phe Phe Ser Ile Ile Gly Gly Met Gly Thr Ile Ala Thr
1               5                   10                  15

Glu Ser Tyr Val Arg Leu Ile Asn His Arg Val Lys Ile Ala Arg Asp
            20                  25                  30

Gln Asp Tyr Leu Asn Tyr Ile Leu Val Asn Asp Ala Gln Val Pro Asp
        35                  40                  45

Arg Thr Ala Tyr Ile Lys Asp His Ser Lys Pro Asn Phe Phe Tyr Asp
    50                  55                  60

Leu Lys Asp Asp Val Glu Gly Gln Asp Lys Leu Gly Thr Asp Phe Leu
65                  70                  75                  80

Val Met Pro Cys Asn Thr Ala His Tyr Phe Tyr Asp Asp Leu Ala Ala
                85                  90                  95

Leu Thr Asp Lys Pro Phe Leu His Met Met Arg Ile Ala Val His Asn
            100                 105                 110

Phe Leu Asp Asn Tyr Pro Asp Glu Glu Lys Ile Gly Leu Ile Ala Thr
        115                 120                 125

Glu Gly Ser Ile Tyr Asp His Leu Tyr Ala Asp Glu Ile Lys Lys Val
    130                 135                 140

Gly Arg Lys Val Glu Leu Gly Gly Pro Glu Ile Gln Pro Met Val Asn
145                 150                 155                 160

Glu Leu Ile Tyr Ser Asp Ile Lys Glu Lys Gly Thr Val Asp His Asp
                165                 170                 175

Leu Tyr His Lys Ile Leu Gln Thr Met His Asp Lys Tyr Gly Cys Asn
            180                 185                 190

Val Ile Leu Leu Gly Cys Thr Glu Leu Ser Leu Ala Gln Glu Lys Ala
        195                 200                 205

Pro Asp His Pro Tyr Asn Val Ile Asp Pro Gln Ser Ile Ile Ala Asp
    210                 215                 220

Val Ser Ile Glu Leu Ala Leu Lys Ile Arg Asn Gly Met Asp Pro Lys
225                 230                 235                 240

Glu Ala Cys Ala Lys Tyr Met Tyr Glu
                245
```

```
<210> SEQ ID NO 117
<211> LENGTH: 1569
<212> TYPE: DNA
<213> ORGANISM: Lactobacillus acidophilus
<220> FEATURE:
<221> NAME/KEY: CDS
<222> LOCATION: (1)..(1569)
<223> OTHER INFORMATION: UDP-N-acetylmuramyl synthase ORF# 1818

<400> SEQUENCE: 117 atg agt att tct tta aat acc tgt ata tta att tta aaa gag cac cat     48
Met Ser Ile Ser Leu Asn Thr Cys Ile Leu Ile Leu Lys Glu His His
1               5                   10                  15 ttg ctc aag tca agc gca gtg caa gat act gta gca acc aag atg gac     96
Leu Leu Lys Ser Ser Ala Val Gln Asp Thr Val Ala Thr Lys Met Asp
            20                  25                  30 tac gtt tct tat gac tca cgc gat att caa act aac aca ttg ttt ttc    144
Tyr Val Ser Tyr Asp Ser Arg Asp Ile Gln Thr Asn Thr Leu Phe Phe
        35                  40                  45 tgt aag gga gca ggc ttt aga cca act tat tta tca atg gct aaa agt    192
Cys Lys Gly Ala Gly Phe Arg Pro Thr Tyr Leu Ser Met Ala Lys Ser
50                  55                  60 aat gga gca aat tgt tac gtt gct gaa caa cca tat cct gaa ggt aaa    240
Asn Gly Ala Asn Cys Tyr Val Ala Glu Gln Pro Tyr Pro Glu Gly Lys
65                  70                  75                  80 gga atg cac gct tta att gtt cgc gat gtt tca aag gca atg gca tta    288
Gly Met His Ala Leu Ile Val Arg Asp Val Ser Lys Ala Met Ala Leu
                85                  90                  95 ttg tca gcg gca ttt ttc cgt ttc cca caa gat gat ttg tat gtt gtt    336
Leu Ser Ala Ala Phe Phe Arg Phe Pro Gln Asp Asp Leu Tyr Val Val
            100                 105                 110 gca ttc act ggt act aag gga aag act act tcg gca tac ttt ttg aag    384
Ala Phe Thr Gly Thr Lys Gly Lys Thr Thr Ser Ala Tyr Phe Leu Lys
        115                 120                 125 ggg atg ctt gat caa gca aac ggt ggt aga aca gct tta att tct tca    432
Gly Met Leu Asp Gln Ala Asn Gly Gly Arg Thr Ala Leu Ile Ser Ser
130                 135                 140 gtt aat gat gtt gtt ggg cca aag cca gaa gat agc ttt aaa tca agt    480
Val Asn Asp Val Val Gly Pro Lys Pro Glu Asp Ser Phe Lys Ser Ser
145                 150                 155                 160 tta act aca cca gaa agt ttg gac ttg ttc cgt gat atg cgt act gct    528
Leu Thr Thr Pro Glu Ser Leu Asp Leu Phe Arg Asp Met Arg Thr Ala
                165                 170                 175 gtt gat aac ggt atg act cac ctt gta atg gaa gtt tca agt caa gct    576
Val Asp Asn Gly Met Thr His Leu Val Met Glu Val Ser Ser Gln Ala
            180                 185                 190 tat aag aag aac cgt gta ttt gga tta act tat gat tta ggt ttc ttt    624
Tyr Lys Lys Asn Arg Val Phe Gly Leu Thr Tyr Asp Leu Gly Phe Phe
        195                 200                 205 tta aat atc agt ccg gat cat att gga cca aat gaa cac cct aac ttt    672
Leu Asn Ile Ser Pro Asp His Ile Gly Pro Asn Glu His Pro Asn Phe
210                 215                 220 gcg gat tac ttg cac tgc aag ttg caa ttg atg gtt aac tca cgt aaa    720
Ala Asp Tyr Leu His Cys Lys Leu Gln Leu Met Val Asn Ser Arg Lys
225                 230                 235                 240 tgt att att aac gca gaa act gct aac ttt aat gaa gta tat gca gca    768
Cys Ile Ile Asn Ala Glu Thr Ala Asn Phe Asn Glu Val Tyr Ala Ala
                245                 250                 255 gca aca acg act act aat cca gat agc att tac ttg ttt gca aga gaa    816
Ala Thr Thr Thr Thr Asn Pro Asp Ser Ile Tyr Leu Phe Ala Arg Glu
```

-continued

```
                        260                 265                 270
gat ttt gaa aat cca gat ttg gat gtg cca att gac ttt aga ttt gct       864
Asp Phe Glu Asn Pro Asp Leu Asp Val Pro Ile Asp Phe Arg Phe Ala
        275                 280                 285 tcc caa gaa ttg gat atg aaa gaa act cgc ttt aag ttg ttc tgt gcc       912
Ser Gln Glu Leu Asp Met Lys Glu Thr Arg Phe Lys Leu Phe Cys Ala
    290                 295                 300 act gat aag gct aag aag ttg cct att aat ggt gat tac act tta aag       960
Thr Asp Lys Ala Lys Lys Leu Pro Ile Asn Gly Asp Tyr Thr Leu Lys
305                 310                 315                 320 atg ttg ggt gac ttt aat gaa tca aat ggt aca gct gcc atc att ggt      1008
Met Leu Gly Asp Phe Asn Glu Ser Asn Gly Thr Ala Ala Ile Ile Gly
                325                 330                 335 gca gga ctt gcc ggt ctt aac cat gat caa tgt gct aag ggg atc cgt      1056
Ala Gly Leu Ala Gly Leu Asn His Asp Gln Cys Ala Lys Gly Ile Arg
            340                 345                 350 aat gtt act atc cct ggt cgt atg caa act gaa aga act aaa gaa cac      1104
Asn Val Thr Ile Pro Gly Arg Met Gln Thr Glu Arg Thr Lys Glu His
        355                 360                 365 ggt atg gtt gtt gtt gat tat gcc cac aat aag gct tcg atg atg gct      1152
Gly Met Val Val Val Asp Tyr Ala His Asn Lys Ala Ser Met Met Ala
    370                 375                 380 ttg atg aga ttc atg caa aat gaa ttt aac gat cct aag atc atc gta      1200
Leu Met Arg Phe Met Gln Asn Glu Phe Asn Asp Pro Lys Ile Ile Val
385                 390                 395                 400 gtt gtt ggt gca cct ggt gat aaa ggc gtt tca cgt cgt cca ggc ttt      1248
Val Val Gly Ala Pro Gly Asp Lys Gly Val Ser Arg Arg Pro Gly Phe
                405                 410                 415 agt gaa agt ttg agt gca tat gct gat aag gca ttt ttg aca act gat      1296
Ser Glu Ser Leu Ser Ala Tyr Ala Asp Lys Ala Phe Leu Thr Thr Asp
            420                 425                 430 gat cca gga ttt gaa gat cca aag tct att gct gaa gaa att gat gct      1344
Asp Pro Gly Phe Glu Asp Pro Lys Ser Ile Ala Glu Glu Ile Asp Ala
        435                 440                 445 ggt att gat cac tct aag tgt gat gta aca att gaa ttg gac cgt aag      1392
Gly Ile Asp His Ser Lys Cys Asp Val Thr Ile Glu Leu Asp Arg Lys
    450                 455                 460 aaa gct att cat gat gca att gct tca gct ggt cca gat gat gta gtt      1440
Lys Ala Ile His Asp Ala Ile Ala Ser Ala Gly Pro Asp Asp Val Val
465                 470                 475                 480 tta atc tgt ggt aag ggt gct gac gct ttc caa aag att cgc ggc gta      1488
Leu Ile Cys Gly Lys Gly Ala Asp Ala Phe Gln Lys Ile Arg Gly Val
                485                 490                 495 gac act cca tat cca tca gat att gtg gtt gct caa cag gta att aac      1536
Asp Thr Pro Tyr Pro Ser Asp Ile Val Val Ala Gln Gln Val Ile Asn
            500                 505                 510 gaa tta gaa ggc caa gac gag cac ttt aga aaa                          1569
Glu Leu Glu Gly Gln Asp Glu His Phe Arg Lys
        515                 520
```

<210> SEQ ID NO 118
<211> LENGTH: 523
<212> TYPE: PRT
<213> ORGANISM: Lactobacillus acidophilus

<400> SEQUENCE: 118

```
Met Ser Ile Ser Leu Asn Thr Cys Ile Leu Ile Leu Lys Glu His His
1               5                   10                  15

Leu Leu Lys Ser Ser Ala Val Gln Asp Thr Val Ala Thr Lys Met Asp
            20                  25                  30
```

-continued

```
Tyr Val Ser Tyr Asp Ser Arg Asp Ile Gln Thr Asn Thr Leu Phe Phe
         35                  40                  45
Cys Lys Gly Ala Gly Phe Arg Pro Thr Tyr Leu Ser Met Ala Lys Ser
         50                  55                  60
Asn Gly Ala Asn Cys Tyr Val Ala Glu Gln Pro Tyr Pro Glu Gly Lys
 65                  70                  75                  80
Gly Met His Ala Leu Ile Val Arg Asp Val Ser Lys Ala Met Ala Leu
                 85                  90                  95
Leu Ser Ala Ala Phe Phe Arg Phe Pro Gln Asp Asp Leu Tyr Val Val
             100                 105                 110
Ala Phe Thr Gly Thr Lys Gly Lys Thr Thr Ser Ala Tyr Phe Leu Lys
             115                 120                 125
Gly Met Leu Asp Gln Ala Asn Gly Gly Arg Thr Ala Leu Ile Ser Ser
         130                 135                 140
Val Asn Asp Val Val Gly Pro Lys Pro Glu Asp Ser Phe Lys Ser Ser
145                 150                 155                 160
Leu Thr Thr Pro Glu Ser Leu Asp Leu Phe Arg Asp Met Arg Thr Ala
                 165                 170                 175
Val Asp Asn Gly Met Thr His Leu Val Met Glu Val Ser Ser Gln Ala
             180                 185                 190
Tyr Lys Lys Asn Arg Val Phe Gly Leu Thr Tyr Asp Leu Gly Phe Phe
         195                 200                 205
Leu Asn Ile Ser Pro Asp His Ile Gly Pro Asn Glu His Pro Asn Phe
         210                 215                 220
Ala Asp Tyr Leu His Cys Lys Leu Gln Leu Met Val Asn Ser Arg Lys
225                 230                 235                 240
Cys Ile Ile Asn Ala Glu Thr Ala Asn Phe Asn Glu Val Tyr Ala Ala
                 245                 250                 255
Ala Thr Thr Thr Thr Asn Pro Asp Ser Ile Tyr Leu Phe Ala Arg Glu
             260                 265                 270
Asp Phe Glu Asn Pro Asp Leu Asp Val Pro Ile Asp Phe Arg Phe Ala
         275                 280                 285
Ser Gln Glu Leu Asp Met Lys Glu Thr Arg Phe Lys Leu Phe Cys Ala
         290                 295                 300
Thr Asp Lys Ala Lys Lys Leu Pro Ile Asn Gly Asp Tyr Thr Leu Lys
305                 310                 315                 320
Met Leu Gly Asp Phe Asn Glu Ser Asn Gly Thr Ala Ala Ile Ile Gly
                 325                 330                 335
Ala Gly Leu Ala Gly Leu Asn His Asp Gln Cys Ala Lys Gly Ile Arg
             340                 345                 350
Asn Val Thr Ile Pro Gly Arg Met Gln Thr Glu Arg Thr Lys Glu His
         355                 360                 365
Gly Met Val Val Asp Tyr Ala His Asn Lys Ala Ser Met Met Ala
         370                 375                 380
Leu Met Arg Phe Met Gln Asn Glu Phe Asn Asp Pro Lys Ile Ile Val
385                 390                 395                 400
Val Val Gly Ala Pro Gly Asp Lys Gly Val Ser Arg Arg Pro Gly Phe
                 405                 410                 415
Ser Glu Ser Leu Ser Ala Tyr Ala Asp Lys Ala Phe Leu Thr Thr Asp
             420                 425                 430
Asp Pro Gly Phe Glu Asp Pro Lys Ser Ile Ala Glu Glu Ile Asp Ala
         435                 440                 445
```

```
         Gly Ile Asp His Ser Lys Cys Asp Val Thr Ile Glu Leu Asp Arg Lys
             450                 455                 460

Lys Ala Ile His Asp Ala Ile Ala Ser Ala Gly Pro Asp Asp Val Val
         465                 470                 475                 480

Leu Ile Cys Gly Lys Gly Ala Asp Ala Phe Gln Lys Ile Arg Gly Val
                         485                 490                 495

Asp Thr Pro Tyr Pro Ser Asp Ile Val Val Ala Gln Gln Val Ile Asn
                     500                 505                 510

Glu Leu Glu Gly Gln Asp Glu His Phe Arg Lys
                 515                 520

<210> SEQ ID NO 119
<211> LENGTH: 1863
<212> TYPE: DNA
<213> ORGANISM: Lactobacillus acidophilus
<220> FEATURE:
<221> NAME/KEY: CDS
<222> LOCATION: (1)..(1863)
<223> OTHER INFORMATION: ABC multidrug transporter ORF# 1821

<400> SEQUENCE: 119
```

| | | | | | | | | | | | | | | | | |
|---|---|---|---|---|---|---|---|---|---|---|---|---|---|---|---|---|
| ttg | gat | aat | gca | aat | gca | gta | gaa | aat | aaa | aat | caa | act | aaa | ggc | aat | 48 |
| Leu | Asp | Asn | Ala | Asn | Ala | Val | Glu | Asn | Lys | Asn | Gln | Thr | Lys | Gly | Asn | |
| 1 | | | | 5 | | | | | 10 | | | | | 15 | | |
| aga | att | aag | att | tta | att | cgt | ttg | ctt | aag | tta | gtt | ggt | agc | aca | agt | 96 |
| Arg | Ile | Lys | Ile | Leu | Ile | Arg | Leu | Leu | Lys | Leu | Val | Gly | Ser | Thr | Ser | |
| | | | 20 | | | | | 25 | | | | | 30 | | | |
| cca | tgg | atg | ctc | atc | atc | tcc | atg | att | acg | att | gtt | ttg | gca | gca | gcc | 144 |
| Pro | Trp | Met | Leu | Ile | Ile | Ser | Met | Ile | Thr | Ile | Val | Leu | Ala | Ala | Ala | |
| | | | | 35 | | | | | 40 | | | | | 45 | | |
| agc | aac | gtt | att | ggt | tca | tta | ttt | att | gaa | cga | ttg | atc | aat | aac | tat | 192 |
| Ser | Asn | Val | Ile | Gly | Ser | Leu | Phe | Ile | Glu | Arg | Leu | Ile | Asn | Asn | Tyr | |
| | | | 50 | | | | | 55 | | | | | 60 | | | |
| att | gtc | cct | tta | aca | aaa | gaa | cga | gtt | ccc | aat | tat | ggt | ccg | ctt | gct | 240 |
| Ile | Val | Pro | Leu | Thr | Lys | Glu | Arg | Val | Pro | Asn | Tyr | Gly | Pro | Leu | Ala | |
| 65 | | | | | 70 | | | | | 75 | | | | | 80 | |
| aca | gca | att | gcg | gta | atg | ttt | gga | att | tat | gca | att | ggt | ttt | ttg | tct | 288 |
| Thr | Ala | Ile | Ala | Val | Met | Phe | Gly | Ile | Tyr | Ala | Ile | Gly | Phe | Leu | Ser | |
| | | | | 85 | | | | | 90 | | | | | 95 | | |
| aac | tat | ctt | ttt | aac | atg | cta | atg | ggt | gtt | tta | gcc | caa | aaa | gtt | caa | 336 |
| Asn | Tyr | Leu | Phe | Asn | Met | Leu | Met | Gly | Val | Leu | Ala | Gln | Lys | Val | Gln | |
| | | | | 100 | | | | | 105 | | | | | 110 | | |
| ttc | cgt | gtt | cgt | aat | gaa | atg | ttt | atc | cac | atg | gaa | agt | ttg | ccg | att | 384 |
| Phe | Arg | Val | Arg | Asn | Glu | Met | Phe | Ile | His | Met | Glu | Ser | Leu | Pro | Ile | |
| | | | 115 | | | | | 120 | | | | | 125 | | | |
| tca | tat | ttt | gat | caa | aat | gaa | ttt | ggt | gat | atc | atg | tct | cgt | tat | acc | 432 |
| Ser | Tyr | Phe | Asp | Gln | Asn | Glu | Phe | Gly | Asp | Ile | Met | Ser | Arg | Tyr | Thr | |
| | | | 130 | | | | | 135 | | | | | 140 | | | |
| aac | gat | att | gat | acc | ttg | atg | caa | atg | att | tcg | caa | tct | atc | cca | caa | 480 |
| Asn | Asp | Ile | Asp | Thr | Leu | Met | Gln | Met | Ile | Ser | Gln | Ser | Ile | Pro | Gln | |
| 145 | | | | | 150 | | | | | 155 | | | | | 160 | |
| ttt | act | aat | tca | gct | ttg | agt | ttg | att | ttt | gtt | gtg | att | gcg | atg | ttt | 528 |
| Phe | Thr | Asn | Ser | Ala | Leu | Ser | Leu | Ile | Phe | Val | Val | Ile | Ala | Met | Phe | |
| | | | | 165 | | | | | 170 | | | | | 175 | | |
| gta | ctt | agt | tgg | caa | tta | act | gtc | ttc | tca | ttt | att | atc | ttt | gct | ttg | 576 |
| Val | Leu | Ser | Trp | Gln | Leu | Thr | Val | Phe | Ser | Phe | Ile | Ile | Phe | Ala | Leu | |
| | | | | 180 | | | | | 185 | | | | | 190 | | |
| tca | ttt | gga | att | gtt | cgc | tac | ttg | act | gtg | aga | tca | agt | cgt | tat | ttc | 624 |
| Ser | Phe | Gly | Ile | Val | Arg | Tyr | Leu | Thr | Val | Arg | Ser | Ser | Arg | Tyr | Phe | |
| | | | 195 | | | | | 200 | | | | | 205 | | | |

-continued

```
caa att cag cag aag aaa ctt ggt caa atc aat ggt tat aac gaa gaa      672
Gln Ile Gln Gln Lys Lys Leu Gly Gln Ile Asn Gly Tyr Asn Glu Glu
    210             215                 220 atg ctt aac gga ttg aag gtc att aaa gtc ttc agt cac gaa cct gaa      720
Met Leu Asn Gly Leu Lys Val Ile Lys Val Phe Ser His Glu Pro Glu
225             230                 235                 240 tca aaa gct ggt ttt gac aag tat aac gaa gaa ttg cgt caa gcc tct      768
Ser Lys Ala Gly Phe Asp Lys Tyr Asn Glu Glu Leu Arg Gln Ala Ser
                245                 250                 255 ggt aga gct aat act ttt gcc aca att ctt ttc cca att atg ggt aac      816
Gly Arg Ala Asn Thr Phe Ala Thr Ile Leu Phe Pro Ile Met Gly Asn
            260                 265                 270 atg ggt aac tta ctc tat gtt tta att gcc ttt gtc ggt gga gct gct      864
Met Gly Asn Leu Leu Tyr Val Leu Ile Ala Phe Val Gly Gly Ala Ala
        275                 280                 285 gcg att aat caa tgg gct cca tta tca ctg ggt gct att ggt tca ttc      912
Ala Ile Asn Gln Trp Ala Pro Leu Ser Leu Gly Ala Ile Gly Ser Phe
    290                 295                 300 cta caa tta tca aaa caa ttt agt atg ccg att gcc caa att tct caa      960
Leu Gln Leu Ser Lys Gln Phe Ser Met Pro Ile Ala Gln Ile Ser Gln
305             310                 315                 320 cag tta aac tca att gtc atg gct tta gct ggc gct gag aga atc ttt     1008
Gln Leu Asn Ser Ile Val Met Ala Leu Ala Gly Ala Glu Arg Ile Phe
                325                 330                 335 aac ttg gaa gat caa gct tca gaa atg gat aat ggt aac gtt act att     1056
Asn Leu Glu Asp Gln Ala Ser Glu Met Asp Asn Gly Asn Val Thr Ile
            340                 345                 350 tct aag ggt gat gaa gtt ggt agt aac tgg aat tgg aac gta cct caa     1104
Ser Lys Gly Asp Glu Val Gly Ser Asn Trp Asn Trp Asn Val Pro Gln
        355                 360                 365 aaa gat ggt tca att aag aag gtt ccg gta cga ggt cac att gtt ttt     1152
Lys Asp Gly Ser Ile Lys Lys Val Pro Val Arg Gly His Ile Val Phe
    370                 375                 380 gat cat gta aac ttt agt tat gtg cca aat cat caa att ctg tat gac     1200
Asp His Val Asn Phe Ser Tyr Val Pro Asn His Gln Ile Leu Tyr Asp
385             390                 395                 400 att tca att aat gct aag cct ggt atg aag gtg gct tta gtt ggt gag     1248
Ile Ser Ile Asn Ala Lys Pro Gly Met Lys Val Ala Leu Val Gly Glu
                405                 410                 415 act ggt gct ggt aaa acc act att tct aac atg ctt aac cgt ttc tac     1296
Thr Gly Ala Gly Lys Thr Thr Ile Ser Asn Met Leu Asn Arg Phe Tyr
            420                 425                 430 gat att gat tca ggt aaa att act tac gat ggt atc cca att aag gat     1344
Asp Ile Asp Ser Gly Lys Ile Thr Tyr Asp Gly Ile Pro Ile Lys Asp
        435                 440                 445 att aaa aaa gat gat ttg cgt aga tca tta tcc att gtt ttg cag gaa     1392
Ile Lys Lys Asp Asp Leu Arg Arg Ser Leu Ser Ile Val Leu Gln Glu
    450                 455                 460 aca cac ttg ttt aca ggc act att atg gat aat atc cgc ttt ggt aat     1440
Thr His Leu Phe Thr Gly Thr Ile Met Asp Asn Ile Arg Phe Gly Asn
465             470                 475                 480 cct gaa gca agt gat gat gat gtt tat caa gca gct aaa ttg tct cac     1488
Pro Glu Ala Ser Asp Asp Asp Val Tyr Gln Ala Ala Lys Leu Ser His
                485                 490                 495 gca gat gaa ttt atc cat gat ctt gat aag ggt tat gac aca gta att     1536
Ala Asp Glu Phe Ile His Asp Leu Asp Lys Gly Tyr Asp Thr Val Ile
            500                 505                 510 gat ggt gat ggc gga gat tta tca caa gga caa atg caa cta ctt agt     1584
Asp Gly Asp Gly Gly Asp Leu Ser Gln Gly Gln Met Gln Leu Leu Ser
        515                 520                 525
```

```
att gcc cga gca atg att gca gat gaa cca gta atg att ctt gat gaa    1632
Ile Ala Arg Ala Met Ile Ala Asp Glu Pro Val Met Ile Leu Asp Glu
            530                 535                 540 gca act tca agt att gat acc aga act gaa aag atg gta caa gct ggt    1680
Ala Thr Ser Ser Ile Asp Thr Arg Thr Glu Lys Met Val Gln Ala Gly
545                 550                 555                 560 atg gac aat tta ctc gca ggt cga aca agt ttt gtt atc gct cac cgt    1728
Met Asp Asn Leu Leu Ala Gly Arg Thr Ser Phe Val Ile Ala His Arg
                565                 570                 575 tta tca act att gtt aac tca gat tta atc ttg gtt ctt gac cat ggt    1776
Leu Ser Thr Ile Val Asn Ser Asp Leu Ile Leu Val Leu Asp His Gly
            580                 585                 590 cac atc att gaa cgt ggt aat cat gaa gag ctt ttg aaa gaa aaa ggc    1824
His Ile Ile Glu Arg Gly Asn His Glu Glu Leu Leu Lys Glu Lys Gly
        595                 600                 605 tat tac tac gaa cta tat act ggt aaa aaa gaa att caa                1863
Tyr Tyr Tyr Glu Leu Tyr Thr Gly Lys Lys Glu Ile Gln
610                 615                 620

<210> SEQ ID NO 120
<211> LENGTH: 621
<212> TYPE: PRT
<213> ORGANISM: Lactobacillus acidophilus

<400> SEQUENCE: 120

Leu Asp Asn Ala Asn Ala Val Glu Asn Lys Asn Gln Thr Lys Gly Asn
1               5                   10                  15

Arg Ile Lys Ile Leu Ile Arg Leu Leu Lys Leu Val Gly Ser Thr Ser
            20                  25                  30

Pro Trp Met Leu Ile Ser Met Ile Thr Ile Val Leu Ala Ala Ala
        35                  40                  45

Ser Asn Val Ile Gly Ser Leu Phe Ile Glu Arg Leu Ile Asn Asn Tyr
    50                  55                  60

Ile Val Pro Leu Thr Lys Glu Arg Val Pro Asn Tyr Gly Pro Leu Ala
65                  70                  75                  80

Thr Ala Ile Ala Val Met Phe Gly Ile Tyr Ala Ile Gly Phe Leu Ser
                85                  90                  95

Asn Tyr Leu Phe Asn Met Leu Met Gly Val Leu Ala Gln Lys Val Gln
            100                 105                 110

Phe Arg Val Arg Asn Glu Met Phe Ile His Met Glu Ser Leu Pro Ile
        115                 120                 125

Ser Tyr Phe Asp Gln Asn Glu Phe Gly Asp Ile Met Ser Arg Tyr Thr
    130                 135                 140

Asn Asp Ile Asp Thr Leu Met Gln Met Ile Ser Gln Ser Ile Pro Gln
145                 150                 155                 160

Phe Thr Asn Ser Ala Leu Ser Leu Ile Phe Val Val Ile Ala Met Phe
                165                 170                 175

Val Leu Ser Trp Gln Leu Thr Val Phe Ser Phe Ile Ile Phe Ala Leu
            180                 185                 190

Ser Phe Gly Ile Val Arg Tyr Leu Thr Val Arg Ser Ser Arg Tyr Phe
        195                 200                 205

Gln Ile Gln Gln Lys Leu Gly Gln Ile Asn Gly Tyr Asn Glu Glu
    210                 215                 220

Met Leu Asn Gly Leu Lys Val Ile Lys Val Phe Ser His Glu Pro Glu
225                 230                 235                 240

Ser Lys Ala Gly Phe Asp Lys Tyr Asn Glu Glu Leu Arg Gln Ala Ser
```

```
                    245                 250                 255
Gly Arg Asn Thr Phe Ala Thr Ile Leu Phe Pro Ile Met Gly Asn
                260                 265                 270

Met Gly Asn Leu Leu Tyr Val Leu Ile Ala Phe Val Gly Ala Ala
                275                 280                 285

Ala Ile Asn Gln Trp Ala Pro Leu Ser Leu Gly Ala Ile Gly Ser Phe
            290                 295                 300

Leu Gln Leu Ser Lys Gln Phe Ser Met Pro Ile Ala Gln Ile Ser Gln
305                 310                 315                 320

Gln Leu Asn Ser Ile Val Met Ala Leu Ala Gly Ala Glu Arg Ile Phe
                325                 330                 335

Asn Leu Glu Asp Gln Ala Ser Glu Met Asp Asn Gly Asn Val Thr Ile
                340                 345                 350

Ser Lys Gly Asp Glu Val Gly Ser Asn Trp Asn Trp Asn Val Pro Gln
                355                 360                 365

Lys Asp Gly Ser Ile Lys Lys Val Pro Val Arg Gly His Ile Val Phe
                370                 375                 380

Asp His Val Asn Phe Ser Tyr Val Pro Asn His Gln Ile Leu Tyr Asp
385                 390                 395                 400

Ile Ser Ile Asn Ala Lys Pro Gly Met Lys Val Ala Leu Val Gly Glu
                405                 410                 415

Thr Gly Ala Gly Lys Thr Thr Ile Ser Asn Met Leu Asn Arg Phe Tyr
                420                 425                 430

Asp Ile Asp Ser Gly Lys Ile Thr Tyr Asp Gly Ile Pro Ile Lys Asp
                435                 440                 445

Ile Lys Lys Asp Asp Leu Arg Arg Ser Leu Ser Ile Val Leu Gln Glu
                450                 455                 460

Thr His Leu Phe Thr Gly Thr Ile Met Asp Asn Ile Arg Phe Gly Asn
465                 470                 475                 480

Pro Glu Ala Ser Asp Asp Val Tyr Gln Ala Ala Lys Leu Ser His
                485                 490                 495

Ala Asp Glu Phe Ile His Asp Leu Asp Lys Gly Tyr Asp Thr Val Ile
                500                 505                 510

Asp Gly Asp Gly Gly Asp Leu Ser Gln Gly Gln Met Gln Leu Leu Ser
                515                 520                 525

Ile Ala Arg Ala Met Ile Ala Asp Glu Pro Val Met Ile Leu Asp Glu
                530                 535                 540

Ala Thr Ser Ser Ile Asp Thr Arg Thr Glu Lys Met Val Gln Ala Gly
545                 550                 555                 560

Met Asp Asn Leu Leu Ala Gly Arg Thr Ser Phe Val Ile Ala His Arg
                565                 570                 575

Leu Ser Thr Ile Val Asn Ser Asp Leu Ile Leu Val Leu Asp His Gly
                580                 585                 590

His Ile Ile Glu Arg Gly Asn His Glu Glu Leu Leu Lys Glu Lys Gly
                595                 600                 605

Tyr Tyr Tyr Glu Leu Tyr Thr Gly Lys Lys Glu Ile Gln
                610                 615                 620

<210> SEQ ID NO 121
<211> LENGTH: 1728
<212> TYPE: DNA
<213> ORGANISM: Lactobacillus acidophilus
<220> FEATURE:
<221> NAME/KEY: CDS
<222> LOCATION: (1)..(1728)
```

<223> OTHER INFORMATION: ABC multidrug transporter ORF# 1821

<400> SEQUENCE: 121

```
atg gtc aaa acg ttg agc aag tcg ata cga caa tat aaa aaa ttg tcg      48
Met Val Lys Thr Leu Ser Lys Ser Ile Arg Gln Tyr Lys Lys Leu Ser
1               5                   10                  15 ctg ctc tca cca ttg ttc gtt atc ggt gaa gtt att atc gaa atg ctg      96
Leu Leu Ser Pro Leu Phe Val Ile Gly Glu Val Ile Ile Glu Met Leu
            20                  25                  30 atc cca tat ttg gtt ggt atc ttg atc gat aat gga att atg aaa ggg     144
Ile Pro Tyr Leu Val Gly Ile Leu Ile Asp Asn Gly Ile Met Lys Gly
        35                  40                  45 aac atg tct tat att agt aaa atg ggg ctt att ttg ctt gta tta acg     192
Asn Met Ser Tyr Ile Ser Lys Met Gly Leu Ile Leu Leu Val Leu Thr
50                  55                  60 att gtt tcg tta atc tta ggt gcg agt gcc agt tat gtt tca gct cac     240
Ile Val Ser Leu Ile Leu Gly Ala Ser Ala Ser Tyr Val Ser Ala His
65                  70                  75                  80 gct gct gcc ggt ttt gca gct aat ttg cgt aaa gat atg ttc tat cac     288
Ala Ala Ala Gly Phe Ala Ala Asn Leu Arg Lys Asp Met Phe Tyr His
                85                  90                  95 atg cag gat tat tct ttt gaa aat att gat cat ttt tca agt gcc agt     336
Met Gln Asp Tyr Ser Phe Glu Asn Ile Asp His Phe Ser Ser Ala Ser
            100                 105                 110 cta gtt acg cgt cta aca acc gac gtt aac aac gta caa atg gct tac     384
Leu Val Thr Arg Leu Thr Thr Asp Val Asn Asn Val Gln Met Ala Tyr
        115                 120                 125 caa atg att atc aga att gcg gta aga gca cca atg atg ttt ata gtt     432
Gln Met Ile Ile Arg Ile Ala Val Arg Ala Pro Met Met Phe Ile Val
130                 135                 140 tca atc atc atg tct gta att att agt cca aga tta tca ttg att ttc     480
Ser Ile Ile Met Ser Val Ile Ile Ser Pro Arg Leu Ser Leu Ile Phe
145                 150                 155                 160 ttg gta tta gga cca att ttt gca att gcc tta ggt tta att att aga     528
Leu Val Leu Gly Pro Ile Phe Ala Ile Ala Leu Gly Leu Ile Ile Arg
                165                 170                 175 tca gct tat cca tat ttc cct aag att ttt aga gga tat gac cgc atg     576
Ser Ala Tyr Pro Tyr Phe Pro Lys Ile Phe Arg Gly Tyr Asp Arg Met
            180                 185                 190 aac caa gtt gtt cgt gaa aac gtt cgt ggt att cgc gaa gtt aag act     624
Asn Gln Val Val Arg Glu Asn Val Arg Gly Ile Arg Glu Val Lys Thr
        195                 200                 205 tat gtt caa gaa aaa cca caa att gag aaa ttc gaa aaa tca tcg ggt     672
Tyr Val Gln Glu Lys Pro Gln Ile Glu Lys Phe Glu Lys Ser Ser Gly
210                 215                 220 ttt att tat aag tta ttt gca acc gca caa aag att atg tct ttg aat     720
Phe Ile Tyr Lys Leu Phe Ala Thr Ala Gln Lys Ile Met Ser Leu Asn
225                 230                 235                 240 gca ctt gta gta gct gct gtt ttg aat att tca act ttg gca att tgc     768
Ala Leu Val Val Ala Ala Val Leu Asn Ile Ser Thr Leu Ala Ile Cys
                245                 250                 255 tgg ttt ggt gct aaa gaa gta gtt ggc ggt acc ttg caa aca ggt caa     816
Trp Phe Gly Ala Lys Glu Val Val Gly Gly Thr Leu Gln Thr Gly Gln
            260                 265                 270 ctt att tct atg ttt act tat tca aat tca gtg tta ttt agt ttg aat     864
Leu Ile Ser Met Phe Thr Tyr Ser Asn Ser Val Leu Phe Ser Leu Asn
        275                 280                 285 att ttg gca atg att acc acc caa tta gta att tca ggt gct agc ggt     912
Ile Leu Ala Met Ile Thr Thr Gln Leu Val Ile Ser Gly Ala Ser Gly
290                 295                 300
```

-continued

```
cgt cgt att gct gct gta att aat gaa aaa cct act att gaa aat cca      960
Arg Arg Ile Ala Ala Val Ile Asn Glu Lys Pro Thr Ile Glu Asn Pro
305                 310                 315                 320 aag aaa cca ctt aag cgt ttg act aat ggt gaa att att ttt gac cat     1008
Lys Lys Pro Leu Lys Arg Leu Thr Asn Gly Glu Ile Ile Phe Asp His
            325                 330                 335 gta aac ttt aag tat gaa tta gct gat aaa aat gag gct ctt agc gat     1056
Val Asn Phe Lys Tyr Glu Leu Ala Asp Lys Asn Glu Ala Leu Ser Asp
        340                 345                 350 att aat ctg cgg att aag cca ggg gaa aca atc ggt att att ggt gaa     1104
Ile Asn Leu Arg Ile Lys Pro Gly Glu Thr Ile Gly Ile Ile Gly Glu
    355                 360                 365 aca gga tca tct aaa tct act tta gta tca atg atc cct cgt ctt tat     1152
Thr Gly Ser Ser Lys Ser Thr Leu Val Ser Met Ile Pro Arg Leu Tyr
370                 375                 380 gat gta acg tca ggt gct gtt cgt gta gcg gga cat aac gtc aag tca     1200
Asp Val Thr Ser Gly Ala Val Arg Val Ala Gly His Asn Val Lys Ser
385                 390                 395                 400 tat gat cta aag acc tta cgt gat aac gta gcg atg gtt ttg caa aag     1248
Tyr Asp Leu Lys Thr Leu Arg Asp Asn Val Ala Met Val Leu Gln Lys
            405                 410                 415 aat gtt ttg ttc act ggt aca gtt aaa gac aac tta aag tgg ggt aac     1296
Asn Val Leu Phe Thr Gly Thr Val Lys Asp Asn Leu Lys Trp Gly Asn
        420                 425                 430 gaa aac gct act gat gaa caa gtt gtt gct gct gcc aag att gct cat     1344
Glu Asn Ala Thr Asp Glu Gln Val Val Ala Ala Ala Lys Ile Ala His
    435                 440                 445 gct gac ggc ttc att cgt gaa atg cca gac ggt tac gat acc atg gtt     1392
Ala Asp Gly Phe Ile Arg Glu Met Pro Asp Gly Tyr Asp Thr Met Val
450                 455                 460 gaa caa ggt ggt aac aat gtt tct ggt ggt caa aag caa aga att act     1440
Glu Gln Gly Gly Asn Asn Val Ser Gly Gly Gln Lys Gln Arg Ile Thr
465                 470                 475                 480 att gcc aga gca tta ctt aag gat cct aaa att ttg att ttg gat gat     1488
Ile Ala Arg Ala Leu Leu Lys Asp Pro Lys Ile Leu Ile Leu Asp Asp
            485                 490                 495 tcc act tca gct gtt gat acc agc aca gaa cgt gaa att aga atg tct     1536
Ser Thr Ser Ala Val Asp Thr Ser Thr Glu Arg Glu Ile Arg Met Ser
        500                 505                 510 ctt gca aaa gat atg ccc gaa aca act aag att att att tcc cag aga     1584
Leu Ala Lys Asp Met Pro Glu Thr Thr Lys Ile Ile Ile Ser Gln Arg
    515                 520                 525 att gtt tca att aag gat gct gac aga att atc gtg atg gat cat gga     1632
Ile Val Ser Ile Lys Asp Ala Asp Arg Ile Ile Val Met Asp His Gly
530                 535                 540 aag atc caa gat atc ggt act cac gat gaa ttg atg aag act aat gaa     1680
Lys Ile Gln Asp Ile Gly Thr His Asp Glu Leu Met Lys Thr Asn Glu
545                 550                 555                 560 ctt tac agt tca atc gct aag ttc caa gaa gaa caa gga aag ggt gag     1728
Leu Tyr Ser Ser Ile Ala Lys Phe Gln Glu Glu Gln Gly Lys Gly Glu
            565                 570                 575
```

<210> SEQ ID NO 122
<211> LENGTH: 576
<212> TYPE: PRT
<213> ORGANISM: Lactobacillus acidophilus

<400> SEQUENCE: 122

```
Met Val Lys Thr Leu Ser Lys Ser Ile Arg Gln Tyr Lys Lys Leu Ser
1               5                   10                  15
```

-continued

```
Leu Leu Ser Pro Leu Phe Val Ile Gly Glu Val Ile Ile Glu Met Leu
             20                  25                  30
Ile Pro Tyr Leu Val Gly Ile Leu Ile Asp Asn Gly Ile Met Lys Gly
         35                  40                  45
Asn Met Ser Tyr Ile Ser Lys Met Gly Leu Ile Leu Leu Val Leu Thr
     50                  55                  60
Ile Val Ser Leu Ile Leu Gly Ala Ser Ala Ser Tyr Val Ser Ala His
 65                  70                  75                  80
Ala Ala Ala Gly Phe Ala Ala Asn Leu Arg Lys Asp Met Phe Tyr His
                 85                  90                  95
Met Gln Asp Tyr Ser Phe Glu Asn Ile Asp His Phe Ser Ser Ala Ser
            100                 105                 110
Leu Val Thr Arg Leu Thr Thr Asp Val Asn Asn Val Gln Met Ala Tyr
        115                 120                 125
Gln Met Ile Ile Arg Ile Ala Val Arg Ala Pro Met Met Phe Ile Val
    130                 135                 140
Ser Ile Ile Met Ser Val Ile Ile Ser Pro Arg Leu Ser Leu Ile Phe
145                 150                 155                 160
Leu Val Leu Gly Pro Ile Phe Ala Ile Ala Leu Gly Leu Ile Ile Arg
                165                 170                 175
Ser Ala Tyr Pro Tyr Phe Pro Lys Ile Phe Arg Gly Tyr Asp Arg Met
            180                 185                 190
Asn Gln Val Val Arg Glu Asn Val Arg Gly Ile Arg Glu Val Lys Thr
        195                 200                 205
Tyr Val Gln Glu Lys Pro Gln Ile Glu Lys Phe Glu Lys Ser Ser Gly
    210                 215                 220
Phe Ile Tyr Lys Leu Phe Ala Thr Ala Gln Lys Ile Met Ser Leu Asn
225                 230                 235                 240
Ala Leu Val Val Ala Ala Val Leu Asn Ile Ser Thr Leu Ala Ile Cys
                245                 250                 255
Trp Phe Gly Ala Lys Glu Val Val Gly Gly Thr Leu Gln Thr Gly Gln
            260                 265                 270
Leu Ile Ser Met Phe Thr Tyr Ser Asn Ser Val Leu Phe Ser Leu Asn
        275                 280                 285
Ile Leu Ala Met Ile Thr Thr Gln Leu Val Ile Ser Gly Ala Ser Gly
    290                 295                 300
Arg Arg Ile Ala Ala Val Ile Asn Glu Lys Pro Thr Ile Glu Asn Pro
305                 310                 315                 320
Lys Lys Pro Leu Lys Arg Leu Thr Asn Gly Glu Ile Ile Phe Asp His
                325                 330                 335
Val Asn Phe Lys Tyr Glu Leu Ala Asp Lys Asn Glu Ala Leu Ser Asp
            340                 345                 350
Ile Asn Leu Arg Ile Lys Pro Gly Glu Thr Ile Gly Ile Ile Gly Glu
        355                 360                 365
Thr Gly Ser Ser Lys Ser Thr Leu Val Ser Met Ile Pro Arg Leu Tyr
    370                 375                 380
Asp Val Thr Ser Gly Ala Val Arg Val Ala Gly His Asn Val Lys Ser
385                 390                 395                 400
Tyr Asp Leu Lys Thr Leu Arg Asp Asn Val Ala Met Val Leu Gln Lys
                405                 410                 415
Asn Val Leu Phe Thr Gly Thr Val Lys Asp Asn Leu Lys Trp Gly Asn
            420                 425                 430
```

-continued

```
Glu Asn Ala Thr Asp Glu Gln Val Ala Ala Lys Ile Ala His
    435                 440                 445

Ala Asp Gly Phe Ile Arg Glu Met Pro Asp Gly Tyr Asp Thr Met Val
    450                 455                 460

Glu Gln Gly Gly Asn Asn Val Ser Gly Gly Gln Lys Gln Arg Ile Thr
465                 470                 475                 480

Ile Ala Arg Ala Leu Leu Lys Asp Pro Lys Ile Leu Ile Leu Asp Asp
                485                 490                 495

Ser Thr Ser Ala Val Asp Thr Ser Thr Glu Arg Glu Ile Arg Met Ser
                500                 505                 510

Leu Ala Lys Asp Met Pro Glu Thr Thr Lys Ile Ile Ile Ser Gln Arg
            515                 520                 525

Ile Val Ser Ile Lys Asp Ala Asp Arg Ile Ile Val Met Asp His Gly
530                 535                 540

Lys Ile Gln Asp Ile Gly Thr His Asp Glu Leu Met Lys Thr Asn Glu
545                 550                 555                 560

Leu Tyr Ser Ser Ile Ala Lys Phe Gln Glu Glu Gly Lys Gly Glu
                565                 570                 575
```

<210> SEQ ID NO 123
<211> LENGTH: 1356
<212> TYPE: DNA
<213> ORGANISM: Lactobacillus acidophilus
<220> FEATURE:
<221> NAME/KEY: CDS
<222> LOCATION: (1)..(1356)
<223> OTHER INFORMATION: YycH protein ORF# 80

<400> SEQUENCE: 123

```
atg act ggg atg aga ttt aaa ttc aaa ttt ggt gaa ttt ttc tta ggt    48
Met Thr Gly Met Arg Phe Lys Phe Lys Phe Gly Glu Phe Phe Leu Gly
1               5                   10                  15 tta gga act ttt ctt gtc ata gct ctt tcg ata gtt cta tgg att ttc    96
Leu Gly Thr Phe Leu Val Ile Ala Leu Ser Ile Val Leu Trp Ile Phe
                20                  25                  30 att atg aca agc gat cag cgt ttt agt aat att gga cag aat caa aac   144
Ile Met Thr Ser Asp Gln Arg Phe Ser Asn Ile Gly Gln Asn Gln Asn
            35                  40                  45 aac aca tct aag caa gaa gcg aga aat cat agt gcc aag tct ctt tat   192
Asn Thr Ser Lys Gln Glu Ala Arg Asn His Ser Ala Lys Ser Leu Tyr
        50                  55                  60 gat ttg ttt att cct act aca gcg tat ggt ttt tct gat ggt aaa ctt   240
Asp Leu Phe Ile Pro Thr Thr Ala Tyr Gly Phe Ser Asp Gly Lys Leu
65                  70                  75                  80 tgc caa tta tat gat tct aac aat aat tta act ctt gag ttt act aag   288
Cys Gln Leu Tyr Asp Ser Asn Asn Asn Leu Thr Leu Glu Phe Thr Lys
                85                  90                  95 gag ata aaa aag gca aag gca gat aat aaa att aaa aaa att gtt aac   336
Glu Ile Lys Lys Ala Lys Ala Asp Asn Lys Ile Lys Lys Ile Val Asn
                100                 105                 110 tca agg gat gca tat gaa aat tat tta aat agt cca gaa tat gtt caa   384
Ser Arg Asp Ala Tyr Glu Asn Tyr Leu Asn Ser Pro Glu Tyr Val Gln
            115                 120                 125 ctt gtt tat cct gat gaa atc aca ttt tct ttg ttt aat cat ttg aat   432
Leu Val Tyr Pro Asp Glu Ile Thr Phe Ser Leu Phe Asn His Leu Asn
        130                 135                 140 aat aaa act ggt gat aat cgt gaa ttt aat cga ttt ttt gtt tct aaa   480
Asn Lys Thr Gly Asp Asn Arg Glu Phe Asn Arg Phe Phe Val Ser Lys
145                 150                 155                 160
```

```
tct aat cat tgg att tat tta ggt aat gat caa acc agt gaa att tat      528
Ser Asn His Trp Ile Tyr Leu Gly Asn Asp Gln Thr Ser Glu Ile Tyr
            165                 170                 175 cgt ata aaa att cga ggt gct aat ttt aat aag ctg cgt aaa tat gcc      576
Arg Ile Lys Ile Arg Gly Ala Asn Phe Asn Lys Leu Arg Lys Tyr Ala
        180                 185                 190 aaa gat gct aaa agt aag aat cct gtt cgt ttc gtt cga tta aaa gaa      624
Lys Asp Ala Lys Ser Lys Asn Pro Val Arg Phe Val Arg Leu Lys Glu
    195                 200                 205 gga tac tca cct ttt tac agt aga gaa act gag ggg aga gtt tat agt      672
Gly Tyr Ser Pro Phe Tyr Ser Arg Glu Thr Glu Gly Arg Val Tyr Ser
210                 215                 220 tac tta gtt aac cat caa tca tat tca tat ttt gtt tca cgg cta ctt      720
Tyr Leu Val Asn His Gln Ser Tyr Ser Tyr Phe Val Ser Arg Leu Leu
225                 230                 235                 240 ggt acg tct ggc gta act agt aaa aca aat aag aat ggt caa acg ata      768
Gly Thr Ser Gly Val Thr Ser Lys Thr Asn Lys Asn Gly Gln Thr Ile
                245                 250                 255 tac tca ctt aac tat tac act aga tta aga gtg cca gac caa aaa tca      816
Tyr Ser Leu Asn Tyr Tyr Thr Arg Leu Arg Val Pro Asp Gln Lys Ser
            260                 265                 270 ggt gaa cat aat tac tta tat act cat ttt gag aaa aat aag att cca      864
Gly Glu His Asn Tyr Leu Tyr Thr His Phe Glu Lys Asn Lys Ile Pro
        275                 280                 285 aat gcg acg aat cgt ttg ctt gat agt gtt tat tat gtt cat caa cta      912
Asn Ala Thr Asn Arg Leu Leu Asp Ser Val Tyr Tyr Val His Gln Leu
    290                 295                 300 gga tta act gag caa gat ttg cgt ttc ttt gat gct gat ggt act aat      960
Gly Leu Thr Glu Gln Asp Leu Arg Phe Phe Asp Ala Asp Gly Thr Asn
305                 310                 315                 320 gtt agc tat ttg aac tat att gaa gga att cct gta ttt tta aac cag     1008
Val Ser Tyr Leu Asn Tyr Ile Glu Gly Ile Pro Val Phe Leu Asn Gln
                325                 330                 335 cat gac tta caa ata aga act act ttt tca aca gat tca atc aat gta     1056
His Asp Leu Gln Ile Arg Thr Thr Phe Ser Thr Asp Ser Ile Asn Val
            340                 345                 350 gca ttt aat agt att aac ttt caa att cct atc cca ttc gat ggg caa     1104
Ala Phe Asn Ser Ile Asn Phe Gln Ile Pro Ile Pro Phe Asp Gly Gln
        355                 360                 365 act caa gca ctt aag ccg act gat gat gtg gtt gag gaa ttg tct gct     1152
Thr Gln Ala Leu Lys Pro Thr Asp Asp Val Val Glu Glu Leu Ser Ala
    370                 375                 380 cat gga tta agc gaa ggt gat att caa aga atc gtt gtt ggg ttc aga     1200
His Gly Leu Ser Glu Gly Asp Ile Gln Arg Ile Val Val Gly Phe Arg
385                 390                 395                 400 atg gaa aaa gat act agt cat cat agt tta att aac tta att cca act     1248
Met Glu Lys Asp Thr Ser His His Ser Leu Ile Asn Leu Ile Pro Thr
                405                 410                 415 tat tat gta aaa gcc tat gat gag tgg aag agt gtc agt gaa tgg aaa     1296
Tyr Tyr Val Lys Ala Tyr Asp Glu Trp Lys Ser Val Ser Glu Trp Lys
            420                 425                 430 aag caa gac tta gct act tat cgt aaa ttt aat aaa tct aat agt agt     1344
Lys Gln Asp Leu Ala Thr Tyr Arg Lys Phe Asn Lys Ser Asn Ser Ser
        435                 440                 445 gaa ggg gtg aga                                                     1356
Glu Gly Val Arg
    450

<210> SEQ ID NO 124
<211> LENGTH: 452
```

<212> TYPE: PRT
<213> ORGANISM: Lactobacillus acidophilus

<400> SEQUENCE: 124

```
Met Thr Gly Met Arg Phe Lys Phe Lys Phe Gly Glu Phe Phe Leu Gly
1               5                   10                  15

Leu Gly Thr Phe Leu Val Ile Ala Leu Ser Ile Val Leu Trp Ile Phe
            20                  25                  30

Ile Met Thr Ser Asp Gln Arg Phe Ser Asn Ile Gly Gln Asn Gln Asn
        35                  40                  45

Asn Thr Ser Lys Gln Glu Ala Arg Asn His Ser Ala Lys Ser Leu Tyr
    50                  55                  60

Asp Leu Phe Ile Pro Thr Thr Ala Tyr Gly Phe Ser Asp Gly Lys Leu
65                  70                  75                  80

Cys Gln Leu Tyr Asp Ser Asn Asn Leu Thr Leu Glu Phe Thr Lys
                85                  90                  95

Glu Ile Lys Lys Ala Lys Ala Asp Asn Lys Ile Lys Lys Ile Val Asn
                100                 105                 110

Ser Arg Asp Ala Tyr Glu Asn Tyr Leu Asn Ser Pro Glu Tyr Val Gln
            115                 120                 125

Leu Val Tyr Pro Asp Glu Ile Thr Phe Ser Leu Phe Asn His Leu Asn
        130                 135                 140

Asn Lys Thr Gly Asp Asn Arg Glu Phe Asn Arg Phe Phe Val Ser Lys
145                 150                 155                 160

Ser Asn His Trp Ile Tyr Leu Gly Asn Asp Gln Thr Ser Glu Ile Tyr
                165                 170                 175

Arg Ile Lys Ile Arg Gly Ala Asn Phe Asn Lys Leu Arg Lys Tyr Ala
            180                 185                 190

Lys Asp Ala Lys Ser Lys Asn Pro Val Arg Phe Val Arg Leu Lys Glu
        195                 200                 205

Gly Tyr Ser Pro Phe Tyr Ser Arg Glu Thr Glu Gly Arg Val Tyr Ser
    210                 215                 220

Tyr Leu Val Asn His Gln Ser Tyr Ser Tyr Phe Val Ser Arg Leu Leu
225                 230                 235                 240

Gly Thr Ser Gly Val Thr Ser Lys Thr Asn Lys Asn Gly Gln Thr Ile
                245                 250                 255

Tyr Ser Leu Asn Tyr Tyr Thr Arg Leu Arg Val Pro Asp Gln Lys Ser
            260                 265                 270

Gly Glu His Asn Tyr Leu Tyr Thr His Phe Glu Lys Asn Lys Ile Pro
        275                 280                 285

Asn Ala Thr Asn Arg Leu Leu Asp Ser Val Tyr Tyr Val His Gln Leu
    290                 295                 300

Gly Leu Thr Glu Gln Asp Leu Arg Phe Phe Asp Ala Asp Gly Thr Asn
305                 310                 315                 320

Val Ser Tyr Leu Asn Tyr Ile Glu Gly Ile Pro Val Phe Leu Asn Gln
                325                 330                 335

His Asp Leu Gln Ile Arg Thr Thr Phe Ser Thr Asp Ser Ile Asn Val
            340                 345                 350

Ala Phe Asn Ser Ile Asn Phe Gln Ile Pro Ile Pro Phe Asp Gly Gln
        355                 360                 365

Thr Gln Ala Leu Lys Pro Thr Asp Val Val Glu Glu Leu Ser Ala
    370                 375                 380

His Gly Leu Ser Glu Gly Asp Ile Gln Arg Ile Val Val Gly Phe Arg
385                 390                 395                 400
```

<210> SEQ ID NO 125
<211> LENGTH: 822
<212> TYPE: DNA
<213> ORGANISM: Lactobacillus acidophilus
<220> FEATURE:
<221> NAME/KEY: CDS
<222> LOCATION: (1)..(822)
<223> OTHER INFORMATION: YycI protein ORF# 81

<400> SEQUENCE: 125

```
Met Glu Lys Asp Thr Ser His His Ser Leu Ile Asn Leu Ile Pro Thr
            405                 410                 415
Tyr Tyr Val Lys Ala Tyr Asp Glu Trp Lys Ser Val Ser Glu Trp Lys
        420                 425                 430
Lys Gln Asp Leu Ala Thr Tyr Arg Lys Phe Asn Lys Ser Asn Ser Ser
    435                 440                 445
Glu Gly Val Arg
450
```

```
ttg gat tat aaa cga att gaa tgg ttg ttt ttt att gtt ttc tta tta       48
Leu Asp Tyr Lys Arg Ile Glu Trp Leu Phe Phe Ile Val Phe Leu Leu
1               5                   10                  15 atc gat ata tat tta gga ata gag att cta cgt tca ccc gtt aac cta       96
Ile Asp Ile Tyr Leu Gly Ile Glu Ile Leu Arg Ser Pro Val Asn Leu
            20                  25                  30 agt aat gca gat act tct tca aga agc gta act agt att cgt tca gaa      144
Ser Asn Ala Asp Thr Ser Ser Arg Ser Val Thr Ser Ile Arg Ser Glu
        35                  40                  45 atg aaa tct gat aat att gat cta cca aat aaa att tcg agc aca cca      192
Met Lys Ser Asp Asn Ile Asp Leu Pro Asn Lys Ile Ser Ser Thr Pro
    50                  55                  60 tct tct ggt tat tat tta gct act aaa aat aaa gat ttt att tca ggt      240
Ser Ser Gly Tyr Tyr Leu Ala Thr Lys Asn Lys Asp Phe Ile Ser Gly
65                  70                  75                  80 aaa gta agc acg tta act aac gta gat gct cgt tat tct aag gca gat      288
Lys Val Ser Thr Leu Thr Asn Val Asp Ala Arg Tyr Ser Lys Ala Asp
                85                  90                  95 aat gca tta tac gct aca cct aaa gtg act act ttg atc agt aaa aag      336
Asn Ala Leu Tyr Ala Thr Pro Lys Val Thr Thr Leu Ile Ser Lys Lys
            100                 105                 110 cct gat gag gcg ttg aaa caa ttg aat aaa ttt aaa aat gat ccc aaa      384
Pro Asp Glu Ala Leu Lys Gln Leu Asn Lys Phe Lys Asn Asp Pro Lys
        115                 120                 125 aac gtc cca tat ggt aaa gag ttt aaa tat gag cca gat atg tct agt      432
Asn Val Pro Tyr Gly Lys Glu Phe Lys Tyr Glu Pro Asp Met Ser Ser
    130                 135                 140 gat gat aat tat gtt ttc gta cag act tca gat ttt ggt gaa att tat      480
Asp Asp Asn Tyr Val Phe Val Gln Thr Ser Asp Phe Gly Glu Ile Tyr
145                 150                 155                 160 gct aat tct gct cag ctg acc att gca gtt aaa gat aat caa atc atc      528
Ala Asn Ser Ala Gln Leu Thr Ile Ala Val Lys Asp Asn Gln Ile Ile
                165                 170                 175 aac tat act gaa act tat atg gga aaa gct agc cca gta aga gag tta      576
Asn Tyr Thr Glu Thr Tyr Met Gly Lys Ala Ser Pro Val Arg Glu Leu
            180                 185                 190 caa tca acg att agt gca tgg cgt gca att cga gct atg tat act gat      624
Gln Ser Thr Ile Ser Ala Trp Arg Ala Ile Arg Ala Met Tyr Thr Asp
        195                 200                 205 cgt gaa tta act aat aat tcc aga gta acg cga atc aaa ttg gga tat      672
Arg Glu Leu Thr Asn Asn Ser Arg Val Thr Arg Ile Lys Leu Gly Tyr
    210                 215                 220
```

```
                      210                 215                 220
tca aaa tta act gag gtt cga ggc agt act att ttg ctt cca act tgg      720
Ser Lys Leu Thr Glu Val Arg Gly Ser Thr Ile Leu Leu Pro Thr Trp
225                 230                 235                 240 tta gtt tgg gta gaa aat aag act act aag aat att acg cta aag aga      768
Leu Val Trp Val Glu Asn Lys Thr Thr Lys Asn Ile Thr Leu Lys Arg
                245                 250                 255 gtt aat gca tac aca gca caa atg ctg cag tcg agt act tat aac gta      816
Val Asn Ala Tyr Thr Ala Gln Met Leu Gln Ser Ser Thr Tyr Asn Val
                260                 265                 270 gaa aag                                                              822
Glu Lys
```

<210> SEQ ID NO 126
<211> LENGTH: 274
<212> TYPE: PRT
<213> ORGANISM: Lactobacillus acidophilus

<400> SEQUENCE: 126

```
Leu Asp Tyr Lys Arg Ile Glu Trp Leu Phe Phe Ile Val Phe Leu Leu
1               5                   10                  15

Ile Asp Ile Tyr Leu Gly Ile Glu Ile Leu Arg Ser Pro Val Asn Leu
            20                  25                  30

Ser Asn Ala Asp Thr Ser Ser Arg Ser Val Thr Ser Ile Arg Ser Glu
        35                  40                  45

Met Lys Ser Asp Asn Ile Asp Leu Pro Asn Lys Ile Ser Ser Thr Pro
    50                  55                  60

Ser Ser Gly Tyr Tyr Leu Ala Thr Lys Asn Lys Asp Phe Ile Ser Gly
65                  70                  75                  80

Lys Val Ser Thr Leu Thr Asn Val Asp Ala Arg Tyr Ser Lys Ala Asp
                85                  90                  95

Asn Ala Leu Tyr Ala Thr Pro Lys Val Thr Thr Leu Ile Ser Lys Lys
            100                 105                 110

Pro Asp Glu Ala Leu Lys Gln Leu Asn Lys Phe Lys Asn Asp Pro Lys
        115                 120                 125

Asn Val Pro Tyr Gly Lys Glu Phe Lys Tyr Glu Pro Asp Met Ser Ser
    130                 135                 140

Asp Asp Asn Tyr Val Phe Val Gln Thr Ser Asp Phe Gly Glu Ile Tyr
145                 150                 155                 160

Ala Asn Ser Ala Gln Leu Thr Ile Ala Val Lys Asp Asn Gln Ile Ile
                165                 170                 175

Asn Tyr Thr Glu Thr Tyr Met Gly Lys Ala Ser Pro Val Arg Glu Leu
            180                 185                 190

Gln Ser Thr Ile Ser Ala Trp Arg Ala Ile Arg Ala Met Tyr Thr Asp
        195                 200                 205

Arg Glu Leu Thr Asn Asn Ser Arg Val Thr Arg Ile Lys Leu Gly Tyr
    210                 215                 220

Ser Lys Leu Thr Glu Val Arg Gly Ser Thr Ile Leu Leu Pro Thr Trp
225                 230                 235                 240

Leu Val Trp Val Glu Asn Lys Thr Thr Lys Asn Ile Thr Leu Lys Arg
                245                 250                 255

Val Asn Ala Tyr Thr Ala Gln Met Leu Gln Ser Ser Thr Tyr Asn Val
            260                 265                 270

Glu Lys
```

<210> SEQ ID NO 127
<211> LENGTH: 795
<212> TYPE: DNA
<213> ORGANISM: Lactobacillus acidophilus
<220> FEATURE:
<221> NAME/KEY: CDS
<222> LOCATION: (1)..(795)
<223> OTHER INFORMATION: Hypothetical protein ORF# 82

<400> SEQUENCE: 127

```
ttg aaa att tct gtt tta gca agt ggc tca act ggt aat aca agt tta      48
Leu Lys Ile Ser Val Leu Ala Ser Gly Ser Thr Gly Asn Thr Ser Leu
 1               5                  10                  15 att atg aca ggc cag cat aag atc cta atg gat gct ggc ctt tct ggt      96
Ile Met Thr Gly Gln His Lys Ile Leu Met Asp Ala Gly Leu Ser Gly
                20                  25                  30 aaa aag act aag caa tta cta gat gaa gtt ggt ata gat att aat gag     144
Lys Lys Thr Lys Gln Leu Leu Asp Glu Val Gly Ile Asp Ile Asn Glu
            35                  40                  45 att gat atg gcc ttt ttg agt cat gat cat aca gat cat agt gga ggc     192
Ile Asp Met Ala Phe Leu Ser His Asp His Thr Asp His Ser Gly Gly
        50                  55                  60 tta ggc gtt tta atg cgg cga tat cct aaa atc gat gca ttt gct aac     240
Leu Gly Val Leu Met Arg Arg Tyr Pro Lys Ile Asp Ala Phe Ala Asn
 65                  70                  75                  80 agt gga acg tgg caa tat tta ctt gat acc cat aag atc gga aaa tta     288
Ser Gly Thr Trp Gln Tyr Leu Leu Asp Thr His Lys Ile Gly Lys Leu
                85                  90                  95 cct gca gaa caa atg aat gtg att gag cct ggg caa act aaa act ttt     336
Pro Ala Glu Gln Met Asn Val Ile Glu Pro Gly Gln Thr Lys Thr Phe
            100                 105                 110 gga gat tta gat gtt act gca ttt gct act agc cat gat gca gct gaa     384
Gly Asp Leu Asp Val Thr Ala Phe Ala Thr Ser His Asp Ala Ala Glu
        115                 120                 125 cct cag tat tat gtg ttt act agt ggg ggc aaa aga gca gca ttt tta     432
Pro Gln Tyr Tyr Val Phe Thr Ser Gly Gly Lys Arg Ala Ala Phe Leu
    130                 135                 140 act gat act ggc tat gtt tct gag aca gtt gag ggt aca att gag gat     480
Thr Asp Thr Gly Tyr Val Ser Glu Thr Val Glu Gly Thr Ile Glu Asp
145                 150                 155                 160 gca gac gcc tat atg atg gaa ttc aat tac gat acg atg atg ctt aga     528
Ala Asp Ala Tyr Met Met Glu Phe Asn Tyr Asp Thr Met Met Leu Arg
                165                 170                 175 gat ggc cct tat tct tgg tca tta aag cag cga att ttg tca gat gtg     576
Asp Gly Pro Tyr Ser Trp Ser Leu Lys Gln Arg Ile Leu Ser Asp Val
            180                 185                 190 ggg cat ttg tct aat gag gat gca gct cag gca ttg gtt gat gtt gtt     624
Gly His Leu Ser Asn Glu Asp Ala Ala Gln Ala Leu Val Asp Val Val
        195                 200                 205 aca cca aaa aca aaa cat att ttt ttg gca cat cgc agt caa cat aat     672
Thr Pro Lys Thr Lys His Ile Phe Leu Ala His Arg Ser Gln His Asn
    210                 215                 220 aat aca gaa tat ttg gct cgt gaa acg gca aaa gag atg ctg att gat     720
Asn Thr Glu Tyr Leu Ala Arg Glu Thr Ala Lys Glu Met Leu Ile Asp
225                 230                 235                 240 ggg gag gca aat att aac agt gat tta aaa atc att gat aca gag ccg     768
Gly Glu Ala Asn Ile Asn Ser Asp Leu Lys Ile Ile Asp Thr Glu Pro
                245                 250                 255 aat cac cca aca aaa tta att gaa att                                  795
Asn His Pro Thr Lys Leu Ile Glu Ile
            260                 265
```

<210> SEQ ID NO 128
<211> LENGTH: 265
<212> TYPE: PRT
<213> ORGANISM: Lactobacillus acidophilus

<400> SEQUENCE: 128

```
Leu Lys Ile Ser Val Leu Ala Ser Gly Ser Thr Gly Asn Thr Ser Leu
1               5                   10                  15

Ile Met Thr Gly Gln His Lys Ile Leu Met Asp Ala Gly Leu Ser Gly
            20                  25                  30

Lys Lys Thr Lys Gln Leu Leu Asp Glu Val Gly Ile Asp Ile Asn Glu
        35                  40                  45

Ile Asp Met Ala Phe Leu Ser His Asp His Thr Asp His Ser Gly Gly
    50                  55                  60

Leu Gly Val Leu Met Arg Arg Tyr Pro Lys Ile Asp Ala Phe Ala Asn
65                  70                  75                  80

Ser Gly Thr Trp Gln Tyr Leu Leu Asp Thr His Lys Ile Gly Lys Leu
                85                  90                  95

Pro Ala Glu Gln Met Asn Val Ile Glu Pro Gly Gln Thr Lys Thr Phe
            100                 105                 110

Gly Asp Leu Asp Val Thr Ala Phe Ala Thr Ser His Asp Ala Ala Glu
        115                 120                 125

Pro Gln Tyr Tyr Val Phe Thr Ser Gly Gly Lys Arg Ala Ala Phe Leu
    130                 135                 140

Thr Asp Thr Gly Tyr Val Ser Glu Thr Val Glu Gly Thr Ile Glu Asp
145                 150                 155                 160

Ala Asp Ala Tyr Met Met Glu Phe Asn Tyr Asp Thr Met Met Leu Arg
                165                 170                 175

Asp Gly Pro Tyr Ser Trp Ser Leu Lys Gln Arg Ile Leu Ser Asp Val
            180                 185                 190

Gly His Leu Ser Asn Glu Asp Ala Ala Gln Ala Leu Val Asp Val Val
        195                 200                 205

Thr Pro Lys Thr Lys His Ile Phe Leu Ala His Arg Ser Gln His Asn
    210                 215                 220

Asn Thr Glu Tyr Leu Ala Arg Glu Thr Ala Lys Glu Met Leu Ile Asp
225                 230                 235                 240

Gly Glu Ala Asn Ile Asn Ser Asp Leu Lys Ile Ile Asp Thr Glu Pro
                245                 250                 255

Asn His Pro Thr Lys Leu Ile Glu Ile
            260                 265
```

<210> SEQ ID NO 129
<211> LENGTH: 1269
<212> TYPE: DNA
<213> ORGANISM: Lactobacillus acidophilus
<220> FEATURE:
<221> NAME/KEY: CDS
<222> LOCATION: (1)..(1269)
<223> OTHER INFORMATION: HtrA serine protease ORF# 83

<400> SEQUENCE: 129

```
atg ata tta ggt aat atg agg gga gag tta agt atg gta gaa aat caa      48
Met Ile Leu Gly Asn Met Arg Gly Glu Leu Ser Met Val Glu Asn Gln
1               5                   10                  15 aat aat aat caa cga cca aga aaa aat agt aat gca aag atc atc act      96
Asn Asn Asn Gln Arg Pro Arg Lys Asn Ser Asn Ala Lys Ile Ile Thr
            20                  25                  30
```

```
act gca gct att gta ggt gta gtt ggt ggt ctg atc ggc ggt ggc gtt      144
Thr Ala Ala Ile Val Gly Val Val Gly Gly Leu Ile Gly Gly Gly Val
        35                  40                  45 tca tat tat gca gct gat caa atg aat aac gct act gat act act acg      192
Ser Tyr Tyr Ala Ala Asp Gln Met Asn Asn Ala Thr Asp Thr Thr Thr
    50                  55                  60 gca caa act agt gta tct tca aat agt agt aag gta tcc gaa aaa agt      240
Ala Gln Thr Ser Val Ser Ser Asn Ser Ser Lys Val Ser Glu Lys Ser
65                  70                  75                  80 gct aaa acc agt ggt acg atg act act gct tat aat gat gta aaa ggg      288
Ala Lys Thr Ser Gly Thr Met Thr Thr Ala Tyr Asn Asp Val Lys Gly
                85                  90                  95 gct gta gtg tcc gtt att aac tta aag aga caa tca tcc tca agt agc      336
Ala Val Val Ser Val Ile Asn Leu Lys Arg Gln Ser Ser Ser Ser Ser
            100                 105                 110 gct aac tct ctt tac agc agc tta ttt ggg gat gat agc gat agt tct      384
Ala Asn Ser Leu Tyr Ser Ser Leu Phe Gly Asp Asp Ser Asp Ser Ser
        115                 120                 125 tca ggt aag agc ggc aag ctt gag act tac agt gaa ggt tcc agt gta      432
Ser Gly Lys Ser Gly Lys Leu Glu Thr Tyr Ser Glu Gly Ser Ser Val
    130                 135                 140 gtt tat atg aag tca aat ggt aaa ggc tat att gta act aat aat cac      480
Val Tyr Met Lys Ser Asn Gly Lys Gly Tyr Ile Val Thr Asn Asn His
145                 150                 155                 160 gtt att tca ggc agt gat gca gtt caa gtg caa ctt gct aat ggc aag      528
Val Ile Ser Gly Ser Asp Ala Val Gln Val Gln Leu Ala Asn Gly Lys
                165                 170                 175 act gtt agt gca aag gtt gtt ggg aaa gat agt act act gac tta gct      576
Thr Val Ser Ala Lys Val Val Gly Lys Asp Ser Thr Thr Asp Leu Ala
            180                 185                 190 gtt tta tca att gac gct aag tac gta aca caa aca gcc gaa ttt ggc      624
Val Leu Ser Ile Asp Ala Lys Tyr Val Thr Gln Thr Ala Glu Phe Gly
        195                 200                 205 gat tct aag agt ctt caa gct ggt caa act gta att gct gta ggt tca      672
Asp Ser Lys Ser Leu Gln Ala Gly Gln Thr Val Ile Ala Val Gly Ser
    210                 215                 220 cca ctt ggt agt gaa tat gct tct acg gta acg caa ggt att ata tca      720
Pro Leu Gly Ser Glu Tyr Ala Ser Thr Val Thr Gln Gly Ile Ile Ser
225                 230                 235                 240 gca ccg gct aga act atc tca act tca tct ggt aat cag caa aca gtt      768
Ala Pro Ala Arg Thr Ile Ser Thr Ser Ser Gly Asn Gln Gln Thr Val
                245                 250                 255 att caa aca gat gca gcc att aac cca ggt aac tca ggt ggt gca ttg      816
Ile Gln Thr Asp Ala Ala Ile Asn Pro Gly Asn Ser Gly Gly Ala Leu
            260                 265                 270 gtt aac tca gct ggt caa gtt atc ggt att aat tct atg aag ctt gct      864
Val Asn Ser Ala Gly Gln Val Ile Gly Ile Asn Ser Met Lys Leu Ala
        275                 280                 285 caa tca agt gat ggt act tct gta gaa ggt atg gga ttt gct att cct      912
Gln Ser Ser Asp Gly Thr Ser Val Glu Gly Met Gly Phe Ala Ile Pro
    290                 295                 300 tcg aat gaa gtt gta act atc gta aat gaa ttg gtt aag aag ggt aag      960
Ser Asn Glu Val Val Thr Ile Val Asn Glu Leu Val Lys Lys Gly Lys
305                 310                 315                 320 att act cgt cca caa ctt ggt gta aga gta gtt gct ctt gaa ggt att     1008
Ile Thr Arg Pro Gln Leu Gly Val Arg Val Val Ala Leu Glu Gly Ile
                325                 330                 335 cct gaa gca tac aga agt cgc tta aag att aag tca aac ctt aag agt     1056
Pro Glu Ala Tyr Arg Ser Arg Leu Lys Ile Lys Ser Asn Leu Lys Ser
            340                 345                 350
```

```
ggt atc tat gtt gct tca att aat aag aat agt tca gct gca aat gca    1104
Gly Ile Tyr Val Ala Ser Ile Asn Lys Asn Ser Ser Ala Ala Asn Ala
        355                 360                 365 ggc atg aag agc ggt gat gtc att act aag gta gat ggc aag aag gtt    1152
Gly Met Lys Ser Gly Asp Val Ile Thr Lys Val Asp Gly Lys Lys Val
370                 375                 380 gat gat gta gca tca tta cac agt atc ctt tac agt cac aag gtt ggt    1200
Asp Asp Val Ala Ser Leu His Ser Ile Leu Tyr Ser His Lys Val Gly
385                 390                 395                 400 gac act gtg aac ata act att aat aga aat ggt aga gat gtc aac tta    1248
Asp Thr Val Asn Ile Thr Ile Asn Arg Asn Gly Arg Asp Val Asn Leu
            405                 410                 415 aag gta aaa ctt gaa ggt aat                                        1269
Lys Val Lys Leu Glu Gly Asn
            420

<210> SEQ ID NO 130
<211> LENGTH: 423
<212> TYPE: PRT
<213> ORGANISM: Lactobacillus acidophilus

<400> SEQUENCE: 130

Met Ile Leu Gly Asn Met Arg Gly Glu Leu Ser Met Val Glu Asn Gln
1               5                   10                  15

Asn Asn Asn Gln Arg Pro Arg Lys Asn Ser Asn Ala Lys Ile Ile Thr
            20                  25                  30

Thr Ala Ala Ile Val Gly Val Val Gly Gly Leu Ile Gly Gly Gly Val
        35                  40                  45

Ser Tyr Tyr Ala Ala Asp Gln Met Asn Asn Ala Thr Asp Thr Thr Thr
    50                  55                  60

Ala Gln Thr Ser Val Ser Ser Asn Ser Ser Lys Val Ser Glu Lys Ser
65                  70                  75                  80

Ala Lys Thr Ser Gly Thr Met Thr Thr Ala Tyr Asn Asp Val Lys Gly
                85                  90                  95

Ala Val Val Ser Val Ile Asn Leu Lys Arg Gln Ser Ser Ser Ser Ser
            100                 105                 110

Ala Asn Ser Leu Tyr Ser Ser Leu Phe Gly Asp Asp Ser Asp Ser Ser
        115                 120                 125

Ser Gly Lys Ser Gly Lys Leu Glu Thr Tyr Ser Glu Gly Ser Ser Val
    130                 135                 140

Val Tyr Met Lys Ser Asn Gly Lys Gly Tyr Ile Val Thr Asn Asn His
145                 150                 155                 160

Val Ile Ser Gly Ser Asp Ala Val Gln Val Gln Leu Ala Asn Gly Lys
                165                 170                 175

Thr Val Ser Ala Lys Val Val Gly Lys Asp Ser Thr Thr Asp Leu Ala
            180                 185                 190

Val Leu Ser Ile Asp Ala Lys Tyr Val Thr Gln Thr Ala Glu Phe Gly
        195                 200                 205

Asp Ser Lys Ser Leu Gln Ala Gly Gln Thr Val Ile Ala Val Gly Ser
    210                 215                 220

Pro Leu Gly Ser Glu Tyr Ala Ser Thr Val Thr Gln Gly Ile Ile Ser
225                 230                 235                 240

Ala Pro Ala Arg Thr Ile Ser Thr Ser Ser Gly Asn Gln Gln Thr Val
                245                 250                 255

Ile Gln Thr Asp Ala Ala Ile Asn Pro Gly Asn Ser Gly Gly Ala Leu
            260                 265                 270
```

```
Val Asn Ser Ala Gly Gln Val Ile Gly Ile Asn Ser Met Lys Leu Ala
        275                 280                 285

Gln Ser Ser Asp Gly Thr Ser Val Glu Gly Met Gly Phe Ala Ile Pro
        290                 295                 300

Ser Asn Glu Val Val Thr Ile Val Asn Glu Leu Val Lys Lys Gly Lys
305                 310                 315                 320

Ile Thr Arg Pro Gln Leu Gly Val Arg Val Ala Leu Glu Gly Ile
                325                 330                 335

Pro Glu Ala Tyr Arg Ser Arg Leu Lys Ile Lys Ser Asn Leu Lys Ser
        340                 345                 350

Gly Ile Tyr Val Ala Ser Ile Asn Lys Asn Ser Ser Ala Ala Asn Ala
        355                 360                 365

Gly Met Lys Ser Gly Asp Val Ile Thr Lys Val Asp Gly Lys Lys Val
        370                 375                 380

Asp Asp Val Ala Ser Leu His Ser Ile Leu Tyr Ser His Lys Val Gly
385                 390                 395                 400

Asp Thr Val Asn Ile Thr Ile Asn Arg Asn Gly Arg Asp Val Asn Leu
                405                 410                 415

Lys Val Lys Leu Glu Gly Asn
        420

<210> SEQ ID NO 131
<211> LENGTH: 171
<212> TYPE: DNA
<213> ORGANISM: Lactobacillus acidophilus
<220> FEATURE:
<221> NAME/KEY: CDS
<222> LOCATION: (1)..(171)
<223> OTHER INFORMATION: Oxidoreductase ORF# 1421

<400> SEQUENCE: 131 atg gct gaa tta aac gat tct ttg act ttt aaa cat ggc gca aaa atc      48
Met Ala Glu Leu Asn Asp Ser Leu Thr Phe Lys His Gly Ala Lys Ile
1               5                   10                  15 tct aac cgc ttc gtt caa ccg ccg atg ttg aca aac agt ggt atc gat      96
Ser Asn Arg Phe Val Gln Pro Pro Met Leu Thr Asn Ser Gly Ile Asp
            20                  25                  30 ggc gaa gca agt gaa gac aca att aat tat tgg aga cat cac tca aag     144
Gly Glu Ala Ser Glu Asp Thr Ile Asn Tyr Trp Arg His His Ser Lys
        35                  40                  45 tcg ggt ggt atg tta att act gaa tgt                                 171
Ser Gly Gly Met Leu Ile Thr Glu Cys
    50                  55

<210> SEQ ID NO 132
<211> LENGTH: 57
<212> TYPE: PRT
<213> ORGANISM: Lactobacillus acidophilus

<400> SEQUENCE: 132

Met Ala Glu Leu Asn Asp Ser Leu Thr Phe Lys His Gly Ala Lys Ile
1               5                   10                  15

Ser Asn Arg Phe Val Gln Pro Pro Met Leu Thr Asn Ser Gly Ile Asp
            20                  25                  30

Gly Glu Ala Ser Glu Asp Thr Ile Asn Tyr Trp Arg His His Ser Lys
        35                  40                  45

Ser Gly Gly Met Leu Ile Thr Glu Cys
    50                  55
```

<210> SEQ ID NO 133
<211> LENGTH: 552
<212> TYPE: DNA
<213> ORGANISM: Lactobacillus acidophilus
<220> FEATURE:
<221> NAME/KEY: CDS
<222> LOCATION: (1)..(552)
<223> OTHER INFORMATION: Pyrazinamidase/nicotinamidase ORF# 1422

<400> SEQUENCE: 133

```
atg aca aat gaa gct tta tta atc atc gat tat act aac gat ttc gta        48
Met Thr Asn Glu Ala Leu Leu Ile Ile Asp Tyr Thr Asn Asp Phe Val
1               5                   10                  15 gac gac aag ggt gca ctc act tgt ggc aag cca gca caa gaa tta gac        96
Asp Asp Lys Gly Ala Leu Thr Cys Gly Lys Pro Ala Gln Glu Leu Asp
                20                  25                  30 gat act att gcc aat ttg gct gat aaa ttt tta aaa gag gac aag tgg       144
Asp Thr Ile Ala Asn Leu Ala Asp Lys Phe Leu Lys Glu Asp Lys Trp
            35                  40                  45 gtg atc ttt cca act gac aag cac ttt aag gat aat cca tat cat cct       192
Val Ile Phe Pro Thr Asp Lys His Phe Lys Asp Asn Pro Tyr His Pro
    50                  55                  60 gaa acg aag ctt ttt cca cca cat aat ttg cct aat acc tgg gga cgc       240
Glu Thr Lys Leu Phe Pro Pro His Asn Leu Pro Asn Thr Trp Gly Arg
65                  70                  75                  80 gaa tta tat ggg aaa gta gga aag tgg tat gaa gct cac aaa gat aat       288
Glu Leu Tyr Gly Lys Val Gly Lys Trp Tyr Glu Ala His Lys Asp Asn
                85                  90                  95 aat cat gta att ttg atg gat aaa act cgc tat tct gct ttt gct ggt       336
Asn His Val Ile Leu Met Asp Lys Thr Arg Tyr Ser Ala Phe Ala Gly
                100                 105                 110 acg tca ctt gat ctg ctt ttg cgt gag cgt aag atc gat act ttg cat       384
Thr Ser Leu Asp Leu Leu Leu Arg Glu Arg Lys Ile Asp Thr Leu His
            115                 120                 125 ttg act ggt gtc tgc act gat att tgt gtt ttg cat act gca atg gat       432
Leu Thr Gly Val Cys Thr Asp Ile Cys Val Leu His Thr Ala Met Asp
    130                 135                 140 gct tat aat cat tgc tat aac ttg gtt gta cat gaa aat ggc gta gct       480
Ala Tyr Asn His Cys Tyr Asn Leu Val Val His Glu Asn Gly Val Ala
145                 150                 155                 160 agc ttt gat caa aat ggt cat aag tgg gca ttg aat cat ttt aag act       528
Ser Phe Asp Gln Asn Gly His Lys Trp Ala Leu Asn His Phe Lys Thr
                165                 170                 175 tgt ttg ggt gct aag gtt gta gat                                       552
Cys Leu Gly Ala Lys Val Val Asp
            180
```

<210> SEQ ID NO 134
<211> LENGTH: 184
<212> TYPE: PRT
<213> ORGANISM: Lactobacillus acidophilus

<400> SEQUENCE: 134

```
Met Thr Asn Glu Ala Leu Leu Ile Ile Asp Tyr Thr Asn Asp Phe Val
1               5                   10                  15

Asp Asp Lys Gly Ala Leu Thr Cys Gly Lys Pro Ala Gln Glu Leu Asp
                20                  25                  30

Asp Thr Ile Ala Asn Leu Ala Asp Lys Phe Leu Lys Glu Asp Lys Trp
            35                  40                  45

Val Ile Phe Pro Thr Asp Lys His Phe Lys Asp Asn Pro Tyr His Pro
    50                  55                  60
```

```
Glu Thr Lys Leu Phe Pro Pro His Asn Leu Pro Asn Thr Trp Gly Arg
 65                  70                  75                  80

Glu Leu Tyr Gly Lys Val Gly Lys Trp Tyr Glu Ala His Lys Asp Asn
                 85                  90                  95

Asn His Val Ile Leu Met Asp Lys Thr Arg Tyr Ser Ala Phe Ala Gly
            100                 105                 110

Thr Ser Leu Asp Leu Leu Leu Arg Glu Arg Lys Ile Asp Thr Leu His
        115                 120                 125

Leu Thr Gly Val Cys Thr Asp Ile Cys Val Leu His Thr Ala Met Asp
130                 135                 140

Ala Tyr Asn His Cys Tyr Asn Leu Val Val His Glu Asn Gly Val Ala
145                 150                 155                 160

Ser Phe Asp Gln Asn Gly His Lys Trp Ala Leu Asn His Phe Lys Thr
                165                 170                 175

Cys Leu Gly Ala Lys Val Val Asp
            180

<210> SEQ ID NO 135
<211> LENGTH: 132
<212> TYPE: DNA
<213> ORGANISM: Lactobacillus acidophilus
<220> FEATURE:
<221> NAME/KEY: CDS
<222> LOCATION: (1)..(132)
<223> OTHER INFORMATION: Unknown ORF# 1423

<400> SEQUENCE: 135 atg aaa aga act act aaa tta ggc gtg agt gcc ttg ctt gtt agt ctg     48
Met Lys Arg Thr Thr Lys Leu Gly Val Ser Ala Leu Leu Val Ser Leu
  1               5                  10                  15 ttc gct tta ttt gtt ggt aaa aaa tta gat gat gaa gta aat aaa gat     96
Phe Ala Leu Phe Val Gly Lys Lys Leu Asp Asp Glu Val Asn Lys Asp
                 20                  25                  30 gac gca agc gat gac cgc ggc gtt gga ccg cta gat                    132
Asp Ala Ser Asp Asp Arg Gly Val Gly Pro Leu Asp
            35                  40

<210> SEQ ID NO 136
<211> LENGTH: 44
<212> TYPE: PRT
<213> ORGANISM: Lactobacillus acidophilus

<400> SEQUENCE: 136

Met Lys Arg Thr Thr Lys Leu Gly Val Ser Ala Leu Leu Val Ser Leu
  1               5                  10                  15

Phe Ala Leu Phe Val Gly Lys Lys Leu Asp Asp Glu Val Asn Lys Asp
                 20                  25                  30

Asp Ala Ser Asp Asp Arg Gly Val Gly Pro Leu Asp
            35                  40

<210> SEQ ID NO 137
<211> LENGTH: 1494
<212> TYPE: DNA
<213> ORGANISM: Lactobacillus acidophilus
<220> FEATURE:
<221> NAME/KEY: CDS
<222> LOCATION: (1)..(1494)
<223> OTHER INFORMATION: Amino acid permease ORF# 1424

<400> SEQUENCE: 137 atg aag caa gat aat cac gtt aag att aaa cta ggc agt tta gtc tta     48
```

```
       Met Lys Gln Asp Asn His Val Lys Ile Lys Leu Gly Ser Leu Val Leu
       1               5                   10                  15 atg att ttc tct tct att ttt gga ttt agt aat tca ttg acg gcc ttt         96
Met Ile Phe Ser Ser Ile Phe Gly Phe Ser Asn Ser Leu Thr Ala Phe
            20                  25                  30 tac cag atg gga tat tca agt atc att tgg tat att gta act gcc gtt        144
Tyr Gln Met Gly Tyr Ser Ser Ile Ile Trp Tyr Ile Val Thr Ala Val
                35                  40                  45 ttg ttc ttc ttg cca tcc gca ctt atc ttt gcg gaa tac ggt gca gct        192
Leu Phe Phe Leu Pro Ser Ala Leu Ile Phe Ala Glu Tyr Gly Ala Ala
        50                  55                  60 ttt aag ggg att aaa ggt ggt atc ttt tct tgg ctt gaa ggt tct act        240
Phe Lys Gly Ile Lys Gly Gly Ile Phe Ser Trp Leu Glu Gly Ser Thr
65                  70                  75                  80 aat gaa aag gta gca ttt atc gga acg ttt att tgg cta tct gcc tgg        288
Asn Glu Lys Val Ala Phe Ile Gly Thr Phe Ile Trp Leu Ser Ala Trp
                85                  90                  95 gtt gtc tgg ctg gta tct tct act cag ttt ttc ttg gta tcg gtt tca        336
Val Val Trp Leu Val Ser Ser Thr Gln Phe Phe Leu Val Ser Val Ser
            100                 105                 110 acc gct ata ttc gga cat gat act act caa agt tgg cat ttg gga gga        384
Thr Ala Ile Phe Gly His Asp Thr Thr Gln Ser Trp His Leu Gly Gly
                115                 120                 125 tta act tca aca caa tta tta ggg att ctt gaa gtt atc ttt tta gca        432
Leu Thr Ser Thr Gln Leu Leu Gly Ile Leu Glu Val Ile Phe Leu Ala
        130                 135                 140 gtt gtt act ttt tgt gcc gca aag gga atc gac aaa ata aag gcg atc        480
Val Val Thr Phe Cys Ala Ala Lys Gly Ile Asp Lys Ile Lys Ala Ile
145                 150                 155                 160 aat aat att ggt ggg att ttt act ttg gcg att gct att ggt ttt aca        528
Asn Asn Ile Gly Gly Ile Phe Thr Leu Ala Ile Ala Ile Gly Phe Thr
                165                 170                 175 gtt gtt tca ttg ctg gtg ttc ttt tta aat cat ggc caa ttg gct gaa        576
Val Val Ser Leu Leu Val Phe Phe Leu Asn His Gly Gln Leu Ala Glu
            180                 185                 190 cct att act tcc cag aat ttg gtt cat tca cca aat cca tca ttc caa        624
Pro Ile Thr Ser Gln Asn Leu Val His Ser Pro Asn Pro Ser Phe Gln
                195                 200                 205 tcc cca att gca gtt gtt tca ttc att gtt tat gca tta ttt gct tat        672
Ser Pro Ile Ala Val Val Ser Phe Ile Val Tyr Ala Leu Phe Ala Tyr
        210                 215                 220 ggt ggt ctt gaa act act tct ggt gtg att gac tca gtt gat aaa cct        720
Gly Gly Leu Glu Thr Thr Ser Gly Val Ile Asp Ser Val Asp Lys Pro
225                 230                 235                 240 gaa aag act tac cct aag ggg ttg atc att gcg atg att atg atg act        768
Glu Lys Thr Tyr Pro Lys Gly Leu Ile Ile Ala Met Ile Met Met Thr
                245                 250                 255 gca ctt tat gtt gta aat att ttt atg tgt ggg gta gct gtt aac tgg        816
Ala Leu Tyr Val Val Asn Ile Phe Met Cys Gly Val Ala Val Asn Trp
            260                 265                 270 aat aag gac tta ggt gtt aaa ggt gtt gac ctt gct aac gtt gaa tat        864
Asn Lys Asp Leu Gly Val Lys Gly Val Asp Leu Ala Asn Val Glu Tyr
                275                 280                 285 gtt ttg att aac aat ctt ggt gtg gtc act ggt aag agc tta ggc ttg        912
Val Leu Ile Asn Asn Leu Gly Val Val Thr Gly Lys Ser Leu Gly Leu
        290                 295                 300 tct cat tca gca tct ttg gca atc ggt tca gca ttt tca cac ttt gct        960
Ser His Ser Ala Ser Leu Ala Ile Gly Ser Ala Phe Ser His Phe Ala
305                 310                 315                 320
```

-continued

```
ggt att gct gat gtt tta tca ggt atc gct gct gca ttt ttg atg gtt      1008
Gly Ile Ala Asp Val Leu Ser Gly Ile Ala Ala Ala Phe Leu Met Val
                325                 330                 335 tac tca cca att aag tca ttt att gaa ggt tgt gat cca cga ctt tta      1056
Tyr Ser Pro Ile Lys Ser Phe Ile Glu Gly Cys Asp Pro Arg Leu Leu
            340                 345                 350 cct aaa aaa ttg gtt gaa ctt aat aag cac ggg atg cca gaa cgt tca      1104
Pro Lys Lys Leu Val Glu Leu Asn Lys His Gly Met Pro Glu Arg Ser
        355                 360                 365 atg tgg cta caa gca att att gtt agt gta att att ttg ttt att tca      1152
Met Trp Leu Gln Ala Ile Ile Val Ser Val Ile Ile Leu Phe Ile Ser
    370                 375                 380 ttt ggt ggt aat gct gcc aat caa ttc tac aca atc ttg atg gat atg      1200
Phe Gly Gly Asn Ala Ala Asn Gln Phe Tyr Thr Ile Leu Met Asp Met
385                 390                 395                 400 atg aat gta tct tca tct gcg cca tat tta ttc ttg att gca gct tat      1248
Met Asn Val Ser Ser Ser Ala Pro Tyr Leu Phe Leu Ile Ala Ala Tyr
                405                 410                 415 cca ttc ttt aag gca aaa aag gat att gat cgt cca ttt gtt ttc att      1296
Pro Phe Phe Lys Ala Lys Lys Asp Ile Asp Arg Pro Phe Val Phe Ile
            420                 425                 430 gaa ggc aaa aag aag gtt tgg gca acc act att gtt gtt tgg tta gtc      1344
Glu Gly Lys Lys Lys Val Trp Ala Thr Thr Ile Val Val Trp Leu Val
        435                 440                 445 gtc gca att ggt att atc ttt act tgt att gaa cct tta ttt aca gga      1392
Val Ala Ile Gly Ile Ile Phe Thr Cys Ile Glu Pro Leu Phe Thr Gly
    450                 455                 460 gat tat caa aca tca ttc tgg act gca att ggt cca gtt gca ttt ggt      1440
Asp Tyr Gln Thr Ser Phe Trp Thr Ala Ile Gly Pro Val Ala Phe Gly
465                 470                 475                 480 att gta gct tgg gta tat tat gca tat cgt gag cgc aaa gat aaa gcc      1488
Ile Val Ala Trp Val Tyr Tyr Ala Tyr Arg Glu Arg Lys Asp Lys Ala
                485                 490                 495 gca tta                                                              1494
Ala Leu <210> SEQ ID NO 138
<211> LENGTH: 498
<212> TYPE: PRT
<213> ORGANISM: Lactobacillus acidophilus

<400> SEQUENCE: 138

Met Lys Gln Asp Asn His Val Lys Ile Lys Leu Gly Ser Leu Val Leu
1               5                   10                  15

Met Ile Phe Ser Ser Ile Phe Gly Phe Ser Asn Ser Leu Thr Ala Phe
            20                  25                  30

Tyr Gln Met Gly Tyr Ser Ser Ile Ile Trp Tyr Ile Val Thr Ala Val
        35                  40                  45

Leu Phe Phe Leu Pro Ser Ala Leu Ile Phe Ala Glu Tyr Gly Ala Ala
    50                  55                  60

Phe Lys Gly Ile Lys Gly Gly Ile Phe Ser Trp Leu Glu Gly Ser Thr
65                  70                  75                  80

Asn Glu Lys Val Ala Phe Ile Gly Thr Phe Ile Trp Leu Ser Ala Trp
                85                  90                  95

Val Val Trp Leu Val Ser Ser Thr Gln Phe Phe Leu Val Ser Val Ser
            100                 105                 110

Thr Ala Ile Phe Gly His Asp Thr Thr Gln Ser Trp His Leu Gly Gly
        115                 120                 125
```

```
Leu Thr Ser Thr Gln Leu Leu Gly Ile Leu Glu Val Ile Phe Leu Ala
    130                 135                 140

Val Val Thr Phe Cys Ala Ala Lys Gly Ile Asp Lys Ile Lys Ala Ile
145                 150                 155                 160

Asn Asn Ile Gly Gly Ile Phe Thr Leu Ala Ile Ala Ile Gly Phe Thr
                165                 170                 175

Val Val Ser Leu Leu Val Phe Phe Leu Asn His Gly Gln Leu Ala Glu
            180                 185                 190

Pro Ile Thr Ser Gln Asn Leu Val His Ser Pro Asn Pro Ser Phe Gln
        195                 200                 205

Ser Pro Ile Ala Val Val Ser Phe Ile Val Tyr Ala Leu Phe Ala Tyr
    210                 215                 220

Gly Gly Leu Glu Thr Thr Ser Gly Val Ile Asp Ser Val Asp Lys Pro
225                 230                 235                 240

Glu Lys Thr Tyr Pro Lys Gly Leu Ile Ile Ala Met Ile Met Met Thr
                245                 250                 255

Ala Leu Tyr Val Val Asn Ile Phe Met Cys Gly Val Ala Val Asn Trp
            260                 265                 270

Asn Lys Asp Leu Gly Val Lys Gly Val Asp Leu Ala Asn Val Glu Tyr
        275                 280                 285

Val Leu Ile Asn Asn Leu Gly Val Val Thr Lys Ser Leu Gly Leu
    290                 295                 300

Ser His Ser Ala Ser Leu Ala Ile Gly Ser Ala Phe Ser His Phe Ala
305                 310                 315                 320

Gly Ile Ala Asp Val Leu Ser Gly Ile Ala Ala Phe Leu Met Val
                325                 330                 335

Tyr Ser Pro Ile Lys Ser Phe Ile Glu Gly Cys Asp Pro Arg Leu Leu
            340                 345                 350

Pro Lys Lys Leu Val Glu Leu Asn Lys His Gly Met Pro Glu Arg Ser
        355                 360                 365

Met Trp Leu Gln Ala Ile Ile Val Ser Val Ile Ile Leu Phe Ile Ser
    370                 375                 380

Phe Gly Gly Asn Ala Ala Asn Gln Phe Tyr Thr Ile Leu Met Asp Met
385                 390                 395                 400

Met Asn Val Ser Ser Ser Ala Pro Tyr Leu Phe Leu Ile Ala Ala Tyr
                405                 410                 415

Pro Phe Phe Lys Ala Lys Lys Asp Ile Asp Arg Pro Phe Val Phe Ile
            420                 425                 430

Glu Gly Lys Lys Lys Val Trp Ala Thr Thr Ile Val Val Trp Leu Val
        435                 440                 445

Val Ala Ile Gly Ile Ile Phe Thr Cys Ile Glu Pro Leu Phe Thr Gly
    450                 455                 460

Asp Tyr Gln Thr Ser Phe Trp Thr Ala Ile Gly Pro Val Ala Phe Gly
465                 470                 475                 480

Ile Val Ala Trp Val Tyr Tyr Ala Tyr Arg Glu Arg Lys Asp Lys Ala
                485                 490                 495

Ala Leu

<210> SEQ ID NO 139
<211> LENGTH: 693
<212> TYPE: DNA
<213> ORGANISM: Lactobacillus acidophilus
<220> FEATURE:
<221> NAME/KEY: CDS
<222> LOCATION: (1)..(693)
```

<223> OTHER INFORMATION: Consensus hypothetical protein ORF# 1425

<400> SEQUENCE: 139

```
atg gtg caa gca att aga aat gct ggt att act aac agt gta att cgt      48
Met Val Gln Ala Ile Arg Asn Ala Gly Ile Thr Asn Ser Val Ile Arg
1               5                   10                  15 gtt aac gta act agg agt ggt gag gtt atc ttg cat ggg aag ttt aaa      96
Val Asn Val Thr Arg Ser Gly Glu Val Ile Leu His Gly Lys Phe Lys
            20                  25                  30 aag aat gcc caa aat cca att att gaa gta aat ttt gat gat aat aag     144
Lys Asn Ala Gln Asn Pro Ile Ile Glu Val Asn Phe Asp Asp Asn Lys
        35                  40                  45 tta agc gac tac ggt aat gat tat gtt cgt ggt tat gag aca gcc ggc     192
Leu Ser Asp Tyr Gly Asn Asp Tyr Val Arg Gly Tyr Glu Thr Ala Gly
    50                  55                  60 gca cgc tat gtt aga aat gct att aga act gtt aac aga aag tgt ggc     240
Ala Arg Tyr Val Arg Asn Ala Ile Arg Thr Val Asn Arg Lys Cys Gly
65                  70                  75                  80 ttc agc aaa gta aac atc gtg gct cat tca atg ggt aat ctt gaa acg     288
Phe Ser Lys Val Asn Ile Val Ala His Ser Met Gly Asn Leu Glu Thr
                85                  90                  95 gcc tat ttc ttt aaa aac tac ggt aat gaa att cca gta gaa cac ttt     336
Ala Tyr Phe Phe Lys Asn Tyr Gly Asn Glu Ile Pro Val Glu His Phe
            100                 105                 110 gtt tcc atc gct ggt cac tat gat ggt att ctt ggc atg aac gat aag     384
Val Ser Ile Ala Gly His Tyr Asp Gly Ile Leu Gly Met Asn Asp Lys
        115                 120                 125 gct aac caa ttg aaa att aat tct aag act ggt aag cca agc cgc atg     432
Ala Asn Gln Leu Lys Ile Asn Ser Lys Thr Gly Lys Pro Ser Arg Met
    130                 135                 140 caa cca gaa tat cgc ggt tta tta tca ctt aga aaa aca ttc cca aga     480
Gln Pro Glu Tyr Arg Gly Leu Leu Ser Leu Arg Lys Thr Phe Pro Arg
145                 150                 155                 160 aat acg cgt gtg tta aac atc tat ggc aac tta gaa aat ggt act aat     528
Asn Thr Arg Val Leu Asn Ile Tyr Gly Asn Leu Glu Asn Gly Thr Asn
                165                 170                 175 tct gat ggt tca gtt tct aat gca tca tca aga tca tta cgt tac ttg     576
Ser Asp Gly Ser Val Ser Asn Ala Ser Ser Arg Ser Leu Arg Tyr Leu
            180                 185                 190 tta aat ggt cgt gca aag tca tac cgt gaa ttg atg att cgc ggc agc     624
Leu Asn Gly Arg Ala Lys Ser Tyr Arg Glu Leu Met Ile Arg Gly Ser
        195                 200                 205 aat gca caa cat agt aag ttg cac aat aat aat gaa gta aac caa gca     672
Asn Ala Gln His Ser Lys Leu His Asn Asn Asn Glu Val Asn Gln Ala
    210                 215                 220 att tcc aac ttc ttg tgg aaa                                         693
Ile Ser Asn Phe Leu Trp Lys
225                 230
```

<210> SEQ ID NO 140
<211> LENGTH: 231
<212> TYPE: PRT
<213> ORGANISM: Lactobacillus acidophilus

<400> SEQUENCE: 140

```
Met Val Gln Ala Ile Arg Asn Ala Gly Ile Thr Asn Ser Val Ile Arg
1               5                   10                  15

Val Asn Val Thr Arg Ser Gly Glu Val Ile Leu His Gly Lys Phe Lys
            20                  25                  30

Lys Asn Ala Gln Asn Pro Ile Ile Glu Val Asn Phe Asp Asp Asn Lys
```

```
                    35                  40                  45
Leu Ser Asp Tyr Gly Asn Asp Tyr Val Arg Gly Tyr Glu Thr Ala Gly
 50                  55                  60

Ala Arg Tyr Val Arg Asn Ala Ile Arg Thr Val Asn Arg Lys Cys Gly
 65                  70                  75                  80

Phe Ser Lys Val Asn Ile Val Ala His Ser Met Gly Asn Leu Glu Thr
                     85                  90                  95

Ala Tyr Phe Phe Lys Asn Tyr Gly Asn Glu Ile Pro Val Glu His Phe
            100                 105                 110

Val Ser Ile Ala Gly His Tyr Asp Gly Ile Leu Gly Met Asn Asp Lys
        115                 120                 125

Ala Asn Gln Leu Lys Ile Asn Ser Lys Thr Gly Lys Pro Ser Arg Met
130                 135                 140

Gln Pro Glu Tyr Arg Gly Leu Leu Ser Leu Arg Lys Thr Phe Pro Arg
145                 150                 155                 160

Asn Thr Arg Val Leu Asn Ile Tyr Gly Asn Leu Glu Asn Gly Thr Asn
                165                 170                 175

Ser Asp Gly Ser Val Ser Asn Ala Ser Ser Arg Ser Leu Arg Tyr Leu
            180                 185                 190

Leu Asn Gly Arg Ala Lys Ser Tyr Arg Glu Leu Met Ile Arg Gly Ser
        195                 200                 205

Asn Ala Gln His Ser Lys Leu His Asn Asn Asn Glu Val Asn Gln Ala
    210                 215                 220

Ile Ser Asn Phe Leu Trp Lys
225                 230

<210> SEQ ID NO 141
<211> LENGTH: 756
<212> TYPE: DNA
<213> ORGANISM: Lactobacillus acidophilus
<220> FEATURE:
<221> NAME/KEY: CDS
<222> LOCATION: (1)..(756)
<223> OTHER INFORMATION: Unknown ORF# 1426

<400> SEQUENCE: 141 atg aat aca aga aaa tta att act tca atg gca gcg gct gta atg ctt      48
Met Asn Thr Arg Lys Leu Ile Thr Ser Met Ala Ala Ala Val Met Leu
  1               5                  10                  15 tct aca ggt tta gct ggt gtg ggt act gca atg aca aac caa cca gca      96
Ser Thr Gly Leu Ala Gly Val Gly Thr Ala Met Thr Asn Gln Pro Ala
             20                  25                  30 caa gct gct act caa tcc ggt agt tca atc agt att aga cgt aga tca     144
Gln Ala Ala Thr Gln Ser Gly Ser Ser Ile Ser Ile Arg Arg Arg Ser
         35                  40                  45 gta act gct aca gta aat tct gat aag cct caa ctt att gca tat gat     192
Val Thr Ala Thr Val Asn Ser Asp Lys Pro Gln Leu Ile Ala Tyr Asp
     50                  55                  60 cca tct act aat aag ttt gtt aag gct ctt gat tca aca tat gta aaa     240
Pro Ser Thr Asn Lys Phe Val Lys Ala Leu Asp Ser Thr Tyr Val Lys
 65                  70                  75                  80 ggt caa act att cca gtt tac tat gct att act gct aca tct act gct     288
Gly Gln Thr Ile Pro Val Tyr Tyr Ala Ile Thr Ala Thr Ser Thr Ala
                 85                  90                  95 aat ggt aca agc caa aac gtt act ttc tac ttc ctt gaa aat aga aca     336
Asn Gly Thr Ser Gln Asn Val Thr Phe Tyr Phe Leu Glu Asn Arg Thr
            100                 105                 110 gta gat ggc aag agt tgt atg ata ctt att cca tca act tct gta aca     384
Val Asp Gly Lys Ser Cys Met Ile Leu Ile Pro Ser Thr Ser Val Thr
```

```
Val Asp Gly Lys Ser Cys Met Ile Leu Ile Pro Ser Thr Ser Val Thr
        115                 120                 125 cca gct tca act gtg cca aca gca gaa gaa ttc caa aag acg gct gaa    432
Pro Ala Ser Thr Val Pro Thr Ala Glu Glu Phe Gln Lys Thr Ala Glu
        130                 135                 140 aat gat gct aaa act att caa gat gct tat gca aat aga act atc aag    480
Asn Asp Ala Lys Thr Ile Gln Asp Ala Tyr Ala Asn Arg Thr Ile Lys
145                 150                 155                 160 tcc att act gtc act cca aaa tcc aaa aag ggc gcc aaa atc tat tac    528
Ser Ile Thr Val Thr Pro Lys Ser Lys Lys Gly Ala Lys Ile Tyr Tyr
                165                 170                 175 gct tat aaa aag agc gca aaa tca aag aag att gtc ttc aaa gca acc    576
Ala Tyr Lys Lys Ser Ala Lys Ser Lys Lys Ile Val Phe Lys Ala Thr
            180                 185                 190 aat aag aag atc aaa tat ggc aag aaa tat aag tca tca atg att gtt    624
Asn Lys Lys Ile Lys Tyr Gly Lys Lys Tyr Lys Ser Ser Met Ile Val
        195                 200                 205 aag aat ggt aag agt aga tat gta tat att ggt aag aag aga tat ctt    672
Lys Asn Gly Lys Ser Arg Tyr Val Tyr Ile Gly Lys Lys Arg Tyr Leu
    210                 215                 220 aaa tca act gct gta aaa gta acc aat gtt aag tac tca cca ctt aac    720
Lys Ser Thr Ala Val Lys Val Thr Asn Val Lys Tyr Ser Pro Leu Asn
225                 230                 235                 240 tta cca gat gat att aag aat tta atc gtt aat aac                    756
Leu Pro Asp Asp Ile Lys Asn Leu Ile Val Asn Asn
                245                 250

<210> SEQ ID NO 142
<211> LENGTH: 252
<212> TYPE: PRT
<213> ORGANISM: Lactobacillus acidophilus

<400> SEQUENCE: 142

Met Asn Thr Arg Lys Leu Ile Thr Ser Met Ala Ala Val Met Leu
1               5                   10                  15

Ser Thr Gly Leu Ala Gly Val Gly Thr Ala Met Thr Asn Gln Pro Ala
            20                  25                  30

Gln Ala Ala Thr Gln Ser Gly Ser Ser Ile Ser Ile Arg Arg Arg Ser
        35                  40                  45

Val Thr Ala Thr Val Asn Ser Asp Lys Pro Gln Leu Ile Ala Tyr Asp
    50                  55                  60

Pro Ser Thr Asn Lys Phe Val Lys Ala Leu Asp Ser Thr Tyr Val Lys
65                  70                  75                  80

Gly Gln Thr Ile Pro Val Tyr Tyr Ala Ile Thr Ala Thr Ser Thr Ala
                85                  90                  95

Asn Gly Thr Ser Gln Asn Val Thr Phe Tyr Phe Leu Glu Asn Arg Thr
            100                 105                 110

Val Asp Gly Lys Ser Cys Met Ile Leu Ile Pro Ser Thr Ser Val Thr
        115                 120                 125

Pro Ala Ser Thr Val Pro Thr Ala Glu Glu Phe Gln Lys Thr Ala Glu
    130                 135                 140

Asn Asp Ala Lys Thr Ile Gln Asp Ala Tyr Ala Asn Arg Thr Ile Lys
145                 150                 155                 160

Ser Ile Thr Val Thr Pro Lys Ser Lys Lys Gly Ala Lys Ile Tyr Tyr
                165                 170                 175

Ala Tyr Lys Lys Ser Ala Lys Ser Lys Lys Ile Val Phe Lys Ala Thr
            180                 185                 190
```

```
Asn Lys Lys Ile Lys Tyr Gly Lys Tyr Lys Ser Ser Met Ile Val
        195                 200                 205

Lys Asn Gly Lys Ser Arg Tyr Val Tyr Ile Gly Lys Lys Arg Tyr Leu
210                 215                 220

Lys Ser Thr Ala Val Lys Val Thr Asn Val Lys Tyr Ser Pro Leu Asn
225                 230                 235                 240

Leu Pro Asp Asp Ile Lys Asn Leu Ile Val Asn Asn
                245                 250
```

<210> SEQ ID NO 143
<211> LENGTH: 690
<212> TYPE: DNA
<213> ORGANISM: Lactobacillus acidophilus
<220> FEATURE:
<221> NAME/KEY: CDS
<222> LOCATION: (1)..(690)
<223> OTHER INFORMATION: Oxidoreductase ORF# 1427

<400> SEQUENCE: 143

```
atg act tta tta gat gaa gcc gtt gta ttg aat gat ggt agt ttg atg        48
Met Thr Leu Leu Asp Glu Ala Val Val Leu Asn Asp Gly Ser Leu Met
1               5                   10                  15 cca aaa gtt ggt gtt gtt gta ggt aat aaa cca gca gat gat gca att        96
Pro Lys Val Gly Val Val Val Gly Asn Lys Pro Ala Asp Asp Ala Ile
                20                  25                  30 aaa gca ggt tat aga tta att gac tgc agc ctt gat caa aaa aca aaa       144
Lys Ala Gly Tyr Arg Leu Ile Asp Cys Ser Leu Asp Gln Lys Thr Lys
            35                  40                  45 ttg aaa gct gaa aat ccg caa cta tat gtg gaa gtt cag gtc cca gaa       192
Leu Lys Ala Glu Asn Pro Gln Leu Tyr Val Glu Val Gln Val Pro Glu
        50                  55                  60 gat gtg att act cgt gat gat ttt aaa aag att aga caa gat att ata       240
Asp Val Ile Thr Arg Asp Asp Phe Lys Lys Ile Arg Gln Asp Ile Ile
65                  70                  75                  80 gac cat cat gct gat ctg tgc tta ttg aag cta agt gat aat aag gaa       288
Asp His His Ala Asp Leu Cys Leu Leu Lys Leu Ser Asp Asn Lys Glu
                85                  90                  95 aaa aat ggt cag att tgg caa gaa tta gag caa tta aaa att caa ggc       336
Lys Asn Gly Gln Ile Trp Gln Glu Leu Glu Gln Leu Lys Ile Gln Gly
            100                 105                 110 tgg att aaa aat att ggt gtt att aat atc agc gtc gat gca ttg aat       384
Trp Ile Lys Asn Ile Gly Val Ile Asn Ile Ser Val Asp Ala Leu Asn
        115                 120                 125 gaa tta tta aat cat act cag gtt aga cca tgt gta gcg caa att agt       432
Glu Leu Leu Asn His Thr Gln Val Arg Pro Cys Val Ala Gln Ile Ser
    130                 135                 140 tat gaa gat caa gga tta att aac tta gct cgt gaa aat aga att caa       480
Tyr Glu Asp Gln Gly Leu Ile Asn Leu Ala Arg Glu Asn Arg Ile Gln
145                 150                 155                 160 gta gaa att cca gtt cat ggt gat att aat gct tta gct gaa att gct       528
Val Glu Ile Pro Val His Gly Asp Ile Asn Ala Leu Ala Glu Ile Ala
                165                 170                 175 agt cat tat ggt acc agc tct gtc gaa tta gtc atg cgc tat ttc agt       576
Ser His Tyr Gly Thr Ser Ser Val Glu Leu Val Met Arg Tyr Phe Ser
            180                 185                 190 caa aag ggt att gtt cca ttg ttt gaa att gaa gat gta gta gaa aat       624
Gln Lys Gly Ile Val Pro Leu Phe Glu Ile Glu Asp Val Val Glu Asn
        195                 200                 205 cca aga att aac ttc act att aat gct gaa gat tta gct aca att ggt       672
Pro Arg Ile Asn Phe Thr Ile Asn Ala Glu Asp Leu Ala Thr Ile Gly
    210                 215                 220
```

```
caa ctt ttt gct caa aag                                              690
Gln Leu Phe Ala Gln Lys
225                 230

<210> SEQ ID NO 144
<211> LENGTH: 230
<212> TYPE: PRT
<213> ORGANISM: Lactobacillus acidophilus

<400> SEQUENCE: 144

Met Thr Leu Leu Asp Glu Ala Val Val Leu Asn Asp Gly Ser Leu Met
1               5                   10                  15

Pro Lys Val Gly Val Val Gly Asn Lys Pro Ala Asp Asp Ala Ile
            20                  25                  30

Lys Ala Gly Tyr Arg Leu Ile Asp Cys Ser Leu Asp Gln Lys Thr Lys
        35                  40                  45

Leu Lys Ala Glu Asn Pro Gln Leu Tyr Val Glu Val Gln Val Pro Glu
    50                  55                  60

Asp Val Ile Thr Arg Asp Asp Phe Lys Lys Ile Arg Gln Asp Ile Ile
65                  70                  75                  80

Asp His His Ala Asp Leu Cys Leu Leu Lys Leu Ser Asp Asn Lys Glu
                85                  90                  95

Lys Asn Gly Gln Ile Trp Gln Glu Leu Glu Gln Leu Lys Ile Gln Gly
            100                 105                 110

Trp Ile Lys Asn Ile Gly Val Ile Asn Ile Ser Val Asp Ala Leu Asn
        115                 120                 125

Glu Leu Leu Asn His Thr Gln Val Arg Pro Cys Val Ala Gln Ile Ser
    130                 135                 140

Tyr Glu Asp Gln Gly Leu Ile Asn Leu Ala Arg Glu Asn Arg Ile Gln
145                 150                 155                 160

Val Glu Ile Pro Val His Gly Asp Ile Asn Ala Leu Ala Glu Ile Ala
                165                 170                 175

Ser His Tyr Gly Thr Ser Ser Val Glu Leu Val Met Arg Tyr Phe Ser
            180                 185                 190

Gln Lys Gly Ile Val Pro Leu Phe Glu Ile Glu Asp Val Val Glu Asn
        195                 200                 205

Pro Arg Ile Asn Phe Thr Ile Asn Ala Glu Asp Leu Ala Thr Ile Gly
    210                 215                 220

Gln Leu Phe Ala Gln Lys
225                 230

<210> SEQ ID NO 145
<211> LENGTH: 462
<212> TYPE: DNA
<213> ORGANISM: Lactobacillus acidophilus
<220> FEATURE:
<221> NAME/KEY: CDS
<222> LOCATION: (1)..(462)
<223> OTHER INFORMATION: Hypothetical ORF#1428

<400> SEQUENCE: 145 ttg gcg caa gag att gaa tgg tgc gat aga tca cca tta aag aaa ggt     48
Leu Ala Gln Glu Ile Glu Trp Cys Asp Arg Ser Pro Leu Lys Lys Gly
1               5                   10                  15 aga aat tcg atg agt gat tat tta gta aaa tct caa cta gaa aat aaa     96
Arg Asn Ser Met Ser Asp Tyr Leu Val Lys Ser Gln Leu Glu Asn Lys
            20                  25                  30 gaa tgg caa att tct aat cat gtc cgt gat cac aac ttt att tgt gat    144
```

```
Glu Trp Gln Ile Ser Asn His Val Arg Asp His Asn Phe Ile Cys Asp
        35                  40                  45 gct aat gat aaa aag tac gat gct ggt cct aat ccg gtt gaa tat tta      192
Ala Asn Asp Lys Lys Tyr Asp Ala Gly Pro Asn Pro Val Glu Tyr Leu
 50                  55                  60 tgt gga agt gta aat tct tgt att gta atg tca gca gga atg atc act      240
Cys Gly Ser Val Asn Ser Cys Ile Val Met Ser Ala Gly Met Ile Thr
 65                  70                  75                  80 aaa gca cat caa tta gat gta aag aat ttt aat gta aaa aat tat gcc      288
Lys Ala His Gln Leu Asp Val Lys Asn Phe Asn Val Lys Asn Tyr Ala
                 85                  90                  95 aag act gaa aaa atg ggt tat ggt aaa tca gta gtt act gag atg aga      336
Lys Thr Glu Lys Met Gly Tyr Gly Lys Ser Val Val Thr Glu Met Arg
            100                 105                 110 att gaa gtc tct ttt gac tca gaa atg tca aag gaa gaa aaa gaa gag      384
Ile Glu Val Ser Phe Asp Ser Glu Met Ser Lys Glu Glu Lys Glu Glu
        115                 120                 125 ttt tta gct cat gtt tta cat gta tct acg att tac caa act att aaa      432
Phe Leu Ala His Val Leu His Val Ser Thr Ile Tyr Gln Thr Ile Lys
130                 135                 140 gaa gca ata aaa att tat gta gaa tta acc                              462
Glu Ala Ile Lys Ile Tyr Val Glu Leu Thr
145                 150
```

<210> SEQ ID NO 146
<211> LENGTH: 154
<212> TYPE: PRT
<213> ORGANISM: Lactobacillus acidophilus

<400> SEQUENCE: 146

```
Leu Ala Gln Glu Ile Glu Trp Cys Asp Arg Ser Pro Leu Lys Lys Gly
  1               5                  10                  15

Arg Asn Ser Met Ser Asp Tyr Leu Val Lys Ser Gln Leu Glu Asn Lys
             20                  25                  30

Glu Trp Gln Ile Ser Asn His Val Arg Asp His Asn Phe Ile Cys Asp
         35                  40                  45

Ala Asn Asp Lys Lys Tyr Asp Ala Gly Pro Asn Pro Val Glu Tyr Leu
 50                  55                  60

Cys Gly Ser Val Asn Ser Cys Ile Val Met Ser Ala Gly Met Ile Thr
 65                  70                  75                  80

Lys Ala His Gln Leu Asp Val Lys Asn Phe Asn Val Lys Asn Tyr Ala
                 85                  90                  95

Lys Thr Glu Lys Met Gly Tyr Gly Lys Ser Val Val Thr Glu Met Arg
            100                 105                 110

Ile Glu Val Ser Phe Asp Ser Glu Met Ser Lys Glu Glu Lys Glu Glu
        115                 120                 125

Phe Leu Ala His Val Leu His Val Ser Thr Ile Tyr Gln Thr Ile Lys
130                 135                 140

Glu Ala Ile Lys Ile Tyr Val Glu Leu Thr
145                 150
```

<210> SEQ ID NO 147
<211> LENGTH: 1176
<212> TYPE: DNA
<213> ORGANISM: Lactobacillus acidophilus
<220> FEATURE:
<221> NAME/KEY: CDS
<222> LOCATION: (1)..(1176)
<223> OTHER INFORMATION: Transporter ORF# 1429

<400> SEQUENCE: 147

```
ttg gca aaa aga aaa tca att tat act aaa gac gtt att tta gtt atg      48
Leu Ala Lys Arg Lys Ser Ile Tyr Thr Lys Asp Val Ile Leu Val Met
1               5                   10                  15 gca gcg tcc ttc ttt ttc atg ttc agt act atg ttt gtt aat ccg ttg      96
Ala Ala Ser Phe Phe Phe Met Phe Ser Thr Met Phe Val Asn Pro Leu
            20                  25                  30 att aat ggc tat gcc aaa aat tta gga gca agt agt gct ttt gca gga     144
Ile Asn Gly Tyr Ala Lys Asn Leu Gly Ala Ser Ser Ala Phe Ala Gly
        35                  40                  45 att atc gta ggt att atg agt gtg gcc gct atg ttt tta cgc ccc gtt     192
Ile Ile Val Gly Ile Met Ser Val Ala Ala Met Phe Leu Arg Pro Val
    50                  55                  60 gct ggt aat tta act gat aaa ttt tct aag tat cgt tta tcc ttt att     240
Ala Gly Asn Leu Thr Asp Lys Phe Ser Lys Tyr Arg Leu Ser Phe Ile
65                  70                  75                  80 ggt gga att tta ata tta atc gga ata gta gga tat atc ctt act cct     288
Gly Gly Ile Leu Ile Leu Ile Gly Ile Val Gly Tyr Ile Leu Thr Pro
                85                  90                  95 tca agc ggt tgg ttg ctg tta ttt aga ctg att aat ggt acg ggg tat     336
Ser Ser Gly Trp Leu Leu Leu Phe Arg Leu Ile Asn Gly Thr Gly Tyr
            100                 105                 110 gtt tta tgt act gtt tgt atg aca act tgg ctg gca ttt ttg gtt cca     384
Val Leu Cys Thr Val Cys Met Thr Thr Trp Leu Ala Phe Leu Val Pro
        115                 120                 125 cgg caa cac gtt ggt gaa gca atg ggt ttc tat ggc tta atg aat gcc     432
Arg Gln His Val Gly Glu Ala Met Gly Phe Tyr Gly Leu Met Asn Ala
    130                 135                 140 ttg gca atg gca tta gca cca gca ctt tca att aat att tat caa aaa     480
Leu Ala Met Ala Leu Ala Pro Ala Leu Ser Ile Asn Ile Tyr Gln Lys
145                 150                 155                 160 att ggt tat cgt gaa agt ctg att gca tcg gct att tca gct tta ttg     528
Ile Gly Tyr Arg Glu Ser Leu Ile Ala Ser Ala Ile Ser Ala Leu Leu
                165                 170                 175 atg gtt atc tct att caa ttt gta ggt aat cat gct aag cct aat gca     576
Met Val Ile Ser Ile Gln Phe Val Gly Asn His Ala Lys Pro Asn Ala
            180                 185                 190 gaa atg tgc caa aga gct gct aaa aag cac ttt aag att att caa gta     624
Glu Met Cys Gln Arg Ala Ala Lys Lys His Phe Lys Ile Ile Gln Val
        195                 200                 205 aat gtt tta ccg gta gct att tta acc act tta ttt gca ata cca tat     672
Asn Val Leu Pro Val Ala Ile Leu Thr Thr Leu Phe Ala Ile Pro Tyr
    210                 215                 220 ttt gtt acc caa gca gat att gta act tat gtt gaa caa atg cat tta     720
Phe Val Thr Gln Ala Asp Ile Val Thr Tyr Val Glu Gln Met His Leu
225                 230                 235                 240 agt gtt gca gta gga tca tat ttc ttg att tat gca att gta ctc tta     768
Ser Val Ala Val Gly Ser Tyr Phe Leu Ile Tyr Ala Ile Val Leu Leu
                245                 250                 255 att att aga att gga ttc aaa cgc tac ttt gat act gtg cgc ttt ggc     816
Ile Ile Arg Ile Gly Phe Lys Arg Tyr Phe Asp Thr Val Arg Phe Gly
            260                 265                 270 gtg tgg ttc tgg att agc ttg gtg tca aca gct gct tat att att ttg     864
Val Trp Phe Trp Ile Ser Leu Val Ser Thr Ala Ala Tyr Ile Ile Leu
        275                 280                 285 ctg gcg gtt atg aat aat aat tgg caa atg gcc tta gca gct gct ggg     912
Leu Ala Val Met Asn Asn Asn Trp Gln Met Ala Leu Ala Ala Ala Gly
    290                 295                 300 atg gcc atg ggg tac ggc att att tat tca gtt tta caa tca acc gct     960
```

```
Met Ala Met Gly Tyr Gly Ile Ile Tyr Ser Val Leu Gln Ser Thr Ala
305                 310                 315                 320 tta ctt ctt gca cca att gaa gaa cag gga tta gct agc tca act ttt     1008
Leu Leu Leu Ala Pro Ile Glu Glu Gln Gly Leu Ala Ser Ser Thr Phe
                325                 330                 335 tat tta gga ttg gat att gct atg gct ttt ggt cct atg att agt ggt     1056
Tyr Leu Gly Leu Asp Ile Ala Met Ala Phe Gly Pro Met Ile Ser Gly
                340                 345                 350 gta att gac agt act ttt cct att aaa tgg ttt tat ccg atc gaa tta     1104
Val Ile Asp Ser Thr Phe Pro Ile Lys Trp Phe Tyr Pro Ile Glu Leu
                355                 360                 365 atc tta att cca ttt ata ctt tta gtt tac ttt att tgg cgc aag aga     1152
Ile Leu Ile Pro Phe Ile Leu Leu Val Tyr Phe Ile Trp Arg Lys Arg
                370                 375                 380 ttg aat ggt gcg ata gat cac cat                                     1176
Leu Asn Gly Ala Ile Asp His His
385                 390

<210> SEQ ID NO 148
<211> LENGTH: 392
<212> TYPE: PRT
<213> ORGANISM: Lactobacillus acidophilus

<400> SEQUENCE: 148

Leu Ala Lys Arg Lys Ser Ile Tyr Thr Lys Asp Val Ile Leu Val Met
1               5                   10                  15

Ala Ala Ser Phe Phe Phe Met Phe Ser Thr Met Phe Val Asn Pro Leu
            20                  25                  30

Ile Asn Gly Tyr Ala Lys Asn Leu Gly Ala Ser Ser Ala Phe Ala Gly
        35                  40                  45

Ile Ile Val Gly Ile Met Ser Val Ala Ala Met Phe Leu Arg Pro Val
    50                  55                  60

Ala Gly Asn Leu Thr Asp Lys Phe Ser Lys Tyr Arg Leu Ser Phe Ile
65                  70                  75                  80

Gly Gly Ile Leu Ile Leu Ile Gly Ile Val Gly Tyr Ile Leu Thr Pro
                85                  90                  95

Ser Ser Gly Trp Leu Leu Leu Phe Arg Leu Ile Asn Gly Thr Gly Tyr
            100                 105                 110

Val Leu Cys Thr Val Cys Met Thr Thr Trp Leu Ala Phe Leu Val Pro
        115                 120                 125

Arg Gln His Val Gly Glu Ala Met Gly Phe Tyr Gly Leu Met Asn Ala
    130                 135                 140

Leu Ala Met Ala Leu Ala Pro Ala Leu Ser Ile Asn Ile Tyr Gln Lys
145                 150                 155                 160

Ile Gly Tyr Arg Glu Ser Leu Ile Ala Ser Ala Ile Ser Ala Leu Leu
                165                 170                 175

Met Val Ile Ser Ile Gln Phe Val Gly Asn His Ala Lys Pro Asn Ala
            180                 185                 190

Glu Met Cys Gln Arg Ala Ala Lys Lys His Phe Lys Ile Ile Gln Val
        195                 200                 205

Asn Val Leu Pro Val Ala Ile Leu Thr Thr Leu Phe Ala Ile Pro Tyr
    210                 215                 220

Phe Val Thr Gln Ala Asp Ile Val Thr Tyr Val Glu Gln Met His Leu
225                 230                 235                 240

Ser Val Ala Val Gly Ser Tyr Phe Leu Ile Tyr Ala Ile Val Leu Leu
                245                 250                 255
```

```
Ile Ile Arg Ile Gly Phe Lys Arg Tyr Phe Asp Thr Val Arg Phe Gly
            260                 265                 270

Val Trp Phe Trp Ile Ser Leu Val Ser Thr Ala Ala Tyr Ile Ile Leu
        275                 280                 285

Leu Ala Val Met Asn Asn Asn Trp Gln Met Ala Leu Ala Ala Ala Gly
        290                 295                 300

Met Ala Met Gly Tyr Gly Ile Ile Tyr Ser Val Leu Gln Ser Thr Ala
305                 310                 315                 320

Leu Leu Leu Ala Pro Ile Glu Glu Gln Gly Leu Ala Ser Ser Thr Phe
                325                 330                 335

Tyr Leu Gly Leu Asp Ile Ala Met Ala Phe Gly Pro Met Ile Ser Gly
            340                 345                 350

Val Ile Asp Ser Thr Phe Pro Ile Lys Trp Phe Tyr Pro Ile Glu Leu
        355                 360                 365

Ile Leu Ile Pro Phe Ile Leu Leu Val Tyr Phe Ile Trp Arg Lys Arg
        370                 375                 380

Leu Asn Gly Ala Ile Asp His His
385                 390

<210> SEQ ID NO 149
<211> LENGTH: 612
<212> TYPE: DNA
<213> ORGANISM: Lactobacillus acidophilus
<220> FEATURE:
<221> NAME/KEY: CDS
<222> LOCATION: (1)..(612)
<223> OTHER INFORMATION: Consensus hypothetical protein ORF# 1432

<400> SEQUENCE: 149 atg ttg aat att tac gga aaa tac gcc cca gca ctg gat agg ata ctc        48
Met Leu Asn Ile Tyr Gly Lys Tyr Ala Pro Ala Leu Asp Arg Ile Leu
1               5                   10                  15 aac cag ttg ctt aat cgt ttc gat gaa ttg aat aaa aat tat gaa caa        96
Asn Gln Leu Leu Asn Arg Phe Asp Glu Leu Asn Lys Asn Tyr Glu Gln
                20                  25                  30 gtt cat cat gaa cgt tta tat gaa cac ttg cgt ggt cga gtt aaa agt       144
Val His His Glu Arg Leu Tyr Glu His Leu Arg Gly Arg Val Lys Ser
            35                  40                  45 gaa gcc agc atg gaa caa aaa tgt aaa aga aag aat ttg ccc tta acg       192
Glu Ala Ser Met Glu Gln Lys Cys Lys Arg Lys Asn Leu Pro Leu Thr
        50                  55                  60 ccg cga tct gct tta aga gat aat cgc gat agt ata ggg ctg cga gtt       240
Pro Arg Ser Ala Leu Arg Asp Asn Arg Asp Ser Ile Gly Leu Arg Val
65                  70                  75                  80 atc tgc aac ttt att gac gat att tat aag ttt att gct tat att aga       288
Ile Cys Asn Phe Ile Asp Asp Ile Tyr Lys Phe Ile Ala Tyr Ile Arg
                85                  90                  95 agt tgg gat gat gta act att gtt aaa gag aaa gat tac att act aat       336
Ser Trp Asp Asp Val Thr Ile Val Lys Glu Lys Asp Tyr Ile Thr Asn
                100                 105                 110 gct aag cct aat ggt tat cgt tct tat cat atg att ttg gat gtt act       384
Ala Lys Pro Asn Gly Tyr Arg Ser Tyr His Met Ile Leu Asp Val Thr
            115                 120                 125 gta atg gat gaa gat gtt gac ggt aat gta ccc ggt cat tat ttc gtt       432
Val Met Asp Glu Asp Val Asp Gly Asn Val Pro Gly His Tyr Phe Val
        130                 135                 140 gaa gtt cag ctt agg aca att gca atg gat acg tgg gca agt ttg gaa       480
Glu Val Gln Leu Arg Thr Ile Ala Met Asp Thr Trp Ala Ser Leu Glu
145                 150                 155                 160
```

```
cat gaa atg aaa tac aag cat caa att aaa aat cca gaa atg att gga    528
His Glu Met Lys Tyr Lys His Gln Ile Lys Asn Pro Glu Met Ile Gly
            165                 170                 175 cga gaa tta aag cgg gta gct gat gaa tta gct tct tgt gat gta agt    576
Arg Glu Leu Lys Arg Val Ala Asp Glu Leu Ala Ser Cys Asp Val Ser
        180                 185                 190 atg caa act atc cgt cag cta att aga gaa gag gat                    612
Met Gln Thr Ile Arg Gln Leu Ile Arg Glu Glu Asp
        195                 200
```

<210> SEQ ID NO 150
<211> LENGTH: 204
<212> TYPE: PRT
<213> ORGANISM: Lactobacillus acidophilus

<400> SEQUENCE: 150

```
Met Leu Asn Ile Tyr Gly Lys Tyr Ala Pro Ala Leu Asp Arg Ile Leu
1               5                   10                  15

Asn Gln Leu Leu Asn Arg Phe Asp Glu Leu Asn Lys Asn Tyr Glu Gln
            20                  25                  30

Val His His Glu Arg Leu Tyr Glu His Leu Arg Gly Arg Val Lys Ser
        35                  40                  45

Glu Ala Ser Met Glu Gln Lys Cys Lys Arg Lys Asn Leu Pro Leu Thr
    50                  55                  60

Pro Arg Ser Ala Leu Arg Asp Asn Arg Asp Ser Ile Gly Leu Arg Val
65                  70                  75                  80

Ile Cys Asn Phe Ile Asp Asp Ile Tyr Lys Phe Ile Ala Tyr Ile Arg
                85                  90                  95

Ser Trp Asp Asp Val Thr Ile Val Lys Glu Lys Asp Tyr Ile Thr Asn
            100                 105                 110

Ala Lys Pro Asn Gly Tyr Arg Ser Tyr His Met Ile Leu Asp Val Thr
        115                 120                 125

Val Met Asp Glu Asp Val Asp Gly Asn Val Pro Gly His Tyr Phe Val
    130                 135                 140

Glu Val Gln Leu Arg Thr Ile Ala Met Asp Thr Trp Ala Ser Leu Glu
145                 150                 155                 160

His Glu Met Lys Tyr Lys His Gln Ile Lys Asn Pro Glu Met Ile Gly
                165                 170                 175

Arg Glu Leu Lys Arg Val Ala Asp Glu Leu Ala Ser Cys Asp Val Ser
            180                 185                 190

Met Gln Thr Ile Arg Gln Leu Ile Arg Glu Glu Asp
        195                 200
```

<210> SEQ ID NO 151
<211> LENGTH: 780
<212> TYPE: DNA
<213> ORGANISM: Lactobacillus acidophilus
<220> FEATURE:
<221> NAME/KEY: CDS
<222> LOCATION: (1)..(780)
<223> OTHER INFORMATION: Uncharacterized membrane-bound protein ORF#
      1823

<400> SEQUENCE: 151

```
atg gct gaa gaa aca aag aaa gag caa agt agc gca aat att aac gct    48
Met Ala Glu Glu Thr Lys Lys Glu Gln Ser Ser Ala Asn Ile Asn Ala
1               5                   10                  15 gaa aag caa gaa aag tta aag aaa aaa tct gaa act gat act aaa gat    96
Glu Lys Gln Glu Lys Leu Lys Lys Lys Ser Glu Thr Asp Thr Lys Asp
            20                  25                  30
```

```
gaa gag tta aaa aaa gaa gat cct aag att ctt cgt caa aag tta agt      144
Glu Glu Leu Lys Lys Glu Asp Pro Lys Ile Leu Arg Gln Lys Leu Ser
         35                  40                  45 aac aaa aac caa gat tac gtt ttt cgt tta gaa aaa gaa tta caa att      192
Asn Lys Asn Gln Asp Tyr Val Phe Arg Leu Glu Lys Glu Leu Gln Ile
 50                  55                  60 caa ggc tca atg tct aga caa gaa gct atg gca atg aca gat ggg ctt      240
Gln Gly Ser Met Ser Arg Gln Glu Ala Met Ala Met Thr Asp Gly Leu
 65                  70                  75                  80 ctt ggt gaa att gta att gcg caa cgt cac ggt caa cca gct aat ggt      288
Leu Gly Glu Ile Val Ile Ala Gln Arg His Gly Gln Pro Ala Asn Gly
                 85                  90                  95 tta tac tta gct tca cct aag atc aaa gca gaa caa atg ctt cac cca      336
Leu Tyr Leu Ala Ser Pro Lys Ile Lys Ala Glu Gln Met Leu His Pro
            100                 105                 110 gac caa aag cca gtt gaa aca cca ttt tgg caa tca gca att gat ggt      384
Asp Gln Lys Pro Val Glu Thr Pro Phe Trp Gln Ser Ala Ile Asp Gly
        115                 120                 125 gca ctt tta tac tta gca att ttt gta ggt tta ttt ggg atc att gca      432
Ala Leu Leu Tyr Leu Ala Ile Phe Val Gly Leu Phe Gly Ile Ile Ala
130                 135                 140 tta ttt gaa aat gat aaa tct caa gcc aac tct caa atg ggt att tta      480
Leu Phe Glu Asn Asp Lys Ser Gln Ala Asn Ser Gln Met Gly Ile Leu
145                 150                 155                 160 act tta gct agt gtt ggt atc tta atg ggt atc ttt atg gtt aag tac      528
Thr Leu Ala Ser Val Gly Ile Leu Met Gly Ile Phe Met Val Lys Tyr
                165                 170                 175 aac gaa tgg att acc cct aag aat ggt caa cgt att ggt tgg gct aga      576
Asn Glu Trp Ile Thr Pro Lys Asn Gly Gln Arg Ile Gly Trp Ala Arg
            180                 185                 190 tta ctt tta agt gga tta ggt att gcg gca gta tta ttt gtg tgg att      624
Leu Leu Leu Ser Gly Leu Gly Ile Ala Ala Val Leu Phe Val Trp Ile
        195                 200                 205 tgg att tta tct ctt cca gct atc cgg atg atc aat cca gtt tta cca      672
Trp Ile Leu Ser Leu Pro Ala Ile Arg Met Ile Asn Pro Val Leu Pro
210                 215                 220 ggc gct gct gat att gta att gct gct ata gca tat ggt gtt cgt tac      720
Gly Ala Ala Asp Ile Val Ile Ala Ala Ile Ala Tyr Gly Val Arg Tyr
225                 230                 235                 240 ttg ttc aga aga cat tat cac att gtg ggg tca aca ttt gca ccg cgt      768
Leu Phe Arg Arg His Tyr His Ile Val Gly Ser Thr Phe Ala Pro Arg
                245                 250                 255 cca caa cat aaa                                                      780
Pro Gln His Lys
            260

<210> SEQ ID NO 152
<211> LENGTH: 260
<212> TYPE: PRT
<213> ORGANISM: Lactobacillus acidophilus

<400> SEQUENCE: 152

Met Ala Glu Glu Thr Lys Lys Glu Gln Ser Ser Ala Asn Ile Asn Ala
 1               5                  10                  15

Glu Lys Gln Glu Lys Leu Lys Lys Lys Ser Glu Thr Asp Thr Lys Asp
             20                  25                  30

Glu Glu Leu Lys Lys Glu Asp Pro Lys Ile Leu Arg Gln Lys Leu Ser
         35                  40                  45

Asn Lys Asn Gln Asp Tyr Val Phe Arg Leu Glu Lys Glu Leu Gln Ile
 50                  55                  60
```

-continued

```
                    50                  55                  60
Gln Gly Ser Met Ser Arg Gln Glu Ala Met Ala Met Thr Asp Gly Leu
 65                  70                  75                  80

Leu Gly Glu Ile Val Ile Ala Gln Arg His Gly Gln Pro Ala Asn Gly
                 85                  90                  95

Leu Tyr Leu Ala Ser Pro Lys Ile Lys Ala Glu Gln Met Leu His Pro
                100                 105                 110

Asp Gln Lys Pro Val Glu Thr Pro Phe Trp Gln Ser Ala Ile Asp Gly
            115                 120                 125

Ala Leu Leu Tyr Leu Ala Ile Phe Val Gly Leu Phe Gly Ile Ile Ala
        130                 135                 140

Leu Phe Glu Asn Asp Lys Ser Gln Ala Asn Ser Gln Met Gly Ile Leu
145                 150                 155                 160

Thr Leu Ala Ser Val Gly Ile Leu Met Gly Ile Phe Met Val Lys Tyr
                165                 170                 175

Asn Glu Trp Ile Thr Pro Lys Asn Gly Gln Arg Ile Gly Trp Ala Arg
            180                 185                 190

Leu Leu Leu Ser Gly Leu Gly Ile Ala Ala Val Leu Phe Val Trp Ile
        195                 200                 205

Trp Ile Leu Ser Leu Pro Ala Ile Arg Met Ile Asn Pro Val Leu Pro
    210                 215                 220

Gly Ala Ala Asp Ile Val Ile Ala Ala Ile Ala Tyr Gly Val Arg Tyr
225                 230                 235                 240

Leu Phe Arg Arg His Tyr His Ile Val Gly Ser Thr Phe Ala Pro Arg
                245                 250                 255

Pro Gln His Lys
            260

<210> SEQ ID NO 153
<211> LENGTH: 1098
<212> TYPE: DNA
<213> ORGANISM: Lactobacillus acidophilus
<220> FEATURE:
<221> NAME/KEY: CDS
<222> LOCATION: (1)..(1098)
<223> OTHER INFORMATION: Predicted GTPase ORF# 1824

<400> SEQUENCE: 153 atg tca tta act gct ggt att gtt ggt tta cca aat gtt ggt aag tca      48
Met Ser Leu Thr Ala Gly Ile Val Gly Leu Pro Asn Val Gly Lys Ser
  1               5                  10                  15 act ttg ttt aac gcg att act aag gct ggg gct gaa atg gcc aac tat      96
Thr Leu Phe Asn Ala Ile Thr Lys Ala Gly Ala Glu Met Ala Asn Tyr
             20                  25                  30 cca ttt gcc acc att gaa cca aac gtc gga atg gtt gaa gtt cct gac     144
Pro Phe Ala Thr Ile Glu Pro Asn Val Gly Met Val Glu Val Pro Asp
         35                  40                  45 aag cgt ctg gca aga att caa gaa ttg att cct gct aaa aag att gtt     192
Lys Arg Leu Ala Arg Ile Gln Glu Leu Ile Pro Ala Lys Lys Ile Val
     50                  55                  60 cat act act ttt gaa ttt acc gat att gct ggt tta gta aaa ggt gct     240
His Thr Thr Phe Glu Phe Thr Asp Ile Ala Gly Leu Val Lys Gly Ala
 65                  70                  75                  80 tcc aag ggt gaa ggt ctt ggt aac aaa ttc ctt gaa aat att cgt caa     288
Ser Lys Gly Glu Gly Leu Gly Asn Lys Phe Leu Glu Asn Ile Arg Gln
                 85                  90                  95 act gat gct att gtt cat gta gta cgt gcc ttt gat gat gat aat att     336
Thr Asp Ala Ile Val His Val Val Arg Ala Phe Asp Asp Asp Asn Ile
```

-continued

```
                 100                 105                 110
act tca gtt act ggt aaa gtt gat cca gaa gaa gac att aat act att    384
Thr Ser Val Thr Gly Lys Val Asp Pro Glu Glu Asp Ile Asn Thr Ile
        115                 120                 125 aac tta gag ctt gct att gct gac ctt gat gcg gtt aat aag cgt att    432
Asn Leu Glu Leu Ala Ile Ala Asp Leu Asp Ala Val Asn Lys Arg Ile
    130                 135                 140 ggt aag gtg caa aag atc gct caa caa ggc gat aag gat gcc aag gca    480
Gly Lys Val Gln Lys Ile Ala Gln Gln Gly Asp Lys Asp Ala Lys Ala
145                 150                 155                 160 gaa atg gct gta ctt gaa aaa ttg aag cca gtt ctt gaa gaa gga aac    528
Glu Met Ala Val Leu Glu Lys Leu Lys Pro Val Leu Glu Glu Gly Asn
                165                 170                 175 gcc gct cgt tca att gac ttt aat aaa gat gaa caa aag att gtt aag    576
Ala Ala Arg Ser Ile Asp Phe Asn Lys Asp Glu Gln Lys Ile Val Lys
            180                 185                 190 ggc ttg ttc tta ctt act tct aag cca atc atc tat gta gca aat att    624
Gly Leu Phe Leu Leu Thr Ser Lys Pro Ile Ile Tyr Val Ala Asn Ile
        195                 200                 205 gca gaa gat tca atg gct gat cca gaa agc gac aag tac tac caa atc    672
Ala Glu Asp Ser Met Ala Asp Pro Glu Ser Asp Lys Tyr Tyr Gln Ile
    210                 215                 220 gtc aaa aga cat gca gaa agt gaa ggc gca gaa tgc tta ggt att tct    720
Val Lys Arg His Ala Glu Ser Glu Gly Ala Glu Cys Leu Gly Ile Ser
225                 230                 235                 240 gca gct aca gaa gaa gaa att gcc ggt atg gaa gac gat gaa aag aaa    768
Ala Ala Thr Glu Glu Glu Ile Ala Gly Met Glu Asp Asp Glu Lys Lys
                245                 250                 255 gaa ttc ctt gaa atg gaa ggc gtt gaa gaa tct ggt ttg gat cgt ctg    816
Glu Phe Leu Glu Met Glu Gly Val Glu Glu Ser Gly Leu Asp Arg Leu
            260                 265                 270 att cgt gca gcc tac cat att ttg ggt ctt aga act ttc ttt act gct    864
Ile Arg Ala Ala Tyr His Ile Leu Gly Leu Arg Thr Phe Phe Thr Ala
        275                 280                 285 ggt ggt cct gaa act cgt gct tgg act ttc cac aag ggg atg aaa gct    912
Gly Gly Pro Glu Thr Arg Ala Trp Thr Phe His Lys Gly Met Lys Ala
    290                 295                 300 cca caa gtt gca ggt gtt att cac tca gac ttt gaa cgt gga ttc att    960
Pro Gln Val Ala Gly Val Ile His Ser Asp Phe Glu Arg Gly Phe Ile
305                 310                 315                 320 cgt gcc gaa gta gtt tca tac gat gac tta gac gaa ctt gaa act atg   1008
Arg Ala Glu Val Val Ser Tyr Asp Asp Leu Asp Glu Leu Glu Thr Met
                325                 330                 335 caa aag gtt aaa gaa gct ggt aag ctt cgc ctt gaa ggt aaa gat tac   1056
Gln Lys Val Lys Glu Ala Gly Lys Leu Arg Leu Glu Gly Lys Asp Tyr
            340                 345                 350 gaa gtt caa gac ggt gac att atc gaa ttt aga ttt aac gtc             1098
Glu Val Gln Asp Gly Asp Ile Ile Glu Phe Arg Phe Asn Val
        355                 360                 365

<210> SEQ ID NO 154
<211> LENGTH: 366
<212> TYPE: PRT
<213> ORGANISM: Lactobacillus acidophilus

<400> SEQUENCE: 154

Met Ser Leu Thr Ala Gly Ile Val Gly Leu Pro Asn Val Gly Lys Ser
1               5                   10                  15

Thr Leu Phe Asn Ala Ile Thr Lys Ala Gly Ala Glu Met Ala Asn Tyr
            20                  25                  30
```

Pro Phe Ala Thr Ile Glu Pro Asn Val Gly Met Val Glu Val Pro Asp
                35                  40                  45

Lys Arg Leu Ala Arg Ile Gln Glu Leu Ile Pro Ala Lys Lys Ile Val
 50                  55                  60

His Thr Thr Phe Glu Phe Thr Asp Ile Ala Gly Leu Val Lys Gly Ala
 65                  70                  75                  80

Ser Lys Gly Glu Gly Leu Gly Asn Lys Phe Leu Glu Asn Ile Arg Gln
                 85                  90                  95

Thr Asp Ala Ile Val His Val Arg Ala Phe Asp Asp Asn Ile
                100                 105                 110

Thr Ser Val Thr Gly Lys Val Asp Pro Glu Glu Asp Ile Asn Thr Ile
                115                 120                 125

Asn Leu Glu Leu Ala Ile Ala Asp Leu Asp Ala Val Asn Lys Arg Ile
130                 135                 140

Gly Lys Val Gln Lys Ile Ala Gln Gln Gly Asp Lys Asp Ala Lys Ala
145                 150                 155                 160

Glu Met Ala Val Leu Glu Lys Leu Lys Pro Val Leu Glu Glu Gly Asn
                165                 170                 175

Ala Ala Arg Ser Ile Asp Phe Asn Lys Asp Glu Gln Lys Ile Val Lys
                180                 185                 190

Gly Leu Phe Leu Leu Thr Ser Lys Pro Ile Ile Tyr Val Ala Asn Ile
                195                 200                 205

Ala Glu Asp Ser Met Ala Asp Pro Glu Ser Asp Lys Tyr Tyr Gln Ile
                210                 215                 220

Val Lys Arg His Ala Glu Ser Glu Gly Ala Glu Cys Leu Gly Ile Ser
225                 230                 235                 240

Ala Ala Thr Glu Glu Glu Ile Ala Gly Met Glu Asp Asp Glu Lys Lys
                245                 250                 255

Glu Phe Leu Glu Met Glu Gly Val Glu Glu Ser Gly Leu Asp Arg Leu
                260                 265                 270

Ile Arg Ala Ala Tyr His Ile Leu Gly Leu Arg Thr Phe Phe Thr Ala
                275                 280                 285

Gly Gly Pro Glu Thr Arg Ala Trp Thr Phe His Lys Gly Met Lys Ala
                290                 295                 300

Pro Gln Val Ala Gly Val Ile His Ser Asp Phe Glu Arg Gly Phe Ile
305                 310                 315                 320

Arg Ala Glu Val Val Ser Tyr Asp Asp Leu Asp Glu Leu Glu Thr Met
                325                 330                 335

Gln Lys Val Lys Glu Ala Gly Lys Leu Arg Leu Glu Gly Lys Asp Tyr
                340                 345                 350

Glu Val Gln Asp Gly Asp Ile Ile Glu Phe Arg Phe Asn Val
                355                 360                 365

<210> SEQ ID NO 155
<211> LENGTH: 261
<212> TYPE: DNA
<213> ORGANISM: Lactobacillus acidophilus
<220> FEATURE:
<221> NAME/KEY: CDS
<222> LOCATION: (1)..(261)
<223> OTHER INFORMATION: Unknown protein ORF# 1825

<400> SEQUENCE: 155 atg gct aaa gaa att att tat aat ttg gct gat aca gtg caa atg aag        48
Met Ala Lys Glu Ile Ile Tyr Asn Leu Ala Asp Thr Val Gln Met Lys
 1               5                   10                  15

```
aaa ccc cat gct tgt caa acc aat gac tgg gaa att tta cgc atg ggt        96
Lys Pro His Ala Cys Gln Thr Asn Asp Trp Glu Ile Leu Arg Met Gly
         20                  25                  30 gca gat atc aag ctt aaa tgt ttg gga tgt ggt cgg atg gta atg atg       144
Ala Asp Ile Lys Leu Lys Cys Leu Gly Cys Gly Arg Met Val Met Met
         35                  40                  45 cca cgt agt gag ttt aat cgt aaa gtg aaa aaa gtt tta acc aag gct       192
Pro Arg Ser Glu Phe Asn Arg Lys Val Lys Lys Val Leu Thr Lys Ala
 50                  55                  60 aat gat ccg gtt aat ctg aaa aaa gag cat tat gta cca aaa gat cgt       240
Asn Asp Pro Val Asn Leu Lys Lys Glu His Tyr Val Pro Lys Asp Arg
 65                  70                  75                  80 atc gtt cgt cca aat ttt gga                                           261
Ile Val Arg Pro Asn Phe Gly
                 85

<210> SEQ ID NO 156
<211> LENGTH: 87
<212> TYPE: PRT
<213> ORGANISM: Lactobacillus acidophilus

<400> SEQUENCE: 156

Met Ala Lys Glu Ile Ile Tyr Asn Leu Ala Asp Thr Val Gln Met Lys
 1               5                  10                  15

Lys Pro His Ala Cys Gln Thr Asn Asp Trp Glu Ile Leu Arg Met Gly
             20                  25                  30

Ala Asp Ile Lys Leu Lys Cys Leu Gly Cys Gly Arg Met Val Met Met
         35                  40                  45

Pro Arg Ser Glu Phe Asn Arg Lys Val Lys Lys Val Leu Thr Lys Ala
 50                  55                  60

Asn Asp Pro Val Asn Leu Lys Lys Glu His Tyr Val Pro Lys Asp Arg
 65                  70                  75                  80

Ile Val Arg Pro Asn Phe Gly
                 85

<210> SEQ ID NO 157
<211> LENGTH: 882
<212> TYPE: DNA
<213> ORGANISM: Lactobacillus acidophilus
<220> FEATURE:
<221> NAME/KEY: CDS
<222> LOCATION: (1)..(882)
<223> OTHER INFORMATION: Predicted transcriptional regulator ORF# 1826

<400> SEQUENCE: 157 atg gta aga gac tca aaa agt aaa gat act aga aaa aaa ggc ggc tta        48
Met Val Arg Asp Ser Lys Ser Lys Asp Thr Arg Lys Lys Gly Gly Leu
 1               5                  10                  15 ggc cgt ggt att gaa gct ctt ttc gaa gat gaa cct caa gtt gaa gaa        96
Gly Arg Gly Ile Glu Ala Leu Phe Glu Asp Glu Pro Gln Val Glu Glu
             20                  25                  30 act gaa gaa gta caa gaa ctt gag tta agt gat att cgc cct aat cca       144
Thr Glu Glu Val Gln Glu Leu Glu Leu Ser Asp Ile Arg Pro Asn Pro
         35                  40                  45 tat cag cct aga aaa cat ttt gac gat aaa agt tta aag gaa tta tca       192
Tyr Gln Pro Arg Lys His Phe Asp Asp Lys Ser Leu Lys Glu Leu Ser
 50                  55                  60 gat tca att aaa gaa aat ggt gtc ttt caa cca att att gtt cgt aag       240
Asp Ser Ile Lys Glu Asn Gly Val Phe Gln Pro Ile Ile Val Arg Lys
 65                  70                  75                  80
```

```
tct gtg aat ggt tat gaa att att gca ggt gaa cgt aga tat cgc gct     288
Ser Val Asn Gly Tyr Glu Ile Ile Ala Gly Glu Arg Arg Tyr Arg Ala
            85                  90                  95 tct aaa tta gcc aag aag acg act att cca gct att att cgt aaa ttt     336
Ser Lys Leu Ala Lys Lys Thr Thr Ile Pro Ala Ile Ile Arg Lys Phe
        100                 105                 110 gac gag agt caa atg atg gaa gtt gcg gta tta gaa aat ttg caa cgt     384
Asp Glu Ser Gln Met Met Glu Val Ala Val Leu Glu Asn Leu Gln Arg
            115                 120                 125 gaa gat ttg act ccg ctt gaa gaa gcg caa gct tat gaa atg ttg caa     432
Glu Asp Leu Thr Pro Leu Glu Glu Ala Gln Ala Tyr Glu Met Leu Gln
        130                 135                 140 aaa aat ctg gga cta act caa gaa gaa gtt tct aag cgg atg ggt aag     480
Lys Asn Leu Gly Leu Thr Gln Glu Glu Val Ser Lys Arg Met Gly Lys
145                 150                 155                 160 tca cgt cca tat att gcc aac tat ttg cgt tta ttg act ttg cca agt     528
Ser Arg Pro Tyr Ile Ala Asn Tyr Leu Arg Leu Leu Thr Leu Pro Ser
                165                 170                 175 aaa act aaa cgt tta ttg caa cat ggt gaa tta tca atg gga caa gct     576
Lys Thr Lys Arg Leu Leu Gln His Gly Glu Leu Ser Met Gly Gln Ala
        180                 185                 190 aga aca ctt ttg ggc tta aag gat aaa gat aag att gat gtt tta gct     624
Arg Thr Leu Leu Gly Leu Lys Asp Lys Asp Lys Ile Asp Val Leu Ala
            195                 200                 205 aaa aaa gtg gtc caa gaa ggg atg cct gtt cgt aaa gtt gaa gca ctt     672
Lys Lys Val Val Gln Glu Gly Met Pro Val Arg Lys Val Glu Ala Leu
        210                 215                 220 gtt ggt gaa atg aat gcg aaa aaa cct cag aaa aag gta gtt aaa aaa     720
Val Gly Glu Met Asn Ala Lys Lys Pro Gln Lys Lys Val Val Lys Lys
225                 230                 235                 240 tct gct ttt att cgt gca agt gaa acg caa ctt tct gat aaa ttt ggt     768
Ser Ala Phe Ile Arg Ala Ser Glu Thr Gln Leu Ser Asp Lys Phe Gly
                245                 250                 255 gca agc gta agt atc tca gaa aac aaa aag gga aag gga cat ctt tcc     816
Ala Ser Val Ser Ile Ser Glu Asn Lys Lys Gly Lys Gly His Leu Ser
            260                 265                 270 att gat ttt gct tct gca gat gaa ttg aat cga att ctt gat ttg tta     864
Ile Asp Phe Ala Ser Ala Asp Glu Leu Asn Arg Ile Leu Asp Leu Leu
        275                 280                 285 ggt gtt gat tta gat ggc                                             882
Gly Val Asp Leu Asp Gly
    290

<210> SEQ ID NO 158
<211> LENGTH: 294
<212> TYPE: PRT
<213> ORGANISM: Lactobacillus acidophilus

<400> SEQUENCE: 158

Met Val Arg Asp Ser Lys Ser Lys Asp Thr Arg Lys Gly Gly Leu
1               5                   10                  15

Gly Arg Gly Ile Glu Ala Leu Phe Glu Asp Glu Pro Gln Val Glu Glu
            20                  25                  30

Thr Glu Glu Val Gln Glu Leu Glu Leu Ser Asp Ile Arg Pro Asn Pro
        35                  40                  45

Tyr Gln Pro Arg Lys His Phe Asp Asp Lys Ser Leu Lys Glu Leu Ser
    50                  55                  60

Asp Ser Ile Lys Glu Asn Gly Val Phe Gln Pro Ile Ile Val Arg Lys
65                  70                  75                  80
```

```
Ser Val Asn Gly Tyr Glu Ile Ile Ala Gly Glu Arg Arg Tyr Arg Ala
                85                  90                  95

Ser Lys Leu Ala Lys Lys Thr Thr Ile Pro Ala Ile Ile Arg Lys Phe
                100                 105                 110

Asp Glu Ser Gln Met Met Glu Val Ala Val Leu Glu Asn Leu Gln Arg
            115                 120                 125

Glu Asp Leu Thr Pro Leu Glu Glu Ala Gln Ala Tyr Glu Met Leu Gln
        130                 135                 140

Lys Asn Leu Gly Leu Thr Gln Glu Glu Val Ser Lys Arg Met Gly Lys
145                 150                 155                 160

Ser Arg Pro Tyr Ile Ala Asn Tyr Leu Arg Leu Leu Thr Leu Pro Ser
                165                 170                 175

Lys Thr Lys Arg Leu Leu Gln His Gly Glu Leu Ser Met Gly Gln Ala
                180                 185                 190

Arg Thr Leu Leu Gly Leu Lys Asp Lys Asp Lys Ile Asp Val Leu Ala
            195                 200                 205

Lys Lys Val Val Gln Glu Gly Met Pro Val Arg Lys Val Glu Ala Leu
        210                 215                 220

Val Gly Glu Met Asn Ala Lys Lys Pro Gln Lys Lys Val Val Lys Lys
225                 230                 235                 240

Ser Ala Phe Ile Arg Ala Ser Glu Thr Gln Leu Ser Asp Lys Phe Gly
                245                 250                 255

Ala Ser Val Ser Ile Ser Glu Asn Lys Lys Gly Lys Gly His Leu Ser
                260                 265                 270

Ile Asp Phe Ala Ser Ala Asp Glu Leu Asn Arg Ile Leu Asp Leu Leu
            275                 280                 285

Gly Val Asp Leu Asp Gly
        290

<210> SEQ ID NO 159
<211> LENGTH: 777
<212> TYPE: DNA
<213> ORGANISM: Lactobacillus acidophilus
<220> FEATURE:
<221> NAME/KEY: CDS
<222> LOCATION: (1)..(777)
<223> OTHER INFORMATION: ATPase ORF# 1827

<400> SEQUENCE: 159 atg gta aat gta att tcg gtt gct aac caa aaa ggt gga gtt ggt aaa      48
Met Val Asn Val Ile Ser Val Ala Asn Gln Lys Gly Gly Val Gly Lys
1               5                   10                  15 act acc act act att aat tta gcg gcc tca att gcc gac cgt ggt tat      96
Thr Thr Thr Thr Ile Asn Leu Ala Ala Ser Ile Ala Asp Arg Gly Tyr
            20                  25                  30 cgc gtt tta atc gtt gat atc gat cct caa ggt aac gct acc tct ggt      144
Arg Val Leu Ile Val Asp Ile Asp Pro Gln Gly Asn Ala Thr Ser Gly
        35                  40                  45 tta gga att gaa aaa tca gag att gac cag gac att tac aat gtt ttg      192
Leu Gly Ile Glu Lys Ser Glu Ile Asp Gln Asp Ile Tyr Asn Val Leu
    50                  55                  60 att gat gaa gtt cct att caa gat aca att cat cat act tcg act gct      240
Ile Asp Glu Val Pro Ile Gln Asp Thr Ile His His Thr Ser Thr Ala
65                  70                  75                  80 aag ctt gat atg gtt ccg gca aca att aac tta tct ggt gcc gaa acc      288
Lys Leu Asp Met Val Pro Ala Thr Ile Asn Leu Ser Gly Ala Glu Thr
                85                  90                  95 gaa ttg att agt atg atg gcc cga gag act cgc ctt aag tca tct ctt      336
```

-continued

```
Glu Leu Ile Ser Met Met Ala Arg Glu Thr Arg Leu Lys Ser Ser Leu
            100                 105                 110 gat gca gtt agt gat caa tat gac ttt atc ttt atc gat tgt ccc cca      384
Asp Ala Val Ser Asp Gln Tyr Asp Phe Ile Phe Ile Asp Cys Pro Pro
            115                 120                 125 tca ttg ggc caa ctt tca att aat gct ttt act gca tct gat tca atc      432
Ser Leu Gly Gln Leu Ser Ile Asn Ala Phe Thr Ala Ser Asp Ser Ile
    130                 135                 140 ttg att cca gtg caa agt gaa tat tat gca atg gaa ggg tta agt caa      480
Leu Ile Pro Val Gln Ser Glu Tyr Tyr Ala Met Glu Gly Leu Ser Gln
145                 150                 155                 160 ttg cta aac act att cgt tta gta caa aag cac ttt aac aaa gac tta      528
Leu Leu Asn Thr Ile Arg Leu Val Gln Lys His Phe Asn Lys Asp Leu
                165                 170                 175 ggc gtt gaa ggc gta ctt tta act atg ctt gat gct aga acc aat tta      576
Gly Val Glu Gly Val Leu Leu Thr Met Leu Asp Ala Arg Thr Asn Leu
            180                 185                 190 ggg gcc gag gtt gtt aaa gaa gtt caa tct tac ttt agc aag aaa gta      624
Gly Ala Glu Val Val Lys Glu Val Gln Ser Tyr Phe Ser Lys Lys Val
        195                 200                 205 tat aaa aca att atc cct aga att act aaa ttg gct gaa gct cca agc      672
Tyr Lys Thr Ile Ile Pro Arg Ile Thr Lys Leu Ala Glu Ala Pro Ser
210                 215                 220 tac ggt caa cca att act gaa tat gct cca aga tct cgt ggc gcg aag      720
Tyr Gly Gln Pro Ile Thr Glu Tyr Ala Pro Arg Ser Arg Gly Ala Lys
225                 230                 235                 240 gta tat gat gag tta gca aaa gag gtg tta aaa gct cat ggt aag aga      768
Val Tyr Asp Glu Leu Ala Lys Glu Val Leu Lys Ala His Gly Lys Arg
            245                 250                 255 ctc aaa aag                                                          777
Leu Lys Lys
```

<210> SEQ ID NO 160
<211> LENGTH: 259
<212> TYPE: PRT
<213> ORGANISM: Lactobacillus acidophilus

<400> SEQUENCE: 160

```
Met Val Asn Val Ile Ser Val Ala Asn Gln Lys Gly Val Gly Lys
1               5                   10                  15

Thr Thr Thr Thr Ile Asn Leu Ala Ala Ser Ile Ala Asp Arg Gly Tyr
            20                  25                  30

Arg Val Leu Ile Val Asp Ile Asp Pro Gln Gly Asn Ala Thr Ser Gly
        35                  40                  45

Leu Gly Ile Glu Lys Ser Glu Ile Asp Gln Asp Ile Tyr Asn Val Leu
    50                  55                  60

Ile Asp Glu Val Pro Ile Gln Asp Thr Ile His His Thr Ser Thr Ala
65                  70                  75                  80

Lys Leu Asp Met Val Pro Ala Thr Ile Asn Leu Ser Gly Ala Glu Thr
                85                  90                  95

Glu Leu Ile Ser Met Met Ala Arg Glu Thr Arg Leu Lys Ser Ser Leu
            100                 105                 110

Asp Ala Val Ser Asp Gln Tyr Asp Phe Ile Phe Ile Asp Cys Pro Pro
        115                 120                 125

Ser Leu Gly Gln Leu Ser Ile Asn Ala Phe Thr Ala Ser Asp Ser Ile
    130                 135                 140

Leu Ile Pro Val Gln Ser Glu Tyr Tyr Ala Met Glu Gly Leu Ser Gln
145                 150                 155                 160
```

```
Leu Leu Asn Thr Ile Arg Leu Val Gln Lys His Phe Asn Lys Asp Leu
            165                 170                 175

Gly Val Glu Gly Val Leu Leu Thr Met Leu Asp Ala Arg Thr Asn Leu
        180                 185                 190

Gly Ala Glu Val Val Lys Glu Val Gln Ser Tyr Phe Ser Lys Lys Val
    195                 200                 205

Tyr Lys Thr Ile Ile Pro Arg Ile Thr Lys Leu Ala Glu Ala Pro Ser
210                 215                 220

Tyr Gly Gln Pro Ile Thr Glu Tyr Ala Pro Arg Ser Arg Gly Ala Lys
225                 230                 235                 240

Val Tyr Asp Glu Leu Ala Lys Glu Val Leu Lys Ala His Gly Lys Arg
                245                 250                 255

Leu Lys Lys

<210> SEQ ID NO 161
<211> LENGTH: 828
<212> TYPE: DNA
<213> ORGANISM: Lactobacillus acidophilus
<220> FEATURE:
<221> NAME/KEY: CDS
<222> LOCATION: (1)..(828)
<223> OTHER INFORMATION: Predicted transcriptional regulator ORF# 1828

<400> SEQUENCE: 161 atg tca tta ttt tct ttt atg cgt cat gac gag gaa gtc cct aag aac      48
Met Ser Leu Phe Ser Phe Met Arg His Asp Glu Glu Val Pro Lys Asn
1               5                   10                  15 aaa caa atc caa gat ttg gaa ttg gat aag att gta cct aat cgt tac      96
Lys Gln Ile Gln Asp Leu Glu Leu Asp Lys Ile Val Pro Asn Arg Tyr
            20                  25                  30 caa cca cga cgt gaa ttt tca gaa gat tca att aaa gag tta gct gaa     144
Gln Pro Arg Arg Glu Phe Ser Glu Asp Ser Ile Lys Glu Leu Ala Glu
        35                  40                  45 aca ctt gat aag gat ggc tta ctt caa cca ata gta gtt cgt gaa gat     192
Thr Leu Asp Lys Asp Gly Leu Leu Gln Pro Ile Val Val Arg Glu Asp
    50                  55                  60 ggt gat caa tat gag atc att gcc ggt gag cgt aga tat cgt gct gct     240
Gly Asp Gln Tyr Glu Ile Ile Ala Gly Glu Arg Arg Tyr Arg Ala Ala
65                  70                  75                  80 aag agc tta ggc tgg gaa aca att cca gca atc gtt aaa aat atg gac     288
Lys Ser Leu Gly Trp Glu Thr Ile Pro Ala Ile Val Lys Asn Met Asp
                85                  90                  95 gat gat caa gca gct tct ctt gct tta att gaa aac tta caa cgt gaa     336
Asp Asp Gln Ala Ala Ser Leu Ala Leu Ile Glu Asn Leu Gln Arg Glu
            100                 105                 110 gac tta aat cca att gat gaa gca aaa gca tac act aat ttg atg aag     384
Asp Leu Asn Pro Ile Asp Glu Ala Lys Ala Tyr Thr Asn Leu Met Lys
        115                 120                 125 tta aat aat tta act caa aca gct tta gct aaa gat atg gga aag tca     432
Leu Asn Asn Leu Thr Gln Thr Ala Leu Ala Lys Asp Met Gly Lys Ser
    130                 135                 140 caa tca tat gtt gct aat aaa ttg cgt tta ctt aaa ttg ggt gat gaa     480
Gln Ser Tyr Val Ala Asn Lys Leu Arg Leu Leu Lys Leu Gly Asp Glu
145                 150                 155                 160 gtt caa caa gct tta atc gaa ggt aaa att act gct cgt cat ggt cgt     528
Val Gln Gln Ala Leu Ile Glu Gly Lys Ile Thr Ala Arg His Gly Arg
                165                 170                 175 gct tta att ggt ctt agc gaa gat gat caa aaa cgc gtt tta gca gaa     576
Ala Leu Ile Gly Leu Ser Glu Asp Asp Gln Lys Arg Val Leu Ala Glu
```

```
                    180                 185                 190
atc gaa gct aag ggc tta aat gtt aaa caa act gaa gaa atc gct aaa       624
Ile Glu Ala Lys Gly Leu Asn Val Lys Gln Thr Glu Glu Ile Ala Lys
        195                 200                 205 gat gtt gaa gca tac ttt aat cct aag cct aag gca aaa tct gaa caa       672
Asp Val Glu Ala Tyr Phe Asn Pro Lys Pro Lys Ala Lys Ser Glu Gln
    210                 215                 220 aaa cgt gta gta aac cgc att cct aag gat cta aaa gtt caa atc aat       720
Lys Arg Val Val Asn Arg Ile Pro Lys Asp Leu Lys Val Gln Ile Asn
225                 230                 235                 240 aca att aaa aag gct gtt aaa tta gct gaa gac tca ggt atc aaa gtt       768
Thr Ile Lys Lys Ala Val Lys Leu Ala Glu Asp Ser Gly Ile Lys Val
                245                 250                 255 aaa att aaa gaa gat aaa aat cct gat gac tac aag att act atc gaa       816
Lys Ile Lys Glu Asp Lys Asn Pro Asp Asp Tyr Lys Ile Thr Ile Glu
            260                 265                 270 ctg aag aga aaa                                                       828
Leu Lys Arg Lys
        275

<210> SEQ ID NO 162
<211> LENGTH: 276
<212> TYPE: PRT
<213> ORGANISM: Lactobacillus acidophilus

<400> SEQUENCE: 162

Met Ser Leu Phe Ser Phe Met Arg His Asp Glu Glu Val Pro Lys Asn
1               5                   10                  15

Lys Gln Ile Gln Asp Leu Glu Leu Asp Lys Ile Val Pro Asn Arg Tyr
            20                  25                  30

Gln Pro Arg Glu Phe Ser Glu Asp Ser Ile Lys Glu Leu Ala Glu
        35                  40                  45

Thr Leu Asp Lys Asp Gly Leu Leu Gln Pro Ile Val Arg Glu Asp
    50                  55                  60

Gly Asp Gln Tyr Glu Ile Ile Ala Gly Glu Arg Arg Tyr Arg Ala Ala
65                  70                  75                  80

Lys Ser Leu Gly Trp Glu Thr Ile Pro Ala Ile Val Lys Asn Met Asp
                85                  90                  95

Asp Asp Gln Ala Ala Ser Leu Ala Leu Ile Glu Asn Leu Gln Arg Glu
            100                 105                 110

Asp Leu Asn Pro Ile Asp Glu Ala Lys Ala Tyr Thr Asn Leu Met Lys
        115                 120                 125

Leu Asn Asn Leu Thr Gln Thr Ala Leu Ala Lys Asp Met Gly Lys Ser
    130                 135                 140

Gln Ser Tyr Val Ala Asn Lys Leu Arg Leu Leu Lys Leu Gly Asp Glu
145                 150                 155                 160

Val Gln Gln Ala Leu Ile Glu Gly Lys Ile Thr Ala Arg His Gly Arg
                165                 170                 175

Ala Leu Ile Gly Leu Ser Glu Asp Gln Lys Arg Val Leu Ala Glu
            180                 185                 190

Ile Glu Ala Lys Gly Leu Asn Val Lys Gln Thr Glu Glu Ile Ala Lys
        195                 200                 205

Asp Val Glu Ala Tyr Phe Asn Pro Lys Pro Lys Ala Lys Ser Glu Gln
    210                 215                 220

Lys Arg Val Val Asn Arg Ile Pro Lys Asp Leu Lys Val Gln Ile Asn
225                 230                 235                 240
```

```
Thr Ile Lys Lys Ala Val Lys Leu Ala Glu Asp Ser Gly Ile Lys Val
            245                 250                 255

Lys Ile Lys Glu Asp Lys Asn Pro Asp Asp Tyr Lys Ile Thr Ile Glu
        260                 265                 270

Leu Lys Arg Lys
        275

<210> SEQ ID NO 163
<211> LENGTH: 720
<212> TYPE: DNA
<213> ORGANISM: Lactobacillus acidophilus
<220> FEATURE:
<221> NAME/KEY: CDS
<222> LOCATION: (1)..(720)
<223> OTHER INFORMATION: Predicted S-adenosylmethionine transferase ORF#
      1829

<400> SEQUENCE: 163 atg aat cct gaa gaa ttt atc tta gaa cta tca aaa cat aat ttt gaa     48
Met Asn Pro Glu Glu Phe Ile Leu Glu Leu Ser Lys His Asn Phe Glu
1               5                   10                  15 tta tct gat aag cag aag caa caa ttt aaa ctt tat ttt aaa tat ttg     96
Leu Ser Asp Lys Gln Lys Gln Gln Phe Lys Leu Tyr Phe Lys Tyr Leu
            20                  25                  30 atc gaa gtt aat gag cat gtc aat tta act cgg atc act gaa gaa aat    144
Ile Glu Val Asn Glu His Val Asn Leu Thr Arg Ile Thr Glu Glu Asn
        35                  40                  45 gaa gtt tat tta aag cac ttc ttt gat agt gtg act cca tta ttt act    192
Glu Val Tyr Leu Lys His Phe Phe Asp Ser Val Thr Pro Leu Phe Thr
    50                  55                  60 ttt ggt gaa gta ttt aaa gat ggt gca aca tta tgt gat gtt ggg gcc    240
Phe Gly Glu Val Phe Lys Asp Gly Ala Thr Leu Cys Asp Val Gly Ala
65                  70                  75                  80 ggg gcc ggt ttt cct tca att ccg ctt aag att tta aat cca aca ctt    288
Gly Ala Gly Phe Pro Ser Ile Pro Leu Lys Ile Leu Asn Pro Thr Leu
                85                  90                  95 aag gtg act att gtt gat tct ctt gct aaa aga tta act ttt tta aag    336
Lys Val Thr Ile Val Asp Ser Leu Ala Lys Arg Leu Thr Phe Leu Lys
            100                 105                 110 aac tta att gaa aaa tta ggt tta act gat gtc gaa tta gtt cat ggt    384
Asn Leu Ile Glu Lys Leu Gly Leu Thr Asp Val Glu Leu Val His Gly
        115                 120                 125 cgt gca gaa gat gtt ggt caa aat aaa ctt tat cgt gaa aaa ttt gat    432
Arg Ala Glu Asp Val Gly Gln Asn Lys Leu Tyr Arg Glu Lys Phe Asp
    130                 135                 140 ctt gtc aca gct cgg gct gtt gct aga atg agt gtg tta agt gaa tat    480
Leu Val Thr Ala Arg Ala Val Ala Arg Met Ser Val Leu Ser Glu Tyr
145                 150                 155                 160 tgt tta cca ctt gtt aaa aaa ggt gga tat ttc att gca ctt aaa ggc    528
Cys Leu Pro Leu Val Lys Lys Gly Gly Tyr Phe Ile Ala Leu Lys Gly
                165                 170                 175 cct aag gca gaa gat gaa cta gat gac ggc caa aaa gct ctt gaa gtg    576
Pro Lys Ala Glu Asp Glu Leu Asp Asp Gly Gln Lys Ala Leu Glu Val
            180                 185                 190 ctt ggt ggt aaa tta gtt aaa gaa gaa gaa tta act ttg cca cat agt    624
Leu Gly Gly Lys Leu Val Lys Glu Glu Glu Leu Thr Leu Pro His Ser
        195                 200                 205 aag gaa gag aga act tta att tta gta aaa aaa atc aag caa acg cca    672
Lys Glu Glu Arg Thr Leu Ile Leu Val Lys Lys Ile Lys Gln Thr Pro
    210                 215                 220 aag aag tat cca cgt caa gct gga acg ccg cgg cgt aaa cca ata cat    720
```

```
Lys Lys Tyr Pro Arg Gln Ala Gly Thr Pro Arg Arg Lys Pro Ile His
225                 230                 235                 240

<210> SEQ ID NO 164
<211> LENGTH: 240
<212> TYPE: PRT
<213> ORGANISM: Lactobacillus acidophilus

<400> SEQUENCE: 164

Met Asn Pro Glu Glu Phe Ile Leu Glu Leu Ser Lys His Asn Phe Glu
1               5                   10                  15

Leu Ser Asp Lys Gln Lys Gln Gln Phe Lys Leu Tyr Phe Lys Tyr Leu
            20                  25                  30

Ile Glu Val Asn Glu His Val Asn Leu Thr Arg Ile Thr Glu Glu Asn
        35                  40                  45

Glu Val Tyr Leu Lys His Phe Phe Asp Ser Val Thr Pro Leu Phe Thr
    50                  55                  60

Phe Gly Glu Val Phe Lys Asp Gly Ala Thr Leu Cys Asp Val Gly Ala
65                  70                  75                  80

Gly Ala Gly Phe Pro Ser Ile Pro Leu Lys Ile Leu Asn Pro Thr Leu
                85                  90                  95

Lys Val Thr Ile Val Asp Ser Leu Ala Lys Arg Leu Thr Phe Leu Lys
            100                 105                 110

Asn Leu Ile Glu Lys Leu Gly Leu Thr Asp Val Glu Leu Val His Gly
        115                 120                 125

Arg Ala Glu Asp Val Gly Gln Asn Lys Leu Tyr Arg Glu Lys Phe Asp
    130                 135                 140

Leu Val Thr Ala Arg Ala Val Ala Arg Met Ser Val Leu Ser Glu Tyr
145                 150                 155                 160

Cys Leu Pro Leu Val Lys Gly Gly Tyr Phe Ile Ala Leu Lys Gly
                165                 170                 175

Pro Lys Ala Glu Asp Glu Leu Asp Asp Gly Gln Lys Ala Leu Glu Val
            180                 185                 190

Leu Gly Gly Lys Leu Val Lys Glu Glu Leu Thr Leu Pro His Ser
        195                 200                 205

Lys Glu Glu Arg Thr Leu Ile Leu Val Lys Lys Ile Lys Gln Thr Pro
    210                 215                 220

Lys Lys Tyr Pro Arg Gln Ala Gly Thr Pro Arg Arg Lys Pro Ile His
225                 230                 235                 240

<210> SEQ ID NO 165
<211> LENGTH: 1056
<212> TYPE: DNA
<213> ORGANISM: Lactobacillus acidophilus
<220> FEATURE:
<221> NAME/KEY: misc_feature
<222> LOCATION: (1)..(1056)
<223> OTHER INFORMATION: Nucleotides 1,818,098-1,819,153 of NCFM genome

<400> SEQUENCE: 165
agagataata ccaaattcgt atgagaaaac agtattagtt tataaaatag ctagattggt       60
tcattttatt tctaatagct gttatgttga tatcctttat atgtaagttg aaatgagata      120 aaatctcaa  aaagtagtta tttaggaggt aactaaaatg gaaagttaa  tggtattaaa      180 tgaagaaaaa ttgagttatg taattggtgg aggaaatcct aaagtagcac attgtgctag      240
tcaaattggt agatcaacgg cttggggtgc agttagcggt gcagctactg gaactgcagt      300
tggtcaggca gttggtgcat tgggtggtgc tcttttcggt gggagtatgg gcgttatcaa      360
```

```
aggctcagca gcatgtgtaa gttatttaac gcgtcataga catcattaat tgttttttgag    420 taaaatgtga aaggcaaaaa atatggttaa aaataaattg gttattaaag gaataacagc    480
tagtattata tattgtcttc tcggaataat atttgactat attgatagta atttatcaat    540
tatttcaatt attgaaaata ttggagaagg tatagtattc ggcttactta tgtattggct    600
attaaaaagt aataatgtta gatcaatatc aaagcataaa attaatcctt taagttcatt    660
tgttattggt ttcttcggca gttgtttatt actgacttta cttctatttc taaaaatagg    720
ttatgtatca attgattttt ataagagtaa tttttatatt attagtatga tttacttgat    780
tactggattt attggtggtg gagctttatg ttttctttcc tatgtttata gacataagaa    840
agagtaacat ctttaagata atccataacc ttactagttt gtagatattt ctaatctatt    900
ttttgtcagt ttactatttt gaaatgttaa aaatactaaa ttagttatta aattaaccaa    960 tttggtatt tttttatttg attcttctgt catgaaataa tgaacatatc ttaataaaaa    1020
cgtaaaggta gggagagcta tgctactaca atataa                              1056

<210> SEQ ID NO 166
<211> LENGTH: 302
<212> TYPE: DNA
<213> ORGANISM: Lactobacillus acidophilus

<400> SEQUENCE: 166
gttttagcaa ataatatgat aaacaatcaa agaaatttag ctttgattgt ttttcatct     60 tgttttaggg tcattttaa agtatccttt aattataaaa acatttttta attaatttat    120
tatgtattag aaaaccaaat tgattctacg aggaattgaa ttaacatggc aaaaattcta    180
attattgaag atgaaaagaa tttggctcga tttgttagac tagaattaca acacgaaaat    240
tatgagactc gtagtagaaa ataatggtcg taaagggtta gatgacgctc ttgcccaaga    300
tt                                                                   302

<210> SEQ ID NO 167
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 167
gcagcatgta gtagtaataa                                                 20

<210> SEQ ID NO 168
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 168
cagaatcacg taatgtgtaa                                                 20

<210> SEQ ID NO 169
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 169
```
atgcaatagc ttgacgaaga                                              20

<210> SEQ ID NO 170
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 170
atgcaatatg gtgctgaatc                                              20

<210> SEQ ID NO 171
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 171
gatctctaga cagcgctcta gca                                          23

<210> SEQ ID NO 172
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 172
gatcagatct tcggccaatg tg                                           22

<210> SEQ ID NO 173
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 173
gatctctaga cacgaaccgt ctt                                          23

<210> SEQ ID NO 174
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 174
gatcagatct ttggctcgat ttg                                          23

<210> SEQ ID NO 175
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 175
tcgtagttga cggtaagaag                                              20

<210> SEQ ID NO 176
<211> LENGTH: 20
<212> TYPE: DNA
<213> ORGANISM: Artificial Sequence

```
<220> FEATURE:
<223> OTHER INFORMATION: oligonucleotide primer

<400> SEQUENCE: 176
acctgcagta gttaccatag                                              20

<210> SEQ ID NO 177
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 177
gttgttacag acggtgaagg                                              20

<210> SEQ ID NO 178
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 178
taatgcacga ccatcagtcc                                              20

<210> SEQ ID NO 179
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 179
gatctctaga ttccgcttct tact                                         24

<210> SEQ ID NO 180
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 180
gatcagatct atctgacgaa tacg                                         24
```

NUCLEIC ACID SEQUENCES ENCODING TWO-COMPONENT SENSING AND REGULATORY PROTEINS, ANTIMICROBIAL PROTEINS AND USES THEREFOR

CROSS REFERENCE TO RELATED APPLICATION

This application claims the benefit of U.S. Provisional Application Ser. No. 60/599,972, filed Aug. 9, 2004, the contents of which are herein incorporated by reference in their entirety.

REFERENCE TO SEQUENCE LISTING SUBMITTED ON COMPACT DISK

The official copy of the sequence listing is submitted on compact disk (CD). Three CDs, labeled Copy 1, Copy 2, and CRF Copy containing an ASCII formatted sequence listing with a file named seqlist295793.txt, created on Aug. 8, 2005, and having a size of 563,412 bytes are filed concurrently with the specification. The sequence listing contained on these compact disks is part of the specification and is herein incorporated by reference in its entirety.

FIELD OF THE INVENTION

This invention relates to polynucleotides and polypeptides encoded by them, as well as methods for using the polypeptides and microorganisms producing them.

BACKGROUND OF THE INVENTION

*Lactobacillus acidophilus* is a Gram-positive, rod-shaped, non-spore forming, homofermentative bacterium that is a normal inhabitant of the gastrointestinal and genitourinary tracts. Since its original isolation by Moro (1900) from infant feces, the "acid loving" organism has been found in the intestinal tract of humans, breast-fed infants, and persons consuming high milk, lactose, or dextrin diets. Historically, *L. acidophilus* is the *Lactobacillus* species most often implicated as an intestinal probiotic capable of eliciting beneficial effects on the microflora of the gastrointestinal tract (Klaenhammer and Russell (2000) "Species of the *Lactobacillus acidophilus* complex" *Encyclopedia of Food Microbiology*, Volume 2, pp. 1151-1157. Robinson et al., eds. (Academic Press, San Diego, Calif.). *L. acidophilus* can ferment hexoses, including lactose and more complex oligosaccharides, to produce lactic acid and lower the pH of the environment where the organism is cultured. Acidified environments (e.g., food, vagina, and regions within the gastrointestinal tract) can interfere with the growth of undesirable bacteria, pathogens, and yeasts. The organism is well known for its acid tolerance, survival in cultured dairy products, and viability during passage through the stomach and gastrointestinal tract. *Lactobacilli* and other commensal bacteria, some of which are considered as probiotic bacteria that "favor life," are generally recognized for their role in flavor and aroma development and to spoilage retardation in fermented food products, and have been studied extensively for their effects on human health, particularly in the prevention or treatment of enteric infections, diarrheal disease, prevention of cancer, and stimulation of the immune system.

During fermentation, lactic acid bacteria are exposed to toxic byproducts of their growth, such as lactic acid and hydrogen peroxide, antimicrobial agents produced by neighboring microorganisms, and the harsh environmental conditions that is encountered during proper fermentation of a raw food item. They must also adapt to the extreme conditions found in the stomach during ingestion, and severe temperatures associated with storage or production conditions, as well as compete with other microorganisms for resources. These bacteria have evolved sensory and regulatory mechanisms, which enable them to monitor external conditions and respond accordingly. One such mechanism is referred to as the "two-component" system, and is structured around two proteins: a histidine protein kinase and a response regulator protein. Furthermore, one of the major responses controlled by these sensory and regulatory systems of these bacteria is the production of their own antimicrobial agents, of which bacteriocins are an example. Two-component regulatory systems have been shown to control many diverse processes in bacteria, such as sporulation, chemotaxis, nitrogen assimilation, outer membrane protein expression, response to osmolarity, regulation of competence and virulence, as well as the production of antimicrobials.

Microorganisms that can respond to changes in the environment, such as those present during commercial fermentation and storage, as well as those microorganisms that can compete more effectively with other microorganisms are advantageous. Therefore, isolated nucleic acid sequences encoding these proteins are desirable for use in engineering microorganisms, including *Lactobacillus acidophilus*, to have an increased ability to tolerate changes in growth environment and an improved ability to inhibit food-borne pathogens.

BRIEF SUMMARY OF THE INVENTION

Compositions and methods for modifying *Lactobacillus* organisms are provided. Compositions of the invention include isolated nucleic acid molecules encoding proteins involved in and those produced under the control of two-component sensing and regulatory systems.

Compositions comprise isolated nucleic acid molecules comprising a) a nucleic acid molecule comprising any one of even numbered SEQ ID NOS:1-164; b) a nucleic acid molecule comprising a nucleotide sequence having at least 80% sequence identity to any one of even numbered SEQ ID NOS:1-164; c) a nucleic acid molecule that encodes a polypeptide comprising the amino acid sequence as set forth in any one of odd numbered SEQ ID NOS:1-164; d) a nucleic acid molecule comprising a nucleotide sequence encoding a polypeptide having at least 80% amino acid sequence identity to the amino acid sequence as set forth in any one of odd numbered SEQ ID NOS:1-164; and e) a complement of any of a)-d).

Additional compositions include a polypeptide selected from the group consisting of a) a polypeptide comprising the amino acid sequence as set forth in any one of odd numbered SEQ ID NOS:1-164; b) a polypeptide comprising an amino acid sequence having at least 80% sequence identity to the amino acid sequence as set forth in any one of odd numbered SEQ ID NOS:1-164, wherein said polypeptide retains activity; c) a polypeptide encoded by the nucleotide sequence as set forth in any one of odd numbered SEQ ID NOS:1-164; and d) a polypeptide that is encoded by a nucleic acid molecule comprising a nucleotide sequence having at least 80% sequence identity to the nucleotide sequence as set forth in any one of odd numbered SEQ ID NOS:1-164.

Variant nucleic acid molecules, peptides and polypeptides sufficiently identical to and/or functionally equivalent to the nucleotide and amino acid sequences set forth in the attached Sequence Listing are encompassed by the present invention.

Additionally, fragments and sufficiently identical fragments of the nucleotide and amino acid sequences are encompassed. Nucleotide sequences that are complementary to a nucleotide sequence of the invention, or that hybridize to a sequence of the invention, are also encompassed.

Compositions of this invention further include vectors and cells comprising the nucleic acid molecules described herein, as well as, cells and transgenic microbial populations comprising the vectors. Also included in the invention are methods for the recombinant production of the peptides and polypeptides of the invention, and methods for their use. Further included are methods and kits for detecting the presence of a nucleic acid and/or peptide and/or polypeptide sequence of the invention in a sample. Additionally provided are antibodies that bind to a peptide and/or polypeptide of the invention, methods of making the antibodies of this invention and methods for using the antibodies of this invention to detect a peptide and/or polypeptide of this invention.

Compositions also provided herein include a polypeptide of the invention further comprising one or more heterologous amino acid sequences, and antibodies that selectively bind to a polypeptide of the invention.

The two-component sensing and regulatory response molecules and molecules under the control of two-component sensing and regulatory response molecules of the present invention are useful for the selection and production of recombinant bacteria, particularly the production of bacteria with improved ability to survive under stressful conditions.

Additionally provided herein are methods for producing a polypeptide, comprising culturing a cell of the invention under conditions in which a nucleic acid molecule encoding the polypeptide is expressed, said polypeptide being selected from the group consisting of: a) a polypeptide comprising the amino acid sequence as set forth below; b) a polypeptide encoded by the nucleic acid sequence as set forth below; c) a polypeptide comprising an amino acid sequence having at least 80% sequence identity to the amino acid sequence as set forth below, wherein said polypeptide retains activity; and d) a polypeptide encoded by a nucleotide sequence having at least 80% sequence identity to the nucleotide sequence as set forth below, wherein said polypeptide retains activity.

Additionally provided are methods for detecting the presence of a polypeptide of the invention in a sample comprising contacting the sample with a compound that selectively binds to a polypeptide and determining whether the compound binds to the polypeptide in the sample.

Further provided are methods for detecting the presence of a polypeptide in a sample wherein the compound that binds to the polypeptide is an antibody, as well as kits comprising a compound for use in methods of the invention for detecting the presence of a polypeptide in a sample and instructions for use.

The present invention also provides methods for detecting the presence of a nucleic acid molecule and/or fragments thereof, of this invention in a sample, comprising: a) contacting the sample with a nucleic acid probe or primer that selectively hybridizes to the nucleic acid molecule; and b) detecting hybridization of the nucleic acid probe or primer with the nucleic acid molecule.

Also provided are methods for detecting the presence of a nucleic acid molecule and/or fragment of the invention in a sample wherein the sample comprises mRNA molecules and is contacted with a nucleic acid probe. Additionally provided herein is a kit comprising a compound that selectively hybridizes to a nucleic acid of the invention, and instructions for use.

Further provided herein are methods for increasing the ability of a microorganism to survive stressful conditions, comprising introducing into said microorganism a nucleic acid molecule of the invention and expressing the nucleic acid molecule. In specific embodiments, the nucleotide sequence encodes a protein of a two-component regulatory system, a histidine protein kinase and/or a response regulator of a two-component regulatory system, a protein under the control of a two-component regulatory system, or a bacteriocin. In further aspects of the invention, the stressful conditions comprise osmotic stress, oxidative stress and/or starvation conditions.

Methods are also provided herein for enhancing the ability of a microorganism to survive passage through the gastrointestinal tract, comprising introducing into the microorganism a nucleic acid molecule comprising at least one nucleotide sequence selected from the group consisting of: a) the nucleotide sequence as set forth in any one of odd numbered SEQ ID NO:1-164; b) a nucleotide sequence encoding a polypeptide comprising the amino acid sequence as set forth in any one of even numbered SEQ ID NO:1-164; c) a nucleotide sequence that is at least 80% identical to the sequence as set forth in any one of odd numbered SEQ ID NO:1-164, wherein said nucleotide sequence encodes a polypeptide that retains activity; and, d) a nucleotide sequence encoding a polypeptide comprising an amino acid sequence having at least 80% sequence identity to the amino acid sequence as set forth in any one of even numbered SEQ ID NO:1-164, wherein said polypeptide retains activity.

Methods are also provided herein for enhancing the ability of a microorganism to survive passage through the gastrointestinal tract, comprising introducing into the microorganism at least one nucleic acid molecule of the invention. In specific embodiments, the nucleotide sequence encodes a protein of a two-component regulatory system, a histidine protein kinase of a two-component regulatory system, a response regulator of a two-component regulatory system, a bacteriocin, and/or encodes a protein under the control of a two-component regulatory system.

Additional aspects of the invention comprise methods for increasing the ability of a microorganism to survive in the presence of an antimicrobial, comprising introducing into said microorganism a nucleic acid molecule comprising at least one nucleotide sequence of the invention. In specific embodiments, the nucleotide sequence encodes a protein of a two-component regulatory system, the nucleotide sequence encodes a histidine protein kinase of a two-component regulatory system and/or a response regulator of a two-component regulatory system, and/or the nucleotide sequence encodes a protein or proteins that is under the control of a two-component regulatory system.

Also provided are methods for enabling an organism to respond to environmental stimuli, comprising introducing into the organism a vector comprising at least one nucleotide sequence of the invention. In specific embodiments, the nucleotide sequence encodes a protein of a two-component regulatory system, a histidine protein kinase of a two-component regulatory system, a response regulator of a two-component regulatory system, a bacteriocin, and/or encodes a protein under the control of a two-component regulatory system. The environmental stimuli can be selected from the group consisting of turgor pressure, a chemical stimulus, heavy-metal cations, oxygen, iron, an antimicrobial compound, various carbohydrates, including glucose.

Yet another embodiment of the invention comprises a *Lactobacillus acidophilus* cell with an increased ability to survive stressful conditions compared to a wild-type *Lactobacillus acidophilus* cell, wherein said increased ability to survive stressful conditions is the result of overexpression of a nucleic acid molecule encoding an amino acid sequence as set forth herein. In specific embodiments, the stressful conditions comprise osmotic stress, oxidative stress, starvation, or the presence of antimicrobials.

DETAILED DESCRIPTION OF THE INVENTION

Figure 1:
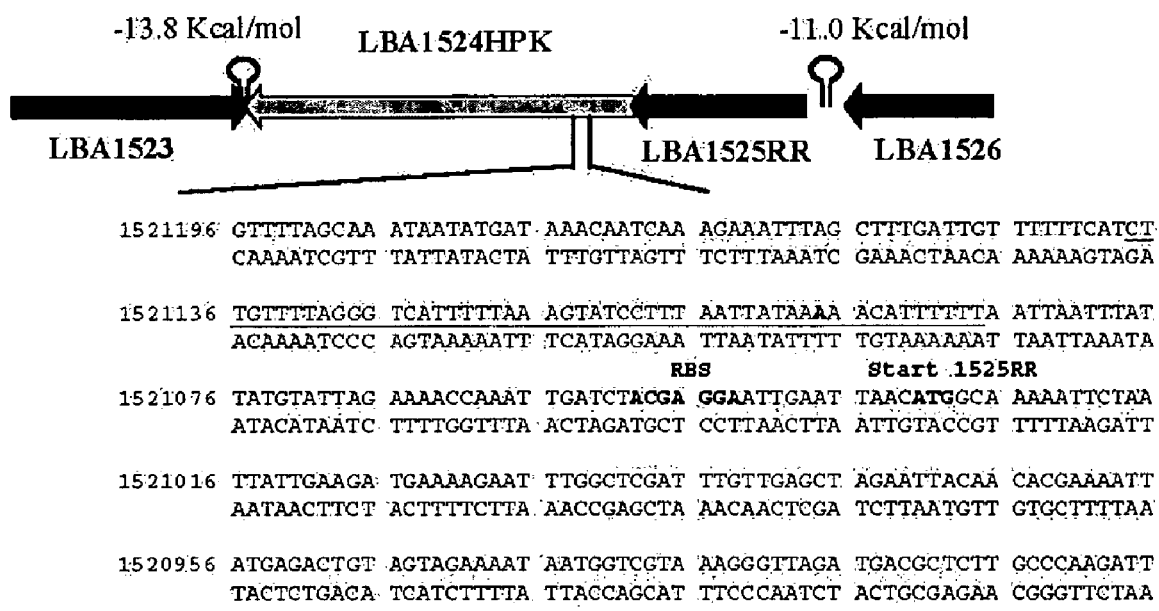
FIG. 1 shows the organization of 1524HPK-1525RR two-component regulatory system in *Lactobacillus acidophilus* NCFM. The disrupted HPK gene is represented by a grey arrow. Putative terminator regions and their calculated free energy are indicated by hairpin structures. The start, putative ribosome binding site, potential promoter and transcription start are indicated. The sequence is set forth in SEQ ID NO:166.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention relates to two-component sensing and regulatory system proteins and proteins under the control of the two-component regulatory system. These proteins include, but are not limited to, histidine protein kinases, response regulators and bacteriocins. Examples of nucleic acid sequences encoding two-component sensing and regulatory system, related antimicrobial proteins and proteins under the control of two-component sensing and regulatory molecules are provided in Table 1.

Two-component regulatory system molecules and molecules expressed under the control of two-component regulatory system molecules are provided. The full-length gene sequences, referred to as "two-component regulatory system sequences," have similarity to two-component regulatory system genes. The invention further provides fragments and variants of these two-component regulatory system sequences, which can also be used to practice the methods of the present invention. As used herein, the terms "gene" and "recombinant gene" refer to nucleic acid molecules comprising an open reading frame, particularly those encoding a two-component regulatory system protein. Isolated nucleic acid molecules of the present invention comprise nucleic acid sequences encoding two-component regulatory system proteins and proteins under the control of two-component regulatory system proteins, nucleic acid sequences encoding the amino acid sequences set forth in SEQ ID NOS:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 146, 148, 150, 152, 154, 156, 158, 160, 162, 164, the nucleic acid sequences set forth in SEQ ID NOS:1, 3, 5, 7, 9, 11, 13, 15, 17, 19, 21, 23, 25, 27, 29, 31, 33, 35, 37, 39, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 132, 135, 137, 139, 1143, 145, 147, 149, 151, 153, 155, 157, 159, 161, 163, 164, and variants and fragments thereof. The present invention also encompasses antisense nucleic acid molecules, as described herein.

In addition, isolated peptides, polypeptides and proteins of a two-component regulatory system or that are produced under the control of a two-component regulatory system, and variants and fragments thereof are encompassed, as well as, methods for producing all of these. For purposes of the present invention, the terms "protein" and "polypeptide" are used interchangeably. A representative amino acid sequence of the present invention is set forth in SEQ ID NO:2. In some embodiments, peptides and/or polypeptides of the present invention affect a stress-related protective activity. Stress-related protective activity refers to a biological or functional activity as determined in vivo or in vitro according to standard assay techniques. These techniques could involve, for example, measuring bacterial survival or growth under adverse environmental conditions. See, for example, Varcamonti et al. (2003) *Appl. Environ. Microbiol.* 69:1287-1289, herein incorporated by reference. By "adverse environmental conditions" or "stressful environmental conditions" is meant an environmental condition or state that is not conducive for growth of the microorganism, and includes, but is not limited to, acidic conditions, alkaline conditions, non-optimal osmotic stress conditions, non-optimal oxidative stress conditions, starvation conditions, and in the presence of antimicrobials.

As used herein, the terms peptide and polypeptide are used to describe a chain of amino acids, which correspond to those encoded by a nucleic acid. A peptide usually describes a chain of amino acids of from two to about 30 amino acids and polypeptide usually describes a chain of amino acids having more than about 30 amino acids. The term polypeptide can refer to a linear chain of amino acids or it can refer to a chain of amino acids, which have been processed and folded into a functional protein. It is understood, however, that 30 is an arbitrary number with regard to distinguishing peptides and polypeptides and the terms may be used interchangeably for a chain of amino acids around 30. The peptides and polypeptides of the present invention are obtained by isolation and purification of the peptides and polypeptides from cells where they are produced naturally or by expression of a recombinant and/or synthetic nucleic acid encoding the peptide or polypeptide. The peptides and polypeptides of this invention can be obtained by chemical synthesis, by proteolytic cleavage of a polypeptide and/or by synthesis from nucleic acid encoding the peptide or polypeptide.

It is also understood that the peptides and polypeptides of this invention may also contain conservative substitutions where a naturally occurring amino acid is replaced by one having similar properties and which does not alter the function of the polypeptide. Such conservative substitutions are well known in the art. Thus, it is understood that, where desired, modifications and changes, which are distinct from the substitutions which enhance immunogenicity, may be made in the nucleic acid and/or amino acid sequence of the peptides and polypeptides of the present invention and still obtain a peptide or polypeptide having like or otherwise desirable characteristics. Such changes may occur in natural isolates or may be synthetically introduced using site-specific mutagenesis, the procedures for which, such as mis-match polymerase chain reaction (PCR), are well known in the art. One of skill in the art will also understand that polypeptides and nucleic acids that contain modified amino acids and nucleotides, respectively (e.g., to increase the half-life and/or the therapeutic efficacy of the molecule), can be used in the methods of the invention.

The nucleic acid and protein compositions encompassed by the present invention are isolated or substantially purified. By "isolated" or "substantially purified" is intended that the nucleic acid or protein molecules, or biologically active fragments or variants, are substantially or essentially free from components normally found in association with the nucleic acid or protein in its natural state. Such components include other cellular material, culture media from recombinant production, and various chemicals used in chemically synthesizing the proteins or nucleic acids. Preferably, an "isolated" nucleic acid of the present invention is free of nucleic acid sequences that flank the nucleic acid of interest in the genomic DNA of the organism from which the nucleic acid was derived (such as coding sequences present at the 5' or 3' ends). However, the molecule can include some additional bases or moieties, which do not deleteriously affect the basic characteristics of the composition. For example, in various embodiments, the isolated nucleic acid contains less than 5 kb, 4 kb, 3 kb, 2 kb, 1 kb, 0.5 kb, or 0.1 kb of nucleic acid sequence normally associated with the genomic DNA in the cells from which it was derived. Similarly, an isolated or substantially purified protein has less than about 30%, 20%, 10%, 5%, or 1% (by dry weight) of contaminating protein, or non-two-component regulatory protein. When the protein is recombinantly produced, preferably culture medium represents less than 30%, 20%, 10%, or 5% of the volume of the protein preparation, and when the protein is produced chemically, preferably the preparations have less than about 30%, 20%, 10%, or 5% (by dry weight) of chemical precursors, or non-two-component regulatory chemicals.

The compositions and methods of the present invention can be used to modulate the function of the two-component regulatory molecules of the invention or the sequences under the control of the two component sensing or regulatory molecules. By "modulate," "alter," or "modify" is intended the up- or down-regulation of a target biological activity. In accordance with the present invention, the level or activity of a sequence of the invention is modulated (i.e., overexpressed or underexpressed) if the level and/or activity of the sequence is statistically lower or higher than the level and/or activity of the same sequence in an appropriate control. Concentration and/or activity can be increased or decreased by at least 0.5%, 1%, 5%, 10%, 20%, 30%, 40%, 50%, 60%, 70%, 80%, or 90% relative to an appropriate control. Proteins of the invention are useful in modifying the biological activities of lactic acid bacteria, especially lactic acid bacteria that are used to ferment foods with nutritional or health-promoting characteristics. Nucleic acid molecules of the invention are useful in modulating production of the sequences of the invention by lactic acid bacteria. Up- or down-regulation of expression of a nucleic acid of the present invention is encompassed. Up-regulation can be accomplished by providing multiple nucleic acid copies, modulating expression by modifying regulatory elements, promoting transcriptional or translational mechanisms, or other means. Down-regulation can be accomplished by using known antisense and gene silencing techniques.

By "lactic acid bacteria" is intended bacteria from a genus selected from the following: *Aerococcus, Carnobacterium, Enterococcus, Lactococcus, Lactobacillus, Leuconostoc, Oenococcus, Pediococcus, Streptococcus, Melissococcus, Alloiococcus, Dolosigranulum, Lactosphaera, Tetragenococcus, Vagococcus,* and *Weissella* (Holzapfel et al. (2001) *Am. J. Clin. Nutr.* 73:365S-373S; *Bergey's Manual of Systematic Bacteriology,* Vol. 2 (Williams and Wilkins, Baltimore (1986)) pp. 1075-1079).

Microorganisms expressing the nucleic acid molecules to produce the polypeptides of the present invention are useful as additives in dairy and fermentation processing. The nucleic acid sequences, encoded polypeptides, and microorganisms expressing them are useful in the manufacture of milk-derived products, such as cheeses, yogurt, fermented milk products, sour milks, and buttermilk. Microorganisms that produce polypeptides of the invention may be probiotic organisms. By "probiotic" is intended a live microorganism that survives passage through the gastrointestinal tract and has a beneficial effect on the subject. By "subject" is intended an organism that comes into contact with a microorganism producing a protein of the present invention. Subject may refer to humans and other animals.

In addition to the sequences disclosed herein, and fragments and variants thereof, the isolated nucleic acid molecules of the current invention also encompass homologous nucleic acid sequences identified and isolated from other organisms or cells by hybridization with entire or partial sequences obtained from the two-component regulatory nucleotide sequences disclosed herein, or variants and fragments thereof.

In another embodiment of the invention, nucleotide sequences and fragments thereof that are expressed under the control of proteins and polypeptides of a two-component regulatory system and the proteins and polypeptides encoded by those nucleotide sequences are provided. In a preferred embodiment, the protein or polypeptide produced from a nucleotide sequence under control of a two-component regulatory system is a bacteriocin. By "bacteriocin" is intended a group of polypeptides produced by a bacterium as an antimicrobial substance. Included in this group are: Class I bacteriocins or lantibiotics which contain the unusual amino acids lantionine, β-methyl-lanthionine and dehydrated residues dehydroalanine and dehydrobutyrine; Class II bacteriocins, i.e., small heat-stable, non-lanthionine containing, membrane-active peptides; and Class III bacteriocins, i.e., large, heat-labile proteins.

Fragments and Variants

The invention provides isolated nucleic acid molecules comprising nucleotide sequences encoding two-component regulatory proteins, as well as peptides and/or proteins encoded thereby. By "two-component regulatory protein" or "two-component sensing protein" is meant proteins comprising, consisting of and/or consisting essentially of the amino acid sequences set forth in even numbered SEQ ID NOS:1-38. By "proteins under the control of two-component sensing and regulatory molecules" is meant proteins having the amino acid sequences set forth in even numbered SEQ ID NOS:40-164. Fragments and variants of these nucleotide sequences and encoded proteins are also provided. By "fragment" of a nucleotide sequence or protein is intended a portion of the nucleotide or amino acid sequence.

Fragments and variants of the nucleic acid molecules disclosed herein can be used as hybridization probes to identify two-component regulatory protein-encoding nucleic acids and/or proteins under the control of two-component sensing and regulatory molecules, or they can be used as primers in amplification protocols (e.g., polymerase chain reaction) or mutation of two-component regulatory nucleic acid molecules, proteins under the control of two-component sensing and regulatory molecules and/or stress-related nucleic acid molecules. Such fragments or variants need not encode function polypeptides. Fragments of nucleic acids can also be bound to a physical substrate to comprise a macro- or microarray (for example, U.S. Pat. No. 5,837,832; U.S. Pat. No. 5,861,242). Such arrays of nucleic acids can be used to study gene expression or to identify nucleic acid molecules with sufficient identity to the target sequences.

By "nucleic acid molecule" is meant DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. A fragment of a nucleic acid molecule encoding a protein of the invention may encode a protein fragment that is biologically active, or it may be used as a hybridization probe or PCR primer as described below. A biologically active fragment of a polypeptide disclosed herein can be prepared by isolating a portion of one of the nucleotide sequences of the invention, expressing the encoded portion of the protein (e.g., by recombinant expression in vitro), and assessing the activity of the encoded portion.

Fragments of nucleic acid molecules of the invention comprise at least about 15, 20, 50, 75, 100, 200, 250, 300, 350, 400, 450, 500, 550, 600, 650, 700, 750, 800, 850, 900, 950, 1000, 1100, 1200, 1400, 1600, 1800, 2000, 2200, 2415 nucleotides (for example, 714 for SEQ ID NO:1, 1854 for SEQ ID NO:3, etc.), including any value between these numbers recited here, e.g., 36 nucleotides or 423 nucleotides up to the total number of nucleotides present in a full-length nucleotide sequence as disclosed herein.

Fragments of amino acid sequences of this invention can include polypeptide fragments that function as immunogens for example, for the production of antibodies to two-component regulatory system proteins or to proteins under the control of two-component sensing and regulatory molecules. Fragments of this invention include peptides comprising amino acid sequences sufficiently identical to and/or derived from the amino acid sequence of a protein of the invention, or partial-length protein of the invention and exhibiting at least one activity of the protein, but which include fewer amino acids than the full-length proteins disclosed herein. Typically, biologically active fragments of this invention comprise a domain or motif with at least one activity of the protein. A biologically active portion or fragment of a two-component regulatory protein or a protein under the control of two-component sensing and regulatory molecules can be a peptide or polypeptide that is, for example, 10, 25, 50, 100, 150, 200, 250, 300, 400, 500, 600, 700, 805 contiguous amino acids in length, or up to the total number of amino acids present in a full-length protein of the current invention (for example, 238 for SEQ ID NO:2, 618 for SEQ ID NO:4, etc.), including any value in between these explicitly listed herein, e.g., 17 amino acids or 106 amino acids up to the total number of amino acids present in a full-length protein sequence of the invention. Such biologically active fragments can be prepared by recombinant techniques and evaluated for one or more of the functional activities according to standard protocols. As used herein, a fragment can comprise at least 5 contiguous amino acids of even numbered SEQ ID NOS:1-164. The invention encompasses other fragments, however, such as any fragment of a protein of this invention comprising greater than 6, 7, 8, or 9 amino acids.

Variants of the nucleotide and amino acid sequences are encompassed in the present invention. By "variant" is meant a sufficiently identical sequence. Accordingly, the invention encompasses isolated nucleic acid molecules that are sufficiently identical to the nucleotide sequences of the invention set forth in the odd numbered SEQ ID NOS:1-164, or nucleic acid molecules that hybridize to a nucleic acid molecule of odd numbered SEQ ID NOS:1-164, or a complement thereof, under stringent conditions. Variants also include variant polypeptides encoded by the nucleotide sequences of the present invention. In addition, polypeptides of the current invention have an amino acid sequence that is sufficiently identical to an amino acid sequence set forth in even numbered SEQ ID NOS:1-164. By "sufficiently identical" is meant that one amino acid or nucleotide sequence contains or encodes a sufficient or minimal number of equivalent or identical amino acid residues or nucleotides as compared to a second amino acid or nucleotide sequence, thus providing a common structural domain and/or a common functional activity. Conservative variants include those sequences that differ due to the degeneracy of the genetic code.

In general, amino acids or nucleotide sequences that have at least about 45%, 55%, 65%, 70%, 75%, 80%, 85%, 90%, 91%, 92%, 93%, 94%, 95%, 95%, 96%, 97%, 98%, 99%, or 99.5% sequence identity to any of the amino acid sequences of even numbered SEQ ID NOS:1-164 or any of the nucleotide sequences of odd numbered SEQ ID NOS:1-164, respectively, are defined herein as sufficiently identical. Variant proteins encompassed by the present invention are biologically active, that is they retain a desired biological activity of the native protein. Such activities are discussed in detail elsewhere herein. By "two-component regulatory system activity" is intended the ability of an organism to respond to an environmental stimuli to enable the organism to better survive. This encompasses both stressful environmental conditions, as described above, and beneficial environmental conditions, wherein a molecule desired by the organism is present, such as glucose. Assays to measure the activity of two-component regulatory system proteins or the proteins under the control of the two-component sensing and regulatory molecules are well known in the art. See, for example, Lee et al. (2004) *Infect. Immun.* 72:3968-3973; Walker and Miller (2004) *J. Bacteriol.* 186:4056-4066; Saini et al. (2004) *Microbiology.* 150:865-875; Abo-Amer et al. (2004) *J. Bacteriol.* 186:1879-1889. A biologically active variant of a protein of the invention can differ from that protein by as few as 1-15 amino acid residues, as few as 1-10, such as 6-10, as few as 5, as few as 4, 3, 2, or even 1 amino acid residue.

In one embodiment, the sequence according to the present invention or for use in the methods of the invention may be one or more of the nucleotide sequences set forth in 3, 7, 13, 15, 19, 23, 29, 33, and 35, which can encode a histidine kinase. Variants of such nucleotide sequences are also included including sequences that have at least about 45%, 55%, 65%, 70%, 75%, 80%, 85%, 90%, 91%, 92%, 93%, 94%, 95%, 95%, 96%, 97%, 98%, 99%, or 99.5%.

In one embodiment, the sequence according to the present invention or for use in the methods of the invention may be one or more of the nucleotide sequences set forth in 73, 75, 85, 89, 91, 95, and 113, which can encode a bacteriocin. Variants of such nucleotide sequences are also included including sequences that have at least about 45%, 55%, 65%, 70%, 75%, 80%, 85%, 90%, 91%, 92%, 93%, 94%, 95%, 95%, 96%, 97%, 98%, 99%, or 99.5%.

In one embodiment, the sequence according to the present invention or for use in the methods of the invention may be one or more of the nucleotide sequences set forth in 1, 9, 11, 17, 21, 25, 27, 31, and 37, which can encode a response regulator. Variants of such nucleotide sequences are also included including sequences that have at least about 45%, 55%, 65%, 70%, 75%, 80%, 85%, 90%, 91%, 92%, 93%, 94%, 95%, 95%, 96%, 97%, 98%, 99%, or 99.5%.

In one embodiment, the sequence according to the present invention or for use in the methods of the invention may be one or more of the nucleotide sequences set forth in 5, 49, 51, 53, 73, 75, 77, 79, 81, 83, 85, 87, 89, 91, 93, 95, 97, 99, 101, 113, 115, 117, 119, 121, 151, 153, 155, 157, 159, 161, and 163, which can encode a polypeptide produced under the control of a two-component regulatory system. Variants of such nucleotide sequences are also included including sequences that have at least about 45%, 55%, 65%, 70%, 75%, 80%, 85%, 90%, 91%, 92%, 93%, 94%, 95%, 95%, 96%, 97%, 98%, 99%, or 99.5%.

In one embodiment, the sequence according to the present invention or for use in the methods of the invention may be one or more of the amino acid sequences set forth in 4, 8, 14, 16, 20, 24, 30, 34, and 36, which can encode a histidine kinase. Variants of such amino acid sequences are also included including sequences that have at least about 45%, 55%, 65%, 70%, 75%, 80%, 85%, 90%, 91%, 92%, 93%, 94%, 95%, 95%, 96%, 97%, 98%, 99%, or 99.5%.

In one embodiment, the sequence according to the present invention or for use in the methods of the invention may be one or more of the amino acid sequences set forth in 74, 76, 90, 92, 96, and 114, which can encode a bacteriocin. Variants of such amino acid sequences are also included including sequences that have at least about 45%, 55%, 65%, 70%, 75%, 80%, 85%, 90%, 91%, 92%, 93%, 94%, 95%, 95%, 96%, 97%, 98%, 99%, or 99.5%.

In one embodiment, the sequence according to the present invention or for use in the methods of the invention may be one or more of the amino acid sequences set forth in 2, 10, 12, 18, 22, 26, 28, 32, and 38, which can encode a response regulator. Variants of such amino acid sequences are also included including sequences that have at least about 45%, 55%, 65%, 70%, 75%, 80%, 85%, 90%, 91%, 92%, 93%, 94%, 95%, 95%, 96%, 97%, 98%, 99%, or 99.5%.

In one embodiment, the sequence according to the present invention or for use in the methods of the invention may be one or more of the amino acid sequences set forth in 6, 50, 52, 54, 74, 76, 78, 80, 82, 84, 66, 68, 90, 92, 94, 96, 98, 100, 102, 114, 116, 118, 120, 122, 152, 154, 156, 158, 160, 163, and 164, which can encode a polypeptide produced under the control of a two-component regulatory system. Variants of such amino acid sequences are also included including sequences that have at least about 45%, 55%, 65%, 70%, 75%, 80%, 85%, 90%, 91% 92%, 93%, 94%, 95%, 95%, 96%, 97%, 98%, 99%, or 99.5%.

Full-length or partial nucleic acid sequences can be used to obtain homologues and orthologs encompassed by the present invention. By "orthologs" is intended genes derived from a common ancestral gene and which are found in different species as a result of speciation. Genes found in different species are considered orthologs when their nucleotide sequences and/or their encoded amino acid sequences share substantial identity as defined elsewhere herein. Functions of orthologs are often highly conserved among species.

Naturally occurring variants can exist within a population (e.g., the *Lactobacillus acidophilus* population). Such variants can be identified by using well-known molecular biology techniques, such as the polymerase chain reaction (PCR), and hybridization as described herein. Synthetically derived nucleotide sequences, for example, sequences generated by site-directed mutagenesis or PCR-mediated mutagenesis that still encode a two-component regulatory protein, are also included as variants. One or more nucleotide or amino acid substitutions, additions, and/or deletions can be introduced into a nucleotide or amino acid sequence disclosed herein, such that the substitutions, additions, or deletions are introduced into the encoded protein. The additions (insertions) and/or deletions (truncations) can be made at the N-terminal and/or C-terminal end of the native protein, and/or at one or more sites in the native protein. Similarly, a substitution of one or more nucleotides or amino acids can be made at one or more sites in the native protein.

For example, conservative amino acid substitutions can be made at one or more predicted, preferably nonessential amino acid residues. A "nonessential" amino acid residue is a residue that can be altered from the wild-type sequence of a protein without altering the biological activity, whereas an "essential" amino acid is required for biological activity. A "conservative amino acid substitution" is one in which the amino acid residue is replaced with an amino acid residue with a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, where such residues are essential for protein activity.

Alternatively, mutations can be made randomly along all or part of the length of the two-component regulatory coding sequence or along all or part of the length of the sequences under the control of two-component sensing and regulatory molecules, such as by saturation mutagenesis. The mutants can be expressed recombinantly, and screened for those that retain biological activity e.g., by assaying for two-component regulatory system activity using standard assay techniques. Methods for mutagenesis and nucleotide sequence alterations are known in the art. See, for example, Kunkel (1985) *Proc. Natl. Acad Sci. USA* 82:488-492, Kunkel et al. (1987) *Methods in Enzymol. Molecular Biology* (MacMillan Publishing Company, New York) and the references sited therein. Obviously the mutations made in the DNA encoding the variant must not disrupt the reading frame and preferably will not create complementary regions that could produce secondary mRNA structure. See, EP Patent Application Publication No. 75,444. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference in its entirety for these teachings.

The deletions, insertions, and substitutions of the amino acid sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by comparing the activity of the modified sequence with the activity of the original sequence. See, for example, Baruah et al. (2004) *J. Bacteriol.* 186:1694-1704; Wang et al. (2001) *J. Bacteriol.* 183:2795-2802; and, Piazza et al. (1999) *J. Bacteriol.* 181:4540-4548), each of which is herein incorporated by reference in their entireties for these teachings.

Variant nucleotide and amino acid sequences of the present invention also encompass sequences derived from mutagenic and recombinogenic procedures such as DNA shuffling. With such a procedure, one or more different polypeptides of the invention can be used to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest can be shuffled between the two-component regulatory nucleic acid of the invention and other known two-component regulatory nucleic acid to obtain a new nucleic acid encoding for a peptide, polypeptide or protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad Sci. USA* 94:4504-4509; Crameri et al. (1998) *Nature* 391:288-291; and U.S. Pat. Nos. 5,605,793 and 5,837,458.

Variants of the two-component regulatory proteins can function as either two-component-related agonists (mimetics) or as two-component-related antagonists. An agonist of the two-component-related protein can retain substantially the same, or a subset, of the biological activities of the naturally occurring form of the two-component regulatory protein. An antagonist of the two-component regulatory protein can inhibit one or more of the activities of the naturally occurring form of the two-component regulatory protein by, for example, competitively binding to a downstream or upstream member of a cellular signaling cascade that includes the two-component regulatory protein.

Variants of a two-component regulatory protein or variants of polypeptides under the control of the two-component sensing and regulatory molecules that function as either agonists or antagonists can be identified by screening combinatorial libraries of mutants, e.g., truncation mutants, of a two-component regulatory protein for stress-related protein agonist or antagonist activity. In one embodiment, a variegated library of two-component regulatory variants is generated by combinatorial mutagenesis at the nucleic acid level and is encoded by a variegated gene library. A variegated library of two-component regulatory variants can be produced by, for example, enzymatically ligating a mixture of synthetic oligonucleotides into gene sequences such that a degenerate set of potential two-component regulatory sequences is expressible as individual polypeptides, or alternatively, as a set of larger fusion proteins (e.g., for phage display) containing the set of two-component regulatory sequences therein. There are a variety of methods that can be used to produce libraries of variants from a degenerate oligonucleotide sequence. Chemical synthesis of a degenerate gene sequence can be performed in an automatic DNA syntheizer, and the synthetic gene then ligated into an appropriate expression vector. Use of a degenerate set of genes allows for the provision, in one mixture, of all of the sequences encoding the desired set of potential two-component regulatory sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acids Res.* 11:477).

In addition, libraries of fragments of a two-component regulatory protein coding sequence can be used to generate a variegated population of two-component regulatory fragments for screening and subsequent selection of variants of a two-component regulatory protein. In one embodiment, a library of coding sequence fragments can be generated by treating a double-stranded PCR fragment of a two-component regulatory coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify two-component regulatory variants (Arkin and Yourvan (1992) *Proc. Natl. Acad. Sci. USA* 89:7811-7815; Delgrave et al. (1993) *Protein Engineering* 6(3):327-331).

Sequence Identity

The two-component regulatory sequences and the sequences under the control of two-component sensing and regulatory molecules are members of various families of molecules with conserved functional features. By "family" is intended two or more proteins or nucleic acid molecules having sufficient nucleotide or amino acid sequence identity. By "sequence identity" is intended the nucleotide or amino acid residues that are the same when aligning two sequences for maximum correspondence over a specified comparison window. By "comparison window" is intended a contiguous segment of the two nucleotide or amino acid sequences for optimal alignment, wherein the second sequence can contain additions or deletions (i.e., gaps) as compared to the first sequence. Generally, for nucleic acid alignments, the comparison window is at least 20 contiguous nucleotides in length, and optionally can be 30, 40, 50, 100, or longer. For amino acid sequence alignments, the comparison window is at least 6 contiguous amino acids in length, and optionally can be 10, 15, 20, 30, or longer. Those of skill in the art understand that to avoid a high similarity due to inclusion of gaps, a gap penalty is typically introduced and is subtracted from the number of matches.

Family members can be from the same or different species, and can include homologues as well as distinct proteins. Often, members of a family display common functional characteristics. Homologues can be isolated based on their identity to the *Lactobacillus acidophilus* nucleic acid sequences disclosed herein using the cDNA, or a portion thereof, as a hybridization probe according to standard hybridization techniques under stringent hybridization conditions as disclosed herein.

To determine the percent identity of two amino acid or nucleotide sequences, an alignment is performed. Percent identity of the two sequences is a function of the number of identical residues shared by the two sequences in the comparison window (i.e., percent identity=number of identical residues/total number of residues×100). In one embodiment, the sequences are the same length. Methods similar to those mentioned below can be used to determine the percent identity between two sequences. The methods can be used with or without allowing gaps. Alignment can also be performed manually by inspection.

When amino acid sequences differ in conservative substitutions, the percent identity can be adjusted upward to correct for the conservative nature of the substitution. Means for making this adjustment are known in the art. Typically the conservative substitution is scored as a partial, rather than a full mismatch, thereby increasing the percentage sequence identity.

Mathematical algorithms can be used to determine the percent identity of two sequences. Non-limiting examples of mathematical algorithms are the algorithm of Karlin and Altschul (1990) *Proc. Natl. Acad Sci. USA* 87:2264, modified as in Karlin and Altschul (1993) *Proc. Natl. Acad. Sci. USA* 90:5873-5877; the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; and the search-for-local alignment-method of Pearson and Lipman (1988) *Proc. Natl. Acad. Sci. USA* 85:2444-2448.

Various computer implementations based on these mathematical algorithms have been designed to enable the determination of sequence identity. The BLAST programs of Altschul et al. (1990) *J. Mol. Biol.* 215:403 are based on the algorithm of Karlin and Altschul (1990) supra. Searches to obtain nucleotide sequences that are homologous to nucleotide sequences of the present invention can be performed with the BLASTN program, score=100, wordlength=12. To identify amino acid sequences homologous to amino acid sequences of the proteins of the present invention, the BLASTX program can be used, score=50, wordlength=3. Gapped alignments can be obtained by using Gapped BLAST (in BLAST 2.0) as described in Altschul et al. (1997) *Nucleic Acids Res.* 25:3389. To detect distant relationships between molecules, PSI-BLAST can be used. See Altschul et al. (1997) supra. For all of the BLAST programs, the default parameters of the respective programs can be used. Alignment can also be performed manually by inspection.

Another program that can be used to determine percent sequence identity is the ALIGN program (version 2.0), which uses the mathematical algorithm of Myers and Miller (1988) supra. A PAM120 weight residue table, a gap length penalty of 12, and a gap penalty of 4 can be used with this program when comparing amino acid sequences.

In addition to the ALIGN and BLAST programs, the BESTFIT, GAP, FASTA and TFASTA programs are part of the GCG Wisconsin Genetics Software Package, Version 10 (available from Accelrys Inc., 9685 Scranton Rd., San Diego, Calif., USA), and can be used for performing sequence alignments. The preferred program is GAP version 10, which used the algorithm of Needleman and Wunsch (1970) supra. Unless otherwise stated, the sequence identity similarity values provided herein refer to the value obtained using GAP Version 10 with the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2, and the BLOSUM62 scoring matrix; or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10

Identification and Isolation of Homologous Sequences

Two-component regulatory nucleotide sequences or proteins under the control of two-component sensing and regulatory molecules identified based on their sequence identity to the sequences set forth herein or to fragments and variants thereof are encompassed by the present invention. Methods such as PCR or hybridization can be used to identify sequences from a cDNA or genomic library, for example, that are substantially identical to a sequence of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, New York). Methods for construction of such cDNA and genomic libraries are generally known in the art and are also disclosed in the above reference.

In hybridization techniques, the hybridization probes can be genomic DNA fragments, cDNA fragments, RNA fragments, and/or other oligonucleotides, and can consist of all or part of a known nucleotide sequence disclosed herein. In addition, they can be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known two-component regulatory nucleotide sequences disclosed herein. Degenerate primers designed on the basis of conserved nucleotides or amino acid residues in a known two-component regulatory nucleotide sequence or encoded amino acid sequence can additionally be used. The hybridization probe typically comprises a region of nucleotide sequence that hybridizes under stringent conditions to at least about 10, or about 20, or about 50, 75, 100, 125, 150, 175, 200, 250, 300, 350, or 400 consecutive nucleotides of a two-component regulatory nucleotide sequence of the invention or a fragment or variant thereof. To achieve specific hybridization under a variety of conditions, such probes include sequences that are unique among two-component regulatory protein sequences or unique among proteins under the control of two-component sensing and regulatory molecules. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference in its entirety for these teachings.

In one embodiment, the entire nucleotide sequence of the invention is used as a probe to identify novel sequences and messenger RNAs. In another embodiment, the probe is a fragment of a nucleotide sequence disclosed herein. In some embodiments, the nucleotide sequence that hybridizes under stringent conditions to the probe can be at least about 300, 325, 350, 375, 400, 425, 450, 500, 550, 600, 650, 700, 800, 900, 1000, 1500, 2000, 2500, 3000, 3500, or 4000 nucleotides in length (including any value not explicitly stated herein).

Substantially identical sequences will hybridize to each other under stringent conditions. By "stringent conditions" is meant conditions under which a probe will hybridize to its target sequence to a detectably greater degree than to other sequences (e.g., at least 2-fold over background). Generally, stringent conditions encompass those conditions for hybridization and washing under which nucleotides having at least about 60%, 65%, 70%, preferably 75% sequence identity typically remain hybridized to each other. Stringent conditions (e.g., high, medium, low stringency) are known in the art and can be found in *Current Protocols in Molecular Biology* (John Wiley & Sons, New York (1989)), 6.3.1-6.3.6, the entire contents of which are incorporated herein by reference for these teachings. Hybridization typically occurs for less than about 24 hours, usually about 4 to about 12 hours.

Stringent conditions are sequence dependent and will differ in different circumstances. When using probes, stringent conditions can be, e.g., those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

The post-hybridization washes are instrumental in controlling specificity. The two factors are ionic strength and temperature. For the detection of sequences that hybridize to a full-length or approximately full-length target sequence, the temperature under stringent conditions is selected to be about 5° C. lower than the thermal melting point ($T_m$) for the specific sequence at a defined ionic strength and pH. However, stringent conditions would encompass temperatures in the range of 1° C. to 20° C. lower than the $T_m$, depending on the desired degree of stringency as otherwise qualified herein. For DNA-DNA hybrids, the $T_m$ can be determined using the equation of Meinkoth and Wahl (1984) *Anal. Biochem.* 138:267-284: $T_m$=81.5° C.+16.6 (log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

The ability to detect sequences with varying degrees of homology can be obtained by varying the stringency of the hybridization and/or washing conditions. To target sequences that are 100% identical (homologous probing), stringency conditions must be obtained that do not allow mismatching. By allowing mismatching of nucleotide residues to occur, sequences with a lower degree of similarity can be detected (heterologous probing). For every 1% of mismatching, the $T_m$ is reduced about 1° C.; therefore, hybridization and/or wash conditions can be manipulated to allow hybridization of sequences of a target percentage identity. For example, if sequences with ≧90% sequence identity are preferred, the $T_m$ can be decreased by 10° C. Two nucleotide sequences could be substantially identical, but fail to hybridize to each other under stringent conditions, if the polypeptides they encode are substantially identical. This situation could arise, for example, if the maximum codon degeneracy of the genetic code is used to create a copy of a nucleic acid.

Exemplary low stringency conditions include hybridization with a buffer solution of 30-35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers can comprise about 0.1% to about 1% SDS. Duration of hybridization is generally less than about 24 hours, and is usually about 4 to about 12 hours. An extensive guide to the hybridization of nucleic acids is found in Tijssen (1993) *Laboratory Techniques in Biochemistry and Molecular Biology—Hybridization with Nucleic Acid Probes,* Part I, Chapter 2 (Elsevier, N.Y.); and Ausubel et al., eds. (1995) Current Protocols in Molecular Biology, Chapter 2 (Greene Publishing and Wiley-Interscience, New York). See Sambrook et al. (1989) *Molecular Cloning: A Laboratory Manual* (2d ed.; Cold Spring Harbor Laboratory Press, Plainview, N.Y.), the entire contents of which are incorporated herein by reference for these teachings.

In a PCR approach, oligonucleotide primers can be designed for use in PCR reactions to amplify corresponding DNA sequences from cDNA or genomic DNA extracted from any organism of interest. PCR primers can be preferably at least about 10 nucleotides in length, or at least about 20 nucleotides in length. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York), the entire contents of which are incorporated herein by reference for these teachings. Known methods of PCR include, but are not limited to, methods using paired primers, nested primers, single specific primers, degenerate primers, gene-specific primers, vector-specific primers, partially-mismatched primers, and the like.

Assays

Diagnostic assays to detect expression of the peptides, polypeptides and/or nucleic acid molecules of this invention, as well as, their disclosed activity in a sample are disclosed. An exemplary method for detecting the presence or absence of a nucleic acid or protein of this invention in a sample comprises obtaining a sample from a food/dairy/feed product, starter culture (mother, seed, bulk/set, concentrated, dried, lyophilized, frozen), cultured food/dairy/feed product, dietary supplement, bioprocessing fermentate, a subject (e.g., a subject that has ingested a probiotic material), etc., and contacting the sample with a compound or an agent that interacts with or combines with the peptides, polypeptides or nucleic acids of this invention in a detectable manner (e.g., an mRNA or genomic DNA comprising the disclosed nucleic acid or fragment thereof) such that the presence of the peptide or nucleic acid is detected in the sample. Results obtained with a sample from the food, supplement, culture, product, or subject can be compared to results obtained with a sample from a control culture, product, or subject and a qualitative and/or quantitative determination of the presence of a polypeptide or nucleic acid of this invention in the sample can be made.

One agent for detecting the mRNA and/or genomic DNA comprising a disclosed nucleotide sequence of this invention is a labeled nucleic acid probe capable of hybridizing to the nucleotide sequence present in the mRNA and/or genomic DNA. The nucleic acid probe can be, for example, a disclosed nucleic acid molecule, such as the nucleic acid of odd numbered SEQ ID NOS:1-164, or a fragment thereof, such as a nucleic acid molecule of at least 15, 30, 50, 100, 250, or 500 nucleotides in length and sufficient to specifically hybridize under stringent conditions to the mRNA or genomic DNA comprising the disclosed nucleic acid sequence. Other suitable probes for use in the diagnostic assays of the invention are described herein.

One agent for detecting a protein of this invention is an antibody or ligand that specifically binds a peptide or protein of this invention. In some embodiments, the antibody or ligand can comprise a detectable label. Antibodies of this invention can be polyclonal, or monoclonal. An intact antibody, or a fragment thereof (e.g., Fab or F(abN)$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody, by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

An isolated peptide, polypeptide or protein of the present invention can be used as an antigen or immunogen to generate antibodies that specifically bind two-component regulatory proteins or proteins under the control of two-component sensing and regulatory molecules or generate antibodies that stimulate production of antibodies in vivo. The full-length polypeptide of the invention can be used as an immunogen or, alternatively, antigenic peptide fragments. The antigenic peptide can comprise at least 8, 10, 15, 20, or 30 or more amino acid residues of the amino acid sequence shown in even numbered SEQ ID NOS:1-164 and encompasses an epitope of a two-component regulatory protein or a protein under the control of two-component sensing and regulatory molecules such that an antibody raised against the peptide forms a specific immune complex with the protein or fragment thereof. An epitope encompassed by the antigenic peptide can comprise are regions of a protein that are located on the surface of the protein, e.g., a hydrophilic region.

The term "sample" is intended to include tissues, cells, and biological fluids present in or isolated from a subject, as well as cells from starter cultures or food products carrying such cultures, or derived from the use of such cultures. That is, the detection method of the invention can be used to detect mRNA, protein, or genomic DNA comprising a nucleic acid molecule or amino acid sequence of this invention in a sample both in vitro and in vivo. In vitro techniques for detection of mRNA comprising a disclosed sequence include, but are not limited to, Northern hybridizations and in situ hybridizations. In vitro techniques for detection of a protein comprising a disclosed polypeptide include, but are not limited to, enzyme linked immunosorbent assays (ELISAs), Western blots, immunoprecipitations, and immunofluorescence. In vitro techniques for detection of genomic DNA comprising the disclosed nucleotide sequences include, but are not limited to, Southern hybridizations. Furthermore, in vivo techniques for detection of a protein of this invention include introducing into a subject a labeled antibody or ligand that specifically binds the protein. For example, the antibody or ligand can be labeled with a radioactive marker whose presence and location in a subject can be detected by standard imaging techniques.

In one embodiment, the sample of this invention comprises protein molecules from a subject that has consumed a probiotic material. Alternatively, the sample can contain mRNA or genomic DNA from a starter culture.

The invention also encompasses kits for detecting the presence of the nucleic acids or proteins of this invention in a sample. Such kits can be used to determine if a microbe producing a specific polypeptide of the invention is present in a food product or starter culture, or in a subject that has consumed a probiotic material. For example, the kit can comprise a labeled compound or agent capable of detecting a disclosed polypeptide or mRNA in a sample and means for determining the amount of a the disclosed polypeptide in the sample (e.g., an antibody or ligand that specifically binds the disclosed polypeptide or nucleic acid probe that hybridizes with nucleic acid sequences encoding a disclosed polypeptide, e.g., odd numbered SEQ ID NOS:1-164). Kits can also include instructions detailing the use of such compounds.

For antibody-based kits, the kit can comprise, for example: (1) a first antibody (e.g., attached to a solid support) that binds to a disclosed polypeptide; and, optionally, (2) a second, different antibody that binds to the disclosed polypeptide or the first antibody and is conjugated to a detectable agent. For nucleic acid-based kits, the kit can comprise, for example: (1) a nucleic acid molecule, e.g., a detectably labeled oligonucleotide, that hybridizes to a disclosed nucleic acid sequence or (2) a pair of primers useful for amplifying a disclosed nucleic acid molecule.

The kit can also comprise, e.g., a buffering agent, a preservative, and/or a protein stabilizing agent. The kit can also comprise components necessary for detecting the detectable agent (e.g., an enzyme or a substrate). The kit can also contain a control sample or a series of control samples that can be assayed and compared to the test sample. Each component of the kit can be enclosed within an individual container, and all of the various containers can be within a single package along with instructions for use.

In one embodiment, the kit comprises multiple probes in an array format, such as those described, for example, in U.S. Pat. Nos. 5,412,087 and 5,545,531, and International Publication No. WO 95/00530, herein incorporated by reference in their entireties. Probes for use in the array can be synthesized either directly onto the surface of the array, as disclosed in International Publication No. WO 95/00530, or prior to immobilization onto the array surface (Gait, ed. (1984), *Oligonucleotide Synthesis a Practical Approach* IRL Press Oxford, England). The probes can be immobilized onto the surface using techniques well known to one of skill in the art, such as those described in U.S. Pat. No. 5,412,087. Probes can be a nucleic acid or amino acid sequence, preferably purified, or an antibody.

The arrays can be used to screen organisms, samples, or products for differences in their genomic, cDNA, polypeptide, or antibody content, including the presence or absence of specific sequences or proteins, as well as the concentration of those materials. Binding to a capture probe is detected, for example, by signal generated from a label attached to the nucleic acid molecule comprising the disclosed nucleic acid sequence, a polypeptide comprising the disclosed amino acid sequence, or an antibody. The method can include contacting the molecule comprising the disclosed nucleic acid, polypeptide, or antibody with a first array having a plurality of capture probes and a second array having a different plurality of capture probes. The results of each hybridization can be compared to analyze differences in expression between a first and second sample. The first plurality of capture probes can be from a control sample, e.g., a wild type lactic acid bacteria, or control subject, e.g., a food, dietary supplement, starter culture sample or a biological fluid. The second plurality of capture probes can be from an experimental sample, e.g., a mutant type lactic acid bacteria, or subject that has consumed a probiotic material, e.g., a starter culture sample, or a biological fluid.

These assays can be especially useful in microbial selection and quality control procedures where the detection of unwanted materials is essential. The detection of particular nucleotide sequences or polypeptides can also be useful in determining the genetic composition of food, fermentation products, or industrial microbes, or microbes present in the digestive system of animals or humans that have consumed probiotics.

The present invention further provides a nucleic acid array or chip, i.e., a multitude of nucleic acids (e.g., DNA) as molecular probes precisely organized or arrayed on a solid support, which allow for the sequencing of genes, the study of mutations contained therein and/or the analysis of the expression of genes, as such arrays and chips are currently of interest given their very small size and their high capacity in terms of number of analyses.

For an analysis, the carrier, such as in a DNA array/chip, is coated with DNA probes (e.g., oligonucleotides) that are arranged at a predetermined location or position on the carrier. A sample containing a target nucleic acid and/or fragments thereof to be analyzed, for example DNA or RNA or cDNA, that has been labeled beforehand, is contacted with the DNA array/chip leading to the formation, through hybridization, of a duplex. After a washing step, analysis of the surface of the chip allows any hybridizations to be located by means of the signals emitted by the labeled target. A hybridization fingerprint results, which, by computer processing, allows retrieval of information such as the expression of genes, the presence of specific fragments in the sample, the determination of sequences and/or the identification of mutations.

In one embodiment of this invention, hybridization between target nucleic acids and nucleic acids of the invention, used in the form of probes and deposited or synthesized in situ on a DNA chip/array, can be determined by means of fluorescence, radioactivity, electronic detection or the like, as are well known in the art.

In another embodiment, the nucleotide sequences of the invention can be used in the form of a DNA array/chip to carry out analyses of the expression of *Lactobacillus acidophilus* genes. This analysis is based on DNA array/chips on which probes, chosen for their specificity to characterize a given gene or nucleotide sequence, are present. The target sequences to be analyzed are labeled before being hybridized onto the chip. After washing, the labeled complexes are detected and quantified. Comparative analyses of the signal intensities obtained with respect to the same probe for different samples and/or for different probes with the same sample, allows, for example, for differential transcription of RNA derived from the sample.

In yet another embodiment, arrays/chips containing nucleotide sequences of the invention can comprise nucleotide sequences specific for other microorganisms, which allows for serial testing and rapid identification of the presence of a microorganism in a sample.

In a further embodiment, the principle of the DNA array/chip can also be used to produce protein arrays/chips on which the support has been coated with a polypeptide and/or an antibody of this invention, or arrays thereof, in place of the nucleic acid. These protein arrays/chips make it possible, for example, to analyze the biomolecular interactions induced by the affinity capture of targets onto a support coated, e.g., with proteins, by surface plasma resonance (SPR). The polypeptides or antibodies of this invention, capable of specifically binding antibodies or polypeptides derived from the sample to be analyzed, can be used in protein arrays/chips for the detection and/or identification of proteins and/or peptides in a sample.

Thus, the present invention provides a microarray or microchip comprising various nucleic acids of this invention in any combination, including repeats, as well as a microarray comprising various polypeptides of this invention in any combination, including repeats. Also provided is a microarray comprising one or more antibodies that specifically react with various polypeptides of this invention, in any combination, including repeats.

Antisense Nucleotide Sequences

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire sequence, or to only a portion thereof, e.g., all or part of the protein coding region (or open reading frame). An antisense nucleic acid molecule can be antisense to a noncoding region of the coding strand of a nucleotide sequence of the invention. The noncoding regions are the 5' and 3' sequences that flank the coding region and are not translated into amino acids. Antisense nucleotide sequences are useful in disrupting the expression of the target gene. Antisense constructs having 70%, 80%, or 85% sequence identity to the corresponding sequence can be used.

Given the coding-strand sequence encoding a protein disclosed herein (e.g., odd numbered SEQ ID NOS:1-164), antisense nucleic acids of the invention can be designed according to the rules of Watson and Crick base pairing. The antisense nucleic acid molecule can be complementary to the entire coding region of the mRNA, but can also be an oligonucleotide that is antisense to only a portion of the coding or noncoding region of the mRNA. An antisense oligonucleotide can be, for example, about 5, 10, 15, 20, 25, 30, 35, 40, 45, or 50 nucleotides in length, or it can be 100, 200 nucleotides, or greater in length, including any value in between those listed herein. An antisense nucleic acid of the invention can be constructed using chemical synthesis and enzymatic ligation procedures known in the art.

An antisense nucleic acid molecule of the invention can be an α-anomeric nucleic acid molecule (Gaultier et al. (1987) *Nucleic Acids Res.* 15:6625-6641). The antisense nucleic acid molecule can also comprise a 2'-O-methylribonucleotide (Inoue et al. (1987) *Nucleic Acids Res.* 15:6131-6148) or a chimeric RNA-DNA analogue (Inoue et al. (1987) *FEBS Lett.* 215:327-330). The invention also encompasses ribozymes, which are catalytic RNA molecules with ribonuclease activity that are capable of cleaving a single-stranded nucleic acid, such as an mRNA, to which they have a complementary region. The invention also encompasses nucleic acid molecules that form triple helical structures. See generally Helene (1991) *Anticancer Drug Des.* 6(6):569; Helene (1992) *Ann. N.Y Acad. Sci.* 660:27; and Maher (1992) *Bioassays* 14(12):807, the entire contents of each of which are incorporated herein by reference for these teachings.

In some embodiments, the nucleic acid molecules of the invention can be modified at the base moiety, sugar moiety, or phosphate backbone to improve, e.g., the stability, hybridization, or solubility of the molecule. As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described, for example, in Hyrup et al. (1996) supra; Perry-O'Keefe et al. (1996) *Proc. Natl. Acad. Sci. USA* 93:14670, the entire contents of each of which are incorporated herein by reference for these teachings.

In another embodiment, PNAs of a sequence can be modified, e.g., to enhance stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996) supra; Finn et al. (1996) *Nucleic Acids Res.* 24(17):3357-3363; Mag et al. (1989) *Nucleic Acids Res.* 17:5973; and Peterson et al. (1975) *Bioorganic Med. Chem. Lett.* 5:1119, the entire contents of each of which are incorporated herein by reference for these teachings.

Fusion Proteins

The invention also includes chimeric or fusion proteins. A "chimeric protein" or "fusion protein" of this invention comprises a peptide or polypeptide as described herein operably linked (e.g., in frame) to a heterologous peptide or polypeptide. "Heterologous" in reference to a sequence is a sequence that originates from a foreign species, or, if from the same species, is substantially modified from its native form in composition and/or genomic locus by deliberate human intervention. For example, a promoter operably linked to a heterologous polypeptide is from a species different from the species from which the polynucleotide was derived, or, if from the same/analogous species, one or both are substantially from their original genomic locus, or the promoter is not the native promoter for the operably linked polynucleotide. A "heterologous peptide or polypeptide" refers to a peptide or polypeptide having an amino acid sequence corresponding to a protein that is not substantially identical to the amino acid sequence or protein of this invention, and which is derived from the same or a different organism. Within a fusion protein of this invention, the two-component regulatory peptide or polypeptide or the protein under the control of two-component sensing and regulatory molecules can comprise all or a portion of a polypeptide of the invention, preferably including at least one biologically active portion of the polypeptide. Within the fusion protein, the term "linked" is intended to indicate that the two-component regulatory peptide or polypeptide or the protein under the control of two-component sensing and regulatory molecules and the heterologous peptide or polypeptide are fused or joined or connected in-frame to each other. The heterologous peptide or polypeptide can be fused to the N-terminus and/or C-terminus of a peptide or polypeptide of this invention.

Expression of the linked coding sequences (e.g., a nucleotide sequence encoding the peptide or polypeptide of the invention linked in frame with a nucleotide sequence encoding the heterologous peptide or polypeptide) in some embodiments results in production of the fusion protein. The heterologous sequence can be a polypeptide that potentiates or increases production of the fusion protein in a cell. The portion of the fusion protein encoded by the heterologous sequence, i.e., the heterologous polypeptide, can be a protein fragment or peptide, an entire functional moiety, or an entire protein sequence. The heterologous peptide or polypeptide can be designed to be used in purifying the fusion protein, either with antibodies or with affinity purification specific for the heterologous polypeptide. Likewise, physical properties of the heterologous polypeptide can be exploited to allow selective purification of the fusion protein.

Particular heterologous polypeptides of interest include superoxide dismutase (SOD), maltose-binding protein (MBP), glutathione-S-transferase (GST), an N-terminal histidine (His) tag, GST, immunoglobulin, and the like. This list is not intended to be limiting, as any heterologous polypeptide (e.g., a protein that potentiates production of the two-component regulatory protein as a fusion protein can be used in the compositions and methods of the invention. In one embodiment, the fusion protein is a GST-two-component regulatory fusion protein in which the two-component regulatory sequences are fused to the C-terminus of the GST sequences. In another embodiment, the fusion protein is a two-component regulatory-immunoglobulin fusion protein in which all or part of a two-component regulatory protein is fused to sequences derived from a member of the immunoglobulin protein family.

The immunoglobulin fusion proteins of the invention can be used as immunogens to produce antibodies in a subject to purify ligands, and in screening assays to identify molecules that inhibit the interaction of a protein of the invention with a ligand.

One of skill in the art will recognize that the particular heterologous polypeptide is chosen with the purification scheme in mind. For example, His tags, GST, and maltose-binding protein represent heterologous polypeptides that have readily available affinity columns to which they can be bound and eluted. Thus, where the heterologous polypeptide is an N-terminal His tag such as hexahistidine (His$_6$ tag), the two-component regulatory fusion protein can be purified using a matrix comprising a metal-chelating resin, for example, nickel nitrilotriacetic acid (Ni—NTA), nickel iminodiacetic acid (Ni—IDA), and cobalt-containing resin (Co-resin). See, for example, Steinert et al. (1997) *QIAGEN News* 4:11-15, herein incorporated by reference in its entirety for these teachings. Where the heterologous polypeptide is GST, the fusion protein can be purified using a matrix comprising glutathione-agarose beads (Sigma or Pharmacia Biotech); where the heterologous polypeptide is a maltose-binding protein (MBP), the fusion protein can be purified using a matrix comprising an agarose resin derivatized with amylose.

Preferably, a chimeric or fusion protein of the invention is produced by standard recombinant DNA techniques. For example, nucleic acid fragments coding for the different polypeptide sequences can be ligated together in-frame, or the fusion nucleic acid can be synthesized, such as with automated DNA synthesizers. Alternatively, PCR amplification of gene fragments can be carried out using anchor primers that give rise to complementary overhangs between two consecutive nucleic fragments, which can subsequently be annealed and re-amplified to generate a chimeric nucleic acid sequence (see, e.g., Ausubel et al., eds. (1995) *Current Protocols in Molecular Biology* (Greene Publishing and Wiley-Interscience, New York). Moreover, the sequences of the invention can be cloned into a commercially available expression vector such that it is linked in-frame to an existing fusion moiety. Thus, the present invention also provides a vector comprising a nucleic acid encoding a fusion protein of this invention.

A fusion protein expression vector is typically designed for ease of removing the heterologous polypeptide to allow the two-component regulatory protein or the protein under the control of two-component sensing and regulatory molecules to retain the native biological activity associated with it. Methods for cleavage of fusion proteins are known in the art. See, for example, Ausubel et al., eds. (1998) *Current Protocols in Molecular Biology* (John Wiley & Sons, Inc.). Chemical cleavage of the fusion protein can be accomplished with reagents such as cyanogen bromide, 2-(2-nitrophenylsulphenyl)-3-methyl-3'-bromoindolenine, hydroxylamine, or low pH. Chemical cleavage is often accomplished under denaturing conditions to cleave otherwise insoluble fusion proteins.

Where separation of the polypeptide from the heterologous polypeptide is desired and a cleavage site at the junction between these fused polypeptides is not naturally occurring, the fusion construct can be designed to contain a specific protease cleavage site to facilitate enzymatic cleavage and removal of the heterologous polypeptide. In this manner, a linker sequence comprising a coding sequence for a peptide that has a cleavage site specific for an enzyme of interest can be fused in-frame between the coding sequence for the heterologous polypeptide (for example, MBP, GST, SOD, or an N-terminal His tag) and the coding sequence for the two-component regulatory polypeptide. Suitable enzymes having specificity for cleavage sites include, but are not limited to, factor Xa, thrombin, enterokinase, remin, collagenase, and tobacco etch virus (TEV) protease. Cleavage sites for these enzymes are well known in the art. Thus, for example, where factor Xa is to be used to cleave the heterologous polypeptide from the two-component regulatory polypeptide, the fusion construct can be designed to comprise a linker sequence encoding a factor Xa-sensitive cleavage site, for example, the sequence IEGR (see, for example, Nagai and Thøgersen (1984) *Nature* 309:810-812, Nagai and Thøgersen (1987) *Meth. Enzymol.* 153:461-481, and Pryor and Leiting (1997) *Protein Expr. Purif.* 10(3):309-319, herein incorporated by reference). Where thrombin is to be used to cleave the heterologous polypeptide from the two-component regulatory polypeptide, the fusion construct can be designed to comprise a linker sequence encoding a thrombin-sensitive cleavage site, for example the sequence LVPRGS or VIAGR (see, for example, Pryor and Leiting (1997) *Protein Expr. Purif.* 10(3): 309-319, and Hong et al. (1997) *Chin. Med. Sci. J.* 12(3):143-147, respectively, herein incorporated by reference). Cleavage sites for TEV protease are known in the art. See, for example, the cleavage sites described in U.S. Pat. No. 5,532,142, herein incorporated by reference in its entirety. See also the discussion in Ausubel et al., eds. (1998) *Current Protocols in Molecular Biology* (John Wiley & Sons, Inc.), Chapter 16.

Antibodies

An isolated polypeptide of the present invention can be used as an immunogen to generate antibodies that specifically bind to the sequence of the invention or stimulate production of antibodies in vivo. A full-length polypeptide of the invention can be used as an immunogen or, alternatively, antigenic peptide fragments of the polypeptides described herein can be used. The antigenic peptide of the polypeptide comprises at least 8, preferably 10, 15, 20, or 30 amino acid residues of the amino acid sequence shown in even SEQ ID NOS:2-164 and encompasses an epitope of a protein of the invention such that an antibody raised against the peptide forms a specific immune complex with the related protein. Specific epitopes encompassed by the antigenic peptide are regions of can be located on the surface of the protein, e.g., hydrophilic regions.

Recombinant Expression Vectors and Cells

The nucleic acid molecules of the present invention can be included in vectors, which can be expression vectors. "Vector" refers to a nucleic acid molecule capable of transporting another nucleic acid to which it has been linked. Expression vectors include one or more regulatory sequences and direct the expression of nucleic acids to which they are operably linked. By "operably linked" is intended that the nucleotide sequence of interest is linked to the regulatory sequence(s) such that expression of the nucleotide sequence is allowed (e.g., in an in vitro transcription/translation system or in a cell when the vector is introduced into the cell). The term "regulatory sequence" is intended to include controllable transcriptional promoters, operators, enhancers, transcriptional terminators, and other expression control elements such as translational control sequences (e.g., Shine-Dalgarno consensus sequence, initiation and termination codons). These regulatory sequences will differ, for example, depending on the cell being used.

The vectors can be autonomously replicated in a cell (episomal vectors), or can be integrated into the genome of a cell, and replicated along with the host genome (non-episomal mammalian vectors). Integrating vectors can contain at least one sequence homologous to the bacterial chromosome that allows for recombination to occur between homologous DNA in the vector and the bacterial chromosome. Integrating vectors can also comprise bacteriophage or transposon sequences. Episomal vectors, or plasmids are circular double-stranded DNA loops into which additional DNA segments can be ligated. Plasmids capable of stable maintenance in a cell are generally the preferred form of expression vectors when using recombinant DNA techniques.

The expression constructs or vectors encompassed in the present invention comprise a nucleic acid construct of the invention in a form suitable for expression of the nucleic acid in a cell. Expression in prokaryotic cells is encompassed in the present invention. It will be appreciated by those skilled in the art that the design of the expression vector can depend on such factors as the choice of the cell to be transformed, the level of expression of protein desired, etc. The expression vectors of the invention can be introduced into cells to thereby produce proteins or peptides, including fusion proteins or peptides, encoded by nucleic acids as described herein (e.g., two-component regulatory proteins, mutant forms of two-component regulatory proteins, fusion proteins, etc.).

Regulatory sequences include those that direct constitutive expression of a nucleotide sequence as well as those that direct inducible expression of the nucleotide sequence only under certain conditions. A bacterial promoter is any DNA sequence capable of binding bacterial RNA polymerase and initiating the downstream (3') transcription of a coding sequence into mRNA. A promoter can have a transcription initiation region, which is usually placed proximal to the 5' end of the coding sequence. This transcription initiation region typically includes an RNA polymerase binding site and a transcription initiation site. A bacterial promoter can also have a second domain called an operator, which can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence.

An example of a gene activator protein is the catabolite activator protein (CAP), which helps initiate transcription of the lac operon in *Escherichia coli* (Raibaud et al. (1984) *Annu. Rev. Genet.* 18:173). Regulated expression can therefore be either positive or negative, thereby either enhancing or reducing transcription. Other examples of positive and negative regulatory elements are well known in the art. Various promoters that can be included in the protein expression system include, but are not limited to, a T7/LacO hybrid promoter, a trp promoter, a T7 promoter, a lac promoter, and a bacteriophage lambda promoter. Any suitable promoter can be used to carry out the present invention, including the native promoter or a heterologous promoter. Heterologous promoters can be constitutively active or inducible. A non-limiting example of a heterologous promoter is given in U.S. Pat. No. 6,242,194 to Kullen and Klaenhammer.

Sequences encoding metabolic pathway enzymes provide particularly useful promoter sequences. Examples include promoter sequences derived from sugar metabolizing enzymes, such as galactose, lactose (lac) (Chang et al. (1987) *Nature* 198:1056), and maltose. Additional examples include promoter sequences derived from biosynthetic enzymes such as tryptophan (trp) (Goeddel et al. (1980) *Nucleic Acids Res.* 8:4057; Yelverton et al. (1981) *Nucleic Acids Res.* 9:731; U.S. Pat. No. 4,738,921; EPO Publication Nos. 36,776 and 121, 775). The beta-lactamase (bla) promoter system (Weissmann, (1981) "The Cloning of Interferon and Other Mistakes," in Interferon 3 (ed. I. Gresser); bacteriophage lambda PL (Shimatake et al. (1981) *Nature* 292:128); the arabinose-inducible araB promoter (U.S. Pat. No. 5,028,530); and T5 (U.S. Pat. No. 4,689,406) promoter systems also provide useful promoter sequences. See also Balbas (2001) *Mol. Biotech.* 19:251-267, where *E. coli* expression systems are discussed.

In addition, synthetic promoters that do not occur in nature also function as bacterial promoters. For example, transcription activation sequences of one bacterial or bacteriophage promoter can be joined with the operon sequences of another bacterial or bacteriophage promoter, creating a synthetic hybrid promoter (U.S. Pat. No. 4,551,433). For example, the tac (Amann et al. (1983) *Gene* 25:167; de Boer et al. (1983) *Proc. Natl. Acad. Sci.* 80:21) and trc (Brosius et al. (1985) *J. Biol. Chem.* 260:3539-3541) promoters are hybrid trp-lac promoters comprised of both trp promoter and lac operon sequences that are regulated by the lac repressor. The tac promoter has the additional feature of being an inducible regulatory sequence. Thus, for example, expression of a coding sequence operably linked to the tac promoter can be induced in a cell culture by adding isopropyl-1-thio-β-D-galactoside (IPTG). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al. (1986) *J. Mol. Biol.* 189:113; Tabor et al. (1985) *Proc. Natl. Acad. Sci.* 82:1074). In addition, a hybrid promoter can also be comprised of a bacteriophage promoter and an *E. coli* operator region (EPO Publication No. 267, 851).

The vector can additionally contain a nucleotide sequence encoding the repressor (or inducer) for that promoter. For example, an inducible vector of the present invention can regulate transcription from the Lac operator (LacO) by expressing the nucleotide sequence encoding the LacI repressor protein. Other examples include the use of the lexA gene to regulate expression of pRecA, and the use of trpO to regulate ptrp. Alleles of such genes that increase the extent of repression (e.g., lacIq) or that modify the manner of induction (e.g., lambda CI857, rendering lambda pL thermo-inducible, or lambda CI+, rendering lambda pL chemo-inducible) can be employed.

In addition to a functioning promoter sequence, an efficient ribosome-binding site is also useful for the expression of the fusion construct. In prokaryotes, the ribosome binding site is called the Shine-Dalgarno (SD) sequence and includes an initiation codon (ATG) and a sequence 3-9 nucleotides in length located 3-11 nucleotides upstream of the initiation codon (Shine et al. (1975) *Nature* 254:34). The SD sequence is thought to promote binding of mRNA to the ribosome by the pairing of bases between the SD sequence and the 3' end of bacterial 16S rRNA (Steitz et al. (1979) "Genetic Signals and Nucleotide Sequences in Messenger RNA," in *Biological Regulation and Development: Gene Expression* (ed. R. F. Goldberger, Plenum Press, NY).

Two-component regulatory proteins and proteins under the control of two-component sensing and regulatory molecules can also be secreted from the cell by creating chimeric DNA molecules that encode a protein comprising a signal peptide sequence fragment that provides for secretion of the two-component regulatory polypeptides in bacteria (U.S. Pat. No. 4,336,336). The signal sequence fragment typically encodes a signal peptide comprised of hydrophobic amino acids that direct the secretion of the protein from the cell. The protein is either secreted into the growth medium (Gram-positive bacteria) or into the periplasmic space, located between the inner and outer membrane of the cell (Gram-negative bacteria). Preferably there are processing sites, which can be cleaved either in vivo or in vitro, encoded between the signal peptide fragment and the protein of the invention.

DNA encoding suitable signal sequences can be derived from genes for secreted bacterial proteins, such as the *E. coli* outer membrane protein gene (ompA) (Masui et al. (1983) FEBS Lett. 151(1): 159-164; Ghrayeb et al. (1984) *EMBO J.* 3:2437-2442) and the *E. coli* alkaline phosphatase signal sequence (phoA) (Oka et al. (1985) *Proc. Natl. Acad. Sci.* 82:7212). Other prokaryotic signals include, for example, the signal sequence from penicillinase, Ipp, or heat stable enterotoxin II leaders.

Typically, transcription termination sequences recognized by bacteria are regulatory regions located 3' to the translation stop codon and thus, together with the promoter, flank the coding sequence. These sequences direct the transcription of an mRNA that can be translated into the polypeptide encoded by the DNA. Transcription termination sequences frequently include DNA sequences (of about 50 nucleotides) that are capable of forming stem loop structures that aid in terminating transcription. Examples include transcription termination sequences derived from genes with strong promoters, such as the trp gene in *E. coli* as well as other biosynthetic genes.

Bacteria such as *Lactobacillus acidophilus* generally utilize the translation start codon ATG, which specifies the amino acid methionine (which is modified to N-formylmethionine in prokaryotic organisms). Bacteria also recognize alternative translation start codons, such as the codons GTG and TTG, which code for valine and leucine, respectively. However, when these alternative translation start codons are used as the initiation codon, these codons direct the incorporation of methionine rather than of the amino acid that they normally encode. *Lactobacillus acidophilus* NCFM recognizes these alternative translation start sites and incorporates methionine as the first amino acid.

The expression vectors will have a plurality of restriction sites for insertion of the sequence of the invention so that it is under transcriptional regulation of the regulatory regions. Selectable marker genes that ensure maintenance of the vector in the cell can also be included in the expression vector. Preferred selectable markers include those which confer resistance to drugs such as ampicillin, chloramphenicol, erythromycin, kanamycin (neomycin), and tetracycline (Davies et al. (1978) *Annu. Rev. Microbiol.* 32:469). Selectable markers can also allow a cell to grow on minimal medium, or in the presence of toxic metabolite and can include biosynthetic genes, such as those in the histidine, tryptophan, and leucine biosynthetic pathways.

The regulatory regions can be native (homologous), or can be foreign (heterologous) to the cell and/or the nucleotide sequence of the invention. The regulatory regions can also be natural or synthetic. Where the region is "foreign" or "heterologous" to the cell, it is intended that the region is not found in the native cell into which the region is introduced. Where the region is "foreign" or "heterologous" to the sequence of the invention, it is intended that the region is not the native or naturally occurring region for the operably linked two-component regulatory nucleotide sequence of the invention. For example, the region can be derived from phage. While the sequences could be expressed using heterologous regulatory regions, native regions can be used. Such constructs would be expected in some cases to alter expression levels of two-component regulatory proteins in the cell. Thus, the phenotype of the cell could be altered.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction, annealing, resubstitutions, e.g., transitions and transversions, can be involved.

The invention further provides a vector comprising a nucleic acid molecule of the invention cloned into the vector in an antisense orientation. That is, the nucleic acid molecule is operably linked to a regulatory sequence in a manner that allows for expression (by transcription of the DNA molecule) of an RNA molecule that is antisense to two-component regulatory mRNA. Regulatory sequences operably linked to a nucleic acid cloned in the antisense orientation can be chosen to direct the continuous or inducible expression of the antisense RNA molecule. The antisense expression vector can be in the form of a recombinant plasmid or phagemid in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics*, Vol. 1(1).

Alternatively, some of the above-described components can be put together in transformation vectors. Transformation vectors are typically comprised of a selectable marker that is either maintained in a replicon or developed into an integrating vector, as described above.

Microbial or Bacterial Cells

The production of bacteria containing heterologous genes, the preparation of starter cultures of such bacteria, and methods of fermenting substrates, particularly food substrates such as milk, can be carried out in accordance with known techniques, including but not limited to those described in Mäyräi-Mäkinen and Bigret (1993) *Lactic Acid Bacteria.* Salminen and vonWright eds. Marcel Dekker, Inc. New York. 65-96; Sandine (1996) *Dairy Starter Cultures* Cogan and Accolas eds. VCH Publishers, New York. 191-206; Gilliland (1985) *Bacterial Starter Cultures for Food.* CRC Press, Boca Raton, Fla.

By "fermenting" is intended the energy-yielding, metabolic breakdown of organic compounds by microorganisms that generally proceeds under anaerobic conditions and with the evolution of gas.

Nucleic acid molecules of the invention can be introduced into cells by methods known in the art. By "introducing" is intended introduction into prokaryotic cells via conventional transformation or transfection techniques, or by phage-mediated infection. As used herein, the terms "transformation," "transduction," "conjugation," and "protoplast fusion" are intended to refer to a variety of art-recognized techniques for introducing foreign nucleic acid (e.g., DNA) into a cell, including calcium phosphate or calcium chloride co-precipitation, DEAE-dextran-mediated transfection, lipofection, or electroporation. Suitable methods for transforming or transfecting cells can be found in Sambrook et al. (1989) *Molecular Cloning: A Laboratory Manual* (2d ed., Cold Spring Harbor Laboratory Press, Plainview, N.Y.) and other laboratory manuals.

Bacterial cells used to express the sequences of the invention are cultured in suitable media, as described generally in Sambrook et al. (1989) *Molecular Cloning, A Laboratory Manual* (2d ed., Cold Spring Harbor Laboratory Press, Plainview, N.Y.).

Two-Component Regulatory Response System Proteins and Related Domains

Bacteria respond to their environment through the interation of two regulatory proteins in a two-component transduction system. One protein, generally located in the cytoplasmic membrane, is a sensor that monitors the environment, while the other is a response regulator that mediates an adaptive response, often through effecting a change in the expression of one or more genes. Two-component regulatory system proteins from different bacterial species share considerable amino acid sequence homology. The sensor protein, a histidine kinase, has an N-terminal domain (input domain) (PFAM Accession No. PF00512) that detects stimuli either directly, or though interaction with a receptor. This domain is a dimerization and phosphoacceptor domain. The cytoplasmic region (transmitter domain) of the sensor protein is highly conserved, and comprises two independently folding domains: the phosphotransfer domain and the ATP-binding kinase domain (PFAM Accession No. PF02518). The N-terminal domain may be linked through the phosphotransfer domain to the kinase domain by a HAMP domain (PFAM Accession PF00672). The phosphotransfer domain has a histidine residue in a region called the H box, that is involved in protein autophosphorylation and phosphatase activity. The catalytic (ATP-binding) domain contains regions of amino acid similarity, including the N, G1, F, and G2 boxes, which have been classically defined in alignments of the histidine kinase superfamily. The G1 and G2 boxes are glycine-rich sequences that resemble the nucleotide-binding motifs of other proteins, and the F box is named by a conserved phenylalanine residue. Histidine kinases fall into three subfamilies, with proteins containing the transmitter domain preceded by an amino-terminal input domain, as described above, in the classical protein subfamily. More complex histidine kinases possess a receiver domain that follows the transmitter domain. This receiver domain is similar to those from response regulators and is linked to an Hpt module (Histidine containing PhosphoTransfer). The phosphotransfer domain is remote from the kinase domain and separate from the sensor domain. These proteins are members of the unorthodox protein subfamily. The third subfamily, the hybrid proteins, are similar to the unorthodox proteins, but the Hpt module is not linked to the receiver.

Histidine kinases may also act as phosphoprotein phosphatases, increasing the dephosphorylation of their cognate response regulators in an ATP-dependent fashion. These phosphorylation/dephosphorylation reactions allow precise control over the amount of the phosphorylated form of the response regulator in the cell.

Assays to measure histidine kinase activity are well known in the art (see, for example, Stewart et al. (1998) *Biochemistry* 37:12269-12279; Levit et al. (1999) *Biochemistry.* 38:6651-6658). Methods for identifying active variants of histidine kinase proteins are well known in the art (see, for example, Tawa and Stewart (1994) *J. Bacteriol.* 176:4210-4218; Hirschman et al. (2001) *Biochemistry.* 40:13876-13887; Marina et al. (2001) *J. Biol. Chem.* 276:41182-41190). Methods to identify essential amino acids in the HAMP domain are well known in the art (see, for example, Appleman and Stewart (2003) J. Bacteriol. 185:89-97).

The response regulator generally has two domains, a conserved amino-terminal region termed the receiver domain (PFAM Accession No. PF00072), and a C-terminal output domain (or effector domain) (PFAM Accession No. PF00486), which is typically a transcriptional regulator (Pao and Saier (1995) *J. Mol. Evol.* 40:136-154). The receiver domain contains three conserved aspartyl and one conserved lysine residue that characterize the response regulator family. The conserved residues fold together to form the active site, where an aspartate residue accepts the phosphoryl group from the transmitter histidine residue, or alternatively, from a variety of small molecules (not ATP). The phosphorylation state of the receiver domain affects the activity of the output domain to elicit a response.

The transcriptional regulatory protein, C terminal domain is almost always found associated with the response regulator receiver domain. It may play a role in DNA binding (Martinez-Hackert and Stock (1997) *Structure* January 5:109-124). Most output domains have a helix-turn-helix DNA-binding motif. Assays to measure activity of two-component regulatory systems are well known in the art (see, for example, Lee et al. (2004) *Infect. Immun.* 72:3968-3973; Walker and Miller (2004) *J. Bacteriol.* 186:4056-4066; Saini et al. (2004) *Microbiology.* 150:865-875; Abo-Amer et al. (2004) *J. Bacteriol.* 186:1879-1889). Methods to identify variants that retain activity are well known in the art (see, for example, Baruah et al. (2004) *J. Bacteriol.* 186:1694-1704; Wang et al. (2001) *J. Bacteriol.* 183:2795-2802; Piazza et al. (1999) *J. Bacteriol.* 181:4540-4548).

Proteins of the present invention having a response regulator receiver domain and/or a transcriptional regulatory protein, C terminal domain include those set forth in SEQ ID NOS:2, 12, 22, 26 and 28. Proteins with a histidine kinase A (phosphoacceptor) N-terminal domain of the present invention include those set forth in SEQ ID NOS:4, 14, 20, 24, 30 and 36. Proteins with a histidine kinase-, DNA gyrase B-, and HSP90-like ATPase domain of the present invention include those set forth in SEQ ID NOS:4, 14, 20, 24, 30, 34, and 36. Proteins with a HAMP domain of the present invention include those set forth in SEQ ID NOS:4, 14 and 24. Additional proteins with a response regulator domain of PFAM 00072 include SEQ ID NO:32.

The GGDEF domain (PFAM Accession No. PF00990) is found linked to a wide range of non-homologous domains in a variety of bacteria. It has been shown to be homologous to the adenyl cyclase catalytic domain (Pei and Grishin (2001) *Proteins* 42:210-216) and has diguanylate cyclase activity (Paul et al. (2004) *Genes Dev.* 18:715-727; Galperin et al. (2001) *FEMS Microbiol. Lett.* 203:11-21). This observation correlates with the functional information available on two GGDEF-containing proteins, namely diguanylate cyclase and phosphodiesterase A of *Acetobacter xylinum,* both of which regulate the turnover of cyclic diguanosine monophosphate. Assays to measure diguanylate cyclase activity are well known in the art (see, for example, Paul et al. (2004) *Genes Dev.* 18:715-727). Proteins with a GGDEF domain of the present invention include those set forth in SEQ ID NO:16.

The EAL domain (PFAM Accession No. PF00563) is found in diverse bacterial signaling proteins. It is called EAL for its conserved residues. The EAL domain is a good candidate for a diguanylate phosphodiesterase function (Galperin et al. (2001) *FEMS Microbiol. Lett.* 203:11-21). The domain contains many conserved acidic residues that could participate in metal binding and might form the phosphodiesterase active site. It often but not always occurs along with PAS and DUF9 domains that are also found in many signaling proteins. Assays to measure phosphodiesterase activity are well known in the art (see, for example, Ausmees et al. (2001) *FEMS Microbiol. Lett.* 204:163-167). Proteins with a EAL domain of the present invention include those set forth in SEQ ID NO:18.

Many bacterial transcription regulatory proteins bind DNA via a helix-turn-helix (HTH) motif. These proteins are very diverse, but for convenience may be grouped into subfamilies on the basis of sequence similarity (Dehoux and Cossart (1995) *Mol. Microbiol.* 15:591). The deoR family (PFAM Accession No. PF00455) groups together a range of proteins, including lacR, deor, fucR and gutR. Within this family, the HTH motif is situated towards the N-terminus (Mortensen et al. (1989) *EMBO J.* 8:325-331; Rosey and Stewart (1992) *J. Bacteriol.* 174:6159-6170; Lu and Lin (1989) *Nucleic Acids Res.* 17:4883-4884). One other such family, marR, groups together a range of proteins, including emrR, hpcR, hpR, marR, pecS, petP, papX, prsX, ywaE, yxaD and yybA. The Mar proteins are involved in the multiple antibiotic resistance, a non-specific resistance system. The expression of the mar operon is controlled by a repressor, MarR. A large number of compounds induce transcription of the mar operon. This is thought to be due to the compound binding to MarR, and the resulting complex stops MarR binding to the DNA. With the MarR repression lost, transcription of the operon proceeds (Sulavik et al. (1997) *J. Bacteriol.* 179:1857-1866). Assays to measure transcription factor activity are well known in the art (see, for example, Sulavik et al. (1997) *J. Bacteriol.* 179:1857-1866). Proteins with a bacterial regulatory protein, deoR domain of the present invention include those set forth in SEQ ID NO:40. Proteins in the marR family of the present invention include those set forth in SEQ ID NO:58.

Proteins Under the Control of Two-Component Regulatory System Proteins

The Patatin-like phospholipase family (PFAM Accession No. PF01734) consists of various patatin glycoproteins from the total soluble protein in potato tubers, with some members also found in vertebrates. Patatin is a storage protein but it also has the enzymatic activity of lipid acyl hydrolase, catalysing the cleavage of fatty acids from membrane lipids (Mignery et al. (1988) *Gene* 62:27-44). Proteins in the patatin-like phospholipase family of the present invention include those set forth in SEQ ID NO:44.

The band 7 protein (PFAM Accession No. PF01145) is an integral membrane protein which is thought to regulate cation conductance by interacting with other proteins of the junctional complex of the membrane skeleton. A variety of proteins belong to this family. These include the prohibiting, cytoplasmic anti-proliferative proteins and stomatin, an erythrocyte membrane protein. Bacterial HflC protein also belongs to this family. Structurally, these proteins consist of a short N-terminal domain which is followed by a transmembrane region and a variable size (from 170 to 350 residues) C-terminal domain. Proteins in the band 7 protein family of the present invention include those set forth in SEQ ID NO:50.

ABC transporters form a large family of proteins responsible for translocation of a variety of compounds across biological membranes. They are minimally composed of four domains, with two transmembrane domains (TMDs) (PFAM Accession PF00664) responsible for allocrite binding and transport and two nucleotide-binding domains (NBDs) (PFAM Accession PF00005) responsible for coupling the energy of ATP hydrolysis to conformational changes in the TMDs. Both NBDs are capable of ATP hydrolysis, and inhibition of hydrolysis at one NBD effectively abrogates hydrolysis at the other. The proteins belonging to this family also contain one or two copies of the 'A' consensus sequence (Walker et al. (1982) *EMBO J.* 1:945-951) or the 'P-loop' (Saraste et al. (1990) *Trends Biochem Sci.* 15:430-434). Methods for measuring ATP-binding and transport are well known in the art (see, for example, Hung et al. (1998) *Nature* 396:703-707; Higgins et al. (1990) *J. Bioenerg. Biomembr.* 22:571-592). ABC transporter proteins of the present invention include those set forth in SEQ ID NOS:60 and 82.

Characterized members of the Multi Antimicrobial Extrusion (MATE) family (PFAM Accession No. PF01554) function as drug/sodium antiporters. These proteins mediate resistance to a wide range of cationic dyes, fluroquinolones, aminoglycosides and other structurally diverse antibiotics and drugs. MATE proteins are found in bacteria, archaea and eukaryotes. These proteins are predicted to have 12-helical transmembrane regions, some of the animal proteins may have an additional C-terminal helix. Methods for measuring antibiotic and drug resistance are well known in the art (see, for example, Mitchell et al. (1998) *Antimicrob. Agents Chemother.* 42:475-477; Mitchell et al. (1999) *J. Biol. Chem.* 274:3541-3548). Multi Antimicrobial Extrusion (MATE) family proteins of the present invention include those set forth in SEQ ID NO:72.

Lantibiotic and non-lantibiotic bacteriocins are synthesized as precursor peptides containing N-terminal extensions (leader peptides), which are cleaved off during maturation. Most non-lantibiotics and also some lantibiotics have leader peptides of the so-called double-glycine type. These leader peptides share consensus sequences and also a common processing site with two conserved glycine residues in positions-1 and -2. The double-glycine-type leader peptides are unrelated to the N-terminal signal sequences, which direct proteins across the cytoplasmic membrane via the sec pathway. Various methods can be used to assay for bacteriocin activity including, for example, the experimental section herein, Ogunbanwo et al. (2003) *Afr. J. Biotechnology* 2: 219-227, Allison et al. (1994) *J. Bacteriol.* 176:2235-2241 and Van Loveren et al. (2000) *Caries Research* 34:481-485. Examples of amino acid sequences of the present invention that have double-glycine-type leader peptides include those set forth in SEQ ID NOS:74, 76, 84, 86, 90, 92, 96 and 114.

The processing sites of these peptides are different from typical signal peptidase cleavage sites, suggesting that a different processing enzyme is involved. Peptide bacteriocins are exported across the cytoplasmic membrane by a dedicated ATP-binding cassette (ABC) transporter. The ABC transporter is the maturation protease and its proteolytic domain resides in the N-terminal part of the protein (Havarstein et al. (1995) *Mol. Microbiol.* 16:229-240). This peptidase domain is found in a wide range of ABC transporters, however the presumed catalytic cysteine and histidine are not conserved in all members of this family.

Peptidases are grouped into clans and families. Clans are groups of families for which there is evidence of common ancestry. Families are grouped by their catalytic type, the first character representing the catalytic type: S, serine; T, threonine; C, cysteine; A, aspartic; M, metallo and U, unknown. A clan that contains families of more than one type is described as being of type P. The serine, threonine and cysteine peptidases utilise the catalytic part of an amino acid as a nucleophile and form an acyl intermediate—these peptidases can also readily act as transferases. In the case of aspartic and metallopeptidases, the nucleophile is an activated water molecule.

Cysteine peptidases have characteristic molecular topologies, which can be seen not only in their three-dimensional structures, but commonly also in the two-dimensional structures. The peptidase domain is responsible for peptide bond hydrolysis; in Merops this is termed the peptidase unit. These are peptidases in which the nucleophile is the sulphydryl group of a cysteine residue. Cysteine proteases are divided into clans (proteins which are evolutionary related), and further sub-divided into families, on the basis of the architecture of their catalytic dyad or triad (Barrett and Rawlings (2001) *Biol. Chem.* 382:727-733). The peptidase C39 family (clan CA) (PFAM Accession No. PF03412) is found in a wide range of ABC transporters, which are maturation proteases for peptide bacteriocins, the proteolytic domain residing in the N-terminal region of the protein (Rawlings and Barrett (1995) *Methods Enzymol.* 248:183-228). Assays for measuring peptidase activity are well known in the art (see, for example, (Havarstein et al. (1995) *Mol. Microbiol.* 16:229-240). Proteins of the present invention in the peptidase C39 family include those set forth in SEQ ID NO:82.

RelE and RelB form a toxin-antitoxin system. RelE represses translation, probably through binding ribosomes (Pedersen et al. (2002) *Mol Microbiol* 45:501-510 and Terry et al. (2001) *J. Bacteriol* 183:2700-2703). A polypeptide having a RelE and RelB domain is set forth in SEQ ID NO:52.

Viruses, parasites and bacteria are covered in protein and sugar molecules that help them gain entry into a host by counteracting the host's defences. One such molecule is the M protein produced by certain streptococcal bacteria. M proteins embody a motif that is now known to be shared by many Gram-positive bacterial surface proteins. The motif includes a conserved hexapeptide, which precedes a hydrophobic C-terminal membrane anchor, which itself precedes a cluster of basic residues. It has been proposed that this hexapeptide sequence is responsible for a post-translational modification necessary for the proper anchoring of the proteins which bear it, to the cell wall. A polypeptide having such a domain is found in SEQ ID NO:78.

The LytTr domain is found in a variety of bacterial transcriptional regulators. The domain binds to a specific DNA sequence pattern (see Nikolskya et al. (2002) *Nucleic Acid Research* 30:2453-459). The LytTr domain is a DNA-binding, potential winged helix-turn-helix domain (~100 residues) present in a variety of bacterial transcriptional regulators of the algR/agrA/lytR family. It is named after the lytr response regulators involved in the regulation of cell autolysis. The LytTr domain binds to a specific DNA sequence pattern in the upstream regions of target genes. The N-terminal of the protein contains a response regulator receiver domain. The consensus sequence for this domain is in PFAM04397. A polypeptide having this domain is set forth in SEQ ID NO:32.

Members of the CAAX amino terminal protease family are probably proteases. The family contains CAAX prenyl protease. The proteins contain a highly conserved Glu-Glu motif at the amino end of the alignment. The alignment also contains two histidine residues that may be involved in zinc binding. This family consists of various hypothetical protein sequences for which the function is unknown. One of the proteins is an abortive infection protein that confers resistance to the bacteriophage Phi 712. AbiG is an abortive infection (Abi) mechanism encoded by the conjugative plasmid pCI750 originally isolated from *Lactococcus lactis* subsp. *cremoris* UC653. The resistance mechanism acts at neither the phage adsorption or phage DNA restriction level. Also in this family is a series of bacteriocin-like peptides PlnP, PlnI, PlnT, PlnP and PlnU from *Lactobacillus plantarum* C11. *Lactobacillus plantarum* C11 secretes a small cationic peptide, plantaricin A, that serves as an induction signal for bacteriocin production as well as transcription of plnABCD. The plnABCD operon encodes the plantaricin A precursor (PlnA) itself and determinants (PlnBCD) for a signal transducing pathway. The consensus sequence for this domain is in PFAM12517. A polypeptide having this domain is set forth in SEQ ID NO:98 and 102.

Glycosyl hydrolases are key enzymes of carbohydrate metabolism. Family 31 comprises of enzymes that are, or similar to, alpha-galactosidases. O-Glycosyl hydrolases (EC 3.2.1.-) are a widespread group of enzymes that hydrolyse the glycosidic bond between two or more carbohydrates, or between a carbohydrate and a non-carbohydrate moiety. A classification system for glycosyl hydrolases, based on sequence similarity, has led to the definition of 85 different families. This classification is available on the CAZy (CArbohydrate-Active EnZymes) web site PUBMED: PUB00007032. Because the fold of proteins is better conserved than their sequences, some of the families can be grouped in 'clans'. Glycoside hydrolase family 31 comprises enzymes with several known activities; α-glucosidase (EC: 3.2.1.20), α-galactosidase (EC:3.2.1.22); glucoamylase (EC: 3.2.1.3), sucrase-isomaltase (EC:3.2.1.48) (EC:3.2.1.10); α-xylosidase (EC:3.2.1); α-glucan lyase (EC:4.2.2.13). Glycoside hydrolase family 31 groups a number of glycosyl hydrolases on the basis of sequence similarities PUBMED: 1747104, PUBMED:1761061, PUBMED:1743281 An aspartic acid has been implicated PUBMED:1856189 in the catalytic activity of sucrase, isomaltase, and lysosomal α-glucosidase. The consensus sequence for this domain is in PFAM01055. A polypeptide having this domain is set forth in SEQ ID NO:116.

The mur ligase family, glutamate ligase domain contains a number of related ligase enzymes which have EC numbers 6.3.2. This family includes: MurC, MurD, MurE, MurF, Mpl and FolC. MurC, MurD, Mure and MurF catalyse consecutive steps in the synthesis of peptidoglycan. Peptidoglycan consists of a sheet of two sugar derivatives, with one of these N-acetylmuramic acid attaching to a small pentapeptide. The pentapeptide is is made of L-alanine, D-glutamic acid, Meso-diaminopimelic acid and D-alanyl alanine. The peptide moiety is synthesised by successively adding these amino acids to UDP-N-acetylmuramic acid. MurC transfers the L-alanine, MurD transfers the D-glutamate, MurE transfers the diaminopimelic acid, and MurF transfers the D-alanyl alanine. This family also includes Folylpolyglutamate synthase that transfers glutamate to folylpolyglutamate. Proteins containing this domain include a number of related ligase enzymes that catalyse consecutive steps in the synthesis of peptidoglycan. Proteins also include folylpolyglutamate synthase that transfers glutamate to folylpolyglutamate and cyanophycin synthetase that catalyses the biosynthesis of the cyanobacterial reserve material multi-L-arginyl-poly-L-aspartate (cyanophycin). The C-terminal domain is almost always associated with the cytoplasmic peptidoglycan synthetases, N-terminal domain. The consensus sequence for this domain is in PFAM02875. A polypeptide having this domain is set forth in SEQ ID NO:118.

ATP-binding cassette (ABC) transporters are multidomain membrane proteins, responsible for the controlled efflux and influx of substances (allocrites) across cellular membranes. They are minimally composed of four domains, with two transmembrane domains (TMDs) responsible for allocrite binding and transport and two nucleotide-binding domains (NBDs) responsible for coupling the energy of ATP hydrolysis to conformational changes in the TMDs. Both NBDs are capable of ATP hydrolysis, and inhibition of hydrolysis at one NBD effectively abrogates hydrolysis at the other. Hydrolysis at the two NBDs may occur in an alternative fashion although they appear substantially functionally symmetrical in terms of their binding to diverse nucleotides. A number of bacterial transport systems have been found to contain integral membrane components that have similar sequences: these systems fit the characteristics of ATP-binding cassette transporters. The proteins form homo- or hetero-oligomeric channels, allowing ATP-mediated transport. Hydropathy analysis of the proteins has revealed the presence of 6 possible transmembrane regions. These proteins belong to family 2 of ABC transporters. The consensus sequence for this domain is in PFAM01061. A polypeptide having this domain is set forth in SEQ ID NO:120 and 122.

ATP-binding cassette (ABC) transporters are multidomain membrane proteins, responsible for the controlled efflux and influx of substances (allocrites) across cellular membranes. They are minimally composed of four domains, with two transmembrane domains (TMDs) responsible for allocrite binding and transport and two nucleotide-binding domains (NBDs) responsible for coupling the energy of ATP hydrolysis to conformational changes in the TMDs. Both NBDs are capable of ATP hydrolysis, and inhibition of hydrolysis at one NBD effectively abrogates hydrolysis at the other. Hydrolysis at the two NBDs may occur in an alternative fashion although they appear substantially functionally symmetrical in terms of their binding to diverse nucleotides. A variety of ATP-binding transport proteins have a six transmembrane helical region. They are all integral membrane proteins involved in a variety of transport systems. Members of this family include; the cystic fibrosis transmembrane conductance regulator (CFTR), bacterial leukotoxin secretion ATP-binding protein, multidrug resistance proteins, the yeast leptomycin B resistance protein, the mammalian sulphonylurea receptor and antigen peptide transporter 2. Many of these proteins have two such regions. The consensus sequence for this domain is in PFAM00664. A polypeptide having this domain is set forth in SEQ ID NO:120 and 122.

GTPase of unknown function family is a member of the G-protein superfamily clan. This clan includes the following Pfam members: NOG1; MMR_HSR1; IIGP; GTP_EFTU; GTP_CDC; Dynamin_N; DUF258; Arf; AIG1; Human HSR1, has been localized to the human MHC class I region and is highly homologous to a putative GTP-binding protein, MMR1 from mouse. These proteins represent a new subfamily of GTP-binding proteins that has both prokaryote and eukaryote members. The consensus sequence for this domain is in PFAM01926. A polypeptide having this domain is set forth in SEQ ID NO:154.

Proteins containing the ParB-like nuclease domain, appear to be related to the *Escherichia coli* plasmid protein ParB, which preferentially cleaves single-stranded DNA. ParB also nickssupercoiled plasmid DNA preferably at sites with potential single-stranded character, like AT-rich regions and sequences that can form cruciform structures. ParB also exhibits 5-3 exonuclease activity. The consensus sequence for this domain is in PFAM02195. A polypeptide having this domain is set forth in SEQ ID NO:158 and 162.

The CobQ/CobB/MinD/ParA nucleotide binding domain family consists of various cobyrinic acid a,c-diamide synthases. These include CbiA and CbiP from *S. typhimurium* (Pollich et al. (1995) J. Bacteriol 177:1487-4487, and CobQ from R. capsulatus (Roth et al. (1993) *J Bacteriol* 175:3303-3316. These amidases catalyse amidations to various side chains of hydrogenobyrinic acid or cobyrinic acid a,c-diamide in the biosynthesis of cobalamin (vitamin B12) from uroporphyrinogen III. Vitamin B12 is an important cofactor and an essential nutrient for many plants and animals and is primarily produced by bacteria (Pollich et al. (1995) *J. Bacteriol* 177:1487-4487). The family also contains dethiobiotin synthetases as well as the plasmid partitioning proteins of the MinD/ParA family (Raux et al. (1998) *Biochem J* 335:159-166). This entry consists of various cobyrinic acid a,c-diamide synthases. These include CbiA and CbiP from *Salmonella typhimurium,* and CobQ from *Rhodobacter capsulatus.* These amidases catalyse amidations to various side chains of hydrogenobyrinic acid or cobyrinic acid a,c-diamide in the biosynthesis of cobalamin (vitamin B 12) from uroporphyrinogen III. Vitamin B12 is an important cofactor and an essential nutrient for many plants and animals and is primarily produced by bacteria. The consensus sequence for this domain is in PFAM01656. A polypeptide having this domain is set forth in SEQ ID NO:160.

Glucose inhibited division protein is a family of bacterial Glucose inhibited division proteins these are probably involved in the regulation of cell division. This family is a member of the Methyltransferase superfamily clan. This clan includes the following Pfam members: CheR; CMAS; Cons_hypoth95; DNA_methylase; DOT1; Eco57I; Fibrillarin; FtsJ; GidB; MethyltransfD12; Methyltransf_10; Methyltransf_2; Methyltransf_3; Methyltransf_4; Methyltransf_5; Methyltransf_8; Methyltransf_9; Met_10; Mg-por_mtran_C; MT-A70; MTS; N6_Mtase; N6_N4_Mtase; NNMT_PNMT_TEMT; NodS; Nol1_Nop2_Fmu; PARP_regulatory; PCMT; PrmA; RrnaAD; rRNA_methylase; Spermine_synth; TehB; TPMT; TRM; tRNA_U5-meth_tr; Ubie_methyltran; UPF0020. GidB (glucose-inhibited division protein B) appears to be present and in a single copy in all complete eubacterial genomes so far. Its mode of action is unknown, but a methytransferase fold is reported from the crystal structure. It may be a family of bacterial glucose inhibited division proteins that are involved in the regulation of cell division. A polypeptide having this domain is set forth in SEQ ID NO:164.

Methods of Use

Many two-component response systems are known in bacteria, including, but not limited to, the Arc two-component signal transduction system of *E. coli,* which regulates numerous operons in response to respiratory growth conditions (see, for example, Kwon et al. (2000) *J. Bacteriol.* 182:2960-2966); PhoQ/PhoP, which responds to changes in environmental levels of $Mg^{2+}$ (see, for example, Marina et al. (2001) *J. Biol. Chem.* 276:41182-41190; PmrAB, which modulates resistance to cationic antimicrobial peptides (see, for example, Moskowitz et al. (2004) *J. Bact.* 186:575-579); EnvZ/OmpR, which respond to changes in osmotic conditions (see, for example, Cai and Inouye (2002) *J. Biol. Chem.* 277:24155-24161); NarX/NarL, which respond to nitrite levels (see, for example, Stewart (1994) *Antonie Van Leeuwenhoek* 66:37-45); PhoR/PhoB, which responds to low phosphate concentrations in the environment and periplasmic space (see, for example, Pragai et al. (2004) *J. Bacteriol.* 186:1182-1190); covRS, which regulates expression of fructosyltransferase (see, for example, Lee et al. (2004) *Infect Immun.* 72:3968-3973); and RegB/RegA, which is a highly conserved redox-responding global two-component regulatory system from *Rhodobacter capsulatus* and *Rhodobacter sphaeroides* (see, for example, Elsen et al. (2004) *Microbiol. Mol. Biol. Rev.* 68:263-279).

The two-component regulatory system proteins of the present are useful in regulating the response of an organism to various environmental conditions. Methods are provided wherein properties of microbes used in fermentation are modified to provide bacterial strains able to survive stressful conditions, such as acid or alkaline stress, osmotic or oxidative stress, starvation, or in the presence of other microorganisms (see, for example, Wick and Egli (2004) *Adv. Biochem. Eng. Biotechnol.* 89:1-45). This ability to survive stressful environmental conditions will increase the utility of these microorganisms in fermenting various foods, as well as allowing them to provide longer-lasting probiotic activity after ingestion. One way this may occur is by enhancing the ability of an organism to survive passage through the gastrointestinal tract. In general the methods comprise overexpressing one or more proteins controlled by two-component sensing and regulatory systems. In one embodiment, the protein is a bacteriocin. By "overexpressing" is meant that the protein of interest is produced in an increased amount in the modified bacterium compared to its production in a wild-type bacterium.

The proteins and nucleic acid sequences encoding them may increase the ability of a microorganism to survive in the presence of an antimicrobial (see, for example, Moskowitz et al. (2004) *J. Bact.* 186:575-579). They may also enable an microorganism to form a biofilm (see, for example, Danhorn et al. (2004) *J. Bacteriol.* 186:4492-4501).

The proteins and nucleic acid sequences encoding them may enable an organism to respond to an environmental stimuli, including, but not limited to, turgor pressure, a chemical stimulus, heavy-metal cations, oxygen, iron, an antimicrobial, and glucose.

TABLE 1

Two-Component Sensing and Regulatory Proteins of the Present Invention

| ORF# | SEQ ID NO: | GENE | FUNCTION |
|---|---|---|---|
| 78 | 1, 2 | VicR response regulator | DNA binding/transcription regulation |
| 79 | 3, 4 | VicK histidine kinase | Two-component sensing/signal transduction/ATP binding |
| 248 | 5, 6 | Two-component response regulator | DNA binding/transcription regulation |
| 602 | 7, 8 | Histidine kinase | Two-component sensing/signal transduction/ATP binding |
| 603 | 9, 10 | Response regulator | DNA binding/transcription regulation |
| 746 | 11, 12 | Response regulator | DNA binding/transcription regulation |
| 747 | 13, 14 | Histidine kinase | Two-component sensing/signal transduction/ATP binding |
| 1413 | 15, 16 | Sensory transduction system regulatory components (Histidine kinase?) | Two-component sensing/signal transduction/ATP binding |
| 1414 | 17, 18 | Response regulator | DNA binding/transcription regulation |
| 1430 | 19, 20 | Histidine kinase | Two-component sensing/signal transduction/ATP binding |
| 1431 | 21, 22 | Response regulator | DNA binding/transcription regulation |
| 1524 | 23, 24 | LisK histidine kinase | Two-component sensing/signal transduction/ATP binding |
| 1525 | 25, 26 | LisR response regulator | DNA binding/transcription regulation |
| 1659 | 27, 28 | Response regulator | DNA binding/transcription regulation |
| 1660 | 29, 30 | Sensory protein kinase | Two-component sensing/signal transduction/ATP binding |
| 1798 | 31, 32 | Response regulator | DNA binding/transcription regulation |
| 1799 | 33, 34 | Sensory histidine kinase | Two-component sensing/signal transduction/ATP binding |
| 1819 | 35, 36 | Sensory histidine kinase | Two-component sensing/signal transduction/ATP binding |

TABLE 1-continued

Two-Component Sensing and Regulatory Proteins of the Present Invention

| ORF# | SEQ ID NO: | GENE | FUNCTION |
|---|---|---|---|
| 1820 | 37, 38 | Response regulator | DNA binding/transcription regulation |
| 599 | 39, 40 | Transcriptional regulator DeoR | Transcription regulation |
| 600 | 41, 42 | Phosphoketolase | |
| 601 | 43, 44 | Patatin-like phospholipase/protease | Nutrient reservoir activity |
| 604 | 45, 46 | PlnI | Bacteriocin immunity |
| 1563 | 47, 48 | Flavodoxin | |
| 1564 | 49, 50 | Membrane protein | Cation conductance regulation |
| 1565 | 51, 52 | DNA-damage-inducible protein J | |
| 1566 | 53, 54 | Helveticin | Antimicrobial |
| 595 | 55, 56 | Hydrolase | |
| 596 | 57, 58 | MarR transcriptional regulator | Transcription regulation |
| 597 | 59, 60 | Multidrug resistance ABC transporter | ATP binding/transport |
| 598 | 61, 62 | Immunity protein | Antimicrobial immunity |
| 1567 | 63, 64 | Aminopeptidase | |
| 1568 | 65, 66 | Surface protein | |
| 1569 | 67, 68 | Transposase | |
| 1570 | 69, 70 | Transposase | |
| 1571 | 71, 72 | MatE membrane protein | Antiporter/multidrug transport |
| 1791 | 73, 74 | Bacteriocin | Antimicrobial |
| 1792 | 75, 76 | Bacteriocin | Antimicrobial |
| 1793 | 77, 78 | Hypothetical protein | |
| 1794 | 79, 80 | ORF2, gassericin accessory protein | |
| 1796 | 81, 82 | PlnG | Peptidase/ATP binding/transport |
| 1797 | 83, 84 | Acidocin J1132 two-component bacteriocin | Antimicrobial |
| 1800 | 85, 86 | Bacteriocin | Antimicrobial |
| 1801 | 87, 88 | Unknown protein | |
| 1802 | 89, 90 | Bacteriocin | Antimicrobial |
| 1803 | 91, 92 | Bacteriocin | Antimicrobial |
| 1804 | 93, 94 | Hypothetical protein | |
| 1805 | 95, 96 | Bacteriocin | Antimicrobial |
| 1808 | 97, 98 | Immunity protein | Antimicrobial immunity |
| 1809 | 99, 100 | Hypothetical protein | |
| 1810 | 101, 102 | Immunity protein | Antimicrobial immunity |
| 1811 | 103, 104 | Hypothetical protein | |
| 1812 | 105, 106 | Alpha-glucosidase II | |
| 1813 | 107, 108 | Hypothetical protein | |
| 1814 | 109, 110 | Unknown protein | |
| 1815 | 111, 112 | Hypothetical protein | |
| 1816 | 113, 114 | Bacteriocin | Antimicrobial |
| 1817 | 115, 116 | Aspartate racemase | |
| 1818 | 117, 118 | UDP-N-acetylmuramyl TP synthase | |
| 1821 | 119, 120 | Transporter | |
| 1822 | 121, 122 | Transporter | |
| 80 | 123, 124 | YycH protein | |
| 81 | 125, 126 | YycI protein | |
| 82 | 127, 128 | Hypothetical protein | |
| 83 | 129, 130 | HtrA serine protease | |
| 1421 | 131, 132 | Oxidoreductase | |
| 1422 | 133, 134 | Pyrazinamidase/nicotinamidase | |
| 1423 | 135, 136 | Unknown protein | |
| 1424 | 137, 138 | Amino acid permease | |
| 1425 | 139, 140 | Hypothetical protein | |
| 1426 | 141, 142 | Unknown protein | |
| 1427 | 143, 144 | Oxidoreductase | |
| 1428 | 145, 146 | Hypothetical protein | |
| 1429 | 147, 148 | Transporter | |
| 1432 | 149, 150 | Hypothetical protein | |
| 1823 | 151, 152 | Uncharacterized membrane protein | |
| 1824 | 153, 154 | GTPase | |
| 1825 | 155, 156 | Unknown protein | |
| 1826 | 157, 158 | Predicted transcription regulator | |
| 1827 | 159, 160 | ParA ATPase | |
| 1828 | 161, 162 | Predicted transcription regulator | |
| 1829 | 163, 164 | Predicted S-adenosylmethionine transferase | |

The following examples are offered by way of illustration and not by way of limitation.

EXPERIMENTAL

EXAMPLE 1

The *Lactobacillus acidophlius* NCFM Genome

The complete genome of *Lactobacillus acidophilus* NCFM consists of 1,993,570 nucleotides with an average GC content of 34.71%. In silico analyses revealed the presence of 1864 open reading frames (ORFs) resulting in a coding percentage of 87.9%. One or more protein families (PFam) were attributed to 75% of these ORFs and 89% showed similarities to at least one COG (cluster of orthologous groups of proteins). As a result of the manual annotation curation, only 11.7% of the ORFs remained unknown and 15.8% showed similarities to unclassified genes of other organisms. Of the predicted ORFs, 72.5% were assigned to a defined fuinction. Sequences from the genome of *Lactobacillus acidophilus* NCFM have been described in U.S. Provisional Patent Application No. 60/465,621 filed on Apr. 23, 2003, U.S. Provisional Patent Application No. 60/480,764 filed on Jun. 23, 2003, U.S. Provisional Patent Application No. 60/546,745 filed on Feb. 23, 2004, U.S. Provisional Patent Application No. 60/551,121 filed on Mar. 8, 2004, U.S. Provisional Patent Application No. 60/551,161 filed on Mar. 8, 2004 and U.S. Provisional Patent Application No. 60/662,712 filed on Oct. 27, 2004, and U.S. patent application Ser. No. 10/831,070 filed on Apr. 23,2004, U.S. patent application Ser. No. 10/873,467 filed on Jun. 22, 2004, U.S. patent application Ser. No. 11/074,176 filed on Mar. 7, 2005 and U.S. patent application Ser. No. 11/074,226 filed on Mar. 7, 2005, the disclosures of which are incorporated herein by reference in their entireties.

The Origin of Replication was predicted by GC-skew analysis and the ORF orientation shift. Directly adjacent to this locus, a gene showing significant similarities to dnaA was identified. Further analyses revealed the presence of a highly conserved gene arrangement (rnpA, ORF La1978; rpmh, ORF La1979; dnaA, ORF La1; dnaN, ORF La2; recF, ORF La4; and gyrB, ORF La5) which can be found in a wide range of other prokaryotes, including *Bacillus subtilis, Escherichia coli,* and *Synechococcus* (Liu and Tsinoremas (1996) *Gene* 172:105-109, Ogasawara et al. (1985) *EMBO J.* 4:3345-3350). In order to initiate the chromosome replication, DnaA requires the presence of several DnaA-boxes (Fujikawa et al. (2003) *Nucleic Acids Res.* 31:2077-2086). Seven DnaA-boxes with a length of 8 nucleotides were determined directly upstream of dnaA, whereas only one was identified downstream of dnaA. Accordingly, this region was designated oriC and most likely represents the DNA replication initiation locus. Subsequently, the genome sequence was rotated and starts 30 nucleotides upstream of dnaA. The Terminus of DNA replication was identified similarly by GC-skew and ORF orientation shift analysis. The exact position could not be determined, since no replication terminator protein could be identified (Griffiths et al. (1998) *J. Bacteriol.* 180:3360-3367). However, a chromosome segregation helicase (ORF La1077) and DnaD (ORF La1161) were identified at the proposed Terminus locus. In addition, a genome region of ~300 kilobase pairs with the predicted Terminus in its center showed a significantly lower average GC content. This lower GC content could aid in the separation of the chromosomal strands. The Origin and the Terminus of DNA replication are placed fairly symmetrical in the genome.

Sixty-one tRNAs were identified within the genome. Only 8 tRNAs were located on the lagging strand, mostly clustered around an rRNA locus. tRNAs for all 21 amino acids were found with redundant tRNAs for all amino acids except cysteine and tryptophan. Ribosomal proteins were mainly assembled around one locus at 260 kilobase pairs. Four ribosomal RNA loci were identified throughout the genome. Three of them were clustered within the first 500 kilobase pairs and oriented in the same sense-direction, whereas the fourth rRNA locus, located at 1.6 megabases, is oriented in the opposite direction. Thus, all rRNA loci were in phase with the direction of DNA replication.

The COG database classifies paralogous proteins of at least three lineages into functionally related groups. Three major sections are currently described and a forth section includes proteins with poorly characterized functions. The graphical representation of the COG distribution shows that the majority of predicted proteins (64.4%) could be classified into the three functional classes and only 19% were assigned to the "poorly characterized" group. However, 6.6% of COGs could not be assigned into any classification, designated here as COG category 5. Of those, five genome regions stand out, due to their visual dominance (COG-I to COG-V). Functional annotation revealed that all of the genes present in these COG category 5 regions I to V were predicted to be involved in cell-adherence and initial host-cell recognition (i.e., ORF La1016-ORF La1020, ORF La1377, ORF La1392: mucus binding proteins; ORF La1606-ORF La1612: fibronectin binding proteins; and ORF La1633-ORF La1636: surface bound proteins). Further analyses of other organisms might lead to a separate COG group within the extracellular structures (functional category W) to reflect this set of proteins and their common function.

Analysis of the GC-content distribution showed localized peak deviations from the average GC content of the genome. Without exceptions, GC-content spikes were found to harbor the four rRNA loci (average GC content of 50.88%), whereas the two neighboring low GC-regions at 1.75 megabases (average GC content of 28.5%) revealed the presence of a large uncharacterized region unique to *Lactobacillus acidophilus* NCFM and an EPS cluster. The EPS cluster consisted of fourteen genes including the highly conserved proteins EpsA-EpsF (ORF La1732-ORF La1737), EpsJ (ORF La1725 and ORF La1726), and EpsI (ORF La1724) and five variable proteins (ORF La1727-ORF La1731) representing glycosyl transferases and polysaccharide polymerases. Together, this set shows high synteny to reported exopolysaccharide (EPS) clusters in streptococci (Stingele et al. (1996) *J. Bacteriol.* 178:1680-1690) and recently reported in *L. gasseri* and *L. johnsonii* (Pridmore et al. (2004) *Proc. Natl. Acad. Sci. U.S.A.* 101:2512-2517). Scanning electron microscopy of NCFM did not detect an external polysaccharide layer (Hood and Zottola (1987) *J. Food Sci.* 52:791), and it remains unclear whether the EPS cluster is functional or if any EPS produced is excreted rather than anchored. Three ORFs in the NCFM EPS cluster encode for two UDP-galactopyranose mutases and a membrane protein involved with the export of O-antigen and teichoic acid. Other teichoic acid associated ORFs include a tandem set of teichoic acid biosynthesis and transport proteins (ORF La524 and ORF La525), another predicted biosynthetic protein (ORF La519), two more polysaccharide transporters specific to O-antigen and teichoic acid (ORF La1614 and ORF La1917), along with a cell wall teichoic acid glycosylation protein (ORF La621). An exaggerated inflammatory response from intestinal epithelial cells to gram-negative bacteria can be tempered by teichoic acids from *lactobacilli* (Vidal et al. (2002) *Infect. Immun.* 70:2057-

2064) suggesting an intimate involvement of teichoic acids and the immune system. The uncharacterized low GC regions and the EPS cluster are centered on two divergently oriented transposases (ORF La1722, ORF La1721, and ORF La1720). The exceptionally low GC content and the presence of mobile elements could indicate the acquisition of this region via horizontal gene transfer.

The NCFM genomic DNA sequence was analyzed for repetitive DNA by a "repeat and match analysis." One intergenic region between ORF La1550 (DNA polymerase I, polA) and ORF La1551 (putative phosphoribosylamine-glycine ligase, purD) had features characteristic of a SPIDR (SPacers Interspersed Direct Repeats) locus. This region was approximately 2.4 kilobases long and contained 32 nearly perfect repeats of 29 base pairs separated by unique 32 base pair spacers. The SPIDR locus constitutes a novel family of repeat sequences that are present in *Bacteria* and *Archaea* but not in *Eukarya* (Jansen et al. (2002) *OMICS* 6:23-33). The repeat loci typically consist of repetitive stretches of nucleotides with a length of 25 to 37 base pairs alternated by nonrepetitive DNA spacers of approximately equal size as the repeats. To date, SPIDR loci have been identified in more than forty microorganisms (Jansen et al. (2002) *OMICS* 6:23-33), but from the lactic acid bacteria, have only been described from *Streptococcus* spp. Despite their discovery over 15 years ago in *E. coli* (Ishino et al. (1987) *J. Bacteriol.* 169:5429-5433), no physiological function has yet been elucidated.

EXAMPLE 2

Gapped BlastP Results for Amino Acid Sequences

A Gapped BlastP sequence alignment showed that SEQ ID NO:2 (238 amino acids) has about 83% identity from amino acids 1-237 with a protein from *Lactobacillus johnsonii* that is a two-component regulatory system response regulator (Accession No. NP_964081), about 83% identity from amino acids 1-237 with a protein from *Lactobacillus gasseri* that is a response regulator consisting of a CheY-like receiver domain and a winged-helix DNA-binding domain (ZP_00046798), about 71% identity from amino acids 1-237 with a protein from *Lactobacillus sakei* that is a putative response regulator (Accession No. AAD10263), about 72% identity from amino acids 3-237 with a protein from *Enterococcus faecalis* that is a DNA-binding response regulator VicR (Accession No. NP_814922), and about 72% identity from amino acids 3-237 with a protein from *Enterococcus faecalis* that is a response regulator VicR (Accession No. CAB64972).

A Gapped BlastP sequence alignment showed that SEQ ID NO:4 (618 amino acids) has about 67% identity from amino acids 7-618 with a protein from *Lactobacillus johnsonii* that is a two-component regulatory system histidine kinase (Accession No. NP_964082), about 66% identity from amino acids 7-618 with a protein from *Lactobicillus gasseri* that is a signal transduction histidine kinase (Accession No. ZP_00046799), about 54% identity from amino acids 2-618 with a protein from *Lactobacillus sakei* that is a putative histidine kinase (Accession No. AAD10264), about 52% identity from amino acids 4-617 with a protein from *Lactobacillus plantarum* that is a histidine kinase sensor protein (Accession No. NP_783897), and about 47% identity from amino acids 12-616 with a protein from *Enterococcus faecalis* that is a sensory box histidine kinase VicK (Accession No. NP_814923).

A Gapped BlastP sequence alignment showed that SEQ ID NO:6 (150 amino acids) has about 79% identity from amino acids 1-150 with a hypothetical protein LJ0247 from *Lactobacillus johnsonii* (Accession No. NP_964263), about 70% identity from amino acids 45-150 with a protein from *Lactobacillus gasseri* that is a response regulator of the LytR/AlgR family (Accession No. ZP_00046165), about 37% identity from amino acids 4-150 with a protein from *Streptococcus mutans* that is a putative transcriptional regulator (Accession No. NP_720879), about 40% identity from amino acids 18-150 with a protein from *Oenococcus oeni* that is a response regulator of the LytR/AlgR family (Accession No. ZP_00069670), and about 31% identity from amino acids 1-148 with a protein from *Leuconostoc mesenteroides* that is a response regulator of the LytR/AlgR family (Accession No. ZP_00063955).

A Gapped BlastP sequence alignment showed that SEQ ID NO:8 (426 amino acids) has about 32% identity from amino acids 20-425 with a protein from *Lactobacillus johnsonii* that is a lactacin F two-component system histidine kinase (Accession No. NP_964617), about 32% identity from amino acids 10-425 with a protein from *Lactobacillus salvarius* that is AbpK (Accession No. AAM61782), about 27% identity from amino acids 22-426 with a protein from *Lactobacillus johnsonii* that is a two-component system histidine kinase (Accession No. NP_964473), about 34% identity from amino acids 141-426 with a protein from *Carnobacterium piscicola* that is a putative histidine kinase PisK (Accession No. AAK69421), and about 31% identity from amino acids 132-426 with a protein from *Lactobacillus sakei* that is a histidine kinase homolog SapK (Accession No. CAA86944).

A Gapped BlastP sequence alignment showed that SEQ ID NO:10 (265 amino acids) has about 41% identity from amino acids 2-259 with a protein from *Lactobacillus salivarius* that is AbpR (Accession No. AAM61783), about 40% identity from amino acids 1-256 with a protein from *Lactobacillus johnsonii* that is a lactacin F two-component system response regulator (Accession No. NP_964619), about 32% identity from amino acids 3-242 with a protein from *Lactobacillus johnsonii* that is a two-component system response regulator (Accession No. NP_964474), about 29% identity from amino acids 1-250 with a protein from *Lactobacillus sakei* that is a sakacin A production response regulator SapR (Accession No. CAA86945), and about 29% identity from amino acids 1-246 with a protein from *Carnobacterium piscicola* that is a response regulator (Accession No. AAB81306).

A Gapped BlastP sequence alignment showed that SEQ ID NO:12 (240 amino acids) has about 73% identity from amino acids 3-239 with a protein from *Lactobacillus gasseri* that is a response regulator consisting of a CheY-like receiver domain and a winged-helix DNA-binding domain (Accession No. ZP_00046225), about 63% identity from amino acids 3-239 with a protein from *Lactobacillus sakei* that is a putative response regulator (Accession No. AAD10267), about 63% identity from amino acids 3-236 with a protein from *Enterococcus faecium* that is a response regulator consisting of a CheY-like receiver domain and a winged-helix DNA-binding domain (ZP_00036862), about 62% identity from amino acids 3-240 with a protein from *Lactobacillus plantarum* that is a response regulator (Accession No. NP_785945), and about 62% identity from amino acids 3-236 with a protein from *Enterococcus faecalis* that is a DNA-binding response regulator (Accession No. NP_814983).

A Gapped BlastP sequence alignment showed that SEQ ID NO:14 (483 amino acids) has about 61% identity form amino acids 1-482 with a protein from *Lactobacillus johnsonii* that is a two-component system histidine kinase (Accession No. NP_964774), about 61% identity from amino acids 8-482 with a protein from *Lactobacillus gasseri* that is a signal transduction histidine kinase (Accession No. ZP_00046226), about 45% identity from amino acids 1-475 with a protein from *Lactobacillus sakei* that is a putative histidine kinase (Accession No. AAD10268;), about 44% identity from amino acids 1-479 with a protein from *Lactobacillus plantarum* that is a histidine kinase sensor protein (Accession No. CAD64795), and about 41% homology from amino acids 1-474 with a protein from *Enterococcus faecalis* that is a sensor histidine kinase (Accession No. NP_814984).

A Gapped BlastP sequence alignment showed that SEQ ID NO:16 (367 amino acids) has about 27% identity from amino acids 10-363 with a protein from *Oenococcus oeni* that is a COG2199: FOG: GGDEF domain (Accession No. ZP_00069778), about 32% identity from amino acids 114-366 with a protein from *Listeria monocytogenes* that is similar to unknown proteins (hypothetical sensory transduction histidine kinase) (Accession No. NP_465435), about 30% identity from amino acids 114-366 with a protein from *Listeria innocua* that is a hypothetical sensory transduction histidine kinase (Accession No. NP_471359), about 38% identity from amino acids 200-366 with a protein from *Leuconostoc mesenteroides* that is a COG2199: FOG: GGDEF domain (Accession No. ZP_00062660), and about 33% identity with a protein from *Vibrio vulnificus* that is a GGDEF family protein (Accession No. NP_936516).

A Gapped BlastP sequence alignment showed that SEQ ID NO:18 (236 amino acids) has about 33% identity from amino acids 12-228 with a protein from *Leuconostoc mesenteroides* that is a COG2200: FOG: EAL domain (Accession No. ZP_00062661), about 33% identity from amino acids 12-223 with a protein from *Leuconostoc mesenteroides* that is a COG2200: FOG: EAL domain (Accession No. ZP_00062662), about 28% identity from amino acids 12-224 with a protein from *Lactococcus lactis* that is a hypothetical protein (Accession No. CAA04442), about 26% identity from amino acids 6-228 with a protein from *Listeria monocytogenes* that is 1 mo0111 (Accession No. NP_463644), and about 26% identity from amino acids 8-228 with a protein from *Listeria innocua* that is lin0158 (Accession No. NP_469503).

A Gapped BlastP sequence alignment showed that SEQ ID NO:20 (427 amino acids) has about 59% identity from amino acids 4-427 with a protein from *Lactobacillus gasseri* that is a signal transduction histidine kinase (Accession No. ZP_00046476), about 62% identity from amino acids 38-427 with a protein from *Lactobacillus johnsonii* that is a two-component system histidine kinase (Accession No. NP_965390), about 37% identity from amino acids 4-421 with an unknown protein from *Streptococcus algalactiae* (Accession No. NP_735834), about 37% identity from amino acids 4-421 with a protein from *Streptococcus algalactiae* that is sensor histidine kinase (Accession No. NP_688325), and about 37% identity from amino acids 4-423 with a protein from *Streptococcus mutans* that is a putative histidine kinase (Accession No. NP_721328).

A Gapped BlastP sequence alignment showed that SEQ ID NO:22 (221 amino acids) has about 77% identity from amino acids 1-220 with a protein from *Lactobacillus johnsonii* that is a two-component response regulator (Accession No. NP_965391), about 77% identity from amino acids 1-220 with proteins from *Lactobacillus gasseri* that are response regulators consisting of a CheY-like receiver domain and a winged-helix DNA-binding domain (Accession No. ZP_00046475), about 59% identity from amino acids 1-221 with a protein from *Streptococcus pyogenes* that is a putative two-component response regulator (Accession No. NP_269073), about 57% identity from amino acids 1-221 with an unknown protein from *Streptococcus agalactiae* (Accession No. NP_735835), and about 58% identity from amino acids 1-221 with a protein from *Streptococcus agalactiae* that is a DNA-binding response regulator (Accession No. NP_688326).

A Gapped BlastP sequence alignment showed that SEQ ID NO:24 (525 amino acids) has about 53% identity from amino acids 1-502 with a protein from *Lactobacillus johnsonii* that is a two-component system histidine kinase (Accession No. NP_965436), about 55% identity from amino acids 100-509 with a protein from *Lactobacillus gasseri* that is a signal transduction histidine kinase (Accession No. ZP_00047348), about 39% identity from amino acids 52-518 with a protein from *Lactobacillus plantarum* that is a histidine protein kinase sensor protein (Accession No. NP_785147), about 39% identity from amino acids 12-500 with a protein from *Enterococcus faecalis* that is a sensor histidine kinase (Accession No. NP_814784), and about 47% identity from amino acids 211-507 with a protein from *Leuconostoc mesenteroides* that is a signal transduction histidine kinase (Accession No. ZP_00063323).

A Gapped BlastP sequence alignment showed that SEQ ID NO:26 (238 amino acids) has about 74% identity from amino acids 1-237 with a protein from *Lactobacillus johnsonii* that is a two-component regulatory system response regulator (Accession No. NP_965437), about 61% identity from amino acids 1-237 with a protein from *Lactobacillus gasseri* that are response regulators consisting of a CheY-like receiver domain and a winged-helix DNA-binding domain (Accession No. ZP_00047347), about 63% identity from amino acids 1-231 with a protein from *Lactobacillus plantarum* that is a response regulator (Accession No. NP_785146), about 61% identity from amino acids 1-231 with a protein from *Enterococcus faecalis* that is a DNA-binding response regulator (Accession No.814783), and about 59% identity from amino acids 1-231 with a protein from *Listeria innocua* that is a two-component response regulator (Accession No. NP_470750).

A Gapped BlastP sequence alignment showed that SEQ ID NO:28 (247 amino acids) has about 73% identity from amino acids 21-247 with a protein from *Lactobacillus johnsonii* that is a two-component system response regulator (Accession No. NP_964988), about 48% identity from amino acids 21-241 with a protein from *Clostridium tetani* that is a transcriptional regulatory protein (Accession No. NP_781768), about 47% identity from amino acids 22-245 with a protein from *Lactobacillus plantarum* that is a response regulator (Accession No. NP_784099), about 48% identity from amino acids 21-247 with proteins from *Thermobacter tengcongensis* that are response regulators consisting of a CheY-like receiver domain and a HTH DNA-binding domain (Accession No. NP_622667), and about 46% identity from amino acids 21-241 with a protein from *Clostridium acetobutylicum* that is a response regulator (Accession No. NP_348326).

A Gapped BlastP sequence alignment showed that SEQ ID NO:30 (441 amino acids) has about 49% identity from amino acids 2-439 with a protein from *Lactobacillus johnsonii* that is a two-component system histidine kinase (Accession No. NP_964989), about 32% identity from amino acids 3-434 with a protein from *Lactococcus lactis* that is a sensor protein kinase (Accession No. NP_267160), about 32% identity from amino acids 2-434 with a protein from *Lactococcus lactis* that is a histidine kinase (Accession No. AAC45387), about 31% identity from amino acids 3-438 with a protein from *Oenococcus oeni* that is signal transduction histidine kinase (Accession No. ZP_00069020), and 36% identity from amino acids 79-437 with a protein from *Lactobacillus plantarum* that is a histidine protein kinase sensor protein (Accession No. NP_784098).

A Gapped BlastP sequence alignment showed that SEQ ID NO:32 (274 amino acids) has about 55% identity from amino acids 11-274 with a protein from *Lactobacillus johnsonii* that is a lactacin F two-component system response regulator (Accession No. NP_964619), about 38% identity from amino acids 9-268 with a protein from *Lactobacillus salvarius* that is AbpR (Accession No. AAM61783), about 32% identity from amino acids 9-262 with a protein from *Lactobacillus johnsonii* that is a two-component system response regulator (Accession No. NP_964474), about 47% identity from amino acids 140-274 with a protein from *Lactobacillus johnsonii* that is a lactacin F two-component system response regulator (Accession No. 964627), and 33% identity from amino acids 12-262 with a protein from *Lactobacillus sakei* that is a response regulator (Accession No. CAA86945).

A Gapped BlastP sequence alignment showed that SEQ ID NO:34 (440 amino acids) has about 39% identity from amino acids 2-435 with a protein from *Lactobacillus johnsonii* that is a lactacin F two-component system histidine kinase (Accession No. NP_964617), about 31% identity from amino acids 58-431 with a protein from *Lactobacillus salvarius* that is AbpK (Accession No. AAM61782), about 31% identity from amino acids 73-431 with a protein from *Lactobacillus johnsonii* that is a two-component histidine kinase (Accession No. NP_964473), about 24% identity from amino acids 59-418 with a protein from *Carnobacterium piscicola* that is a histidine protein kinase (Accession No. AAB81305), and about 25% identity from amino acids 59-412 with a protein from *Carnobacterium piscicola* that is a histidine kinase CbaK (Accession No. AAF18146).

A Gapped BlastP sequence alignment showed that SEQ ID NO:36 (381 amino acids) has about 63% identity from amino acids 1-381 with a protein from *Lactobacillus gasseri* that is a signal transduction histidine kinase (Accession No. ZP_00046636), about 63% identity from amino acids 1-381 with a protein from *Lactobacillus johnsonii* that is a two-component system histidine kinase (Accession No. NP_965691), about 52% identity from amino acids 4-375 with a protein from *Lactobacillus sakei* that is a putative histidine kinase (Accession No. AAD10266), about 53% identity from amino acids 6-375 with a protein from *Lactobacillus plantarum* that is a histidine kinase sensor protein (Accession No. NP_786468), and 52% identity from amino acids 2-379 with a protein from *Enterococcus faecium* that is a signal transduction histidine kinase (Accession No. ZP_00036366).

A Gapped BlastP sequence alignment showed that SEQ ID NO:38 (228 amino acids) has about 89% identity from amino acids 1-228 with proteins from *Lactobacillus gasseri* that are response regulators consisting of a CheY-like receiver domain and a winged-helix DNA-binding domain (Accession No. ZP_00046635), about 85% identity from amino acids 1-227 with a protein from *Lactobacillus sakei* that is a putative response regulator (Accession No. AAD10265), about 81% identity from amino acids 1-228 with a protein from *Lactobacillus plantarum* that is a response regulator (Accession No. NP_786469), about 80% identity from amino acids 2-227 with proteins from *Oenococcus onei* that are response regulators consisting of a CheY-like receiver domain and a winged-helix DNA-binding domain (Accession No. ZP_00069111), and about 80% identity from amino acids 1-228 with a protein from *Enterococcus faecalis* that is a DNA-binding response regulator (Accession No. NP_816885).

A Gapped BlastP sequence alignment showed that SEQ ID NO:40 (254 amino acids) has about 42% identity from amino acids 3-254 with a protein from *Lactobacillus johnsonii* that is a hypothetical protein LJ0802 (Accession No. NP_964657), about 42% identity from amino acids 3-254 with proteins from *Lactobacillus gasseri* that are transcriptional regulators of sugar metabolism (Accession No. ZP_00046400), about 30% identity from amino acids 1-239 with a protein from *Listeria monocytogenes* that is similar to a transcriptional regulator (DeoR) (Accession No. NP_465631), about 30% identity from amino acids 1-231 with a protein from *Oceanobacillus iheyensis* that is a transcriptional repressor of the phosphotransferase system (Accession No. NP_693730), and about 28% identity from amino acids 1-239 with a protein from *Listeria innocua* that is similar to a transcriptional regulator (DeoR family) (Accession No. NP_471545).

A Gapped BlastP sequence alignment showed that SEQ ID NO:42 (805 amino acids) has about 84% identity from amino acids 7-805 with a protein from *Lactobacillus johnsonii* that is a probable xylulose-5-phosphate/fructose-6-phosphste phosphoketolase (Accession No. NP_964658), about 65% identity from amino acids 7-805 with a protein from *Lactobacillus plantarum* that is a phosphoketolase (Accession No. NP_786060), about 65% identity from amino acids 7-805 with a protein from *Lactobacillus pentosus* that is similar to a phosphoketolase (Accession No. CAC84393), about 65% identity from amino acids 6-805 with a protein from *Oenococcus onei* that is a phosphoketolase (Accession No. ZP_00069369), and 65% identity from amino acids 7-805 with a protein from *Lactobacillus paraplantarum* that is a xylulose-5-phosphate phosphoketolase (Accession No. AAQ64626).

A Gapped BlastP sequence alignment showed that SEQ ID NO:44 (286 amino acids) has about 59% identity from amino acids 5-286 with a protein from *Lactobacillus johnsonii* that is a hypothetical protein LJ0785 (Accession No. NP_964640), about 59% identity from amino acids 5-286 with a protein from *Lactobacillus gasseri* that is a predicted esterase of the alpha-beta hydrolase superfamily (Accession No. ZP_00045972), about 41% identity from amino acids 5-284 with a protein from *Fusobacterium nucleatum* that is a serine protease (Accession No. ZP_00143830), about 41% identity from amino acids 5-284 with a protein from *Fusobacterium nucleatum* that is a Serine protease (Accession No. NP_603405), and 41% identity from amino acids 5-284 with a protein from *Streptococcus agalactiae* that is a protein of unknown function (Accession No. NP_689045).

A Gapped BlastP sequence alignment showed that SEQ ID NO:46 (402 amino acids) has about 35% identity from amino acids 74-387 with a protein from *Lactobacillus gasseri* that is a predicted metal-dependent membrane protease (Accession No. ZP_00046861), about 29% identity from amino acids 1-389 with a protein from *Lactobacillus johnsonii* that is a hypothetical protein LJ1642 (Accession No. NP_965449), about 26% identity from amino acids 113-392 with a protein from *Lactobacillus plantarum* that is a CAAX family membrane-bound protease (Accession No. NP_786255), about 27% identity from amino acids 90-383 with a hypothetical protein from *Lactobacillus gasseri* (Accession No. ZP_00047041), and 23% identity from amino acids 104-389 with a protein from *Lactobacillus johnsonii* that is hypothetical protein LJ0777 (Accession No. NP_964632).

A Gapped BlastP sequence alignment showed that SEQ ID NO:48 (224 amino acids) has about 31% identity from amino acids 64-222 with proteins from *Methanosarcina barkeri* that are flavodoxins (Accession No. ZP_00079137), about 27% identity from amino acids 37-224 with proteins from *Leuconostoc mesenteroides* that are flavodoxins (Accession No. ZP_00062708), about 29% identity from amino acids 64-222 with a protein from *Porphyromonas gingivalis* that is a putative flavodoxin (Accession No. NP_905330), about 29% identity from amino acids 63-224 with a protein from *Azobacter vinelandii* that is a flavodoxin (Accession No. ZP_00092501), and about 33% identity from amino acids 74-224 with a protein from *Methanosarcina barkeri* that is a flavodoxin (Accession No. ZP_00079128).

A Gapped BlastP sequence alignment showed that SEQ ID NO:50 (293 amino acids) has about 85% identity from amino acids 20-287 with a protein from *Lactobacillus johnsonii* that is a hypothetical protein LJ1250 (Accession No. NP_965105), about 83% identity from amino acids 22-291 with proteins from *Lactobacillus gasseri* that are membrane protease subunits, stomatin/prohibitin homologs (Accession No. ZP_00045910), about 60% identity from amino acids 22-286 with proteins from *Leuconostoc mesenteroides* that are membrane protease subunits, stomatin/prohibitin homologs (Accession No. ZP_00063597), about 57% identity from amino acids 22-289 with proteins from *Oenococcus oeni* that are membrane protease subunits, stomatin/prohibitin homologs (Accession No. ZP_00069250), and about 43% identity from amino acids 23-283 with an unknown protein from *Lactobacillus plantarum* (Accession No. NP_784144).

A Gapped BlastP sequence alignment showed that SEQ ID NO:52 (105 amino acids) has about 30% identity from amino acids 7-100 with a hypothetical protein from *Streptococcus pyogenes* (Accession No. NP_664197), about 30% identity from amino acids 7-100 with a hypothetical protein from *Streptococcus pyogenes* (Accession No. NP_606807), about 34% identity from amino acids 3-72 with a hypothetical protein from *Streptococcus pyogenes* (Accession No. NP_268822), about 40% identity from amino acids 8-60 with a protein from *Treponema denticola* that is a putative DNA-damage-inducible protein J (Accession No. NP_971120), and about 30% identity from amino acids 3-58 with a protein from *Desulfitobacterium hafniense* that is a DNA-damage-inducible protein J (Accession No. ZP_00099746).

A Gapped BlastP sequence alignment showed that SEQ ID NO:54 (325 amino acids) has about 42% identity from amino acids 1-323 with a hypothetical protein from *Lactobacillus gasseri* (Accession No. ZP_00047284), about 41% identity from amino acids 9-323 with a hypothetical protein LJ0696 from *Lactobacillus johnsonii* (Accession No. NP_964548), about 35% identity from amino acids 17-322 with a protein from *Lactobacillus helveticus* that is a helveticin (Accession No. AAA63274), about 24% identity from amino acids 116-258 with a protein from *Rattus norvgicus* that is similar to Gli3 protein (Accession No. XP_225411), and about 21% identity from amino acids 153-289 with a protein from *Saccharomyces cerevisiae* that is Tom1p (Accession No. NP_010745).

A Gapped BlastP sequence alignment showed that SEQ ID NO:56 (272 amino acids) has about 38% identity from amino acids 3-272 with proteins from *Lactobacillus gasseri* that are predicted hydrolases of the HAD superfamily (Accession No. ZP_00046918), about 36% identity from amino acids 7-270 with a protein from *Streptococcus mutans* that is a conserved hypothetical protein (Accession No. NP_721496), about 34% identity from amino acids 7-272 with a protein from *Streptococcus agalactiae* that is unknown (Accession No. NP_735618), about 33% identity from amino acids 7-272 with a protein from *Streptococcus agalactiae* that is a halo-acid dehalogenase-like family hydrolase (Accession No. AAM99986), and about 33% identity from amino acids 7-272 with a protein from *Listeria innocua* that is a conserved hypothetical protein lin0440 (Accession No. NP_469785).

A Gapped BlastP sequence alignment showed that SEQ ID NO:58 (146 amino acids) has about 35% identity from amino acids 26-145 with proteins from *Lactobacillus gasseri* that are transcriptional regulators (Accession No. ZP_00045996), about 35% identity from amino acids 28-142 with a protein from *Lactococcus lactis* that is a transcriptional regulator (Accession No. NP_267638), about 31% identity from amino acids 29-142 with a protein from *Clostridium acetobutylicum* that is a MarR/EmrR family transcriptional regulator (Accession No. NP_349100), about 34% identity from amino acids 14-104 with a protein from *Methanothermobacter thermautotrophicus* that is a transcription regulator (Accession No. NP_275456), and about 27% identity from amino acids 14-142 with a protein from *Staphylococcus aureus* that is a hypothetical protein (Accession No. NP_370857).

A Gapped BlastP sequence alignment showed that SEQ ID NO:60 (585 amino acids) has about 57% identity from amino acids 16-582 with a protein from *Lactobacillus brevis* that is a Hop-resistant MDR (multidrug resistance)-like gene (Accession No. BAA21552), about 57% identity from amino acids 16-584 with a protein from *Lactobacillus plantarum* that is a multidrug ABC transporter ATP-binding and permease protein (Accession No. NP_786297), about 51% identity from amino acids 11-582 with a protein from *Lactococcus lactis* that is a multidrug resistance protein LmrA (Accession No. AAB49750), about 51% identity from amino acids 11-582 with a protein from *Lactococcus lactis* that is a multidrug resistance ABC transporter ATP-binding and permease protein (Accession No. Q9CHL8), and about 51% identity from amino acids 11-582 with a protein from *Lactococcus lactis* that is a multidrug resistance ABC transporter ATP-binding and permease protein (Accession No. NP_266867).

A Gapped BlastP sequence alignment showed that SEQ ID NO:62 (118 amino acids) has about 33% identity from anino acids 4-115 with a protein from *Lactobacillus gasseri* that is a hypothetical protein (Accession No. ZP_00046399), about 26% identity from amino acids 29-115 with a protein from *Carnobacterium divergens* that is dvnI (Accession No. CAA11807), about 26% identity from amino acids 29-115 with a protein from *Lactobacillus plantarum* that is a bacteriocin immunity protein (Accession No. NP_786516), about 38% identity from amino acids 74-117 with a protein from Equine coronavirus NC99 that is a spike protein (Accession No. AAQ67205), and about 25% identity from amino acids 20-115 with a protein from *Clostridium acetobutylicum* that is an uncharacterized protein similar to the mesC/lccI/entI family bacteriocin immunity protein (Accession No. NP_149170).

A Gapped BlastP sequence alignment showed that SEQ ID NO:64 (505 amino acids) has about 27% identity from amino acids 3-481 with a protein from *Thermoanaerobacter tengcongensis* that is aminopeptidase N (Accession No. NP_624209), about 33% identity from amino acids 122-369 with a protein from *Streptomyces avermitilis* that is a putative metallopeptidase (Accession No. NP_821429), about 31% identity from amino acids 122-371 with a protein from *Streptomyces coelicolor* that is a putative metallopeptidase (Accession No. NP_631646), about 24% identity from amino acids 11-480 with a protein from *Chloroflexus auranticus* that is a hypothetical protein (Accession No. ZP_00017564), and about 23% identity from amino acids 282-499 with a protein from *Xylella fastidiosa* that is aminopeptidase N (Accession No. ZP_00042138).

A Gapped BlastP sequence alignment showed that SEQ ID NO:66 (353 amino acids) has about 22% identity from amino acids 128-344 with proteins from *Haemophilus somnus* that are proteins involved in heme utilization (Accession No. ZP_00133280), and about 21% identity with a protein from Homo sapiens that is unknown (Accession No. AAH62424)

A Gapped BlastP sequence alignment showed that SEQ ID NO:68 (201 amino acids) has about 27% identity from amino acids 1-134 with a protein from *Xylella fastidiosa* that is a transposase and inactivated derivatives (Accession No. ZP_00038374), about 58% identity from amino acids 159-201 with a protein from *Lactobacillus delbrueckii* that is a transposase for insertion sequence element (Accession No. AAQ06905), about 26% identity from amino acids 1-134 with a protein from *Xylella fastidiosa* that is a transposase and inactivated derivatives (Accession No. ZP_00038149), about 24% identity from amino acids 27-196 with a protein from *Nostoc* sp. that is a transposase (Accession No. NP_490351), and about 25% identity from amino acids 1-132 with a protein from *Xylella fastidiosa* that is a transposase and inactivated derivatives (Accession No. ZP_00038301).

A Gapped BlastP sequence alignment showed that SEQ ID NO:70 (180 amino acids) has about 67% identity from amino acids 1-138 with a protein from *Lactobacillus debruekii* that is a transposase for insertion sequence element (Accession No. AAQ06905), about 36% identity from amino acids 2-179 with a protein from *Clostridium perfringens* that is a probable transposase (Accession No. NP_561584), about 36% identity from amino acids 2-178 with a protein from *Clostridium tetani* that is a transposase (Accession No. NP_781063), about 36% identity from amino acids 2-179 with a protein from *Clostridium perfringens* that is a probable transposase (Accession No. NP_562803), and about 35% identity from amino acids 2-179 with a protein from *Clostridium tetani* that is a transposase (Accession No. AAO35235).

A Gapped BlastP sequence alignment showed that SEQ ID NO:72 (444 amino acids) has about 55% identity from amino acids 1-432 with a protein from *Lactobacillus plantarum* that is a cation efflux protein (Accession No. NP_783937), about 42% identity from amino acids 2-432 with a protein from *Bifidobacterium longum* that is a $Na^{30}$-driven multidrug efflux pump (Accession No. ZP_00120269), about 33% identity from amino acids 3-421 with a protein from *Clostridium tetani* that is a $Na^+$-driven multidrug efflux pump (Accession No. NP_781116), about 31% identity from amino acids 3-431 with a protein from *Methanosarcina acetivorans* that is an integral membrane protein (Accession No. NP_616062), and about 29% identity from amino acids 7-432 with a protein from *Clostridium acetobutlycum* that is a predicted membrane protein and probable cation efflux pump (MDR-type) (Accession No. NP_349099).

A Gapped BlastP sequence alignment showed that SEQ ID NO:74 (64 amino acids) has about 28% identity from amino acids 4-49 with a protein from *Nostoc* sp. that is a hypothetical protein (Accession No. NP_478212).

A Gapped BlastP sequence alignment showed that SEQ ID NO:76 (63 amino acids) has about 40% identity from amino acids 9-39 with a protein from *Bacillus subtilis* that is an assimilatory nitrate reductase (Accession No. NP_388214), and about 40% identity from amino acids 9-41 with a protein from *Bacillus subtilis* that is an assimilatory nitrite reductase (Accession No. NP_388212).

A Gapped BlastP sequence alignment showed that SEQ ID NO:78 (438 amino acids) has about 40% identity from amino acids 66-188 with a protein from *Lactobacillus salavarius* that is unknown (Accession No. AAM61773), about 28% identity from amino acids 4-297 with a protein from *Streptococcus mutans* that is a hypothetical protein (Accession No. NP_722210), about 26% identity from amino acids 101-220 with a protein from *Streptococcus agalactiae* that is a putative bacteriocin transport accessory protein (Accession No. NP_687482), about 27% identity from amino acids 86-216 with a protein from *Brochothrix campestris* that is a transport accessory protein (Accession No. AAC95141), and about 25% identity from amino acids 101-220 with a protein from *Streptococcus agalactiae* that is unknown (Accession No. NP_734963).

A Gapped BlastP sequence alignment showed that SEQ ID NO:80 (196 amino acids) has about 56% identity from amino acids 1-196 with a protein from *Lactobacillus gasseri* that is a putative gassericin K7 B accessory protein (Accession No. AAP73779), about 56% identity from amino acids 1-196 with a protein from *Lactobacillus gasseri* that is ORF2 (Accession No. BAA82351), about 55% identity from amino acids 10-196 with a protein from *Lactobacillus gasseri* that is unknown (Accession No. AAP56342), about 49% identity from amino acids 10-196 with a protein from *Lactobacillus* sp. that is a hypothetical protein in the LAF 5' region (ORF1) (Accession No. AAA16635), and about 28% identity from amino acids 41-195 with a protein from *Lactobacillus casei* that is an ABC-transporter accessory factor (Accession No. NP_542220).

A Gapped BlastP sequence alignment showed that SEQ ID NO:82 (720 amino acids) has about 68% identity from amino acids 1-720 with a protein from *Lactobacillus salvarius* that is AbpT (Accession No. AAM61785), about 62% identity from amino acids 9-720 with a protein from *Lactobacillus plantarum* that is an ATP-binding and permease protein PlnG bacteriocin ABC-transporter (Accession No. NP_784218), about 62% identity from amino acids 9-720 with a protein from *Lactobacillus plantarum* that is the ABC-transporter PlnG (Accession No. CAA64189), about 62% identity from amino acids 6-720 with a protein from *Lactobacillus sakei* that is the probable ATP-dependent translocation protein sppT (Accession No. AAA16635), and about 62% identity from amino acids 2-720 with a protein from *Lactobacillus sakei* that is an ABC-exporter (Accession No. CAA86946).

A Gapped BlastP sequence alignment showed that SEQ ID NO:84 (83 amino acids) has about 100% identity from amino acids 20-42 with a protein from *Lactobacillus acidophilus* that is the acidocin J1132 alpha peptide (N-terminal) (Accession No. AAB49523), and about 100% identity from amino acids 19-42 with a protein from *Lactobacillus acidophilus* that is the acidocin J1132 beta peptide (Accession No. AAB49524).

A Gapped BlastP sequence alignment showed that SEQ ID NO:94 (208 amino acids) has about 25% identity from amino acids 23-125 with a hypothetical protein from *Lactobacillus helveticus* (Accession No. CAA57507).

A Gapped BlastP sequence alignment showed that SEQ ID NO:98 (197 amino acids) has about 35% identity from amino acids 3-196 with a protein from *Lactobacillus gasseri* that is a predicted metal-dependent membrane protease (Accession No. ZP_00046861), about 38% identity from amino acids 1-151 with a protein from *Lactobacillus gasseri* that is a hypothetical protein (Accession No. ZP_00047041), about 26% identity from amino acids 3-183 with a protein from *Lactobacillus plantarum* that is a CAAX family membrane-bound protease (Accession No. NP_786255), about 30% identity from amino acids 1-142 with a protein from *Lactobacillus gasseri* that is a predicted metal-dependent membrane protease (Accession No. ZP_00047281), and about 35% identity from amino acids 80-156 with a protein from *Lactobacillus plantarum* that is the CAAX family membrane-bound protease immunity protein PlnI (Accession No. NP_784215).

A Gapped BlastP sequence alignment showed that SEQ ID NO:100 (263 amino acids) has about 23% identity from amino acids 57-263 with a protein from *Lactobacillus gasseri* that is a hypothetical protein (Accession No. ZP_00047041), about 33% identity from amino acids 134-201 with a protein from *Halobacterium* sp. that is the 3-oxoacyl-[acyl-carrier protein]reductase FabG (Accession No. NP_280196), about 29% identity from amino acids 62-245 with a protein from *Lactobacillus gasseri* that is a prediceted metal-dependent protease (Accession No. ZP_00046861), about 30% identity from amino acids 26-109 with a protein from *Plasmodium falciparum* that is a conserved hypothetical protein (Accession No. NP_701942), and about 26% identity from amino acids 83-229 with a protein from Avian infectious prochitis virus that is the replicase polyprotein 1ab (Accession No. AAP92673).

A Gapped BlastP sequence alignment showed that SEQ ID NO:102 (398 amino acids) has about 30% identity from amino acids 6-396 with a protein from *Lactobacillus gasseri* that is a predicted metal-dependent membrane protease (Accession No. ZP_00046861), about 27% identity from amino acids 4-392 with a protein from *Lactobacillus gasseri* that is hypothetical protein (Accession No. ZP_00047041), about 30% identity from amino acids 201-381 with a protein from *Lactobacillus gasseri* that is a predicted metal-dependent membrane protease (Accession No. ZP_00047281), about 24% identity from amino acids 103-394 with a protein from *Lactobacillus plantarum* that is a CAAX family membrane-bound protease (Accession No. NP_786255), and about 35% identity from amino acids 256-360 with a protein from *Lactobacillus plantarum* that is the CAAX family membrane-bound protease immunity protein PlnP (Accession No. NP_784209).

A Gapped BlastP sequence alignment showed that SEQ ID NO:104 (103 amino acids) has about 48% identity from amino acids 51-83 with a protein from *Pyrococcus abyssi* that is a hypothetical molybdenum cofactor (Accession No. NP_126386), about 28% identity from amino acids 1-92 with a protein from *Dictyostelium discoideum* that is a vacuolar proton ATPase 100 kDa subunit (Accession No. AAB49621), about 28% identity from amino acids 34-102 with a protein from *Agrobacterium tumefaciens* that is a conserved hypothetical protein (Accession No. NP_535397), about 40% identity from amino acids 53-94 with a protein from *Ralstonia solanacearum* that is a putative hemaglutanin-related protein (Accession No. NP_521309), and about 44% identity from amino acids 48-76 with a protein from *Lactobacillus gasseri* that is ORF3 (Accession No. BAA82352).

A Gapped BlastP sequence alignment showed that SEQ ID NO:106 (767 amino acids) has about 71% identity from amino acids 3-766 with proteins from *Lactobacillus gasseri* that is that are alpha-glucosidases (Accession No. ZP_00046641), about 65% identity from amino acids 5-761 with a protein from *Lactobacillus plantarum* that is an alpha-glucosidase (Accession No. NP_621719), about 40% identity from amino acids 15-767 with a protein from *Thermoanaerobacter tengcongensis* that is an alpha-glucosidase (Accession No. NP_535397), about 40% identity from amino acids 20-717 with a protein from *Bacillus thermoamyloliquefaciens* that is alpha-glucosidase II (Accession No. Q9F234), and about 38% identity from amino acids 10-750 with proteins from *Nostoc punctiforme* that are alpha-glucosidases (Accession No. ZP_00110705).

A Gapped BlastP sequence alignment showed that SEQ ID NO:116 (249 amino acids) has about 90% identity from amino acids 1-249 with a protein from *Lactobacillus gasseri* that is an aspartate racemase (Accession No. ZP_00046638), about 87% identity from amino acids 1-249 with a protein from *Lactobacillus johnsonii* that is an aspartate racemace (Accession No. NP_965689), about 52% identity from amino acids 1-234 with a protein from *Pediococcus pentosaceus* that is an aspartate racemance (Accession No. CAA43598), and about 48% identity from amino acids 1-235 with a protein from *Streptococcus thermophilus* that is an aspartate racemase (ZP00285115).

A Gapped BlastP sequence alignment showed that SEQ ID NO:118 (523 amino acids) has about 85% identity from amino acids 2-519 with a protein from *Lactobacillius johnsonii* that is a UDP-N-acetylmuramoyl-L-alanyl-D-glutamate lysine ligase (Accession No. NP_965690), about 85% identity from amino acids 2-519 with a protein from *Lactobaillus johnsonii* that is a UDP-N-acetylmuramyl tripeptide synthase (Accession No. ZP_00046637), about 52% identity from amino acids 1-510 with a protein from *Pediococcus pentosaceus* that is a UDP-N-acetylmuramyl tripeptide synthase (Accession No. ZP_00323229), and about 45% identity from amino acids 1-515 with a protein from *Leuconostoc mesenteroides* that is a UDP-N-acetylmuramyl tripeptide synthase (Accession No. ZP_00062837).

A Gapped BlastP sequence alignment showed that SEQ ID NO:120 (621 amino acids) has about 84% identity from amino acids 7-620 with a protein from *Lactobacillus johnsonii* that are ABC transporter ATPase and permease components (Accession No. NP_965693), about 82% identity from amino acids 10-620 with a protein from *Lactobacillus gasseri* that are ABC-type multidrug transport system, ATPase and permease components (Accession No. ZP_00046634), about 52% identity with a protein from *Clostridium acetobutylicum* that is an ABC-type multidrug/protein/lipid transport system, ATPase component (Accession No. NP_350005), and about 52% identity from amino acids 40-621 with a protein from *Desulfitobacterium hafniense* that are ABC-type multidrug transport system, APTase and permease components (Accession No. ZP_00099385). A Gapped BlastP sequence alignment showed that SEQ ID NO:122 (576 amino acids) has about 83% identity from amino acids 1-576 with a protein from *Lactobacillus gasseri* that are ABC-type multidrug transport system ATPase and permease components (Accession No. ZP_00046633), about 83% identity from amino acids 1-576 with a protein from *Lactobacillus johnsonii* that are ABC transporter ATPase and permease components (Accession No. NP_965694), about 51% identity from amino acids 1-574 with a protein from *Desulfitobacterium hafniense* that are ABC-type multidrug transport system ATPase and permease components (Accession No. ZP_00099386), and about 50% identity from amino acids 1-569 with a protein from *Bifidobacterium longum* that is an ATP-binding protein of an ABC transporter (Accession No. NP_696913).

A Gapped BlastP sequence alignment showed that SEQ ID NO:124 (452 amino acids) has about 40% identity from amino acids 4-431 with a protein from *Lactobacillus gasseri* that is an uncharacterized protein conserved in bacteria (Accession No. ZP_00341762), about 39% identity from amino acids 4-431 with a protein from *Lactobacillus johnsonii* that is a hypothetical protein (Accession No. NP_964083), about 26% identity from amino acids 9-427 with a protein from *Lactobacillus plantarum* that is a hypothetical protein (Accession No. NP_783898), and about 25% identity from amino acids 21-427 with a protein from *Pediococcus pentosaceus* that is an uncharacterized protein conserved in bacteria (Accession No. ZP_00323558).

A Gapped BlastP sequence alignment showed that SEQ ID NO:126 (274 amino acids) has about 42% identity from amino acids 1-268 with a protein from *Lactobacilus johnsonii* that is a hypothetical protein (Accession No. NP_964084), about 40% identity from amino acids 1-268 with a protein from *Lactobacillus gasseri* that is an uncharacterized protein conserved in bacteria (Accession No. ZP_0046801), about 33% identity from amino acids 1-269 with a protein from *Lactobacillus plantarum* that is a hypothetical protein (Accession No. NP_783899), and about 27% identity from amino acids 1-266 with a protein from *Pediococcus pentosaceus* that is an uncharacterized protein conserved in bacteria (Accession No. ZP_00323559).

A Gapped BlastP sequence alignment showed that SEQ ID NO:128 (265 amino acids) has about 74% identity from amino acids 1-265 with a protein from *Lactobacillus gasseri* that are metal-dependent hydrolases of the beta-lactamase superfamily (Accession No. ZP_00046802), about 73% identity from amino acids 1-265 with a protein from *Lactobacillus johnsonii* that is a hypothetical protein (Accession No. NP_964085), about 52% identity from amino acids 1-265 with a protein from *Lactobacillus plantarum* that is a hydrolase (Accession No. NP_783900), and about 52% identity from amino acids 1-255 with a protein from *Pediococcus pentosaceus* that are metal-dependent hydrolases of the beta-lactamase superfamily (Accession No. ZP_00323560).

A Gapped BlastP sequence alignment showed that SEQ ID NO:130 (423 Amino acids) has about 86% identity from amino acids 12-423 with a protein from *Lactobacillus helveticus* that is HtrA (Accession No. CAA06668), about 60% identity from amino acids 18-420 with a protein from *Lactobacillus johnsonii* that is a serine protease do-like HtrA (Accession No. NP_964086), about 50% identity from amino acids 36-412 with a protein from *Pediococcus pentosaceus* that are trypsin-like serine proteases (Accession No. ZP_00323561), and about 41% identity from amino acids 22-420 with a protein from *Exiguobacterium* sp. that is a trypsin-like serine protease (Accession No. ZP_00184047).

A Gapped BlastP sequence alignment showed that SEQ ID NO:118 (236 amino acids) has about 35% identity from amino acids 25 to 221 with a protein from *Oenococcus oeni* that is an EAL domain (Accession No. ZP_00319350), about 33% identity from amino acids 7 to 223 with a protein from *Leuconostocmesesenteroides* subsp. *mesenteroides* ATCC 8293 that are EAL domains (Accession No. ZP_00062661), and about 33% identity with a protein from *Leuconostocmesenteroides* subsp. *mesenteroides* ATCC 8293 that is an EAL domain (Accession No. ZP_00062662).

A Gapped BlastP sequence alignment showed that SEQ ID NO:132 (56 amino acids) has about 55% identity from amino acids 1 to 56 with a protein from *Oenococcus oeni* PSU-1 that is a NADH:flavin oxidoreductases (Accession No. ZP_00318642), about 51% identity from amino acids 1 to 56 with a protein from *Leuconostoc mesenteroides* subsp. *mesenteroides* ATCC 8293 that are NADH:flavin oxidoreductases (Accession No. ZP_00064370), and about 50% identity from amino acids 3 to 56 with proteins from *Lactococcus lactis* subsp. *lactis* that are NADH-dependent oxidoreductase (Accession Nos. NP_267851, AAK05793, and G86836).

A Gapped BlastP sequence alignment showed that SEQ ID NO:134 (184 amino acids) has about 68% identity from amino acids 3 to 184 with a protein from *Oenocossus oeni* PSU-1 that is an amidase related to nicotinamidase (Accession No. ZP_00318699), about 63% identity from amino acids 2 to 183 with a protein from *Lactobacillus plantarum* WCFS1 that is a pyrazinamidase/nicotinamidase (Accession Nos. NP_786021 and CAD64878), and about 59% identity from amino acids 2 to 182 with the protein from *Pediococcus pentosaceus* ATCC 25745 that is an amidase related to nicotinamidase (Accession No. ZP_00323805).

A Gapped BlastP sequence alignment showed that SEQ ID NO:138 (498 amino acids) has about 83% identity from amino acids 1 to 493 with a protein from *Lactobacillus johnsonii* NCC533 that is an amino acid transporter (Accession No. NP_965275), about 82% identity from amino acids 1 to 493 with a protein from *Lactobacillus gasseri* that is an amino acid transporter (Accession No. ZP_00046566), and about 46% identity from amino acids 8 to 492 with the protein from *Pediococcus pentosaceus* ATCC 25745 that is an amino acid transporter (Accession No. ZP_00323277).

A Gapped BlastP sequence alignment showed that SEQ ID NO:140 (231 amino acids) has about 46% identity from amino acids 1 to 230 with a protein from *Lactobacillus plantarum* WCFS1 that is a cell surface hydrolase (putative) (Accession No. NP_785474), about 46% identity from amino acids 1 to 231 with a protein from *Lactobacillus johnsonii* NCC533 that is a hypothetical protein LJ0748 (Accession No. NP_964600), and about 45% identity with the protein from *Lactobacillus gasseri* that is an uncharacterized protein with an alpha/beta hydrolase fold (Accession No. ZP_00045991).

A Gapped BlastP sequence alignment showed that SEQ ID NO:144 (230 amino acids) has about 27% identity from amino acids 1 to 226 with a protein from *Oenocossus oeni* PSU-1 that is an aldo/keto reductases, related to diketogulonate reductases (Accession No. ZP_00319386), about 26% identity from amino acids 4 to 226 with a protein from *Bifidobacterium longum* NCC2705 that is a morphine 6-dehydrogenace (Accession No. NP_696457), and about 26% identity from amino acids 9 to 226 with a protein from *Bifidobactrium longum* DJO 10A that is an aldo/keto reductases related to *diketogulonate reductase* (Accession No. ZP_00120718).

A Gapped BlastP sequence alignment showed that SEQ ID NO:148 (392 amino acids) has about 68% identity from amino acids 1 to 389 with a protein from *Lactobacillus gasseri* that is a permeases of the major facilitator super family (Accession No. ZP_00046919), about 68% identity from amino acids 1 to 391 with a protein from *Lactobaccillus johnsonii* NCC 533 that is a major facilitator super family permease (Accession No. NP_965415), and about 46% identity from amino acids 1 to 385 with a protein from *Lactobacillus plantarum* WCFS1 that is a multi-drug transport protein (Accession No. NP_784617).

A Gapped BlastP sequence alignment showed that SEQ ID NO:22 (221 amino acids) has about 77% identity with a protein from *Lactobacillus johnsonii* NCC 533 that is a 2-component system response regulator (Accession No. NP_965391), about 77% identity from amino acids 1 to 220 with a protein from *Lactobacillus gasseri* that is a response regulator consisting of a CheY-like receiver domain and a winged-helix DNA-binding domain (Accession No. ZP_00046475), and about 59% identity from amino acids 1 to 221 with a protein from *Streptococcus pyogenes* SSI-1 that are putative to component response regulators (Accession No. NP_607078).

A Gapped BlastP sequence alignment showed that SEQ ID NO:108 (63 amino acids) has about 59% identity from amino acids 1 to 63 with a protein from *Bacillus thuringiensis serovar konkukian* str. 97-27 that is a flagellar hook-associated protein 1 (Accession No. YP_035858), and about 40% identity from amino acids 32 to 63 with a protein from *Bacillus cereusZK* that is a flagellar hook-associated protein 1 (Accession No. YP-083109).

A Gapped BlastP sequence alignment showed that SEQ ID NO:122 (576 amino acids) has about 83% identity from amino acids 1 to 576 with a protein from *Lactobacillus gasseri* that is an ABC-type multi-drug transport system, ATPace and permease components (Accession No. ZP_00046633), about 83% identity from amino acids 1 to 576 with a protein from *Lactobacillus johnsonii* NCC 533 that is an ABC transporter ATPace and permease components (Accession Nos. NP_965694 and AAS09660), and about 51% identity from amino acids 1 to 574 with a protein from *Desulfitobacterium hafniense* DCB-2 that is an ABC-type multi-drug transport system, ATPace and permease components (Accession No. ZP_00099386).

A Gapped BlastP sequence alignment showed that SEQ ID NO:152 (260 amino acids) has about 45% identity from amino acids 2 to 249 with a protein from *Lactobacillus gasseri* that is an uncharacterized membrane-bound protein conserved in bacterium (Accession No. ZP_00046632).

A Gapped BlastP sequence alignment showed that SEQ ID NO:154 (366 amino acids) has about 93% identity from amino acids 1 to 366 with a protein from *Lactobacillus johnsonii* NCC533 that is a probable GTP-binding protein (Accession No. AAS09662), about 93% identity from amino acids 1 to 366 with a protein from *Lactobacillus gasseri* that is a predicted GTPase, probable translation factor (Accession No. ZP_00046631), and about 77% identity from amino acids 1 to 366 with a protein from *Pediococcus pentosaceus* ATCC 25745 that is a predicted GTPase, probable translation factor (Accession No. ZP_00322452) and 76% identity from amino acid 1 to 366 with a protein from *Lactobacillus plantarum* WCFS1 that is a GTP-binding protein (Accession No. NP_786473).

A Gapped BlastP sequence alignment showed that SEQ ID NO:158 (294 amino acids) has about 80% identity from amino acids 1 to 293 with a protein from *Lactobacillus gasseri* that is a predicted transcriptional regulator (Accession No. ZP_00046630), about 78% identity from amino acids 1 to 293 with a protein from *Lactobacillus johnsonii* NCC 533 which is a chromosome partitioning protein ParB (Accession No. NP_965698), and about 60% identity from amino acids 5 to 293 of a protein from *Lactobacillus plantarum* WCFS1 that is a chromosome partitioning protein (Accession No. NP_786475) and about 59% identity from amino acids 12 to 293 to a protein from *Entrococcus faecalis* V583 which is a chromosome partitioning protein ParB family (Accession No. NP_816893).

A Gapped BlastP sequence alignment showed that SEQ ID NO:160 (259 amino acids) has about 85% identity from amino acids 1 to 257 to a protein from *Lactobacillus johnsonii* NCC533 that is a chromosome partitioning protein ParA (Accession No. NP_965699), about 85% identity from amino acids 1 to 257 to a protein from *Lactobacillus gasseri* that is an ATPases involved in chromosome partitioning (Accession No. ZP_00046629), and permease components (Accession No. ZP_00046629), and about 68% identity from amino acids 1 to 251 of a protein from *enterococcus faecalis* V583 that is an ATPase, ParA family (Accession No. NP_816894).

A Gapped BlastP sequence alignment showed that SEQ ID NO:162 (276 amino acids) has about 57% identity from amino acids 1 to 276 with a protein from *Lactobacillus johnsonii* NCC533 which is a probable chromosome partitioning protein ParB (Accession No. NP_96570), about 58% identity from amino acids 1 to 276 of a protein from *Lactobacillus gasseri* that is a predicted transcriptional regulator (Accession No. ZP_00046628), and about 50% identity from amino acids 14 to 275 of a protein from *Lactobacillus plantarum* WCFS1 that is a chromosome partitioning protein, DNA binding protein (Accession No. NP_786477) and about 50% identity from amino acids 19 to 276 with a protein from *Geobacillus kaustophilus* HTA426 which is a hypothetical protein GK3491 (Accession No. YP_149344).

A Gapped BlastP sequence alignment showed that SEQ ID NO:164 (240 amino acids) has about 67% identity from amino acids 1 to 239 with a protein from *Lactobacillus johnsonii* NCC533 which is a glucose inhibited division protein B (Accession No. NP_965701), and about 66% identity from amino acids 1 to 239 to a protein from *Lactobacillus gasseri* that is a predicted S-adenosylmethionine-dependent methyltransferase involved in bacterial cell division (Accession No. ZP_00046627), and about 62% identity from amino acids 1 to 239 a protein from *Pediococcus pentosaceus* ATCC 25745 that is a predicted S-adenosylmethionine-dependent methyltransferase involved in bacterial cell division (Accession No. ZP_00322449).

EXAMPLE 3

PFAM Results for Amino Acid Sequences

SEQ ID NO:2 contains a predicted Response_reg domain located from about amino acids 3 to 92 and a predicted Trans_reg_C domain located from about amino acids 84 to 225, and is a member of the Response regulator receiver domain family (Response_reg) (PFAM Accession PF00072) and a member of the Transcriptional regulatory protein C family (Trans_reg_C) (PFAM Accession PF00486).

SEQ ID NO:4 contains a predicted HAMP domain from about amino acids 184 to 253, a predicted HisKA domain located from about amino acids 376 to 443 and a predicted HATPase_c domain from about amino acids 496 to 607, and is a member of the HAMP domain family (HAMP) (PFAM Accession PF00672), a member of the His Kinase A (phosphoacceptor) domain family (HisKA) (PFAM accession PF00512), and a member of the Histidine kinase-, DNA gyrase B-, and HSP90-like ATPase family (HATPase_c) (PFAM Accession PF02518).

SEQ ID NO:12 contains a predicted Response_reg domain from about amino acids 3 to 124 and a Trans_reg_C domain from about amino acids 160 to 131, and is a member of the Response regulator receiver domain family (Response_reg) (PFAM Accession PF00072) and a member of the Transcriptional regulatory protein C family (Trans_reg_C) (PFAM Accession PF00496).

SEQ ID NO:14 contains a predicted HAMP domain from about amino acids 173 to 242, a predicted HisKA domain located from about amino acids 253 to 319 and a predicted HATPase_c domain from about amino acids 364 to 475, and is a member of the HAMP domain family (HAMP) (PFAM Accession PF00672), a member of the His Kinase A (phosphoacceptor) domain family (HisKA) (PFAM accession PF00512), and a member of the Histidine kinase-, DNA gyrase B-, and HSP90-like ATPase family (HATPase_c) (PFAM Accession PF02518).

SEQ ID NO:16 contains a predicted GGDEF domain from about amino acids 200-363, and is a member of the GGDEF domain family (GGDEF) (PFAM Accession PF00990).

SEQ ID NO:18 contains a predicted EAL domain from about amino acids 4 to 234, and is a member of the EAL domain family (EAL) (PFAM Accession PF00563).

SEQ ID NO:20 contains a predicted HisKA domain located from about amino acids 208 to 270, a predicted HATPase_c domain from about amino acids 314 to 426, and is a member of the His Kinase A (phosphoacceptor) domain family (HisKA) (PFAM accession PF00512), and a member of the Histidine kinase-, DNA gyrase B-, and HSP90-like ATPase family (HATPase_c) (PFAM Accession PF02518).

SEQ ID NO:22 contains a predicted Response_reg domain from about amino acids 1 to 120, and is a member of the Response regulator receiver domain family (Response_reg) (PFAM Accession PF00072).

SEQ ID NO:24 contains a predicted HAMP domain from about amino acids 203 to 274, a predicted HisKA domain from about amino acids 278 to 345, a predicted HATPase_c domain from about amino acids 391 to 502, and is a member of the HAMP domain family (HAMP) (PFAM Accession PF00672), a member of the His Kinase A (phosphoacceptor) domain family (HisKA) (PFAM accession PF00512) and a member of the Histidine kinase-, DNA gyrase B-, and HSP90-like ATPase family (HATPase_c) (PFAM Accession PF02518).

SEQ ID NO:26 contains a predicted Response_reg domain from about amino acids 2 to 120 and a predicted Trans_reg_C domain from about amino acids 156 to 227, and is a member of the response regulator receiver domain family (Response_reg) (PFAM Accession PF00072) and a member of the Transcriptional regulatory protein C family (Trans_reg_C) (PFAM Accession PF00486).

SEQ ID NO:28 contains a predicted Response_reg domain from about amino acids 20 to 138 and a predicted Trans_reg_C domain from about amino acids 170 to 240, and is a member of the Response regulator receiver domain family (Response_reg) (PFAM Accession PF00072) and a member of the transcriptional regulatory protein C family (Trans_reg_C) (PFAM Accession PF00486).

SEQ ID NO:30 contains a predicted HisKA domain from about amino acids 223 to 290 and a predicted HATPase_c domain from about amino acids 330 to 441, and is a member of the His Kinase A (phosphoacceptor) domain family (HisKA) (PFAM accession PF00512) and a member of the Histidine kinase-, DNA gyrase B-, and HSP90-like ATPase family (HATPase_c) (PFAM Accession PF02518).

SEQ ID NO:36 contains a predicted HisKA domain from about amino acids 153 to 219 and a predicted HATPase_c domain from about amino acids 265 to 376, and is a member of the His Kinase A (phosphoacceptor) domain family (HisKA) (PFAM accession PF00512) and a member of the Histidine kinase-, DNA gyrase B-, and HSP90-like ATPase family (HATPase_c) (PFAM Accession PF02518).

SEQ ID NO:38 contains a Response_reg domain from about amino acids 1 to 120 and a predicted Trans_reg_C domain from about amino acids 150 to 226, and is a member of the Response regulator receiver domain family (Response_reg) (PFAM Accession PF00072) and a member of the Transcriptional regulatory protein C family (Trans_reg_C) (PFAM Accession PF00486).

SEQ ID NO:40 contains a predicted DeoR domain from about amino acids 6 to 231, and is a member of the Bacterial regulatory proteins, DeoR family (DeoR, PFAM Accession PF00455).

SEQ ID NO:44 contains a predicted Patatin domain from about amino acids 9 to 176, and is a member of the Patatin-like phospholipase family (Patatin) (PFAM Accession PF01734).

SEQ ID NO:50 contains a predicted Band_7 domain from about amino acids 21 to 194, and is a member of the SPFH domain/Band 7 family (Band_7) (PFAM Accession PF01145).

SEQ ID NO:58 contains a predicted MarR domain from about amino acids 35 to 138, and is a member of the MarR family (MarR) (PFAM Accession PF01047).

SEQ ID NO:60 contains an ABC_membrane domain from about amino acids 41 to 307 and an ABC_tran domain from about amino acids 377 to 582, and is a member of the ABC transporter transmembrane region family (ABC_membrane) (PFAM Accession PF00664) and a member of the ABC transporter family (ABC_tran) (PFAM Accession PF00005).

SEQ ID NO:72 contains a MatE domain from about amino acids 27 to 189, and is a member of the MatE domain family (MatE) (PFAM Accession PF01554).

SEQ ID NO:82 contains a Peptidase_C39 domain from about amino acids 10 to 145, an ABC_membrane domain from about amino acids 164 to 440 and an ABC_tran domain from about amino acids 512 to 696, and is a member of the Peptidase C39 family (Peptidase_C39) (PFAM Accession PF03412), a member of the ABC transporter transmembrane region family (ABC_membrane) (PFAM Accession PF00664) and a member of the ABC transporter family (ABC_tran) (PFAM Accession PF00005).

SEQ ID NO:124 contains a predicted YycH domain from about amino acids 12 to 429 and is a member of the YycH domain family (PFAM Accession No. PF07435).

SEQ ID NO:128 contains a predicted Lactamase_B domain from about amino acids 11 to 219 and is a member of the Lactamase_B domain family (PFAM Accession No. PF00753).

SEQ ID NO:130 contains a predicted PDZ domain from about amino acids 315 to 408, a predicted trypsin domain from about amino acids 132 to 312, and is a member of the PDZ domain family (PFAM Accession No. PF00595) and a member of the trypsin domain family (PFAM Accession No. PF00089).

SEQ ID NO:56 contains a predicted hydrolase domain from about amino acids 6 to 243, and is a member of the hydrolase domain family (PFAM Accession No. PF00702).

SEQ ID NO:8 contains a domain with an E-value of 0.015 to a predicted HAT Pase_C domain from amino acids 321 to 425, and is a member of the HATPase_C domain family (PFAM Accession No. PF02518).

SEQ ID NO:10 contains a predicted response_reg domain from about amino acids 3 to 140, a predicted LyTR domain from about amino acids 160 to 254, and is a member of the response_reg domain family (PFAM Accession No. PF00072) and a member of the LytTR domain family (PFAM Accession No. PF04397).

SEQ ID NO:138 contains a predicted amino acid permease domain from about amino acids 13 to 498, and is a member of the AA_permease domain family (PFAM Accession No. PF00324).

SEQ ID NO:144 contains a predicted aldo/keto reductase domain from about amino acids 10 to 228, and is a member of the Aldo/keto reductase family (PFAM Accession No. PF00248).

SEQ ID NO:148 contains a predicted major facilitator super family domain from about amino acid 15 to 356 and is a member of the major facilitator super family (MFS_1) domain family (PFAM Accession No. PF07609).

SEQ ID NO:150 contains a predicted region found in RelA/SpoT proteins from about amino acids 44 to 169, and is a member of the RelA_SpoT domain family (PFAM Accession No. PF04607).

SEQ ID NO:48 contains a predicted flavodoxin domain from about amino acids 67 to 224 (E-value equals 0.021) and is a member of the flavodoxin_1 domain family (PFAM Accession No. PF00258).

SEQ ID NO:52 contains a predicted RelB antitoxin domain from about amino acids 5 to 76 with an E-value of 0.0001 and is a member of the RelB domain family (PFAM Accession No. PF04221).

SEQ ID NO:64 contains a predicted peptidase family Ml domain from about amino acids 31 to 416, and is a member of the peptidase M1 domain family (PFAM Accession No. PF01433).

SEQ ID NO:70 contains a punitive transposase DNA-binding domain from about amino acids 97 to 178, and is a member of the transposase_35 domain family (PFAM Accession No. PF07282).

SEQ ID NO:78 contains a predicted gram positive anchor domain from about amino acids 393 to 433, which is a member of the gram positive anchor domain family (PFAM Accession No. PF00746).

SEQ ID NO:32 contains a predicted LytTr DNA-binding domain from about amino acids 172 to 266, a predicted response regulator receiver domain from about amino acids 12 to 152, and is a member of the LytTR DNA-binding domain family (PFAM Accession No. PF04397) and a member of the response regulator receiver domain family (PFAM Accession No. PF00072).

SEQ ID NO:34 contains a HATPase_C domain from about amino acids 320 to 434, and is a member of the histidine kinase-, DNA gyrase B-, and HSP90-like ATPace family (HATPase_C) (PFAM Accession No. PF02518).

SEQ ID NO:98 contains a predicted CAAX amino terminal protease family domain from about amino acids 38 to 148, with an E-value of 0.00025, which is a member of the ABI domain family (PFAM Accession No. PF02517).

SEQ ID NO:102 contains a predicted CAAX amino terminal protease family domain from about amino acids 243 to 353, with an E-value of 8.9e-06 and is a member of the ABI domain family (PFAM Accession No. PF02517).

SEQ ID NO:106 contains a predicted glycosylhydrolases family domain from about amino acids 185 to 296, and is a member of the glycosylhydrolases family (Gylco_hydro_31) (PFAM Accession No. PF01055).

SEQ ID NO:116 contains a predicted asp/glu/hydantoin racemase from about amino acids 2 to 231, and is a member of the asp/glu/hydantoin racemase domain family (PFAM Accession No. PF01055).

SEQ ID NO:118 contains a predicted mur ligase family, glutamate ligase domain from about amino acids 30 to 102, and is a member of the mur ligase family, glutamate ligase domain family (PFAM Accession No. PF02875).

SEQ ID NO:120 contains a predicted ABC transporter domain from about amino acids 408 to 592 and a predicted ABC transporter transmembrane region located about amino acids 36 to 315, and is a member of the ABC transporter domain family (PFAM Accession No. PF01061) and a member of the ABC transporter transmembrane region domain family (PFAM Accession No. PF00664).

SEQ ID NO:122 contains a predicted ABC transporter domain from about amino acids 360 to 544 and a predicted ABC transporter transmembrane region located from about amino acids 16 to 287, and is a member of the ABC transporter domain family (PFAM Accession No. PF01061) and a member of the ABC transporter transmembrane region domain family (PFAM Accession No. PF00664).

SEQ ID NO:154 contains a predicted GTPase of unknown function from about amino acids 3 to 145, which is a member of the MMR_HSR1 domain family (PFAM Accession No. PF01926).

SEQ ID NO:158 contains a predicted ParB-like nuclease domain from about amino acids 37 to 126, and is a member of the ParB-like nuclease domain family (PFAM Accession No. PF02195).

SEQ ID NO:160 contains a predicted CobQ-CobB/MinD/ParA nucleotide binding domain from about amino acids 5 to 221, and is a member of the CbiA domain family (PFAM Accession No. PF01656).

SEQ ID NO:162 contains a predicted ParB-like nuclease domain from about amino acids 20 to 109, and is a member of the ParBc domain family (PFAM Accession No. PF02195).

SEQ ID NO:164 contains a predicted glucose inhibited division protein from about amino acids 21 to 215, and is a member of the GidB domain family (PFAM Accession No. PF02527).

EXAMPLE 4

Microarray Analysis of a Two-component Regulatory System Involved in Acid Tolerance and Oligopeptide Transport Activity in *Lactobacillus acidophilus*

Survival of microorganisms during their transit through the gastrointestinal tract requires the capability to sense and respond to the various and changing conditions present in that environment. Two-component regulatory systems (2CRS) are one of the most important mechanisms for environmental sensing and signal transduction. They are found in the majority of gram-positive and gram-negative bacteria and control housekeeping functions, as well as regulating proteins important for pathogenesis, stress and adherence (Cotter et al. (1999) *J. Bacteriol* 181:6840-6843; Sebert et al. (2002) *Infect. Immun.* 70:4059-4067; Teng et al. (2002) *Infect. Immun.* 70:1991-1996). A typical 2CRS consists of a membrane-associated histidine protein kinase (HPK), which detects specific environmental signals, and a cytoplasmic response regulator (RR), which regulates expression of one or more genes in a regulon (Parkinson (1993) *Cell* 73:857871). 2CRS are located in modules with varying arrangements of conserved domains (West and Stock (2001) *TRENDS Biochem. Sci.* 26:369-376). HPKs generally consist of a signal input domain and an autokinase domain, which can be divided into two sub domains: a histidine phosphotransferase sub domain and an ATP-binding sub domain. The RR is typically composed of a regulatory (receiver) domain and a DNA binding (output) domain (Hoch and Varughese (2001) *J. Bacteriol.* 183:4941-4949). Detection of an external signal by the input domain of the kinase controls its own activation. The active kinases will autophosphorylate via ATP hydrolysis, on a histidine residue. This phosphoryl group is then transferred to an aspartate residue in the receiver domain of the RR that activates the regulatory protein and promotes the transcriptional response (Foussard et al. (2001) *Microbes Infect.* 3:417-424).

Genomic sequencing of microorganisms has uncovered the presence of many 2CRS and promoted global analysis of their responses to different environments. For those studies, DNA microarray technology involving high-density arrays of open reading frame-specific fragments has been instrumental. Fabret et al. (Fabret et al. (1999) *J. Bacteriol.* 181:1975-

1983) identified and grouped 2CRS in *Bacillus subtilis* in five different groups and the function of these 2CRS have been investigated by microarray analysis (Kobayashi et al. (2001) *J. Bacteriol.* 183:7365-7370; Ogura et al. (2001) *Nucleic Acids Res.* 29:3804-3813).

In lactic acid bacteria (LAB), production of some class II bacteriocins (plantaricin, sakacin P, sakacin A, carnobacteriocin 132) is transcriptionally regulated through a signal transduction pathway which consists of three components: an inducer bacteriocin-like peptide, a HPK, and a RR (for a review see 25). In fact, the production of many small antimicrobial peptides appears to be modulated by a cell-density response mechanism. Additionally, multiple 2CRS have been identified in a number of LAB (Miller and Bassler (2001) *Annu. Rev. Microbiol.* 55:165-199; Morel-Deville et al. (1997) *Microbiology* 143:1513-1520). For example, six 2CRS were detected in *Lactococcus lactis*, with four of them implicated in cellular responses to stress (O'Connell-Motherway et al. (2000) *Microbiology* 46:935-947).

*Lactobacillus acidophilus* NCFM is a probiotic organism that has been used extensively in yogurt, fermented foods, and dietary supplements (Sanders and Klaenhammer (2001) *J. Dairy Sci.* 84:319-331). The annotated genome sequence of *L. acidophilus* NCFM encodes nine putative 2CRS (Altermann et al. (2004) *Proc. Natl. Acad. Sci. U.S.A.* 102:3906-3912). In this study, we identified a 2CRS similar to the lisRK system described in *Listeria monocytogenes* (Cotter et al. (1999) *J. Bacteriol.* 181:6840-6843), which participates in both stress response and virulence in *L. monocytogenes*. The HPK gene from the LBA1524HPK-LBA1525RR system was disrupted to investigate its putative role in acid tolerance. A whole genome array containing 97.4% *L. acidophilus* annotated genes was constructed and used to compare genome-wide transcriptional patterns of the control and the HPK mutant, exposed to three different pHs.

Materials and Methods

Bacterial Strains and Growth Conditions

The bacterial strains used in this study were *Escherichia coli* EC 1000 (RepA$^+$ MC1000, Km$^R$; host for pORI28-based plasmids, [Law et al. (1995) *J. Bacteriol.* 177:7011-7018]), and *L. acidophilus* strains: NCFM (human intestinal isolate; [Barefoot and Klaenhammer (1983) *Appl. Environ. Microbiol.* 45:1808-1815]), NCK1398 (NCFM lacL::pTRK685, [Russell and Klaenhammer (2001) *Appl. Environ. Microbiol.* 67:4361-4364]) and NCK1686 (NCFM LBA1524:: pTRK807, [this example]).

*E. coli* strains were propagated at 37° C. in Luria-Bertani (LB, Difco Laboratories Inc., Detroit, Mich.) broth with shaking. Erythromycin (Em) resistant clones of *E. coli* were selected on brain heart infusion (BHI) agar (Difco) supplemented with Em (150 μg/ml). *Lactobacilli* were propagated statically at 37° C. in MRS (Difco) or on MRS supplemented with 1.5% agar. When appropriate, Em (5.0 μg/ml) and/or chloramphenicol (Cm, 7.0 μg/ml) was added. Reconstituted skim milk (10% SM) and 10% SM supplemented with 1% yeast extract (Difco) or 0.25% casaminoacids (Difco) were used for determination of acidification rates.

Standard DNA Techniques

Restriction enzymes (Roche Molecular Biochemicals, Indianapolis, Ind.) and T4 DNA ligase (New England Biolabs, Beverly, Mass.) were used according to the suppliers' recommendations. Plasmid preparations from *E. coli* were performed using the QIAprep Spin Plasmid Minipreps kit (QIAGEN Inc., Valencia, Calif.). Chromosomal DNA from *L. acidophilus* was extracted according to Walker and Klaenhammer (Walker and Klaenhammer (1994) *J. Bacteriol.* 176:5330-5340). Electrotransformation of *L. acidophilus* was carried out as described by Walker et al. (Walker et al. (1996) *FEMS Microbiol. Lett.* 138:233-237). PCR was performed by standard protocols using Taq DNA polymerase (RocheMolecular Biochemicals).

DNA Sequence Analysis and Data Submission

Potential coding sequences were derived from the genomic sequence of *L. acidophilus* NCFM (Genbank accession number CP000033, [Altermann et al. (2004) *Proc. Natl. Acad. Sci. U.S.A.* 102:3906-3912]). Protein sequence similarity analysis was conducted using the BlastP module (Altschul et al. (1997) *Nucleic Acids Res.* 25: 3389-3402) at NCBI (nebi.nlm.nih.gov/). TMHMM (cbs.dtu.dklservices/TMHMM) was used to predict transmembrane helices in proteins. CD-Search (Marchler-Bauer et al. (2003) *Nucleic Acids Res.* 31:383-387) was employed to identify conserved domains in protein sequences.

Microarray platform and data are available at the Gene Expression Omnibus (GEO rhtto://www.nebi.nlm.nih.goy/ge2]) under accession numbers GPL1401 (platform) and GSE1976 (series).

RNA Isolation and RNA Slot Blots

Aliquots (10 ml) of *L. acidophilus* cultures grown on MRS to $A_{600}$=0.3 were transferred to MRS (adjusted to desired pH with lactic acid). After 30 minutes, cells were harvested by centrifugation and frozen immediately in a dry ice/ethanol bath. One ml Trizol (Life Technologies, Rockville, Md.) was added to the cell pellets and they were homogenized in a Mini-Beadbeater-8 cell disruptor (Biospec Products, Bartlesville, Okla.) for five 1-min cycles (and chilled on ice for 1 min between the cycles), the phases were separated by centrifugation (14,000 rpm, 15 min, 4° C.). The aqueous phase was removed to a fresh tube and 0.4 ml of Trizol and 0.2 ml of chloroform were added. The mixture was vortexed for 15 s and centrifuged to separate the 10 phases. The Trizol step was repeated twice and RNA was precipitated from the final aqueous phase by adding 1 volume of isopropanol, followed by incubation at room temperature for 10 min and centrifugation (12,000 rpm, 10 min, 4° C.). Concentration and purity of RNA samples were determined by electrophoresis on agarose gels and standard spectrophotometer measurements.

Total RNA hybridizations using a slot-blot apparatus (Bio-Dot SF, Bio-Rad) and Zeta-Probe membrane (Bio-Rad Laboratories, Inc.) were carried out as previously described (Durmaz et al. (2002) *J. Bacteriol.* 184:6532-6543). [α-$^{32}$P] dCTP-labeled probes were generated from PCR fragments using the Multiprime DNA labeling system (Amersham Pharmacia Biotech Inc., Piscataway, N.J.) and purified using the NucTrap Probe purification columns (Stratagene, La Jolla, Calif.). The primers utilized are listed in Table 2. Radioactive signals were detected by using a Kodak Biomax film and autoradiographs were analyzed by densitometry using the SpotDenso function with auto-linked background on an Alphalmager 2000 (Innotech Scientific). Primers as set forth in table 2 are denoted in the sequence listing as follows LBA 0197 (SEQ ID NO:167), for LBA 1300 (SEQ ID NO:168), for LBA 1524 (SEQ ID NO:169), for LBA 1525 (SEQ ID NO:170), for LBA 0698 (SEQ ID NO:171), for LBA 1075 (SEQ ID NO:175), for LBA 1196 (SEQ ID NO:176).

TABLE 2

Primers utilized for probe generation in Northern blot analysis.

| ORF | Description | Primers* |
|---|---|---|
| LBA0197 | ABC transporter, oligopeptide binding protein OppA1 | F:5' gcagcatgtagtagtaataa 3'<br>R:5' cagaatcacgtaatgtgtaa 3' |
| LBA1300 | Oligopeptide ABC transporter, substrate binding protein OppA2 | F:5' atgcaatagcttgacgaaga 3'<br>R:5' atgcaatatggtgctgaatc 3' |
| LBA1524 | Two component sensor histidine kinase | F:5' gatctctaga-cagcgctctagca 3'<br>R:5' gatcagatct-tcggccaatgtg 3' |
| LBA1525 | Two-component system regulator | F:5' gatctctaga-cacgaaccgtctt 3'<br>R:5' gatcagatct-ttggctcgatttg 3' |
| LBA0698 | Glyceraldehyde-3-P dehydrogenase | F:5' tcgtagttgacggtaagaag 3'<br>R:5' acctgcagtagttaccatag 3' |
| LBA1075 | Malolactic enzyme | F:5' gttgttacagacggtgaagg 3'<br>R:5' taatgcacgaccatcagtcc 3' |
| LBA1196 | RNA polymerase sigma factor RpoD | F:5' gatctctaga-ttccgcttcttact 3'<br>R:5' gatcagatct-atctgacgaatacg 3' |

*Dashes indicate the introduction of restriction enzyme sites.

Generation of *Lactobacillus acidophilus* DNA Microarray

A whole genome DNA microarray based on the PCR products of predicted ORFs from the *L. acidophilus* genome was used for global gene expression analysis. PCR primers for 1,966 genes were designed using GAMOLA software (Altermann and Klaenhammer (2003) *OMJCS* 7:161-169) and purchased from Qiagen Operon (Alameda, Calif.). Total genomic DNA from *L. acidophilus* NCFM was used as a template for 96-well PCR amplifications. To amplify gene-specific PCR products, a 100 µl reaction mix contained: 1 µl *L. acidophilus* DNA (100 ng/l), 10 µl specific primer pairs (10 µM), 0.5 µl of dNTP mix (10 mM), 10 µl PCR buffer (10×), and 1 µl Taq DNA polymerase (5 U/µl [Roche Molecular Biochemicals]). The following PCR protocol was used: an initial denaturation step for 5 min at 94° C. followed by 40 cycles of denaturation at 94° C. for 15 sec, annealing at 50° C. for 30 sec and polymerization at 72° C. for 45 sec. Approximately 95% of ORFs produced a unique PCR product between 100-800 bp. The size of fragments was confirmed by electrophoresis in 1% agarose gels. DNA from 96-well plates were purified using the Qiagen Purification Kit. In general, the total quantity of each PCR product was greater than 1 µg. The purified PCR fragments were spotted three times in a random pattern on glass slides (Corning, Acton, Mass.) using the Affymetrix® 417™ Arrayer at the NCSU Genome Research Laboratory (cals.ncsu.edu:8050/grl/). To prevent carry-over contaminations, pins were washed between uses in different wells. Humidity was controlled at 50-55% during printing. DNA was cross-linked to the surface of the slide by UV (300 mJ) and posterior incubation of the slides for 2 h at 80° C. The reliability of the microarray data was assessed by hybridization of two cDNA samples prepared from the same total RNA, labeled with Cy3 and Cy5. Hybridization data revealed a linear correlation in the relative expression level of 98.6% of 5685 spots (each gene by triplicate) with no more than a two-fold change.

cDNA Probe Preparation and Microarray Hybridization

Identical amounts (25 µg) of DNAse treated (Invitrogen) RNA were aminoallyl-labeled by reverse transcription with random hexamers in the presence of amino-allyl dUTP (Sigma Chemical Co.), using Superscript II reverse transcriptase (Life Technologies) at 42° C. overnight, followed by fluorescence-labeling of aminoallylated cDNA with N-hydroxysuccinimide-activated Cy3 or Cy5 esters (Amersham Pharmacia Biotech). Labeled cDNA probes were purified using the PCR Purification Kit (Qiagen). Coupling of the Cy3 and Cy5 dyes to the AA-dUTP labeled cDNA and hybridization of samples to microarrays were performed according to the protocols outlined in the TIGR protocols website (tigr.org/tdb/microarray/protocosTGR.shtml). Briefly, combined Cy5- and Cy3-labeled cDNA probes were hybridized to the arrays for 16 h at 42° C. After hybridization, the slides were washed twice in low stringency buffer (1×SSC containing 0.2% SDS) for 5 min each. The first wash was performed at 42° C. and the second one at room temperature. Subsequently, the slides were washed in a high stringency buffer (0.1×SSC containing 0.2% SDS, for 5 min at room temperature) and finally in 0.1 ×SSC (2 washes of 2.5 min each at room temperature).

Data Normalization and Gene Expression Analysis

Immediately after washing of the arrays, fluorescence intensities were acquired at 10 µm resolution using a ScanArray 4000 Microarray Scanner (Packard Biochip BioScience, Biochip Technologies LLC, Mas.) and stored as TIFF images. Signal intensities were quantified, the background was subtracted and data was normalized using the QuantArray 3.0 software package (Perkin Elmer). Two slides (each containing triplicate arrays) were hybridized reciprocally to Cy3- and Cy5-labeled probes per experiment (dye swap). Spots were analyzed by adaptive quantitation. Data was median normalized. When the local background intensity was higher than the spot signal (negative values) no data was considered for those spots. The median of the six ratios per gene was recorded. The ratio between the average absolute pixel values for the replicated spots of each gene with and without treatment represented the fold change in gene expression. All genes belonging to a potential operon were considered for analysis if at least one gene of the operon showed significant expression changes, and the remaining genes showed trends toward that expression. Confidence intervals and P values on the fold change were also calculated with the use of a two-sample t test. P values of 0.05 or less were considered significant (Knudsen (2002) "A Biologist's Guide to Analysis of DNA Microarray Data," (John Wiley & Sons, Inc., New York)).

Construction of the Histidine Protein Kinase Mutant

A 766-bp internal fragment of ORF LBA1524 was amplified using *L. acidophilus* NCFM chromosomal DNA as template and the primers 11 524F (5'-gatctagacagcgctctagca-3') and 11 524R (5'-gatcgatcttcggccaatgtg-3'). The internal fragment was cloned in the integrative vector pORI28 (Law et al. (1995) *J. Bacteriol.* 177:7011-7018) generating pTRK807, and introduced by electroporation in *L. acidophilus* NCFM containing pTRK669 (Russell and Klaenhamrnmer (2001) *Appl. Environ. Microbiol.* 67:4361-4364).

Subsequent steps to facilitate the integration event were carried out according to Russell and Klaenhammer (Russell and Klaenhammer (2001) *Appl. Environ. Microbiol.* 67:4361-4364). The suspected integrants were confirmed by PCR and Southern hybridization analysis, using standard procedures.

Acid Challenge and Adaptation Assays

For acid challenge analysis, cells were grown to an absorbance at 600 nm ($A_{600}$) of 0.25-0.3 (pH>5.8) from a 2% inoculum in MRS broth. Cultures were centrifuged and resuspended in the same volume of MRS adjusted to pH 3.5 with lactic acid at 37° C. Survival was determined at 30 minutes intervals by plating serial dilutions in a 10% MRS broth diluent onto MRS agar using a Whitley Automatic Spiral Plater (Don Whitley Scientific Limited, West Yorkshire, England).

For acid adaptation assays, cells were grown to an $A_{600}$ of 0.25-0.3 (pH>5.8). Cells were centrifuged and resuspended in the same volume of MRS pH 5.5 (adjusted with lactate) and incubation continued for 1 hour at 37° C. as described previously (Azcarate-Peril et al. (2004) *Appl. Environ. Microbiol.* 70:5315-5322). Controls were resuspended in MRS broth at pH 6.8. The cells from the adapted (pH 5.5) and control (pH 6.8) cultures were then centrifuged and resuspended in MRS broth at pH 3.5 (adjusted with lactic acid). Viable-cell counts were performed at 30 minutes intervals for 2.5 h by plating on MRS agar.

Ethanol Tolerance

Log phase_cells at an $A_{600}$ of 0.25-0.3 (pH>5.8) from a 2% inoculum in MRS broth were centrifuged and resuspended in the same volume of NMS, or MRS containing 15 or 20% (v/v) ethanol. CFU/ml were determined at 30 minutes intervals by serial dilutions in 10% MRS and enumeration on MRS agar as described above.

Results

Two-component Regulatory Systems (2CRS)

Using CD-search (Marchler-Bauer et al. (2003) *Nucleic Acids Res.* 31:383-387) and BlastP (Altschul et al. (1997) *Nucleic Acids Res.* 25: 3389-3402) programs, we identified nine signal transduction systems consisting of a histidine protein kinase (HPK) and a response regulator (RR; [Altermann et al. (2004) *Proc. Natl. Acad. Sci. US.A.* 102:3906-3912]). These 2CRS represented almost 1% of *L. acidophilus* NCFM ORFs. Additionally, four RRs were identified containing a LytTR DNA binding motif that were not associated with a histidine kinase. HPKs share a characteristic kinase core composed of a dimerization domain and a catalytic domain for ATP binding and phosphate transfer. The C-terminal half of the HPK proteins showed five conserved amino acid motifs: the H box, containing the His residue that will be phosphorylated, and the N, G1, F and G2 boxes (Stock et al. (2000) *Annu. Rev. Biochem.* 69:183-215). ORFs LBA0079HPK, LBA0747HPK, LBA1524HPK, LBA1430HPK, LBA1660HPK and LBAI819HPK were assigned to the group IIIA/OmpR of HPKs in accordance with the region surrounding the histidine that becomes phosphorylated; whereas the HPKs LBA0602HPK and LBA1799HPK, were categorized in the Class IV (Fabret et al. (1999) *J. Bacteriol.* 181:1975-1983). The remaining 2CRS (LBA1413-LBA1414) could not be classified into any known category. LBA1413 showed a Domain of Unknown Function with GGDEF motif (smart00267, DUF 1), which apparently occurs exclusively in eubacteria and might participate in prokaryotic signaling processes. LBA1414 showed also a domain of unknown function (cd01948, EAL), which is found in diverse bacterial signaling proteins. Together with the GGDEF domain, EAL might be involved in regulating cell surface adhesiveness in bacteria (Galperin et al. (2001) *FEMS Microbiol Lett.* 203:11-21).

Response regulators contain two conserved domains. First a regulator, which receives the signal from the sensor partner in bacterial 2CRS. It contains a phosphoaceeptor site that is phosphorylated by the histidine kinase. Second, a DNA binding effector domain in the C terminus of the protein. RRs present in *L. acidophilus* contained these two conserved domains. The RRs ranged from 221 to 274 amino acids in size. ORFs LBA0078RR, LBA0746RR, LBA1525RR, LBA1431RR, LBA1659RR and LBA1820RR can be included in the OmpR family of response regulators according to the amino acid sequence of their output domains, where the residues involved in the hydrophobic core of the domain are conserved (Martinez-Hackert and Stock (1997) *Structure* 5:109124). The response regulators encoded by LBA603RR and LBAi 798RR can be defined as members of the AlgR/AgrA/LytR family of RRs (Nikolskaya and Galperin (2002) *Nucleic Acids Res.* 30:2453-2459).

The 2CRS composed of LBA1524HPK and LBA1525RR formed an operon flanked by two terminators with a free energy of −11.0 and −13.8 Kcal/mol, respectively. Also, a typical RBS sequence and a putative promoter were positioned upstream of LBA1525RR (FIG. 1). The histidine protein kinase gene showed a 36% identity with the HPK in the lisRK system described in *Listeria monocytogenes* (Cotter et al. (1999) *J. Bacteriol.* 181:6840-6843). This two component signal transduction system was shown to participate in the stress response and virulence of *L. monocytogenes*. A lisRK-defective mutant, generated by random insertional mutagenesis, grew at higher concentrations of ethanol than the parental strain, but was more sensitive to acid stress during logarithmic phase of growth (Cotter et al. (1999) *J. Bacteriol.* 181:6840-6843). LBA1524HPK also showed homology (32% identity and 55% similarity) to the HPK gene of csrRS, a system that represses the expression of the hyaluronic acid capsid and virulence factors of *Streptococcus*, SLS and SpeB (Heath et al. (1999) *Infect. Immun.* 67:5298-5305).

Insertional Inactivation of LBA1524UPK and Acid Stress Assays

To investigate the physiological function of LBA I 524HPK-LBA I 525RR 2CRS and to examine its putative association with acid tolerance in *L. acidophilus*, a chromosomally interrupted LBA1524HPK mutant was constructed. For insertional inactivation of the HPK, a 766-bp internal region was amplified by PCR using the primers 11524F-11524R described in Materials and Methods. This fragment was cloned into pORI28 and the resulting plasmid, pTRK807, was then transferred by electroporation into *L. acidophilus* NCFM, already harboring the helper plasmid pTRK669. Integrants were isolated as described by Russell and Klaenhammer (Russell and Klaenhammer (2001) *Appl. Environ. Microbiol.* 67:4361-4364) to generate strain NCK1686. PCR experiments and Southern hybridizations were performed to confirm the integration event via junction amplicons and fragments (data not shown). Because this operon was flanked by two putative terminators, polar effects from the inactivation of LBA1524HPK were not expected. Phase-contrast microscopy analyses of the HPK mutant revealed a decrease in cell size and chain length compared to the wild type, NCFM cells (data not shown).

Two strong transmembrane regions can be predicted, by in silico analysis, in the histidine protein kinase of LBA I 524BPK-LBA 15 25RR 2CRS (from 24 to 42 aa, and 202 to 226 aa). The ATP-binding phosphotransfer (catalytic domain) and the dimerization domain can be located in the carboxy termini of the protein from 396 to 499 as and from 276 to 341 aa, respectively. The 766-bp internal region of LBA1524HPK, amplified by PCR using primers I 1524F-11524R, used to inactivate the HPK spanned from 51 to 347 aa. As a consequence, insertion of the vector would have affected the second transmembrane and/or the dimerization domain of the HPK.

Figure 3:
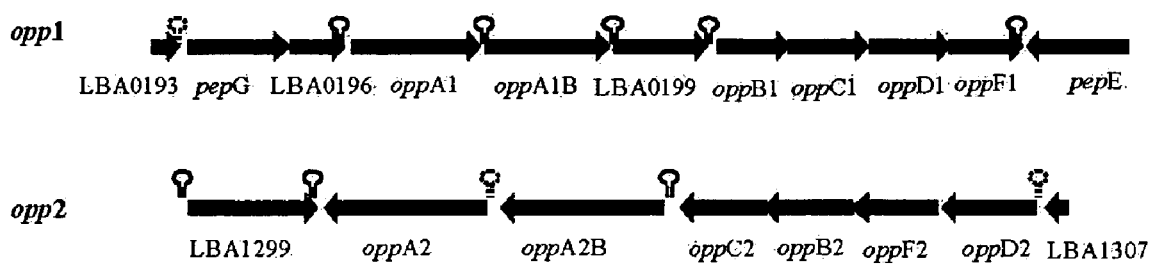
FIG. 3 shows the organization of the oligopeptide transport (opp) operons in *Lactobacillus acidophilus* NCFM. Predicted rho-independent terminators with a free energy over −10 kcal/mol (continuous line) and under −10 Kcal/mol (dotted line) are indicated.

The response of log phase cells to pH 3.5 was compared between the HPK mutant strain NCK1686 and control, *L. acidophilus* NCK1398 (NCFM::lacL). Strain NCK1398 was used as a control throughout the study so that the effects of antibiotic pressure could be accounted for. When log phase cells of NCK1686 were exposed to pH 3.5, more than a 2-log reduction in cfu was observed after 2.5 hours, compared to a half-log reduction in the control (FIG. 3A). Therefore, similar to *L. monocytogenes* (Cotter et al. (1999) *J. Bacteriol.* 181: 6840-6843), the HPK mutant was more sensitive to acid indicating that the LBA1524HPK-LBA1525RR 2CRS plays a significant role in acid resistance of *L. acidophilus*.

Acid Adaptation of *L. acidophilus*

Figure 2:
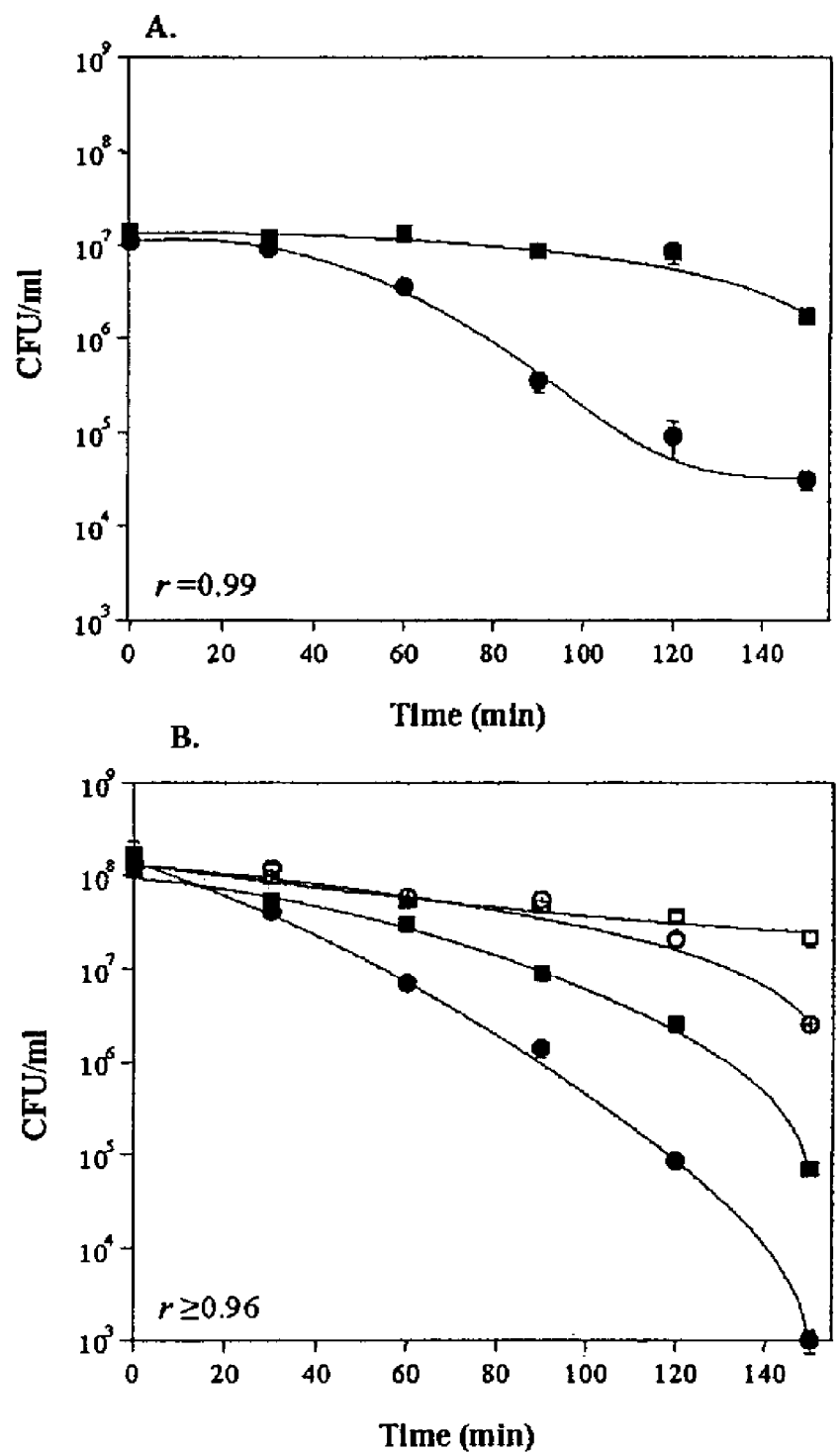
FIG. 2A shows the survival of *Lactobacillus acidophilus* NCK1398 (NCFMΔlacL, squares) and the HPK mutant NCK1686 (circles) in MRS adjusted to pH 3.5 with lactic acid.
FIG. 2B shows the survival of *Lactobacillus acidophilus* NCK1398 (NCFMΔlacL, squares) and the HPK mutant NCK1686 (circles) following exposure to pH 5.5 (open symbols) or pH 6.8 (filled symbols) for 1 h prior to challenge at pH 3.5 (adjusted with lactate).

Log phase cells of *L. acidophilus* NCK1398 and NCK1686 were exposed to pH 5.5 for 1 h, prior to challenge by pH 3.5. Remarkably, both the control and HPK mutant exhibited a high tolerance to acid challenge (FIG. 2B). Exposure to pH 5.5 appeared to adapt the cells to a higher level of acid tolerance during challenge at pH 3.5. Acid sensitivity incurred by the LBA1524HPK mutant over 150 min was nearly abolished by the adaptation period at pH 5.5, but after 2.5 h at pH 3.5 the mutant still remained more sensitive than the control.

Global Gene Expression of the HPK Mutant

In an attempt to identify genes regulated by the 2CRS, and potentially affected by inactivation of the LBA1524HPK ORF, parallel cultures of the control strain NCK1398 (NCFM::lacL) and the HPK mutant (NCK1686) were grown in MRS broth to an optical density of 0.3 and transferred to MRS adjusted to pH 6.8, 5.5, or 4.5. After 30 minutes, RNA was isolated and used for hybridization to microarray slides printed with representative sequences of the majority of the identified ORFs on the *L. acidophilus* genome. Statistically significant ($P \leq 0.05$) gene expression changes were considered for ORFs exhibiting at least a two-fold change.

Comparison of the expression profiles identified 80 differentially-expressed genes showing at least two-fold changes in expression patterns (Table 3). As expected, the components of the LBA I 524HPK-LBA I 525RR 2CRS, as well as the large and small subunits of the (i-galactosidase and UDP-glucose 4-epimerase were differentially expressed, owing to the inactivation of these genes in the compared strains. Surprisingly, the inactivated HPK gene and the RR were over expressed in the NCK1686 mutant. This might be attributable to amplification of the vector in the chromosome and/or a readthrough event where a longer transcript is generated, but not translated into a functional protein. The same effect was observed for NCFM::lacL where the disrupted operon appeared to be highly expressed. Alternatively, a non-functional HPK could result in elevated transcriptional expression of the 2CRS, if the phosphorylated form of the RR was involved in the auto regulation of the 2CRS.

TABLE 3

Open reading frames differently expressed in the HPK mutant (NCK 1686) compared to the control *L. acidophilus* NCK1398 (NCFM::lacL) under different pH conditions[1].

| COG[2] Functional Classification/Gene | Relative mRNA ratio (HPK/WT)[3] | | |
|---|---|---|---|
| | pH 6.8 | pH 5.5 | pH 4.5 |
| Amino acid transport and metabolism [E] | | | |
| LBA0111 Putative ABC transporter (glutamine), ATP binding protein | 0.36 | 0.47 | 0.57 |
| LBA0112 Putative ABC transporter (glutamine), substrate binding protein | 0.53 | 0.71 | 0.83 |
| LBA0197 ABC transporter, oligopeptide binding protein oppA1 | 6.22 | 4.43 | 1.92 |
| LBA0198 ABC transporter, oligopeptide binding protein oppA 1B | 7.42 | 1.96 | 1.59 |
| LBA0200 ABC transporter, oligopeptide permease protein oppB1 | 6.70 | 6.31 | 1.67 |
| LBA0201 ABC transporter, oligopeptide permease protein oppC1 | 7.27 | 8.09 | 2.55 |
| LBA0202 Oligopeptide ABC transporter, ATP binding protein oppD1 | 7.44 | 7.09 | 3.89 |
| LBA0203 Oligopeptide ABC transporter, ATP binding protein oppF1 | 8.01 | 7.10 | 5.57 |
| LBA0849 Diaminopimelate epimerase | 1.30 | 2.15 | 0.91 |
| LBA0850 Aspartokinase/homoserine dehydrogenase | 1.33 | 1.89 | 0.79 |
| LBA0911 Aminopeptidase pepC | 1.79 | 1.79 | 0.72 |
| LBA0943 Cationic amino acid transporter | 2.94 | 2.90 | 1.51 |
| LBA1042 ABC transporter (glutamine) membrane-spanning permease | 0.93 | 0.44 | 0.71 |
| LBA1044 ABC transporter (glutamine) membrane-spanning permease | 0.91 | 0.47 | 0.72 |
| LBA1045 ABC transporter (glutamine) ATP-binding protein | 0.78 | 0.39 | 0.82 |
| LBA1046 ABC transporter (glutamine) substrate-binding protein | 0.84 | 0.43 | 0.71 |
| LBA1080 Putative methionine synthase metK | 6.96 | 5.51 | 4.32 |
| LBA1086 Amino acid permease | 3.44 | 1.73 | 1.64 |
| LBA1135 Macrolide efflux protein | 1.12 | 2.00 | 1.21 |

TABLE 3-continued

Open reading frames differently expressed in the HPK mutant (NCK 1686) compared to the control *L. acidophilus* NCK1398 (NCFM::lacL) under different pH conditions[1].

| COG[2] Functional Classification/Gene | Relative mRNA ratio (HPK/WT)[3] | | |
|---|---|---|---|
| | pH 6.8 | pH 5.5 | pH 4.5 |
| LBA1211 Homoserine kinase khsE | 1.84 | 1.67 | 1.32 |
| LBA1212 Homoserine dehydrogenase hdh | 2.25 | 1.50 | 1.20 |
| LBA1300 Oligopeptide ABC trasporter, substrate binding protein oppA2 | 0.35 | 0.47 | 0.36 |
| LBA 1301 Oligopeptide ABC trasporter, substrate binding protein oppA2B | 4.92 | 1.74 | 1.37 |
| LBA1302 Oligopeptide ABC transporter, permease protein oppC2 | 1.29 | 2.14 | 1.43 |
| LBA1303 ABC transporter, oligopeptide permease protein oppB2 | 1.50 | 1.98 | 1.49 |
| LBA1305 Oligopeptide ABC transporter, ATP binding protein oppF2 | 1.50 | 2.00 | 1.33 |
| LBA1306 Oligopeptide ABC transporter, ATP binding protein oppD2 | 1.24 | 2.22 | 1.35 |
| LBA1341 Branched-chain amino acid aminotransferase ILVE | 2.13 | 1.08 | 1.26 |
| LBA1515 Peptidase T pepT | 2.26 | 2.05 | 1.32 |
| LBA1665 Oligopeptide ABC transporter, substrate binding protein | 0.38 | 0.15 | 0.58 |
| LBA1837 Cytosol non-specific dipeptidase pepD/A | 1.03 | 1.55 | 3.10 |
| LBA1961 Oligopeptide ABC transporter, substrate binding protein | 2.05 | 1.91 | 1.08 |
| Carbohydrate transport and metabolism [G] | | | |
| LBA0600 Xylulose-5-phosphate/fructose phosphoketolase | 1.31 | 3.22 | 0.78 |
| LBA1467 Beta-gatactosidase large subunit (lactase) | 0.07 | 0.17 | 0.27 |
| LBA1468 Beta-galactosidase small subunit | 0.17 | 0.43 | 1.05 |
| LBA1777 PTS system, fructose-specific enzyme II | 0.98 | 1.26 | 0.41 |
| LBA1778 Fructose-1-phosphate kinase | 1.00 | 1.30 | 0.29 |
| LBA1779 Transcriptional repressor (fructose operon) | 0.92 | 1.32 | 0.35 |
| LBA1870 Maltose phosphorylase | 0.67 | 0.90 | 0.21 |
| LBA1872 Oligo-1,6-glucosidase | 0.97 | 0.88 | 0.46 |
| Inorganic ion transport and metabolism [P] | | | |
| LBA0319 ABC transporter, ATP binding protein | 1.19 | 1.06 | 1.88 |
| LBA0320 ABC transporter, ATP binding protein | 1.25 | 0.87 | 1.96 |
| LBA0321 ABC transporter, permease protein | 1.34 | 1.33 | 2.21 |
| LBA0904 Outer membrane lipoprotein precursor | 2.11 | 2.11 | 1.19 |
| LBA0905 ABC transporter, ATP binding protein | 2.08 | 2.07 | 1.40 |
| LBA0906 ABC transporter, permease protein | 1.99 | 2.88 | 2.19 |
| LBA1683 Cation-transporting ATPase | 7.95 | 1.92 | 1.83 |
| Signal transduction mechanisms [T] | | | |
| LBA0149 Hypothetical protein | 1.28 | 1.01 | 0.56 |
| LBA0403 Hypothetical protein | 1.01 | 1.30 | 1.21 |
| LBA1081 Autoinducer-2 production protein luxS | 1.69 | 2.27 | 1.51 |
| LBA1524 Two-component sensor histidine kinase | 1.17 | 2.82 | 0.97 |
| LBA1525 Two-component system regulator | 2.09 | 1.54 | 1.03 |
| Defense mechanisms [V] | | | |
| LBA0074 ABC transporter, ATP binding and permease protein | 2.27 | 0.96 | 1.07 |
| LBA0075 ABC transporter, ATP binding and permease protein | 3.01 | 3.90 | 2.94 |
| LBA1838 ABC transporter, ATP-binding protein | 1.55 | 4.15 | 7.37 |
| LBA1839 Putative permease | 1.48 | 5.16 | 8.72 |
| LBA1876 ABC transporter, ATP-binding/membrane spanning protein | 1.79 | 1.98 | 1.59 |
| Posttranslational modification, protein turnover, chaperones [O] | | | |
| LBA0165 Neutral endopeptidase pepO | 2.91 | 3.28 | 1.97 |
| LBA1512 Proteinase P precursor prtP | 7.53 | 7.02 | 1.58 |
| LBA1564 Putative membrane protein | 1.42 | 1.47 | 2.08 |
| Cell wall/membrane/envelope biogenesis [M] | | | |
| LBA0018 Unknown | 0.90 | 1.00 | 0.55 |
| LBA1469 UDP-glucose 4-epimerase | 0.18 | 0.51 | 0.67 |
| Transcription [K] | | | |
| LBA1840 Transcriptional regulator (TetR/AcrR family) | 1.33 | 3.52 | 12.60 |
| General function prediction only [R] | | | |
| LBA0367 Putative receptor | 1.04 | 1.74 | 1.26 |
| Energy production and conversion [C] | | | |
| LBA0463 Acetate kinase | 2.31 | 1.12 | 1.27 |
| Translation, ribosomal structure and biogenesis [J] | | | |
| LBA0672 Putative phosphate starvation induced protein yvyD | 1.12 | 0.93 | 0.43 |
| Intracellular trafficking, secretion, and vesicular transport [U] | | | |
| LBA1496 Putative fibrinogen-binding protein | 3.56 | 2.35 | 1.22 |

TABLE 3-continued

Open reading frames differently expressed in the HPK mutant (NCK1686)
compared to the control L. acidophilus NCK1398 (NCFM::lacL) under different
pH conditions[1].

| COG[2] Functional Classification/Gene | Relative mRNA ratio (HPK/WT)[3] | | |
|---|---|---|---|
| | pH 6.8 | pH 5.5 | pH 4.5 |
| Replication, recombination and repair [L] | | | |
| LBA1565 Unknown | 2.02 | 1.43 | 1.37 |
| Function unknown/General function prediction only [S], [R] | | | |
| LBA0555 Myosin-crossreactive antigen | 1.05 | 0.98 | 0.43 |
| LBA0872 Putative membrane protein | 2.14 | 5.27 | 2.97 |
| LBA1119 Putative inner membrane protein | 4.22 | 3.46 | 6.24 |
| LBA1869 Beta-phosphoglucomutase | 0.69 | 0.70 | 0.24 |
| LBA1952 Hypothetical protein | 1.07 | 0.89 | 2.26 |
| No COG found | | | |
| LBA0352 Hypothetical protein | 0.94 | 0.87 | 0.47 |
| LBA0402 Unknown | 1.01 | 0.81 | 1.38 |
| LBA0404 Hypothetical protein | 0.88 | 0.60 | 0.95 |
| LBA1495 >>Putative fibrinogen-binding protein<< | 1.62 | 0.97 | 1.15 |
| LBA1611 Surface protein fmtB | 0.56 | 0.93 | 0.94 |
| LBA1690 Putative membrane protein | 1.62 | 1.32 | 2.34 |

[1]Array ratios from two biological replicates and two technical replicates for each condition were averaged.
[2]Clusters of Orthologous Groups (37). Genes were classified according to the COG domain present in the potentially encoded protein sequence.
[3]Values in boldface indicate ratios that meet the P criteria (P < 0.05).

The most dramatic changes in expression in the HPK mutant were observed in genes predicted to encode components of the proteolytic enzyme system. Proteolyitc systems of lactic acid bacteria are divided into three functional categories 1) proteinases (that degrade casein into small peptides); 2) transport systems, (that import those peptides) and 3) peptidases (Kunji et al. (1996) *Antonie van Leeuwenhoek* 70:187-221). The expression of ORF LBA1512 encoding the proteinase precursor in *L. acidophilus,* PAP (39% identical and 53% similar to the cell envelope proteinase PrtR from *L. rhamnosus* GI27527536), increased in the HPK mutant more than 7-fold at pH 6.8 and 5.5 (Table 3). However, PrtM (LBA1588), the protein putatively involved in the maturation of the proteinase, showed expression levels comparable to the control strain (ratios between 0.8 and 1.1).

Two operons potentially encoding oligopeptide ABC transporters are present in the *L. acidophilus* genome (FIG. 3), opp1 (ORFs LBA0197 to LBA0203) and opp2 (ORFs LBA1300 to LBA1306). Each consist of six genes, opp1 consists of oppD1, oppF1, oppB1, oppC1, oppA1, and oppA1B, and opp2 consists of oppD2, oppF2, oppB2, oppC2, oppA2, and oppA2B, coding for two ATP-binding proteins (OppD, OppF), two membrane proteins (OppB, OppC and two substrate-binding proteins (oppA and OppA-B). The oppA and oppA-B genes in both operons are separated by terminators from the downstream genes. Expression of the opp1 operon was significantly increased in the HPK mutant at pH 6.8 and 5.5 showing increments of 6 to 8-fold in most of the genes in the operon. The ORFs encoded by opp2 showed an increased expression in the mutant at pH 5.5. Interestingly, oppA2 (LBA1300) was down regulated in the mutant under all the evaluated conditions, but the expression of oppA2B (LBA1301) increased significantly at pH 6.8 in the mutant (Table 3). Two other ORFs encoding putative oligopeptide binding proteins were differentially expressed in the mutant. LBA1665 was consistently under expressed in the HPK mutant at the three pHs. In contrast, LBA1961 was over expressed at pH 6.8 and 5.5.

Four peptidases were also differentially expressed in the HPK mutant strain. A neutral endopeptidase PepO (LBAO 165) was up regulated at all pHs evaluated. The aminopeptidase encoded by LBA0911, and peptidase T (LBA1515) were up regulated at pH 5.5. Finally, a cytosol non-specific dipeptidase encoded by ORF LBA1837 was significantly up regulated at pH 4.5.

Figure 4:
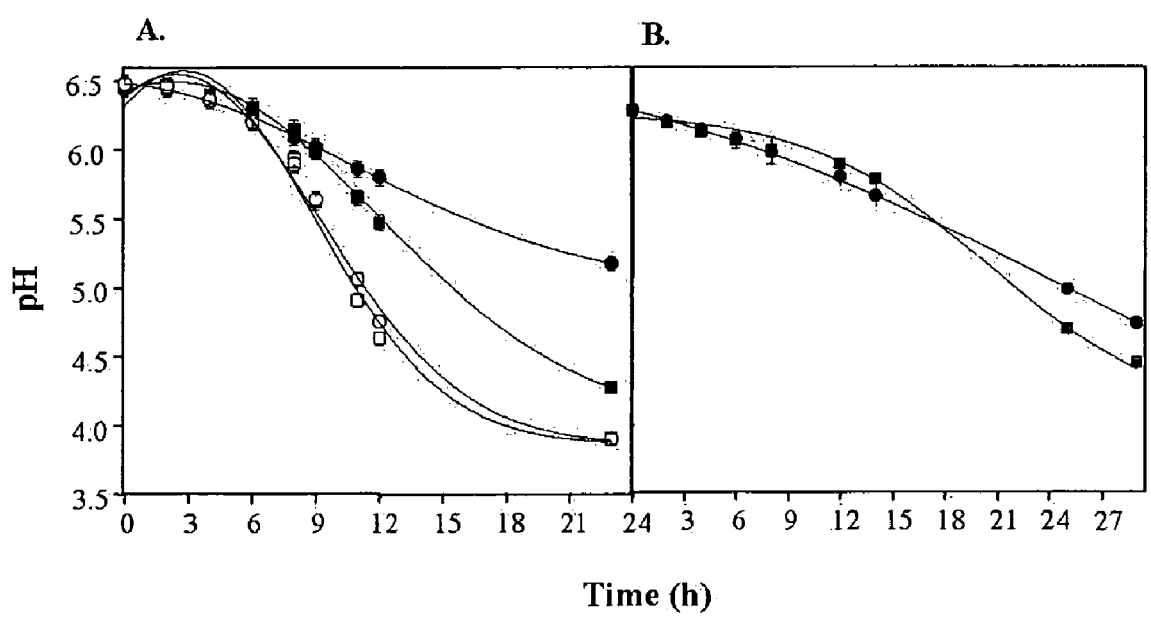
FIG. 4A shows the growth of *Lactobacillus acidophilus* NCFM (■) and NCK1686 (NCFMΔ1524HPK, ●) in milk (filled symbols) and milk supplemented with yeast extract (open symbols).
FIG. 4B shows the growth of *Lactobacillus acidophilus* NCFM (■) and NCK1686 (NCFMΔ1524HPK, ●) in milk (filled symbols) and milk supplemented with 0.25% casamino acids. r=0.99

To investigate potential alterations in the proteolytic system of the HPK mutant, we compared the acidification rates of *L. acidophilus* NCFM (wt; since NCK 1398 does not grow in milk) versus the HPK mutant in 10% skim milk (SM) and in 10% SM plus yeast extract (FIG. 4A). The HPK mutant was not able to acidify SM below pH 5.0, compared to the control where the pH dropped to nearly pH 4.0. Supplementation of SM with 0.5% yeast extract completely restored a wild-type level of acidification activity in the HPK mutant. In addition, supplementation of SM with 0.25% casamino acids also nearly abolished the difference between the wt and the HPK mutant (FIG. 4B). These data suggest that the mutant was deficient in proteolytic activity. In addition, other component(s) present in yeast extract further stimulated the acidification rates of both the parent and mutant to equal levels in skim milk.

Expression of LBA1080 (a putative methionine synthase) and LBA1081 (luxS) was increased up to 6.9-fold under all conditions in the HPK mutant. At the amino acid level, the LuxS (LBA1081) homolog in the genome sequence of *L. acidophilus* was 77% identical and 84% similar to the S-ribosylhomocysteinase (autoinducer-2 production protein LuxS) from *L. plantarum* (Kleerebezem et al. (2003) *Proc. Natl. Acad. Sci. U.S.A.* 100:1990-1995), and 73% identical and 89% similar to LuxS from *S. pyogenes* (Lyon et al. (2001) *Mol. Microbiol.* 42: 145-157). Examination of the surrounding chromosomal region suggested that luxS is the second member of an operon consisting of five genes whose function is poorly characterized. A putative rho-independent terminator with a low free energy of 31 8.5 Kcal/mol was present downstream of luxS.

Among the global transcriptional changes observed in the HPK mutant, two key enzymes involved in lysine biosynthesis, aspartate kinase (EC 2.7.2.4, LBA0850) and diaminopimelate epimerase (EC 5.1.1.7, LBA0849), were up_regulated at pH 5.5. Additionally, a putative operon composed of a cytosol non-specific dipeptidase, an ABC transporter and a transcriptional regulator from theTetR/AcrR family (ORFs LBA1737 to LBA 1840) was highly up regulated at pH 4.5.

Given the similarity of LBA1524HPK with lisK, the HPK from *L. monocytogenes* (Barefoot and Klaenhammer (1983) *Appl. Environ. Microbiol.* 45:1808-1815), and the fact that a lisK-deficient mutant was able to grow at a higher concentration of ethanol than its parent strain, survival of the *L. acidophilus* HPK mutant was investigated in the presence of ethanol. No differences were observed when log-phase cells were exposed to 15% (v/v) ethanol indicating that *L. acidophilus* is naturally highly resistant. However, at 20% ethanol the HPK mutant showed a 4-log reduction in survival after 90 min compared to only a 1-log reduction in the control (data not shown).

Confirmation of DNA Microarray Results by Northern Blotting

Cells of the control and the HPK mutant strains were harvested at an $A_{600}$ of 0.3 and exposed to pH 6.8, 5.5, and 4.5 in MRS broth for 30 minutes. Total RNA was prepared and hybridized with several labeled probes. For analysis of gene expression, DNAs of the ORFs indicated in Table 2 were amplified by PCR and labeled with $\alpha$-$^{32}$p. Selected for analysis by Northern blot, were oppA1 (LBA0197, up regulated in the HPK mutant), oppA2 (LBA1300, down regulated in the HPK mutant cells), and LBA1524HPK and LBA1525RR (components of the inactivated 2CRS) genes. Genes encoding a glyceraldehyde-3-P dehydrogenase (LBA0698), malolactic enzyme (LBA1075), and RNA polymerase sigma factor rpoD (LBA1196) were also evaluated as controls because these were not differentially expressed at the different pH conditions when evaluated in the microarrays (data not shown).

Figure 5:
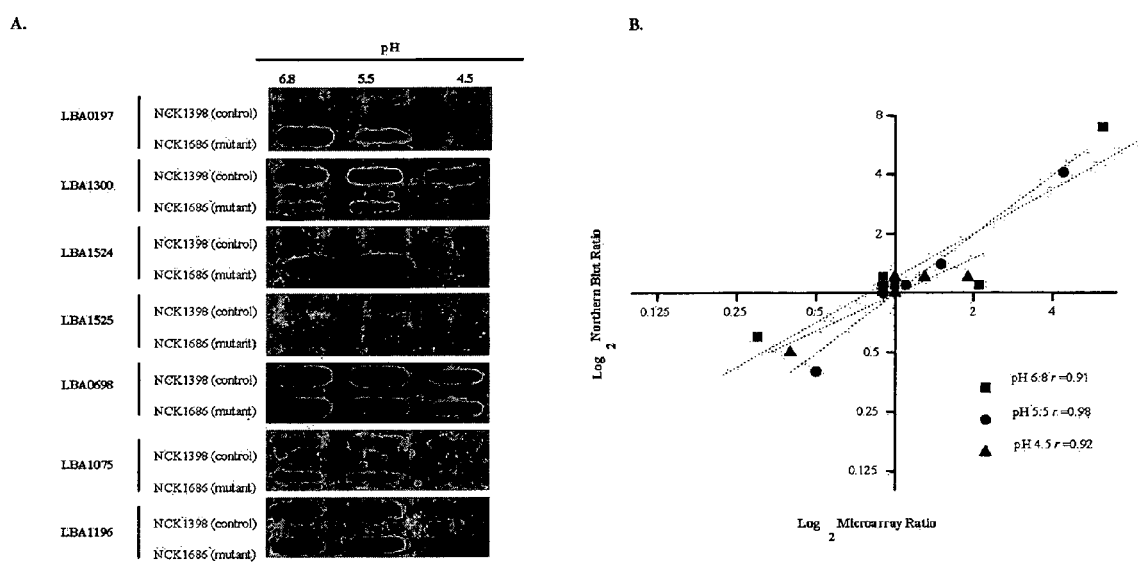
FIG. 5A shows a Northern blot analysis of seven genes which was performed using RNA isolated in three independent experiments from *Lactobacillus acidophilus* NCK1398 (NCFMΔlacL) and NCK1686 (NCFMΔ1524HPK) exposed to pH 6.8, 5.5 and 4.5 for 30 minutes. RNA ratios were calculated from data obtained by the Northern blot by densitometry analysis.
FIG. 5B shows a comparison of expression measurements by Microarray and Northern blot analysis. The correlation coefficient for each condition is given in the figure.

The hybridized membranes and comparison between relative expression ratios obtained by Microarray and Northern analysis are shown in FIGS. 5A and B. The transcription levels of the selected genes, as measured by the DNA microarray method, were consistent with those measured by Northern hybridizations, with one exception. The amounts of RNA detected for the disrupted gene LBA1524HPK showed 10-fold more RNA when measured by Northern blot, but only 2-fold according to microarray. This suggests that Northern analysis was better able to quantitate gene expression at higher levels.

Discussion

Analysis of the genome sequence of *L. acidophilus* revealed the presence of nine 2CRS (Altermann et al. (2004) *Proc. Natl. Acad. Sci. U.S.A.* 102:3906-3912). All the identified histidine protein kinases showed between two and six transmembrane domains, suggesting their location in the cell membrane. One of the identified 2CRS's, LBA1524HPK-LBA1525RR, showed homology to lisRK, a signal transduction system previously shown to participate in stress response and virulence in *L. monocytogenes* (Cotter et al. (1999) *J. Bacteriol.* 181:6840-6843). When we insertionally interrupted LBA1524HPK, log-phase cells became more sensitive to acid pH. We previously reported that *L. acidophilus* induces an adaptive response at pH 5.5 that provides elevated acid tolerance to the cells (Azcarate-Peril et al. (2004) *Appl. Environ. Microbiol.* 70:5315-5322). Both, the HPK mutant and the control NCFM::lacL exhibited an acid induced tolerance response (ATR), although this response was slightly impaired by the LBA1524HPK mutation. This indicates that while LBA1524HPK-LBA1525RR plays some role, additional mechanisms contribute to acid adaptation in *L. acidophilus* that are not regulated by this 2CRS.

A whole genome array comparing the expression profile between the control and the HPK mutant revealed an altered expression pattern of numerous ORFs encoding genes for major components of the proteolytic enzyme system. Based on its genome sequence, *L. acidophilus* has a limited capacity to synthesize amino acids, with the potential to synthesize only three amino acids (cysteine, serine, and aspartate) de novo. Additionally, cysteine and serine could be synthesized from pyruvate, and aspartate from fumarate. Based on these three amino acids, a series of other derivatives might be generated (asparagine, threonine, glycine, lysine, methionine, glutamine and glutamate). However, neither de novo or conversion pathways were predicted for the remaining 13 amino acids (Altermann et al. (2004) *Proc. Natl. Acad. Sci. U.S.A.* 102:3906-3912). Therefore, amino acid requirements must be satisfied by the uptake of amino acids and oligopeptides. *L. acidophilus* encodes two putative oligopeptide transporting systems (Altermann et al. (2004) *Proc. Natl. Acad. Sci. U.S.A.* 102:3906-3912), opp1 (ORFs LBA0197 to LBA0203) and opp2 (ORFs LBA1300 to LBA1306). As well, six additional genes coding for periplasmic substratebinding proteins (OppA) were identified (LBAI216, LBA1347, LBA1400, LBA1665, LBA1958, and LBA1961). One major function of oligopeptide transport (Opp) systems for bacterial cells is to internalize peptides to be used as carbon and nitrogen sources. They are also involved in the recycling of the cell wall peptides, which are likely one of the first targets of physiochemical stress. Opp systems are members of the ABC transporters family and usually consist of two ATP-binding proteins, two transmembrane proteins, and an extracellular ligand-specific binding protein. In gram-positive bacteria, the substrate-binding protein aligns with the external face of the cytoplasmic membrane (Sutcliffe and Russell (1995) *J. Bacteriol.* 177:1123-1128) and biochemical evidence suggests that they have a chaperone-like function in protein folding, protection against thermal denaturation, and interaction with unfolded proteins (Richarme and Caldas (1997) *J. Biological Chem.* 272:15607-15612). Since several components of the proteolytic system were overexpressed, we expected that the HPK mutant would be able to grow better in milk than the control. On the contrary, the mutant was not able to acidify 10% skim milk (SM) under pH 5.0. However, when SM was supplemented with yeast extract both the parent and the mutant were stimulated to the same degree. Yeast extract is the water-soluble portion of autolyzed yeast, containing vitamin B complex. It provides vitamins, nitrogen, amino acids, and carbon in growth media or supplemented milk. Furthermore, supplementation of SM with casaminoacids essentially abolished differences in acidification rate between the wild type and the mutant strains. These observations provide evidence that the proteolytic system in the HPK mutant was debilitated. An alternative possibility is that inactivation of the 2CRS resulted in the reduced expression of a specific amino acid transporter. The decreased intracellular concentration of that amino acid might trigger the cell to overexpress other options to obtain that amino acid, i.e., through peptide transport and peptidases, or through other pathways such as enzymes involved in the biosynthesis of lysine (LBA0849 and LBA0850). Two genes encoding putative opp binding proteins (LBA1300 and LBA1665) were consistently under expressed in the mutant suggesting that these transport systems are important for the organism's ability to grow in milk. It is not clear, however, why other opp transporters present in the genome would not replace any loss of capacity from the limited expression of LBA1300 and LBA1665, especially when a number of these were overexpressed.

Opp systems are also related to mechanisms of signaling since they transport signal peptides that, once inside the cell, will interact with intracellular receptors to regulate cellular functions (Lazazzera (2001) *Peptides* 22:1519-1527). In gram-positive bacteria, cell-density response mechanisms are well studied. A peptide signal precursor locus is translated into a precursor protein that is cleaved to produce an autoinducer signal that is transported out of the cell. When the extracellular concentration of the peptide signal accumulates to the minimal stimulatory level, a HPK of a 2CRS detects it and the phosphorylated RR activates the transcription of target genes (Miller and Bassler (2001) *Annu. Rev. Microbiol.* 55:165-199).

Interestingly, the autoinducer-2 production gene, luxS, was significantly overexpressed in the BPK mutant. The gene luxS is responsible for the production of an autoinducer molecule AI-2 in Vibrio harveyi and other gram-positive and gram-negative bacteria (Shauder et al. (2001) *Mol. Microbiol.* 41:463-476). LuxS is the autoinducer synthase, responsible for catalysis of the final step in AI-2 biosynthesis. The disruption of luxS in *S. pyogenes* had several effects suggesting that it is an important component of the response machinery that allows this strain to adapt to changing conditions during an infection. These effects include regulation of the SpeB protease and stress response (Lyon et al. (2001) *Mol. Microbiol.* 42: 145-157). The gene located upstream luxS (LBA1080) was also up-regulated in the mutant at both pH 5.5 and 4.5.

Intriguingly, the expression of the aspartate kinase (EC 2.7.2.4, LBA0850) and diaminopimelate epimerase (EC 5.1.1.7, LBA0849) was increased at pH 5.5 in the HPK mutant. These are key enzymes in the biosynthesis of lysine and are organized in an operon in *L. acidophilus*. However, the diaminopimelate decarboxylase (EC 4.1.1.20, LBA0851), enzyme responsible for the last step in the synthesis of lysine, was not over expressed in the HPK mutant. under these conditions, we suggest D,Ldiaminopimelate, instead of being converted to L-lysine, enters the peptidoglycan biosynthesis pathway. It is unclear if the HPK mutant produces more peptidoglycan. If so, that may contribute to the changes observed in cell morphology and chain length. In summary, environmental conditions that included changes in acid concentration and fluctuations of pH were sensed by the 2CRS, LBA1524HPK. It would be expected that this protein then initiates a phosphorylation cascade that regulates expression of a number of genes in the *L. acidophilus* genome. Most of the differentially expressed genes were up regulated in the HPK mutant, suggesting that LBA1525RR may act as a repressor. The inactivation of this 2CRS resulted in alterations in cell morphology, acid sensitivity, ethanol sensitivity, and poor acidification rates in skim milk indicating a loss of proteolytic activity. Microarray data showed that more than 50% of the genes differentially expressed in the BPK mutant encode putative membrane proteins. Additionally, expression of multiple components of the proteolytic enzyme system, i.e. opp transporters, permeases, and peptidases, were dramatically affected by the inactivation of the HPK, but no simple correlation of higher or lower gene expression to proteolytic activity, or the loss thereof, was apparent.

EXAMPLE 5

Genetic Characterization of an Operon Encoding the Bacteriocin, Lactacin B, in *Lactobacillus acidophilus* NCFM Bacteriocins are a diverse group of antimicrobial peptides produced by microorganisms. Their range of inhibition is narrow, typically limited to species that inhabit the same environmental niches such as the gastrointestinal tract. Many bacteriocins are able to elicit their lethal effects by creating pores in the cellular membrane of target organisms. This results in a dissipation of the proton motive force, leakage of ATP and other essential cellular ions leading to cell death. Currently, bacteriocins produced by lactic acid bacteria (LAB), in particular, are widely used within the food industry due to their efficacy against foodborne pathogens such as *Listeria monocytogenes* and *Clostridium botulinum*. Lactacin B is a chromosomally encoded bacteriocin produced by *Lactobacillus acidophilus* NCFM. Recent sequencing of the NCFM genome revealed a primary region of interest possibly responsible for lactacin B production, processing, and export. The overall objective of our study was to investigate the role of this region in lactacin B production and processing The activity of lactacin B, a bacteriocin produced by *L. acidophilus* NCFM, was assayed using the direct method for bacteriocin detection (Barefoot et al. (1983) *Appl. Environ. Microbiol.* 45:1808-1815). Zones of inhibition indicate death of indicator strain. Bacteriocin production by *L. acidophilus* NCFM and its derivatives was carried out under both aerobic and anaerobic conditions.

Stationary phase cultures of NCFM were carried out as follows. 5 µl of culture were aliquotted onto MRS agar plate (1.5% w/v). MRS soft agar (0.75% w/v) containing indicator strain was poured onto surface of plate. After 19-24 hour incubation, zones of inhibition were analyzed.

The consensus genetic elements necessary for production of many LAB bacteriocins have been elucidated. These elements can exist on a plasmid and/or chromosomally and include genes encoding a two-component regulatory system, one or more structural genes encoding the pre-bacteriocin peptide, a gene encoding an immunity protein and finally one or more genes encoding a dedicated export system responsible for export of the bacteriocin molecule from the cell. These coordinated processes yield a mature biologically active antimicrobial peptide as illustrated by Ennahar et al. (2000) *FEMS Microbiol. Lett.* 24: 85-106.

Previous analysis revealed that lactacin B is a 6.5 kDa bacteriocin with antagonistic activity against closely-related species; the genetic determinants were unknown (Barefoot et al. (1983) *Appl. Environ. Microbiol.* 45:1808-1815.). Recent mining of the NCFM genome revealed a region possibly responsible for lactacin B production (Altermann et al. (2004) *Proc. Natl. Acad. Sci. USA* 102: 3906-12). This region is flanked by two strong terminators and includes 11 putative open reading frames (ORFs) with similarities to conventional bacteriocin machinery including a regulation system, an immunity protein, and a dedicated ABC transporter protein involved in bacteriocin export. Seven additional putative open reading frames with unknown functions were also identified in the putative operon (data not shown). Table 4 provides a summary of the various open reading frames and their fulnction.

TABLE 4

| ORF | Size (aa) | Homology (accession no.) | Proposed function |
|---|---|---|---|
| LBA1803 | 53 | | |
| LBA1802 | 63 | | |
| LBA1801 | 38 | | |
| LBA1800 | 47 | | |
| LBA1799 | 440 | Two-component system protein histidine kinase (NP_964617) | Regulation of lactacin B |
| LBA1798 | 270 | Two-component system protein histidine kinase (NP_964619) | Regulation of lactacin B |
| LBA1797 | 83 | | |
| LBA1796 | 720 | ABC transporter permease component (NP_964620) | Lactacin B export |
| LBA1794 | 196 | Transporter auxillary protein (NP_964629) | Lactacin B export |
| LBA1793 | 438 | Immunity/modification protein [Streptococcus thermophilus LMG18311] | Immunity to Lactacin B |
| LBA1792 | 63 | | |
| LBA1791 | 67 | | |

In order to examine the role that this region plays in lactacin B production, the gene encoding the putative ABC transporter protein (LBA1796) was functionally disrupted by homologous recombination using the targeted integration vector pORI28 as described by Russell et al. (2001) *Appl. Environ. Microbiol.* 67: 43614364. An 800 bp internal fragment of LBA1796 was PCR amplified and cloned into pORI28 using XbaI/BglII sites. Subsequent transformation into NCFM containing a temperature sensitive helper plasmid (pTRK669) selects for chromosomal integrants following a temperature increase.

Figure 6:
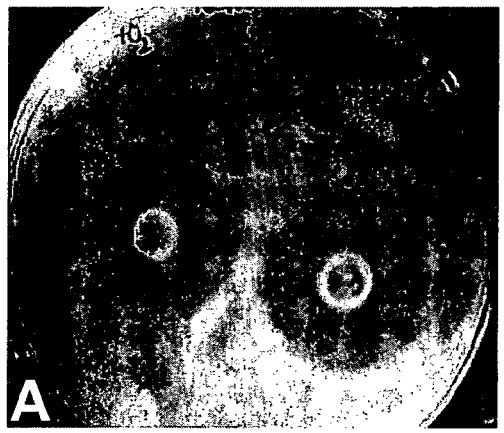
FIGS. 6A and 6B shows a bacteriocin assay which compares the wildtype NCFM (A) versus the NCFM integrant.
Figure 6:
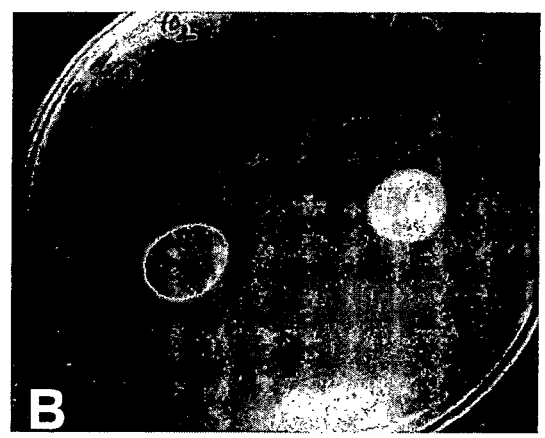

Inactivation of the putative ABC transporter protein was confirmed via Southern hybridization analysis (data not shown) and by PCR to confirm junction fragments using chromosomal DNA as a template (data not shown). The integrant was assayed for lactacin B activity (FIGS. 6A and B). A bacteriocin assay was performed comparing wildtype NCFM (FIG. 6A) versus NCFM integrant (FIG. 6B). Lactacin B activity was abolished in the integrant.

ABC Transporter Protein (LabT) appears crucial for lactacin B export and activity. It is likely that this region also encodes the genetic determinants for lactacin B regulation, production, and immunity.

EXAMPLE 6

Characterization of a Two-Component Regulatory System Implicated in the Bile Tolerance of *Lactobacillus acidophilus* NCFM The effectiveness of any bacterium used as a probiotic or biotheraputic vector intended to act in the intestinal tract depends on its ability to survive in this region where it must be able to withstand stresses imposed by the body's physico-chemical defense system. These stresses include low pH, high osmolality, and the presence of bile (Chowdhury et al. (1996) *Stress Response in Pathogenic Bacteria. Indian Journal of Biosciences* 21:149-160). Bile's amphipathic nature allows it to act as a detergent, dissolving the phospholipid membranes that surround bacteria leading to a loss of membrane integrity and cell death. In addition to its action as a detergent, bile has been shown to cause DNA damage and induce genes involved with DNA repair (Dashkevicz et al. (1989) *Appl Environ Microbiol* 55:11-6, McAuliffe et al. In Press. *Appl Environ Microbiol.*). Bacteria employ a plethora of mechanisms to respond to and defend against bile in their environment, including mechanisms that remove bile from the cell, modify it, and repair damage through general stress responses. The pathway to the induction of genes that mediate these responses is largely unknown, but may be mediated by a histidine protein kinase-response regulator phosphorelay pathway (Begley et al. In Press. The interaction between bacteria and bile. *FEMS Microbiol Rev.*). A whole-genome microarray study has shown that several genes in *L. acidophilus* NCFM are upregulated upon exposure to 5% Oxgall (See, Example 2). Included among these was a group of six tandem genes containing both histidine kinase and response regulator genes. This study examined this putative operon and the influence of its histidine kinase on cell growth in the presence of bile.

A microarray study of the expression of genes in *L. acidophilus* NCFM cells exposed to 5% Oxgall was performed that indicated the upregulation of six tandem genes (LBA1432-LBA1427) with this treatment (see, Example 2). The sequenced *L. acidophilus* NCFM genome (Accession NC_006814) indicates that LBA1430 encodes a histidine protein kinase and LBA1431 encodes a response regulator gene. The function of the other genes in this group remains largely unknown, although LBA1429 consists of 12 transmembrane domains and is believed to encode a transporter (Altermann et al. (2005) *Proc Natl Acad Sci USA* 102:3906-12). Clone Manager software indicated the presence of dyad symmetry that could lead to a stem loop structure, typical of a transcriptional terminator upstream of the putative operon. Reverse transcriptase PCR using primers designed to amplify the intergenic regions in the proposed operon was performed on RNA extracted from cells grown in MRS with no Oxgall or MRS+0.3% Oxgall for 1.5 hours. PCR amplification of cDNA from the intergenic regions indicated that these genes are cotranscribed into RNA.

The putative histidine kinase gene in the six-gene operon was selected for inactivation in order to investigate its role in bile tolerance in *L. acidophilus* NCFM. This inactivation was carried out by insertion of an erythromycin cassette by the method of Russell and Klaenhammer, utilizing the Ori+and RepA-integration plasmid, pORI28 (Flahaut et al. (1996) *Appl. Environ. Microbiol.* 62:2416-2420). The integration vector was created through ligation of a BglII and XbaI digested pORI28 with BglII and XbaI digested PCR fragment of LBA1430. The resulting plasmid, pTRK843 was transformed into *L. acidophilus* NCFM containing pTRK669, a plasmid containing a functional repA gene and a chloramphenicol resistance cassette. A temperature shift from 37° to 42° resulted in the loss of pTRK669 and selection for clones where pTRK843 had integrated into the genome. Integration of pTRK843 was confirmed by Southern blot (data not shown).

Figure 7:
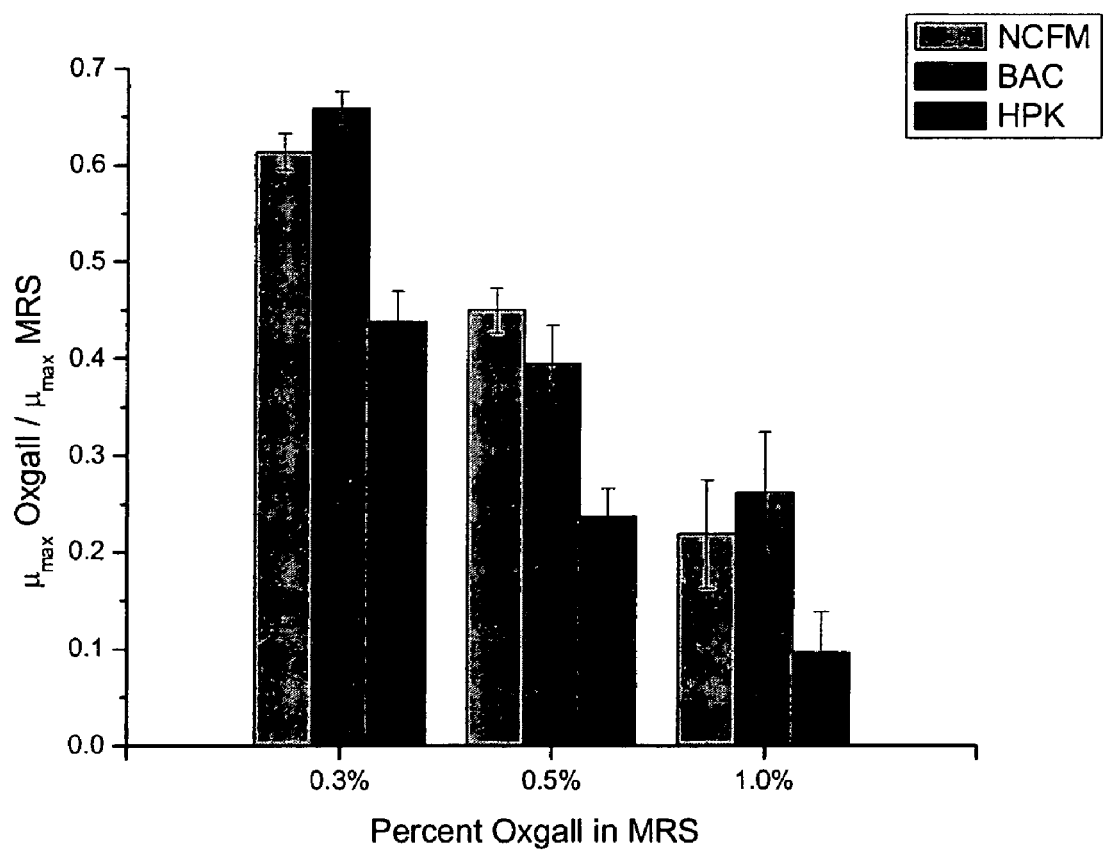
FIG. 7 shows the ratio of maximum growth rates in MRS compared to MRS+Oxgall. Bars with * represent significantly different means within their group. Error bars represent the standard error of the mean.

Cells were grown anaerobically in MRS with 0.0%, 0.3%, or 0.5% Oxgall for 15 hours with OD600 measurements taken every 15 minutes. The resulting growth curves showed decreasing ability for the histidine kinase mutant to grow as the concentration of Oxgall in the medium increases as compared to the wild type strain. An ABC transporter, LBA1796, knockout mutant (Bac) was used in this study as a control so erythromycin pressure could be maintained indicating the continued presence of the insertional knockout (A. Dobson, personal communication). The maximum specific growth rate (μmaxh-1) for the HPK mutant was significantly different than for the controls when grown in MRS with 0.3% and 0.5% Oxgall. See FIG. 7.

Figure 8:
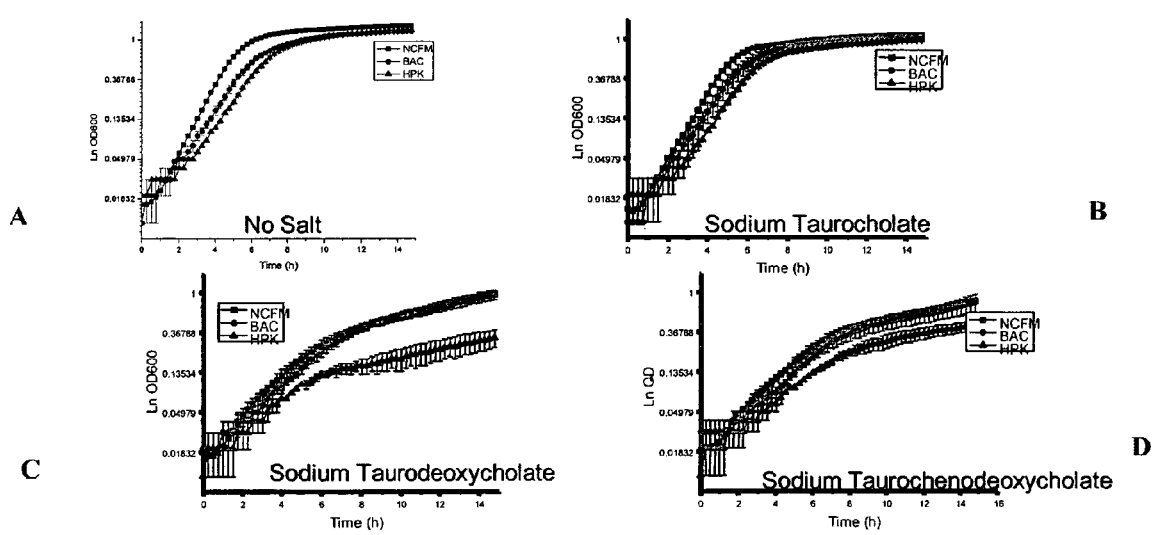
FIG. 8 provides a series of growth curves using 0.3% of individual bile salts: no salt (A), sodium taurocholate (B), sodium taurodeoxycholate (C) and sodium taurochendodeoxycholate (D).

Growth curve experiments were also performed using 0.3% of individual bile salts: taurocholic acid, taurodeoxycholic acid, taurochenodeoxycholic acid, glycocholic acid, glycodeoxycholic acid. Sodium taurodeoxycholate was the only salt that affected the growth of the HPK mutant as compared to wild type, however the maximum specific growth rate between the strains were not significantly different with any of the salts. See FIG. 8.

It is known that some *lactobacilli* and *bifidobacteria* strains, including *L. acidophilus* NCFM, possess the ability to deconjugate bile salts, or separate their amino acid moiety from the cholesterol backbone (Gilliland et al. (1977) *Appl Environ Microbiol* 33:15-8). Although the role of this process in bacteria is not clear, it is believed to confer some positive effect on the cell including protection against the toxic effects of bile (Flahaut et al. (1996) *Appl. Environ. Microbiol.* 62:2416-2420). Functional analysis of the bile salt hydrolase genes has shown that the bshB gene (LBA1078) deconjugates sodium taurodeoxycholate (McAuliffe et al. In Press. *Appl Environ Microbiol.*). Since the growth of the HPK mutant was decreased in this particular salt, it is possible that genes controlled by this particular HPK include the bshB gene. In order to determine if the HPK mutant retained the ability to deconjugate this bile salt, cells were plated onto MRS agar with 0.3% of each of the salts used in the growth experiments. Zones of clearing surrounding the colonies indicated the activity of the bile salt hydrolases (Dashkevicz et al. (1989) *Appl Environ Microbiol* 55:11-6). No difference in deconjugation was seen between the wild type *L. acidophilus* NCFM and the HPK mutant strain.

It has been proposed that since sodium taurodeoxycholate is more hydrophobic than other bile salts, that it imposes a more disruptive effect on bacterial cell membranes (Sung et al. (1993) *Dig Dis Sci* 38:2104-12). Since this particular salt lowers growth of the HPK mutant as compared to the wild type and control strains, it is possible that genes regulated by this particular histidine kinase encode proteins that may counteract this disruptive effect.

LBA1427-1432 in *L. acidophilus* NCFM constitute an operon involved in bile tolerance. LBA1430 in *L. acidophilus* NCFM encodes a histidine kinase involved in bile tolerance. Loss of histidine kinase activity from LBA1430 leads to a decreased ability of cells to grow in the presence of bile. Sodium taurodeoxycholate has a more inhibitory effect on the growth of the HPK mutant than other salts tested.

All publications, patents and patent applications mentioned in the specification are indicative of the level of those skilled in the art to which this invention pertains. All publications, patents and patent applications are herein incorporated by reference in their entireties to the same extent as if each individual publication, publication or patent application was specifically and individually indicated to be incorporated by reference for the teachings disclosed in the sentence and/or paragraph in which the publication, patent or patent application is cited.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence encoding a polypeptide having at least 90% amino acid sequence identity to the full length amino acid sequence of SEQ ID NO: 20, wherein said nucleic acid molecule encodes a polypeptide having histidine kinase activity which activates a transcriptional regulator in response to the presence of bile and thereby increases bile tolerance of a cell.

2. A plasmid comprising a nucleotide sequence that encodes a polypeptide having at least 90% amino acid sequence identity to the full length amino acid sequence of SEQ ID NO: 20, wherein said polypeptide has histidine kinase activity which activates a transcriptional regulator in response to the presence of bile and thereby increases bile tolerance of a cell.

3. The plasmid of claim 2, further comprising a nucleic acid molecule encoding a heterologous polypeptide.

4. A microbial cell comprising a heterologous nucleic acid molecule comprising a nucleotide sequence that encodes a polypeptide having at least 90% amino acid sequence identity to the full length of the amino acid sequence of SEQ ID NO: 20, wherein said nucleic acid molecule encodes a polypeptide having histidine kinase activity which activates a transcriptional regulator in response to the presence of bile and thereby increases bile tolerance of a cell.

5. The cell of claim 4, wherein said cell is a bacterial cell.

6. A method for producing a polypeptide, comprising culturing a cell comprising a heterologous polynucleotide encoding said polypeptide under conditions in which the nucleic acid molecule encoding the polypeptide is expressed, said polypeptide comprises an amino acid sequence having at least 90% sequence identity to the full length amino acid sequence of SEQ ID NO: 20, wherein said polypeptide has histidine kinase activity which activates a transcriptional regulator in response to the presence of bile and thereby increases the bile tolerance of a cell.

7. A kit comprising the nucleic acid molecule of claim 1 and instructions for use.

8. The isolated nucleic acid molecule of claim 1, wherein said nucleic acid molecule comprises a nucleotide sequence having at least 90% sequence identity to the full length sequence of SEQ ID NO: 19.

9. The isolated nucleic acid molecule of claim 1, wherein said nucleic acid molecule comprises a nucleotide sequence having at least 95% sequence identity to the full length sequence of SEQ ID NO: 19.

10. The isolated nucleic acid molecule of claim 1, wherein said nucleic acid molecule comprises SEQ ID NO: 19.

11. The isolated nucleic acid molecule of claim 1, wherein said nucleic acid molecule encodes a polypeptide having the amino acid sequence set forth in SEQ ID NO: 20.

12. The cell of claim 4, wherein said nucleic acid molecule comprises a nucleotide sequence having at least 90% sequence identity to the full length sequence of SEQ ID NO: 19.

13. The cell of claim 4, wherein said nucleic acid molecule comprises a nucleotide sequence having at least 95% sequence identity to the full length sequence of SEQ ID NO: 19.

14. The cell claim 4, wherein said nucleic acid molecule comprises SEQ ID NO: 19.

15. The cell claim 4, wherein said nucleic acid molecule encodes a polypeptide having the amino acid sequence set forth in SEQ ID NO: 20.

16. The host cell of claim 4, wherein said heterologous nucleic acid molecule is in a vector.

17. The method of claim 6, wherein said nucleic acid molecule comprises a nucleotide sequence having at least 90% sequence identity to the full length sequence of SEQ ID NO: 19.

18. The method of claim 6, wherein said nucleic acid molecule comprises a nucleotide sequence having at least 95% sequence identity to the full length sequence of SEQ ID NO: 19.

19. The method of claim 6, wherein said nucleic acid molecule comprises SEQ ID NO: 19.

20. The method of claim 6, wherein said nucleic acid molecule encodes a polypeptide having the amino acid sequence set forth in SEQ ID NO: 20.

21. The cell of claim 5, wherein said bacterial cell comprises a lactic acid bacterial.

22. The cell of claim 21, wherein said lactic acid bacterial cell comprises *Lactobacillus*.

* * * * *

UNITED STATES PATENT AND TRADEMARK OFFICE
CERTIFICATE OF CORRECTION

PATENT NO. : 7,550,576 B2
APPLICATION NO. : 11/199489
DATED : June 23, 2009
INVENTOR(S) : Klaenhammer et al.

It is certified that error appears in the above-identified patent and that said Letters Patent is hereby corrected as shown below:

Column 30,
Line 33, "Mäyräi" should read --Mäyrä--.

Column 33,
Line 38, "prohibiting" should read --prohibitins--.

Column 43,
Line 20, "fuinction" should read --function--.

Column 49,
Lines 9 and 24, "*salvarius*" should read --*salivarius*--.

Column 52,
Line 41, "anino" should read --amino--.

Column 54,
Line 33, "*salvarius*" should read --*salivarius*--.

Column 56,
Line 19, "*Lactobacillius*" should read --*Lactobacillus*--.

Column 67,
Line 49, "Coming" should read --Corning--

Column 69,
Line 13, "Klaenhamrnmer" should read --Klaenhammer--.

Column 70,
Lines 63 and 64, "11524F-11524R" should read --I1524F-I1524R--.

Column 78,
Line 8, "LBA1525RR" should read --LBAi525RR--.

Column 80,
Line 21, "foodbome" should read --foodborne--;
Line 67, "fulnction" should read --function--.

UNITED STATES PATENT AND TRADEMARK OFFICE
CERTIFICATE OF CORRECTION

PATENT NO.        : 7,550,576 B2
APPLICATION NO.   : 11/199489
DATED             : June 23, 2009
INVENTOR(S)       : Klaenhammer et al.

It is certified that error appears in the above-identified patent and that said Letters Patent is hereby corrected as shown below:

Column 81,
Line 29, "43614364" should read --4361-4364--;
Line 31, "Xba1I" should read --XbaI--.

Signed and Sealed this

Seventeenth Day of November, 2009

David J. Kappos
*Director of the United States Patent and Trademark Office*